US012195458B2

(12) United States Patent
Blackaby et al.

(10) Patent No.: US 12,195,458 B2
(45) Date of Patent: *Jan. 14, 2025

(54) POLYHETEROCYCLIC COMPOUNDS AS METTL3 INHIBITORS

(71) Applicant: Storm Therapeutics Limited, Cambridge (GB)

(72) Inventors: Wesley Peter Blackaby, Cambridge (GB); Elizabeth Jane Thomas, Cambridge (GB); David James Hardick, Cambridge (GB); Jon Shepherd, Oxfordshire (GB); Frederick Arthur Brookfield, Oxfordshire (GB); Christian Bubert, Oxfordshire (GB); Mark Peter Ridgill, Oxfordshire (GB)

(73) Assignee: Storm Therapeutics Limited, Cambridge (GB)

( * ) Notice: Subject to any disclaimer, the term of this patent is extended or adjusted under 35 U.S.C. 154(b) by 129 days.

This patent is subject to a terminal disclaimer.

(21) Appl. No.: 17/778,701

(22) PCT Filed: Dec. 1, 2020

(86) PCT No.: PCT/GB2020/053081
§ 371 (c)(1),
(2) Date: May 20, 2022

(87) PCT Pub. No.: WO2021/111124
PCT Pub. Date: Jun. 10, 2021

(65) Prior Publication Data
US 2023/0116403 A1    Apr. 13, 2023

(30) Foreign Application Priority Data

Dec. 2, 2019  (GB) ..................... 1917603
Oct. 2, 2020  (GB) ..................... 2015692
Oct. 6, 2020  (GB) ..................... 2015820

(51) Int. Cl.
*C07D 471/04* (2006.01)
*C07D 403/14* (2006.01)
*C07D 417/14* (2006.01)
*C07D 519/00* (2006.01)

(52) U.S. Cl.
CPC ......... *C07D 471/04* (2013.01); *C07D 403/14* (2013.01); *C07D 417/14* (2013.01); *C07D 519/00* (2013.01)

(58) Field of Classification Search
CPC .................................................. C07D 471/04
USPC ................................................... 514/210.16
See application file for complete search history.

(56) References Cited

U.S. PATENT DOCUMENTS

| 5,668,180 | A | 9/1997 | Lesieur et al. |
| 5,928,323 | A | 7/1999 | Gosling et al. |
| 8,202,524 | B2 * | 6/2012 | Sah .................. A61P 25/18 514/772.3 |
| 9,464,065 | B2 | 10/2016 | Schultz et al. |
| 9,708,348 | B2 | 7/2017 | Castro et al. |
| 11,725,010 | B2 | 8/2023 | Blackaby et al. |
| 2023/0002378 | A1 | 1/2023 | Blackaby et al. |

FOREIGN PATENT DOCUMENTS

| WO | WO-9842698 A1 | 10/1998 |
| WO | WO-200017190 A2 | 3/2000 |
| WO | WO-200250091 A1 | 6/2002 |
| WO | WO-2002066469 A2 | 8/2002 |
| WO | WO-2005048922 A2 | 6/2005 |
| WO | WO-2005097261 A1 | 10/2005 |
| WO | WO-2006100208 A1 | 9/2006 |
| WO | WO-2006138549 A1 | 12/2006 |
| WO | WO-2007/048070 A2 | 4/2007 |
| WO | WO-2007039218 A1 | 4/2007 |
| WO | WO-2007081597 A2 | 7/2007 |
| WO | WO-2007/095124 A2 | 8/2007 |
| WO | WO-2007147217 A1 | 12/2007 |
| WO | WO-2008016666 A2 | 2/2008 |
| WO | WO-2008074068 A1 | 6/2008 |
| WO | WO-2008077188 A1 | 7/2008 |
| WO | WO-2008100448 A2 | 8/2008 |
| WO | WO-2009/025478 A1 | 2/2009 |
| WO | WO-2009/100294 A2 | 8/2009 |
| WO | WO-2009/127678 A1 | 10/2009 |

(Continued)

OTHER PUBLICATIONS

Alvarez et al., "Allosteric Indole Amide Inhibitors of p97: Identification of a Novel Probe of the Ubiquitin Pathway," ACS Medicinal Chemistry Letters, 7(2): 182-187 (2016).

(Continued)

*Primary Examiner* — Niloofar Rahmani
(74) *Attorney, Agent, or Firm* — Foley Hoag LLP; David P. Halstead; Alexander J. Chatterley

(57) ABSTRACT

The present invention relates to compounds of formula (I) that function as inhibitors of METTL3 (N6-adenosine-methyltransferase 70 kDa subunit) enzyme activity:

$$X\text{—}Y\text{—}Z \qquad (I)$$

wherein X, Y and Z are each as defined herein. The present invention also relates to processes for the preparation of these compounds, to pharmaceutical compositions comprising them, and to their use in the treatment of proliferative disorders, such as cancer, and autoimmune diseases, as well as other diseases or conditions in which METTL3 activity is implicated.

21 Claims, No Drawings

(56) References Cited

FOREIGN PATENT DOCUMENTS

| | | |
|---|---|---|
| WO | WO-2010000030 A1 | 1/2010 |
| WO | WO-2010000031 A1 | 1/2010 |
| WO | WO-2010000032 A1 | 1/2010 |
| WO | WO-2010006496 A1 | 1/2010 |
| WO | WO-2010114898 A1 | 10/2010 |
| WO | WO-2010/138600 A2 | 12/2010 |
| WO | WO-2011050245 A1 | 4/2011 |
| WO | WO-2012006680 A1 | 1/2012 |
| WO | WO-2012/131031 A1 | 10/2012 |
| WO | WO-2013119916 A2 | 8/2013 |
| WO | WO-2014148557 A1 | 9/2014 |
| WO | WO-2015105657 A1 | 7/2015 |
| WO | WO-2015192760 A1 | 12/2015 |
| WO | WO-2015192761 A1 | 12/2015 |
| WO | WO-2016027249 A1 | 2/2016 |
| WO | WO-2016054491 A1 | 4/2016 |
| WO | WO-2016/196386 A1 | 12/2016 |
| WO | WO-2017214269 A1 | 12/2017 |
| WO | WO-2018098446 A1 | 5/2018 |
| WO | WO-2018183145 A1 | 10/2018 |
| WO | WO-2019/197024 A1 | 10/2019 |
| WO | WO-2020037079 A1 | 2/2020 |
| WO | WO-2020/112872 A1 | 6/2020 |
| WO | WO-2020/201773 A1 | 10/2020 |
| WO | WO-2021/111124 A1 | 6/2021 |

OTHER PUBLICATIONS

Heidenreich et al., "Structure-Based Approach toward Identification of Inhibitory Fragments for Eleven-Nineteen-Leukemia Protein (ENL)," Journal of Medicinal Chemistry, 61: 10929-10934 (2018).
International Search Report and Written Opinion for International Application No. PCT/GB2020/053081 dated Feb. 16, 2021.
Moustakim et al., "Discovery of an MLLT1/3 Yeats Domain Chemical Probe," Angewandte Chemie International Edition, 57: 16302-16307 (2018).
United Kingdom Search Report for Application No. GB1917603.1 dated May 19, 2020.
Burgess et al., "Targeting the m6A RNA modification pathway blocks SARS-CoV-2 and HCoV-OC43 replication" Genes and Development, 35:1005-1019 (2021).
Cheng et al., "The m6A methyltransferase METTL3 promotes bladder cancer progression via AFF4/NF-KB/MYC signaling network" Oncogene, 38(19):3667-3680 (2019).
Choe et al., "mRNA circularization by METTL3-eIF3h enhances translation and promotes oncogenesis" Nature, 561(7724): (2018).
Cui et al., "m6A RNA Methylation Regulates the Self-Renewal and Tumorigenesis of Glioblastoma Stem Cells" Cell Rep, 18(11):2622-2634 (2017).
Du et al., ""MiR-33a suppresses proliferation of NSCLC cells via targeting METTL3 mRNA"" Biochem Biophys Res Commun, 482(4): 582-589 (2017).
Fang et al., "Transcriptome-Wide Analysis of RNA N6-Methyladenosine Modification in Adriamycin-Resistant Acute Myeloid Leukemia Cells" Frontiers in Genetics, 13(833694): 13 pages (2022).
Han et al., "Anti-tumor immunity controlled through mRNA m6A and YTHDF1 in dendritic cells" Nature, 566(7743):270-274 (2019).
Han et al., "METTL3 promote tumor proliferation of bladder cancer by accelerating pri-miR221/222 maturation in m6A-dependent manner" Mol Cancer, 18(1): (2019).
Li et al., " METTL3 facilitates tumor progression via an m6A-IGF2BP2-dependent mechanism in colorectal carcinoma" Mol Cancer, 18(1):(2019).
Li et al., "METTL3 inhibition reduces N6-methyladenosine levels and prevents allogeneic CD4+ T-cell responses" Immunology and Cell Biology, 100:718-730 (2022).
Lin et al., " RNA m6A methylation regulates the epithelial mesenchymal transition of cancer cells and translation of Snail" Nat Commun May 6, 2019;10(1):2065. doi: 10.1038/s41467-019-09865-9. PMID: 31061416; PMCID: PMC6502834.
Lin et al., "METTL3 promotes translation in human cancer cells" Mol Cell, 62(3):335-345 (2016).
Liu et al., "m6A mRNA methylation regulates AKT activity to promote the proliferation and tumorigenicity of endometrial cancer" Nat Cell Biol, 20(9): 1074-1083 (2018).
Miao et al., "The m6A methyltransferase METTL3 promotes osteosarcoma progression by regulating the m6A level of LEF1" Biochem Biophys Res Commun, 516(3):719-725 (2019).
Visvanathan et al., "Essential role of METTL3-mediated m6A modification in glioma stem-like cells maintenance and radioresistance" Oncogene, 37(4):522-533 (2018).
Visvanathan et al., "N6-Methyladenosine Landscape of Glioma Stem-Like Cells: METTL3 Is Essential for the Expression of Actively Transcribed Genes and Sustenance of the Oncogenic Signaling" Genes (Basel).Feb. 13, 2019;10(2):141. doi: 10.3390/genes10020141. PMID: 30781903; PMCID: PMC6410051.
Wang et al."N6-methyladenosine METTL3 promotes the breast cancer progression via targeting Bcl-2" Gene, Jan. 5, 2020;722:144076. doi: 10.1016/j.gene.2019.144076.
Weng et al., ""METTL14 Inhibits Hematopoietic Stem/Progenitor Differentiation and Promotes Leukemogenesis via mRNA m6A Modification"" Cell Stem Cell, 22(2): 191-205 (2018).
Wu et al., "The Role of RNA Methyltransferase METTL3 in Normal and Malignant Hematopoiesis" Frontiers in Oncology, 12(873903): 10 pages (2022).
Xu et al., "METTL3 promotes intrahepatic cholangiocarcinoma progression by regulating IFIT2 expression in an m6A-YTHDF2-dependent manner" Oncogene, 41:1622-1633 (2022).
Yanakova et al., "Small molecule inhibition of METTL3 as a strategy against myeloid leukaemia" Nature, 593(7860): 597-601 (2021).
Yue et al., "METTL3-mediated N6-methyladenosine modification is critical for epithelial-mesenchymal transition and metastasis of gastric cancer" Mol Cancer, 18(1): (2019).
Zhang et al., "METTL3 regulates m6A methylation of PTCH1 and GLI2 in Sonic hedgehog signaling to promote tumor progression in SHH-medulloblastoma" Cell Reports, 41(111530): 26 pages (2022).
Zhou et al., "METTL3 mediated m6A modification plays an oncogenic role in cutaneous squamous cell carcinoma by regulating ΔNp63" Biochem Biophys Res Commun, 515(2):310-317 (2019).
"Harnessing the Power of RNA Modification: 1st in Class Inhibitors of RNA Modifying Enzymes (RME) to Treat Cancer and Other Diseases" Storm Therapeutics. (2022).
"Oral Administration of STC-15 in Subjects With Advanced Malignancies" ClinicalTrials.gov identifier: NCT05584111, https://clinicaltrials.gov/ct2/show/NCT05584111, last visited Feb. 8, 2023.
Obacz et al., "STC-15, an oral small molecule inhibitor of the RNA methyltransferase METTL3, inhibits tumour growth through activation of anti-cancer immune responses and synergizes with immune checkpoint blockade," Storm Therapeutics, 37th Society for Immunotherapy of Cancer Annual Meeting (SITC 2022), Nov. 2022.
Ofir-Rosenfeld et al., "STC-15, an oral small molecule inhibitor of the RNA methyltransferase METTL3, inhibits tumour growth through activation of anti-cancer immune responses associated with increased interferon signalling, and synergizes with T cell checkpoint blockade," Storm Therapeutics, 34th EORTC-NCI-AACR Symposium on Molecular Targets and Cancer Therapeutics, Oct. 2022.
Ofir-Rosenfeld et al., "STC-15, an oral small molecule inhibitor of the RNA methyltransferase METTL3, inhibits tumour growth through activation of anti-cancer immune responses associated with increased interferon signalling, and synergises with T cell checkpoint blockade," Abstracts, 34th EORTC-NCI AACR Symposium, Poster 345, Poster Session (Oct. 28, 2022), Eur. J. Cancer, vol. 174, suppl. 1, S123, Oct. 2022.
Dyson et al., "Chemistry of Synthetic Medicinal Substances, M." World: 12-19 (1964).
Kümmerer, "Pharmaceuticals in the environment," Annual Review of Environment and Resources 35.1 (2010):57-75.

* cited by examiner

POLYHETEROCYCLIC COMPOUNDS AS METTL3 INHIBITORS

RELATED APPLICATIONS

This application is a U.S. National Stage filing under 35 U.S.C. § 371 of PCT Application No. PCT/GB20/53081, filed Dec. 1, 2020, which claims the benefit of priority to United Kingdom Patent Application Nos. 1917603.1, filed Dec. 2, 2019, 2015692.3, filed Oct. 2, 2020, and 2015820.0, filed Oct. 6, 2020. The contents of the International Patent Application are incorporated herein by reference in their entirety.

FIELD OF THE INVENTION

The present invention relates to certain compounds that function as inhibitors of METTL3 (N6-adenosine-methyltransferase 70 kDa subunit) activity. The present invention also relates to processes for the preparation of these compounds, to pharmaceutical compositions comprising them, and to their use in the treatment of proliferative disorders, such as cancer, autoimmune, neurological, infectious and inflammatory diseases, as well as other diseases or conditions in which METTL3 activity is implicated.

BACKGROUND OF THE INVENTION

N6-methyladenosine (m6A) is the most common and abundant covalent modification of messenger RNA, modulated by 'writers', 'erasers' and 'readers' of this mark (Meyer & Jaffrey 2014, Niu Y et al, 2013, Yue et al 2015). Approximately 0.1 to 0.5% of all mRNA adenosines are m6A modified (Li Y et al 2015). In vitro data have shown that m6A influences fundamental aspects of mRNA biology, mainly mRNA expression, splicing, stability, localisation and translation (Meyer et al, 2015; Sledz & Jinek 2016). M6A modifications are tissue specific and there is significant variability in their occurrence profiles in non-diseased tissues (eg brain, heart, kidney) and diseased tissues and cells (lung, renal, breast, and leukemic cancer cells) (Meyer et al 2012).

The m6A modifications and its erasers and writers such as FTO, ALKBH5, methyltransferase like 3 (METTL3) and METTL14 are associated with major diseases such as solid organ cancers, leukaemia, type 2 diabetes, neuropsychiatric behavioural and depressive disorders (Chandola et al 2015; Koranda et al 2018).

The RNA methyltransferase, METTL3, is the major, but not the sole enzyme, that catalyses m6A modification of RNA. It exists as a hetero-trimeric complex with METTL14 (Liu et al 2014, Wang et al 2016) and Wilm's Tumour Associated Protein (WTAP) (Ping et al 2014). Catalytic activity resides in METTL3, which transfers a methyl group from the co-factor S-adenosyl methionine to the substrate RNA and METTL14 facilitates substrate RNA binding. WTAP localises the complex in specific nuclear regions and also localises RNA substrates to the complex (Wang X et al 2016).

METTL3 has been reported to play a role in many aspects of the development of cancer (Fry et al 2018). Genetic knockdown of METTL3 in lung cancer cell lines (A549, H1299 and H1792) and HeLa cells leads to decreased growth, survival and invasion of human lung cancer cells (Lin S et al 2016). METTL3 is significantly up-regulated in human bladder cancer (Cheng et al 2019). Knockdown of METTL3 drastically reduced bladder cancer cell proliferation, invasion, and survival in vitro and tumorigenicity in vivo. AF4/FMR2 family member 4 (AFF4), two key regulators of NF-κB pathway (IKBKB and RELA) and MYC were further identified as direct targets of METTL3-mediated m6A modification. In renal carcinoma cell lines (CAK-1, CAK-2 and ACHN), genetic knockdown reduced cell proliferation via the phosphatidinylinositol 3-kinase (PI3K)/AKT/mammalian target of rapamycin (mTOR) signalling pathway (Li X et al 2017).

Recently Barbieri et al (2017), defined a set of RNA-modifying enzymes that are necessary for AML leukaemia and identified a key leukemic pathway for the METTL3 RNA methyltransferase. In this pathway, METTL3 is stably recruited by the CCAAT-box binding transcription factor CEBPZ to promoters of a specific set of active genes, resulting in m6A methylation of the respective mRNAs and increased translation. One important target is SP1, an oncogene in several cancers, which regulates c-MYC expression. Consistent with these findings, it has been reported that METTL3 can methylate its targets co-transcriptionally.

The pathway described by Barbieri et al., is critical for AML leukaemia, as three of its components are required for AML cell growth: (i) the m6A RNA methyltransferase METTL3; (ii) the transcription factor CEBPZ, which targets this enzyme to promoters; and (iii) SP1, whose translation is dependent upon the m6A modification by METTL3. Together, the observations of Barbieri et al define METTL3 enzymatic activity as a new candidate target for the treatment of AML.

In separate, independent studies it has been reported that METTL3 plays an essential role in controlling myeloid differentiation of mammalian normal hematopoietic and leukemic cells (Vu et al 2017). Forced expression of wild type METTL3, but not a mutant METTL3 (with defect in catalytic activity), significantly promotes cell proliferation and inhibits cell differentiation of human cord blood-derived CD34+ haematopoietic stem/progenitor cells (HSPCs). Genetic knockdown of METTL3 has the opposite effects. METTL3 is highly expressed in AML compared to normal HSPCs or other types of cancers. Knockdown of METTL3 in human AML cell lines significantly induces cell differentiation and apoptosis and inhibits leukemia progression in mice xeno-transplanted with MOLM-13 AML cells. The biological function of METTL3 is likely attributed to the promotion of translation of its mRNA targets such as MYC, BCL-2, and PTEN in an m6A-dependent manner.

Recently, METTL3 mediated m6A modification has been demonstrated to play an important role in T cell homeostasis and signal dependent induction of mRNA degradation in CD4 positive T cell lineages (Li et al 2017). Deletion of METTL3 in mouse T cells disrupts T cell homeostasis and differentiation. In a lymphopenic mouse adoptive transfer model, naive Mett/3-deficient T cells failed to undergo homeostatic expansion and remained in the naive state for up to 12 weeks, thereby preventing colitis. Consistent with these observations, the mRNAs of SOCS family genes encoding the STAT signalling inhibitory proteins SOCS1, SOCS3 and CISH were marked by m6A, exhibited slower mRNA decay and showed increased mRNAs and levels of protein expression in Mett/3-deficient naive T cells. This increased SOCS family activity consequently inhibited IL-7-mediated STAT5 activation and T cell homeostatic proliferation and differentiation. Thus METTL3 mediated m6A methylation has important roles for inducible degradation of Socs mRNAs in response to IL-7 signalling in order to reprogram naive T cells for proliferation and differentiation, pointing to a role in auto-immunity.

Recent studies have revealed that depletion of METTL3 leads to alterations in the propagation of diverse viruses (Winkler et al). Following viral infection or stimulation of cells with an inactivated virus, deletion of the m6A 'writer' METTL3 led to an increase in the induction of interferon-stimulated genes. Consequently, propagation of different viruses was suppressed in an interferon-signaling-dependent manner. Significantly, the mRNA of IFNB, was m6A modified and was stabilized following repression of METTL3. m6A serves as a negative regulator of interferon response by dictating the fast turnover of interferon mRNAs and consequently facilitating viral propagation.

METTL3-dependent m6A on HBV and HCV viral genome regulates recognition of the viral genome by RIG-1 RNA sensor. Depletion of METTL3 enhances viral dsRNA recognition and induces an anti-viral immune response (Kim et al.).

Therefore METTL3 inhibitors may provide a novel therapeutic approach to treat a range of infectious and inflammatory diseases. In particular, they provide a potential treatments for viral diseases (e.g. DNA and RNA viruses).

Furthermore, METTL3-dependent m6A on endogenous mRNAs regulates recognition of by MAVS-dependent RNA sensors. Depletion of METTL3 enhances endogenous dsRNA recognition and induces an auto-immune response (Gao et al.). This implies that an anti-tumour immune response might be enhanced by METTL3 inhibition.

Thus, METTL3 inhibitors may also provide a novel therapeutic approach to enhance an anti-tumour immune response.

REFERENCES

Barbieri I, Tzelepis K, Pandolfini L, Shi J, Millen-Zambrano G, Robson S C, Aspris D, Migliori V, Bannister A J, Han N, De Braekeleer E, Ponstingl H, Hendrick A, Vakoc C R, Vassiliou G S, Kouzarides T. Nature. 2017 Dec. 7; 552 (7683):126-131.

Chandola U, Das R, Panda B. Brief Funct Genomics. 2015 May; 14(3):169-79.

Cheng M, Gao Q, Wu M, Liang Y, Zhu F, Zhang Y, Zhang X, Li Y, Sheng L, Zhang H, Xiong Q, Yuan Q. Oncogene (2019; e-publication ahead of print).

Fry N J, Law B A, Ilkayeva O R, Carraway K R, Holley C L, Mansfield K D. Oncotarget. 2018 Jul. 27; 9(58):31231-31243.

Koranda J L, Dore L, Shi H, Patel M J, Vaasjo L O, Rao M N, Chen K, Lu Z, Yi Y, Chi W, He C, Zhuang X. Neuron. 2018 Jul. 25; 99(2): 283-292.

Li H B, Tong J, Zhu S, Batista P J, Duffy E E, Zhao J, Bailis W, Cao G, Kroehling L, Chen Y, Wang G, Broughton J P, Chen Y G, Kluger Y, Simon M D, Chang H Y, Yin Z, Flavell R A. Nature. 2017 Aug. 17; 548 (7667):338-342

Li X, Tang J, Huang W, Wang F, Li P, Qin C, Qin Z, Zou Q, Wei J, Hua L, Yang H, Wang Z. Oncotarget. 2017 Oct. 10; 8(56):96103-96116.

Li Y, Wang Y, Zhang Z, Zamudio A V, Zhao J C. RNA. 2015 August; 21(8):1511-8.

Lin S, Choe J, Du P, Triboulet R, Gregory R I. Mol Cell. 2016 May 5; 62(3):335-345.

Liu J, Yue Y, Han D, Wang X, Fu Y, Zhang L, Jia G, Yu M, Lu Z, Deng X, Dai Q, Chen W, He C. Nat Chem Biol. 2014 February; 10(2):93-5.

Meyer K D, Patil D P, Zhou J, Zinoviev A, Skabkin M A, Elemento O, Pestova T A, Qian S B, Jaffrey S R. Cell. 2015 Nov. 5; 163(4): 999-1010.

Meyer K D, Jaffrey S R. Nat Rev Mol Cell Biol. 2014 May; 15(5):313-26.

Meyer K D, Saletore Y, Zumbo P, Elemento O, Mason C E, Jaffrey S R. Cell. 2012 Jun. 22; 149(7):1635-46.

Niu Y, Zhao X, Wu Y S, Li M M, Wang X J, Yang Y G. Genomics Proteomics Bioinformatics. 2013 February; 11(1):8-17.

Ping X L, Sun B F, Wang L, Xiao W, Yang X, Wang W J, Adhikari S, Shi Y, Lv Y, Chen Y S, Zhao X, Li A, Yang Y, Dahal U, Lou X M, Liu X, Huang J, Yuan W P, Zhu X F, Cheng T, Zhao Y L, Wang X, Rendtlew Danielsen J M, Liu F, Yang Y G. Cell Res. 2014 February; 24(2):177-89.

Śledź P, Jinek M. Elife. 2016 Sep. 14; 5.

Vu L P, Pickering B F, Cheng Y, Zaccara S, Nguyen D, Minuesa G, Chou T, Chow A, Saletore Y, MacKay M, Schulman J, Famulare C, Patel M, Klimek V M, Garrett-Bakelman F E, Melnick A, Carroll M, Mason C E, Jaffrey S R, Kharas M G. Nat Med. 2017 November; 23(11): 1369-1376.

Wang X, Feng J, Xue Y, Guan Z, Zhang D, Liu Z, Gong Z, Wang Q, Huang J, Tang C, Zou T, Yin P. Nature. 2016 Jun. 23; 534(7608):575-8

Wang P, Doxtader K A, Nam Y. Mol Cell. 2016 Jul. 21; 63(2):306-317.

Winkler R, Gillis E, Lasman L, Safra M, Geula S, Soyris C, Nachshon A, Tai-Schmiedel J, Friedman N, Le-Trilling Vu T K, Trilling M, Mandelboim M, Hanna, J H, Schwartz S, Stern-Ginossar N. Nature Immunology (2018, e-publication ahead of print).

Yue Y, Liu J, He C. Genes Dev. 2015 Jul. 1; 29(13):1343-55.

Geon-Woo Kim, Hasan Imam, Mohsin Khan, Aleem Siddiqui, J Biol Chem, (27 Jul. 2020; online publication ahead of print).

Yimeng Gao, Radovan Vasic, Yuanbin Song, Rhea Teng, Chengyang Liu, Rana Gbyli, Giulia Biancon, Raman Nelakanti, Kirsten Lobben, Eriko Kudo, Wei Liu, Anastasia Ardasheva, Xiaoying Fu, Xiaman Wang, Poorval Joshi, Veronica Lee, Burak Dura, Gabriella Viero, Akiko Iwasaki, Rong Fan, Andrew Xiao, Richard A Flavell, Hua-Bing Li, Toma Tebaldi, Stephanie Halene; Immunity (16 Jun. 2020; Volume 52; 6; p887-1132).

Rosa M Rubio, Daniel P Depledge, Christopher Bianco, Letitia Thompson, Ian Mohr; Genes Dev. 2018 Dec. 1; 32(23-24):1472-1484.

An object of this invention is to provide inhibitors of METTL3 activity.

SUMMARY OF THE INVENTION

In one aspect, the present invention provides a compound as defined herein, or a pharmaceutically acceptable salt thereof.

In another aspect, the present invention provides a pharmaceutical composition as defined herein which comprises a compound as defined herein, or a pharmaceutically acceptable salt thereof, and one or more pharmaceutically acceptable excipients.

In another aspect, the present invention provides a compound as defined herein, or a pharmaceutically acceptable salt thereof, or a pharmaceutical composition as defined herein, for use in therapy.

In another aspect, the present invention provides a compound as defined herein, or a pharmaceutically acceptable salt thereof, or a pharmaceutical composition as defined herein, for use in the treatment of a proliferative condition.

In another aspect, the present invention provides a compound as defined herein, or a pharmaceutically acceptable salt thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt thereof, or a pharmaceutical composition as defined herein, for use in the inhibition of METTL3 activity.

In another aspect, the present invention provides a compound as defined herein, or a pharmaceutically acceptable salt thereof, or a pharmaceutical composition as defined herein, for use in promoting an immune response (e.g. anti-viral or anti-tumour immune response).

In another aspect, the present invention provides a compound as defined herein, or a pharmaceutically acceptable salt thereof, or a pharmaceutical composition as defined herein, for use in increasing an innate immune response in a subject.

In another aspect, the present invention provides a compound as defined herein, or a pharmaceutically acceptable salt thereof, or a pharmaceutical composition as defined herein, for use in increasing or enhancing an anti-tumour immune response during immune-oncology therapy.

In another aspect, the present invention provides a compound as defined herein, or a pharmaceutically acceptable salt thereof, or a pharmaceutical composition as defined herein, for use in the treatment of an autoimmune disease.

In another aspect, the present invention provides a compound as defined herein, or a pharmaceutically acceptable salt thereof, or a pharmaceutical composition as defined herein, for use in the treatment of a neurological disease.

In another aspect, the present invention provides a compound as defined herein, or a pharmaceutically acceptable salt thereof, or a pharmaceutical composition as defined herein, for use in the treatment of an infectious disease.

In another aspect, the present invention provides a compound as defined herein, or a pharmaceutically acceptable salt thereof, or a pharmaceutical composition as defined herein, for use in the treatment of a viral infection. Suitably, the viral infection is a RNA viral infection. Suitably, the viral infection is human papillomavirus (HPV) or hepatitis.

In another aspect, the present invention provides a compound as defined herein, or a pharmaceutically acceptable salt thereof, or a pharmaceutical composition as defined herein, for use in the treatment of an inflammatory disease.

In another aspect, the present invention provides the use of a compound as defined herein, or a pharmaceutically acceptable salt thereof, in the manufacture of a medicament for use in the treatment of a proliferative condition.

In another aspect, the present invention provides the use of a compound as defined herein, or a pharmaceutically acceptable salt thereof, in the manufacture of a medicament for use in the treatment of cancer. In a particular embodiment, the medicament is for use in the treatment of human cancers.

In another aspect, the present invention provides the use of a compound as defined herein, or a pharmaceutically acceptable salt thereof, in the manufacture of a medicament for the inhibition of METTL3 activity.

In another aspect, the present invention provides the use of a compound as defined herein, or a pharmaceutically acceptable salt thereof, in the manufacture of a medicament for promoting an immune response (e.g. anti-viral or anti-tumour immune response).

In another aspect, the present invention provides the use of a compound as defined herein, or a pharmaceutically acceptable salt thereof, in the manufacture of a medicament for for use in increasing an innate immune response in a subject.

In another aspect, the present invention provides the use of a compound as defined herein, or a pharmaceutically acceptable salt thereof, in the manufacture of a medicament for use in increasing or enhancing an anti-tumour immune response during immune-oncology therapy.

In another aspect, the present invention provides the use of a compound as defined herein, or a pharmaceutically acceptable salt thereof, in the manufacture of a medicament for use in the treatment of an autoimmune disease.

In another aspect, the present invention provides the use of a compound as defined herein, or a pharmaceutically acceptable salt thereof, in the manufacture of a medicament for use in the treatment of a neurological disease.

In another aspect, the present invention provides the use of a compound as defined herein, or a pharmaceutically acceptable salt thereof, in the manufacture of a medicament for use in the treatment of an infectious disease.

In another aspect, the present invention provides the use of a compound as defined herein, or a pharmaceutically acceptable salt thereof, in the manufacture of a medicament for use in the treatment of a viral infection. Suitably, the viral infection is a RNA viral infection. Suitably, the viral infection is human papillomavirus (HPV) or hepatitis.

In another aspect, the present invention provides the use of a compound as defined herein, or a pharmaceutically acceptable salt thereof, in the manufacture of a medicament for use in the treatment of an inflammatory disease.

In another aspect, the present invention provides a method of inhibiting METTL3 activity in vitro or in vivo, said method comprising contacting a cell with an effective amount of a compound as defined herein, or a pharmaceutically acceptable salt thereof, or a pharmaceutical composition as defined herein.

In another aspect, the present invention provides a method of inhibiting cell proliferation in vitro or in vivo, said method comprising contacting a cell with an effective amount of a compound as defined herein, or a pharmaceutically acceptable salt, or a pharmaceutical composition as defined herein.

In another aspect, the present invention provides a method of inhibiting metastasis in vitro or in vivo, said method comprising contacting a cell with an effective amount of a compound as defined herein, or a pharmaceutically acceptable salt, or a pharmaceutical composition as defined herein.

In another aspect, the present invention provides a method of promoting an immune response (e.g. anti-viral or anti-tumour immune response) in a subject in need thereof, said method comprising administering to the subject a therapeutically effective amount of a compound as defined herein, or a pharmaceutically acceptable salt, or a pharmaceutical composition as defined herein.

In another aspect, the present invention provides a method of increasing an innate immune response in a subject in need thereof, said method comprising administering to the subject a therapeutically effective amount of a compound as defined herein, or a pharmaceutically acceptable salt, or a pharmaceutical composition as defined herein.

In another aspect, the present invention provides a method of increasing or enhancing an anti-tumour immune response during immune-oncology therapy, said method comprising administering to a subject in need thereof a therapeutically effective amount of a compound as defined herein, or a pharmaceutically acceptable salt, or a pharmaceutical composition as defined herein.

In another aspect, the present invention provides a method of treating a proliferative disorder, said method comprising administering to a subject in need thereof a therapeutically effective amount of a compound as defined herein, or a pharmaceutically acceptable salt, or a pharmaceutical composition as defined herein.

In another aspect, the present invention provides a method of treating cancer, said method comprising administering to a subject in need thereof a therapeutically effective amount of a compound as defined herein, or a pharmaceutically acceptable salt, or a pharmaceutical composition as defined herein.

In another aspect, the present invention provides a method of treating an autoimmune disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating a neurological disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating an infectious disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating a viral infection, said method comprising administering to a subject in need thereof a therapeutically effective amount of a compound as defined herein, or a pharmaceutically acceptable salt, or a pharmaceutical composition as defined herein. Suitably, the viral infection is a RNA viral infection. Suitably, the viral infection is human papillomavirus (HPV) or hepatitis.

In another aspect, the present invention provides a method of treating an inflammatory disease, said method comprising administering to a subject in need thereof a therapeutically effective amount of a compound as defined herein, or a pharmaceutically acceptable salt, or a pharmaceutical composition as defined herein.

In one aspect, the present invention provides a combination comprising a compound as defined herein, or a pharmaceutically acceptable salt thereof, with one or more additional therapeutic agents.

The present invention further provides a method of synthesising a compound, or a pharmaceutically acceptable salt, as defined herein.

In another aspect, the present invention provides a compound as defined herein, or a pharmaceutically acceptable salt, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl($C_{1-6}$alkyl)" includes phenyl($C_{1-4}$alkyl), benzyl, 1-phenylethyl and 2-phenylethyl.

The term "(m-nC)" or "Cm-n", or "(m-nC) group" or "Cm-n" used alone or as a prefix, refers to any group having m to n carbon atoms.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkylene" group is an alkyl group that is positioned between and serves to connect two other chemical groups. Thus, "$C_{1-3}$alkylene" means a linear saturated divalent hydrocarbon radical of one to three carbon atoms or a branched saturated divalent hydrocarbon radical of three atoms, for example, methylene, ethylene, propylene, and the like.

The term "$C_{m-n}$cycloalkyl" means a hydrocarbon ring containing from m to n carbon atoms, for example "$C_{3-6}$ cycloalkyl" means a hydrocarbon ring containing from 3 to 6 carbon atoms, for example, cyclopropyl, cyclobutyl, cyclopentyl, cyclohexyl. The term "$C_{m-n}$cycloalkyl" also encompasses non-aromatic saturated or partially saturated monocyclic, fused, bridged, or spiro bicyclic carbocyclic ring system(s). The term "$C_{m-n}$cycloalkyl" includes both monovalent species and divalent species. Monocyclic "$C_{m-n}$cycloalkyl" rings contain from about 3 to 12 (suitably from 3 to 8, most suitably from 5 to 6) ring carbon atoms. Bicyclic "$C_{m-n}$cycloalkyl" contain from 7 to 17 ring carbon atoms, suitably 7 to 12 ring carbon atoms. Bicyclic "$C_{m-n}$ cycloalkyl" rings may be fused, spiro, or bridged ring systems.

The term "cycloalkoxy" means a cycloalkyl-O-group in which the cycloalkyl group is as previously defined, for example $C_{3-4}$cycloalkoxy (or —O—$C_{3-4}$cycloalkyl) means a hydrocarbon ring containing from 3 to 4 carbon atoms, linked to an O atom e.g. and

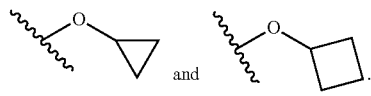 [SMILES: *OC1CC1 ; *OC1CCC1]

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7, most suitably from 5 to 6) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

A "carbon-linked heterocyclyl" means a heterocycle group as defined above that is connected via a carbon atom, rather than a heteroatom such as nitrogen.

By "spirocyclic ring systems" it is meant a compound which at least two rings which have only one atom in common and are not linked by a bridge.

By "fused ring systems" it is meant a compound in which two rings share two adjacent atoms. In other words, the rings share one covalent bond.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
 a benzene ring fused to a 5- or 6-membered ring containing 1, 2 or 3 ring heteroatoms;
 a pyridine ring fused to a 5- or 6-membered ring containing 1, 2 or 3 ring heteroatoms;
 a pyrimidine ring fused to a 5- or 6-membered ring containing 1 or 2 ring heteroatoms;
 a pyrrole ring fused to a 5- or 6-membered ring containing 1, 2 or 3 ring heteroatoms;
 a pyrazole ring fused to a 5- or 6-membered ring containing 1 or 2 ring heteroatoms;
 a pyrazine ring fused to a 5- or 6-membered ring containing 1 or 2 ring heteroatoms;
 an imidazole ring fused to a 5- or 6-membered ring containing 1 or 2 ring heteroatoms;
 an oxazole ring fused to a 5- or 6-membered ring containing 1 or 2 ring heteroatoms;
 an isoxazole ring fused to a 5- or 6-membered ring containing 1 or 2 ring heteroatoms;
 a thiazole ring fused to a 5- or 6-membered ring containing 1 or 2 ring heteroatoms;
 an isothiazole ring fused to a 5- or 6-membered ring containing 1 or 2 ring heteroatoms;
 a thiophene ring fused to a 5- or 6-membered ring containing 1, 2 or 3 ring heteroatoms;
 a furan ring fused to a 5- or 6-membered ring containing 1, 2 or 3 ring heteroatoms;
 a cyclohexyl ring fused to a 5- or 6-membered heteroaromatic ring containing 1, 2 or 3 ring heteroatoms; and
 a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of formula (I) shown below, or a pharmaceutically acceptable salt thereof:

$$X—Y—Z \quad (I)$$

wherein:
 X is selected from:

[chemical structures]

wherein
 $Q_1$ is selected from NH, N—$C_{1-4}$alkyl, O or S;
 $Q_{2a}$ is selected from N or $CR_{2a}$;
 $Q_{2b}$ is selected from N or $CR_{2b}$;
 $Q_{2c}$ is selected from N or $CR_{2c}$;
 $Q_{2d}$ is selected from N or $CR_{2d}$;
 $Q_3$ is selected from N or $CR_{1b}$;
 $Q_4$ is selected from N or $CR_{1x}$;

subject to the proviso that no more than 3 of $Q_1$, $Q_{2a}$, $Q_{2b}$, $Q_{2c}$, $Q_{2d}$, $Q_3$ and $Q_4$ are nitrogen;

$R_{1a}$ is selected from:
(i) $C_{1-4}$alkyl or $C_{1-4}$alkoxy, each of which being optionally substituted by halo, cyano, hydroxy, $C_{3-6}$cycloalkyl, $C_{1-4}$alkoxy, $C_{1-4}$haloalkoxy, aryl or heteroaryl; or
(ii) a group of the formula:

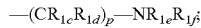
$—(CR_{1c}R_{1d})_p—NR_{1e}R_{1f}$;

wherein
p is an integer selected from 0, 1, 2 or 3
$R_{1c}$ and $R_{1d}$ are independently selected from:
(i) hydrogen (including deuterium),
(ii) $C_{1-6}$alkyl which is optionally substituted by one more substituents selected from cyano, oxo, hydroxy, $C_{1-4}$alkoxy, halo, $C_{1-4}$haloalkoxy, $C_{3-6}$cycloalkyl, —O—$C_{3-6}$cycloalkyl, $NR_{1ca}R_{1da}$ or —S(O)$_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$ cycloalkyl are optionally further substituted with halo, cyano or hydroxy;
(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or —S(O)$_{0-2}R_{1ca}R_{1da}$, wherein $R_{1ca}$ and $R_{1da}$ are H or $C_{1-2}$alkyl; and;
(iv) or $R_{1c}$ and $R_{1d}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$ haloalkoxy, $NR_{1ca}R_{1da}$ or —S(O)$_{0-2}R_{1ca}R_{1da}$, wherein $R_{1ca}$ and $R_{1da}$ are H or $C_{1-2}$alkyl;

$R_{1e}$ and $R_{1f}$ are each independently selected from:
(i) hydrogen (including deuterium);
(ii) $C_{1-6}$alkyl which is optionally substituted by one more substituents selected from cyano, oxo, hydroxy, $C_{1-2}$ alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl;
(iii) a group with the formula:

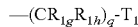
$—(CR_{1g}R_{1h})_q$-$T_1$ wherein:
q is 0, 1, 2, 3, 4, 5 or 6;
$R_{1g}$ and $R_{1h}$ are independently selected from:
a) hydrogen;
b) $C_{1-6}$alkyl which is optionally substituted by one more substituents selected from cyano, hydroxy, $C_{1-4}$alkoxy, halo, $C_{1-4}$haloalkoxy, —O—$C_{3-6}$ cycloalkyl, $NR_{1ga}R_{1ha}$ or —S(O)$_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;
c) an aryl-$C_{1-6}$alkyl, heteroaryl$C_{1-6}$alkyl, $C_{3-6}$-cycloalkyl or $C_{3-6}$cycloalkyl$C_{1-6}$alkyl group, each of which is optionally substituted by one or more substituents selected from $C_{1-2}$alkyl, cyano, $C_{1-2}$haloalkyl, hydroxy, $C_{1-2}$alkoxy, halo, $C_{1-2}$-haloalkoxy, $NR_{1ga}R_{1ha}$ or —S(O)$_{0-2}R_{1ga}R_{1ha}$, wherein $R_{1ga}$ and $R_{1ha}$ are H or $C_{1-2}$alkyl; or d) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —S(O)$_{0-2}R_{1ga}R_{1ha}$, wherein $R_{1ga}$ and $R_{1ha}$ are H or $C_{1-2}$alkyl;

and $T_1$ is selected from hydrogen, cyano, hydroxy, $NR_{1t}R_{2t}$ or —S(O)$_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$-haloalkoxy, $NR_{3t}R_{4t}$ or —S(O)$_{0-2}R_{3t}R_{4t}$, wherein $R_{3t}$ and $R_{4t}$ are H or $C_{1-2}$alkyl;
(iv) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —S(O)$_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —S(O)$_{0-2}R_{1i}R_{1j}$, wherein $R_{1i}$ and $R_{1j}$ are H or $C_{1-4}$alkyl;

$R_{1b}$ is selected from hydrogen, cyano, halo or $C_{1-3}$ alkyl;
$R_{1x}$ is selected from hydrogen, cyano, halo or $C_{1-3}$ alkyl;
$R_{2a}$, $R_{2b}$, $R_{2c}$ and $R_{2d}$ are independently selected from hydrogen, cyano, halo or a group of the formula:

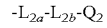
-$L_{2a}$-$L_{2b}$-$Q_2$ wherein
$L_{2a}$ is absent or $C_{1-3}$alkylene optionally substituted by $C_{1-2}$ alkyl or oxo;
$L_{2b}$ is absent or selected from O, S, SO, SO$_2$, N($R_n$), C(O), C(O)O, OC(O), C(O)N($R_n$), N($R_n$)C(O), N($R_n$)C(O)N($R_o$), S(O)$_2$N($R_n$), or N($R_n$)SO$_2$, wherein $R_n$ and $R_o$ are each independently selected from hydrogen or $C_{1-2}$alkyl; and
$Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

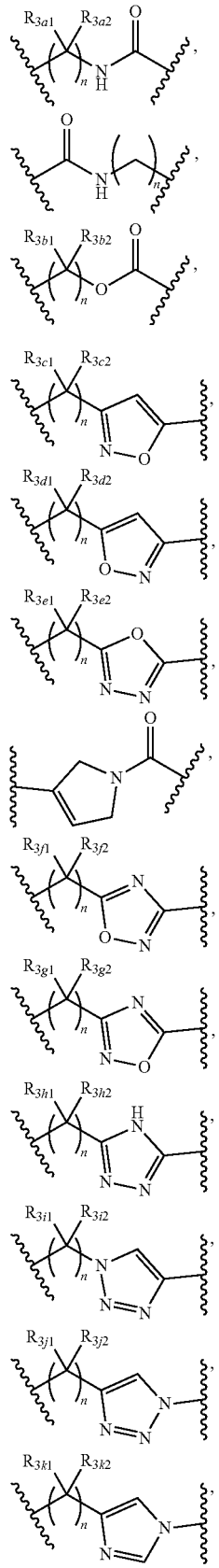
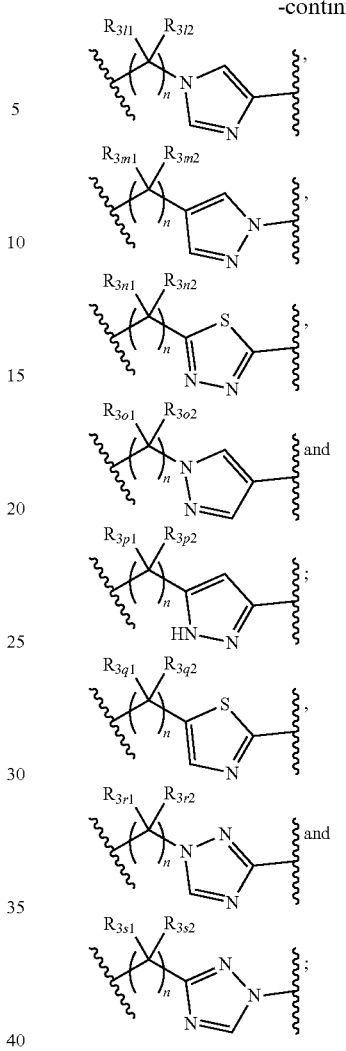

wherein:
R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$, are independently selected from hydrogen (including deuterium), C$_{1-6}$alkyl, C$_{3-4}$ cycloalkyl, hydroxy, and halo; and wherein C$_{1-6}$alkyl, or C$_{3-4}$ cycloalkyl is optionally substituted with one or more substituents selected from halo, amino, cyano, and hydroxy;

R$_{3a2}$, R$_{3b2}$, R$_{3c2}$, R$_{3d2}$, R$_{3e2}$, R$_{3f2}$, R$_{3g2}$, R$_{3h2}$, R$_{3i2}$, R$_{3j2}$, R$_{3k2}$, R$_{3l2}$, R$_{3m2}$, R$_{3n2}$, R$_{3o2}$, R$_{3p2}$, R$_{3q2}$, R$_{3r2}$ and R$_{3s2}$ are hydrogen or halo;

with the proviso that R$_{3a1}$, R$_{3b1}$, R$_{3i1}$, R$_{3l1}$, R$_{3o1}$, R$_{3r1}$, R$_{3a2}$, R$_{3b2}$, R$_{3i2}$, R$_{3l2}$, R$_{3o2}$ and R$_{3s1}$ cannot be halo when n=1 or when n=2 and the carbon atom to which they are attached is linked to an oxygen or nitrogen atom;

or R$_{3a1}$ and R$_{3a2}$, R$_{3b1}$ and R$_{3b2}$, R$_{3c1}$ and R$_{3c2}$, R$_{3d1}$ and R$_{3d2}$, R$_{3e1}$ and R$_{3e2}$, R$_{3f1}$ and R$_{3f2}$, R$_{3g1}$ and R$_{3g2}$, R$_{3h1}$ and R$_{3h2}$, R$_{3i1}$ and R$_{3i2}$, R$_{3j1}$ and R$_{3j2}$, R$_{3k1}$ and R$_{3k2}$, R$_{3l1}$ and R$_{3l2}$, R$_{3m1}$ and R$_{3m2}$, R$_{3n1}$ and R$_{3n2}$, R$_{3o1}$ and R$_{3o2}$, R$_{3p1}$ and R$_{3p2}$, R$_{3q1}$ and R$_{3q2}$, or R$_{3r1}$ and R$_{3r2}$ or R$_{3s1}$ and R$_{3s2}$ may be linked such that, together with the carbon atom to which they are attached, they form a spiro-fused C$_{3-4}$cycloalkyl which is optionally substituted with one or more substituents selected from halo, methyl, amino, cyano, and hydroxy;

n is 0, 1 or 2

Z is selected from one of the following structures:

i)

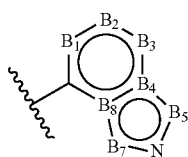

wherein:

- $B_1$ is $A_5$, wherein $A_5$ is selected from $CR_{16}$ and N, wherein $R_{16}$ is selected from hydrogen, halo, cyano, $C_{1-4}$ alkyl, $C_{2-4}$ alkenyl, $C_{2-4}$ alkynyl, a 5- or 6-membered heteroaryl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;
- $B_2$ is $A_6$, wherein $A_6$ is selected from N or $CR_{17}$, wherein $R_{17}$, $R_{H2}$, $R_{H4}$ and $R_{H5}$ are selected from hydrogen, hydroxy, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, —O—$C_{3-6}$cycloalkyl, heterocyclyl, —O-heterocyclyl (carbon-linked), —(OCH$_2$CH$_2$)$_m$—NR$_q$R$_r$, —(OCH$_2$CH$_2$)$_m$—OCH$_3$ wherein m is an integer from 1 to 6, NR$_q$R$_r$, —C(O)—NR$_q$R$_r$, —C(O)OR$_q$,
  wherein R$_q$ and R$_r$ are each independently hydrogen, $C_{1-5}$ alkyl, $C_{3-6}$cycloalkyl, a 3- to 6-membered carbon-linked heterocyclyl, or R$_q$ and R$_r$ are linked together such that, together with the nitrogen atom to which they are attached, they form a 3- to 6-membered heterocyclic ring; wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O— heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl;
- $B_3$ is N or $CR_{Z1}$, wherein $R_{Z1}$ is selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;
- $B_4$ is selected from C or N;
- $B_5$ is selected from $CR_{zi1b}$ or $NR_{B5N}$, wherein:
  $R_{Zi1b}$ is selected from hydrogen, $C_{1-4}$alkyl, cyano, halo, NH$_2$ and $C_{1-4}$alkoxy; and
  $R_{B5N}$ is selected from hydrogen or $C_{1-4}$alkyl;
- $B_7$ is N, NR$_{Z2N}$ or CR$_{Z2}$, wherein $R_{Z2}$ is selected from hydrogen, $C_{1-4}$alkyl, cyano, halo, NH$_2$ and $C_{1-4}$alkoxy; and $R_{Z2N}$ is selected from hydrogen or $C_{1-4}$alkyl;
- $B_8$ is selected from C or N;

with the proviso that no more than four of $B_1$ to $B_8$ are N.

ii)

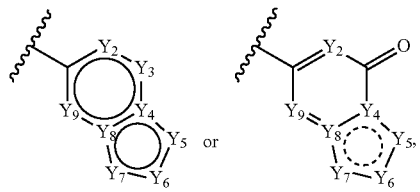

- $Y_2$ is $A_7$, wherein $A_7$ is selected from $CR_{18}$ and N; wherein $R_{18}$ is selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;
- $Y_3$ is N or $CR_{Z1a}$ wherein $R_{Z1a}$, is selected from hydrogen, hydroxy, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$ cycloalkyl, wherein $C_{3-6}$cycloalkyl and —O—$C_{3-6}$cycloalkyl are optionally substituted by one or more of halo, methyl or methoxy;
- $Y_4$ is C or N
- $Y_5$ is C—$R_{Y5}$ or $NR_{Y5N}$, wherein:
  $R_{Y5}$ is selected from hydrogen, $C_{1-4}$alkyl, cyano, halo, NH$_2$ and $C_{1-4}$alkoxy;
  $R_{Y5N}$ is selected from hydrogen or $C_{1-4}$alkyl;
- $Y_6$ is C—$R_{Zi2e}$ or N, wherein $R_{Zi2e}$ is selected from hydrogen, $C_{1-4}$alkyl, cyano, halo, NH$_2$ and $C_{1-4}$alkoxy
- $Y_7$ is O, S, $CR_{Z2a}$ or N, wherein $R_{Z2a}$ is selected from hydrogen, $C_{1-4}$alkyl, cyano, halo, NH$_2$ and $C_{1-4}$alkoxy;
- $Y_8$ Is C or N;
- $Y_9$ is $CR_{Z3a}$ or N; wherein
  $R_{Z3a}$ is selected from hydrogen, $C_{1-4}$alkyl, cyano, halo, NH$_2$ and $C_{1-4}$alkoxy; with the proviso that no more than four of $Y_1$ to $Y_8$ are N.

(iii)

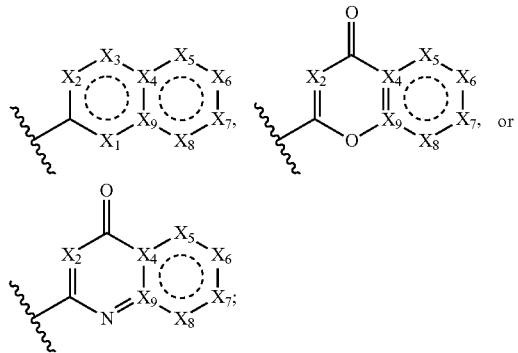

- $X_1$ is N or C—$R_{Z9}$, wherein $R_{Z9}$ is selected from hydrogen, halo, cyano, $C_{1-4}$ alkyl, $C_{1-4}$ haloalkyl, $C_{1-4}$alkoxy, $C_{1-4}$ haloalkoxy;
- $X_2$ is selected from N or $CR_4$ wherein:
  $R_4$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl);
- $X_3$ is N;
- $X_4$ is N or C;
- $X_5$ is selected from N, $CR_5$ and $CRx_{5a}R_{X5b}$ wherein:
  $R_5$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);

Rx$_{5a}$ and R$_{X5b}$ are independently selected from hydrogen, halo, cyano, C$_{1-4}$ alkyl, C$_{1-4}$ haloalkyl, C$_{1-4}$alkoxy, C$_{1-4}$ haloalkoxy (e.g. hydrogen, halo, cyano and methyl);

either:
- X$_6$ is A$_1$ and X$_7$ is A$_2$; or
- X$_6$ is A$_8$ and X$_7$ is A$_9$ or A$_{11}$, wherein:
  A$_1$ is selected from CR$_{12}$ and N; wherein
   R$_{12}$ is selected from selected from hydrogen, halo, cyano, C$_{1-4}$ alkyl, C$_{1-4}$ haloalkyl, C$_{1-4}$alkoxy and C$_{1-4}$ haloalkoxy (e.g. hydrogen, halo, cyano and C$_{1-4}$ alkyl);
  A$_2$ is selected from CR$_{13}$ and N, wherein
   R$_{13}$ selected from hydrogen, halo, cyano, C$_{1-4}$ alkyl, C$_{1-4}$ haloalkyl, C$_{1-4}$ alkoxy, C$_{1-4}$ haloalkoxy (e.g. hydrogen, halo, cyano, methoxy and methyl);
  A$_8$ is selected from CR$_{19}$R$_{20}$ and NR$_{21}$; wherein
   R$_{19}$ and R$_{20}$ are independently selected from hydrogen, halo, cyano, C$_{1-4}$ alkyl, C$_{1-4}$ haloalkyl, C$_{1-4}$alkoxy, C$_{1-4}$ haloalkoxy (e.g hydrogen, halo, cyano and C$_{1-4}$ alkyl);
   R$_{21}$ is hydrogen or C$_{1-4}$alkyl.
  A$_9$ is selected from CR$_{22}$R$_{23}$ and NR$_{24}$;
   wherein R$_{22}$ and R$_{23}$ are independently selected from selected from hydrogen, halo, cyano, C$_{1-4}$ alkyl, C$_{1-4}$ haloalkyl, C$_{1-4}$alkoxy, C$_{1-4}$ haloalkoxy (e.g. hydrogen, halo, cyano and methyl);
   R$_{24}$ is selected from hydrogen or C$_{1-4}$alkyl
  A$_{11}$ is selected from CR$_{28}$R$_{29}$ and NR$_{30}$;
   R$_{28}$ and R$_{29}$ are selected from hydrogen, halo, methoxy and methyl;
   R$_{30}$ is selected from hydrogen or C$_{1-4}$alkyl.
X$_8$ is selected from CR$_6$, N or CR$_{X6a}$R$_{X6b}$;
 wherein R$_6$ is selected from hydrogen, halo, cyano, C$_{1-4}$ alkyl, C$_{1-4}$ haloalkyl, C$_{1-4}$ alkoxy and C$_{1-4}$ haloalkoxy;
 Rx$_{6a}$ and Rx$_{6b}$ are each independently selected from hydrogen, halo, cyano, C$_{1-4}$ alkyl, C$_{1-4}$ haloalkyl, C$_{1-4}$alkoxy and C$_{1-4}$ haloalkoxy;
X$_9$ is N or C;
with the proviso that no more than four of X$_2$ to X$_9$ are N.

(iv)

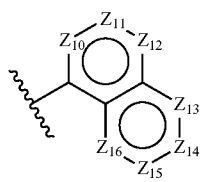

Z$_{10}$ is N or C—R$_{Z10}$, wherein R$_{Z10}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{11}$ is N or C—R$_{Z11}$, wherein R$_{Z11}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{12}$ is N or C—R$_{Z12}$, wherein R$_{Z12}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{13}$ is N or C—R$_{Z13}$, wherein R$_{Z13}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{14}$ is N or C—R$_{Z14}$, wherein R$_{Z14}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{15}$ is N or C—R$_{Z15}$, wherein R$_{Z15}$ is selected from hydrogen, halo, cyano, C$_{1-4}$ alkyl, C$_{1-4}$ haloalkyl, C$_{1-4}$alkoxy, C$_{1-4}$ haloalkoxy;
Z$_{16}$ is N or C—R$_{Z16}$, wherein R$_{Z16}$ is selected from hydrogen, halo, cyano, C$_{1-4}$ alkyl, C$_{1-4}$ haloalkyl, C$_{1-4}$alkoxy, C$_{1-4}$ haloalkoxy;
with the proviso that no more than three of Z$_{10}$ to Z$_{16}$ are N;

(v)

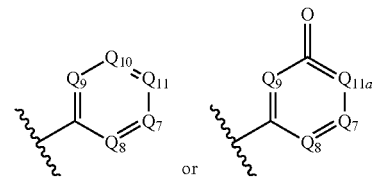

Q$_7$ is CR$_7$ or N;
Q$_8$ is CR$_8$ or N;
Q$_9$ is CR$_9$ or N;
Q$_{10}$ is CR$_{10}$ or N;
Q$_{11}$ is CR$_{11}$ or N;
Q$_{11a}$ is NR$_{11N}$ or CR$_{11a}$R$_{11b}$;
wherein R$_7$, R$_8$, R$_9$, R$_{10}$, R$_{11}$, R$_{11a}$ and R$_{11b}$ are each independently selected from hydrogen, NH$_2$, halo, cyano, C$_{1-4}$ alkoxy, C$_{1-4}$ haloalkoxy, C$_{1-6}$ alkyl, —CH$_2$OCH$_3$, —CH$_2$SO$_2$CH$_3$, —SO$_2$CH$_3$, —NHC(O)CH$_3$ and —C(O)NR$_{v1}$R$_{v2}$, wherein R$_{v1}$ and R$_{v2}$ are independently selected from hydrogen and methyl and; and R$_{11N}$ is selected from hydrogen, NH$_2$, halo, cyano, and C$_{1-6}$ alkyl;
or
R$_9$ and R$_{10}$ may be linked together such that, together to the atoms to which they are attached, they form a fused 5- or 6-membered saturated or unsaturated ring system, or R$_{10}$ and R$_{11}$ may be linked together such that, together to the atoms to which they are attached, they form a fused 5- or 6-membered saturated or unsaturated ring system, wherein either of the fused 5- or 6-membered saturated or unsaturated ring system may be optionally substituted by one or more substituents selected from C$_{1-2}$alkyl, cyano, C$_{1-2}$haloalkyl, hydroxy, C$_{1-2}$alkoxy, halo, C$_{1-2}$haloalkoxy, NR$_{1ia}$R$_{1ja}$ or —S(O)$_{0-2}$R$_{1ia}$R$_{1ja}$, wherein R$_{1ia}$ and R$_{1ja}$ are H or C$_{1-2}$alky;
with the proviso that no more than three of Q$_7$ to Q$_{11}$ are N.

In another aspect, the present invention relates to compounds of formula (I) shown below, or a pharmaceutically acceptable salt thereof:

X—Y—Z (I)

wherein:
X is selected from:

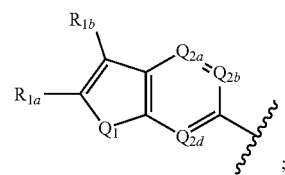

;

-continued

[chemical structure with $R_{1a}$, $Q_1$, $Q_{2a}$, $Q_{2b}$, $Q_{2d}$, N]

;

[chemical structure with $R_{1a}$, $R_{1b}$, $Q_1$, $Q_{2a}$, $Q_{2c}$, $Q_{2d}$]

;

[chemical structure with $R_{1a}$, $Q_1$, $Q_{2a}$, $Q_{2c}$, $Q_{2d}$, N]

;

[chemical structure with $R_{1a}$, $Q_3$, $Q_4$, N, $Q_{2a}$, $Q_{2c}$, $Q_{2d}$]

and

[chemical structure with $R_{1a}$, $Q_3$, $Q_4$, N, $Q_{2a}$, $Q_{2b}$, $Q_{2d}$]

;

wherein
$Q_1$ is selected from NH, N—$C_{1-4}$alkyl, O or S;
$Q_{2a}$ is selected from N or $CR_{2a}$;
$Q_{2b}$ is selected from N or $CR_{2b}$;
$Q_{2c}$ is selected from N or $CR_{2c}$;
$Q_{2d}$ is selected from N or $CR_{2d}$;
$Q_3$ is selected from N or $CR_{1b}$;
$Q_4$ is selected from N or $CR_{1x}$;
subject to the proviso that no more than 3 of $Q_1$, $Q_{2a}$, $Q_{2b}$, $Q_{2c}$, $Q_{2d}$, $Q_3$ and $Q_4$ are nitrogen;
$R_{1a}$ is selected from:
  (i) $C_{1-4}$alkyl or $C_{1-4}$alkoxy, each of which being optionally substituted by halo, cyano, hydroxy, $C_{3-6}$cycloalkyl, 3 to 6 membered heterocyclyl, $C_{1-4}$alkoxy, $C_{1-4}$ haloalkoxy, aryl or heteroaryl; or
  (ii) a group of the formula:

—$(CR_{1c}R_{1d})_p$—$NR_{1e}R_{1f}$;

wherein
    p is an integer selected from 0, 1, 2 or 3
    $R_{1c}$ and $R_{1d}$ are independently selected from:
      (i) hydrogen (including deuterium),
      (ii) $C_{1-6}$alkyl which is optionally substituted by one more substituents selected from cyano, oxo, hydroxy, $C_{1-4}$alkoxy, halo, $C_{1-4}$haloalkoxy, $C_{3-6}$cycloalkyl, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally further substituted with halo, cyano or hydroxy;
      (iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;
      (iv) or $R_{1c}$ and $R_{1d}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;
    $R_{1e}$ and $R_{1f}$ are each independently selected from:
      (i) hydrogen (including deuterium);
      (ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl;
      (iii) a group with the formula:

—$(CR_{1g}R_{1h})_q$-$T_1$ wherein:
        q is 0, 1, 2, 3, 4, 5 or 6;
        $R_{1g}$ and $R_{1h}$ are independently selected from:
          a) hydrogen;
          b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy; or
          c) an aryl-$C_{1-6}$alkyl, heteroaryl$C_{1-6}$alkyl, $C_{3-6}$cycloalkyl or $C_{3-6}$cycloalkyl$C_{1-6}$alkyl group, each of which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;
          d) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;
        and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;
      (iv) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl;

$R_{1b}$ is selected from hydrogen, cyano, halo or $C_{1-4}$ alkyl;
$R_{1x}$ is selected from hydrogen, cyano, halo or $C_{1-3}$ alkyl;
$R_{2a}$, $R_{2b}$, $R_{2c}$ and $R_{2d}$ are independently selected from hydrogen, cyano, halo or a group of the formula:

$$-L_{2a}-L_{2b}-Q_2$$

wherein
$L_{2a}$ is absent or $C_{1-3}$alkylene optionally substituted by $C_{1-2}$ alkyl or oxo;
$L_{2b}$ is absent or selected from O, S, SO, $SO_2$, $N(R_n)$, $C(O)$, $C(O)O$, $OC(O)$, $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and
$Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

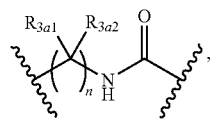,

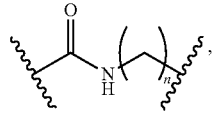,

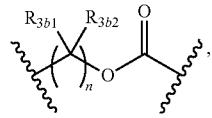,

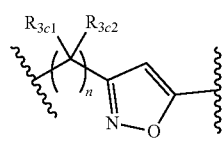,

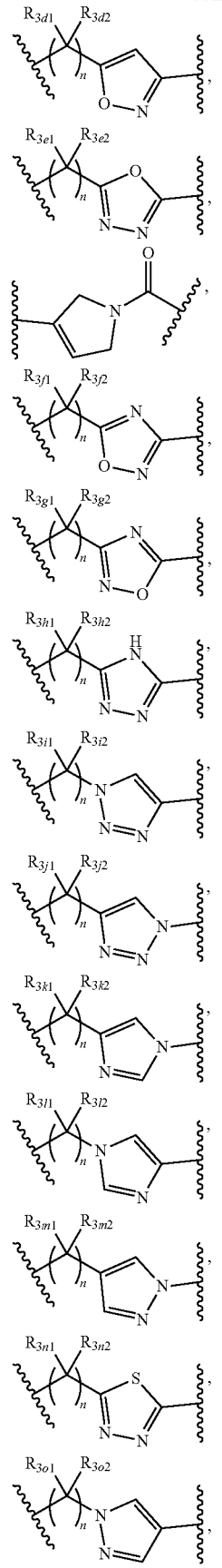

-continued

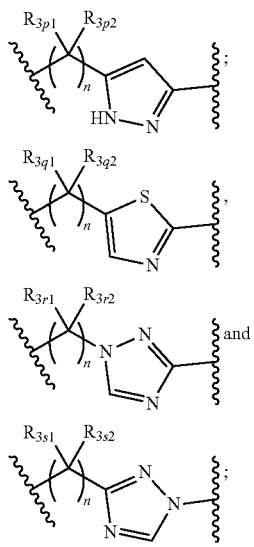

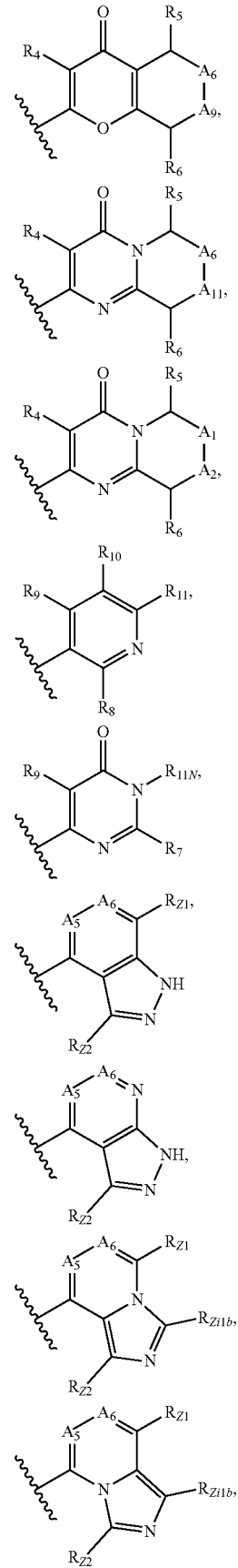

wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen or halo;

with the proviso that $R_{3a1}$, $R_{3b1}$, $R_{3i1}$, $R_{3l1}$, $R_{3o1}$, $R_{3r1}$, $R_{3a2}$, $R_{3b2}$, $R_{3i2}$, $R_{3l2}$, $R_{3o2}$ and $R_{3s1}$ cannot be halo when n=1 or when n=2 and the carbon atom to which they are attached is linked to an oxygen or nitrogen atom;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, or $R_{3r1}$ and $R_{3r2}$ or $R_{3s1}$ and $R_{3s2}$ may be linked such that, together with the carbon atom to which they are attached, they form a spiro-fused $C_{3-4}$cycloalkyl which is optionally substituted with one or more substituents selected from halo, methyl, amino, cyano, and hydroxy;

n is 0, 1 or 2

Z is selected from:

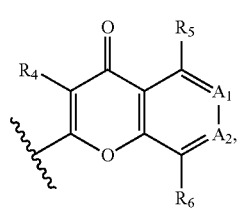

-continued
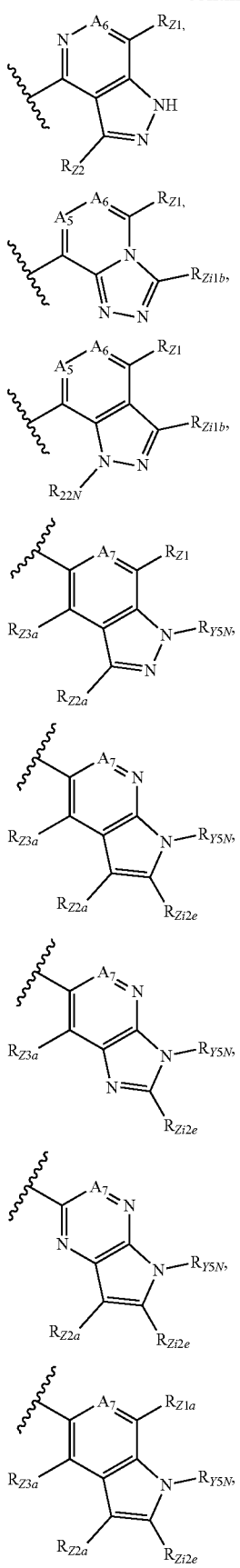
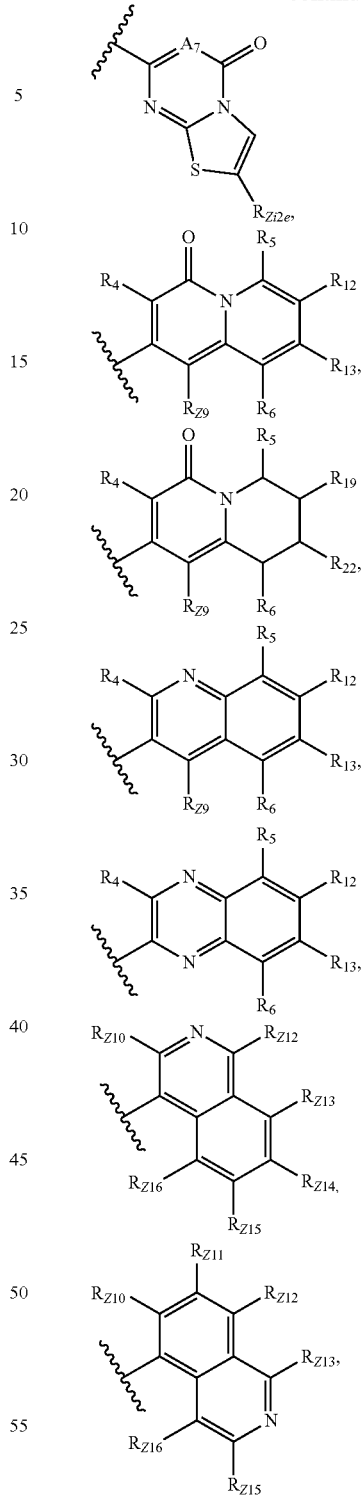
wherein:
$R_4$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);
$R_5$ is selected from hydrogen, halo, cyano, $C_{1-4}$ alkyl, $C_1$a haloalkyl, $C_{1-4}$ alkoxy, $C_{1-4}$ haloalkoxy (e.g. hydrogen, halo, cyano and methyl);

$R_6$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl);

$R_8$, $R_9$, $R_{10}$ and $R_{11}$ are independently selected from hydrogen, $NH_2$, halo, cyano, $C_{1-4}$ alkoxy, $C_{1-4}$ haloalkoxy, $C_{1-6}$ alkyl, —$CH_2OCH_3$, —$CH_2SO_2CH_3$, —$SO_2CH_3$, —$NHC(O)CH_3$ and —$C(O)NR_{v1}R_{v2}$, wherein $R_{v1}$ and $R_{v2}$ are independently selected from hydrogen and methyl; or $R_9$ and $R_{10}$ may be linked together such that, together to the atoms to which they are attached, they form a fused 5- or 6-membered saturated or unsaturated ring system, or $R_{10}$ and $R_{11}$ may be linked together such that, together to the atoms to which they are attached, they form a fused 5- or 6-membered saturated or unsaturated ring system, wherein either of the fused 5- or 6-membered saturated or unsaturated ring system may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ia}R_{1ja}$ or —$S(O)_{0-2}R_{1ia}R_{1ja}$, wherein $R_{1ia}$ and $R_{1ja}$ are H or $C_{1-2}$alky;

$R_7$ and $R_{11N}$ are independently selected from hydrogen, $NH_2$, halo, cyano, and $C_{1-6}$ alkyl;

$R_{Z1}$ and $R_{Z1a}$ selected from hydrogen, $C_{1-4}$alkyl, cyano, halo, $C_{1-4}$haloalkyl, $C_{1-4}$ haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

$R_{Z2}$ and $R_{Z2a}$ are selected from hydrogen, $C_{1-4}$alkyl, cyano, halo, $NH_2$ and $C_{1-4}$alkoxy;

$R_{Z3a}$ is selected from hydrogen, $C_{1-4}$alkyl, cyano, halo, $NH_2$ and $C_{1-4}$alkoxy;

$R_{Zi1b}$ is selected from hydrogen, $C_{1-4}$alkyl, cyano, halo, $NH_2$ and $C_{1-4}$alkoxy;

$R_{Zi2e}$ is selected from hydrogen, $C_{1-4}$alkyl, cyano, halo, $NH_2$ and $C_{1-4}$alkoxy;

$R_{Y5N}$ and $R_{Z2N}$ are selected from hydrogen or $C_{1-4}$alkyl;

$R_{Z9}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z10}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z11}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z12}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z13}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z14}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z15}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z16}$ is selected from hydrogen, halo, cyano, $C_{1-4}$ alkyl, $C_{1-4}$ haloalkyl, $C_{1-4}$alkoxy, $C_{1-4}$ haloalkoxy;

$A_1$ is selected from $CR_{12}$ and N;
$A_2$ is selected from $CR_{13}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{11}$ is selected from $CR_{28}R_{29}$ and $NR_{30}$;

$R_{12}$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and $C_{1-4}$ alkyl);

$R_{13}$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano, methoxy and methyl);

$R_{16}$ and $R_{18}$ are selected from hydrogen, halo, cyano, $C_{1-4}$ alkyl, $C_{1-4}$ alkoxy, $C_{1-4}$ haloalkyl, $C_{1-4}$haloalkoxy, $C_{3-4}$cycloalkyl, a 3- to 4-membered heterocyclyl and $C_{3-4}$-cycloalkoxy;

$R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$ cycloalkyl, —O—$C_{3-6}$cycloalkyl, heterocyclyl, —O-heterocyclyl (carbon-linked), —$(OCH_2CH_2)_m$—$OCH_3$ wherein m is an integer from 1 to 6, $NR_qR_r$, wherein $R_q$ and $R_r$ are each independently hydrogen, $C_{1-5}$ alkyl, $C_{3-6}$cycloalkyl, a 3- to 6-membered carbon-linked heterocyclyl, or $R_q$ and $R_r$ are linked together such that, together with the nitrogen atom to which they are attached, they form a 3- to 6-membered heterocyclic ring; wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O—heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl;

$R_{19}$ and $R_{20}$ are selected from hydrogen, halo, cyano and $C_{1-4}$ alkyl;

$R_{22}$ and $R_{23}$ are selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl;

$R_{28}$ and $R_{29}$ are selected from hydrogen, halo, methoxy and methyl;

$R_{21}$, $R_{24}$ and $R_{30}$ are hydrogen or $C_{1-4}$alkyl.

Particular compounds of the invention include, for example, compounds of formula (I), or pharmaceutically acceptable salts thereof, wherein, unless otherwise stated, each of X, Y, Z, $R_{1a}$, $R_{1b}$, $R_{1c}$, $R_{1d}$, $R_{1e}$, $R_{1f}$, $R_{2a}$, $R_{2b}$, $R_{2c}$, $R_{2d}$, $Q_1\square Q_{2a}$, $Q_{2b}$, $Q_{2c}$, $Q_{2d}$, $Q_3$, $Q_4$, $R_{3a1}$, $R_{3a2}$, $R_{3b1}$, $R_{3b2}$, $R_{3c1}$, $R_{3c2}$, $R_{3d1}$, $R_{3d2}$, $R_{3e1}$, $R_{3e2}$, $R_{3f1}$, $R_{3f2}$, $R_{3g1}$, $R_{3g2}$, $R_{3h1}$, $R_{3h2}$, $R_{3i1}$, $R_{3i2}$, $R_{3j1}$, $R_{3j2}$, $R_{3k1}$, $R_{3k2}$, $R_{3l1}$, $R_{3l2}$, $R_{3m1}$, $R_{3m2}$, $R_{3n1}$, $R_{3n2}$, $R_{3o1}$, $R_{3o2}$, $R_{3p1}$, $R_{3p2}$, n, $R_4$, $R_5$, $R_{X5a}$, $R_{X5b}$, $R_6$, $R_7$, $R_8$, $R_9$, $R_{10}$, $R_{11}$, $R_{11N}$, $R_{12}$, $R_{13}$, $R_{16}$, $R_{17}$, $R_{18}$, $R_{19}$, $R_{20}$, $R_{21}$, $R_{22}$, $R_{23}$, $R_{24}$, $R_{28}$, $R_{29}$, $R_{30}$, $R_{Z1}$, $R_{Z1a}$, $R_{Z1b}$, $R_{Z1c}$, $R_{Z1d}$, $R_{Z2}$, $R_{Z2a}$, $R_{Z3a}$, $R_{Zi1b}$, $R_{Zi2e}$, $R_{Z9}$, $R_{Z10}$, $R_{Z11}$, $R_{Z12}$, $R_{Z13}$, $R_{Z14}$, $R_{Z15}$, $R_{Z16}$, $A_1$, $A_2$, $A_5$, $A_6$, $A_7$, $A_8$, $A_9$, $A_{11}$, and any associated substituent groups has any of the meanings defined hereinbefore or in any one of paragraphs (1) to (193) hereinafter:—

(1) $Q_1$ is selected from O, NH or N—$C_{1-4}$alkyl.
(2) $Q_1$ is selected from NH or N—$C_{1-4}$alkyl.
(3) $Q_1$ is selected from NH or N—$CH_3$.
(4) $Q_1$ is NH.
(5) $Q_{2a}$ is $CR_{2a}$;
(6) $Q_{2b}$ is $CR_{2b}$;
(7) $Q_{2c}$ is $CR_{2c}$;
(8) $Q_{2d}$ is $CR_{2d}$;
(9) $Q_3$ is $CR_{1b}$;
(10) $Q_4$ is $CR_{1x}$;

(11) X is selected from:
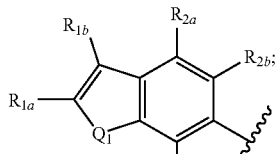
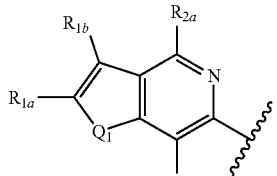
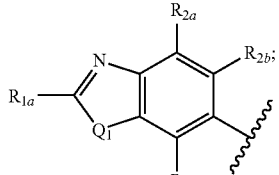
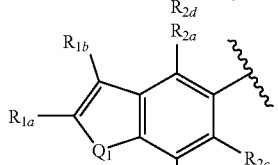
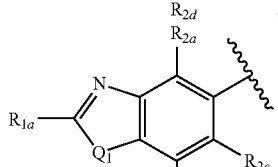
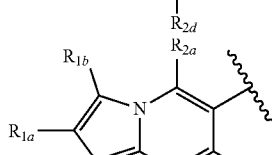; and
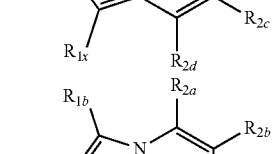
wherein $Q_1$, $R_{1a}$, $R_{1b}$, $R_{1x}$, $R_{2a}$, $R_{2b}$, $R_{2c}$, $R_{2d}$ are as defined herein.
(12) X is selected from:
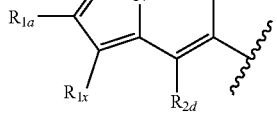
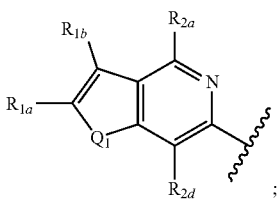
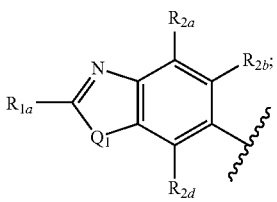
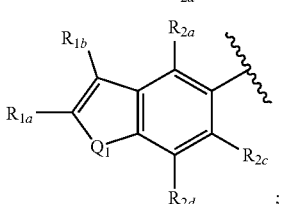
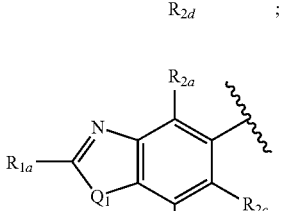; and
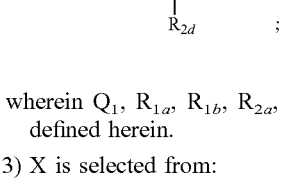;
wherein $Q_1$, $R_{1a}$, $R_{1b}$, $R_{2a}$, $R_{2b}$, $R_{2c}$ and $R_{2d}$ are as defined herein.
(13) X is selected from:
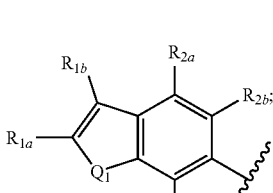
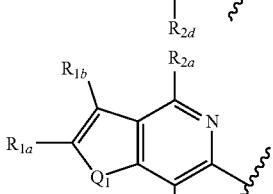; and
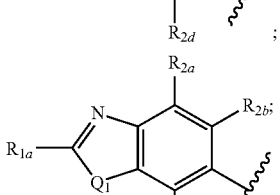
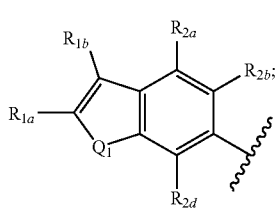
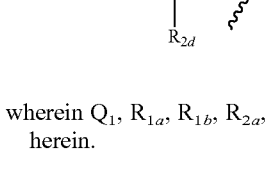
wherein $Q_1$, $R_{1a}$, $R_{1b}$, $R_{2a}$, $R_{2b}$ and $R_{2d}$ are as defined herein.

(14) X is selected from:

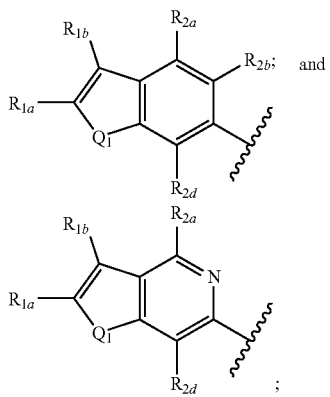

wherein $Q_1$, $R_{1a}$, $R_{1b}$, $R_{2a}$, $R_{2b}$ and $R_{2d}$ are as defined herein.

(15) X is:

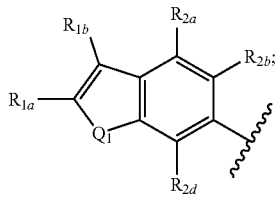

wherein $Q_1$, $R_{1a}$, $R_{1b}$, $R_{2a}$, $R_{2b}$ and $R_{2d}$ are as defined herein.

(16) X is:

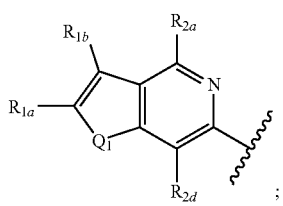

wherein $Q_1$, $R_{1a}$, $R_{1b}$, $R_{2a}$ and $R_{2d}$ are as defined herein.

(17) $R_{1b}$, $R_{2a}$, $R_{2b}$, $R_{2c}$ and $R_{2d}$ are each independently selected from hydrogen, $C_{1-2}$alkyl or halo.

(18) X is selected from:

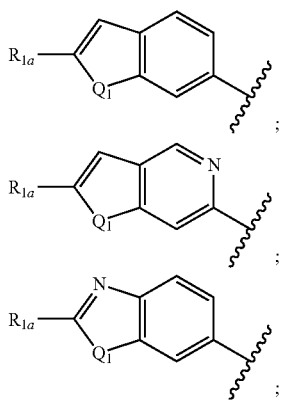

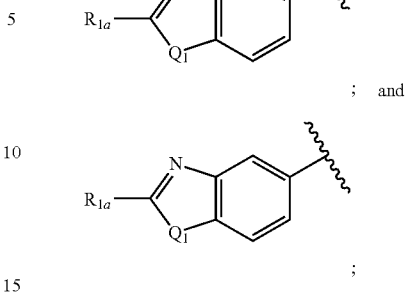

wherein $Q_1$ and $R_{1a}$ are as defined herein.

(19) X is selected from:

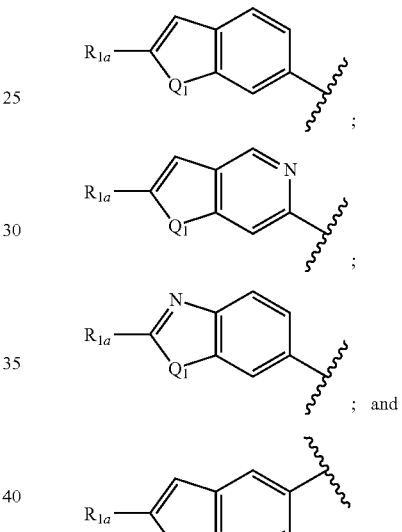

wherein $Q_1$ and $R_{1a}$ are as defined herein.

(20) X is selected from:

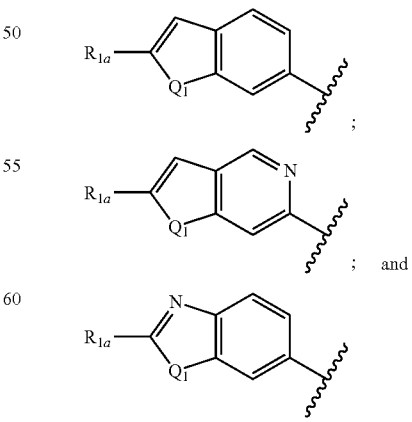

wherein $Q_1$ and $R_{1a}$ are as defined herein.

(21) X is selected from:

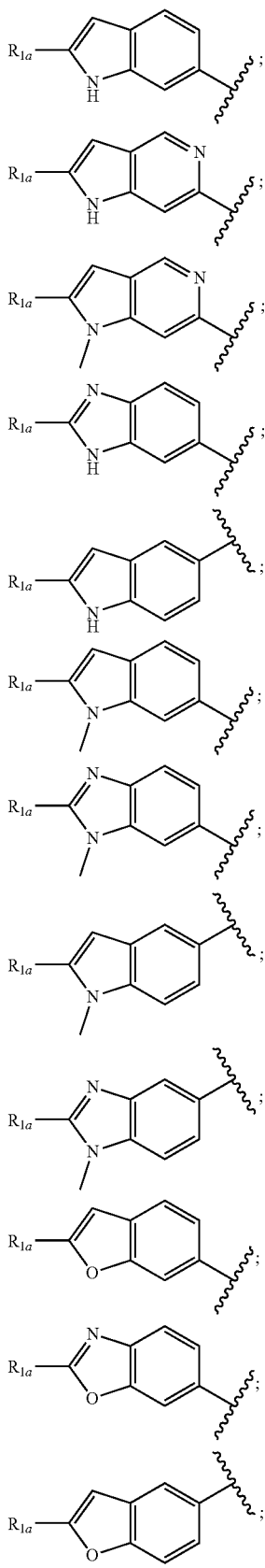

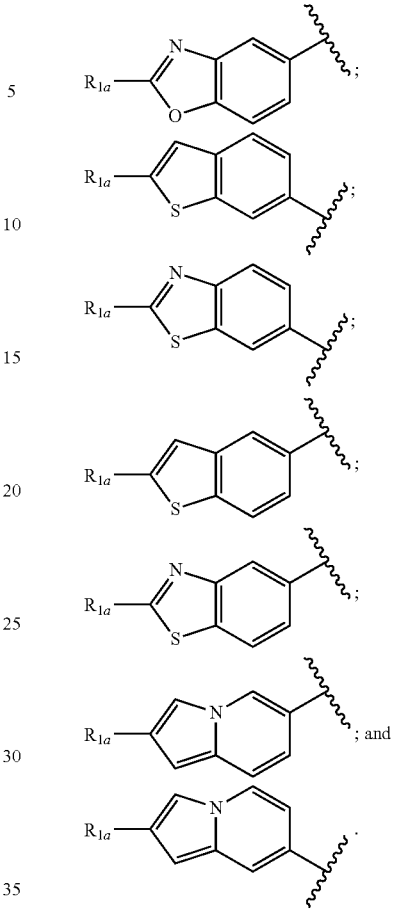

wherein R$_{1a}$ is as defined herein.

(22) X is selected from:

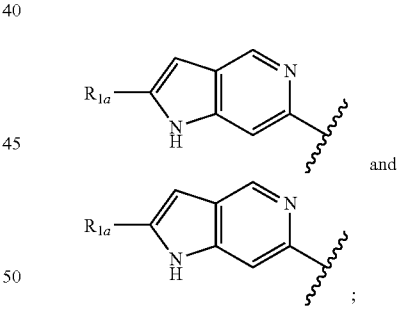

wherein R$_{1a}$ is as defined herein.

(23) R$_{1a}$ is selected from:
   (i) C$_{1-4}$alkyl optionally substituted by halo, cyano, hydroxy, C$_{3-6}$cycloalkyl, C$_{1-4}$-alkoxy, C$_{1-4}$haloalkoxy, aryl or heteroaryl; or
   (ii) a group of the formula:

(CR$_{1c}$R$_{1d}$)$_p$—NR$_{1e}$R$_{1f}$;

wherein
     p is an integer selected from 0, 1, 2 or 3
     R$_{1c}$ and R$_{1d}$ are independently selected from:
       (i) hydrogen (including deuterium),
       (ii) C$_{1-6}$alkyl which is optionally substituted by one or more substituents selected from cyano, hydroxy, C$_{1-4}$alkoxy, halo, C$_{1-4}$haloalkoxy, $C_{3-6}$cycloalkyl, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally further substituted with halo, cyano or hydroxy;

(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; and;

(iv) or $R_{1c}$ and $R_{1d}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$ alkyl, $C_{1-2}$haloalkyl, cyano, hydroxy, $C_{1-2}$alkoxy, halo, $C_{1-2}$ haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{1e}$ and $R_{1f}$ are each independently selected from:
(i) hydrogen (including deuterium);
(ii) $C_{1-6}$alkyl which is optionally substituted by one or more substituents selected from cyano, oxo, hydroxy, $C_{1-2}$ alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl;
(iii) a group with the formula:

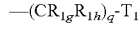
—$(CR_{1g}R_{1h})_q$-$T_1$ wherein:
q is 0, 1, 2, 3, 4, 5 or 6;
$R_{1g}$ and $R_{1h}$ are independently selected from:
a) hydrogen;
b) $C_{1-6}$alkyl which is optionally substituted by one or more substituents selected from cyano, oxo, hydroxy, $C_{1-4}$ alkoxy, halo, $C_{1-4}$haloalkoxy, —O—$C_{3-6}$cycloalkyl, $NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;
c) an aryl-$C_{1-6}$alkyl, heteroaryl$C_{1-6}$alkyl, $C_{3-6}$cycloalkyl or $C_{3-6}$cycloalkyl$C_{1-6}$alkyl group, each of which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl; or
d) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, cyano, $C_{1-2}$haloalkyl, hydroxy, $C_{1-2}$ alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1h}$a are H or $C_{1-2}$alkyl;
and $T_1$ is selected from hydrogen, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{3t}R_{4t}$ or —$S(O)_{0-2}R_{3t}R_{4t}$, wherein $R_{3t}$ and $R_{4t}$ are H or $C_{1-2}$alkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$ haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

(24) $R_{1a}$ is selected from:
(i) $C_{1-4}$alkyl optionally substituted by halo, cyano, hydroxy, $C_{3-6}$cycloalkyl, a 3 to 6 membered heterocyclyl, $C_{1-4}$alkoxy, $C_{1-4}$haloalkoxy, aryl or heteroaryl; or
(ii) a group of the formula:

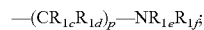
—$(CR_{1c}R_{1d})_p$—$NR_{1e}R_{1f}$;

wherein
p is an integer selected from 1 or 2;
$R_{1c}$ and $R_{1d}$ are independently selected from:
(i) hydrogen (including deuterium),
(ii) $C_{1-3}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally substituted with halo, cyano or hydroxy;

(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; and;

(iv) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{1e}$ and $R_{1f}$ are each independently selected from:
(i) hydrogen (including deuterium);
(ii) $C_{1-6}$alkyl which is optionally substituted by one or more substituents selected from cyano, oxo, hydroxy, $C_{1-2}$alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl;
(iii) a group with the formula:

—$(CR_{1g}R_{1h})_q$-$T_1$ wherein:
q is 0, 1, 2 or 3;
$R_{1g}$ and $R_{1h}$ are independently selected from:
  a) hydrogen (including deuterium); or
  b) $C_{1-3}$alkyl which is optionally substituted by one more substituents selected from cyano, oxo, hydroxy, $C_{1-3}$alkoxy, halo, $C_{1-4}$haloalkoxy, —O—$C_{3-4}$cycloalkyl, wherein —O—$C_{3-4}$cycloalkyl is optionally substituted with halo, cyano or hydroxy, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl;
  c) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;
  and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;
(iv) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;
wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl;
(25) $R_{1a}$ is a group of the formula:

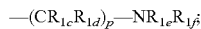
—$(CR_{1c}R_{1d})_p$—$NR_{1e}R_{1f}$;

wherein
  p is an integer selected from 1 or 2;
  $R_{1c}$ and $R_{1d}$ are independently selected from:
    (i) hydrogen (including deuterium); or
    (ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy,
    (iii) $C_{3-4}$cycloalkyl which is optionally substituted by $C_{1-4}$alkyl, $C_{1-4}$haloalkyl, cyano, hydroxy, $C_{1-2}$alkoxy, halo, $C_{1-2}$haloalkoxy or $NR_{1ca}R_{1da}$; and; (iv) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;
$R_{1e}$ and $R_{1f}$ are each independently selected from:
  (i) hydrogen (including deuterium);
  (ii) $C_{1-6}$alkyl which is optionally substituted by one more substituents selected from cyano, oxo, hydroxy, $C_{1-2}$alkoxy, halo, $C_{1-2}$haloalkoxy, $NH_2$;
  (iii) a group with the formula:

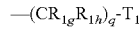
—$(CR_{1g}R_{1h})_q$-$T_1$ wherein:
q is 0, 1, 2 or 3;
$R_{1g}$ and $R_{1h}$ are independently selected from:
  a) hydrogen (including deuterium); or
  b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy,
  c) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;
  and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;
(iv) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$ haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$ wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(26) $R_{1a}$ is a group of the formula:

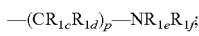

wherein
p is an integer selected from 1 or 2;
$R_{1c}$ and $R_{1d}$ are independently selected from:
(i) hydrogen (including deuterium),
(ii) $C_{1-3}$alkyl which is optionally substituted by one more substituents selected from cyano, oxo, hydroxy, $C_{1-3}$alkoxy, halo, $C_{1-43}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{1e}$ is selected from:
(i) hydrogen (including deuterium);
(ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

and $R_{1f}$ is selected from:
(i) $C_{1-6}$alkyl which is optionally substituted by one more substituents selected from cyano, oxo, hydroxy, $C_{1-2}$alkoxy, halo, $C_{1-2}$haloalkoxy and $NH_2$;
(ii) a group with the formula:

wherein:
q is 1, 2 or 3;
$R_{1g}$ and $R_{1h}$ are independently selected from:
a) hydrogen (including deuterium); or
b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$ cycloalkyl is optionally substituted with halo, cyano or hydroxy;
c) or $R_{1g}$ and $R_{1h}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, halo, $C_{1-4}$alkyl, $C_{1-4}$haloalkyl, cyano, hydroxy, $NR_{1i}R_{2t}$ or —$S(O)_{0-2}R_{1i}R_{2t}$ (wherein $R_{1t}$ and $R_{2t}$ are H or $C_{1-4}$ alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$ alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$ cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring; which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(27) $R_{1a}$ is a group of the formula:

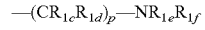

wherein
p is an integer selected from 1 or 2;
$R_{1c}$ and $R_{1d}$ are independently selected from:
(i) hydrogen (including deuterium),
(ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{1e}$ is selected from:
(i) hydrogen (including deuterium);
(ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

$R_{1f}$ is a group with the formula:

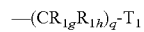

wherein:

q is 1, 2 or 3;

$R_{1g}$ and $R_{1h}$ are independently selected from:
a) hydrogen (including deuterium); or
b) $C_{1-3}$alkyl which is optionally substituted by one or more substituents selected from cyano, oxo, hydroxy, $C_{1-4}$alkoxy, halo, $C_{1-4}$haloalkoxy, —O—$C_{3-6}$cycloalkyl, wherein —O—$C_{3-6}$cycloalkyl is optionally substituted with halo, cyano or hydroxy;
c) or $R_{1g}$ and $R_{1h}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$-haloalkyl, cyano, hydroxy, $C_{1-2}$alkoxy, halo or $C_{1-2}$-haloalkoxy;

and $T_1$ is selected from halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(28) $R_{1a}$ is a group of the formula:

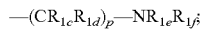—$(CR_{1c}R_{1d})_p$—$NR_{1e}R_{1f}$;

wherein p is an integer selected from 1 or 2;

$R_{1c}$ and $R_{1d}$ are independently selected from:
(i) hydrogen (including deuterium),
(ii) $C_{1-3}$alkyl which is optionally substituted by one or more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{1e}$ is selected from:
(i) hydrogen (including deuterium);
(ii) $C_{1-3}$alkyl which is optionally substituted by one or more substituents selected from cyano, oxo, hydroxy, $C_{1-2}$alkoxy, halo, $C_{1-2}$haloalkoxy and $NH_2$;

$R_{1f}$ is a group with the formula:

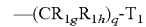—$(CR_{1g}R_{1h})_q$-$T_1$ wherein:

q is 1 or 2;

$R_{1g}$ and $R_{1h}$ are independently selected from:
a) hydrogen (including deuterium); or
b) $C_{1-3}$alkyl, which is optionally substituted by one or more substituents selected from cyano, oxo, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy;

and $T_1$ is selected from $C_{1-4}$alkyl, $C_{3-8}$cycloalkyl, aryl, heterocyclyl, heteroaryl, a spirocyclic carbocyclic or heterocyclic ring system, a bridged $C_{3-8}$cycloalkyl, a bridged bicyclic $C_{5-2}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{3-6}$cycloalkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(29) $R_{1a}$ is a group of the formula:

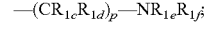—$(CR_{1c}R_{1d})_p$—$NR_{1e}R_{1f}$;

wherein p is an integer selected from 1 or 2;

$R_{1c}$ and $R_{1d}$ are independently selected from:
(i) hydrogen (including deuterium) or
(ii) $C_{1-3}$alkyl which is optionally substituted by one or more substituents selected from cyano, oxo, hydroxy, $C_{1-2}$alkoxy, halo, $C_{1-2}$haloalkoxy, —O—$C_3$cycloalkyl;

$R_{1e}$ is selected from hydrogen (including deuterium) or $C_{1-2}$alkyl; and $R_{1f}$ is a group with the formula:

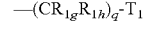—$(CR_{1g}R_{1h})_q$-$T_1$ wherein:
q is 1 or 2;
$R_{1g}$ and $R_{1h}$ are independently selected from:
a) hydrogen (including deuterium); or
b) $C_{1-2}$alkyl, which is optionally substituted by one or more substituents selected from cyano, oxo, hydroxy, $C_{1-2}$alkoxy, halo or $C_{1-2}$haloalkoxy;
and $T_1$ is selected from $C_{1-4}$alkyl, $C_{3-8}$cycloalkyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy or $C_{3-6}$cycloalkyl;
or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$-haloalkyl, $C_{3-6}$cycloalkyl, cyano, hydroxy, $C_{1-2}$alkoxy, halo or $C_{1-2}$haloalkoxy; wherein any wherein any alkyl, alkoxy or $C_{3-6}$cycloalkyl is further optionally substituted by one or more substituents selected from cyano, hydroxy, halo, $NR_{1k}R_{1l}$ or $-S(O)_{0-2}R_{1k}R_{1l}$, wherein $R_{1k}$ and $R_{1l}$ are H or $C_{1-4}$alkyl.

(30) $R_{1a}$ is a group of the formula:

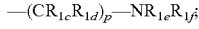
—$(CR_{1c}R_{1d})_p$—$NR_{1e}R_{1f}$;

wherein
p is an integer selected from 1 or 2;
$R_{1c}$ and $R_{1d}$ are independently selected from hydrogen (including deuterium) or $C_{1-2}$ alkyl;
$R_{1e}$ is selected from hydrogen (including deuterium) or $C_{1-2}$alkyl; and
$R_{1f}$ is a group with the formula:

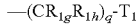
—$(CR_{1g}R_{1h})_q$-$T_1$ wherein:
q is 1 or 2;
$R_{1g}$ and $R_{1h}$ are independently selected from hydrogen (including deuterium) or $C_{1-2}$alkyl;
and $T_1$ is selected from $C_{1-4}$alkyl, $C_{3-4}$cycloalkyl, heterocyclyl, a mono- or bicyclic heteroaryl, a spirocyclic carbocyclic or heterocyclic ring system, a bridged $C_3$-cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;
or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$ cycloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-8}$cycloalkyl is further optionally substituted by one or more substituents selected from cyano, hydroxy, halo, $NR_{1k}R_{1l}$ or $-S(O)_{0-2}R_{1k}R_{1l}$, wherein $R_{1k}$ and $R_{1l}$ are H or $C_{1-4}$alkyl.

(31) $R_{1a}$ is a group of the formula:

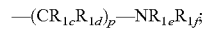
—$(CR_{1c}R_{1d})_p$—$NR_{1e}R_{1f}$;

wherein
p is 1;
$R_{1c}$ and $R_{1d}$ are independently selected from hydrogen (including deuterium) or $C_{1-2}$alkyl;
$R_{1e}$ is selected from hydrogen (including deuterium) or $C_{1-2}$alkyl; and
$R_{1f}$ is a group with the formula:

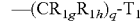
—$(CR_{1g}R_{1h})_q$-$T_1$ wherein:
q is 1 or 2;
$R_{1g}$ and $R_{1h}$ are independently selected from hydrogen (including deuterium) or $C_{1-2}$alkyl;
and $T_1$ is selected from $C_{3-4}$cycloalkyl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;
or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring; which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, wherein any alkyl, alkoxy or $C_{3-6}$cycloalkyl is further optionally substituted by one or more substituents selected from cyano, hydroxy, halo, $NR_{1k}R_{1l}$ or $-S(O)_{0-2}R_{1k}R_{1l}$, wherein $R_{1k}$ and $R_{1l}$ are H or $C_{1-4}$alkyl.

(32) $R_{1a}$ is a group of the formula:

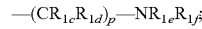
—$(CR_{1c}R_{1d})_p$—$NR_{1e}R_{1f}$;

wherein
p is 1;
$R_{1c}$ and $R_{1d}$ are independently selected from hydrogen (including deuterium) or $C_{1-2}$ alkyl;
$R_{1e}$ is selected from hydrogen (including deuterium) or $C_{1-2}$alkyl; and
$R_{1f}$ is a group with the formula:

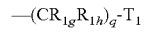
—$(CR_{1g}R_{1h})_q$-$T_1$ wherein:
q is 1;
$R_{1g}$ and $R_{1h}$ are independently selected from hydrogen (including deuterium) or $C_{1-2}$alkyl;
and $T_1$ is selected from $C_{3-4}$cycloalkyl, heterocyclyl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, C$_{1-2}$haloalkyl, cyano, hydroxy, C$_{1-2}$alkoxy, halo, C$_{1-2}$haloalkoxy or C$_{3-6}$cycloalkyl,
wherein any alkyl or alkoxy is optionally further substituted by one or more substituents selected from cyano, hydroxy or halo.

(33) R$_{1a}$ is a group of the formula:

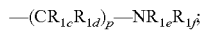

wherein
p is 1;
R$_{1c}$ and R$_{1d}$ are independently selected from hydrogen (including deuterium) or C$_{1-2}$alkyl; and
R$_{1e}$ and R$_{1f}$ are linked such that, together with the nitrogen atom to which they are attached, they form a mono- or bicyclic-heterocyclic ring, which is optionally substituted by one or more substituents selected from C$_{1-2}$alkyl, C$_{1-2}$haloalkyl, C$_{3-6}$cycloalkyl, cyano, hydroxy, C$_{1-2}$alkoxy, halo or C$_{1-2}$haloalkoxy, and/or the mono- or bicyclic heterocyclic ring formed by R$_{1e}$ and R$_{1f}$ is optionally spiro-fused to a C$_{3-6}$cycloalkyl or a heterocyclic ring, which in turn is optionally substituted by one or more substituents selected from C$_{1-2}$alkyl, C$_{1-2}$haloalkyl, cyano, hydroxy, C$_{1-2}$ alkoxy, halo or C$_{1-2}$haloalkoxy.

(34) R$_{1a}$ is

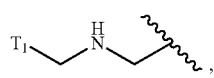

wherein T$_1$ is as defined herein.

(35) R$_{1a}$ is a group of the formula:

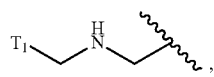

wherein T$_1$ is selected from C$_{3-4}$cycloalkyl, heterocyclyl, a spirocyclic carbocyclic or heterocyclic ring system, a bridged C$_{3-8}$cycloalkyl, a bridged bicyclic C$_{5-12}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy;

(36) R$_{1a}$ is selected from:
methoxy;

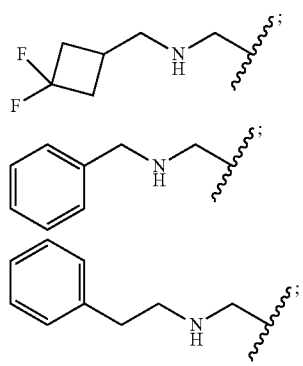

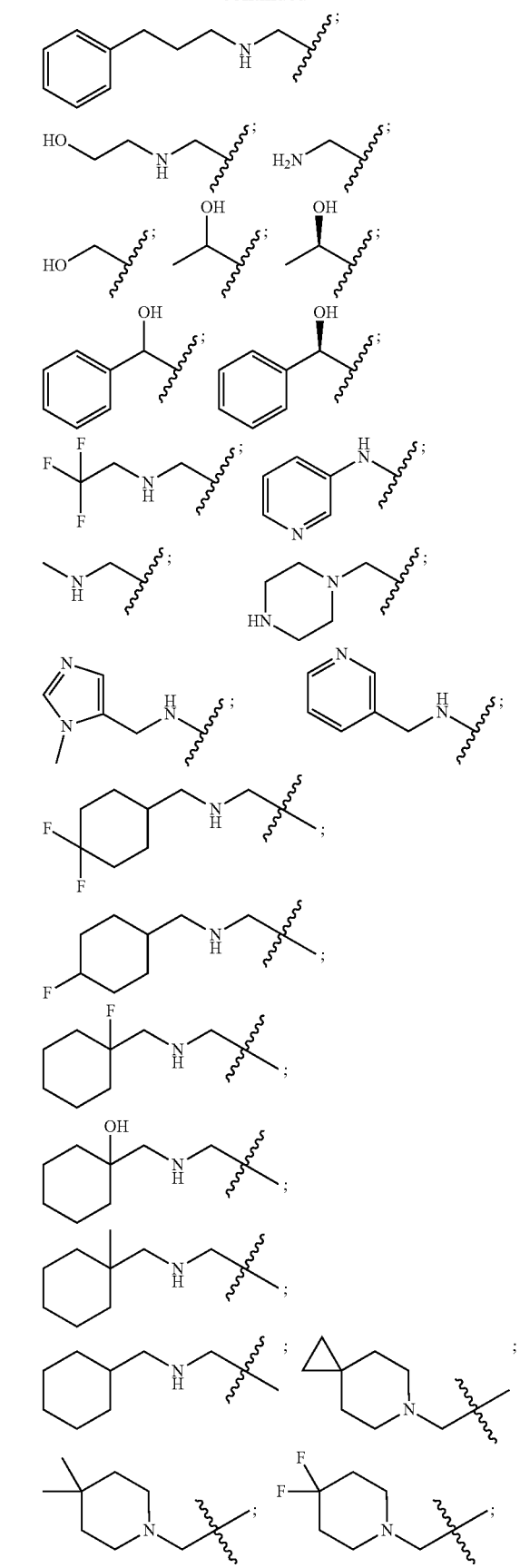

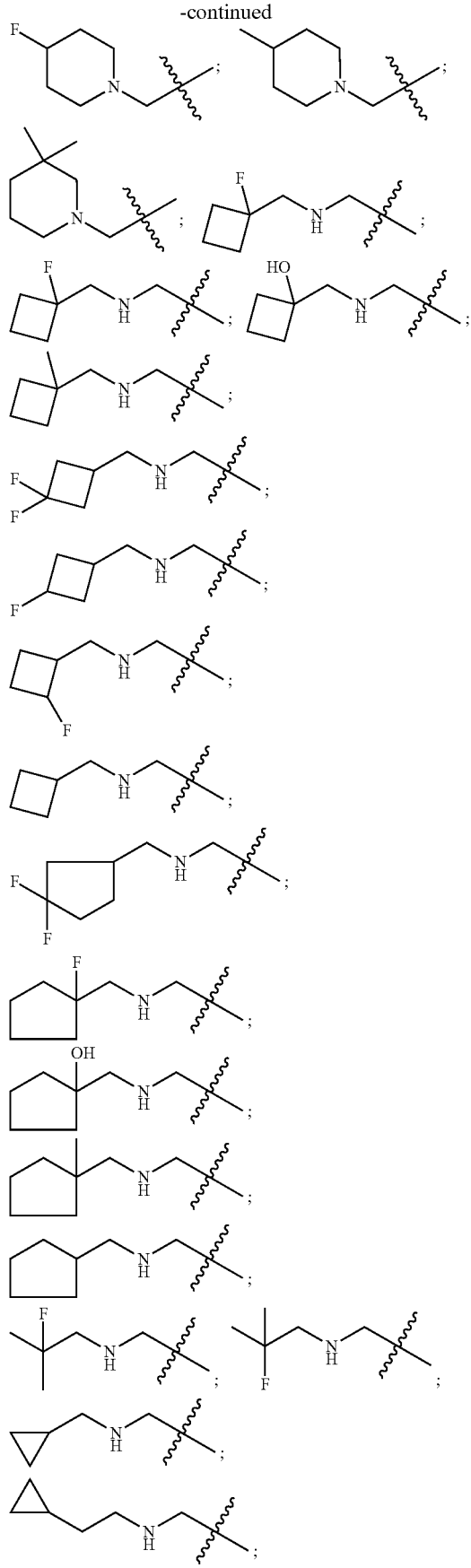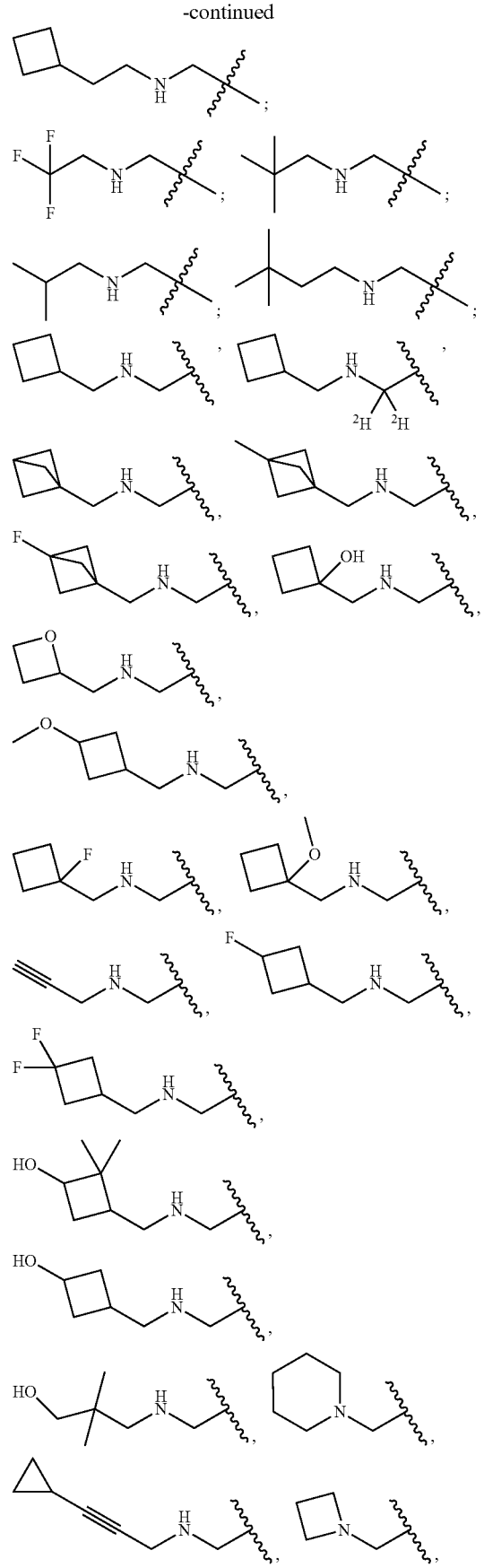

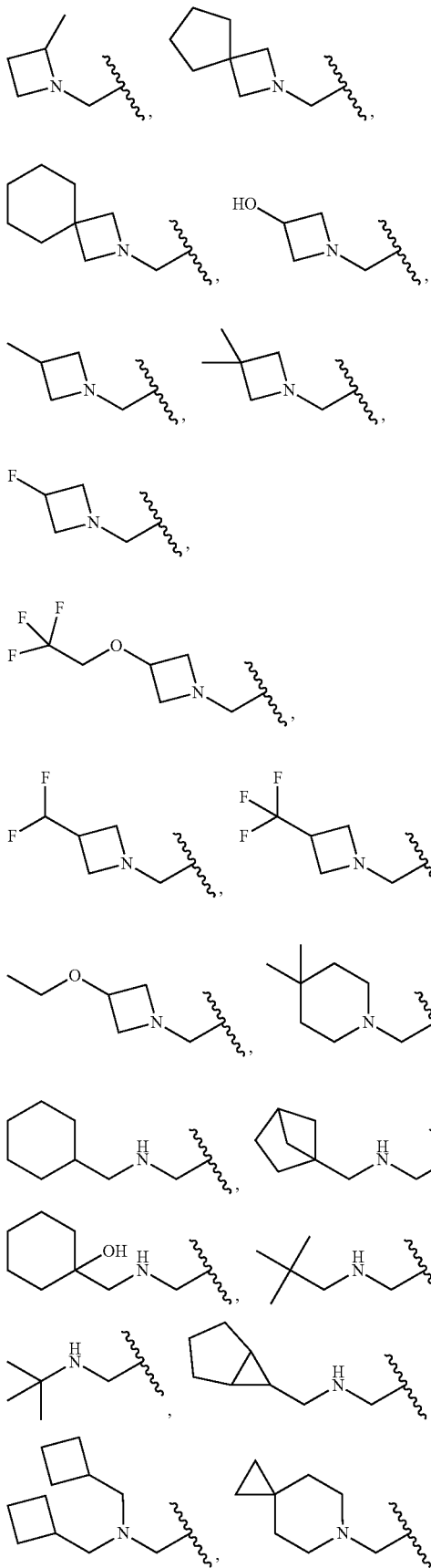
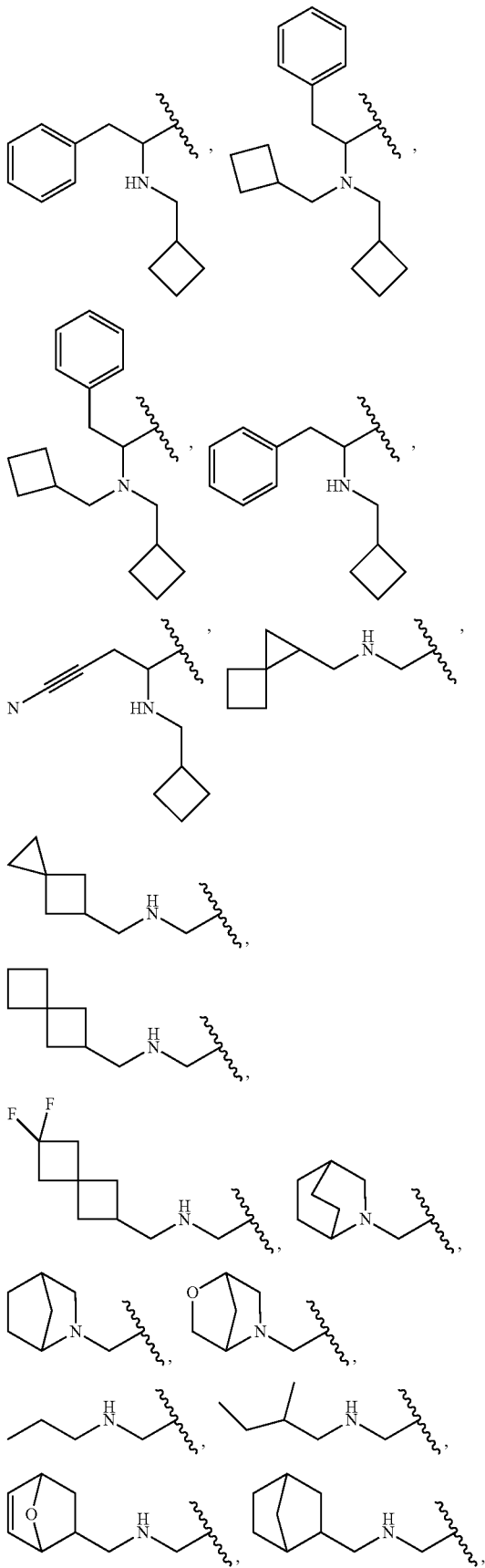

-continued
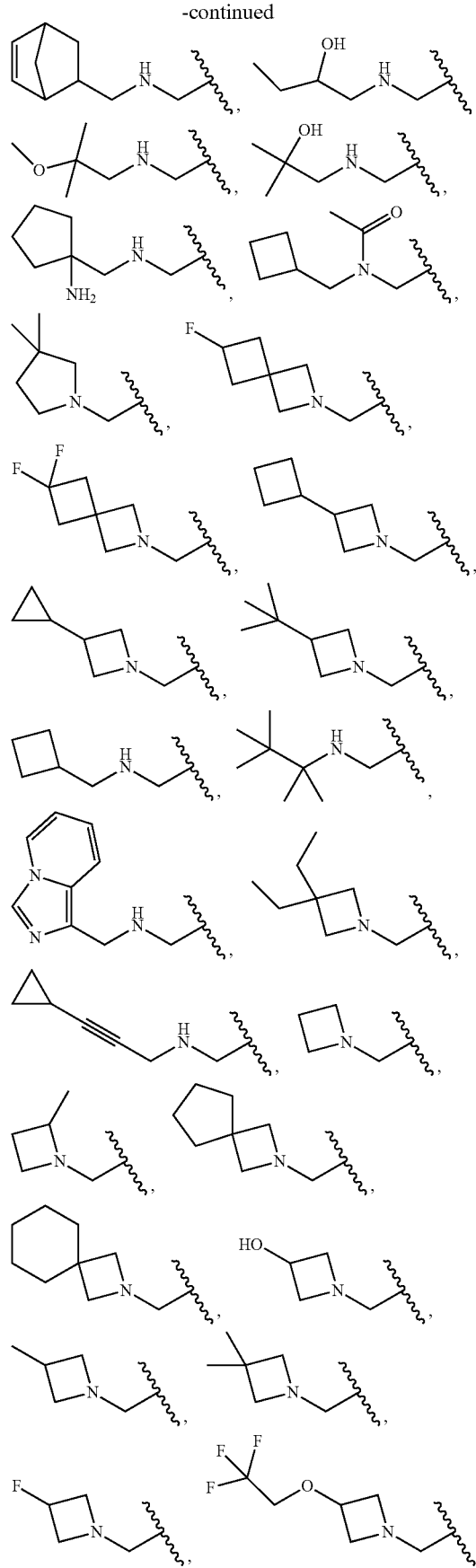
-continued
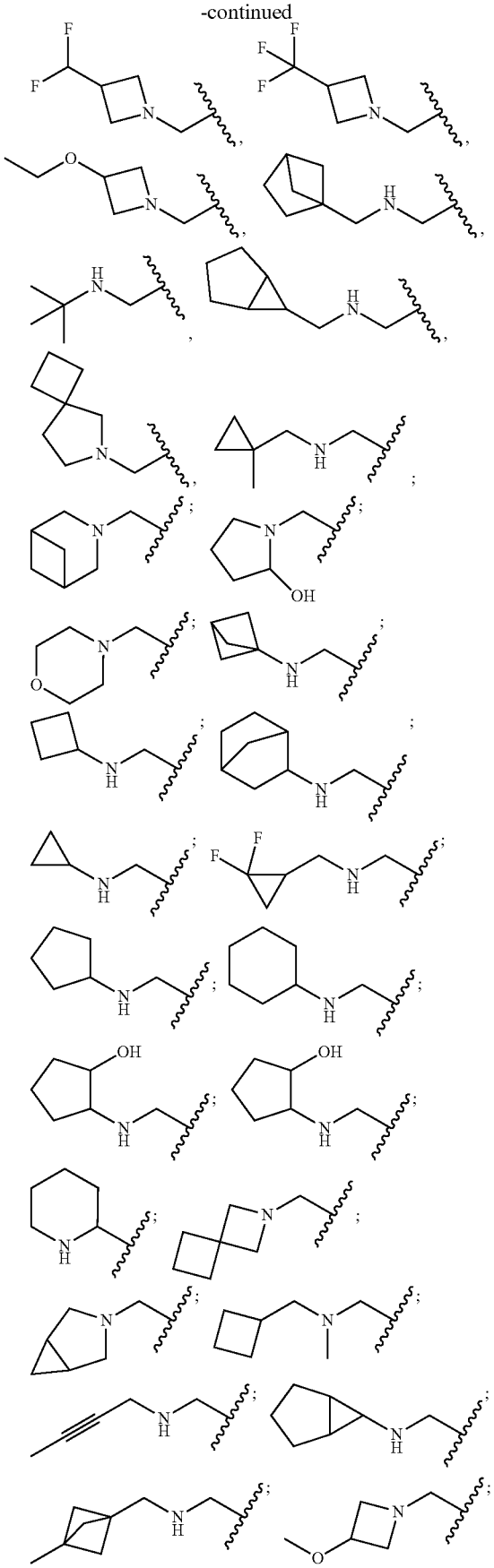

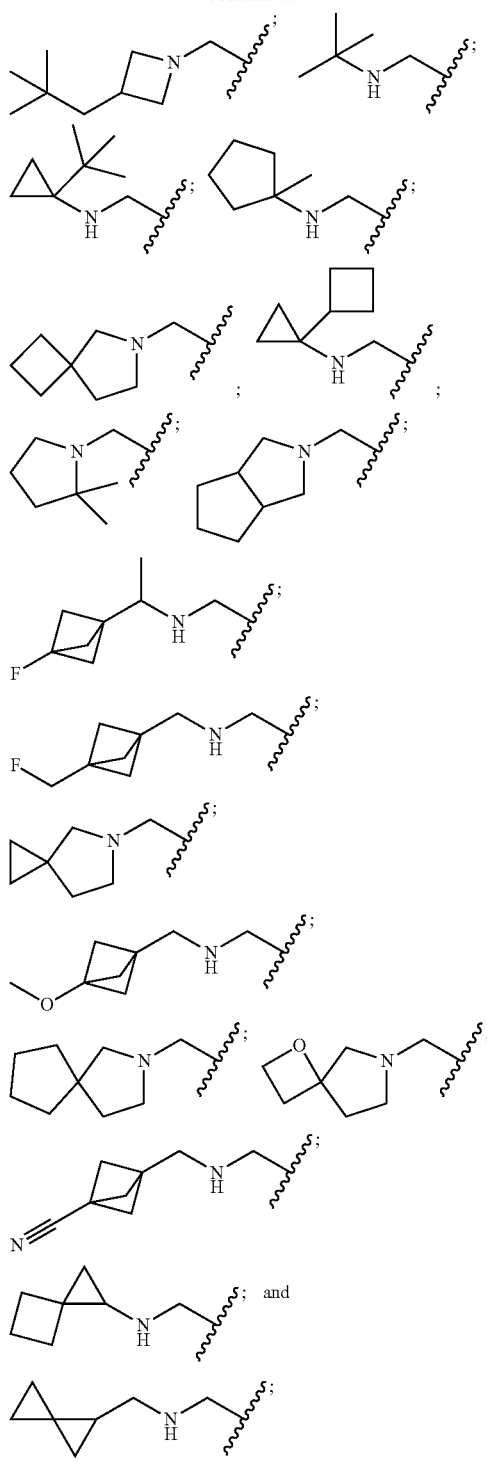
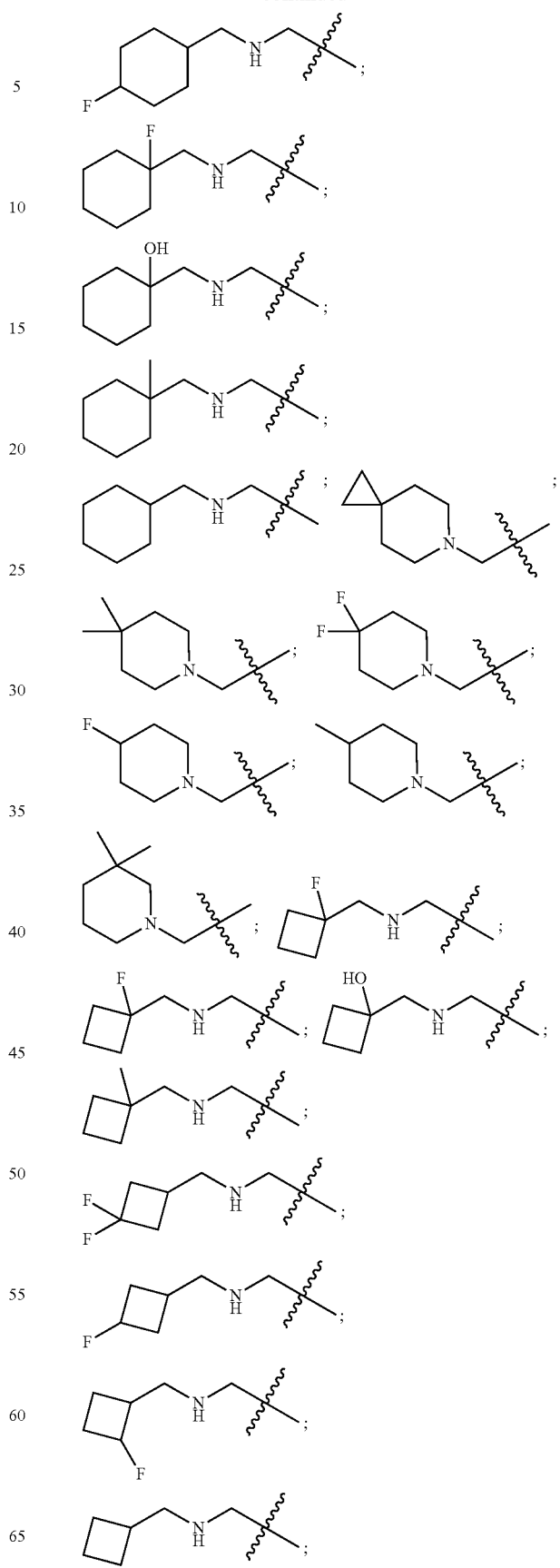
(37) R$_{1a}$ is selected from:
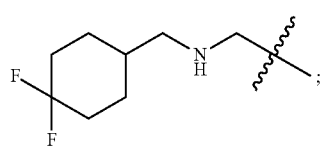

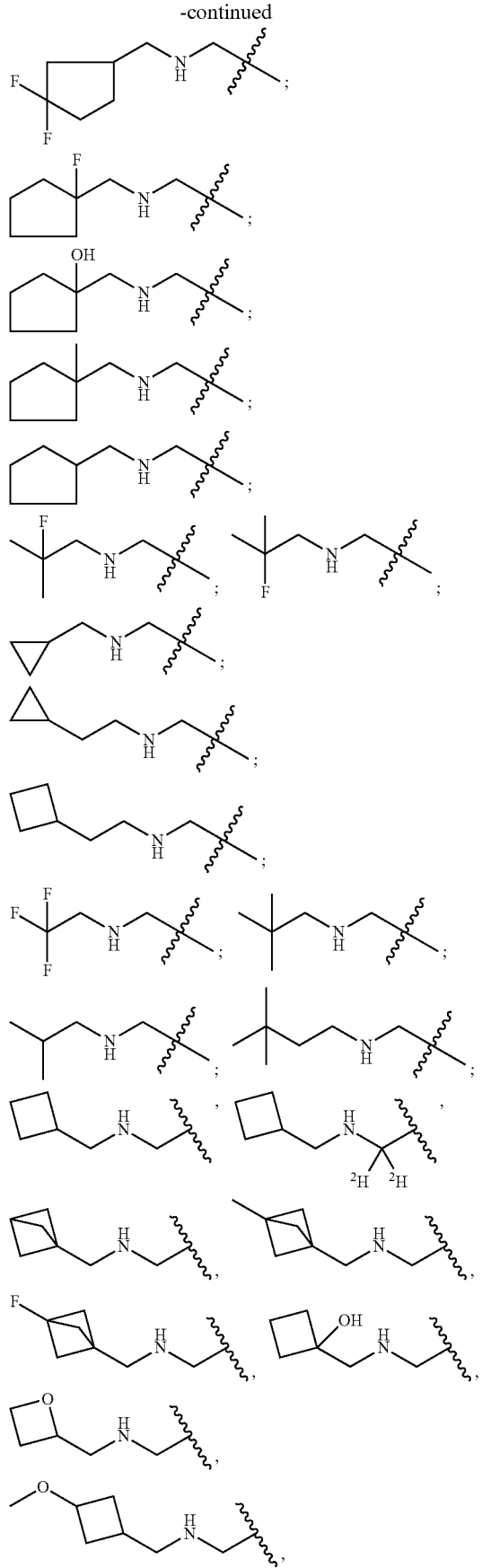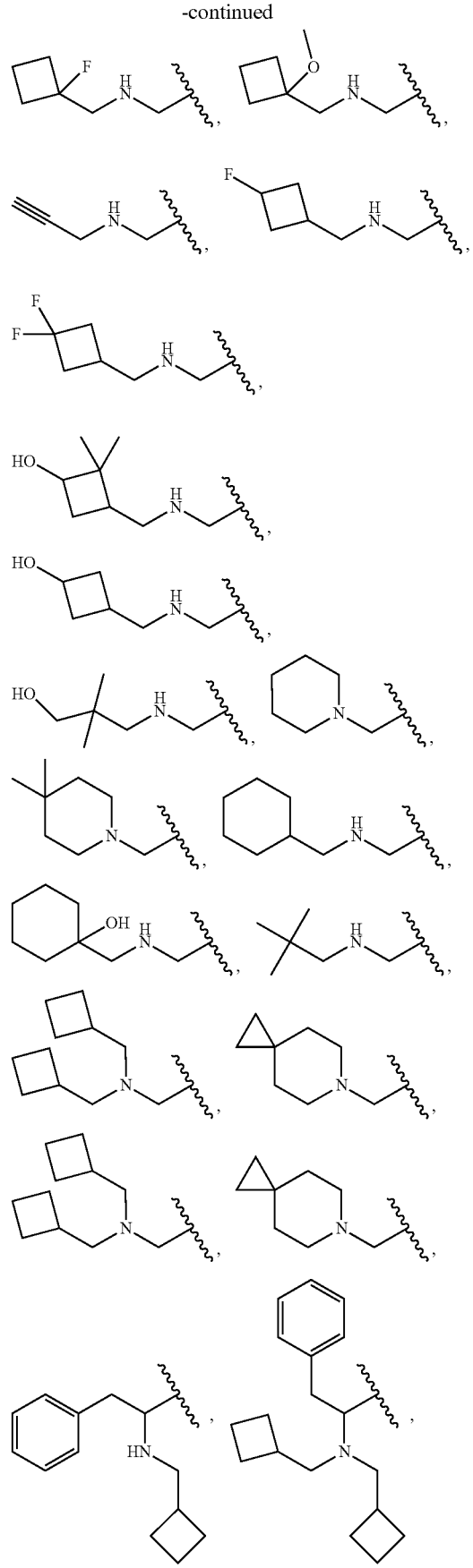

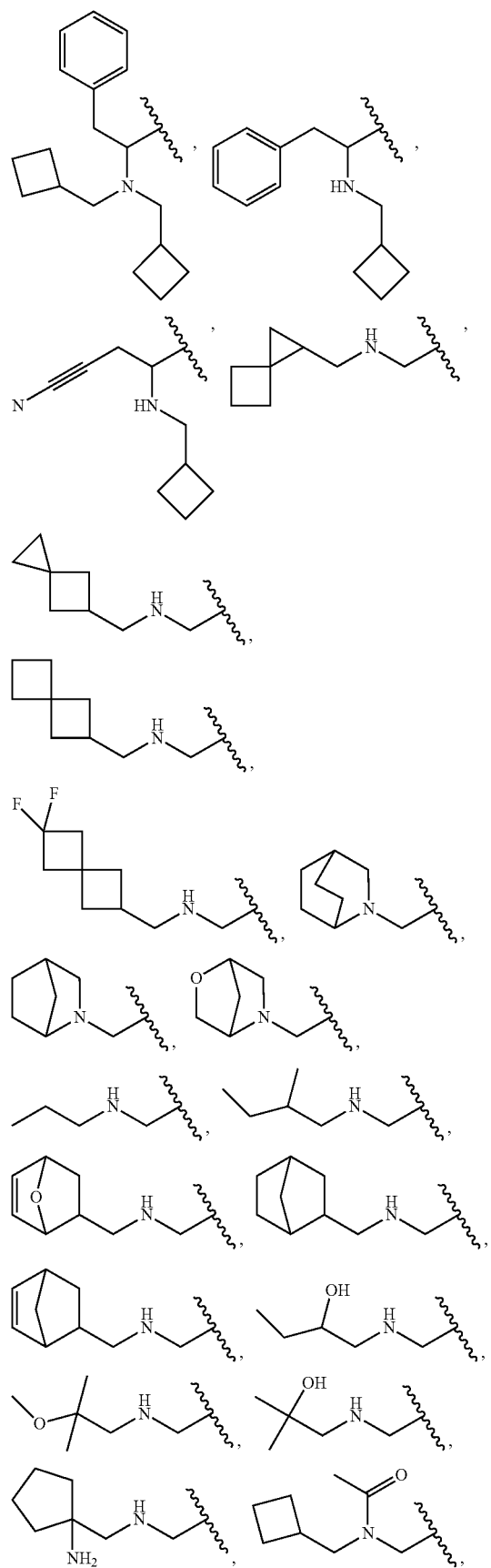
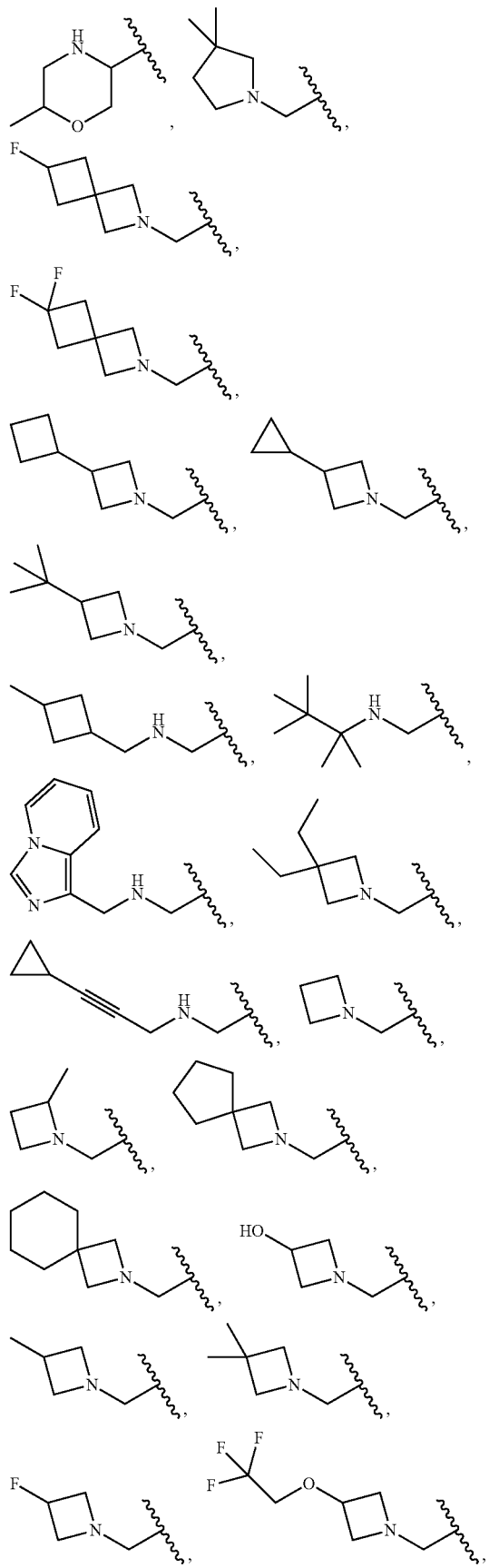

-continued
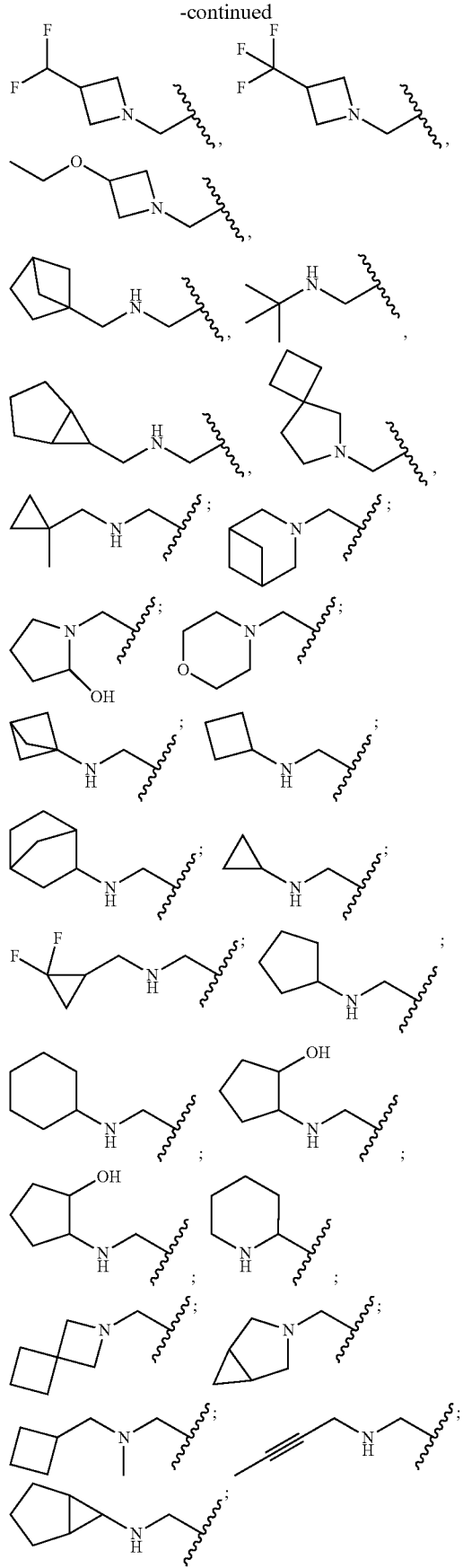
-continued
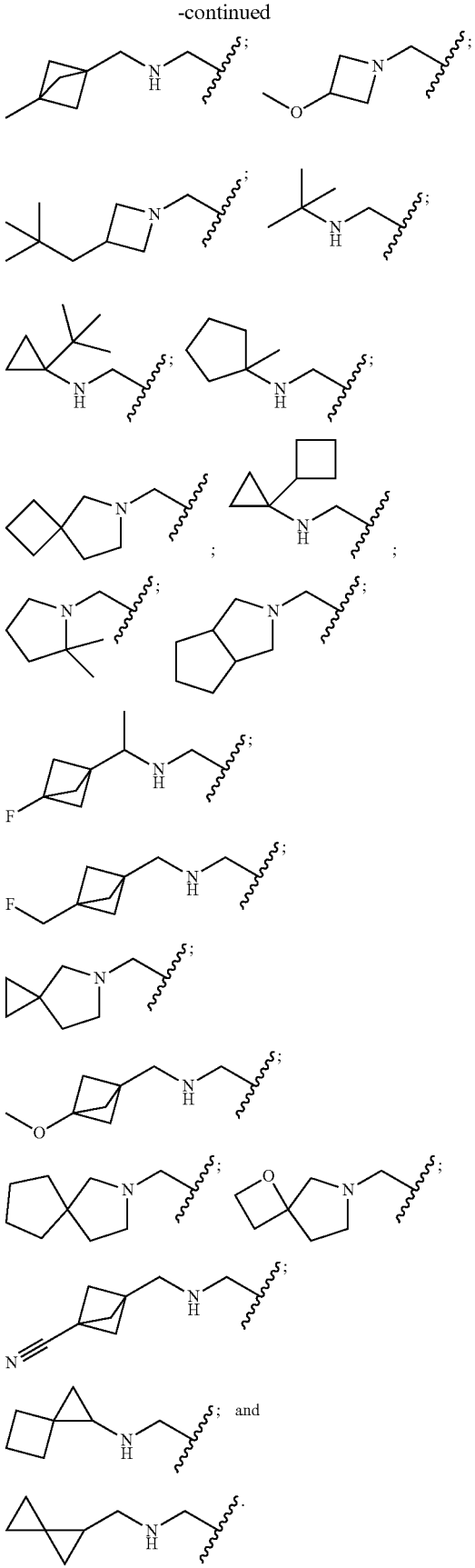

(38) $R_{1a}$ is selected from:
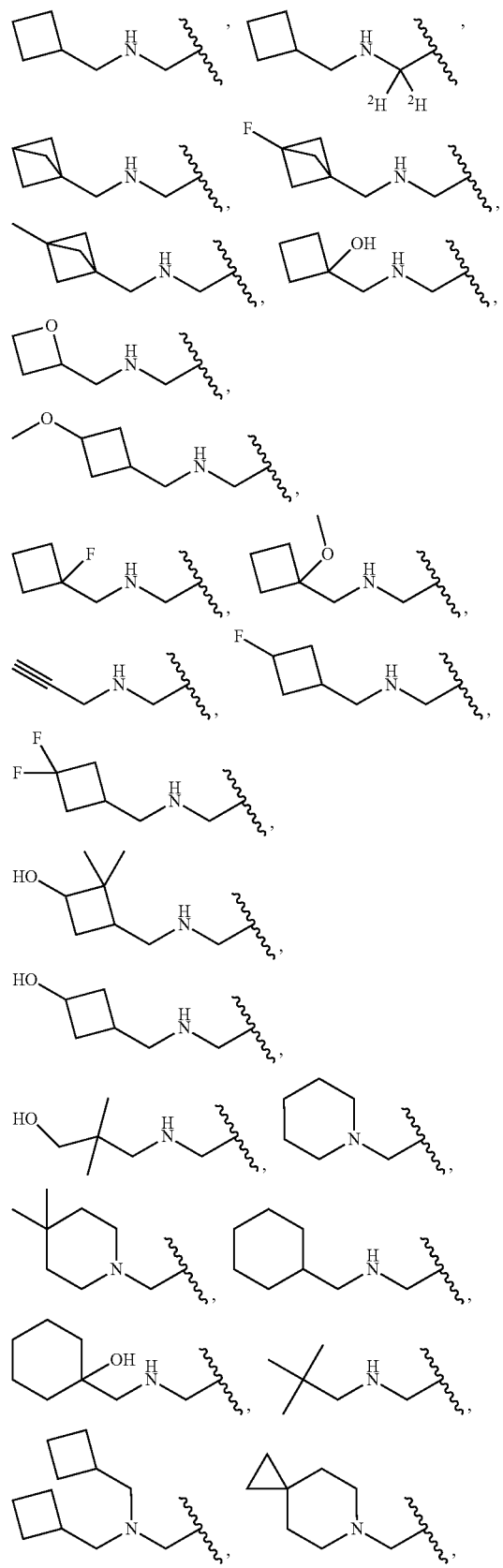
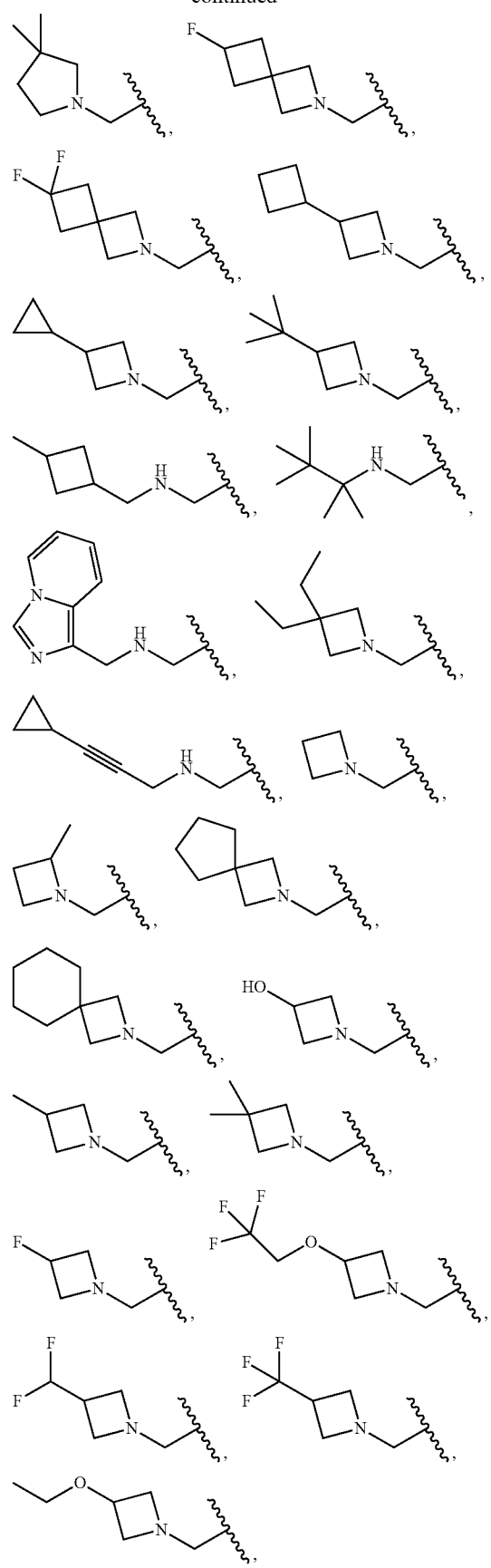

-continued

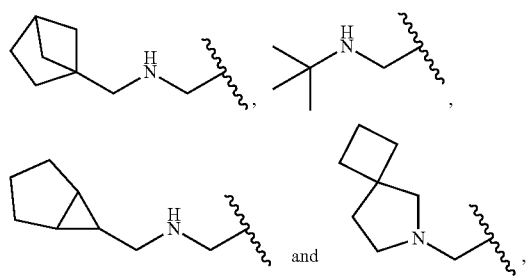

(39) $R_{1a}$ is selected from:

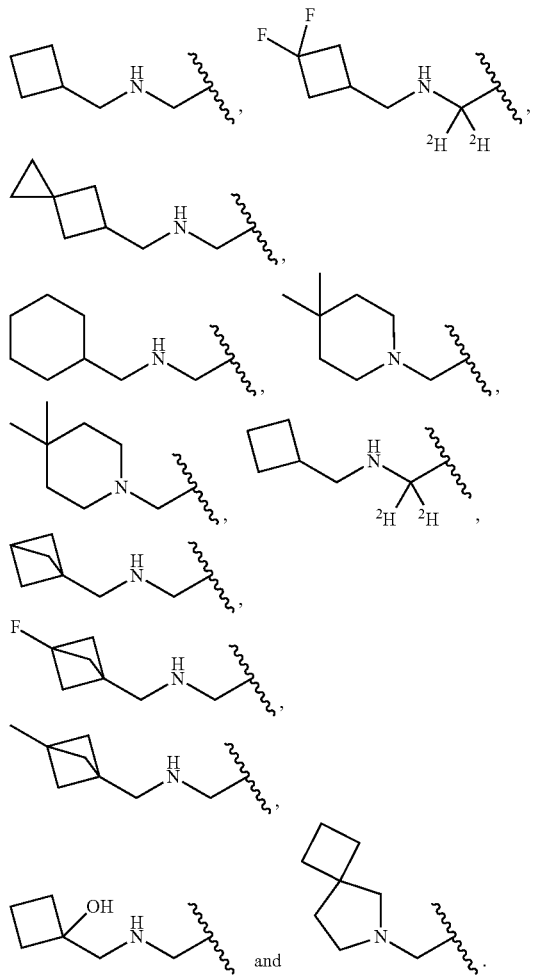

(40) $R_{1a}$ is selected from:

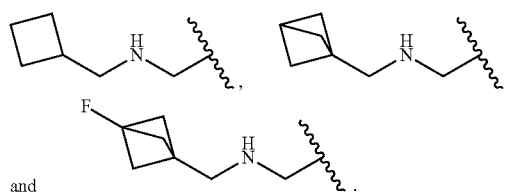

(40a) $R_{1a}$ is selected from:

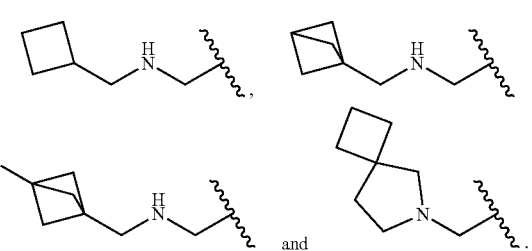

(41) $R_{1a}$ is selected from:

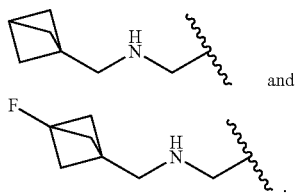

(41a) $R_{1a}$ is:

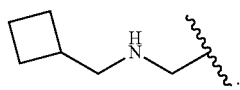 [SMILES: *CNCC1CCC1]

(41b) $R_{1a}$ is:

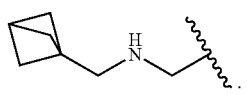 [SMILES: *CNCC12CC(C1)C2]

(41c) $R_{1a}$ is:

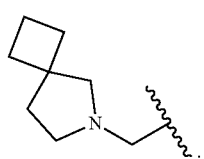 [SMILES: *CN1CCC2(CCC2)C1]

(42) $R_{1a}$ is:

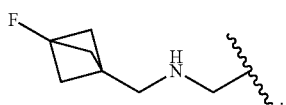 [SMILES: *CNCC12CC(F)(C1)C2]

(43) $R_{1b}$ is selected from hydrogen, halo or $C_{1-2}$ alkyl.
(44) $R_{1b}$ is hydrogen.
(45) $R_{1x}$ is selected from hydrogen, halo or $C_{1-2}$ alkyl.
(46) $R_{1x}$ is hydrogen.
(47) $R_{2a}$, $R_{2b}$, $R_{2c}$ and $R_{2d}$ are independently selected from hydrogen, cyano, halo or a group of the formula:

$$-L_{2a}-L_{2b}-Q_2$$

wherein

L$_{2a}$ is absent or C$_{1-3}$alkylene optionally substituted by C$_{1-2}$ alkyl or oxo;

L$_{2b}$ is absent or selected from O, S, N(R$_n$), C(O), C(O)O, OC(O), C(O)N(R$_n$), N(R$_n$)C(O), N(R$_n$)C(O) N(R$_o$), wherein R$_n$ and R$_o$ are each independently selected from hydrogen or C$_{1-2}$alkyl; and Q$_2$ is hydrogen, cyano, C$_{1-6}$alkyl, C$_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, C$_{1-4}$alkyl, NR$_p$R$_q$, OR$_p$, C(O)R$_p$, wherein R$_p$ and R$_q$ are each independently selected from hydrogen or C$_{1-4}$alkyl.

(48) R$_{2a}$, R$_{2b}$, R$_{2c}$ and R$_{2d}$ are independently selected from hydrogen, cyano, halo or a group of the formula:

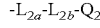

wherein

L$_{2a}$ is absent or C$_{1-3}$alkylene optionally substituted by C$_{1-2}$ alkyl;

L$_{2b}$ is absent or selected from O, S, N(R$_n$), C(O); and

Q$_2$ is hydrogen, cyano, C$_{1-6}$alkyl, C$_{3-6}$cycloalkyl, aryl, heterocyclyl or heteroaryl, each of which is optionally substituted by one or more substituents selected from halo, trifluoromethyl, trifluoromethoxy, amino, cyano and hydroxy.

(49) R$_{2a}$, R$_{2b}$, R$_{2c}$ and R$_{2d}$ are independently selected from hydrogen, cyano, C$_{1-6}$ alkoxy, C$_{1-6}$ haloalkoxy, halo, C$_{1-6}$alkyl, C$_{1-6}$haloalkyl, C$_{3-6}$cycloalkyl, aryl, heterocyclyl or heteroaryl, each of which is optionally substituted by one or more substituents selected from halo, trifluoromethyl, trifluoromethoxy, amino, cyano and hydroxy.

(50) R$_{2a}$, R$_{2b}$, R$_{2c}$ and R$_{2d}$ are independently selected from hydrogen, cyano, halo or C$_{1-3}$alkyl.

(51) R$_{2a}$, R$_{2b}$, R$_{2c}$ and R$_{2d}$ are independently selected from hydrogen or halo.

(52) R$_{2a}$, R$_{2b}$, R$_{2c}$ and R$_{2d}$ are hydrogen.

(53) R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$ are independently selected from hydrogen, C$_{1-6}$alkyl, C$_{3-4}$ cycloalkyl, hydroxy, and halo; and wherein C$_{1-6}$alkyl, or C$_{3-4}$ cycloalkyl is optionally substituted with one or more substituents selected from halo, amino, cyano, and hydroxy; and R$_{3a2}$, R$_{3b2}$, R$_{3c2}$, R$_{3d2}$, R$_{3e2}$, R$_{3f2}$, R$_{3g2}$, R$_{3h2}$, R$_{3i2}$, R$_{3j2}$, R$_{3k2}$, R$_{3l2}$, R$_{3m2}$, R$_{3n2}$, R$_{3o2}$, R$_{3p2}$, R$_{3q2}$, R$_{3r2}$ and R$_{3s2}$ are hydrogen;

(54) R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$ are independently selected from hydrogen and C$_{1-6}$alkyl; and wherein C$_{1-6}$alkyl is optionally substituted with one or more hydroxy substituents;

(55) R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$ are independently selected from hydrogen and methyl; and wherein methyl is optionally substituted with one or more hydroxy substituents;

(56) R$_{3a1}$, R$_{3b1}$, R$_{3c1}$, R$_{3d1}$, R$_{3e1}$, R$_{3f1}$, R$_{3g1}$, R$_{3h1}$, R$_{3i1}$, R$_{3j1}$, R$_{3k1}$, R$_{3l1}$, R$_{3m1}$, R$_{3n1}$, R$_{3o1}$, R$_{3p1}$, R$_{3q1}$, R$_{3r1}$ and R$_{3s1}$ are independently selected from hydrogen and methyl; and wherein methyl is substituted with a hydroxy substituent;

(57) R$_{3a2}$, R$_{3b2}$, R$_{3c2}$, R$_{3d2}$, R$_{3e2}$, R$_{3f2}$, R$_{3g2}$, R$_{3h2}$, R$_{3i2}$, R$_{3j2}$, R$_{3k2}$, R$_{3l2}$, R$_{3m2}$, R$_{3n2}$, R$_{3o2}$, R$_{3p2}$, R$_{3g2}$, R$_{3r2}$ and R$_{3s2}$ are hydrogen;

(58) R$_{3a1}$ and R$_{3a2}$, R$_{3b1}$, and R$_{3b2}$, R$_{3c1}$ and R$_{3c2}$, R$_{3d1}$ and R$_{3d2}$, R$_{3e1}$ and R$_{3e2}$, R$_{3f1}$ and R$_{3f2}$, R$_{3g1}$ and R$_{3g2}$, R$_{3h1}$ and R$_{3h2}$, R$_{3i1}$ and R$_{3i2}$, R$_{3j1}$ and R$_{3j2}$, R$_{3k1}$ and R$_{3k2}$, R$_{3l1}$ and R$_{3l2}$, R$_{3m1}$ and R$_{3m2}$, R$_{3n1}$ and R$_{3n2}$, R$_{3o1}$ and R$_{3o2}$, R$_{3p1}$ and R$_{3p2}$, R$_{3q1}$ and R$_{3q2}$, R$_{3r1}$ and R$_{3r2}$, and R$_{3s1}$, and R$_{3s2}$ are hydrogen.

(59) R$_{3a1}$ and R$_{3a2}$, R$_{3b1}$ and R$_{3b2}$, R$_{3c1}$ and R$_{3c2}$, R$_{3d1}$ and R$_{3d2}$, R$_{3e}$, and R$_{3e2}$, R$_{3f1}$ and R$_{3f2}$, R$_{3g1}$ and R$_{3g2}$, R$_{3h1}$ and R$_{3h2}$, R$_{3i1}$ and R$_{3i2}$, R$_{3j1}$ and R$_{3j2}$, R$_{3k1}$ and R$_{3k2}$, R$_{3l1}$ and R$_{3l2}$, R$_{3m1}$ and R$_{3m2}$, R$_{3n1}$ and R$_{3n2}$, R$_{3o1}$ and R$_{3o2}$, R$_{3p1}$ and R$_{3p2}$, and R$_{3q1}$ and R$_{3q2}$, R$_{3r1}$ and R$_{3r2}$, and R$_{3s1}$ and R$_{3s2}$ are linked to form a spiro-fused C$_{3-4}$cycloalkyl which is optionally substituted with one or more substituents selected from halo, amino, cyano, and hydroxy

(60) n is 0, 1 or 2;

(61) n is 1 or 2;

(62) n is 1;

(63) Y is

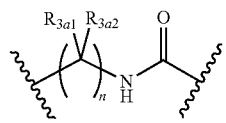

wherein R$_{3a1}$, R$_{3a2}$ and n are as herein defined;

(64) Y is

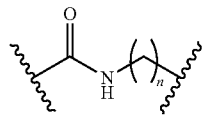

wherein n is herein defined;

(65) Y is

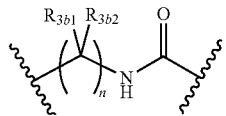

wherein R$_{3b1}$, R$_{3b2}$ and n are as herein defined;

(66) Y is

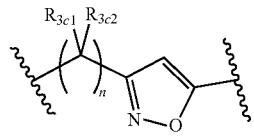

wherein R$_{3c1}$, R$_{3c2}$ and n are as herein defined;

(67) Y is

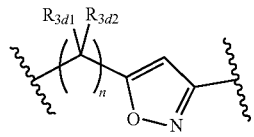

wherein R$_{3d1}$, R$_{3d2}$ and n are as herein defined;

(68) Y is

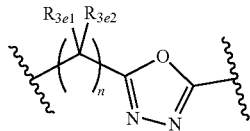

wherein $R_{3e1}$, $R_{3e2}$ and n are as herein defined;

(69) Y is

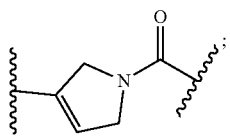 [SMILES: *C(=O)N1CC=C(*)C1]

(70) Y is

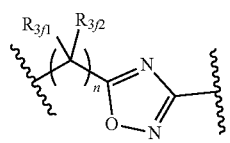

wherein $R_{3f1}$, $R_{3f2}$ and n are as herein defined;

(71) Y is

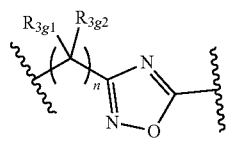

wherein $R_{3g1}$, $R_{3g2}$ and n are as herein defined;

(72) Y is

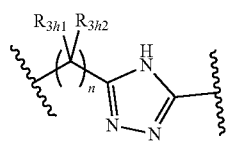

wherein $R_{3h1}$, $R_{3h2}$ and n are as herein defined

(73) Y is

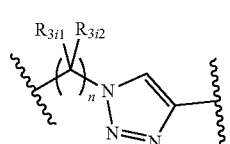

wherein $R_{3i1}$, $R_{3i2}$ and n are as herein defined;

(74) Y is


wherein $R_{3j1}$, $R_{3j2}$ and n are as herein defined;

(75) Y is

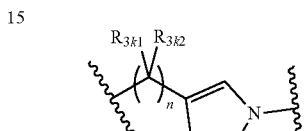

wherein $R_{3k1}$, $R_{3k2}$ and n are as herein defined;

(76) Y is

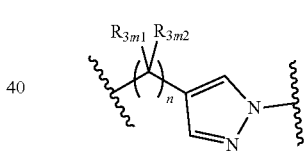

wherein $R_{3l1}$, $R_{3l2}$ and n are as herein defined;

(77) Y is

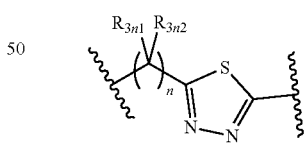

wherein $R_{3m1}$, $R_{3m2}$ and n are as herein defined;

(78) Y is

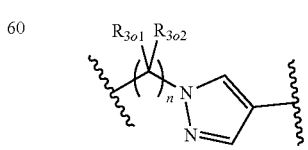

wherein $R_{3n1}$, $R_{3n2}$ and n are as herein defined;

(79) Y is

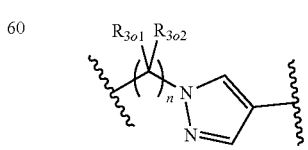

wherein $R_{3o1}$, $R_{3o2}$ and n are as herein defined;

(80) Y is
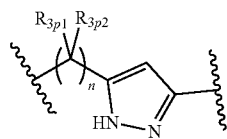
wherein $R_{3p1}$, $R_{3p2}$ and n are as herein defined;
(81) Y is
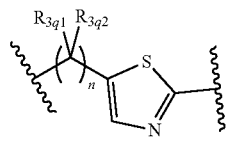
wherein $R_{3q1}$, $R_{3q2}$ and n are as herein defined;
(82) Y is
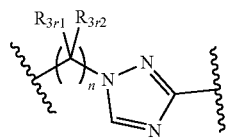
wherein $R_{3r1}$, $R_{3r2}$ and n are as herein defined;
(83) Y is
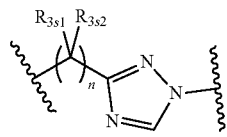
wherein $R_{3s1}$, $R_{3s2}$ and n are as herein defined;
(84) Y is selected from:
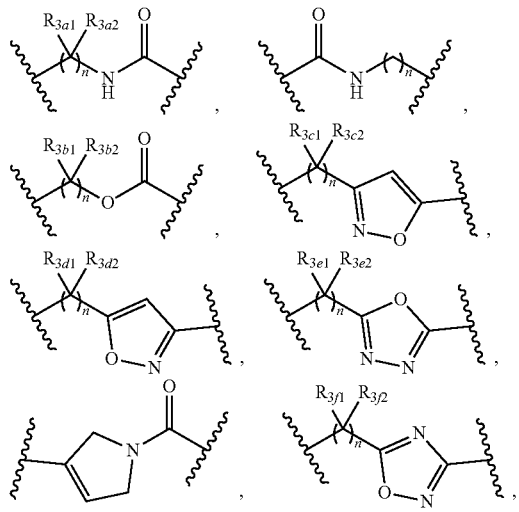
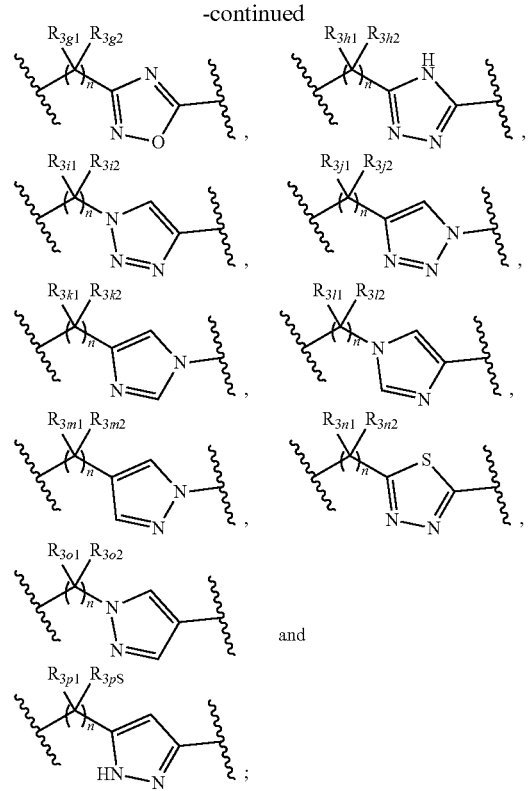
(85) Y is selected from:
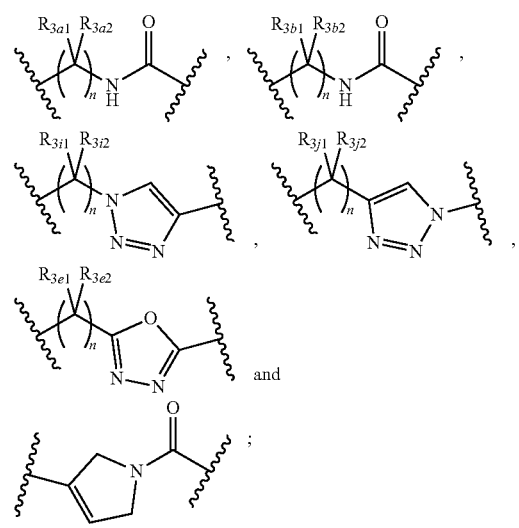
wherein $R_{3a1}$, $R_{3a2}$, $R_{3b1}$, $R_{3b2}$, $R_{3e1}$, $R_{3e2}$, $R_{3i1}$, $R_{3i2}$, $R_{3j1}$ and $R_{3j2}$ are as defined herein.
(86) Y is selected from:
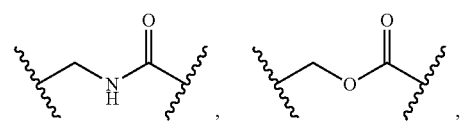

-continued

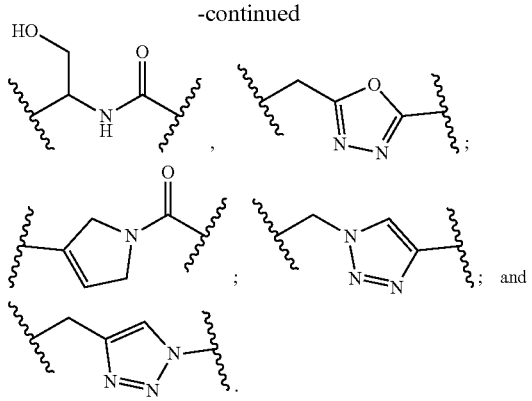

(87) Y is selected from:

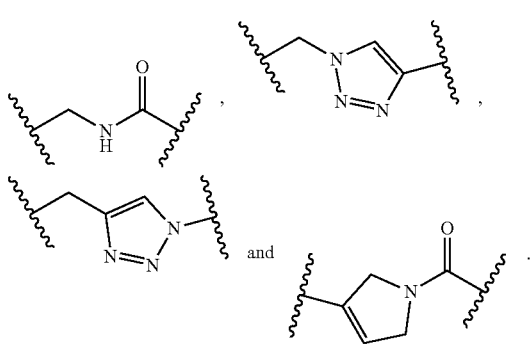

(88) Y is selected from

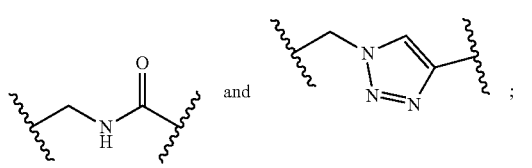 [SMILES: *CNC(*)=O ; *Cn1cc(*)nn1]

(89) Y is

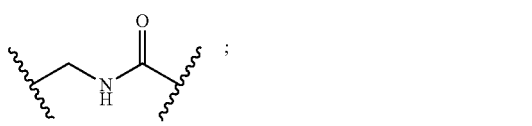 [SMILES: *CNC(*)=O]

(90) R₄, R₅ and R₆ are independently selected from hydrogen and halo;
(91) R₄, R₅ and R₆ are hydrogen;
(92) when Z is

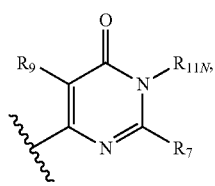

then $R_7$, $R_9$ and $R_{11N}$ are independently selected from hydrogen, halo and cyano;
(93) when Z is

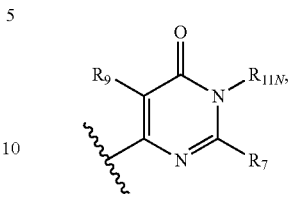

then $R_7$, $R_9$ and $R_{11N}$ are hydrogen;
(94) when Z is

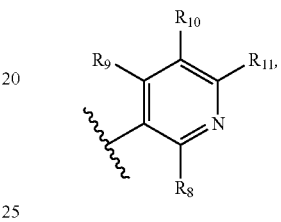

then Ra, $R_9$, $R_{10}$ and $R_{11}$ are independently selected from hydrogen, NH₂, halo, cyano, $C_{1-4}$ alkoxy, $C_{1-4}$ haloalkoxy, $C_{1-6}$ alkyl, —CH₂OCH₃, —CH₂SO₂CH₃, —SO₂CH₃, —NHC(O)CH₃ and —C(O)NR$_{v1}$R$_{v2}$, wherein R$_{v1}$, and R$_{v2}$ are independently selected from hydrogen and methyl; or either $R_9$ and $R_{10}$ may be linked together to form a fused 5- or 6-membered saturated or unsaturated ring system or $R_{10}$ and $R_{11}$ may be linked together to form a fused 5- or 6-membered saturated or unsaturated ring system.
(95) when Z is

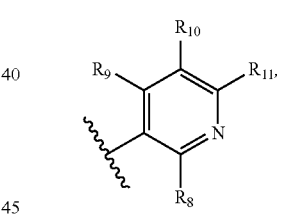

then $R_8$, $R_9$, $R_{10}$ and $R_{11}$ are independently selected from hydrogen, NH₂, halo, cyano, $C_{1-4}$ alkoxy, $C_{1-4}$ haloalkoxy and $C_{1-3}$ alkyl.
(95a) when Z is

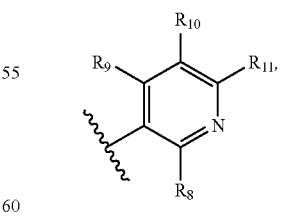

then $R_8$ is selected from hydrogen, cyano, —CH₂OCH₃, —CH₂SO₂CH₃, —SO₂CH₃, —NHC(O)CH₃ and —C(O)NR$_{v1}$R$_{v2}$, wherein R$_{v1}$ and R$_{v2}$ are independently selected from hydrogen and methyl; $R_9$ is hydrogen; $R_{10}$ is selected from halo, $C_{1-4}$alkoxy or $C_{1-4}$haloalkoxy; and $R_{11}$ is hydrogen.

(96) when Z is

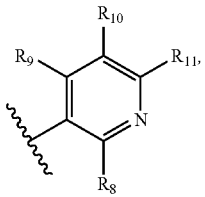

then $R_8$ is hydrogen, cyano, —$CH_2OCH_3$, —$CH_2SO_2CH_3$, —$SO_2CH_3$, —$NHC(O)CH_3$ and —$C(O)NR_{v1}R_{v2}$, wherein $R_{v1}$ and $R_{v2}$ are independently selected from hydrogen and methyl; $R_9$ is hydrogen; $R_{10}$ is $C_{1-4}$alkoxy or $C_{1-4}$haloalkoxy; and $R_{11}$ is hydrogen.

(97) when Z is

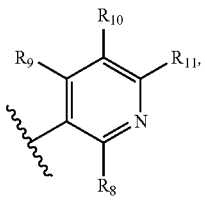

then $R_8$ is hydrogen or cyano; $R_9$ is hydrogen; $R_{10}$ is $C_{1-4}$alkoxy; and $R_{11}$ is hydrogen.

(97a) when Z is

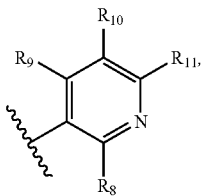

then $R_8$, $R_9$ and $R_{11}$ are hydrogen, and $R_{10}$ is methoxy.

(98) when Z is

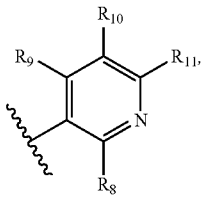

then $R_8$, $R_9$, $R_{10}$ and $R_{11}$ are hydrogen.

(99) $R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

(100) $R_{Z1}$ and $R_{Z1a}$ are selected from hydrogen, $C_{1-2}$alkyl, cyano, halo, $C_{1-2}$haloalkyl, $C_{1-2}$haloalkoxy, $C_{1-2}$alkoxy;

(101) $R_{Z1}$ and $R_{Z1a}$ are selected from hydrogen, $C_{1-2}$alkyl, cyano and halo;

(102) $R_{Z1}$ and $R_{Z1a}$ are hydrogen;

(103) $R_{Z2}$, $R_{Z2a}$, $R_{Z3a}$, $R_{Zi1b}$ and $R_{Zi2e}$ are independently selected from hydrogen, $C_{1-4}$ alkyl, cyano, halo or $C_{1-4}$alkoxy;

(104) $R_{Z2}$, $R_{Z2a}$, $R_{Z3a}$, $R_{Zi1b}$ and $R_{Zi2e}$ are independently selected from hydrogen, cyano or halo;

(105) $R_{Z2}$, $R_{Z2a}$, $R_{Z3a}$, $R_{Zi1b}$ and $R_{Zi2e}$ are hydrogen;

(106) $R_{B5N}$, $R_{Y5N}$, $R_{Z2N}$ and $R_{11N}$ are selected from hydrogen or methyl;

(107) $R_{B5N}$, $R_{Y5N}$, $R_{Z2N}$ and $R_{11N}$ are hydrogen;

(108) $R_{Z4}$, $R_{Z5}$, $R_{Z6}$, $R_{Z7}$, $R_{Z8}$, $R_{Z9}$, $R_{Z10}$, $R_{Z11}$, $R_{Z12}$, $R_{Z13}$, $R_{Z14}$, $R_{Z15}$, and $R_{Z16}$ are independently selected from hydrogen, halo and cyano;

(109) $R_{Z4}$, $R_{Z5}$, $R_{Z6}$, $R_{Z7}$, $R_{Z8}$, $R_{Z9}$, $R_{Z10}$, $R_{Z11}$, $R_{Z12}$, $R_{Z13}$, $R_{Z14}$, $R_{Z15}$ and $R_{Z16}$ are independently selected from hydrogen and halo;

(110) $R_{Z4}$, $R_{Z5}$, $R_{Z6}$, $R_{Z7}$, $R_{Z8}$, $R_{Z9}$, $R_{Z10}$, $R_{Z11}$, $R_{Z12}$, $R_{Z13}$, $R_{Z14}$, $R_{Z15}$, $R_{Z16}$ are hydrogen;

(111) Suitably,
when $X_6$ is $A_1$, $A_1$ is $CR_{12}$;
when $X_7$ is $A_2$, $A_2$ is $CR_{13}$;
$B_1$ is $A_5$, wherein $A_5$ is $CR_{16}$;
$B_2$ is $A_6$, wherein $A_6$ is $CR_{17}$;
$Y_2$ is $A_7$, wherein is $CR_{18}$;
when $X_6$ is $A_8$, $A_8$ is $CR_{19}R_{20}$;
when $X_7$ is $A_9$, $A_9$ is $CR_{22}R_{23}$;
when $X_7$ is $A_{11}$, $A_{11}$ is $CR_{28}R_{29}$;
and wherein $R_{12}$, $R_{13}$, $R_{16}$, $R_{17}$, $R_{13}$, $R_{19}$, $R_{20}$, $R_{21}$, $R_{22}$, $R_{23}$, $R_{28}$ and $R_{29}$ are as defined herein.

(112) $R_{12}$, $R_{13}$, $R_{16}$, $R_{19}$, $R_{20}$, $R_{21}$, $R_{22}$ and $R_{23}$ are independently selected from hydrogen, halo, cyano and methyl;

(113) $R_{12}$, $R_{13}$, $R_{16}$, $R_{19}$, $R_{20}$, $R_{21}$, $R_{22}$ and $R_{23}$ are hydrogen;

(114) $R_{12}$ is selected from hydrogen, halo, cyano and $C_{1-4}$ alkyl;

(115) $R_{12}$ is selected from hydrogen and halo;

(116) $R_{12}$ is selected from hydrogen and chloro;

(117) $R_{12}$ is hydrogen;

(118) $R_{13}$ is selected from hydrogen, halo, cyano and methyl;

(119) $R_{13}$ is hydrogen;

(120) $R_{13}$ is selected from hydrogen, methoxy and methyl; (121) $R_{16}$ and $R_{18}$ are selected from hydrogen, halo, cyano, $C_{1-4}$ alkyl, $C_{1-4}$ alkoxy, $C_{1-4}$haloalkyl and $C_{1-4}$haloalkoxy;

(122) $R_{16}$ and $R_{13}$ are selected from hydrogen, halo, cyano and $C_{1-4}$ alkyl;

(123) $R_{16}$ and $R_{13}$ are selected from hydrogen and halo;

(124) $R_{16}$ and $R_{1s}$ are hydrogen;

(125) $R_{17}$ is selected from hydrogen, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, —O—$C_{3-6}$cycloalkyl, heterocyclyl, —O-heterocyclyl (carbon-linked), —$(OCH_2CH_2)_m$—$OCH_3$ wherein m is an integer from 1 to 6, $NR_qR_r$, wherein $R_q$ and $R_r$ are each independently hydrogen, $C_{1-4}$ alkyl, $C_{3-6}$cycloalkyl, a 3- to 6-membered carbon-linked heterocyclyl, or $R_q$ and $R_r$ are linked together such that, together with the nitrogen atom to which they are attached, they form a 3- to 6-membered heterocyclic ring;
wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $-S(O)_{0-2}R_{1ea}R_{1fa}$, wherein $R_{1ea}$ and $R_{1fa}$ are H or $C_{1-2}$alkyl.

(126) $R_{17}$ is selected from hydrogen, halo, cyano, $C_{1-2}$ alkyl, $C_{1-2}$ haloalkyl, $C_{1-2}$ alkoxy, $C_{1-2}$ haloalkoxy, $C_{2-3}$ alkenyl, $C_{2-3}$ alkynyl, phenyl a 5- or 6-membered or heteroaryl, $C_{3-6}$cycloalkyl, $-O-C_{3-6}$cycloalkyl, heterocyclyl, $-O$-heterocyclyl (carbon-linked), $-(OCH_2CH_2)_m-OCH_3$ wherein m is an integer from 1 to 6, $NR_qR_r$, wherein $R_q$ and $R_r$ are each independently hydrogen, $C_{1-2}$ alkyl or $R_q$ and $R_r$ are linked together such that, together with the nitrogen atom to which they are attached, they form a 3- to 6-membered heterocyclic ring;

wherein any $C_{1}$alkyl, $C_{2-4}$ alkenyl, $C_{2-4}$ alkynyl, phenyl, 5- or 6-membered or heteroaryl, $C_{3-6}$cycloalkyl, $-O-C_{3-6}$cycloalkyl, heterocyclyl or $-O$-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $-S(O)_{0-2}R_{1ea}R_{1fa}$, wherein $R_{1ea}$ and $R_{1fa}$ are H or $C_{1-2}$alkyl.

(127) $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered heteroaryl, $C_{3-6}$cycloalkyl, $-O-C_{3-6}$cycloalkyl, heterocyclyl, $-O$-heterocyclyl (carbon-linked), $-(OCH_2CH_2)_m-OCH_3$ wherein m is 1, 2 or 3, $NR_qR_r$, wherein $R_q$ and $R_r$ are each independently hydrogen, $C_{1-4}$ alkyl; or $R_q$ and $R_r$ are linked together such that, together with the nitrogen atom to which they are attached, they form a 3- to 6-membered heterocyclic ring;

wherein any $C_{1-4}$ alkyl, $C_{2-4}$ alkenyl, $C_{2-4}$ alkynyl, phenyl, 5- or 6-membered or heteroaryl, $C_{3-6}$cycloalkyl, $-O-C_{3-6}$cycloalkyl, heterocyclyl or $-O$-heterocyclyl (carbon-linked) is optionally further substituted by one or more substituents selected from $C_{1-2}$ alkyl, $C_{1-2}$haloalkyl, cyano, hydroxy, $C_{1-2}$alkoxy, halo and $C_{1-2}$haloalkoxy.

(128) $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{3-6}$cycloalkyl, $-O-C_{3-4}$cycloalkyl, heterocyclyl, $-(OCH_2CH_2)_m-OCH_3$ wherein m is 1, 2 or 3, $NR_qR_r$, wherein $R_q$ and $R_r$ are each independently hydrogen or $C_{1-2}$ alkyl;

wherein any $C_{1-4}$ alkyl, $C_{2-4}$ alkenyl, $C_{2-4}$ alkynyl, $C_{3-6}$cycloalkyl, $-O-C_{3-4}$ cycloalkyl, heterocyclyl, system is optionally further substituted by one or more substituents selected from $C_{1-2}$alkyl, $C_{1-2}$haloalkyl, cyano, hydroxy, $C_{1-2}$alkoxy, halo and $C_{1-2}$haloalkoxy.

(129) $R_{17}$ is selected from hydrogen, halo, cyano, $C_{1-4}$ alkyl, $C_{1-4}$ alkoxy, $C_{2-4}$ alkenyl, $C_{2-4}$ alkynyl and a 5- or 6-membered aryl or heteroaryl; wherein any $C_{1-4}$ alkyl, $C_{2-4}$ alkenyl, $C_{2-4}$ alkynyl, 5- or 6-membered aryl or heteroaryl is optionally further substituted by one or more substituents selected from $C_{1-2}$alkyl, $C_{1-2}$haloalkyl, cyano, hydroxy, $C_{1-2}$alkoxy, halo and $C_{1-2}$haloalkoxy.

(130) $R_{17}$ is selected from hydrogen, halo, $C_{1-4}$ alkoxy, $C_{2-4}$ alkynyl and 5- or 6-membered aryl or heteroaryl.

(131) $R_{17}$ is selected from hydrogen, $C_{1-4}$ alkoxy, bromo, ethynyl, and pyrazoyl.

(132) $R_{26}$ and $R_{29}$ are selected from hydrogen or halo, methoxy and methyl;

(133) $R_{28}$ and $R_{29}$ are hydrogen;

(134) $R_{21}$, $R_{24}$ and $R_{30}$, are independently selected from hydrogen or methyl;

(135) $R_{21}$, $R_{24}$ and $R_{30}$, are hydrogen;

(136) Z is selected from

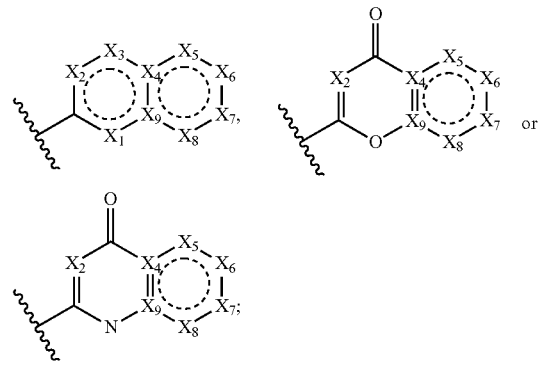

wherein $X_2$, $X_3$, $X_4$, $X_5$, $X_6$, $X_7$, $X_8$ and $X_9$ are as defined herein;

(137) Z is

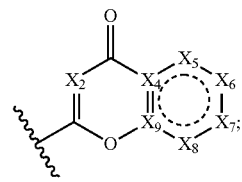

wherein $X_2$, $X_4$, $X_5$, $X_6$, $X_7$, $X_8$ and $X_9$ are as defined herein;

(138) Z is

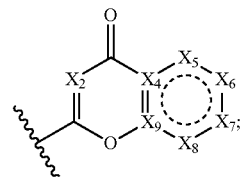

$X_2$ is $CR_4$;

$X_4$ is C or N;

$X_5$ is $CR_5$;

$X_6$ is $A_1$, wherein $A_1$ is $CR_{12}$ $X_7$ is $A_2$, wherein $A_2$ is $CR_{13}$ $X_8$ is N or $CR_6$, $X_9$ is N or C;

wherein $R_4$, $R_5$, $R_6$, $R_{12}$ and $R_{13}$ are as defined herein;

(139) Z is

[chemical structure: chromone-like with $R_4$, $R_5$, $R_6$, $A_1$, $A_2$]

wherein $R_4$, $R_5$, $R_6$, $A_1$ and $A_2$ are as herein defined;

(140) Z is

[chemical structure with $X_2$, $X_4$, $X_5$, $X_6$, $X_7$, $X_8$, $X_9$]

wherein $X_2$, $X_4$, $X_5$, $X_6$, $X_7$, $X_8$ and $X_9$ are as defined herein;

(141) Z is

[chemical structure with $X_2$, $X_4$, $X_5$, $X_6$, $X_7$, $X_8$, $X_9$]

$X_2$ is $CR_4$:
$X_4$ is N;
$X_5$ is $CR_5$:
$X_6$ is $A_1$, wherein $A_1$ is $CR_{12}$
$X_7$ is $A_2$, wherein $A_2$ is $CR_{13}$
$X_8$ is $CR_6$,
$X_9$ is N or C;
wherein $R_4$, $R_5$, $R_6$, $R_{12}$, $R_{13}$, $X_7$, $X_8$ and $X_9$ are as defined herein;

(142) Z is

[chemical structure with $R_4$, $R_5$, $R_6$, $A_1$, $A_2$]

wherein $R_4$, $R_5$, $R_6$, $A_1$ and $A_2$ are as herein defined;

(143) Z is

[chemical structure: bicyclic with $B_1$–$B_8$]

wherein $B_1$, $B_2$, $B_3$, $B_4$, $B_5$, $B_7$ and $B_8$ are as defined herein;

(144) Z is:

[chemical structure: bicyclic with $B_1$–$B_8$]

wherein
$B_1$ is $A_5$, wherein $A_5$ is N or $CR_{16}$;
$B_2$ is $A_6$, wherein $A_6$ is $CR_{17}$
$B_3$ is N or $CR_{Z1}$;
$B_4$ is N or C;
$B_5$ is selected from $CR_{Zi1b}$ or $NR_{B5N}$
$B_7$ is N, $NR_{Z2N}$ or $CR_{Z2}$;
$B_a$ is selected from C or N;
wherein $R_{16}$, $R_{17}$, $R_{Z1}$, $R_{Zi1b}$, $R_{B5N}$, $R_{Z2}$ are as defined herein;

(145) Z is:

[chemical structure: bicyclic with $B_1$–$B_8$]

wherein
$B_1$ is $A_5$, wherein $A_5$ is $CR_{16}$;
$B_2$ is $A_6$, wherein $A_6$ is $CR_{17}$
$B_3$ is $CR_{Z1}$;
$B_4$ is N or C;
$B_5$ is selected from $CR_{Zi1b}$ or $NR_{B5N}$
$B_7$ is N, NH or $CR_{Z2}$;
$B_8$ is C;
wherein $R_{16}$, $R_{17}$, $R_{Z1}$, $R_{zi1b}$, $R_{B5N}$, $R_{Z2}$ are as defined herein;

(146) Z is

[chemical structure: pyrazole with $A_5$, $A_6$, $R_{Z1}$, $R_{Z2}$]

wherein $A_5$, $A_6$, $R_{Z1}$ and $R_{Z2}$ are as herein defined;

(147) Z is

[chemical structure: imidazole with $A_5$, $A_6$, $R_{Z1}$, $R_{Zi1b}$, $R_{Z2}$]

wherein $A_5$, $A_6$, $R_{Z1}$, $R_{Z2}$ are $R_{Zi1b}$ are as herein defined;

(148) Z is

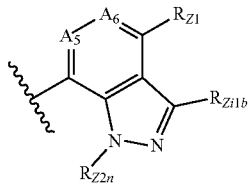

wherein $A_5$, $A_6$, $R_{Z1}$, $R_{Z2}N$ are $R_{Zi1b}$ are as herein defined;

(149) Z is:

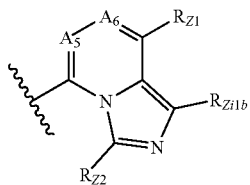

wherein $R_{Z1}$, $R_{Z2}$, $R_{Zi1b}$, $A_5$ and $A_6$ are as herein defined;

(150) Z is:

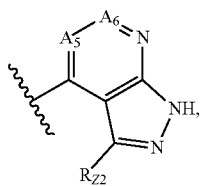

wherein $R_{Z2}$, $A_5$ and $A_6$ are as herein defined;

(151) Z is:

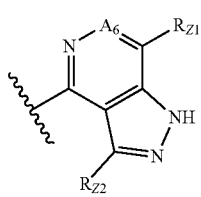

wherein $R_{Z1d}$, $R_{Z2d}$ and $A_6$ are as herein defined;

(152) Z is

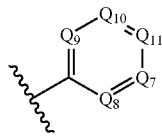

wherein $Q_7$, $Q_8$, $Q_9$, $Q_{11}$ and $Q_{11}$ are as defined herein;

(153) Z is

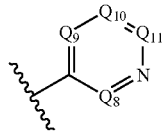

wherein $Q_8$, $Q_9$, $Q_{10}$ and $Q_{11}$ are as defined herein;

(154) Z is selected from:

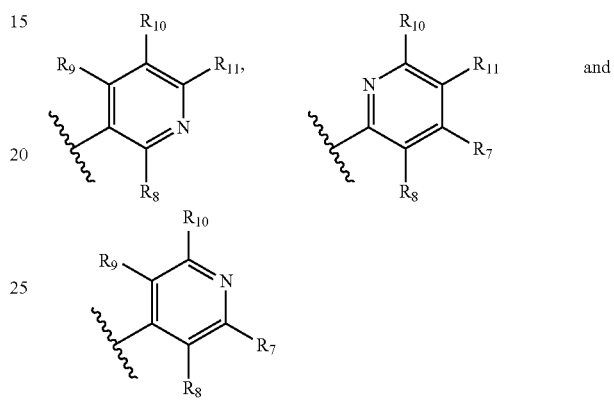

wherein $R_7$, $R_8$, $R_9$, $R_{10}$ and $R_{11}$ are as defined herein;

(155) Z is

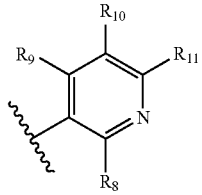

wherein $R_8$, $R_9$, $R_{10}$ and $R_{11}$ are as herein defined;

(156) Z is

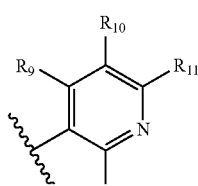

wherein:

$R_8$ is selected from hydrogen, cyano, —CH$_2$OCH$_3$, —CH$_2$SO$_2$CH$_3$, —SO$_2$CH$_3$, —NHC(O)CH$_3$ and —C(O)NR$_{v1}$R$_{v2}$, wherein R$_{v1}$, and R$_{v2}$ are independently selected from hydrogen and methyl $R_{10}$ is selected from halo, $C_{1-4}$alkoxy or $C_{1-4}$haloalkoxy;

$R_9$ and $R_{11}$ are as herein defined;

(157) Z is

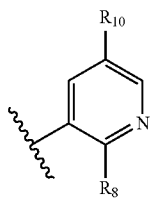

wherein $R_8$ is hydrogen or cyano and $R_{10}$ is $C_{1-4}$ alkoxy;

(157a) Z is

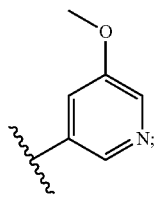 [SMILES: *c1cncc(OC)c1]

(158) Z is

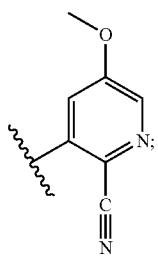 [SMILES: *c1cc(OC)cnc1C#N]

(159) Z is

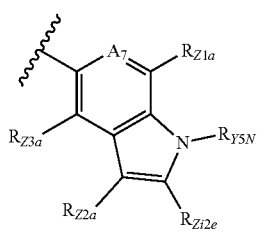

wherein $A_7$, $R_{Y5N}$, $R_{Z1a}$, $R_{Z2a}$ and $R_{Z3a}$ are as herein defined;

(160) Z is

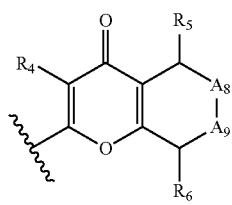

wherein $R_4$, $R_5$, $A_8$ and $A_9$ are as herein defined;

(161) Z is

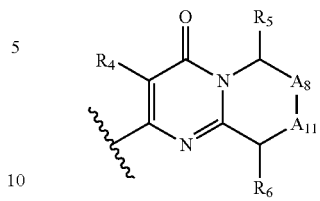

wherein $R_4$, $R_5$, $R_6$, $A_8$ and $A_{11}$ are as herein defined;

(162) Z is

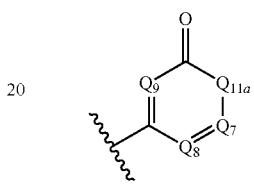

wherein $Q_8$, $Q_9$, $Q_{10}$ and $Q_{11a}$ are as defined herein;

(163) Z is

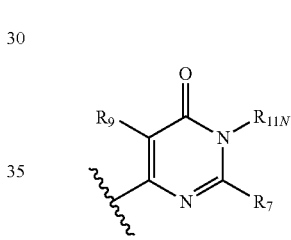

wherein $R_7$, $R_9$ and $R_{11N}$ are as herein defined;

(164) Z is

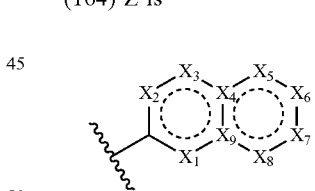

wherein $X_1$ is N or $CR_{Z9}$;

$X_2$ is $CR_4$;

$X_3$ is N;

$X_4$ is C;

$X_5$ is $CR_5$;

$X_6$ is $A_1$, wherein $A_1$ is $CR_{12}$ $X_7$ is $A_2$, wherein $A_2$ is $CR_{13}$ $X_8$ is N or $CR_6$, $X_9$ is N or C;

wherein $R_{Z9}$, $R_4$, $R_5$, $R_6$, $R_{12}$ and $R_{13}$ are as defined herein.

(165) Z is

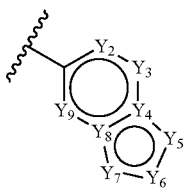

wherein
Y$_2$ is A$_7$, wherein A$_7$ is CR$_{18}$;
Y$_3$ is N or CR$_{Z1a}$;
Y$_4$ is C or N
Y$_5$ is NR$_{Y5N}$;
Y$_6$ is C—R$_{Zi2e}$ or N;
Y$_7$ is CR$_{Z2a}$ or N;
Y$_8$ is C or N;
Y$_9$ is CR$_{Z3a}$ or N;
wherein R$_{18}$, R$_{z1a}$, R$_{Y5N}$, R$_{Zi2e}$, R$_{Z2a}$ and R$_{Z3a}$ are as defined herein;

(166) Z is

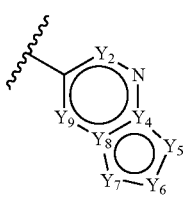

wherein
Y$_2$ is A$_7$, wherein A$_7$ is CR$_{18}$;
Y$_4$ is C or N
Y$_5$ is NR$_{Y5N}$;
Y$_6$ is C—R$_{Zi2e}$ or N;
Y$_7$ is CR$_{Z2a}$ or N;
Y$_8$ is C or N;
Y$_9$ is CR$_{Z3a}$ or N;
wherein R$_{18}$, R$_{Z1a}$, R$_{Y5N}$, R$_{Zi2e}$, R$_{Z2a}$ and R$_{Z3a}$ are as defined herein;

(167) Z is

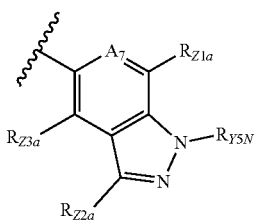

wherein R$_{Y5N}$, R$_{Z1a}$, R$_{Z2a}$, R$_{Z3a}$ and A$_7$ are as herein defined;

(168) Z is

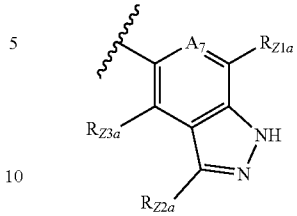

wherein R$_{Z1a}$, R$_{Z2a}$, R$_{Z3a}$ and A$_7$ are as herein defined;

(169) Z is

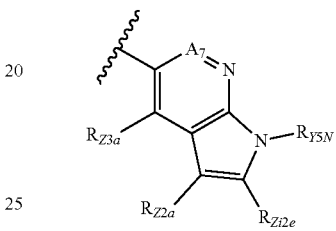

wherein R$_{Y5N}$, R$_{Z2a}$, R$_{Z3a}$, R$_{Zi2e}$ and A$_7$ are as herein defined;

(170) Z is

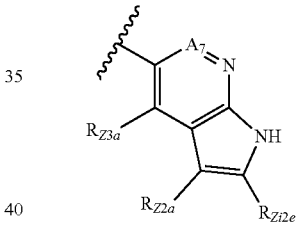

wherein R$_{Z2a}$, R$_{Z3a}$, R$_{Zi2e}$ and A$_7$ are as herein defined;

(171) Z is

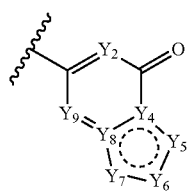

wherein
Y$_2$ is A$_7$, wherein A$_7$ is CR$_{18}$;
Y$_4$ is N
Y$_5$ is C—R$_{Y5}$;
Y$_6$ is C—R$_{Zi2e}$;
Y$_7$ is O or S;
Y$_8$ is C;
Y$_9$ is N;
wherein R$_{18}$, R$_{Y5}$, R$_{Zi2e}$ are as defined herein;

(172) Z is:

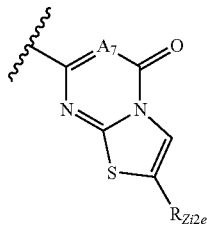

wherein $A_7$ and $R_{Zi2e}$ are as defined herein;

(173) Z is

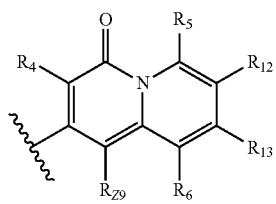

wherein $R_4$, $R_5$, $R_6$, $R_{Z9}$, $R_{12}$ and $R_{13}$ are as herein defined;

(174) Z is

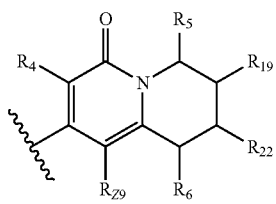

wherein $R_4$, $R_5$, $R_6$, $R_{19}$, $R_{22}$ and $R_{Z9}$ are as herein defined;

(175) Z is

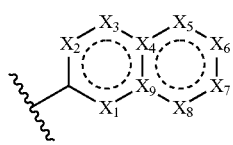

wherein $X_2$, $X_3$, $X_4$, $X_5$, $X_6$, $X_7$, $X_8$ and $X_9$ are as defined herein;

(176) Z is

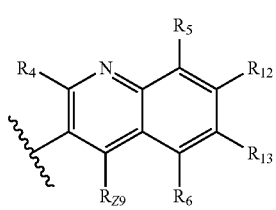

wherein $R_4$, $R_5$, $R_6$, $R_{12}$, $R_{13}$ and $R_{Z9}$ are as herein defined;

(177) Z is

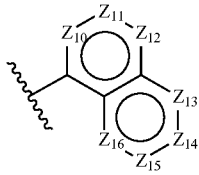

wherein $Z_{10}$, $Z_{11}$, $Z_{12}$, $Z_{13}$, $Z_{14}$, $Z_{15}$ and $Z_{16}$ are as defined herein;

(178) Z is

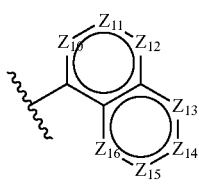

wherein
$Z_{10}$ is $CR_{Z10}$;
$Z_{11}$ is N;
$Z_{12}$ is $CR_{Z12}$;
$Z_{13}$ is $CR_{Z13}$;
$Z_{14}$ is N or $CR_{Z14}$;
$Z_{15}$ is N or $CR_{Z15}$;
$Z_{16}$ is $CR_{Z16}$;
wherein $R_{Z10}$, $R_{Z12}$, $R_{Z13}$, $R_{Z14}$, $R_{Z15}$ and $R_{Z16}$ are as defined herein;

(179) Z is

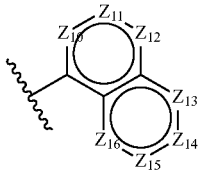

wherein
$Z_{10}$ is $CR_{Z10}$;
$Z_{11}$ is $CR_{Z10}$ or N;
$Z_{12}$ is $CR_{Z12}$;
$Z_{13}$ is $CR_{Z13}$;
$Z_{14}$ is N;
$Z_{15}$ is N or $CR_{Z15}$;
$Z_{16}$ is $CR_{Z16}$;
wherein $R_{Z10}$, $R_{Z12}$, $R_{Z13}$, $R_{Z14}$, $R_{Z15}$ and $R_{Z16}$ are as defined herein;

(180) Z is

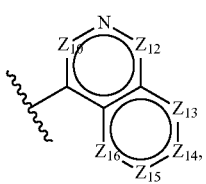

wherein $Z_{10}$, $Z_{12}$, $Z_{13}$, $Z_{14}$, $Z_{15}$ and $Z_{16}$ are as herein defined;

(181) Z is

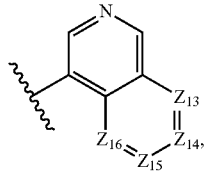

wherein $Z_{13}$, $Z_{14}$, $Z_{15}$ and $Z_{16}$ are as herein defined;

(182) Z is

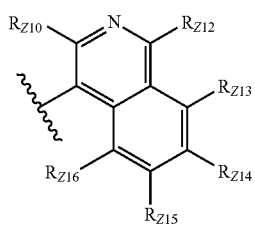

wherein $R_{Z10}$, $R_{Z12}$, $R_{Z13}$, $R_{Z14}$, $R_{Z15}$ and $R_{Z16}$ are as herein defined;

(183) Z is

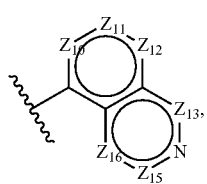

wherein $Z_{10}$, $Z_{11}$, $Z_{12}$, $Z_{13}$, $Z_{15}$ and $Z_{16}$ are as herein defined, (184) Z is

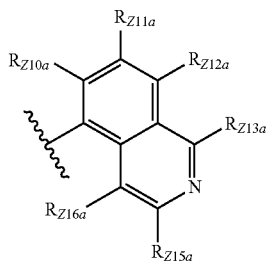

wherein $R_{Z10a}$, $R_{Z11a}$, $R_{Z12a}$, $R_{Z13a}$, $R_{Z15a}$ and $R_{Z16a}$ are as herein defined;

(185) Z is selected from:

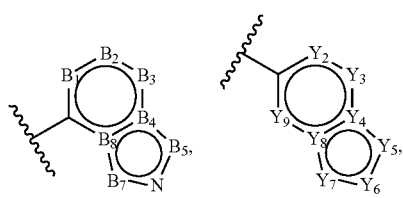

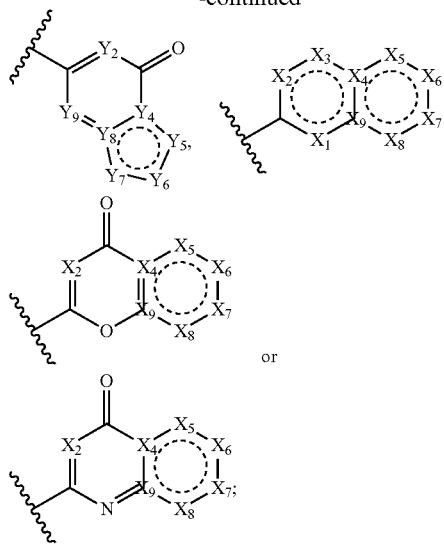

wherein $B_1$, $B_2$, $B_3$, $B_4$, $B_5$, $B_7$, $B_8$, $Y_2$, $Y_3$, $Y_4$, $Y_5$, $Y_6$, $Y_7$, $Y_8$, $Y_9$, $X_1$, $X_2$, $X_3$, $X_4$, $X_5$, $X_6$, $X_7$, $X_8$ and $X_9$ are as defined herein;

(186) Z is selected from:

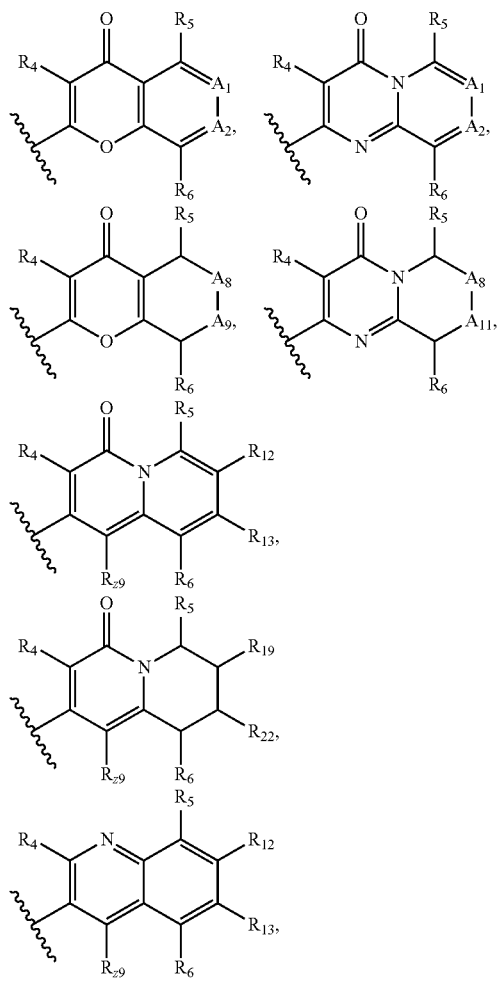

-continued wherein:
A$_1$, A$_2$, A$_5$, A$_6$, A$_7$, A$_8$, A$_9$, A$_{11}$, R$_4$, R$_5$, R$_6$, R$_7$, R$_8$, R$_9$, R$_{10}$, R$_{11}$, R$_{11N}$, R$_{12}$, R$_{13}$, R$_{19}$, R$_{22}$, R$_{Y5N}$, R$_{Z1}$, R$_{Z2}$, R$_{Z9}$, R$_{Z10}$, R$_{Z11}$, R$_{Z12}$, R$_{Z13}$, R$_{Z14}$, R$_{Z15}$, R$_{Z16}$, R$_{Z2a}$, R$_{Z3a}$, R$_{Z1a}$, R$_{Zi1b}$ and R$_{Zi2e}$ are as defined herein;

(187) Z is selected from:

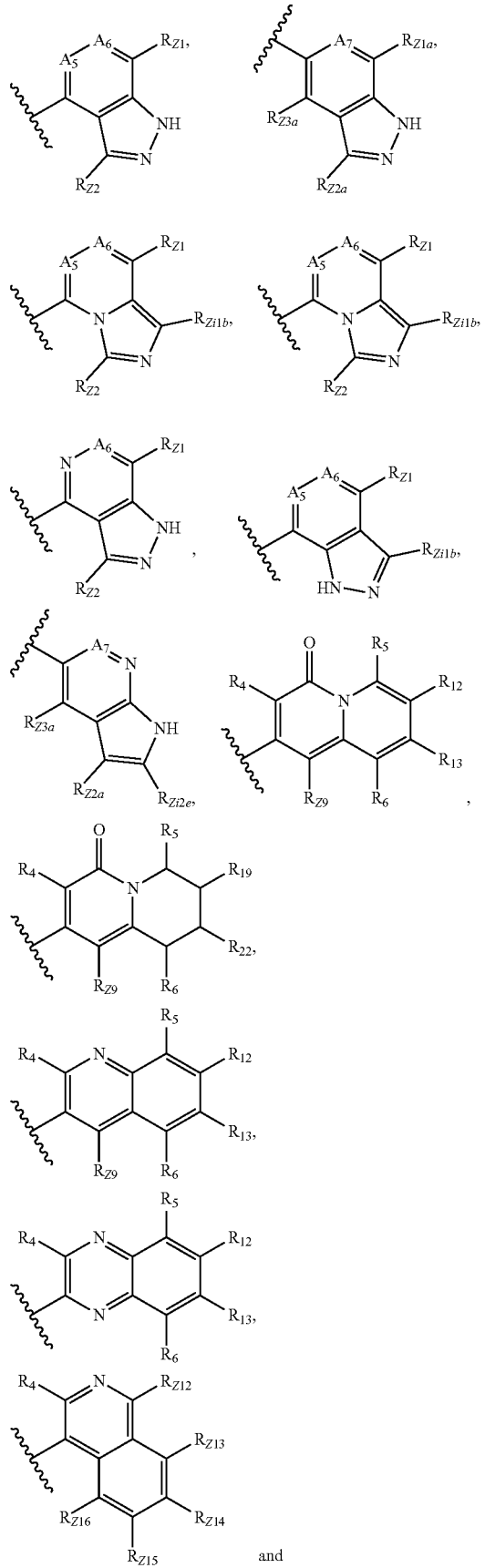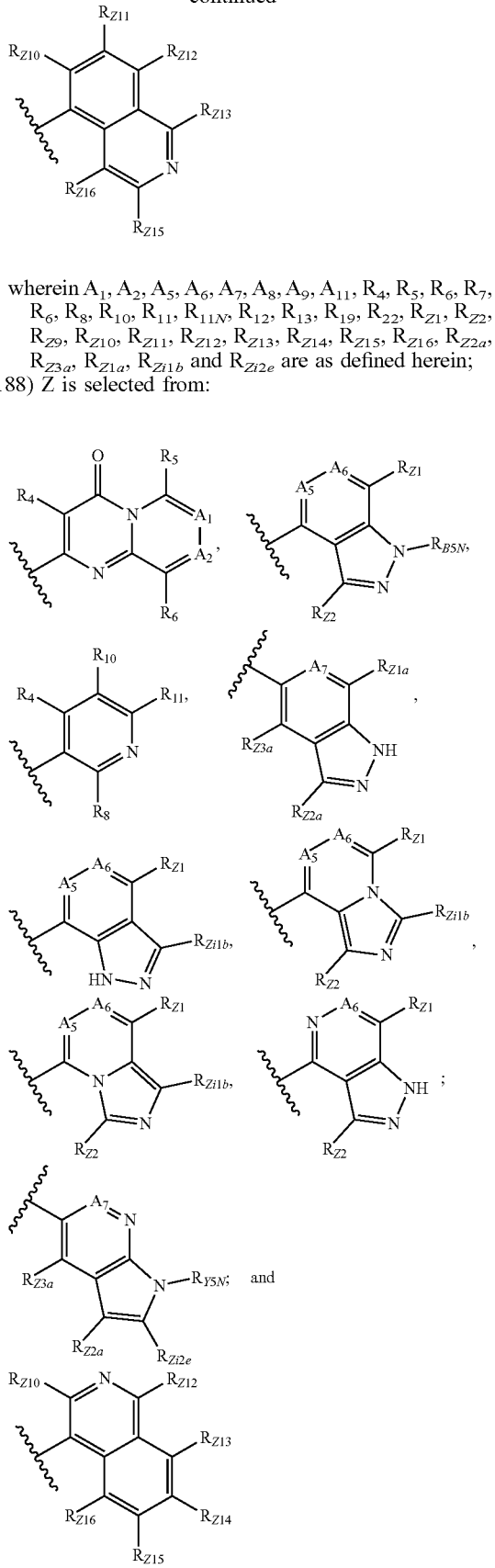
wherein $A_1$, $A_2$, $A_5$, $A_6$, $A_7$, $A_8$, $A_9$, $A_{11}$, $R_4$, $R_5$, $R_6$, $R_7$, $R_6$, $R_8$, $R_{10}$, $R_{11}$, $R_{11N}$, $R_{12}$, $R_{13}$, $R_{19}$, $R_{22}$, $R_{Z1}$, $R_{Z2}$, $R_{Z9}$, $R_{Z10}$, $R_{Z11}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined herein;
(188) Z is selected from:

$A_1$, $A_2$, $A_5$, $A_6$, $A_7$, $A_8$, $A_9$, $A_{11}$, $R_4$, $R_5$, $R_6$, $R_7$, $R_8$, $R_9$, $R_{10}$, $R_{11}$, $R_{Y5N}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined herein;

(189) Z is selected from:

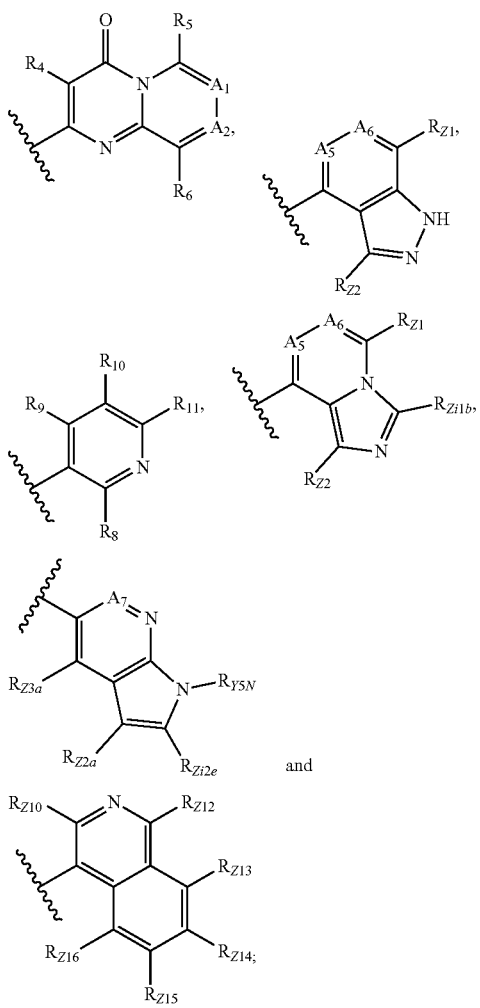

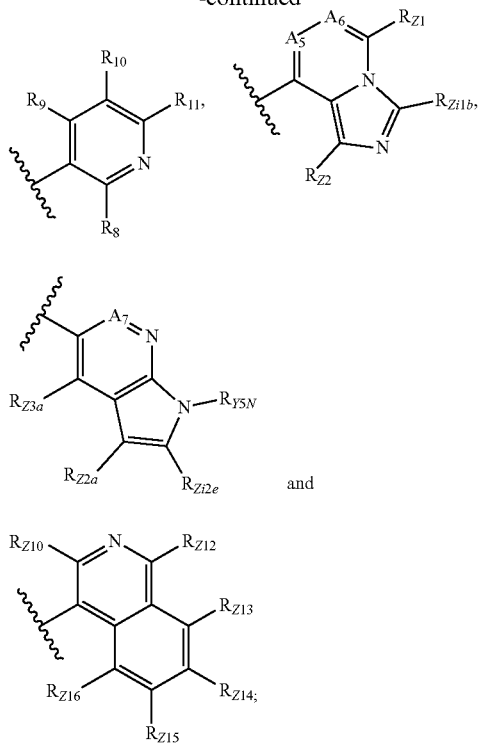

wherein $A_1$, $A_2$, $A_5$, $A_6$, $A_7$, $A_8$, $A_9$, $A_{11}$, $R_4$, $R_5$, $R_6$, $R_7$, $R_8$, $R_9$, $R_{10}$, $R_{11}$, $R_{Y5N}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined herein.

(190) Z is selected from:

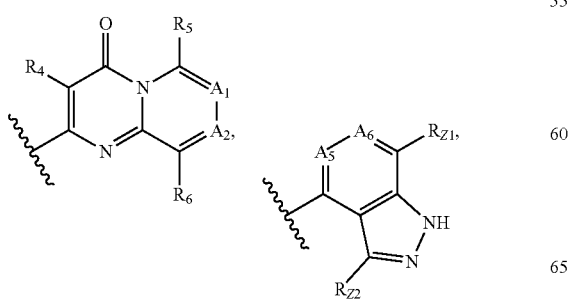

wherein $A_1$, $A_2$, $A_5$, $A_6$, $A_7$, $A_8$, $A_9$, $A_{11}$, $R_4$, $R_5$, $R_6$, $R_7$, $R_8$, $R_9$, $R_{10}$, $R_{11}$, $R_{Y5N}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined herein.

(191) Z is selected from:

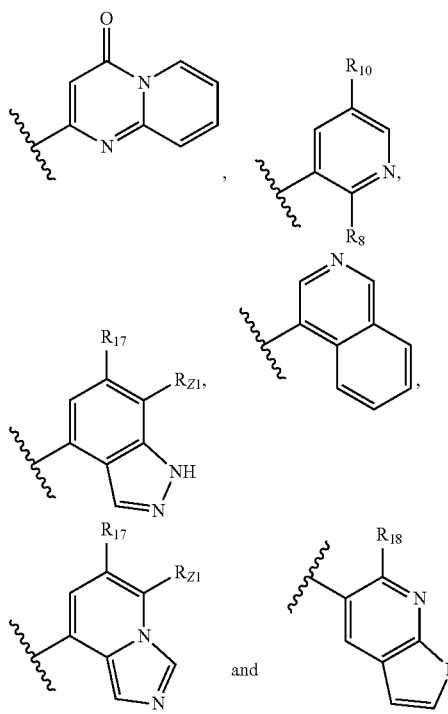

wherein $R_8$, $R_{10}$, $R_{17}$, $R_{18}$ and $R_{Z1}$, are as defined herein.

(192) Z is selected from:
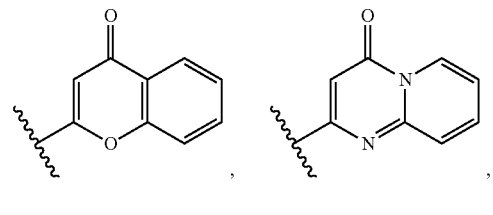
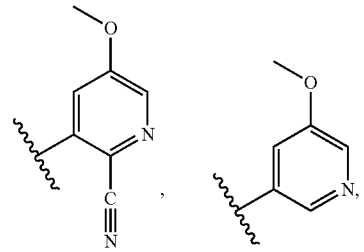
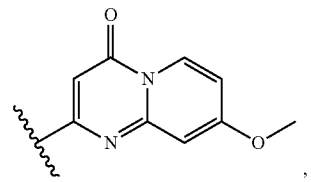
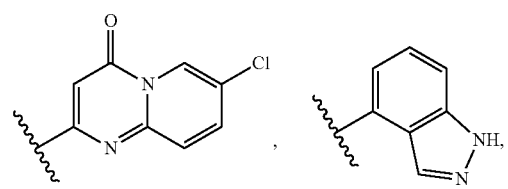
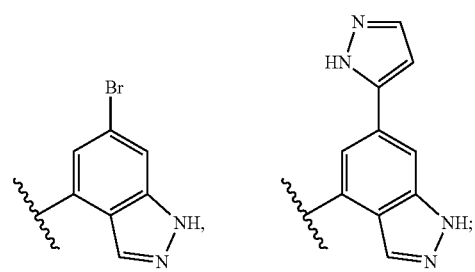
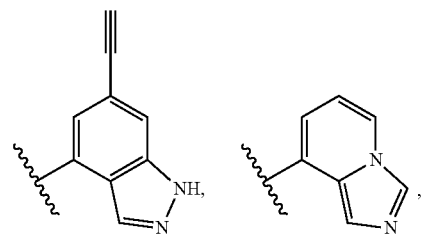
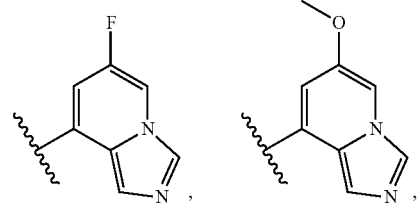
-continued
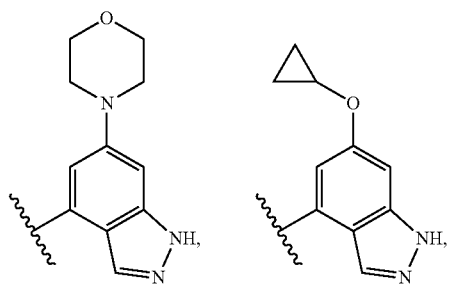
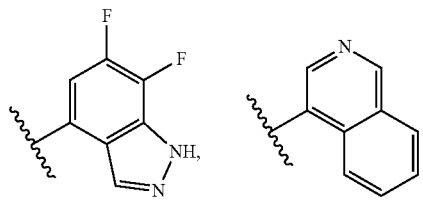
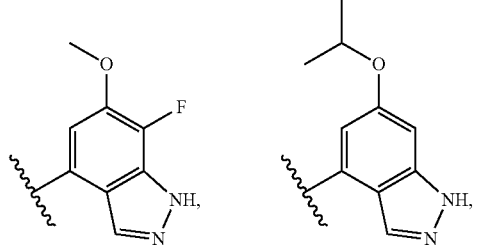
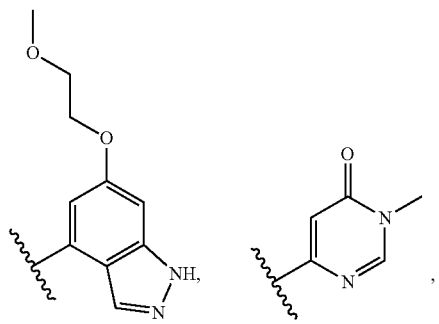
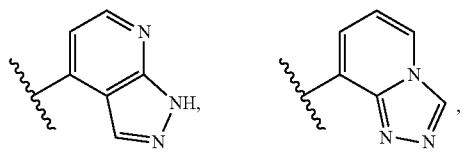
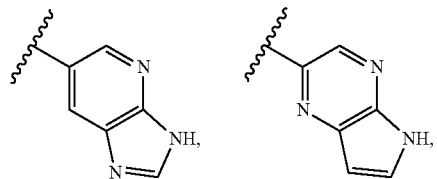
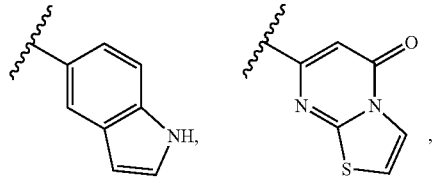

-continued

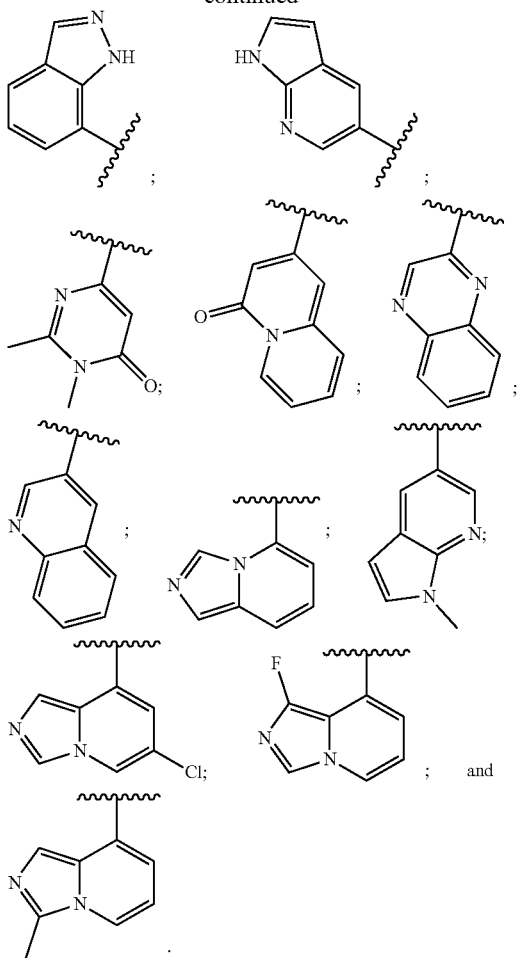

(193) Z is selected from:

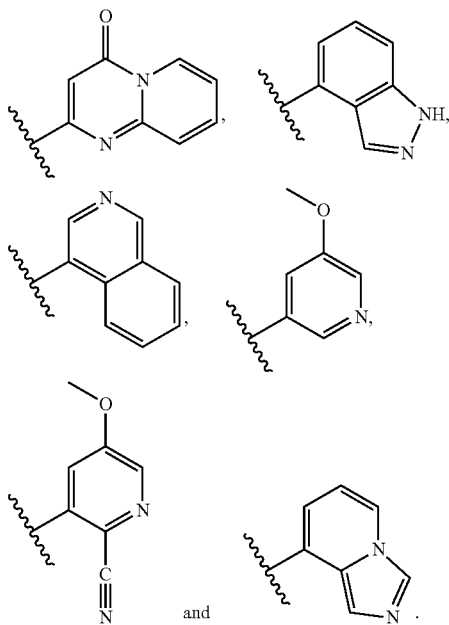

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered aryl or heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably, an aryl group is phenyl.

In an embodiment, X is

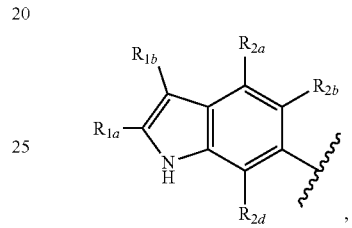

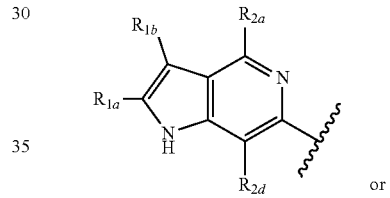

Y is selected form:

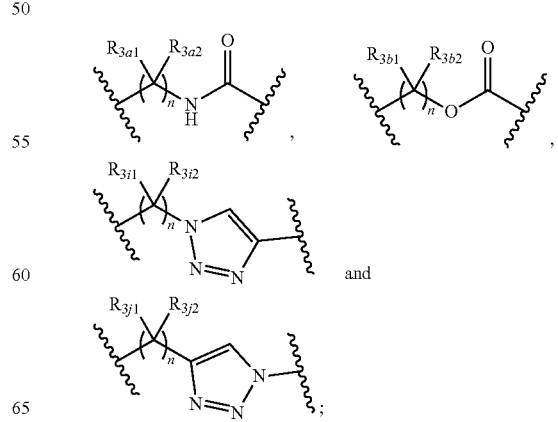

and

Z is selected from:

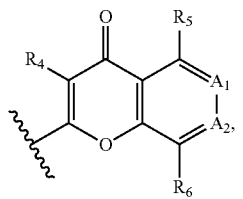 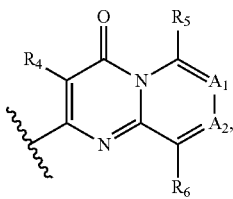

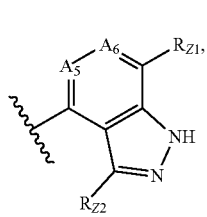 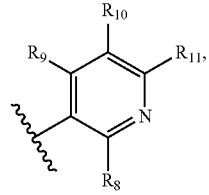

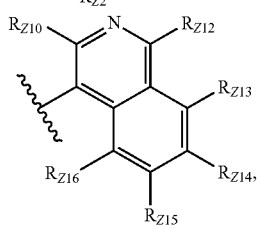

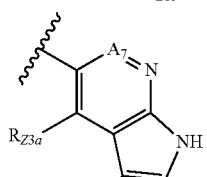

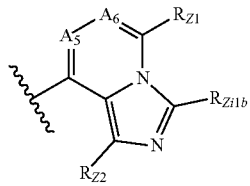

wherein:
(i) $R_{1a}$, $R_{1b}$, $R_{2a}$, $R_{2b}$ and $R_{2d}$ are as defined herein;
(ii) $R_{3a1}$, $R_{3a2}$, $R_{3b1}$, $R_{3b2}$, $R_{3i1}$, $R_{3i2}$, $R_{3j1}$, $R_{3j2}$ and n are as defined herein; and
(iii) $A_1$, $A_2$, $A_5$, $A_6$, $A_7$, $R_4$, $R_5$, $R_6$, $R_8$, $R_9$, $R_{10}$, $R_{11}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Zi2e}$, $R_{Zi1b}$ and $R_{Z2}$ are as defined herein.

In an embodiment,
X is

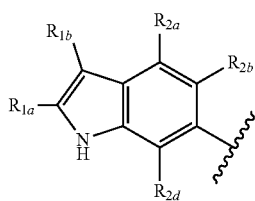   or

-continued

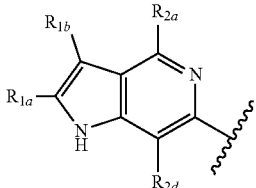

Y is

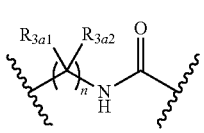   or   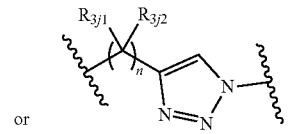

Z is

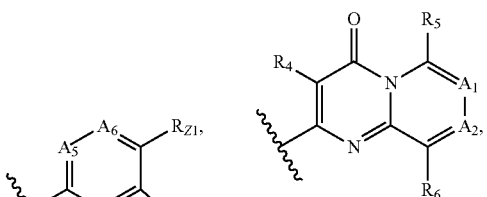

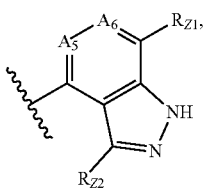

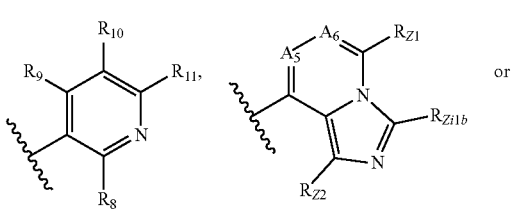 or 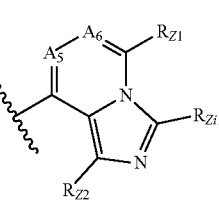

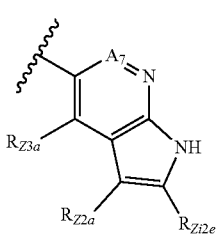

wherein:
(i) $R_{1a}$, $R_{1b}$, $R_{2a}$, $R_{2b}$ and $R_{2d}$ are as defined herein;
(ii) n, $R_{3a1}$, $R_{3a2}$, $R_{3j}$, $R_{3j2}$, are as defined herein; and
(iii) $A_1$, $A_2$, $A_5$, $A_6$, $A_7$, $R_4$, $R_5$, $R_6$, $R_8$, $R_9$, $R_{10}$, $R_{11}$, $R_{Z1}$, $R_{Z2}$, $R_{Z2a}$, $R_{Z3a}$, $R_{Zi2e}$, $R_{Zi1b}$ are as defined herein.

In an embodiment,

X is

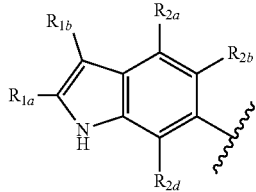

Y is

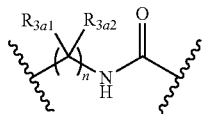

Z is

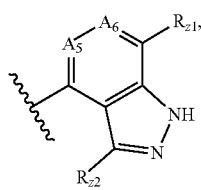

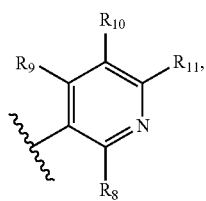

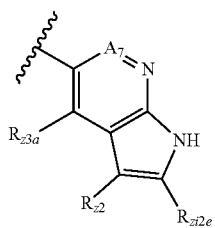

wherein:
  (i) $R_{1a}$, $R_{1b}$, $R_{2a}$, $R_{2b}$ and $R_{2d}$ are as defined herein;
  (ii) n, $R_{3a1}$ and $R_{3a2}$, are as defined herein; and
  (iii) $A_1$, $A_2$, $A_5$, $A_6$, $A_7$, $R_4$, $R_5$, $R_6$, $R_8$, $R_9$, $R_{10}$, $R_{11}$, $R_{Z1}$, $R_{Z2}$, $R_{Z2a}$, $R_{Z3a}$, $R_{Zi2e}$, $R_{Zi1b}$ are as defined herein.

In an embodiment:

X is

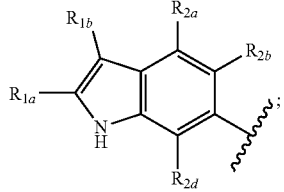

Y is

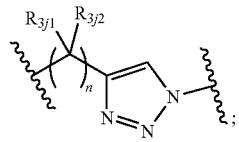

and

Z is

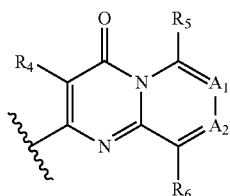 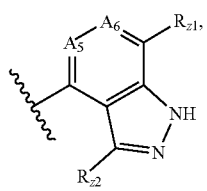

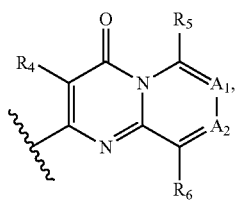

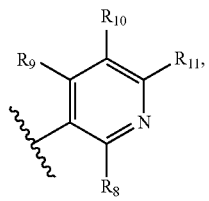 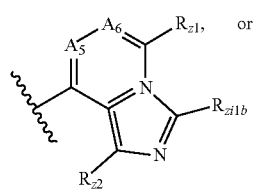

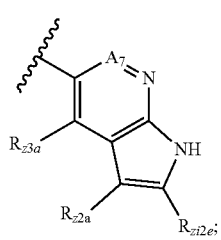

wherein:
  (i) $R_{1a}$, $R_{1b}$, $R_{2a}$, $R_{2b}$ and $R_{2d}$ are as defined herein;
  (ii) n, $R_{3j1}$ and $R_{3j2}$ are as defined herein; and
  (iii) $A_1$, $A_2$, $A_5$, $A_6$, $A_7$, $R_4$, $R_5$, $R_6$, $R_8$, $R_9$, $R_{10}$, $R_{11}$, $R_{Z1}$, $R_{Z2}$, $R_{Z2a}$, $R_{Z3a}$, $R_{Zi2e}$, $R_{Zi1b}$ are as defined herein.

In an embodiment,
X is

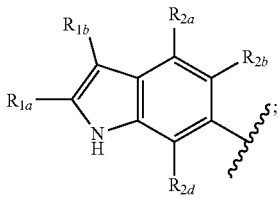

Y is

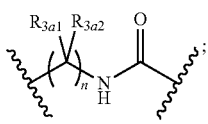

and
Z is

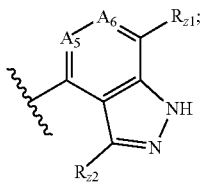

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_5$, $A_6$, $R_{Z1}$ and $R_{Z2}$ are as defined herein.

In an embodiment,
X is

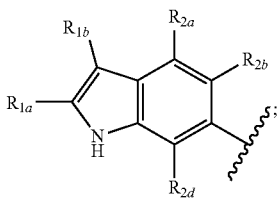

Y is

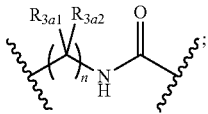

and
Z is

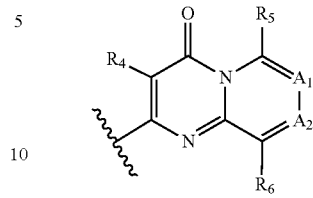

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_1$, $A_2$, $R_4$, $R_5$ and $R_6$ are as defined herein.

In an embodiment,
X is

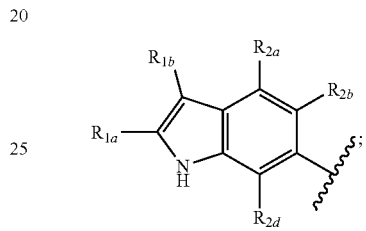

Y is

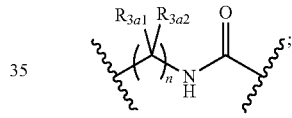

and
Z is

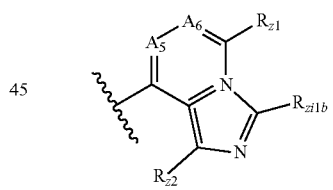

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_5$, $A_6$, $R_{Z1}$, $R_{Zi1b}$, and $R_{Z2}$ are as defined herein.

In an embodiment,
X is

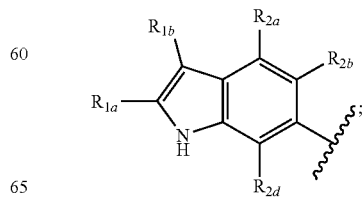

Y is

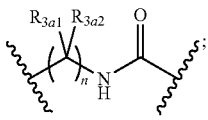

and
Z is

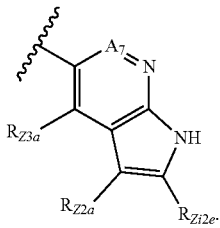

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_{Z6}$, $R_{Z2e}$, $R_{Z3e}$ and $R_{Zi2e}$ are as defined herein.

In an embodiment,
X is

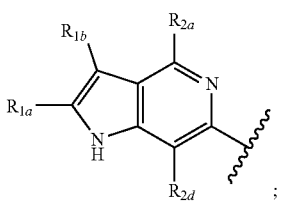

Y is

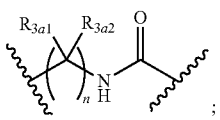

and
Z is

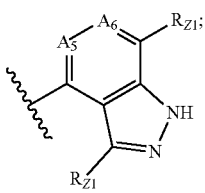

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_5$, $A_6$, $R_{Z1}$ and $R_{Z2}$ are as defined herein.

In an embodiment,
X is

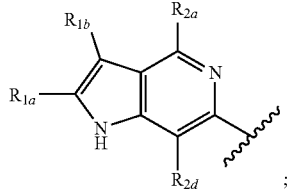

Y is

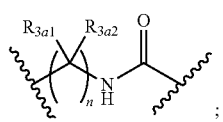

and
Z is

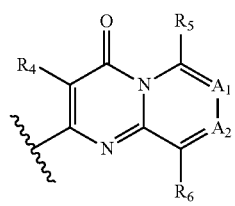

(i) wherein $R_{1a}$, $R_{1b}$, $R_{2a}$, $R_{2b}$ and $R_{2d}$ are as defined herein;
(ii) n, $R_{3a1}$ and $R_{3a2}$ are as defined herein; and
(iii) $A_1$, $A_2$, $R_4$, $R_5$ and $R_6$ are as defined herein.

In an embodiment,
X is

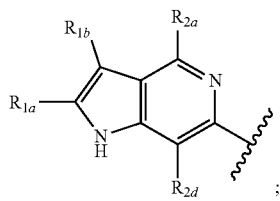

Y is

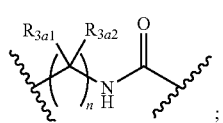

and
Z is

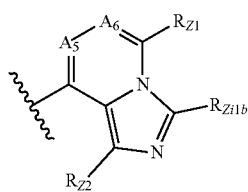

(i) wherein $R_{1a}$, $R_{1b}$, $R_{2a}$ and $R_{2d}$ are as defined herein;
(ii) n, $R_{3a1}$ and $R_{3a2}$ are as defined herein; and
(iii) $A_5$, $A_6$, $R_{Z1}$, $R_{Zi1b}$, and $R_{Z2}$ are as defined herein.
In an embodiment,
X is

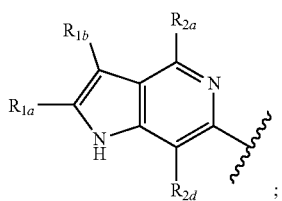

Y is

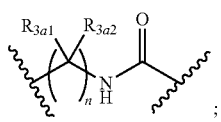

and
z is

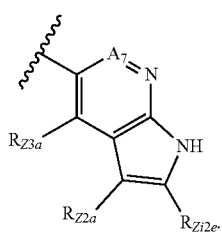

(iv) wherein $R_{1a}$, $R_{1b}$, $R_{2a}$, $R_{2b}$ and $R_{2d}$ are as defined herein;
(v) n, $R_{3a1}$ and $R_{3a2}$ are as defined herein; and
(vi) $A_{Z6}$, $R_{Z2e}$, $R_{Z3e}$ and $R_{Zi2e}$ are as defined herein.
In an embodiment,
X is

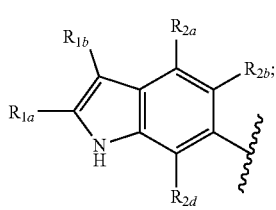

Y is

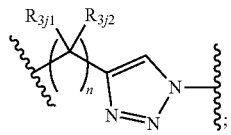

and
Z is

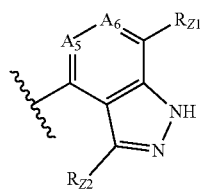

(i) wherein $R_{1a}$, $R_{1b}$, $R_{2a}$, $R_{2b}$ and $R_{2d}$ are as defined herein;
(ii) n, $R_{3j1}$ and $R_{3j2}$ are as defined herein; and
(iii) $A_5$, $A_6$, $R_{Z1}$ and $R_{Z2}$ are as defined herein.
In an embodiment,
X is

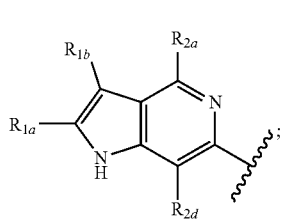

Y is

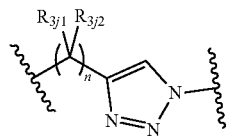

and
Z is

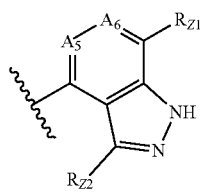

(i) wherein $R_{1a}$, $R_{1b}$, $R_{2a}$, and $R_{2d}$ are as defined herein;
(ii) n, $R_{3j1}$ and $R_{3j2}$ are as defined herein; and
(iii) $A_5$, $A_6$, $R_{Z1}$ and $R_{Z2}$ are as defined herein.

In an embodiment,
X is

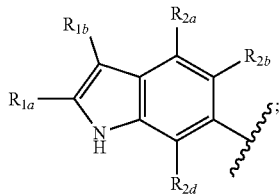

Y is

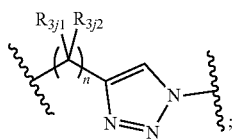

and
Z is

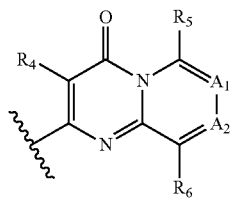

(i) wherein $R_{1a}$, $R_{1b}$, $R_{2a}$, $R_{2b}$ and $R_{2d}$ are as defined herein;
(ii) n, $R_{3j1}$ and $R_{3j2}$ are as defined herein; and
(iii) $A_1$, $A_2$, $R_4$, $R_5$ and $R_6$ are as defined herein.

In an embodiment,
X is

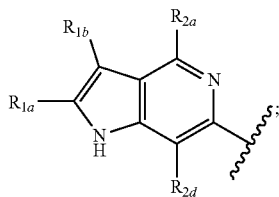

Y is

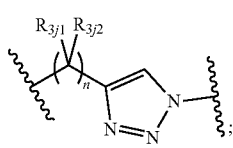

and
Z is

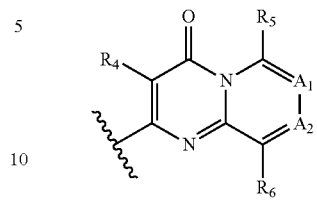

(iv) wherein $R_{1a}$, $R_{1b}$, $R_{2a}$ and $R_{2d}$ are as defined herein;
(v) n, $R_{3j1}$ and $R_{3j2}$ are as defined herein; and
(vi) $A_1$, $A_2$, $R_4$, $R_5$ and $R_6$ are as defined herein.

In an embodiment,
X is

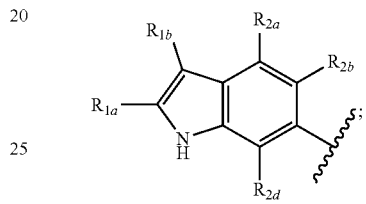

Y is

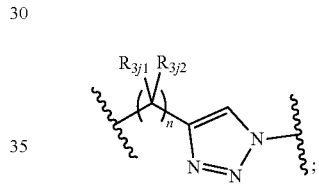

and
Z is

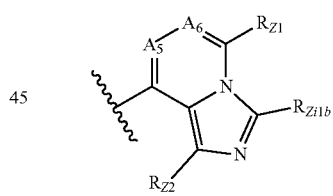

(i) wherein $R_{1a}$, $R_{1b}$, $R_{2a}$, $R_{2b}$ and $R_{2d}$ are as defined herein;
(ii) n, $R_{3j1}$ and $R_{3j2}$ are as defined herein; and
(iii) $A_5$, $A_6$, $R_{Z1}$, $R_{Zi1b}$, and $R_{Z2}$ are as defined herein In an embodiment,
X is

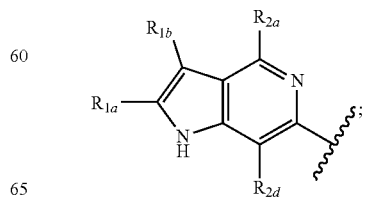

Y is

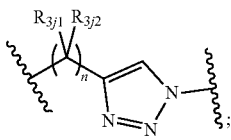

and
Z is

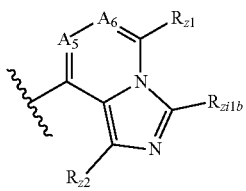

(i) wherein $R_{1a}$, $R_{1b}$, $R_{2a}$, $R_{2b}$ and $R_{2a}$ are as defined herein;
(ii) n, $R_{3j1}$ and $R_{3j2}$ are as defined herein; and
(iii) $A_5$, $A_6$, $R_{Z1}$, $R_{Zi1b}$, and $R_{Z2}$ are as defined herein In an embodiment,
X is

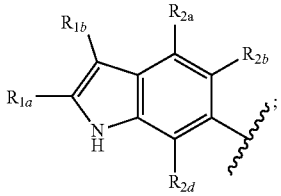

Y is

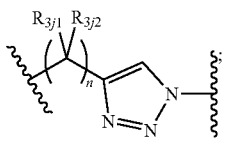

and
Z is

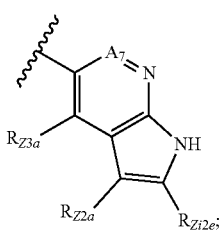

wherein:
(i) $R_{1a}$, $R_{1b}$, $R_{2a}$, $R_{2b}$ and $R_{2d}$ are as defined herein;
(ii) n, $R_{3j1}$ and $R_{3j2}$ are as defined herein; and
(iii) $A_7$, $R_{Z2a}$, $R_{Z3a}$ are $R_{Zi2e}$ are as defined herein.

In an embodiment,
X is

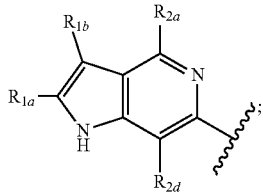

Y is

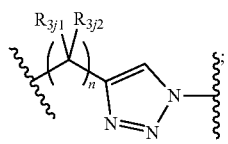

and
Z is

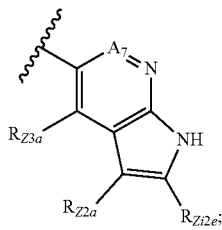

wherein:
(i) $R_{1a}$, $R_{1b}$, $R_{2a}$, $R_{2b}$ and $R_{2d}$ are as defined herein;
(ii) n, $R_{3j1}$ and $R_{3j2}$ are as defined herein; and
(iii) $A_7$, $R_{Z2a}$, $R_{Z3a}$ are $R_{Zi2e}$ are as defined herein.

In an embodiment,
X is

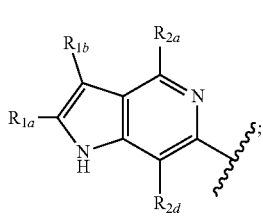

Y is

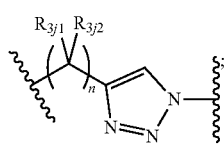

and
Z is

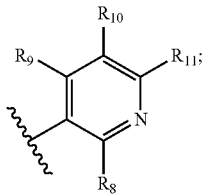

wherein:
(iv) $R_{1a}$, $R_{1b}$, $R_{2a}$, $R_{2b}$ and $R_{2d}$ are as defined herein;
(v) n, $R_{3j1}$ and $R_{3j2}$ are as defined herein; and
(vi) $R_8$, $R_9$, $R_{10}$ and $R_{11}$ are as defined herein.
In an embodiment,
X is

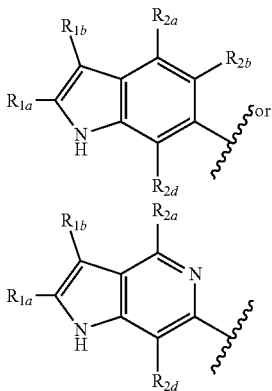

Y is

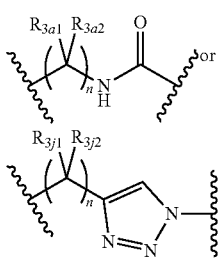

Z is

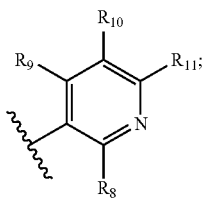

wherein:
(iv) $R_{1a}$, $R_{1b}$, $R_{2a}$, $R_{2b}$ and $R_{2d}$ are as defined herein;
(v) n, $R_{3a1}$, $R_{3a2}$, $R_{3j1}$, $R_{3j2}$, are as defined herein; and
(vi) $R_8$, $R_9$, $R_{10}$, $R_{11}$ are as defined herein.

In an embodiment:
when $X_6$ is $A_1$, $A_1$ is $CR_{12}$;
when $X_7$ is $A_2$, $A_2$ is $CR_{13}$;
$B_1$ is $A_5$, wherein $A_5$ is $CR_{16}$;
$B_2$ is $A_6$, wherein $A_6$ is $CR_{17}$;
$Y_2$ is $A_7$, wherein $A_7$ is $CR_{18}$;
when $X_6$ is $A_8$, $A_8$ is $CR_{19}R_{20}$;
when $X_7$ is $A_9$, $A_9$ is $CR_{22}R_{23}$;
when $X_7$ is $A_{11}$, $A_{11}$ is $CR_{28}R_{29}$;
and wherein $R_{12}$, $R_{13}$, $R_{16}$, $R_{17}$, $R_{18}$, $R_{19}$, $R_{20}$, $R_{21}$, $R_{22}$, $R_{23}$, $R_{28}$ and $R_{29}$ are as defined herein.

In an embodiment: $A_1$ is $CR_{12}$; $A_2$ is $CR_{13}$; $A_5$ is $CR_{16}$; $A_6$ is $CR_{17}$; $A_7$ is $CR_{18}$; $A_8$ is $CR_{19}R_{20}$; $A_9$ is $CR_{22}R_{23}$; $A_{11}$ is $CR_{28}R_{29}$; wherein $R_{12}$, $R_{13}$, $R_{16}$, $R_{17}$, $R_{18}$, $R_{19}$, $R_{20}$, $R_{21}$, $R_{22}$, $R_{23}$, $R_{28}$ and $R_{29}$ are as defined herein In an embodiment:
(i) $R_4$, $R_5$, $R_{X5a}$, $R_{X5b}$, $R_{Y5}$, $R_6$, $R_7$, $R_8$, $R_9$, $R_{10}$, $R_{11}$, $R_{11a}$, $R_{11b}$, $R_{Z2}$, $R_{Z2a}$, $R_{Z3a}$, $R_{Zi1b}$, $R_{Zi2e}$, $R_9$, $R_{Z10}$, $R_{Z11}$, $R_{Z12}$, $R_{Z12a}$, $R_{Z13}$, $R_{Z14}$, $R_{Z15}$ and $R_{Z16}$ are independently selected from hydrogen, methyl, cyano or halo; and
$R_{B5N}$, $R_{Y5N}$, $R_{Z2N}$ and $R_{11N}$ are selected from methyl or hydrogen;
(ii) $R_{Z1}$ and $R_{Z1a}$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl;
(iii) $R_{12}$, $R_{13}$, $R_{16}$, $R_{18}$, $R_{19}$, $R_{20}$, $R_{21}$, $R_{22}$, $R_{23}$, $R_{24}$ and $R_{30}$ are independently selected from hydrogen, halo, cyano and methyl;
(iv) $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl a 5- or 6-membered or heteroaryl, $C_{3-6}$cycloalkyl, —O—$C_{3-6}$cycloalkyl, heterocyclyl, —(OCH$_2$CH$_2$)$_m$—OCH$_3$ wherein m is an integer from 1 to 6, $NR_qR_r$, wherein $R_q$ and $R_r$ are each independently hydrogen, $C_{1-4}$ alkyl or $R_q$ and $R_r$ are linked together such that, together with the nitrogen atom to which they are attached, they form a 3- to 6-membered heterocyclic ring; wherein any $C_{1-4}$ alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl.
(v) $R_{21}$, $R_{24}$ and $R_{30}$, are independently selected from hydrogen or methyl;
(vi) $R_{28}$ and $R_{29}$ are selected from hydrogen or halo, methoxy and methyl.

In an embodiment:
(i) $R_4$, $R_5$, $R_{X5a}$, $R_{X5b}$, $R_{Y5}$, $R_{B5N}$, $R_{Y5N}$, $R_6$, $R_7$, $R_8$, $R_9$, $R_{10}$, $R_{11}$, $R_{11a}$, $R_{11b}$, $R_{11N}$, $R_{Z2}$, $R_{Z2N}$, $R_{Z2a}$, $R_{Z3a}$, $R_{Zi1b}$, $R_{Zi2e}$, $R_{Z9}$, $R_{Z10}$, $R_{Z11}$, $R_{Z12}$, $R_{Z12a}$, $R_{Z13}$, $R_{Z14}$, $R_{Z15}$ and $R_{Z16}$ are hydrogen;
(ii) $R_{Z1}$ and $R_{Z1a}$ are selected from hydrogen, cyano, halo, $C_{1-2}$haloalkyl, $C_{1-2}$haloalkoxy, $C_{1-2}$alkoxy, $C_{3-6}$cycloalkyl and —O—$C_{3-6}$cycloalkyl;
(iii) $R_{12}$, $R_{13}$, $R_{16}$, $R_{18}$, $R_{19}$, $R_{20}$, $R_{21}$, $R_{22}$, $R_{23}$, $R_{24}$ and $R_{30}$ are hydrogen; (iv) $R_{17}$ is selected from hydrogen, halo, cyano, $C_{1-2}$ alkyl, $C_{1-2}$ haloalkyl, $C_{1-2}$ alkoxy, $C_{1-2}$ haloalkoxy, $C_{2-3}$ alkenyl, $C_{2-3}$ alkynyl, phenyl a 5- or 6-membered or heteroaryl, $C_{3-6}$cycloalkyl, —O—$C_{3-6}$cycloalkyl, heterocyclyl, —(OCH$_2$CH$_2$)$_m$—OCH$_3$ wherein m is an integer from 1 to 6, $NR_qR_r$, wherein $R_q$ and $R_r$ are each independently hydrogen, $C_{1-2}$ alkyl or $R_q$ and $R_r$ are linked together such that, together with the nitrogen atom to which they are attached, they form a 3- to 6-membered heterocyclic ring; wherein any $C_{1-4}$ alkyl, $C_{2-4}$ alkenyl, $C_{2-4}$ alkynyl, phenyl, 5- or 6-membered or heteroaryl, $C_{3-6}$ cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl (v) $R_{21}$, $R_{24}$ and $R_{30}$, are hydrogen;

(vi) $R_{28}$ and $R_{29}$ are hydrogen.

Suitably, X is as defined in any one of paragraphs (11) to (22) above. More suitably, X is as defined in paragraph (14), (15), (16) or (22). Most suitably, X is as defined in paragraph (22).

Suitably, $Q_1$ is as defined in any one of paragraphs (1) to (4) above. Most suitably, $Q_1$ is as defined in paragraph (3) or (4).

Suitably, $Q_{2a}$ is as defined in paragraph (5).
Suitably, $Q_{2b}$ is as defined in paragraph (6).
Suitably, $Q_{2c}$ is as defined in paragraph (7).
Suitably, $Q_{2d}$ is as defined in paragraph (8).
Suitably, $Q_3$ is as defined in paragraph (9).
Suitably, $Q_4$ is as defined in paragraph (10).

Suitably, $R_{1a}$ is as defined in any one of paragraphs (23) to (42) above. Suitably, $R_{1a}$ is as defined in any one of paragraphs (30) to (35) or (36) to (42). More suitably, $R_{1a}$ is as defined in any one of paragraphs (32) to (35) or (40) to (42). Most suitably, $R_{1a}$ is as defined in any one of paragraphs (40) to (42), e.g. paragraphs (40a), (41a), (41b), (41c) or (42).

Suitably, $R_{1b}$ is as defined in any one of paragraphs (43) to (44). Most suitably, $R_{1b}$ is as defined in paragraph (44).

Suitably, $R_{1b}$ is as defined in any one of paragraphs (45) or (46). Most suitably, $R_{1x}$ is as defined in paragraph (46).

Suitably, $R_{2a}$, $R_{2b}$, $R_{2c}$ and $R_{2d}$ are as defined in any one of paragraphs (47) to (52) above. Most suitably, $R_{2a}$, $R_{2b}$ and $R_{2c}$ are as defined in paragraph (51) or (52).

Suitably, Y is as defined in any one of paragraphs (63) to (89) above. Most suitably, Y is as defined in any one of paragraphs (86), (87), (88) or (89).

Suitably, n is as defined in any one of paragraphs (60) to (62) above. Most suitably, n is as defined in paragraph (62), i.e. n is 1.

Suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are as defined in any one of paragraphs (53) to (56), and paragraphs (58) to (59) above. Most suitably, $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are as defined in paragraph (56) or (58).

Suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are as defined in any one of paragraphs (57), (58) and (59) above. Most suitably, $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are as defined in paragraph (57) or (58) above.

Suitably, Z is as defined in any one of paragraphs from (136) to (193) above. More suitably, Z is as defined in paragraphs (187) to (193). Most suitably, Z is as defined in any one of paragraphs (190) to (193)

Suitably, $R_4$, $R_5$ and $R_6$ are as defined in any one of paragraphs (90) and (91). Most suitably, $R_4$, $R_5$ and $R_6$ are as defined in paragraph (91), i.e. $R_4$, $R_5$ and $R_6$ are hydrogen.

Suitably, when Z is

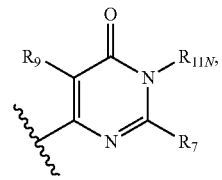

then $R_7$, $R_8$ and $R_{11N}$ are as defined in any one of paragraphs (92) and (93) above. Most suitably, $R_7$, $R_8$ and $R_{11N}$ are as defined in paragraph (93).

Suitably, when Z is

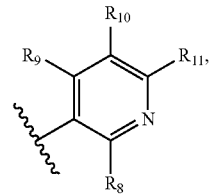

then $R_8$, $R_9$, $R_{10}$ and $R_{11}$ are as defined in any one of paragraphs (94) to (98) above. More suitably, $R_8$, $R_9$, $R_{10}$ and $R_{11}$, are as defined in any one of paragraphs (95) to (98) above. Most Most suitably, $R_8$, $R_9$, $R_{10}$ and $R_{11}$ are as defined in paragraph (97), (97a) or (98).

Suitably, $R_{Z1}$ and $R_{Z1a}$ are as defined in any one of paragraphs (99) to (102). Most suitably, $R_{Z1}$ and $R_{Z1a}$ are as defined in paragraph (102).

Suitably, $R_{Z2}$, $R_{Z2a}$, $R_{Z3a}$, $R_{Zi1b}$ and $R_{Zi2e}$ are as defined in any one of paragraphs (103) to (105). Most suitably, $R_{Z2}$, $R_{Z2a}$, $R_{Z3a}$, $R_{Z3e}$, $R_{Zi1b}$ and $R_{Zi2e}$ are as defined in paragraph (105).

Suitably, $R_{B5N}$, $R_{Y5N}$, $R_{Z2N}$ and $R_{11N}$ are as defined in paragraph (106) or (107). Most suitably, $R_{B5N}$, $R_{Y5N}$, $R_{Z2N}$ and $R_{11N}$ are as defined in paragraph (106).

Suitably, $R_{Z4}$, $R_{Z5}$, $R_{Z6}$, $R_{Z7}$, $R_{Z8}$, $R_{Z9}$, $R_{Z10}$, $R_{Z11}$, $R_{Z12}$, $R_{Z13}$, $R_{Z14}$, $R_{Z15}$, and $R_{Z16}$ are as defined in any one of paragraphs (108) to (110). Most suitably, $R_{Z4}$, $R_{Z5}$, $R_{Z6}$, $R_{Z7}$, $R_{Z8}$, $R_{Z9}$, $R_{Z10}$, $R_{Z11}$, $R_{Z12}$, $R_{Z13}$, $R_{Z14}$, $R_{Z15}$, and $R_{Z16}$ are as defined in paragraph (110).

Suitably, $A_1$, $A_2$, $A_5$, $A_6$, $A_7$, $A_8$, $A_9$ and $A_{11}$ are as defined in paragraph (111)

Suitably, $R_{12}$, $R_{13}$, $R_{16}$, $R_{19}$, $R_{20}$, $R_{21}$, $R_{22}$ and $R_{23}$ are as defined in any one of paragraphs (112) or (113) above. Most suitably, $R_{12}$, $R_{13}$, $R_{16}$, $R_{19}$, $R_{20}$, $R_{21}$, $R_{22}$ and $R_{23}$ are as defined in paragraph (113).

Suitably, $R_{12}$ is as defined in any one of paragraphs (114) to (117) above. Most suitably, $R_{12}$ are as defined in paragraph (117), i.e. $R_{12}$ is hydrogen.

Suitably, $R_{13}$ is as defined in any one of paragraphs (118) to (120) above. Most suitably, $R_{13}$ is as defined in paragraph (119).

Suitably, $R_{16}$ and $R_{18}$ are as defined in any one of paragraphs (121) to (124) above. Most suitably, $R_{16}$ and $R_{18}$ are as defined in paragraph (124), i.e. $R_{16}$ and $R_{18}$ are hydrogen.

Suitably, $R_{17}$ is as defined in any one of paragraphs (125) to (131) above. More suitably, $R_{17}$ is as defined any one of paragraphs (128) to (131). Most suitably, $R_{17}$ is as defined any one of paragraphs (129) to (131).

Suitably, $R_{28}$ and $R_{29}$ are as defined in any one of paragraphs (132) to (133) above. Most suitably, $R_{28}$ and $R_{29}$ are as defined in paragraph (133).

Suitably, $R_{21}$, $R_{24}$ and $R_{30}$ are as defined in any one of paragraphs from (134) to (135) above. Most suitably, $R_{21}$, $R_{24}$ and $R_{30}$ are as defined in paragraph (135).

Suitably, $R_4$, $R_5$, $R_{X5a}$, $R_{X5b}$, $R_6$, $R_7$, $R_8$, $R_9$, $R_{10}$, $R_{11}$, $R_{11N}$, $R_{Z1}$, $R_{Z1a}$, $R_{Z2}$, $R_{Z2a}$, $R_{Z3a}$, $R_{Zi1b}$, $R_{Zi1c}$, $R_{Zi2e}$, $R_{Z9}$, $R_{Z10}$, $R_{Z11}$, $R_{Z12}$, $R_{Z13}$, $R_{Z14}$, $R_{Z15}$ and $R_{Z16}$ are independently selected from hydrogen or methyl. Most suitably, $R_4$, $R_5$, $R_{X5a}$, $R_{X5b}$, $R_6$, $R_7$, $R_8$, $R_9$, $R_{10}$, $R_{11}$, $R_{11N}$, $R_{Z1}$, $R_{Z1a}$, $R_{Z2}$, $R_{Z2a}$, $R_{Z3a}$, $R_{Zi1b}$, $R_{Zi1c}$, $R_{Zi2e}$, $R_{Z9}$, $R_{Z10}$, $R_{Z11}$, $R_{Z12}$, $R_{Z13}$, $R_{Z14}$, $R_{Z15}$ and $R_{Z16}$ are hydrogen.

In a particular group of compounds of the invention, Y is as defined in paragraph (63), i.e. the compounds have the structural formula (II) (a sub-definition of formula (I)) shown below:

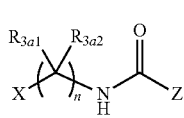
(II)

wherein X, $R_{3a1}$, $R_{3a2}$, n and Z each having any one of the meanings defined herein; or a pharmaceutically acceptable salt thereof.

In an embodiment of the compounds of formula (II):
X is as defined in any one of paragraphs (11) to (22) above;
$R_{3a1}$ is as defined in any one of paragraphs from (53) to (56), and paragraphs (58) to (59) above;
$R_{3a2}$ is as defined in any one of paragraphs (57), (58) and (59) above;
n is as defined in any one of paragraphs (60) to (62) above; and
Z is as defined in any one of paragraphs (136) to (193) above.

In an embodiment of the compounds of formula (II):
X is as defined in paragraph (22) above;
$R_{3a1}$ is as defined in paragraph (56) above;
$R_{3a2}$ is as defined in paragraph (57) above;
n is as defined in paragraph (62) above; and
Z is as defined in any one of paragraphs (136) to (193) above.

In a particular group of the compounds of formula (II):
X is as defined in paragraph (20), (21) or (22) above and $R_{1a}$, is as defined in any one of paragraphs (23) to (42) above;
$R_{3a1}$ is as defined in paragraph (56) above;
$R_{3a2}$ is as defined in paragraph (57) above;
n is as defined in paragraph (62) above; and
Z is as defined in any one of paragraphs (136) to (193) above.

In a particular group of the compounds of formula (II):
X is as defined in paragraph (22) above and $R_{1a}$ is as defined in any one of paragraphs (36) to (42) above;
$R_{3a1}$ is as defined in paragraph (56) above;
$R_{3a2}$ is as defined in paragraph (57) above;
n is as defined in paragraph (62) above; and
Z is as defined in any one of paragraphs (136) to (193) above.

In a particular group of the compounds of formula (II):
X is as defined in paragraph (22) above and $R_{1a}$ is as defined in paragraph (32) or (35) above;
$R_{3a1}$ is as defined in paragraph (56) above;
$R_{3a2}$ is as defined in paragraph (57) above;
n is as defined in paragraph (62) above; and
Z is as defined in any one of paragraphs (136) to (193) above.

In an embodiment of the compounds of formula (II):
X is as defined in paragraph (14) above;
$R_{3a1}$ is as defined in any one of paragraphs from (53) to (56), and paragraphs (58) to (59) above;
$R_{3a2}$ is as defined in any one of paragraphs (57), (58) and (59) above;
n is as defined in any one of paragraphs (60) to (62) above; and
Z is as defined in any one of paragraphs (142), (146) and (156) above.

In a particular group of compounds of the invention, Y is as defined in paragraph (73), i.e. the compounds have the structural formula (III) (a sub-definition of formula (1)) shown below:

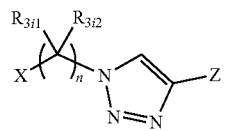
(III)

wherein X, $R_{3i1}$, $R_{3i2}$, n and Z each having any one of the meanings defined herein; or a pharmaceutically acceptable salt thereof.

In an embodiment of the compounds of formula (III):
X is as defined in any one of paragraphs (11) to (22) above;
$R_{3i1}$ is as defined in any one of paragraphs from (53) to (56), and paragraphs (58) to (59) above;
$R_{3i2}$ is as defined in any one of paragraphs (57), (58) and (59) above;
n is as defined in any one of paragraphs (60) to (62) above; and
Z is as defined in any one of paragraphs (136) to (193) above.

In an embodiment of the compounds of formula (III):
X is as defined in paragraph (22) above;
$R_{3i1}$ is as defined in paragraph (56) above;
$R_{3i2}$ is as defined in paragraph (57) above;
n is as defined in paragraph (62) above; and
Z is as defined in any one of paragraphs (136) to (193) above.

In a particular group of the compounds of formula (III):
X is as defined in paragraph (20), (21) or (22) above and $R_{1a}$, is as defined in any one of paragraphs (23) to (42) above;
$R_{3i1}$ is as defined in paragraph (56) above;
$R_{3i2}$ is as defined in paragraph (57) above;
n is as defined in paragraph (62) above; and
Z is as defined in any one of paragraphs (136) to (193) above.

In a particular group of the compounds of formula (III):
X is as defined in paragraph (22) above and $R_{1a}$ is as defined in any one of paragraphs (30) to (35) or (36) to (42) above;
$R_{3i1}$ is as defined in paragraph (56) above;
$R_{3i2}$ is as defined in paragraph (57) above;
n is as defined in paragraph (62) above; and
Z is as defined in any one of paragraphs (136) to (193) above.

In a particular group of compounds of the invention, Y is as defined in paragraph (64), i.e. the compounds have the structural formula (IV) (a sub-definition of formula (1)) shown below:

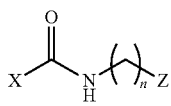

(IV)

wherein X, n and Z each having any one of the meanings defined herein; or a pharmaceutically acceptable salt thereof.

In an embodiment of the compounds of formula (IV):
X is as defined in any one of paragraphs (11) to (22) above;
n is as defined in any one of paragraphs (60) to (62) above; and
Z is as defined in any one of paragraphs (136) to (193) above.

In an embodiment of the compounds of formula (IV):
X is as defined in paragraph (22) above;
n is as defined in paragraph (62) above; and
Z is as defined in any one of paragraphs (136) to (193) above.

In a particular group of the compounds of formula (IV):
X is as defined in paragraph (20), (21) or (22) above and $R_{1a}$, is as defined in any one of paragraphs (23) to (42) above;
n is as defined in paragraph (62) above; and
Z is as defined in any one of paragraphs (136) to (193) above.

In a particular group of the compounds of formula (IV):
X is as defined in paragraph (22) above and $R_{1a}$ is as defined in any one of paragraphs (30) to (35) or (36) to (42) above;
n is as defined in paragraph (62) above; and
Z is as defined in any one of paragraphs (136) to (193) above.

In a particular group of compounds of the invention, Y is as defined in paragraph (74), i.e. the compounds have the structural formula (V) (a sub-definition of formula (1)) shown below:

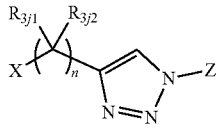

(V)

wherein X, $R_{3j1}$, $R_{3j2}$, n and Z each having any one of the meanings defined herein; or a pharmaceutically acceptable salt thereof.

In an embodiment of the compounds of formula (V):
X is as defined in any one of paragraphs (11) to (22) above;
$R_{3j1}$ is as defined in any one of paragraphs from (53) to (56), and paragraphs (58) to (59) above;
$R_{3j2}$ is as defined in any one of paragraphs (57), (58) and (59) above;
n is as defined in any one of paragraphs (60) to (62) above; and
Z is as defined in any one of paragraphs (136) to (193) above.

In an embodiment of the compounds of formula (V):
X is as defined in paragraph (22) above; $R_{3a1}$ is as defined in paragraph (56) above; $R_{3j2}$ is as defined in paragraph (57) above;

n is as defined in paragraph (62) above; and
Z is as defined in any one of paragraphs (136) to (193) above.

In a particular group of the compounds of formula (V):
X is as defined in paragraph (20), (21) or (22) above and $R_{1a}$, is as defined in any one of paragraphs (23) to (42) above; $R_{3j1}$ is as defined in paragraph (56) above; $R_{3j2}$ is as defined in paragraph (57) above;
n is as defined in paragraph (62) above; and
Z is as defined in any one of paragraphs (136) to (193) above.

In a particular group of the compounds of formula (V):
X is as defined in paragraph (22) above and $R_{1a}$ is as defined in any one of paragraphs (30) to (35) or (36) to (42) above;
$R_{3j1}$ is as defined in paragraph (56) above; $R_{3j2}$ is as defined in paragraph (57) above;
n is as defined in paragraph (62) above; and
Z is as defined in any one of paragraphs (136) to (193) above.

In a particular group of compounds of the invention, X is as defined in paragraph (15), i.e. the compounds have the structural formula (VI) (a sub-definition of formula (I)) shown below:

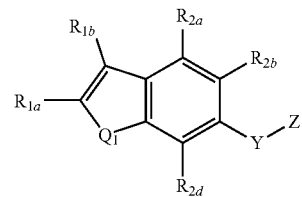

VI wherein $R_{1a}$, $R_{1b}$, $R_{2a}$, $R_{2b}$, $R_{2d}$, Y and Z each having any one of the meanings defined herein; or a pharmaceutically acceptable salt thereof.

In an embodiment of the compounds of formula (VI):
$Q_1$ is as defined in any one of paragraphs (1) to (4)
$R_{1a}$ is as defined in any one of paragraphs (23) to (42) above;
$R_{1b}$ is as defined in any one of paragraphs (43) to (44) above;
$R_{2a}$, $R_{2b}$ and $R_{2d}$ are as defined in any one of paragraphs (47) to (52) above;
Y is as defined in any one of paragraphs (63) to (89) above; and
Z is as defined in any one of paragraphs (136) to (193) above.

In an embodiment of the compounds of formula (VI):
$Q_1$ is as defined in any one of paragraphs (3) or (4);
$R_{1a}$ is as defined in any one of paragraphs (30) to (35) above;
$R_{1b}$ is as defined in paragraph (44) above;
$R_{2a}$, $R_{2b}$, and $R_{2d}$ are as defined in paragraph (51) or (52);
Y is as defined in paragraphs (86), (87), (88) or (89) above; and
Z is as defined in any one of paragraphs (186) to (193) above.

In an embodiment of the compounds of formula (VI):
$Q_1$ is as defined in any one of paragraphs (3) or (4);
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);

Y is as defined in paragraphs (86), (87), (88) or (89) above; and
Z is as defined in any one of paragraphs (136) to (193) above.
In an embodiment of the compounds of formula (VI):
$Q_1$ is as defined in paragraph (3) or (4)
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
Y is as defined in any one of paragraphs (85) to (89) above; and
Z is as defined in any one of paragraphs (189) to (193) above.
In a particular group of the compounds of formula (VI):
$Q_1$ is as defined in paragraph (4)
$R_{1a}$ is as defined in paragraph (32) or (35) above;
$R_{1b}$ is as defined in paragraph (44) above;
$R_{2a}$, $R_{2b}$, and $R_{2d}$ are as defined in paragraph (52);
Y is as defined in paragraph (89) above;
Z is as defined in any one of paragraph (193) above.
In a particular group of the compounds of formula (XI):
$Q_1$ is as defined in paragraph (4)
$R_{1a}$ is as defined in any one of paragraphs (40a), (41a), (41b), (41c) or (42) above;
$R_{1b}$ is as defined in paragraph (44) above;
$R_{2a}$, $R_{2b}$, and $R_{2d}$ are as defined in paragraph (52);
Y is as defined in paragraph (89) above; and
Z is as defined in paragraph (193) above.
In a particular group of compounds of the invention, X is as defined in paragraph (15) and Y is as defined in paragraph (63), i.e. the compounds have the structural formula (VII) (a sub-definition of formula (I)) shown below:

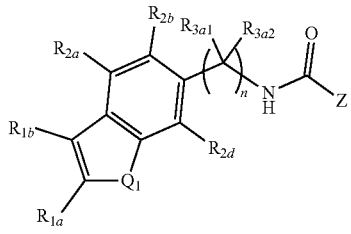

VII wherein $R_{1a}$, $R_{1b}$, $R_{2a}$, $R_{2b}$, $R_{2d}$, $R_{3a1}$, $R_{3a2}$, n and Z each having any one of the meanings defined herein; or a pharmaceutically acceptable salt thereof.
In an embodiment of the compounds of formula (VII):
$Q_1$ is as defined in any one of paragraphs (1) to (4)
$R_{1a}$ is as defined in any one of paragraphs (23) to (42) above;
$R_{1b}$ is as defined in any one of paragraphs (43) to (44) above;
$R_{2a}$, $R_{2b}$ and $R_{2d}$ are as defined in any one of paragraphs (47) to (52) above;
$R_{3a1}$ is as defined in any one of paragraphs from (53) to (56), and paragraphs (58) to (59) above;
$R_{3a2}$ is as defined in any one of paragraphs (57), (58) and (59) above;
n is as defined in any one of paragraphs (60), (61) and (62) above;
Z is as defined in any one of paragraphs (136) to (193) above.
In an embodiment of the compounds of formula (VII):
$Q_1$ is as defined in any one of paragraphs (3) or (4);

$R_{1a}$ is as defined in any one of paragraphs (30) to (35) above;
$R_{1b}$ is as defined in paragraph (44) above;
$R_{2a}$, $R_{2b}$, and $R_{2d}$ are as defined in paragraph (51) or (52);
$R_{3a1}$ is as defined in paragraph (56) above;
$R_{3a2}$ is as defined in paragraph (57) above;
n is as defined in paragraph (62) above; and
Z is as defined in any one of paragraphs (186) to (191) above.
In an embodiment of the compounds of formula (VII):
$Q_1$ is as defined in any one of paragraphs (3) or (4);
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
$R_{3a1}$ is as defined in paragraph (56) above;
$R_{3a2}$ is as defined in paragraph (57) above;
n is as defined in paragraph (62) above; and
Z is as defined in any one of paragraphs (136) to (193) above.
In an embodiment of the compounds of formula (VII):
$Q_1$ is as defined in any one of paragraphs (3) or (4);
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
$R_{3a1}$ is as defined in paragraph (56) above;
$R_{3a2}$ is as defined in paragraph (57) above;
n is as defined in paragraph (62) above; and
Z is as defined in any one of paragraphs (186) to (191) above.
In an embodiment of the compounds of formula (VII):
$Q_1$ is as defined in any one of paragraphs (3) or (4);
$R_{1a}$ is as defined in paragraph (32) or (35) above;
$R_{1b}$ is as defined in paragraph (44) above;
$R_{2a}$, $R_{2b}$, and $R_{2d}$ are as defined in paragraph (51) or (52);
$R_{3a1}$ is as defined in paragraph (56) above;
$R_{3a2}$ is as defined in paragraph (57) above;
n is as defined in paragraph (62) above; and
Z is as defined in any one of paragraphs (186) to (191) above.
In an embodiment of the compounds of formula (VII):
$Q_1$ is as defined in any one of paragraphs (3) or (4);
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
$R_{3a1}$ is as defined in paragraph (56) above;
$R_{3a2}$ is as defined in paragraph (57) above;
n is as defined in paragraph (62) above; and
Z is as defined in paragraph (193) above.
In a particular group of compounds of the invention, X is as defined in paragraph (15) and Z is defined as paragraph (146), i.e. the compounds have the structural formula (VIII) (a sub-definition of formula (I)) shown below:

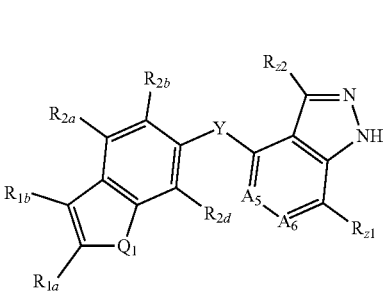

VIII wherein X, $R_{1a}$, $R_{1b}$, $R_{2a}$, $R_{2b}$, $R_{2d}$, Y, $A_5$, $A_6$, $R_{Z1}$ and $R_{Z2}$ each have any one of the meanings defined herein; or a pharmaceutically acceptable salt thereof.

In an embodiment of the compounds of formula (VIII):
$Q_1$ is as defined in any one of paragraphs (3) or (4);
$R_{1a}$ is as defined in any one of paragraphs (23) to (42) above;
$R_{1b}$ is as defined in any one of paragraphs (43) to (44) above;
$R_{2a}$, $R_{2b}$, and $R_{2d}$ are as defined in paragraph (47) or (52) above;
Y is as defined in any one of paragraphs (63) to (89) above;
$R_{Z1}$ is as defined in any one of paragraphs from (99) to (102) above;
$R_{Z2}$ is as defined in any one of paragraphs from (103) to (105) above;
$A_5$ is $CR_{16}$ and $R_{16}$ is as defined in any one of paragraphs (121) to (124) above; and
$A_6$ is $CR_{17}$ and $R_{17}$ is as defined in any one of paragraphs from (125) to (131) above.

In an embodiment of the compounds of formula (VIII):
$Q_1$ is as defined in paragraph (3) or (4)
$R_{1a}$ is as defined in any one of paragraphs (30) to (35) above;
$R_{1b}$ is as defined in paragraph (44) above;
$R_{2a}$, $R_{2b}$, and $R_{2d}$ are as defined in paragraph (51) or (52);
Y is as defined in any one of paragraphs (85) to (89) above; and
$R_{Z1}$ is as defined in any one of paragraphs from (101) to (102) above;
$R_{Z2}$ is as defined in any one of paragraphs from (104) to (105) above;
$A_5$ is $CR_{16}$ and $R_{16}$ is as defined in any one of paragraphs (123) to (124) above; and
$A_6$ is $CR_{17}$ and $R_{17}$ as defined in any one of paragraphs from (128) to (131) above.

In an embodiment of the compounds of formula (VIII):
$Q_1$ is as defined in paragraph (3) or (4)
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
Y is as defined in any one of paragraphs (85) to (89) above; and
$R_{Z1}$ is as defined in any one of paragraphs from (101) to (102) above;
$R_{Z2}$ is as defined in any one of paragraphs from (104) to (105) above;
$A_5$ is $CR_{16}$ and $R_{16}$ is as defined in any one of paragraphs (123) to (124) above; and
$A_6$ is $CR_{17}$ and $R_{17}$ as defined in any one of paragraphs from (128) to (131) above.

In a particular group of the compounds of formula (VIII):
$Q_1$ is as defined in paragraph (4)
$R_{1a}$ is as defined in any one of paragraphs (40a), (41a), (41b), (41c) or (42) above;
$R_{1b}$ is as defined in paragraph (44) above;
$R_{2a}$, $R_{2b}$, and $R_{2d}$ are as defined in paragraph (52);
Y is as defined in any one of paragraphs (87), (88) or (89) above;
$R_{Z1}$ is as defined in any one of paragraphs (102) above;
$R_{Z2}$ is as defined in paragraph (105) above;
$A_5$ is $CR_{16}$ and $R_{16}$ is as defined in paragraph (124) above; and
$A_6$ is $CR_{17}$ and $R_{17}$ as defined in any one of paragraphs from (130) to (131) above.

In a particular group of the compounds of formula (VIII):
$Q_1$ is as defined in paragraph (4)
$R_{1a}$ is as defined in paragraph (32) or (35) above;
$R_{1b}$ is as defined in paragraph (44) above;
$R_{2a}$, $R_{2b}$, and $R_{2d}$ are as defined in paragraph (52);
Y is as defined in any one of paragraphs (87), (88) or (89) above;
$R_{Z1}$ is as defined in any one of paragraphs (102) above;
$R_{Z2}$ is as defined in paragraph (105) above;
$A_5$ is $CR_{16}$ and $R_{16}$ is as defined in paragraph (124) above; and
$A_6$ is $CR_{17}$ and $R_{17}$ as defined in any one of paragraphs from (130) to (131) above.

In a particular group of compounds of the invention, X is as defined in paragraph (14), (15) or (16) and Z is defined as paragraph (142), i.e. the compounds have the structural formula (IX) or (X) (a sub-definition of formula (I)) shown below:

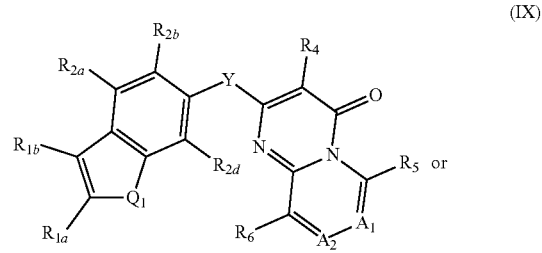

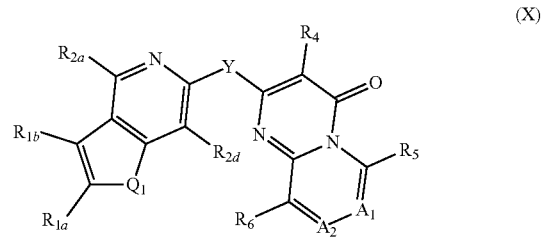

wherein $R_{1a}$, $R_{1b}$, $R_{2a}$, $R_{2b}$, $R_{2d}$, $Q_1$, Y, $A_1$, $A_2$, $R_4$, $R_5$ and $R_6$ each having any one of the meanings defined herein; or a pharmaceutically acceptable salt thereof.

In an embodiment of the compounds of formula (IX):
$Q_1$ is as defined in any one of paragraphs (1) to (4)
$R_{1a}$ is as defined in any one of paragraphs (23) to (42) above;
$R_{1b}$ is as defined in any one of paragraphs (43) to (44) above;
$R_{2a}$, $R_{2b}$ and $R_{2d}$ are as defined in any one of paragraphs (47) to (52) above;
Y is as defined in any one of paragraphs (63) to (89) above;
$A_1$ is $CR_{12}$, and $R_{12}$ is as defined in any one of paragraphs (112), (113), or (114) to (117) above;
$A_2$ is $CR_{13}$ and $R_{13}$ is as defined in any one of paragraphs (112), (113), or (118) to (120) above;
$R_4$ is as defined in paragraph (90) or (91) above;
$R_5$ is as defined in paragraph (90) or (91) above; and
$R_6$ is as defined in paragraph (90) or (91) above.

In an embodiment of the compounds of formula (IX):
$Q_1$ is as defined in paragraph (3) or (4)
$R_{1a}$ is as defined in any one of paragraphs (30) to (35) above;
$R_{1b}$ is as defined in paragraph (44) above;
$R_{2a}$, $R_{2b}$, and $R_{2d}$ are as defined in paragraph (51) or (52);

Y is as defined in any one of paragraphs (85) to (89) above;
A$_1$ is CR$_{12}$, and R$_{12}$ is as defined in any one of paragraphs (114) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (IX):
Q$_1$ is as defined in paragraph (3) or (4)
R$_{1a}$ is as defined in any one of paragraphs (38) to (42) above;
R$_{1b}$ is as defined in paragraph (44) above;
R$_{2a}$, R$_{2b}$, and R$_{2d}$ are as defined in paragraph (51) or (52);
Y is as defined in any one of paragraphs (85) to (89) above;
A$_1$ is CR$_{12}$, and R$_{12}$ is as defined in any one of paragraphs (114) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (IX):
Q$_1$ is as defined in paragraph (4)
R$_{1a}$ is as defined in any one of paragraphs (40a), (41a), (41b), (41c) or (42) above;
R$_{1b}$ is as defined in paragraph (44) above;
R$_{2a}$, R$_{2b}$, and R$_{2d}$ are as defined in paragraph (52);
Y is as defined in any one of paragraphs (88) or (89) above;
A$_1$ is CR$_{12}$, and R$_{12}$ is as defined in any one of paragraphs (116) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (IX):
Q$_1$ is as defined in paragraph (4)
R$_{1a}$ is as defined in paragraph (32) or (35) above;
R$_{1b}$ is as defined in paragraph (44) above;
R$_{2a}$ and R$_{2d}$ are as defined in paragraph (52);
Y is as defined in any one of paragraphs (88) or (89) above;
A$_1$ is CR$_{12}$, and R$_{12}$ is as defined in any one of paragraphs (116) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (X):
Q$_1$ is as defined in any one of paragraphs (1) to (4)
R$_{1a}$ is as defined in any one of paragraphs (23) to (42) above;
R$_{1b}$ is as defined in any one of paragraphs (43) to (44) above;
R$_{2a}$ and R$_{2d}$ are as defined in any one of paragraphs (47) to (52) above;
Y is as defined in any one of paragraphs (63) to (89) above;
A$_1$ is CR$_{12}$, and R$_{12}$ is as defined in any one of paragraphs (112), (113), or (114) to (117) above;
A$_2$ is CR$_{13}$ and R$_{13}$ is as defined in any one of paragraphs (112), (113) or (118) to (120) above;
R$_4$ is as defined in paragraph (90) or (91) above;
R$_5$ is as defined in paragraph (90) or (91) above; and
R$_6$ is as defined in paragraph (90) or (91) above.
In an embodiment of the compounds of formula (X):
Q$_1$ is as defined in paragraph (3) or (4)
R$_{1a}$ is as defined in any one of paragraphs (38) to (42) above;
R$_{1b}$ is as defined in paragraph (44) above;
R$_{2a}$ and R$_{2d}$ are as defined in paragraph (51) or (52);
Y is as defined in any one of paragraphs (85) to (89) above;
A$_1$ is CR$_{12}$, and R$_{12}$ is as defined in any one of paragraphs (114) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (X):
Q$_1$ is as defined in paragraph (4)
R$_{1a}$ is as defined in any one of paragraphs (40a), (41a), (41b), (41c) or (42) above;
R$_{1b}$ is as defined in paragraph (44) above;
R$_{2a}$ and R$_{2d}$ are as defined in paragraph (52);
Y is as defined in any one of paragraphs (88) or (89) above;
A$_1$ is CR$_{12}$, and R$_{12}$ is as defined in any one of paragraphs (116) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In an embodiment of the compounds of formula (X):
Q$_1$ is as defined in paragraph (4)
R$_{1a}$ is as defined in paragraph (32) or (35) above;
R$_{1b}$ is as defined in paragraph (44) above;
R$_{2a}$, R$_{2b}$, and R$_{2d}$ are as defined in paragraph (52);
Y is as defined in any one of paragraphs (88) or (89) above;
A$_1$ is CR$_{12}$, and R$_{12}$ is as defined in any one of paragraphs (116) to (117) above;
A$_2$ is CR$_{13}$ and R$_{13}$ is as defined in paragraph (120) above;
R$_4$ is as defined in paragraph (91) above;
R$_5$ is as defined in paragraph (91) above; and
R$_6$ is as defined in paragraph (91) above.
In a particular group of compounds of the invention, X is as defined in paragraph (15) and Z is defined as paragraph (147), i.e. the compounds have the structural formula (XI) (a sub-definition of formula (I)) shown below:

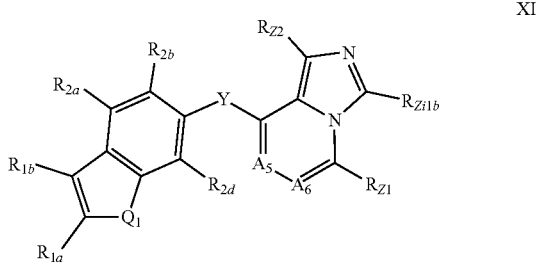

XI wherein X, R$_{1a}$, R$_{1b}$, R$_{2a}$, R$_{2b}$, R$_{2d}$, Y, A$_5$, A$_6$, R$_{Z1}$, R$_{Z2}$ and R$_{Zi1b}$ each have any one of the meanings defined herein; or a pharmaceutically acceptable salt thereof.
In an embodiment of the compounds of formula (XI):
Q$_1$ is as defined in any one of paragraphs (1) to (4)
R$_{1a}$ is as defined in any one of paragraphs (23) to (42) above;
R$_{1b}$ is as defined in any one of paragraphs (43) to (44) above;

$R_{2a}$, $R_{2b}$ and $R_{2d}$ are as defined in any one of paragraphs (47) to (52) above;
Y is as defined in any one of paragraphs (63) to (89) above; and
$A_5$ is $CR_{16}$ and $R_{16}$ is as defined in any one of paragraphs (121) to (124) above;
$A_6$ is $CR_{17}$ and $R_{17}$ is as defined in any one of paragraphs from (125) to (131) above;
$R_{Z1}$ is as defined in any one of paragraphs from (99) to (102) above;
$R_{Z2}$ is as defined in any one of paragraphs from (103) to (105) above; and
$R_{Zi1b}$ is as defined in any one of paragraphs from (103) to (105) above;
In an embodiment of the compounds of formula (XI):
$Q_1$ is as defined in paragraph (3) or (4)
$R_{1a}$ is as defined in any one of paragraphs (38) to (42) above;
$R_{1b}$ is as defined in paragraph (44) above;
$R_{2a}$, $R_{2b}$, and $R_{2d}$ are as defined in paragraph (51) or (52);
Y is as defined in any one of paragraphs (85) to (89) above; and
$A_5$ is $CR_{16}$ and $R_{16}$ is as defined in any one of paragraphs (123) to (124) above;
$A_6$ is $CR_{17}$ and $R_{17}$ as defined in any one of paragraphs from (128) to (131) above;
$R_{Z1}$ is as defined in any one of paragraphs from (101) to (102) above;
$R_{Z2}$ is as defined in any one of paragraphs from (104) to (105) above; and
$R_{Zi1b}$ is as defined in any one of paragraphs from (104) to (105) above.
In an embodiment of the compounds of formula (XI):
$Q_1$ is as defined in paragraph (3) or (4)
$R_{1a}$ is as defined in any one of paragraphs (30) to (35) above;
$R_{1b}$ is as defined in paragraph (44) above;
$R_{2a}$, $R_{2b}$, and $R_{2d}$ are as defined in paragraph (51) or (52);
Y is as defined in any one of paragraphs (85) to (89) above; and
$A_5$ is $CR_{16}$ and $R_{16}$ is as defined in any one of paragraphs (123) to (124) above;
$A_6$ is $CR_{17}$ and $R_{17}$ as defined in any one of paragraphs from (128) to (131) above;
$R_{Z1}$ is as defined in any one of paragraphs from (101) to (102) above;
$R_{Z2}$ is as defined in any one of paragraphs from (104) to (105) above; and
$R_{Zi1b}$ is as defined in any one of paragraphs from (104) to (105) above.
In a particular group of the compounds of formula (XI):
$Q_1$ is as defined in paragraph (4)
$R_{1a}$ is as defined in any one of paragraphs (40a), (41a), (41b), (41c) or (42) above;
$R_{1b}$ is as defined in paragraph (44) above;
$R_{2a}$, $R_{2b}$, and $R_{2d}$ are as defined in paragraph (52);
Y is as defined in any one of paragraphs (87), (88) or (89) above;
$A_5$ is $CR_{16}$ and $R_{16}$ is as defined in paragraph (124) above;
$A_6$ is $CR_{11}$ and $R_{17}$ as defined in any one of paragraphs from (130) to (131) above; and
$R_{Z1}$ is as defined in paragraph (102) above;
$R_{Z2}$ is as defined in paragraph (105) above; and
$R_{Zi1b}$ is as defined in paragraph (105) above.
In a particular group of the compounds of formula (XI):
$Q_1$ is as defined in paragraph (4)
$R_{1a}$ is as defined in paragraph (32) or (35) above;

$R_{1b}$ is as defined in paragraph (44) above;
$R_{2a}$, $R_{2b}$, and $R_{2d}$ are as defined in paragraph (52);
Y is as defined in any one of paragraphs (87), (88) or (89) above;
$A_5$ is $CR_{16}$ and $R_{16}$ is as defined in paragraph (124) above;
$A_6$ is $CR_{17}$ and $R_{17}$ as defined in any one of paragraphs from (130) to (131) above; and
$R_{Z1}$ is as defined in paragraph (102) above;
$R_{Z2}$ is as defined in paragraph (105) above; and
$R_{Zi1b}$ is as defined in paragraph (105) above.
In a particular group of compounds of the invention, X is as defined in paragraph (16), i.e. the compounds have the structural formula (XII) (a sub-definition of formula (I)) shown below:

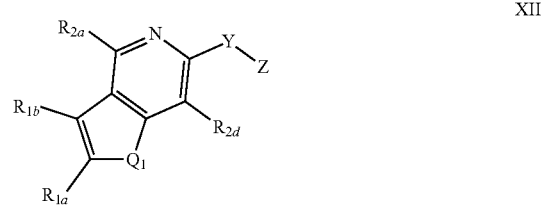

XII wherein X, $R_{1a}$, $R_{1b}$, $R_{2a}$, $R_{2d}$, Y and Z each have any one of the meanings defined herein; or a pharmaceutically acceptable salt thereof.
In an embodiment of the compounds of formula (XII):
$Q_1$ is as defined in any one of paragraphs (1) to (4);
$R_{1a}$ is as defined in any one of paragraphs (23) to (42) above;
$R_{1b}$ is as defined in any one of paragraphs (43) to (44) above;
$R_{2a}$ and $R_{2d}$ are as defined in any one of paragraphs (47) to (52) above;
Y is as defined in any one of paragraphs (63) to (89) above; and
Z is as defined in any one of paragraphs (136) to (193) above.
In an embodiment of the compounds of formula (XII):
$Q_1$ is as defined in paragraph (3) or (4)
$R_{1a}$ is as defined in any one of paragraphs (30) to (35) above;
$R_{1b}$ is as defined in paragraph (44) above;
$R_{2a}$ and $R_{2d}$ are as defined in paragraph (51) or (52);
Y is as defined in any one of paragraphs (85) to (89) above; and
Z is as defined in any one of paragraphs (189) to (193) above.
In an embodiment of the compounds of formula (XII):
$Q_1$ is as defined in paragraph (3) or (4)
$R_{1a}$ is as defined in any one of paragraphs (38) to (42) above;
$R_{1b}$ is as defined in paragraph (44) above;
$R_{2a}$ and $R_{2d}$ are as defined in paragraph (51) or (52);
Y is as defined in any one of paragraphs (85) to (89) above; and
Z is as defined in any one of paragraphs (189) to (193) above.
In a particular group of the compounds of formula (XII):
$Q_1$ is as defined in paragraph (4)
$R_{1a}$ is as defined in paragraph (32) or (35) above;
$R_{1b}$ is as defined in paragraph (44) above;
$R_{2a}$ and $R_{2d}$ are as defined in paragraph (52);
Y is as defined in paragraph (89) above;

Z is as defined in any one of paragraph (193) above.

In a particular group of the compounds of formula (XII):
Q₁ is as defined in paragraph (4)
$R_{1a}$ is as defined in any one of paragraphs (40a), (41a), (41b), (41c) or (42) above;
$R_{1b}$ is as defined in paragraph (44) above;
$R_{2a}$ and $R_{2d}$ are as defined in paragraph (52);
Y is as defined in paragraph (89) above; and
Z is as defined in paragraph (193) above.

In a particular group of compounds of the invention, Z is as defined in paragraph (155), i.e. the compounds have the structural formula (XIII) (a sub-definition of formula (I)) shown below:

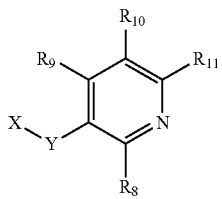

In an embodiment of the compounds of formula (XII):
X is as defined in any one of paragraphs (11) to (22) above;
Y is as defined in any one of paragraphs (63) to (89) above; and
$R_8$, $R_9$, $R_{10}$ and $R_{11}$ are as defined in any one of paragraphs (94) to (98) above.

In an embodiment of the compounds of formula (XIII):
X is as defined in paragraph (14), (15), (16) or (22) above;
Y is as defined in any one of paragraphs (85) to (89) above;
$R_8$, $R_9$, $R_{10}$ and $R_{11}$ are as defined in any one of paragraphs (94) to (98) above.

In an embodiment of the compounds of formula (XIII):
X is as defined in paragraph (14), (15), (16) or (22) above;
Y is as defined in any one of paragraphs (86), (87), (88) or (89);
$R_8$, $R_9$, $R_{10}$ and $R_{11}$ are as defined in any one of paragraphs (95a) to (97) above.

In a particular group of the compounds of formula (XIII):
X is as defined in paragraph (14), (15), (16) or (22) above;
Y is as defined in any one of paragraphs (88) or (89);

In a particular group of the compounds of formula (XIII):
X is as defined in paragraph (22) above;
Y is as defined in paragraph (89);
$R_8$, $R_9$, $R_{10}$ and $R_{11}$ are as defined in paragraph (96), (97) or (97a).

Particular compounds of the present invention include any of the compounds exemplified in the present application, or a pharmaceutically acceptable salt thereof, and, in particular, any of the following:

N-({2-[(4,4-dimethylpiperidin-1-yl)methyl]-1H-indol-6-yl}methyl)-4-oxo-4H-pyrido[1,2-a]pyrimidine-2-carboxamide N-[(2-{[(cyclobutylmethyl)amino]methyl}-1H-indol-6-yl)methyl]-4-oxo-4H-pyrido[1,2-a]pyrimidine-2-carboxamide N-[[2-[[(3,3-difluorocyclobutyl)methylamino]methyl]-1H-indol-6-yl]methyl]-4-oxo-pyrido[1,2-a]pyrimidine-2-carboxamide N-[[2-[[(1-hydroxycyclobutyl)methylamino]methyl]-1H-indol-6-yl]methyl]-4-oxo-pyrido[1,2-a]pyrimidine-2-carboxamide N-[[2-[[(1-fluorocyclobutyl)methylamino]methyl]-1H-indol-6-yl]methyl]-4-oxo-pyrido[1,2-a]pyrimidine-2-carboxamide N-[[2-[[(1-methylcyclopropyl)methylamino]methyl]-1H-indol-6-yl]methyl]-4-oxo-pyrido[1,2-a]pyrimidine-2-carboxamide.

N-[[2-(2-azabicyclo[2.1.1]hexan-2-ylmethyl)-1H-indol-6-yl]methyl]-4-oxo-pyrido[1,2-a]pyrimidine-2-carboxamide N-[[2-(3-azabicyclo[3.1.1]heptanean-3-ylmethyl)-1H-indol-6-yl]methyl]-4-oxo-pyrido[1,2-a]pyrimidine-2-carboxamide N-[[2-[[2-(hydroxymethyl)pyrrolidin-1-yl]methyl]-1H-indol-6-yl]methyl]-4-oxo-pyrido[1,2-a]pyrimidine-2-carboxamide N-[[2-(morpholinomethyl)-1H-indol-6-yl]methyl]-4-oxo-pyrido[1,2-a]pyrimidine-2-carboxamide N-[[2-[(1-adamantylamino)methyl]-1H-indol-6-yl]methyl]-4-oxo-pyrido[1,2-a]pyrimidine-2-carboxamide 4-oxo-N-[[2-(1-piperidylmethyl)-1H-indol-6-yl]methyl]pyrido[1,2-a]pyrimidine-2-carboxamide N-[[2-[(4-fluoro-1-piperidyl)methyl]-1H-indol-6-yl]methyl]-4-oxo-pyrido[1,2-a]pyrimidine-2-carboxamide 4-oxo-N-[[2-[[[rac-(1S,2S,4S)-7-oxabicyclo[2.2.1]heptane-5-en-2-yl]methylamino]methyl]-1H-indol-6-yl]methyl]pyrido[1,2-a]pyrimidine-2-carboxamide N-[[2-[[(1-hydroxycyclopentyl)methylamino]methyl]-1H-indol-6-yl]methyl]-4-oxo-pyrido[1,2-a]pyrimidine-2-carboxamide 4-oxo-N-[[2-[[[rac-(1S,2R,4S)-7-oxabicyclo[2.2.1]heptane-5-en-2-yl]methylamino]methyl]-1H-indol-6-yl]methyl]pyrido[1,2-a]pyrimidine-2-carboxamide N-[[2-[(1-bicyclo[1.1.1]pentanylamino)methyl]-1H-indol-6-yl]methyl]-4-oxo-pyrido[1,2-a]pyrimidine-2-carboxamide N-[[2-[(cyclobutylamino)methyl]-1H-indol-6-yl]methyl]-4-oxo-pyrido[1,2-a]pyrimidine-2-carboxamide N-({2-[({bicyclo[2.2.1]heptanean-2-yl}amino)methyl]-1H-indol-6-yl}methyl)-4-oxo-4H-pyrido[1,2-a]pyrimidine-2-carboxamide N-[[2-[(cyclopropylamino)methyl]-1H-indol-6-yl]methyl]-4-oxo-pyrido[1,2-a]pyrimidine-2-carboxamide N-[[2-(2-azabicyclo[2.2.2]octan-2-ylmethyl)-1H-indol-6-yl]methyl]-4-oxo-pyrido[1,2-a]pyrimidine-2-carboxamide N-[[2-[[(2,2-difluorocyclopropyl)methylamino]methyl]-1H-indol-6-yl]methyl]-4-oxo-pyrido[1,2-a]pyrimidine-2-carboxamide N-[(2-{[({3-fluorobicyclo[1.1.1]pentan-1-yl}methyl)amino]methyl}-1H-indol-6-yl)methyl]-4-oxo-4H-pyrido[1,2-a]pyrimidine-2-carboxamide N-[[2-[(cyclohexylmethylamino)methyl]-1H-indol-6-yl]methyl]-4-oxo-pyrido[1,2-a]pyrimidine-2-carboxamide N-[[2-[[(1-hydroxycyclohexyl)methylamino]methyl]-1H-indol-6-yl]methyl]-4-oxo-pyrido[1,2-a]pyrimidine-2-carboxamide N-[[2-[(cyclopentylamino)methyl]-1H-indol-6-yl]methyl]-4-oxo-pyrido[1,2-a]pyrimidine-2-carboxamide N-[[2-(cyclopentylmethylamino)methyl]-1H-indol-6-yl]methyl]-4-oxo-pyrido[1,2-a]pyrimidine-2-carboxamide N-[[2-[[(1-methoxycyclobutyl)methylamino]methyl]-1H-indol-6-yl]methyl]-4-oxo-pyrido[1,2-a]pyrimidine-2-carboxamide N-[[2-[(isobutylamino)methyl]-1H-indol-6-yl]methyl]-4-oxo-pyrido[1,2-a]pyrimidine-2-carboxamide N-[[2-[(cyclohexylamino)methyl]-1H-indol-6-yl]methyl]-4-oxo-pyrido[1,2-a]pyrimidine-2-carboxamide N-[[2-[(cyclopropylmethylamino)methyl]-1H-indol-6-yl]
methyl]-4-oxo-pyrido[1,2-a]pyrimidine-2-carboxamide
4-oxo-N-[[2-[(prop-2-ynylamino)methyl]-1H-indol-6-yl]
methyl]pyrido[1,2-a]pyrimidine-2-carboxamide
N-[[2-[(oxetan-2-ylmethylamino)methyl]-1H-indol-6-yl]
methyl]-4-oxo-pyrido[1,2-a]pyrimidine-2-carboxamide
N-[[2-[(2,2-dimethylpropylamino)methyl]-1H-indol-6-yl]
methyl]-4-oxo-pyrido[1,2-a]pyrimidine-2-carboxamide
N-[[2-[(1-bicyclo[1.1.1]pentanylmethylamino)methyl]-1H-
indol-6-yl]methyl]-4-oxo-pyrido[1,2-a]pyrimidine-2-car-
boxamide
N-{[2-({[(1S,2S)-2-hydroxycyclopentyl]amino}methyl)-
1H-indol-6-yl]methyl}-4-oxo-4H-pyrido[1,2-a]pyrimi-
dine-2-carboxamide
N-{[2-({[(1R,2R)-2-hydroxycyclopentyl]amino}methyl)-
1H-indol-6-yl]methyl}-4-oxo-4H-pyrido[1,2-a]pyrimi-
dine-2-carboxamide
N-{[2-({[(1S,2R)-2-hydroxycyclopentyl]amino}methyl)-
1H-indol-6-yl]methyl}-4-oxo-4H-pyrido[1,2-a]pyrimi-
dine-2-carboxamide
N-{[2-({[(1R,2S)-2-hydroxycyclopentyl]amino}methyl)-
1H-indol-6-yl]methyl}-4-oxo-4H-pyrido[1,2-a]pyrimi-
dine-2-carboxamide
N-[[2-[(cyclopropylmethylamino)methyl]-5-fluoro-1H-in-
dol-6-yl]methyl]-4-oxo-pyrido[1,2-a]pyrimidine-2-car-
boxamide
N-[[2-[(cyclobutylmethylamino)methyl]-5-fluoro-1H-in-
dol-6-yl]methyl]-4-oxo-pyrido[1,2-a]pyrimidine-2-car-
boxamide
4-oxo-N-[[2-[(2,2,2-trifluoroethylamino)methyl]-1H-indol-
6-yl]methyl]pyrido[1,2-a]pyrimidine-2-carboxamide
N-[(2-{[N-(cyclobutylmethyl)acetamido]methyl}-1H-in-
dol-6-yl)methyl]-4-oxo-4H-pyrido[1,2-a]pyrimidine-2-
carboxamide
4-oxo-N-{[2-(piperidin-2-yl)-1H-indol-6-yl]methyl}-4H-
pyrido[1,2-a]pyrimidine-2-carboxamide
N-[(2-{[(cyclobutylmethyl)amino]methyl}-3-fluoro-1H-in-
dol-6-yl)methyl]-4-oxo-4H-pyrido[1,2-a]pyrimidine-2-
carboxamide
N-[(2-{[(cyclobutylmethyl)amino]methyl}-1-methyl-1H-
indol-6-yl)methyl]-4-oxo-4H-pyrido[1,2-a]pyrimidine-2-
carboxamide
N-[[2-[(Cyclobutylmethylamino)-dideuterio-methyl]-1H-
indol-6-yl]methyl]-4-oxo-pyrido[1,2-a]pyrimidine-2-car-
boxamide
N-[[2-[(cyclobutylmethylamino)methyl]-1H-indol-6-yl]
methyl]-1H-indazole-4-carboxamide
N-[[2-[(cyclobutylmethylamino)methyl]-1H-pyrrolo[3,2-b]
pyridin-6-yl]methyl]-4-oxo-pyrido[1,2-a]pyrimidine-2-
carboxamide
N-(1H-indol-6-ylmethyl)-4-oxo-pyrido[1,2-a]pyrimidine-2-
carboxamide
N-(1H-indol-2-ylmethyl)-4-oxo-pyrido[1,2-a]pyrimidine-2-
carboxamide
N-(indolizin-2-ylmethyl)-4-oxo-pyrido[1,2-a]pyrimidine-2-
carboxamide
N-[(6-{[4-(1H-indazol-4-yl)-1H-1,2,3-triazol-1-yl]methyl}-
1H-indol-2-yl)methyl]cyclopropanamine
(1R,2S)-2-[[6-[[4-(1H-indazol-4-yl)triazol-1-yl]methyl]-
1H-indol-2-yl]methylamino]cyclopentanol
N-[6-[[4-(1H-indazol-4-yl)triazol-1-yl]methyl]-1H-indol-
2-yl]methyl]cyclopentanamine
N-(cyclopropylmethyl)-1-[6-[[4-(1H-indazol-4-yl)triazol-1-
yl]methyl]-1H-indol-2-yl]methanamine
1-[[[6-[[4-(1H-indazol-4-yl)triazol-1-yl]methyl]-1H-indol-
2-yl]methylamino]methyl]cyclobutanol
N-(cyclobutylmethyl)-1-[6-[[4-(1H-indazol-4-yl)triazol-1-
yl]methyl]-1H-indol-2-yl]methanamine
N-(cyclobutylmethyl)-1-[6-[[4-(1H-indazol-4-yl)triazol-1-
yl]methyl]-1H-pyrrolo[3,2-b]pyridin-2-yl]methanamine
N-(cyclobutylmethyl)-1-[6-[[4-(1H-indazol-4-yl)triazol-1-
yl]methyl]-1H-pyrrolo[3,2-c]pyridin-2-yl]methanamine
N-(cyclobutylmethyl)-1-[6-[[4-(1H-indazol-4-yl)triazol-1-
yl]methyl]-1H-pyrrolo[3,2-c]pyridin-2-yl]methanamine
2-[1-[[2-[(cyclobutylmethylamino)methyl]-1H-indol-6-yl]
methyl]triazol-4-yl]pyrido[1,2-a]pyrimidin-4-one
N-(cyclobutylmethyl)-1-[6-[[4-(6-methoxyimidazo[1,5-a]
pyridin-8-yl)triazol-1-yl]methyl]-1H-indol-2-yl]meth-
anamine
N-(cyclobutylmethyl)-1-[6-[[4-(1H-indazol-4-yl)imidazol-
1-yl]methyl]-1H-indol-2-yl]methanamine
N-(cyclobutylmethyl)-1-[6-[[3-(1H-indazol-4-yl)-1,2,4-
oxadiazol-5-yl]methyl]-1H-indol-2-yl]methanamine
N-[[2-(2-azaspiro[3.3]heptanean-2-ylmethyl)-1H-indol-6-
yl]methyl]-4-oxo-pyrido[1,2-a]pyrimidine-2-carboxam-
ide
N-[[2-[(benzylamino)methyl]-1H-indol-6-yl]methyl]-4-
oxo-pyrido[1,2-a]pyrimidine-2-carboxamide
N-[[2-(3-azabicyclo[3.1.0]hexan-3-ylmethyl)-1H-indol-6-
yl]methyl]-4-oxo-pyrido[1,2-a]pyrimidine-2-carboxam-
ide
N-[[2-[[cyclobutylmethyl(methyl)amino]methyl]-1H-indol-
6-yl]methyl]-4-oxo-pyrido[1,2-a]pyrimidine-2-carbox-
amide
N-[[2-[(cyclobutylmethylamino)methyl]-1H-pyrrolo[2,3-b]
pyridin-6-yl]methyl]-4-oxo-pyrido[1,2-a]pyrimidine-2-
carboxamide
N-[(2-{[(cyclobutylmethyl)amino]methyl}-1H-1,3-benzo-
diazol-6-yl)methyl]-4-oxo-4H-pyrido[1,2-a]pyrimidine-
2-carboxamide
N-[(2-{[(but-2-yn-1-yl)amino]methyl}-1H-indol-6-yl)
methyl]-4-oxo-4H-pyrido[1,2-a]pyrimidine-2-carboxam-
ide
N-[(2-{[(3-cyclopropylprop-2-yn-1-yl)amino]methyl}-1H-
indol-6-yl)methyl]-4-oxo-4H-pyrido[1,2-a]pyrimidine-2-
carboxamide
N-({2-[({bicyclo[3.1.0]hexan-6-yl}amino)methyl]-1H-in-
dol-6-yl}methyl)-4-oxo-4H-pyrido[1,2-a]pyrimidine-2-
carboxamide
N-[(2-{[({bicyclo[2.1.1]hexan-1-yl}methyl)amino]
methyl}-1H-indol-6-yl)methyl]-4-oxo-4H-pyrido[1,2-a]
pyrimidine-2-carboxamide
N-[(2-{[({3-methylbicyclo[1.1.1]pentan-1-yl}methyl)
amino]methyl}-1H-indol-6-yl)methyl]-4-oxo-4H-pyrido
[1,2-a]pyrimidine-2-carboxamide
N-({2-[(3-methylazetidin-1-yl)methyl]-1H-indol-6-
yl}methyl)-4-oxo-4H-pyrido[1,2-a]pyrimidine-2-carbox-
amide
N-({2-[(3-fluoroazetidin-1-yl)methyl]-1H-indol-6-
yl}methyl)-4-oxo-4H-pyrido[1,2-a]pyrimidine-2-carbox-
amide
N-({2-[(azetidin-1-yl)methyl]-1H-indol-6-yl}methyl)-4-
oxo-4H-pyrido[1,2-a]pyrimidine-2-carboxamide
N-{[2-({2-azaspiro[3.4]octan-2-yl}methyl)-1H-indol-6-yl]
methyl}-4-oxo-4H-pyrido[1,2-a]pyrimidine-2-carboxam-
ide
N-({2-[(3-hydroxyazetidin-1-yl)methyl]-1H-indol-6-
yl}methyl)-4-oxo-4H-pyrido[1,2-a]pyrimidine-2-carbox-
amide
N-({2-[(3,3-dimethylazetidin-1-yl)methyl]-1H-indol-6-
yl}methyl)-4-oxo-4H-pyrido[1,2-a]pyrimidine-2-carbox-
amide 4-oxo-N-[(2-{[3-(2,2,2-trifluoroethoxy)azetidin-1-yl]
methyl}-1H-indol-6-yl)methyl]-4H-pyrido[1,2-a]pyrimidine-2-carboxamide N-[(2-{[3-(difluoromethyl)azetidin-1-yl]methyl}-1H-indol-6-yl)methyl]-4-oxo-4H-pyrido[1,2-a]pyrimidine-2-carboxamide N-({2-[(3-methoxyazetidin-1-yl)methyl]-1H-indol-6-yl}methyl)-4-oxo-4H-pyrido[1,2-a]pyrimidine-2-carboxamide N-[(2-{[3-(tert-butoxy)azetidin-1-yl]methyl}-1H-indol-6-yl)methyl]-4-oxo-4H-pyrido[1,2-a]pyrimidine-2-carboxamide 4-oxo-N-[(2-{[3-(trifluoromethyl)azetidin-1-yl]methyl}-1H-indol-6-yl)methyl]-4H-pyrido[1,2-a]pyrimidine-2-carboxamide N-({2-[(3-ethoxyazetidin-1-yl)methyl]-1H-indol-6-yl}methyl)-4-oxo-4H-pyrido[1,2-a]pyrimidine-2-carboxamide N-{[2-({2-azaspiro[3.5]nonan-2-yl}methyl)-1H-indol-6-yl]methyl}-4-oxo-4H-pyrido[1,2-a]pyrimidine-2-carboxamide N-({2-[(2-methylazetidin-1-yl)methyl]-1H-indol-6-yl}methyl)-4-oxo-4H-pyrido[1,2-a]pyrimidine-2-carboxamide N-({2-[(3,3-dimethylpyrrolidin-1-yl)methyl]-1H-indol-6-yl}methyl)-4-oxo-4H-pyrido[1,2-a]pyrimidine-2-carboxamide N-{[2-({6-fluoro-2-azaspiro[3.3]heptanean-2-yl}methyl)-1H-indol-6-yl]methyl}-4-oxo-4H-pyrido[1,2-a]pyrimidine-2-carboxamide N-{[2-({6,6-difluoro-2-azaspiro[3.3]heptanean-2-yl}methyl)-1H-indol-6-yl]methyl}-4-oxo-4H-pyrido[1,2-a]pyrimidine-2-carboxamide N-({2-[(3-cyclobutylazetidin-1-yl)methyl]-1H-indol-6-yl}methyl)-4-oxo-4H-pyrido[1,2-a]pyrimidine-2-carboxamide N-({2-[(3-cyclopropylazetidin-1-yl)methyl]-1H-indol-6-yl}methyl)-4-oxo-4H-pyrido[1,2-a]pyrimidine-2-carboxamide N-({2-[(3-tert-butylazetidin-1-yl)methyl]-1H-indol-6-yl}methyl)-4-oxo-4H-pyrido[1,2-a]pyrimidine-2-carboxamide N-[(2-{[(1-tert-butylcyclopropyl)amino]methyl}-1H-indol-6-yl)methyl]-4-oxo-4H-pyrido[1,2-a]pyrimidine-2-carboxamide N-{[2-({[(3-methylcyclobutyl)methyl]amino}methyl)-1H-indol-6-yl]methyl}-4-oxo-4H-pyrido[1,2-a]pyrimidine-2-carboxamide 4-oxo-N-[(2-{[(2,3,3-trimethylbutan-2-yl)amino]methyl}-1H-indol-6-yl)methyl]-4H-pyrido[1,2-a]pyrimidine-2-carboxamide N-[(2-{[({imidazo[1,2-a]pyridin-2-yl}methyl)amino]methyl}-1H-indol-6-yl)methyl]-4-oxo-4H-pyrido[1,2-a]pyrimidine-2-carboxamide N-({2-[(3,3-diethylazetidin-1-yl)methyl]-1H-indol-6-yl}methyl)-4-oxo-4H-pyrido[1,2-a]pyrimidine-2-carboxamide 4-oxo-N-[(2-{[(pent-3-yn-1-yl)amino]methyl}-1H-indol-6-yl)methyl]-4H-pyrido[1,2-a]pyrimidine-2-carboxamide N-{[2-({6-azaspiro[3.4]octan-6-yl}methyl)-1H-indol-6-yl]methyl}-4-oxo-4H-pyrido[1,2-a]pyrimidine-2-carboxamide N-({2-[(2,2-dimethylpyrrolidin-1-yl)methyl]-1H-indol-6-yl}methyl)-4-oxo-4H-pyrido[1,2-a]pyrimidine-2-carboxamide N-{[2-({octahydrocyclopenta[c]pyrrol-2-yl}methyl)-1H-indol-6-yl]methyl}-4-oxo-4H-pyrido[1,2-a]pyrimidine-2-carboxamide N-{[2-({5-azaspiro[2.4]heptanean-5-yl}methyl)-1H-indol-6-yl]methyl}-4-oxo-4H-pyrido[1,2-a]pyrimidine-2-carboxamide N-[(2-{[({3-methoxybicyclo[1.1.1]pentan-1-yl}methyl)amino]methyl}-1H-indol-6-yl)methyl]-4-oxo-4H-pyrido[1,2-a]pyrimidine-2-carboxamide 4-oxo-N-[(2-{[({spiro[2.2]pentan-1-yl}methyl)amino]methyl}-1H-indol-6-yl)methyl]-4H-pyrido[1,2-a]pyrimidine-2-carboxamide 4-oxo-N-({2-[({spiro[2.3]hexan-1-yl}amino)methyl]-1H-indol-6-yl}methyl)-4H-pyrido[1,2-a]pyrimidine-2-carboxamide N-[(2-{[({3-cyanobicyclo[1.1.1]pentan-1-yl}methyl)amino]methyl}-1H-indol-6-yl)methyl]-4-oxo-4H-pyrido[1,2-a]pyrimidine-2-carboxamide N-{[2-({1-oxa-6-azaspiro[3.4]octan-6-yl}methyl)-1H-indol-6-yl]methyl}-4-oxo-4H-pyrido[1,2-a]pyrimidine-2-carboxamide N-{[2-({2-azaspiro[4.4]nonan-2-yl}methyl)-1H-indol-6-yl]methyl}-4-oxo-4H-pyrido[1,2-a]pyrimidine-2-carboxamide N-[(2-{[(1-methylcyclopentyl)amino]methyl}-1H-indol-6-yl)methyl]-4-oxo-4H-pyrido[1,2-a]pyrimidine-2-carboxamide N-{[2-(hydroxymethyl)-1H-indol-6-yl]methyl}-4-oxo-4H-pyrido[1,2-a]pyrimidine-2-carboxamide N-[(2-{[(1-cyclobutylcyclopropyl)amino]methyl}-1H-indol-6-yl)methyl]-4-oxo-4H-pyrido[1,2-a]pyrimidine-2-carboxamide N-{[2-({[(1-methylcyclobutyl)methyl]amino}methyl)-1H-indol-6-yl]methyl}-4-oxo-4H-pyrido[1,2-a]pyrimidine-2-carboxamide 4-oxo-N-[(2-{[({spiro[2.3]hexan-5-yl}methyl)amino]methyl}-1H-indol-6-yl)methyl]-4H-pyrido[1,2-a]pyrimidine-2-carboxamide N-({2-[({[3-(fluoromethyl)bicyclo[1.1.1]pentan-1-yl]methyl}amino)methyl]-1H-indol-6-yl}methyl)-4-oxo-4H-pyrido[1,2-a]pyrimidine-2-carboxamide N-[(2-{[(1-{3-fluorobicyclo[1.1.1]pentan-1-yl}ethyl)amino]methyl}-1H-indol-6-yl)methyl]-4-oxo-4H-pyrido[1,2-a]pyrimidine-2-carboxamide N-({2-[(tert-butylamino)methyl]-1H-indol-6-yl}methyl)-4-oxo-4H-pyrido[1,2-a]pyrimidine-2-carboxamide 4-(1-{[2-({2-azaspiro[3.3]heptanean-2-yl}methyl)-1H-indol-6-yl]methyl}-1H-1,2,3-triazol-4-yl)-1H-indazole N-{[2-(2-{2-azaspiro[3.3]heptanean-2-yl}ethyl)-1H-indol-6-yl]methyl}-4-oxo-4H-pyrido[1,2-a]pyrimidine-2-carboxamide ({3-fluorobicyclo[1.1.1]pentan-1-yl}methyl)({6-[(4-{imidazo[1,5-a]pyridin-8-yl}-1H-1,2,3-triazol-1-yl)methyl]-1H-indol-2-yl}methyl)amine N-[(2-{[({3-fluorobicyclo[1.1.1]pentan-1-yl}methyl)amino]methyl}-1H-indol-6-yl)methyl]-5-oxo-5H-[1,3]thiazolo[3,2-a]pyrimidine-7-carboxamide N-[(2-{[({bicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide N-[(2-{[({3-fluorobicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide N-[(2-{[(cyclobutylmethyl)amino]methyl}-1H-pyrrolo[3,2-b]pyridin-6-yl)methyl]-4-oxo-4H-pyrido[1,2-a]pyrimidine-2-carboxamide N-[(2-{[({3-methylbicyclo[1.1.1]pentan-1-yl}methyl)
amino]methyl}-1H-pyrrolo[3,2-c]pyridin-6-yl)methyl]-
4-oxo-4H-pyrido[1,2-a]pyrimidine-2-carboxamide N-[(2-{[(cyclobutylmethyl)amino]methyl}-1H-pyrrolo[3,2-
c]pyridin-6-yl)methyl]-4-oxo-4H-pyrido[1,2-a]pyrimi-
dine-2-carboxamide N-[(2-{[({bicyclo[1.1.1]pentan-1-yl}methyl)amino]
methyl}-1H-pyrrolo[3,2-c]pyridin-6-yl)methyl]-4-oxo-
4H-pyrido[1,2-a]pyrimidine-2-carboxamide N-[(2-{[({3-fluorobicyclo[1.1.1]pentan-1-yl}methyl)
amino]methyl}-1H-pyrrolo[3,2-c]186yridine-6-yl)
methyl]-4-oxo-4H-pyrido[1,2-a]pyrimidine-2-carboxam-
ide N-[(2-{[(cyclobutylmethyl)amino]methyl}-1H-indol-6-yl)
methyl]-4-oxo-4H,6H,7H,8H,9H-pyrido[1,2-a]pyrimi-
dine-2-carboxamide (cyclobutylmethyl)({6-[(4-{1H-pyrrolo[2,3-b]pyridin-5-
yl}-1H-imidazol-1-yl)methyl]-1H-indol-2-yl}methyl)
amine (cyclobutylmethyl)({6-[(4-{imidazo[1,5-a]pyridin-8-yl}-
1H-1,2,3-triazol-1-yl)methyl]-1H-indol-2-yl}methyl)
amine N-[(2-{[(2,2-dimethylpropyl)amino]methyl}-1H-indol-6-
yl)methyl]-1H-pyrrolo[2,3-b]pyridine-5-carboxamide N-[(2-{[(cyclobutylmethyl)amino]methyl}-1H-indol-6-yl)
methyl]-1H-pyrrolo[2,3-b]pyridine-5-carboxamide (cyclobutylmethyl)({6-[(4-{1H-pyrrolo[2,3-b]pyridin-5-
yl}-1H-1,2,3-triazol-1-yl)methyl]-1H-indol-2-yl}methyl)
amine N-[[2-(2-azabicyclo[2.2.1]heptanean-2-ylmethyl)-1H-in-
dol-6-yl]methyl]-4-oxo-pyrido[1,2-a]pyrimidine-2-car-
boxamide N-[(3-fluoro-1-bicyclo[1.1.1]pentanyl)methyl]-1-[6-[(4-
imidazo[1,5-a]pyridin-8-yltriazol-1-yl)methyl]-1H-pyr-
rolo[3,2-c]pyridin-2-yl]methanamine (cyclobutylmethyl)[(6-{[1-(1H-indazol-4-yl)-1H-1,2,3-tri-
azol-4-yl]methyl}-1H-indol-2-yl)methyl]amine

[(3,3-difluorocyclobutyl)methyl][(6-{[1-(1H-indazol-4-yl)-
1H-1,2,3-triazol-4-yl]methyl}-1H-indol-2-yl)methyl]
amine (cyclobutylmethyl)[(6-{[1-(isoquinolin-4-yl)-1H-1,2,3-tri-
azol-4-yl]methyl}-1H-indol-2-yl)methyl]amine (cyclobutylmethyl)({6-[(1-{imidazo[1,5-a]pyridin-8-yl}-
1H-1,2,3-triazol-4-yl)methyl]-1H-indol-2-yl}methyl)
amine 3-[1-({2-[({(Bicyclo[1.1.1]pent-1-yl)methyl}amino)
methyl]-1H-indol-6-yl}methyl)-1H-1,2,3-triazol-4-yl]-5-
methoxy-2-pyridinecarbonitrile;

3-[1-({2-[({(3-Fluorobicyclo[1.1.1]pent-1-yl)
methyl}amino)methyl]-1H-indol-6-yl}methyl)-1H-1,2,3-
triazol-4-yl]-5-methoxy-2-pyridinecarbonitrile;

5-Methoxy-3-[1-({2-[({(3-methylbicyclo[1.1.1]pent-1-yl)
methyl}amino)methyl]-1H-indol-6-yl}methyl)-1H-1,2,3-
triazol-4-yl]-2-pyridinecarbonitrile;

3-{1-[(2-{[(Cyclobutylmethyl)amino]methyl}-1H-indol-6-
yl)methyl]-1H-1,2,3-triazol-4-yl}-5-methoxy-2-pyridin-
ecarbonitrile;

3-{1-[(2-{(6-Aza-6-spiro[3.4]octyl)methyl}-1H-indol-6-yl)
methyl]-1H-1,2,3-triazol-4-yl}-5-methoxy-2-pyridin-
ecarbonitrile;

3-[1-({2-[(4,4-Dimethyl-1-piperidyl)methyl]-1H-indol-6-
yl}methyl)-1H-1,2,3-triazol-4-yl]-5-methoxy-2-pyridin-
ecarbonitrile;

N-((2-((6-azaspiro[3.4]octan-6-yl)methyl)-1H-pyrrolo[3,2-
c]pyridin-6-yl)methyl)-4-oxo-4H-pyrido[1,2-a]pyrimi-
dine-2-carboxamide 3-(1-((2-(((cyclobutylmethyl)amino)methyl)-1H-indol-6-yl)
methyl)-1H-1,2,3-triazol-4-yl)-5-fluoropicolinonitrile 1-cyclobutyl-N-((6-((4-(5-methoxypyridin-3-yl)-1H-1,2,3-
triazol-1-yl)methyl)-1H-indol-2-yl)methyl)methanamine;

5-chloro-3-(1-((2-(((cyclobutylmethyl)amino)methyl)-1H-
indol-6-yl)methyl)-1H-1,2,3-triazol-4-yl)picolinonitrile 2-((6-azaspiro[3.4]octan-6-yl)methyl)-6-((4-(imidazo[1,5-
a]pyridin-8-yl)-1H-1,2,3-triazol-1-yl)methyl)-1H-pyrrolo
[3,2-c]pyridine.

Further compounds of the invention, or a pharmaceutically acceptable salts thereof, include any one of the following:

3-[1-({2-[({(Bicyclo[1.1.1]pent-1-yl)methyl}amino)
methyl]-1H-indol-6-yl}methyl)-1H-1,2,3-triazol-4-yl]-5-
methoxy-2-pyridinecarbonitrile;

3-[1-({2-[({(3-Fluorobicyclo[1.1.1]pent-1-yl)
methyl}amino)methyl]-1H-indol-6-yl}methyl)-1H-1,2,3-
triazol-4-yl]-5-methoxy-2-pyridinecarbonitrile;

5-Methoxy-3-[1-({2-[({(3-methylbicyclo[1.1.1]pent-1-yl)
methyl}amino)methyl]-1H-indol-6-yl}methyl)-1H-1,2,3-
triazol-4-yl]-2-pyridinecarbonitrile;

3-{1-[(2-{[(Cyclobutylmethyl)amino]methyl}-1H-indol-6-
yl)methyl]-1H-1,2,3-triazol-4-yl}-5-methoxy-2-pyridin-
ecarbonitrile;

3-{1-[(2-{(6-Aza-6-spiro[3.4]octyl)methyl}-1H-indol-6-yl)
methyl]-1H-1,2,3-triazol-4-yl}-5-methoxy-2-pyridin-
ecarbonitrile; and 3-[1-({2-[(4,4-Dimethyl-1-piperidyl)methyl]-1H-indol-6-
yl}methyl)-1H-1,2,3-triazol-4-yl]-5-methoxy-2-pyridin-
ecarbonitrile.

Particular compounds of the present invention include any of the compounds exemplified in the present application, or a pharmaceutically acceptable salt thereof, and, in particular, any of the following:

N-[[2-[[(1-hydroxycyclobutyl)methylamino]methyl]-1H-in-
dol-6-yl]methyl]-4-oxo-pyrido[1,2-a]pyrimidine-2-car-
boxamide;

N-[[2-[[(1-fluorocyclobutyl)methylamino]methyl]-1H-in-
dol-6-yl]methyl]-4-oxo-pyrido[1,2-a]pyrimidine-2-car-
boxamide;

N-[[2-[(4,4-dimethyl-1-piperidyl)methyl]-1H-indol-6-yl]
methyl]-4-oxo-pyrido[1,2-a]pyrimidine-2-carboxamide N-[[2-[(cyclobutylmethylamino)methyl]-1H-indol-6-yl]
methyl]-4-oxo-pyrido[1,2-a]pyrimidine-2-carboxamide N-[[2-[(cyclobutylmethylamino)methyl]-1H-indol-6-yl]
methyl]-1H-pyrrolo[2,3-b]pyridine-5-carboxamide N-(cyclobutylmethyl)-1-[6-[[4-(1H-pyrazolo[4,3-c]pyridin-
4-yl)triazol-1-yl]methyl]-1H-indol-2-yl]methanamine N-(cyclobutylmethyl)-1-[6-[[4-(1H-indazol-4-yl)triazol-1-
yl]methyl]-1H-indol-2-yl]methanamine N-(cyclobutylmethyl)-1-[6-[[4-(1H-pyrrolo[2,3-b]pyridin-
5-yl)triazol-1-yl]methyl]-1H-indol-2-yl]methanamine N-[[2-[(2,2-dimethylpropylamino)methyl]-1H-indol-6-yl]
methyl]-4-oxo-pyrido[1,2-a]pyrimidine-2-carboxamide N-[[2-[(1-bicyclo[1.1.1]pentanylmethylamino)methyl]-1H-
indol-6-yl]methyl]-4-oxo-pyrido[1,2-a]pyrimidine-2-car-
boxamide 1-[[[6-[[4-(1H-indazol-4-yl)triazol-1-yl]methyl]-1H-indol-
2-yl]methylamino]methyl]cyclobutanol N-[[2-[[(3-fluoro-1-bicyclo[1.1.1]pentanyl)methylamino]
methyl]-1H-indol-6-yl]methyl]-4-oxo-pyrido[1,2-a]py-
rimidine-2-carboxamide N-[[2-[[(3,3-difluorocyclobutyl)methylamino]methyl]-1H-
indol-6-yl]methyl]-4-oxo-pyrido[1,2-a]pyrimidine-2-car-
boxamide N-[(3,3-difluorocyclobutyl)methyl]-1-[6-[[1-(1H-indazol-
4-yl)triazol-4-yl]methyl]-1H-indol-2-yl]methanamine N-[[2-[(oxetan-2-ylmethylamino)methyl]-1H-indol-6-yl]methyl]-4-oxo-pyrido[1,2-a]pyrimidine-2-carboxamide N-[[2-[(cyclobutylmethylamino)methyl]-1H-indol-6-yl]methyl]-1H-indazole-4-carboxamide N-[[2-[[(1-fluorocyclobutyl)methylamino]methyl]-1H-indol-6-yl]methyl]-4-oxo-pyrido[1,2-a]pyrimidine-2-carboxamide N-[[2-[(cyclobutylmethylamino)methyl]-3H-benzimidazol-5-yl]methyl]-4-oxo-pyrido[1,2-a]pyrimidine-2-carboxamide N-(cyclobutylmethyl)-1-[6-[[1-(4-isoquinolyl)triazol-4-yl]methyl]-1H-indol-2-yl]methanamine 4-oxo-N-[[2-[(prop-2-ynylamino)methyl]-1H-indol-6-yl]methyl]pyrido[1,2-a]pyrimidine-2-carboxamide N-[[2-[(2,2-dimethylpropylamino)methyl]-1H-indol-6-yl]methyl]-1H-pyrrolo[2,3-b]pyridine-5-carboxamide N-[[2-[(cyclopropylmethylamino)methyl]-1H-indol-6-yl]methyl]-4-oxo-pyrido[1,2-a]pyrimidine-2-carboxamide N-[[2-[(isobutylamino)methyl]-1H-indol-6-yl]methyl]-4-oxo-pyrido[1,2-a]pyrimidine-2-carboxamide N-[[2-[(cyclohexylamino)methyl]-1H-indol-6-yl]methyl]-4-oxo-pyrido[1,2-a]pyrimidine-2-carboxamide.

The various functional groups and substituents making up the compounds of the formula (I) are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula (I) (and compounds of formula (II), (III) and (IV)) may exist in solvated as well as unsolvated forms such as, for example, hydrated forms. It is to be understood that the invention encompasses all such solvated forms that possess antiproliferative activity.

It is also to be understood that certain compounds of the formula (I) (and compounds of formula (II), (Ill) and (IV)) may exhibit polymorphism, and that the invention encompasses all such forms that possess antiproliferative activity.

Compounds of the formula (I) (and compounds of formula (II), (Ill) and (IV)) may exist in a number of different tautomeric forms and references to compounds of the formula (I) include all such forms. For the avoidance of doubt, where a compound can exist in one of several tautomeric forms, and only one is specifically described or shown, all others are nevertheless embraced by formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

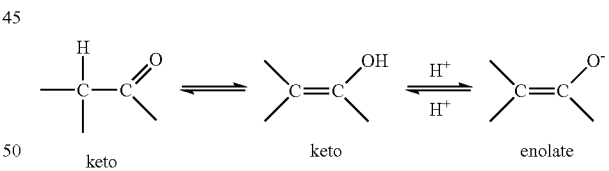

keto            keto            enolate

Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula (I) may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula (I) and in-vivo cleavable amide derivatives that may be formed at a carboxy group or an amino group in a compound of the formula (I).

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymoloqy*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula (I) that possesses a carboxy group is, for example, an in vivo cleavable ester thereof. An in vivo cleavable ester of a compound of the formula (I) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula (I) that possesses a hydroxy group is, for example, an in vivo cleavable ester or ether thereof. An in vivo cleavable ester or ether of a compound of the formula (I) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a $C_{1-4}$alkylamine such as methylamine, a $(C_{1-4}$alkyl)$_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula (I) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction.

The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of the variable groups. Suitable processes for their preparation are described further in the accompanying Examples.

Once a compound of formula I has been synthesised by any one of the processes defined herein, the processes may then further comprise the additional steps of:
 (i) removing any protecting groups present;
 (ii) converting the compound formula I into another compound of formula I;
 (iii) forming a pharmaceutically acceptable salt, hydrate or solvate thereof; and/or
 (iv) forming a prodrug thereof.

The resultant compounds of formula I can be isolated and purified using techniques well known in the art.

Biological Activity

The METTL3 enzyme and cell assays described in accompanying Example section may be used to measure the pharmacological effects of the compounds of the present invention.

Although the pharmacological properties of the compounds of formula I vary with structural change, as expected, the compounds of the invention were found to be active in these METTL3 assays.

In general, the compounds of the invention demonstrate an $IC_{50}$ of 10 µM or less in the METTL3 enzyme assay described herein, with preferred compounds of the invention demonstrating an $IC_{50}$ of 5 µM or less and the most preferred compounds of the invention demonstrating an $IC_{50}$ of 2 µM or less.

In the METTL3 cell assay described in the Example section, the compounds of formula (I) suitably possess an activity of less than 10 µM, with preferred compounds of the invention demonstrating an $IC_{50}$ of 5 µM or less and the most preferred compounds demonstrating an activity of 2 µM or less.

Pharmaceutical Compositions

According to a further aspect of the invention there is provided a pharmaceutical composition which comprises a compound of the invention as defined hereinbefore, or a pharmaceutically acceptable salt thereof, and one or more pharmaceutically acceptable excipients.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition and/or treat or prevent an autoimmune disease referred to herein, slow its progression and/or reduce the symptoms associated with the condition and/or disease.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of METTL3 activity.

The present invention therefore provides a method of inhibiting METTL3 activity in vitro or in vivo, said method comprising contacting a cell with an effective amount of a compound, or a pharmaceutically acceptable salt thereof, or a pharmaceutical composition as defined herein.

The present invention also provides a method of treating a disease or disorder in which METTL3 activity is implicated in a patient in need of such treatment, said method comprising administering to said patient a therapeutically effective amount of a compound, or a pharmaceutically acceptable salt thereof, or a pharmaceutical composition as defined herein. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder, infection (e.g. viral infection) or a depressive disorder.

The present invention provides a method of inhibiting cell proliferation, in vitro or in vivo, said method comprising contacting a cell with an effective amount of a compound, or a pharmaceutically acceptable salt thereof, as defined herein.

The present invention provides a method of treating a proliferative disorder, said method comprising administering to a subject in need thereof a therapeutically effective amount of a compound, or a pharmaceutically acceptable salt thereof, or a pharmaceutical composition as defined herein.

The present invention provides a method of treating cancer, said method comprising administering to a subject in need thereof a therapeutically effective amount of a compound, or a pharmaceutically acceptable salt thereof, or a pharmaceutical composition as defined herein. Suitably the cancer is lung cancer, renal cancer, solid organ cancer, pancreatic cancer or leukaemia suitably AML leukaemia or chronic myeloid leukaemia.

The present invention provides a method of treating leukaemia, said method comprising administering to a subject in need thereof a therapeutically effective amount of a compound, or a pharmaceutically acceptable salt thereof, or a pharmaceutical composition as defined herein.

The present invention provides a method of treating AML leukaemia, said method comprising administering to a subject in need thereof a therapeutically effective amount of a compound, or a pharmaceutically acceptable salt thereof, or a pharmaceutical composition as defined herein.

The present invention provides a method of treating an autoimmune disease, said method comprising administering to a subject in need thereof a therapeutically effective amount of a compound, or a pharmaceutically acceptable salt thereof, or a pharmaceutical composition as defined herein. Suitably the autoimmune disease is colitis, multiple sclerosis, rheumatoid arthritis, lupus, cirrhosis, or dermatitis.

The present invention provides a method of treating a neurological disease, said method comprising administering to a subject in need thereof a therapeutically effective amount of a compound, or a pharmaceutically acceptable salt thereof, or a pharmaceutical composition as defined herein.

The present invention provides a method of treating an infectious disease, said method comprising administering to a subject in need thereof a therapeutically effective amount of a compound, or a pharmaceutically acceptable salt thereof, or a pharmaceutical composition as defined herein.

In another aspect, the present invention provides a method of treating a viral infection, said method comprising administering to a subject in need thereof a therapeutically effective amount of a compound as defined herein, or a pharmaceutically acceptable salt, or a pharmaceutical composition as defined herein. Suitably, the viral infection is a RNA viral infection. Suitably, the viral infection is human papillomavirus (HPV) or hepatitis.

The present invention provides a method of treating an inflammatory disease, said method comprising administering to a subject in need thereof a therapeutically effective amount of a compound, or a pharmaceutically acceptable salt thereof, or a pharmaceutical composition as defined herein.

METTL3 inhibitors are also potentially useful therapeutic agents for treating diseases related to the re-activation of the silenced X-chromosome (Patil et al, Nature, 2016 Sep. 15; 537(7620):369-373). As such, they are potentially effective therapeutic agents for the treatment of Rett syndrome.

The present invention further provides a method of treating a disease related to the re-activation of the silenced X-chromosome, said method comprising administering to a subject in need thereof a therapeutically effective amount of a compound, or a pharmaceutically acceptable salt thereof, or a pharmaceutical composition as defined herein.

The present invention further provides a method of treating Rett syndrome, said method comprising administering to a subject in need thereof a therapeutically effective amount of a compound, or a pharmaceutically acceptable salt thereof, or a pharmaceutical composition as defined herein.

The present invention provides a compound, or a pharmaceutically acceptable salt thereof, or a pharmaceutical composition as defined herein for use in therapy.

The present invention provides a compound, or a pharmaceutically acceptable salt thereof, or a pharmaceutical composition as defined herein for use in the treatment of a proliferative condition.

The present invention provides a compound, or a pharmaceutically acceptable salt thereof, or a pharmaceutical composition as defined herein for use in the treatment of cancer. In a particular embodiment, the cancer is human cancer. Suitably the cancer is lung cancer, renal cancer, solid organ cancer, pancreatic cancer or leukaemia suitably AML leukaemia or chronic myeloid leukaemia.

The present invention provides a compound, or a pharmaceutically acceptable salt thereof, or a pharmaceutical composition as defined herein for use in the treatment of leukaemia.

The present invention provides a compound, or a pharmaceutically acceptable salt thereof, or a pharmaceutical composition as defined herein for use in the treatment of AML leukaemia.

The present invention provides a compound, or a pharmaceutically acceptable salt thereof, or a pharmaceutical composition as defined herein for use in the inhibition of METTL3 activity.

The present invention provides a compound, or a pharmaceutically acceptable salt thereof, or a pharmaceutical composition as defined herein for use in the treatment of an autoimmune disease. Suitably the autoimmune disease is colitis, multiple sclerosis, rheumatoid arthritis, lupus, cirrhosis, or dermatitis.

The present invention provides a compound, or a pharmaceutically acceptable salt thereof, or a pharmaceutical composition as defined herein for use in the treatment of an neurological disease.

The present invention provides a compound, or a pharmaceutically acceptable salt thereof, or a pharmaceutical composition as defined herein for use in the treatment of an infectious disease.

The present invention provides a compound, or a pharmaceutically acceptable salt thereof, or a pharmaceutical composition as defined herein for use in the treatment of an inflammatory disease.

In another aspect, the present invention provides a compound as defined herein, or a pharmaceutically acceptable salt thereof, or a pharmaceutical composition as defined herein, for use in the treatment of a viral infection. Suitably, the viral infection is a RNA viral infection. Suitably, the viral infection is human papillomavirus (HPV) or hepatitis.

The present invention provides a compound, or a pharmaceutically acceptable salt thereof, as defined herein for use in the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The present invention provides a compound, or a pharmaceutically acceptable salt thereof, or a pharmaceutical composition as defined herein, for use in the treatment of a disease related to the re-activation of the silenced X-chromosome.

The present invention provides a compound, or a pharmaceutically acceptable salt thereof, or a pharmaceutical composition as defined herein, for use in the treatment of Rett syndrome.

The present invention provides a use of a compound, or a pharmaceutically acceptable salt thereof, as defined herein in the manufacture of a medicament for the treatment of a proliferative condition.

The present invention provides a use of a compound, or a pharmaceutically acceptable salt thereof, as defined herein in the manufacture of a medicament for the treatment of cancer. Suitably, the medicament is for use in the treatment of human cancers. Suitably the cancer is lung cancer, renal cancer, solid organ cancer, pancreatic cancer or leukaemia suitably AML leukaemia or chronic myeloid leukaemia.

The present invention provides a use of a compound, or a pharmaceutically acceptable salt thereof, as defined herein in the manufacture of a medicament for the treatment of leukaemia.

The present invention provides a use of a compound, or a pharmaceutically acceptable salt thereof, as defined herein in the manufacture of a medicament for the treatment of AML leukaemia.

The present invention provides a use of a compound, or a pharmaceutically acceptable salt thereof, as defined herein in the manufacture of a medicament for the treatment of an autoimmune disease. Suitably the autoimmune disease is colitis, multiple sclerosis, rheumatoid arthritis, lupus, cirrhosis, or dermatitis.

The present invention provides a use of a compound, or a pharmaceutically acceptable salt thereof, as defined herein in the manufacture of a medicament for the treatment of a neurological disease.

The present invention provides a use of a compound, or a pharmaceutically acceptable salt thereof, as defined herein in the manufacture of a medicament for the treatment of an inflammatory disease.

In another aspect, the present invention provides the use of a compound as defined herein, or a pharmaceutically acceptable salt thereof, in the manufacture of a medicament for use in the treatment of a viral infection. Suitably, the viral infection is a RNA viral infection. Suitably, the viral infection is human papillomavirus (HPV) or hepatitis.

The present invention provides a use of a compound, or a pharmaceutically acceptable salt thereof, as defined herein in the manufacture of a medicament for the treatment of an infectious disease.

The present invention provides a use of a compound, or a pharmaceutically acceptable salt thereof, as defined herein in the manufacture of a medicament for the inhibition of METTL3 activity.

The present invention provides a use of a compound, or a pharmaceutically acceptable salt thereof, as defined herein in the manufacture of a medicament for the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The present invention provides a use of a compound, or a pharmaceutically acceptable salt thereof, as defined herein in the manufacture of a medicament for the treatment of a disease related to the re-activation of the silenced X-chromosome.

The present invention provides a use of a compound, or a pharmaceutically acceptable salt thereof, as defined herein in the manufacture of a medicament for the treatment of Rett syndrome.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain and skin.

The anti-proliferative effects of the compounds of the present invention have particular application in the treatment of human cancers (by virtue of their inhibition of METTL3 activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase]; (iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];
(vi) vascular damaging agents such as Combretastatin A4 and compounds disclosed in International Patent Applications WO 99/02166, WO 00/40529, WO 00/41669, WO 01/92224, WO 02/04434 and WO 02/08213;
(vii) an endothelin receptor antagonist, for example zibotentan (ZD4054) or atrasentan;
(viii) antisense therapies, for example those which are directed to the targets listed above, such as ISIS 2503, an anti-ras antisense;
(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;
(x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and
(xi) Agents used to treat AML leukaemia, including for example, cytarabine, FLT3 inhibitors, BCL2 inhibitors (e.g. venetoclax) or IDH1/2 inhibitors.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt thereof, and any one of the anti-tumour agents listed herein above.

In a further aspect of the invention there is provided a compound of the invention or a pharmaceutically acceptable salt thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt thereof, in combination with an anti-tumour agent (optionally selected from one listed herein above), in association with a pharmaceutically acceptable diluent or carrier.

In another embodiment, the invention relates to a therapeutic combination comprising a compound as defined herein and another agent used to treat AML leukaemia e.g., cytarabine, FLT3 inhibitors, BCL2 inhibitors or IDH1/2 inhibitors. Suitably, the agent used to treat AML leukaemia is a BCL2 inhibitor, such as venetoclax.

EXAMPLES

The Following Abbreviations have been Used in the Examples:
AIBN—Azobisisobutyronitrile
DBU—1,8-Diazabicyclo[5.4.0]undec-7-ene
DCE—Dichloroethane
DCM—Dichlorometan
DIBAL—Diisobutylaluminium hydride
DIPEA—N-ethyl-N-isopropyl-propan-2-amine
DMAP—4-Dimethylaminopyridine
DMF—Dimethylformamide
DMSO—Dimethyl sulfoxide
DPPA—Diphenylphosphoryl azide
HATU—[dimethylamino(triazolo[4,5-b]pyridin-3-yloxy)methylene]-dimethyl-ammonium; hexafluorophosphate
HPLC—High performance liquid chromatography
IPA—Isopropanol
LCMS—Liquid chromatograph mass spectrometry
NBS—N-Bromosuccinimide
NMP—N-Methyl-2-pyrrolidone
Phase sep cartridge—Telos phase separator 6 mL
RBF—Round bottomed flask
RM—Reaction mixture
RT—Retention Time
STAB—Sodium triacetoxyborohydride
T3P—Propylphosphonic anhydride
TBAF—Tetra-n-butylammonium fluoride
TEA—Triethylamine
TFA—Trifluoroacetic acid
TFAA—Trifluoroacetic anhydride
THF—Tetrahydrofuran
The Following Methodologies have been Used in the Examples:
LCMS method A refers to low pH analysis using a mobile phase consisting of 0.1% formic acid in a gradient of 5-100% MeCN in water over 1.2 min at a flow rate of 1.2 mL/min. The stationary phase consisted of a Kinetex Core-Shell C18, 2.1 mm×50 mm, 5 μm. The experiment was run at 40° C.

LCMS Method B refers to high pH analysis using a mobile phase consisting of 2 mM ammonium bicarbonate, buffered to pH10 in a gradient of 5-100% MeCN in water over 2.1 min at a flow rate of 1.0 mL/min. The stationary phase consisted of a Phenomenex Gemini-NX C18, 2.0×50 mm, 3 μm. The experiment was run at 40° C.

LCMS Method C refers to high pH analysis using a mobile phase consisting of 2 mM ammonium bicarbonate, buffered to pH10 in a gradient of 5-100% MeCN in water over 5.8 min at a flow rate of 0.6 mL/min. The stationary phase consisted of a Waters UPLC® BEH™ C18, 2.1×100 mm, 1.7 μm. The experiment was run at 40° C.

LCMS Method D refers to high pH analysis using a mobile phase consisting of 2 mM ammonium bicarbonate, buffered to pH10 in a gradient of 5-100% MeCN in water over 5.9 min at a flow rate of 0.6 mL/min. The stationary phase consisted of a Phenomenex Gemini-NX C18, 2.0×100 mm, 3 μm. The experiment was run at 40° C.

LCMS method E refers to low pH analysis using a mobile phase consisting of 0.1% formic acid in a gradient of 5-100% MeCN in water over 5.3 min at a flow rate of 0.6 mL/min. The stationary phase consisted of a Phenomenex Kinetix-XB C18, 2.1 mm×100 mm, 1.7 μm. The experiment was run at 40° C.

LCMS method F refers to high pH analysis using a mobile phase consisting of 2 mM ammonium bicarbonate, buffered to pH10 in a gradient of 5-100% MeCN in water over 0.75 min at a flow rate of 1.0 mL/min. The stationary phase consisted of a Waters UPLC® BEH™ C18, 2.1×100 mm, 1.7 μm. The experiment was run at 40° C.

Method G refers to low pH analysis using a mobile phase consisting of 0.1% Formic acid in water (pH=2.70) in a gradient of 3-100% of 0.1% formic acid in water:acetonitrile (10:90) over 3.00 min at a flow rate of 0.8 mL/min. The stationary phase consisted of C18, 50*2.1 mm, 1.6 μm column. The experiment was run at 35° C.

Method H refers to a high pH analysis using a mobile phase consisting of 5 mM ammonium bicarbonate, (pH 7.35) in a gradient of MeCN in water over 3.0 min at a flow rate of 0.5 mL/min. The stationary phase consisted of C18, 50*2.1 mm, 2.5 μm. The experiment was run at 35° C.

Method I refers to a high pH analysis using a mobile phase consisting of 5 mM ammonium bicarbonate, (pH 7.35) in a gradient of MeCN in water over 3.0 min at a flow rate of 0.5 mL/min. The stationary phase consisted of C18, 50*2.1 mm, 2.5 μm. The experiment was run at 35° C.

Method J refers to high pH analysis using a mobile phase consisting of 2 mM ammonium bicarbonate, buffered to pH10 in a gradient of 1-100% MeCN over 1.35 min at a flow rate of 1 mL/min. The stationary phase consisted of a Waters UPLC® BEH™ C18 2.1×30 mm, 1.7 μm. The experiment was run at 40° C.

Method K refers to a Low pH analysis using a mobile phase consisting of 0.1% Formic acid in water in a gradient of 5-100% of 0.1% formic acid in water: 0.1% formic acid in acetonitrile over 5.4 min at a flow rate of 0.6 mL/min. The stationary phase consisted of Phenomenex Kinetex Core-Shell C8 50×2.1 mm, 2.6 um (protected by a "security Guard" column. The experiment was run at 40° C.

Method L refers to a Low pH analysis using a mobile phase consisting of 0.1% Formic acid in water in a gradient of 5-100% of 0.1% formic acid in water: 0.1% formic acid in acetonitrile over 1.1 min at a flow rate of 0.9 mL/min. The stationary phase consisted of Waters UPLC® BEH™ C18 2.1×50 mm, 1.7 μm. The experiment was run at 40° C.

Method M refers to a Low pH analysis using a mobile phase consisting of 0.1% Formic acid in water in a gradient of 5-100% of 0.1% formic acid in water: 0.1% formic acid in acetonitrile over 2.25 min at a flow rate of 1.2 mL/min. The stationary phase consisted of Phenomenex Kinetex Core-Shell C8 50×2.1 mm, 2.6 um. The experiment was run at 40° C.

LC04_ABF3 refers to high pH analysis using a mobile phase consisting of 5 mM ammonium bicarbonate, buffered to pH10 in a gradient of 50-100% acetonitrile in water over 2.70 min at a flow rate of 1.0 mL/min. The stationary phase consisted of a Waters UPLC® C18 4.6×50 mm, 3.5 μm. The experiment was run at 30° C.

LC04_ABR2 refers to high pH analysis using a mobile phase consisting of 5 mM ammonium bicarbonate, buffered to pH10 in a gradient of 10-100% acetonitrile in water over 9.0 min at a flow rate of 1.0 mL/min. The stationary phase consisted of a Waters UPLC® BEH™ C18 4.6×150 mm, 3.5 μm. The experiment was run at 30° C.

LC03_ABR2 refers to high pH analysis using a mobile phase consisting of 5 mM ammonium bicarbonate, buffered to pH10 in a gradient of 3-100% Acetonitrile in water over 3.0 min at a flow rate of 0.5 mL/min. The stationary phase consisted of a Waters UPLC® BEH™ C18 2.1×50 mm, 2.5 μm. The experiment was run at 30° C.

UC02_FAR1 refers to low pH analysis using a mobile phase consisting of 0.1% Formic acid in water (pH=2.70) in a gradient of 3-100% of 0.1% formic acid in water:acetonitrile (10:90) in water over 3.00 min at a flow rate of 0.8 mL/min. The stationary phase consisted of a Waters UPLC® BEH™ 018 2.1×50 mm, 2.5 μm. The experiment was run at 30° C.

The Following Preparative HPLC Methodologies have Used in the Examples:

Preparative Method A refers to low pH purification using a mobile phase consisting of 0.1% Formic acid in a gradient of 10-95% MeCN in water over 14.4 min at a flow rate of 40 mL/min. The stationary phase consisted of a Waters Sunfire C18, 30×100 mm, 10 μm.

Preparative Method B refers to high pH purification using a mobile phase consisting of 0.2% ammonium hydroxide in a gradient of 30-95% MeCN in water over 10 min at a flow rate of 40 mL/min. The stationary phase consisted of a Waters XBridge™ C18 OBD™, 30×100 mm, 10 μm.

Intermediate 1: 4-Oxopyrido[1,2-a]pyrimidine-2-carboxylic acid

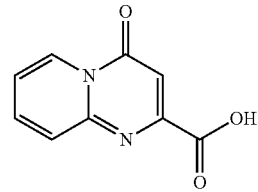 [SMILES: O=C(O)c1cc(=O)n2ccccc2n1]

Methyl 4-oxopyrido[1,2-a]pyrimidine-2-carboxylate [Tetrahedron (2014), 70(17), 2761-2765](3.94 g, 19.3 mmol) was dissolved in hydrogen chloride solution (8M, 7.5 mL) at room temperature (An exotherm was noted on addition) and the mixture was heated at reflux at for 2 h. The mixture was cooled to room temperature and the precipitate was collected by filtration and dried under vacuum to give the title compound (3.00 g, 81%) as a white solid.

Method A: LC-MS (electrospray): m/z=191.1 (M+H)$^+$, RT=0.32 min

Example 1: N-({2-[(4,4-dimethylpiperidin-1-yl)methyl]-1H-indol-6-yl}methyl)-4-oxo-4H-pyrido[1,2-a]pyrimidine-2-carboxamide

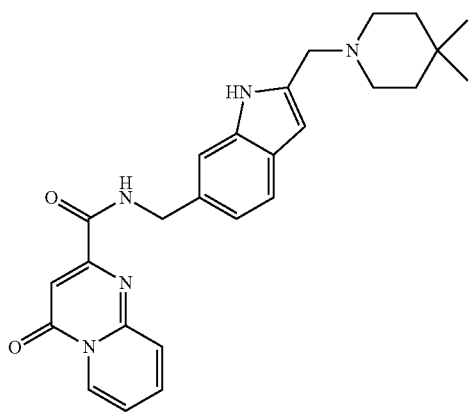 [SMILES: CC1(C)CCN(Cc2cc3ccc(CNC(=O)c4cc(=O)n5ccccc5n4)cc3[nH]2)CC1]

Step 1: 2-(4,4-dimethylpiperidine-1-carbonyl)-1H-indole-6-carbonitrile

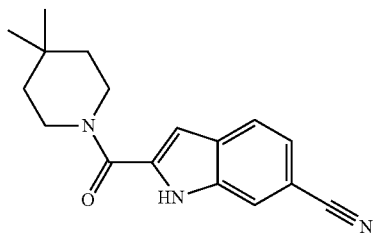 [SMILES: CC1(C)CCN(C(=O)c2cc3ccc(C#N)cc3[nH]2)CC1]

HATU (809 mg, 2.13 mmol) was added to a mixture of 6-cyano-1H-indole-2-carboxylic acid (330 mg, 1.77 mmol) and DIPEA (1.5 mL, 8.86 mmol) in DMF (26 mL), the mixture was stirred at ambient temperature for 5 mins, 4,4-dimethylpiperidine hydrochloride (292 mg, 1.95 mmol) was then added, and the mixture was stirred at ambient temperature for 1 h. The mixture was extracted with EtOAc and H$_2$O, the layers were separated, the mixture was extracted with EtOAc (3×10 mL), the organic layer was washed with brine, dried over MgSO$_4$ and concentrated. Purification by Basic reverse phase HPLC gave the title compound (100 mg, 20%) as a yellow solid.

Method A: LC-MS (electrospray): m/z=281.95 (M+H)$^+$, RT=1.20 min

Step 2: [2-[(4,4-dimethyl-1-piperidyl)methyl]-1H-indol-6-yl]methanamine

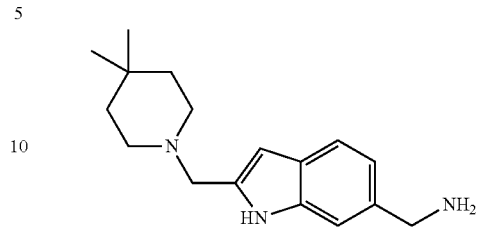

Lithium aluminium hydride (2M in THF, 0.22 mL, 0.44 mmol) was added to a solution of 2-(4,4-dimethylpiperidine-1-carbonyl)-1H-indole-6-carbonitrile (100 mg, 0.355 mmol) in THF-Anhydrous (2 mL) at 0° C. The mixture was stirred at 0° C., then was warmed to room temperature and stirred for 1 h. Further lithium aluminium hydride (2M in THF, 0.22 mL, 0.44 mmol) was added, and the mixture was stirred at ambient temperature for 67 h. The reaction was cooled to 0° C. and treated dropwise with H$_2$O (2 mL), NaOH (1M, 2 mL) and H$_2$O (6 mL). The mixture was stirred for 10 minutes, filtered, and the filter cake washed with THF. The filtrate was concentrated and purified by acidic reverse phase chromatography to give the title compound (86 mg, 89%) as a yellow solid.

Method A: LC-MS (electrospray): m/z=272.1 (M+H)$^+$, RT=0.31 min

Step 3: N-({2-[(4,4-dimethylpiperidin-1-yl)methyl]-1H-indol-6-yl}methyl)-4-oxo-4H-pyrido[1,2-a]pyrimidine-2-carboxamide

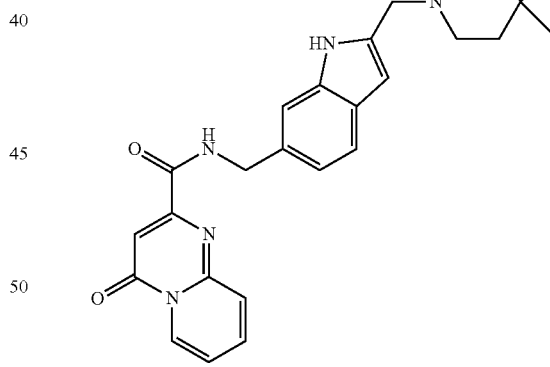

HATU (80 mg, 0.210 mmol) was added to a mixture of 4-oxopyrido[1,2-a]pyrimidine-2-carboxylic acid Intermediate 1 (60%, 61 mg, 0.19 mmol) and DIPEA (0.15 mL, 0.88 mmol) in DMF (2.6 mL), the mixture was stirred at ambient temperature for 5 minutes, [2-[(4,4-dimethyl-1-piperidyl)methyl]-1H-indol-6-yl]methanamine (48 mg, 0.18 mmol) was then added, and the mixture was stirred at ambient temperature for 1 h. Further HATU (45 mg) was added and the stir was continued for 2 h. The mixture was portioned between EtOAc and H$_2$O, the layers were separated, and the mixture was extracted with EtOAc (3×10 mL). The organic layer was washed with brine, dried over MgSO$_4$ and concentrated under vacuum. The crude material was purified by preparative HPLC (Method B) to give the title compound (4.0 mg, 5.1%) as a white solid.

Method B: LC-MS (electrospray): m/z=444.3 (M+H)⁺, RT=4.59 min

Example 2: N-[(2-{[(cyclobutylmethyl)amino]methyl}-1H-indol-6-yl)methyl]-4-oxo-4H-pyrido[1,2-a]pyrimidine-2-carboxamide

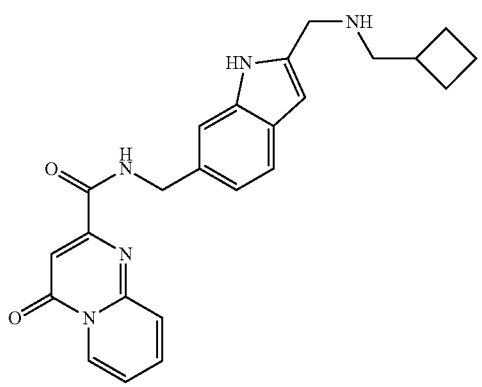 [SMILES: O=C(NCc1ccc2cc(CNCC3CCC3)[nH]c2c1)c1cc(=O)n2ccccc2n1]

Step 1:
3-amino-4-(3,3-diethoxyprop-1-yn-1-yl)benzonitrile

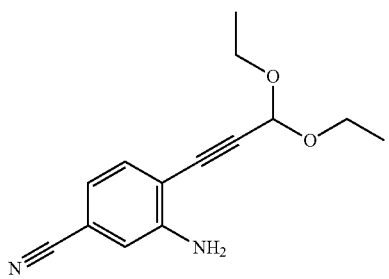 [SMILES: CCOC(C#Cc1ccc(C#N)cc1N)OCC]

gassed by bubbling nitrogen into the solution for 20 minutes. Then copper (1) iodide (125 mg, 0.66 mmol) and 3,3-diethoxyprop-1-yne (5.04 g, 39.3 mmol) were added sequentially and the reaction was stirred under nitrogen atmosphere for 18 hours. The precipitate (triethylamine hydrochloride) was collected by filtration and washed with EtOAc (~20 mL). The filtrate was concentrated at reduced pressure and the residue was purified by chromatography on SiO₂ [Biotage KP-Sil 100 g, eluting with 0-50% EtOAc in heptane]. The product containing fractions were combined and concentrated in vacuo to afford the title compound (8.19 g, Quant) as an orange oil.

Method B: LC-MS (electrospray): m/z=262.3 (M+H)⁺, RT=1.65 min.

Step 2: 2-(diethoxymethyl)-1H-indole-6-carbonitrile

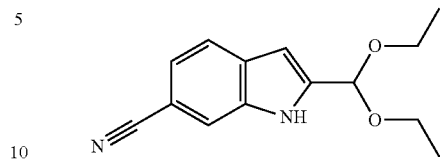

To a stirred solution of 3-amino-4-(3,3-diethoxyprop-1-ynyl)benzonitrile (8.00 g, 31.1 mmol) in NMP (99 mL) was added potassium tert-butoxide (6.98 g, 62.2 mmol) at 0° C. (the colour of the solution turned from orange to dark red). After warming to RT, the solution was stirred at ambient temperature for 16 hours. Saturated aqueous ammonium chloride solution (25 mL) was added and the resulting mixture was partitioned between EtOAc (250 mL) and water (250 mL). The layers were separated and the organic layer washed twice more with water (2×200 mL). The organic layer was dried over sodium sulfate, filtered and concentrated in vacuo to give a brown oil. The first aqueous layer was re-extracted with EtOAc (200 mL) and the layers separated. The organic layer was washed twice with water (2×200 mL). The organic layer was dried over sodium sulfate, filtered and concentrated in vacuo to give an orange oil. The crude material was purified by chromatography on SiO₂ [BIOTAGE KP-Sil 100 g, eluting with 0-50% EtOAc in heptane]. The product containing fractions were combined and concentrated in vacuo. The residue (yellow solid) was recrystallised from EtOAc/heptane to afford the title compound (5.86 g, 24.0 mmol, 77%) as colourless crystalline solid.

Method B: LC-MS (electrospray): m/z=262.3 (M+H)⁺, RT=1.69 min.

Step 3: [2-(diethoxymethyl)-1H-indol-6-yl]methanamine

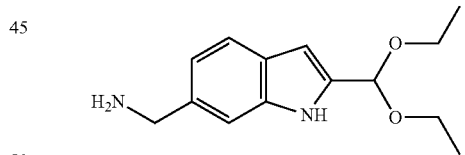

To a degassed solution of 2-(diethoxymethyl)-1H-indole-6-carbonitrile (5.8 g, 24 mmol) in ethanol (70 mL) was added ammonia in MeOH (7M, 20 mL, 0.14 mmol) and the reaction was degassed and backfilled with nitrogen 3 times. Raney nickel (assumed 50%, about 5.4 g, 0.1 mmoL) was added and the reaction evacuated and backfilled with nitrogen 3 times. The flask was evacuated one final time and put under a hydrogen atmosphere and stirred at ambient temperature for 3 hours. More Raney nickel (about 2.7 g) was added and the reaction evacuated and placed under a hydrogen atmosphere and stirred at ambient temperature for 16 hours. The catalyst was removed by filtration (through Kieselguhr) and washed with methanol (50 mL). The filtrate was concentrated under reduced pressure to afford the title compound (5.96 g, 100%) as a colourless oil which crystallised upon standing.

Method C: LC-MS (electrospray): m/z=247.3 (M−H)⁻, RT=2.74 min.

Step 4: N-[(2-formyl-1H-indol-6-yl)methyl]-4-oxo-pyrido[1,2-a]pyrimidine-2-carboxamide

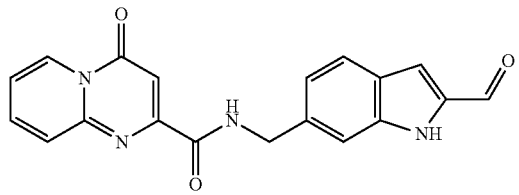

To a stirred solution of 4-oxopyrido[1,2-a]pyrimidine-2-carboxylic acid (455 mg, 2.39 mmol) (Intermediate 1) and DIPEA (1.0 mL, 5.98 mmol) in DMF (10 mL) was added HATU (910 mg, 2.39 mmol). A colour change was observed from colourless to green and a suspension formed. After a further 30 minutes of stirring at ambient temperature, a solution of [2-(diethoxymethyl)-1H-indol-6-yl]methanamine (500 mg, 1.99 mmol) in DMF (5 mL) was added dropwise to the reaction. A colour change of green to red was observed and the reaction became homogeneous and was stirred at ambient temperature overnight.

The mixture was partitioned between EtOAc (100 mL) and sat. NaHCO₃ solution (50 mL). The organic layer was separated, washed with water (80 mL) and brine (20 mL), dried (Na₂SO₄), filtered and concentrated at reduced pressure to give a viscous red oil.

The crude product was dissolved in THF (10 mL), water (1 mL) and acetic acid (0.5 mL) were added and the mixture was stirred at ambient temperature for 2 hours.

The THF was removed in vacuo and water (10 mL) was added to the resulting mixture causing further solid to precipitate out. The brown solid was collected by washed with water (2×5 mL) then ether (3×5 mL) and dried under vacuum to give the title compound (520 mg, 75%) as a brown solid.

Method C: LC-MS (electrospray): m/z=347.2 (M+H)⁺, RT=2.37 min.

Step 5: N-[[2-[(Cyclobutylmethylamino)methyl]-1H-indol-6-yl]methyl]-4-oxo-pyrido[1,2-a]pyrimidine-2-carboxamide

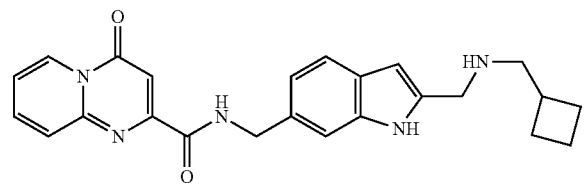

A pressure vial was charged with N-[(2-formyl-1H-indol-6-yl)methyl]-4-oxo-pyrido[1,2-a]pyrimidine-2-carboxamide (185 mg, 0.53 mmol), DCE (5 mL) and 1-cyclobutylmethanamine (0.13 mL, 1.0 mmol) at ambient temperature. The vial was sealed and the mixture was stirred at 65° C. for 2 hours. After cooling to RT, sodium triacetoxyborohydride (340 mg, 1.85 mmol) was added and the mixture was heated to 65° C. for 2 hours.

The mixture was partitioned between EtOAc (40 mL) and sat. sodium bicarbonate solution (30 mL). The organic layer was separated, washed with brine (20 mL), dried (Na₂SO₄), filtered and concentrated at reduced pressure. The residue (pale yellow oil) was purified by reverse phase chromatography (basic method, SNAP ULTRA 30 g Cartridge, eluting with MeCN+0.1% NH₃/H₂O+0.1% NH₃, 10 to 90%). The fractions containing desired product were freeze dried overnight to give the title compound (85 mg, 38%) as an off-white solid.

Method C: LC-MS (electrospray): m/z=416.4 (M+H)⁺, RT=3.14 min.

Example 6: N-[[2-[[(1-methylcyclopropyl)methyl-amino]methyl]-1H-indol-6-yl]methyl]-4-oxo-pyrido[1,2-a]pyrimidine-2-carboxamide

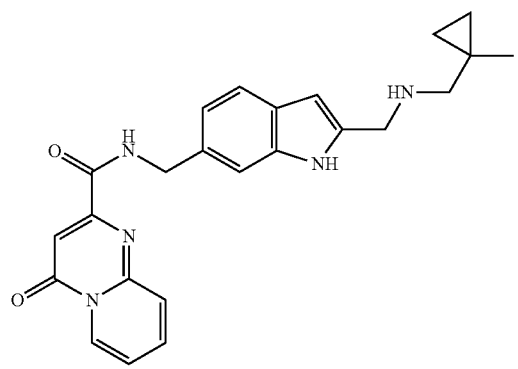 [SMILES: CC1(CNCc2cc3ccc(CNC(=O)c4cc(=O)n5ccccc5n4)cc3[nH]2)CC1]

(1-methylcyclopropyl)methanamine hydrochloride (70 mg, 0.577 mmol) was added to a solution of N-[(2-formyl-1H-indol-6-yl)methyl]-4-oxo-pyrido[1,2-a]pyrimidine-2-carboxamide (100 mg, 0.289 mmol) in DCE (7 mL) in a pressure vial, and the RM was stirred at 60° C. for 3 h. (1-methylcyclopropyl)methanamine hydrochloride (70 mg, 0.577 mmol) was added, along with N-ethyl-N-isopropyl-propan-2-amine (0.30 mL, 1.73 mmol) and the reaction was stirred at 60° C. for 1 h. The mixture was cooled to room temperature and added drop-wise over 5 min to a solution of NaBH₄ (11 mg, 0.289 mmol) in Ethanol (2.5 mL). The mixture was stirred at ambient temperature overnight. NaBH₄ (11 mg, 0.289 mmol) in Ethanol (2.5 mL) was added dropwise, and the reaction stirred at ambient temperature for a further 1 h. The mixture was quenched with water (30 mL), extracted with DCM (3×40 mL), passed through a Telos phase separator and concentrated in vacuo. The residue was purified by preparative HPLC (Method B) and the product containing fractions combined, concentrated in vacuo and freeze dried overnight to afford the title compound (70 mg, 59% as a pale yellow solid.

Method C: LC-MS (electrospray): m/z=416.5 (M+H)⁺, RT=3.16 min

The compounds in Table 1 were prepared in the same manner as Example 2 and 3 using commercial amines or described intermediates.

TABLE 1

| Compound No | Name | Structure | LCMS method | LCMS Retention time | Mass Ion |
|---|---|---|---|---|---|
| 3 | N-[[2-[[(3,3-difluorocyclo-butyl)methyl-amino]methyl]-1H-indol-6-yl]methyl]-4-oxo-pyrido[1,2-a]pyrimidine-2-carboxamide | 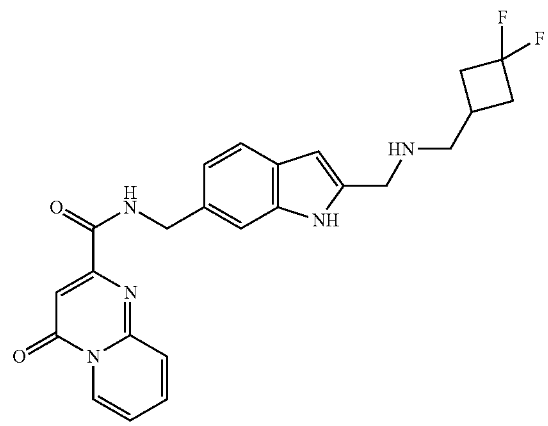 [SMILES: O=C(NCc1ccc2cc(CNCC3CC(F)(F)C3)[nH]c2c1)c1cc(=O)n2ccccc2n1] | C | 2.98 | 452.4 |
| 4 | N-[[2-[[(1-hydroxycyclo-butyl)methyl-amino]methyl]-1H-indol-6-yl]methyl]-4-oxo-pyrido[1,2-a]pyrimidine-2-carboxamide | 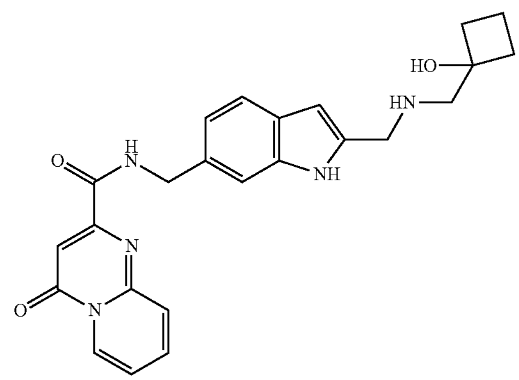 [SMILES: O=C(NCc1ccc2cc(CNCC3(O)CCC3)[nH]c2c1)c1cc(=O)n2ccccc2n1] | C | 2.54 | 432.5 |
| 5 | N-[[2-[[(1-fluorocyclobutyl)methylamino]methyl]-1H-indol-6-yl]methyl]-4-oxo-pyrido[1,2-a]pyrimidine-2-carboxamide | 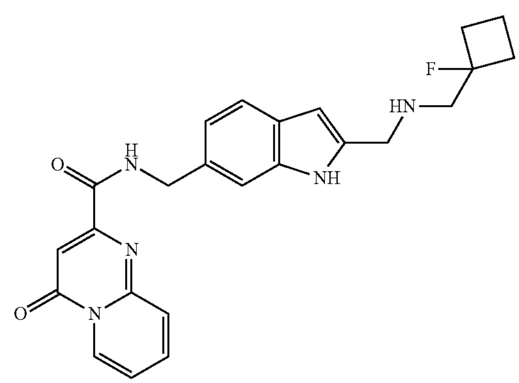 [SMILES: O=C(NCc1ccc2cc(CNCC3(F)CCC3)[nH]c2c1)c1cc(=O)n2ccccc2n1] | C | 3.01 | 434.4 |
| 7 | N-[[2-(2-azabicyclo[2.1.1]hexan-2-ylmethyl)-1H-indol-6-yl]methyl]-4-oxo-pyrido[1,2-a]pyrimidine-2-carboxamide | 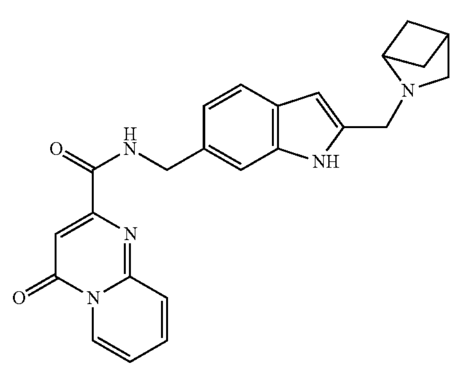 [SMILES: O=C(NCc1ccc2cc(CN3CC4CC3C4)[nH]c2c1)c1cc(=O)n2ccccc2n1] | C | 2.96 | 414.4 |

TABLE 1-continued

| Compound No | Name | Structure | LCMS method | LCMS Retention time | Mass Ion |
|---|---|---|---|---|---|
| 8 | N-[[2-(3-azabicyclo[3.1.1]heptanean-3-ylmethyl)-1H-indol-6-yl]methyl]-4-oxo-pyrido[1,2-a]pyrimidine-2-carboxamide | 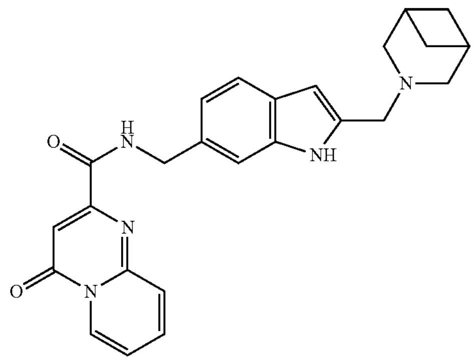 [SMILES: O=C(NCc1ccc2cc(CN3CC4CC(C4)C3)[nH]c2c1)c1cc(=O)n2ccccc2n1] | C | 3.67 | 428.4 |
| 9 | N-[[2-[[2-(hydroxymethyl)pyrrolidin-1-yl]methyl]-1H-indol-6-yl]methyl]-4-oxo-pyrido[1,2-a]pyrimidine-2-carboxamide | 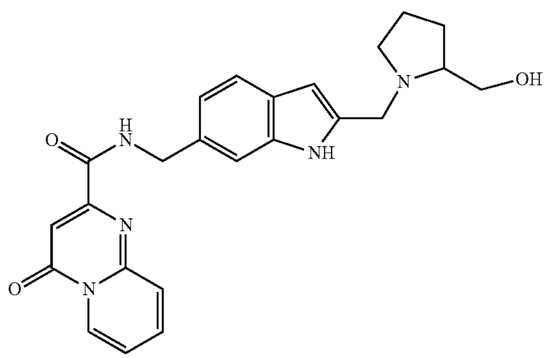 [SMILES: O=C(NCc1ccc2cc(CN3CCCC3CO)[nH]c2c1)c1cc(=O)n2ccccc2n1] | C | 2.66 | 432.4 |
| 10 | N-[[2-(morpholinomethyl)-1H-indol-6-yl]methyl]-4-oxo-pyrido[1,2-a]pyrimidine-2-carboxamide | 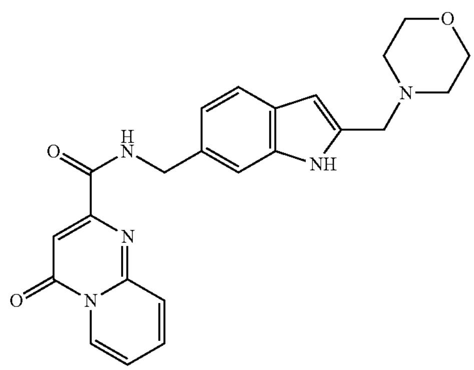 [SMILES: O=C(NCc1ccc2cc(CN3CCOCC3)[nH]c2c1)c1cc(=O)n2ccccc2n1] | C | 2.52 | 418.3 |
| 11 | N-[[2-[(1-adamantylamino)methyl]-1H-indol-6-yl]methyl]-4-oxo-pyrido[1,2-a]pyrimidine-2-carboxamide | 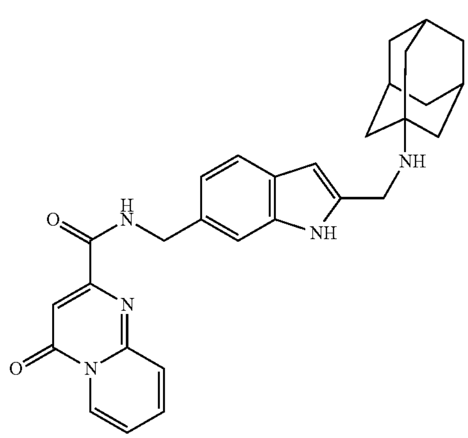 [SMILES: O=C(NCc1ccc2cc(CNC34CC5CC(CC(C5)C3)C4)[nH]c2c1)c1cc(=O)n2ccccc2n1] | C | 4.02 | 482.5 |

TABLE 1-continued

| Compound No | Name | Structure | LCMS method | LCMS Retention time | Mass Ion |
|---|---|---|---|---|---|
| 12 | 4-oxo-N-[[2-(1-piperidylmethyl)-1H-indol-6-yl]methyl]pyrido[1,2-a]pyrimidine-2-carboxamide | 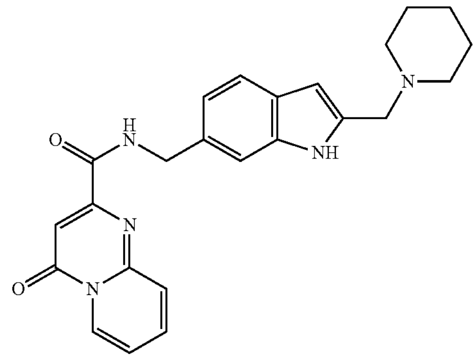 [SMILES: O=C(NCc1ccc2cc(CN3CCCCC3)[nH]c2c1)c1cc(=O)n2ccccc2n1] | C | 3.29 | 416.4 |
| 13 | N-[[2-[(4-fluoro-1-piperidyl)methyl]-1H-indol-6-yl]methyl]-4-oxo-pyrido[1,2-a]pyrimidine-2-carboxamide | 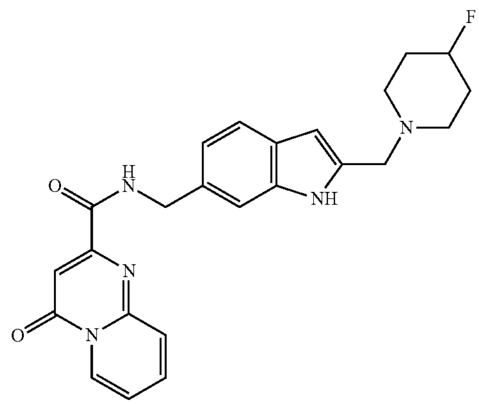 [SMILES: O=C(NCc1ccc2cc(CN3CCC(F)CC3)[nH]c2c1)c1cc(=O)n2ccccc2n1] | C | 3.00 | 434.4 |
| 14 | 4-oxo-N-[[2-[[[rac-(1S,2S,4S)-7-oxabicyclo[2.2.1]heptane-5-en-2-yl]methylamino]methyl]-1H-indol-6-yl]methyl]pyrido[1,2-a]pyrimidine-2-carboxamide | | C | 2.62 | 456.5 |

TABLE 1-continued

| Compound No | Name | Structure | LCMS method | LCMS Retention time | Mass Ion |
|---|---|---|---|---|---|
| 15 | N-[[2-[[(1-hydroxycyclopentyl)methylamino]methyl]-1H-indol-6-yl]methyl]-4-oxo-pyrido[1,2-a]pyrimidine-2-carboxamide | 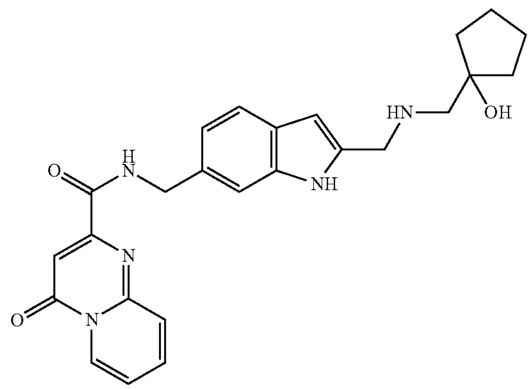 [SMILES: O=C(NCc1ccc2cc(CNCC3(O)CCCC3)[nH]c2c1)c1cc(=O)n2ccccc2n1] | C | 2.74 | 446.4 |
| 16 | 4-oxo-N-[[2-[[[rac-(1S,2R,4S)-7-oxabicyclo[2.2.1]heptane-5-en-2-yl]methylamino]methyl]-1H-indol-6-yl]methyl]pyrido[1,2-a]pyrimidine-2-carboxamide | 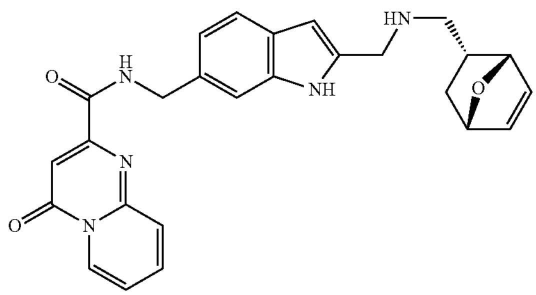 [SMILES: O=C(NCc1ccc2cc(CNC[C@H]3C[C@H]4C=C[C@@H]3O4)[nH]c2c1)c1cc(=O)n2ccccc2n1] | C | 2.57 | 456.4 |
| 17 | N-[[2-[(1-bicyclo[1.1.1]pentanylamino)methyl]-1H-indol-6-yl]methyl]-4-oxo-pyrido[1,2-a]pyrimidine-2-carboxamide | 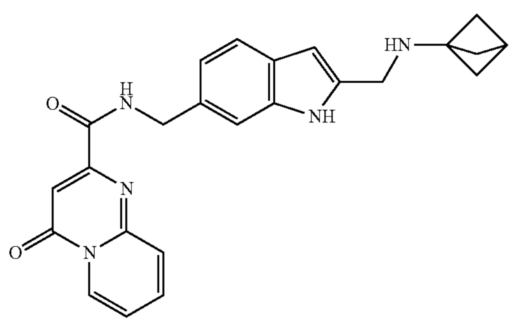 [SMILES: O=C(NCc1ccc2cc(CNC34CC(C3)C4)[nH]c2c1)c1cc(=O)n2ccccc2n1] | C | 3.06 | 414.4 |
| 18 | N-[[2-[(cyclobutylamino)methyl]-1H-indol-6-yl]methyl]-4-oxo-pyrido[1,2-a]pyrimidine-2-carboxamide | 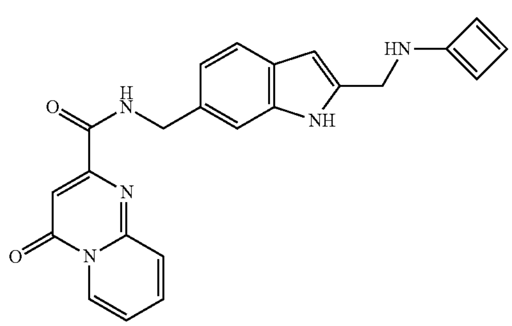 [SMILES: O=C(NCc1ccc2cc(CNC3=CC=C3)[nH]c2c1)c1cc(=O)n2ccccc2n1] | C | 2.90 | 402.4 |

TABLE 1-continued

| Compound No | Name | Structure | LCMS method | LCMS Retention time | Mass Ion |
|---|---|---|---|---|---|
| 19 | N-({2-[({bicyclo[2.2.1]heptanean-2-yl}amino)methyl]-1H-indol-6-yl}methyl)-4-oxo-4H-pyrido[1,2-a]pyrimidine-2-carboxamide | 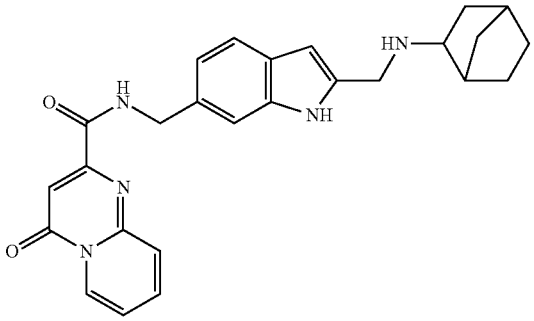 [SMILES: O=C(NCc1ccc2cc(CNC3CC4CCC3C4)[nH]c2c1)c1cc(=O)n2ccccc2n1] | C | 3.52 | 442.4 |
| 20 | N-[[2-[(cyclopropylamino)methyl]-1H-indol-6-yl]methyl]-4-oxo-pyrido[1,2-a]pyrimidine-2-carboxamide | 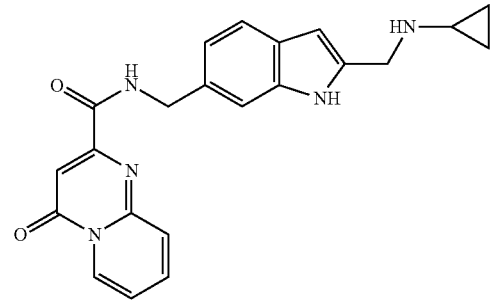 [SMILES: O=C(NCc1ccc2cc(CNC3CC3)[nH]c2c1)c1cc(=O)n2ccccc2n1] | C | 2.69 | 388.4 |
| 21 | N-[[2-(2-azabicyclo[2.2.2]octan-2-ylmethyl)-1H-indol-6-yl]methyl]-4-oxo-pyrido[1,2-a]pyrimidine-2-carboxamide | 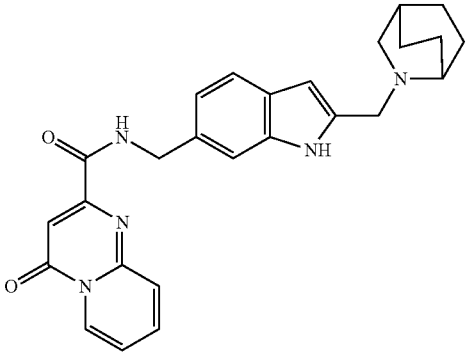 [SMILES: O=C(NCc1ccc2cc(CN3CC4CCC3CC4)[nH]c2c1)c1cc(=O)n2ccccc2n1] | C | 3.69 | 442.4 |
| 22 | N-[[2-[[(2,2-difluorocyclopropyl)methylamino]methyl]-1H-indol-6-yl]methyl]-4-oxo-pyrido[1,2-a]pyrimidine-2-carboxamide | 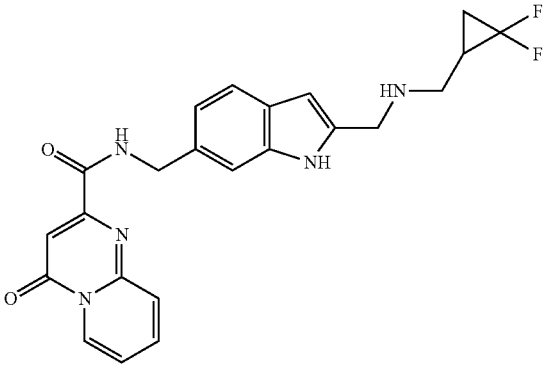 [SMILES: O=C(NCc1ccc2cc(CNCC3CC3(F)F)[nH]c2c1)c1cc(=O)n2ccccc2n1] | C | 2.82 | 438.3 |

TABLE 1-continued

| Compound No | Name | Structure | LCMS method | LCMS Retention time | Mass Ion |
|---|---|---|---|---|---|
| 23 | N-[(2-{[({3-fluorobicyclo[1.1.1]pentan-1-yl}methyl)amino]methyl}-1H-indol-6-yl)methyl]-4-oxo-4H-pyrido[1,2-a]pyrimidine-2-carboxamide | 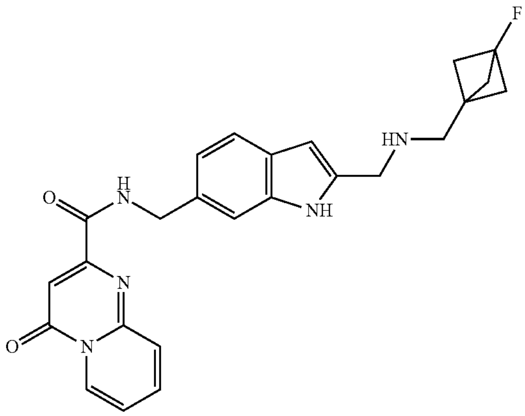 [SMILES: O=C(NCc1ccc2cc(CNCC34CC(F)(C3)C4)[nH]c2c1)c1cc(=O)n2ccccc2n1] | C | 3.01 | 446.4 |
| 24 | N-[[2-[(cyclohexylmethylamino)methyl]-1H-indol-6-yl]methyl]-4-oxo-pyrido[1,2-a]pyrimidine-2-carboxamide | 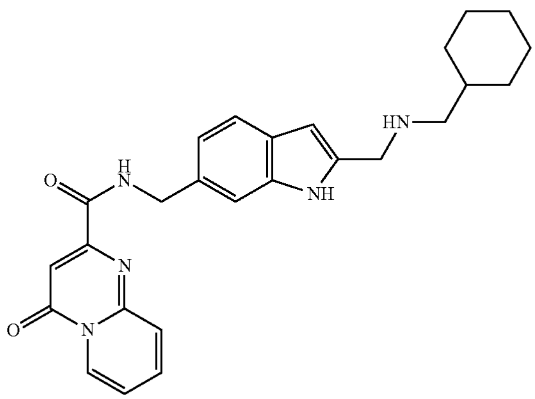 [SMILES: O=C(NCc1ccc2cc(CNCC3CCCCC3)[nH]c2c1)c1cc(=O)n2ccccc2n1] | C | 3.68 | 444.5 |
| 25 | N-[[2-[[(1-hydroxycyclohexyl)methylamino]methyl]-1H-indol-6-yl]methyl]-4-oxo-pyrido[1,2-a]pyrimidine-2-carboxamide | 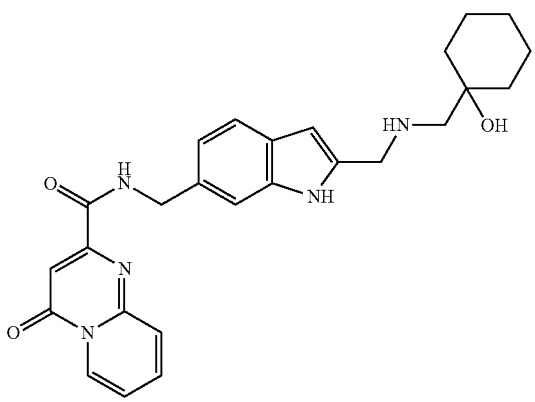 [SMILES: O=C(NCc1ccc2cc(CNCC3(O)CCCCC3)[nH]c2c1)c1cc(=O)n2ccccc2n1] | C | 2.98 | 460.5 |
| 26 | N-[[2-[(cyclopentylamino)methyl]-1H-indol-6-yl]methyl]-4-oxo-pyrido[1,2-a]pyrimidine-2-carboxamide | 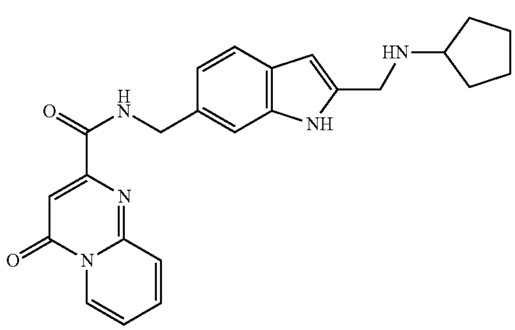 [SMILES: O=C(NCc1ccc2cc(CNC3CCCC3)[nH]c2c1)c1cc(=O)n2ccccc2n1] | C | 3.10 | 416.5 |

TABLE 1-continued

| Compound No | Name | Structure | LCMS method | LCMS Retention time | Mass Ion |
|---|---|---|---|---|---|
| 27 | N-[[2-[(cyclopentylmethylamino)methyl]-1H-indol-6-yl]methyl]-4-oxo-pyrido[1,2-a]pyrimidine-2-carboxamide | 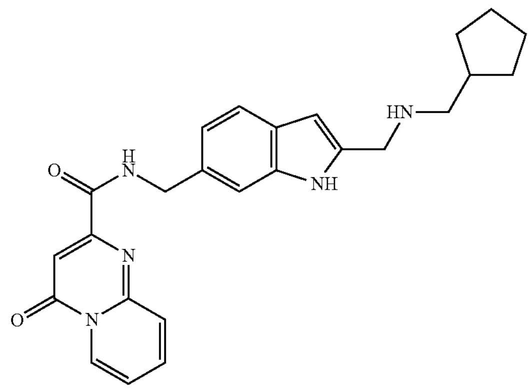 [SMILES: O=C(NCc1ccc2cc(CNCC3CCCC3)[nH]c2c1)c1cc(=O)n2ccccc2n1] | C | 3.40 | 430.5 |
| 28 | N-[[2-[[(1-methoxycyclobutyl)methylamino]methyl]-1H-indol-6-yl]methyl]-4-oxo-pyrido[1,2-a]pyrimidine-2-carboxamide | 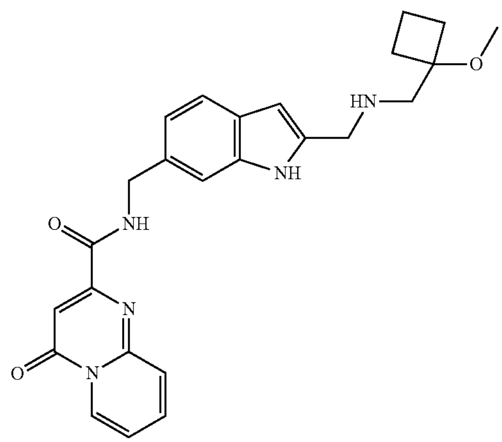 [SMILES: COC1(CNCc2cc3ccc(CNC(=O)c4cc(=O)n5ccccc5n4)cc3[nH]2)CCC1] | C | 2.91 | 446.5 |
| 29 | N-[[2-[(isobutylamino)methyl]-1H-indol-6-yl]methyl]-4-oxo-pyrido[1,2-a]pyrimidine-2-carboxamide | 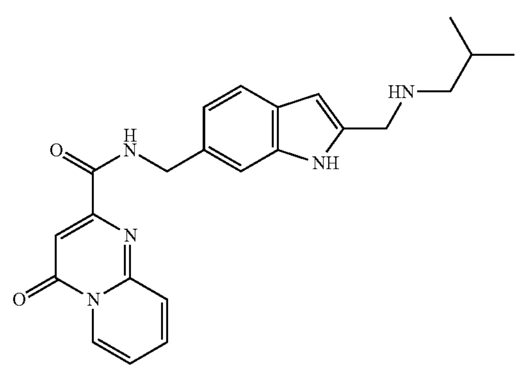 [SMILES: CC(C)CNCc1cc2ccc(CNC(=O)c3cc(=O)n4ccccc4n3)cc2[nH]1] | C | 3.06 | 404.5 |
| 30 | N-[[2-[(cyclohexylamino)methyl]-1H-indol-6-yl]methyl]-4-oxo-pyrido[1,2-a]pyrimidine-2-carboxamide | 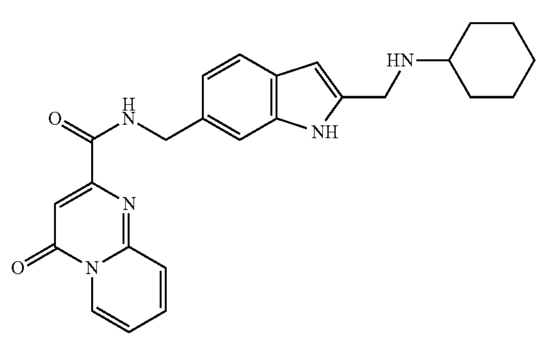 [SMILES: O=C(NCc1ccc2cc(CNC3CCCCC3)[nH]c2c1)c1cc(=O)n2ccccc2n1] | C | 3.29 | 430.5 |

TABLE 1-continued

| Compound No | Name | Structure | LCMS method | LCMS Retention time | Mass Ion |
|---|---|---|---|---|---|
| 31 | N-[[2-[(cyclopropylmethylamino)methyl]-1H-indol-6-yl]methyl]-4-oxo-pyrido[1,2-a]pyrimidine-2-carboxamide | 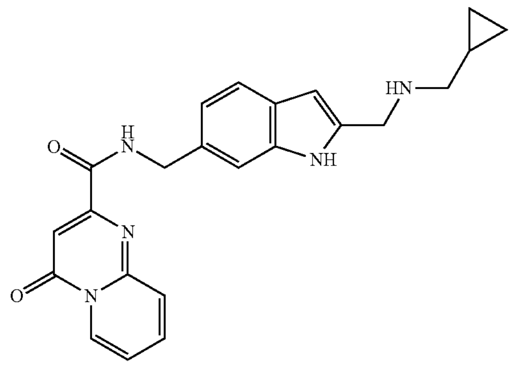 [SMILES: O=C(NCc1ccc2cc(CNCC3CC3)[nH]c2c1)c1cc(=O)n2ccccc2n1] | C | 2.81 | 402.5 |
| 32 | 4-oxo-N-[[2-[(prop-2-ynylamino)methyl]-1H-indol-6-yl]methyl]pyrido[1,2-a]pyrimidine-2-carboxamide | 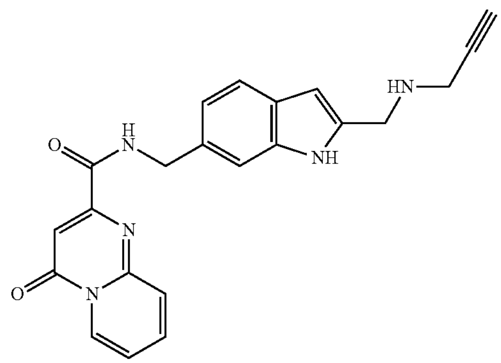 [SMILES: C#CCNCc1cc2ccc(CNC(=O)c3cc(=O)n4ccccc4n3)cc2[nH]1] | C | 2.51 | 386.3 |
| 33 | N-[[2-[(oxetan-2-ylmethylamino)methyl]-1H-indol-6-yl]methyl]-4-oxo-pyrido[1,2-a]pyrimidine-2-carboxamide | 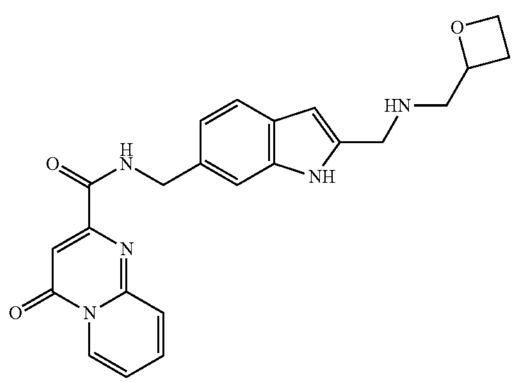 [SMILES: O=C(NCc1ccc2cc(CNCC3CCO3)[nH]c2c1)c1cc(=O)n2ccccc2n1] | C | 2.33 | 418.5 |
| 34 | N-[[2-[(2,2-dimethylpropylamino)methyl]-1H-indol-6-yl]methyl]-4-oxo-pyrido[1,2-a]pyrimidine-2-carboxamide | 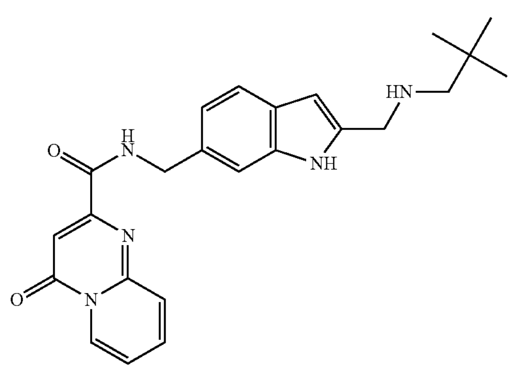 [SMILES: CC(C)(C)CNCc1cc2ccc(CNC(=O)c3cc(=O)n4ccccc4n3)cc2[nH]1] | C | 3.37 | 418.5 |

TABLE 1-continued

| Compound No | Name | Structure | LCMS method | LCMS Retention time | Mass Ion |
|---|---|---|---|---|---|
| 35 | N-[[2-[(1-bicyclo[1.1.1]pentanylmethyl-amino)methyl]-1H-indol-6-yl]methyl]-4-oxo-pyrido[1,2-a]pyrimidine-2-carboxamide | 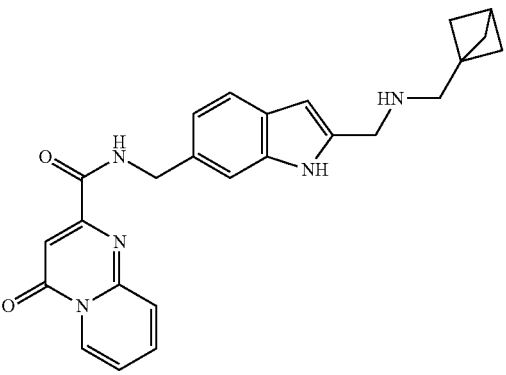 [SMILES: O=C(NCc1ccc2cc(CNCC34CC(C3)C4)[nH]c2c1)c1cc(=O)n2ccccc2n1] | C | 3.23 | 428.4 |
| 36 | N-{[2-({[(1S,2S)-2-hydroxycyclo-pentyl]amino}methyl)-1H-indol-6-yl]methyl}-4-oxo-4H-pyrido[1,2-a]pyrimidine-2-carboxamide | 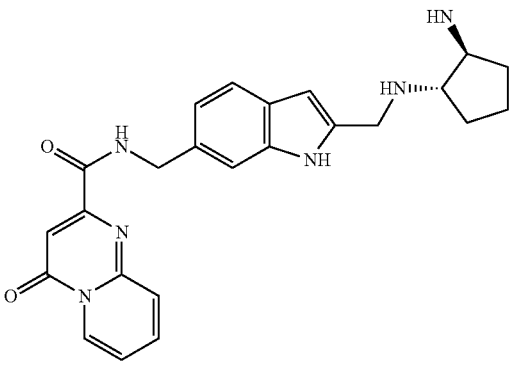 [SMILES: N[C@H]1CCC[C@@H]1NCc1cc2ccc(CNC(=O)c3cc(=O)n4ccccc4n3)cc2[nH]1] | D | 3.15 | 432.3 |
| 37 | N-{[2-({[(1R,2R)-2-hydroxycyclo-pentyl]amino}methyl)-1H-indol-6-yl]methyl}-4-oxo-4H-pyrido[1,2-a]pyrimidine-2-carboxamide | 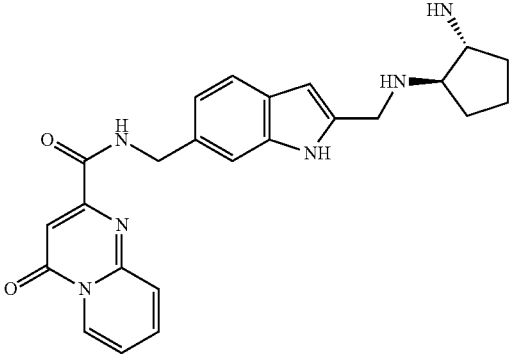 [SMILES: N[C@@H]1CCC[C@H]1NCc1cc2ccc(CNC(=O)c3cc(=O)n4ccccc4n3)cc2[nH]1] | D | 3.15 | 432.3 |
| 38 | N-{[2-({[(1S,2R)-2-hydroxycyclo-pentyl]amino}methyl)-1H-indol-6-yl]methyl}-4-oxo-4H-pyrido[1,2-a]pyrimidine-2-carboxamide | 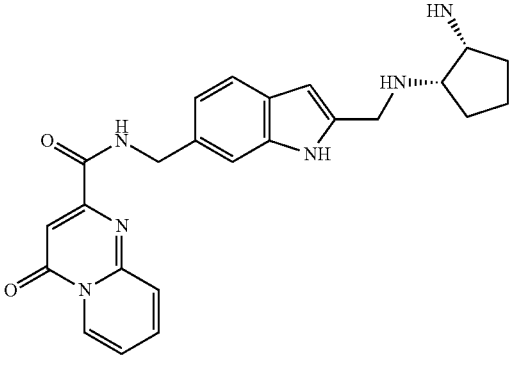 [SMILES: N[C@@H]1CCC[C@@H]1NCc1cc2ccc(CNC(=O)c3cc(=O)n4ccccc4n3)cc2[nH]1] | D | 3.39 | 432.3 |

TABLE 1-continued

| Compound No | Name | Structure | LCMS method | LCMS Retention time | Mass Ion |
|---|---|---|---|---|---|
| 39 | N-{[2-({[(1R,2S)-2-hydroxycyclopentyl]amino}methyl)-1H-indol-6-yl]methyl}-4-oxo-4H-pyrido[1,2-a]pyrimidine-2-carboxamide | 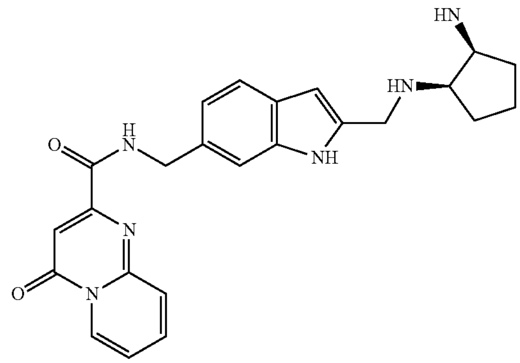 [SMILES: N[C@H]1CCC[C@H]1NCc1cc2ccc(CNC(=O)c3cc(=O)n4ccccc4n3)cc2[nH]1] | D | 3.38 | 432.3 |
| 40 | N-[[2-[(cyclopropylmethylamino)methyl]-5-fluoro-1H-indol-6-yl]methyl]-4-oxo-pyrido[1,2-a]pyrimidine-2-carboxamide | 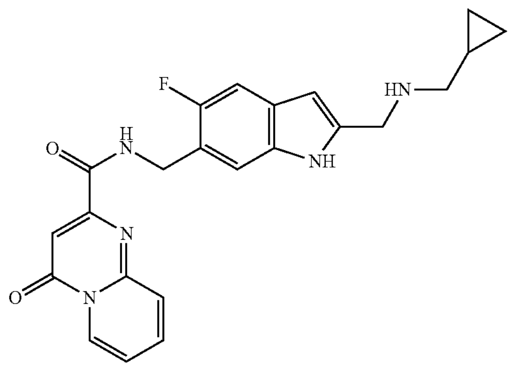 [SMILES: O=C(NCc1cc2[nH]c(CNCC3CC3)cc2cc1F)c1cc(=O)n2ccccc2n1] | C | 2.99 | 420.5 |
| 41 | N-[[2-[(cyclobutylmethylamino)methyl]-5-fluoro-1H-indol-6-yl]methyl]-4-oxo-pyrido[1,2-a]pyrimidine-2-carboxamide | 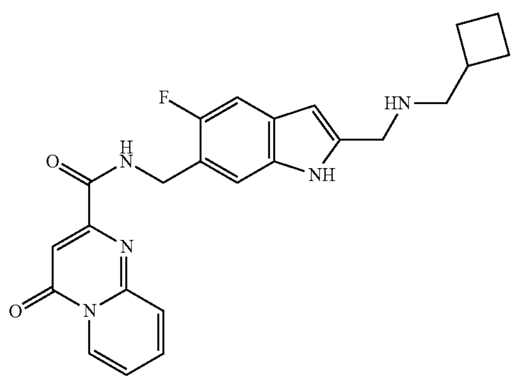 [SMILES: O=C(NCc1cc2[nH]c(CNCC3CCC3)cc2cc1F)c1cc(=O)n2ccccc2n1] | C | 3.28 | 434.5 |
| 67 | N-[[2-(2-azaspiro[3.3]heptanean-2-ylmethyl)-1H-indol-6-yl]methyl]-4-oxo-pyrido[1,2-a]pyrimidine-2-carboxamide | 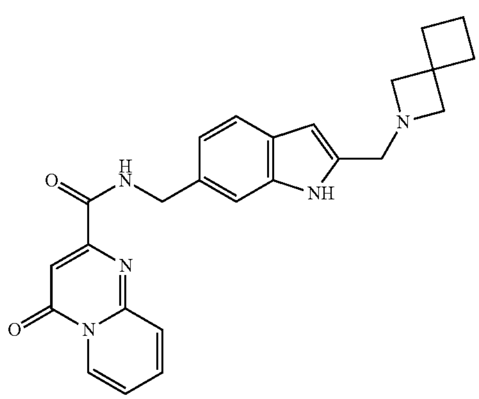 [SMILES: O=C(NCc1ccc2cc(CN3CC4(CCC4)C3)[nH]c2c1)c1cc(=O)n2ccccc2n1] | C | 3.26 | 428.4 |

TABLE 1-continued

| Compound No | Name | Structure | LCMS method | LCMS Retention time | Mass Ion |
|---|---|---|---|---|---|
| 68 | N-[[2-[(benzylamino)methyl]-1H-indol-6-yl]methyl]-4-oxo-pyrido[1,2-a]pyrimidine-2-carboxamide | 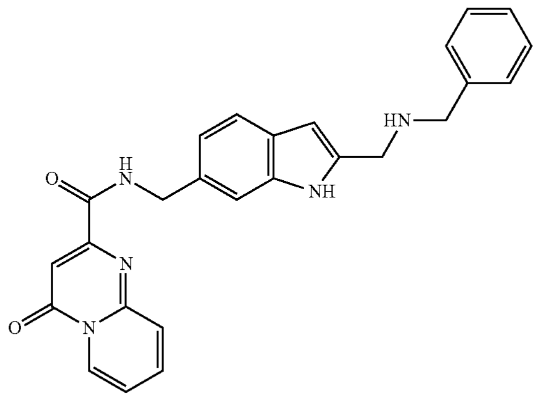 [SMILES: O=C(NCc1ccc2cc(CNCc3ccccc3)[nH]c2c1)c1cc(=O)n2ccccc2n1] | C | 3.16 | 438.5 |
| 69 | N-[[2-(3-azabicyclo[3.1.0]hexan-3-ylmethyl)-1H-indol-6-yl]methyl]-4-oxo-pyrido[1,2-a]pyrimidine-2-carboxamide | 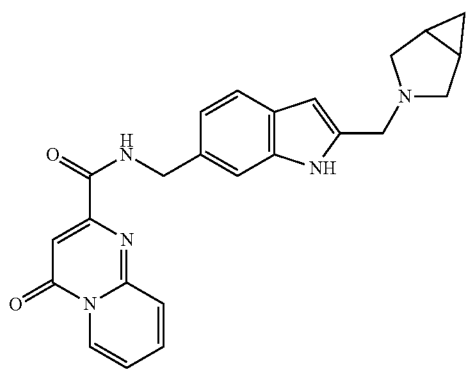 [SMILES: O=C(NCc1ccc2cc(CN3CC4CC4C3)[nH]c2c1)c1cc(=O)n2ccccc2n1] | C | 3.30 | 414.4 |
| 73 | N-[(2-{[(but-2-yn-1-yl)amino]methyl}-1H-indol-6-yl)methyl]-4-oxo-4H-pyrido[1,2-a]pyrimidine-2-carboxamide | 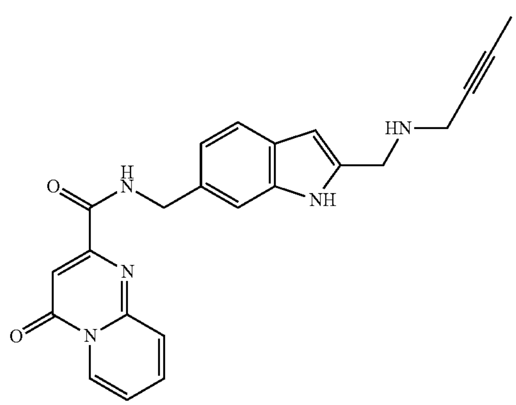 [SMILES: CC#CCNCc1cc2ccc(CNC(=O)c3cc(=O)n4ccccc4n3)cc2[nH]1] | C | 2.74 | 400.474 |

TABLE 1-continued

| Compound No | Name | Structure | LCMS method | LCMS Retention time | Mass Ion |
|---|---|---|---|---|---|
| 74 | N-[(2-{[(3-cyclopropyl-prop-2-yn-1-yl)amino]methyl}-1H-indol-6-yl)methyl]-4-oxo-4H-pyrido[1,2-a]pyrimidine-2-carboxamide | 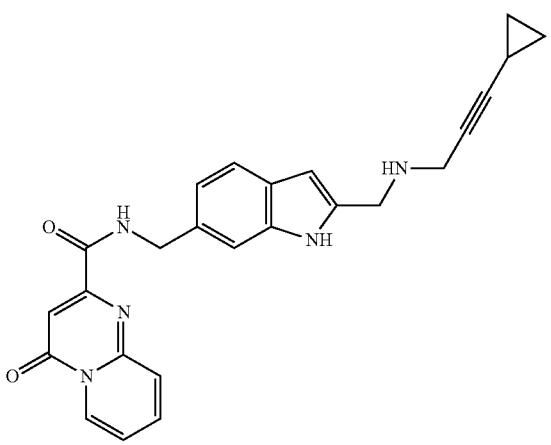 [SMILES: O=C(NCc1ccc2cc(CNCC#CC3CC3)[nH]c2c1)c1cc(=O)n2ccccc2n1] | C | 3.03 | 426.4 |
| 75 | N-({2-[({bicyclo[3.1.0]hexan-6-yl}amino)methyl]-1H-indol-6-yl}methyl)-4-oxo-4H-pyrido[1,2-a]pyrimidine-2-carboxamide | 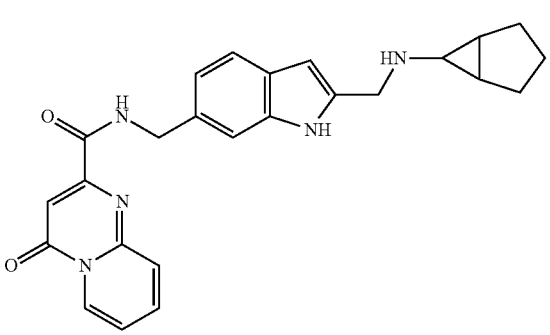 [SMILES: O=C(NCc1ccc2cc(CNC3C4CCCC43)[nH]c2c1)c1cc(=O)n2ccccc2n1] | C | 3.26 | 428.5 |
| 76 | N-[(2-{[({bicyclo[2.1.1]hexan-1-yl}methyl)amino]methyl}-1H-indol-6-yl)methyl]-4-oxo-4H-pyrido[1,2-a]pyrimidine-2-carboxamide | 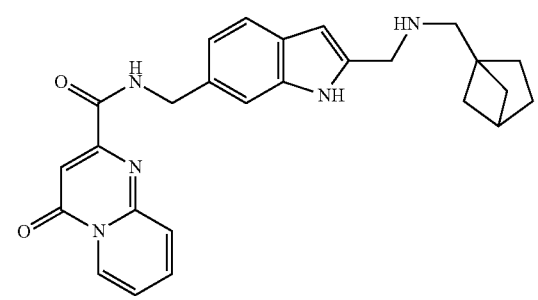 [SMILES: O=C(NCc1ccc2cc(CNCC34CCC(C3)C4)[nH]c2c1)c1cc(=O)n2ccccc2n1] | E | 1.87 | 442.4 |
| 77 | N-[(2-{[({3-methylbicyclo[1.1.1]pentan-1-yl}methyl)amino]methyl}-1H-indol-6-yl)methyl]-4-oxo-4H-pyrido[1,2-a]pyrimidine-2-carboxamide | 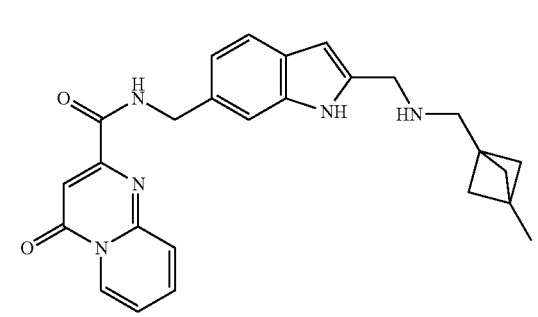 [SMILES: CC12CC(CNCc3cc4ccc(CNC(=O)c5cc(=O)n6ccccc6n5)cc4[nH]3)(C1)C2] | C | 3.52 | 442.6 |

TABLE 1-continued

| Compound No | Name | Structure | LCMS method | LCMS Retention time | Mass Ion |
|---|---|---|---|---|---|
| 78 | N-({2-[(3-methylazetidin-1-yl)methyl]-1H-indol-6-yl}methyl)-4-oxo-4H-pyrido[1,2-a]pyrimidine-2-carboxamide | 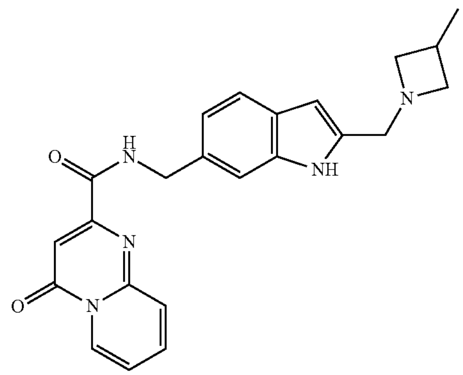 [SMILES: CC1CN(Cc2cc3ccc(CNC(=O)c4cc(=O)n5ccccc5n4)cc3[nH]2)C1] | C | 2.94 | 402.4 |
| 79 | N-({2-[(3-fluoroazetidin-1-yl)methyl]-1H-indol-6-yl}methyl)-4-oxo-4H-pyrido[1,2-a]pyrimidine-2-carboxamide | 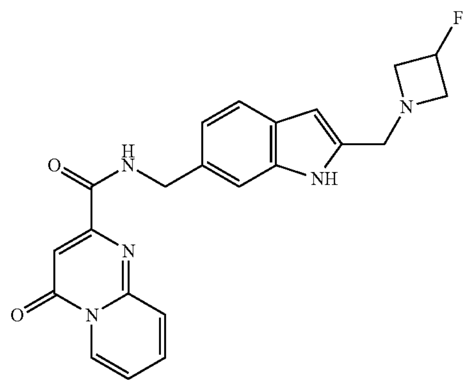 [SMILES: O=C(NCc1ccc2cc(CN3CC(F)C3)[nH]c2c1)c1cc(=O)n2ccccc2n1] | C | 2.63 | 406.4 |
| 80 | N-({2-[(azetidin-1-yl)methyl]-1H-indol-6-yl}methyl)-4-oxo-4H-pyrido[1,2-a]pyrimidine-2-carboxamide | 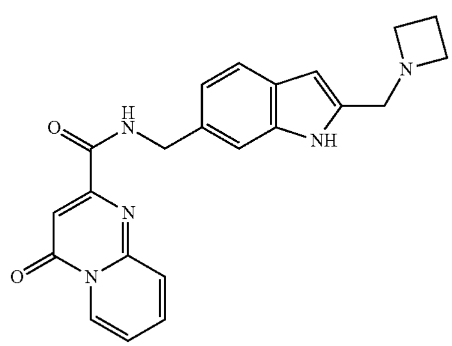 [SMILES: O=C(NCc1ccc2cc(CN3CCC3)[nH]c2c1)c1cc(=O)n2ccccc2n1] | C | 2.73 | 388.5 |
| 81 | N-{[2-({2-azaspiro[3.4]octan-2-yl}methyl)-1H-indol-6-yl]methyl}-4-oxo-4H-pyrido[1,2-a]pyrimidine-2-carboxamide | 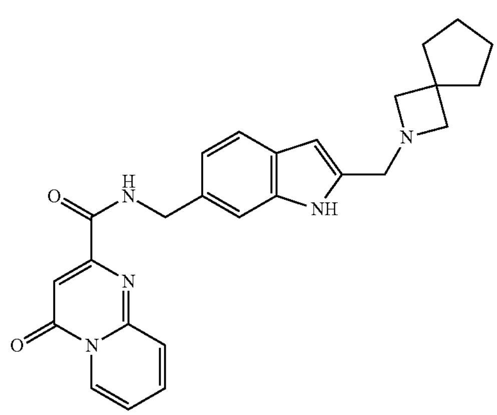 [SMILES: O=C(NCc1ccc2cc(CN3CC4(CCCC4)C3)[nH]c2c1)c1cc(=O)n2ccccc2n1] | C | 3.53 | 442.5 |

TABLE 1-continued

| Compound No | Name | Structure | LCMS method | LCMS Retention time | Mass Ion |
|---|---|---|---|---|---|
| 82 | N-({2-[(3-hydroxyazetidin-1-yl)methyl]-1H-indol-6-yl}methyl)-4-oxo-4H-pyrido[1,2-a]pyrimidine-2-carboxamide | 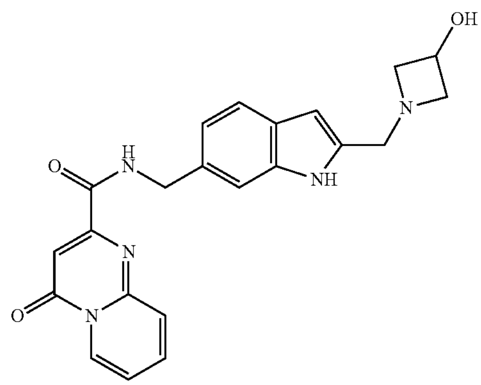 [SMILES: O=C(NCc1ccc2cc(CN3CC(O)C3)[nH]c2c1)c1cc(=O)n2ccccc2n1] | C | 2.10 | 404.4 |
| 83 | N-({2-[(3,3-dimethylazetidin-1-yl)methyl]-1H-indol-6-yl}methyl)-4-oxo-4H-pyrido[1,2-a]pyrimidine-2-carboxamide | 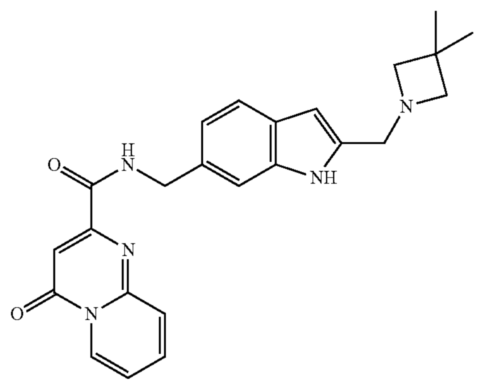 [SMILES: CC1(C)CN(Cc2cc3ccc(CNC(=O)c4cc(=O)n5ccccc5n4)cc3[nH]2)C1] | C | 3.20 | 416.4 |
| 84 | 4-oxo-N-[(2-{[3-(2,2,2-trifluoroethoxy)azetidin-1-yl]methyl}-1H-indol-6-yl)methyl]-4H-pyrido[1,2-a]pyrimidine-2-carboxamide | 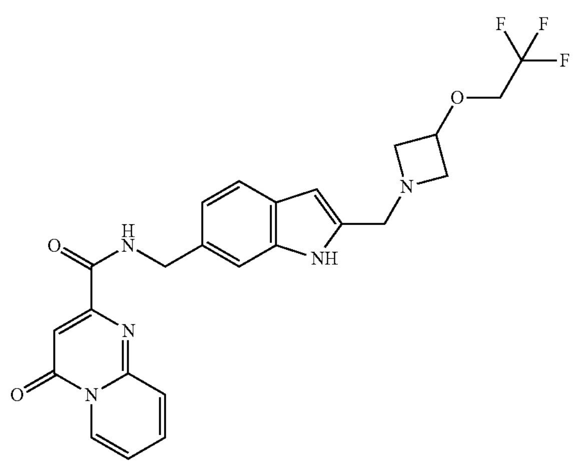 [SMILES: O=C(NCc1ccc2cc(CN3CC(OCC(F)(F)F)C3)[nH]c2c1)c1cc(=O)n2ccccc2n1] | C | 3.16 | 486.5 |

TABLE 1-continued

| Compound No | Name | Structure | LCMS method | LCMS Retention time | Mass Ion |
|---|---|---|---|---|---|
| 85 | N-[(2-{[3-(difluoromethyl)azetidin-1-yl]methyl}-1H-indol-6-yl)methyl]-4-oxo-4H-pyrido[1,2-a]pyrimidine-2-carboxamide | 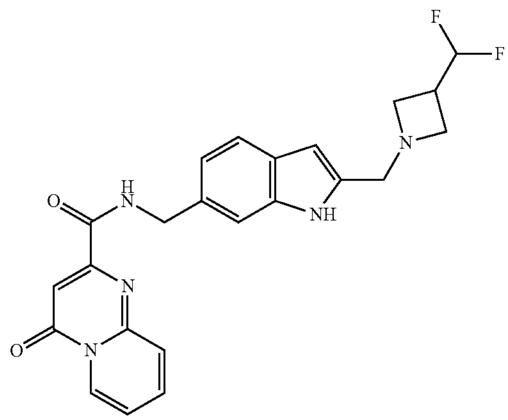 [SMILES: O=C(NCc1ccc2cc(CN3CC(C(F)F)C3)[nH]c2c1)c1cc(=O)n2ccccc2n1] | C | 2.92 | 438.4 |
| 86 | N-({2-[(3-methoxyazetidin-1-yl)methyl]-1H-indol-6-yl}methyl)-4-oxo-4H-pyrido[1,2-a]pyrimidine-2-carboxamide | 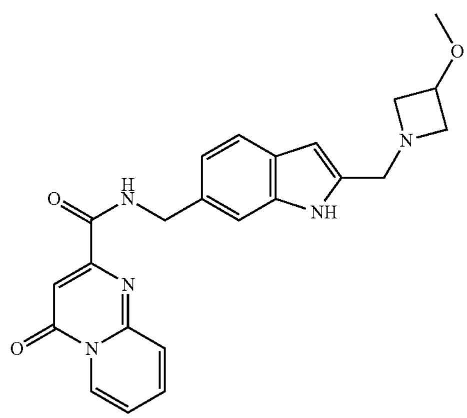 [SMILES: COC1CN(Cc2cc3ccc(CNC(=O)c4cc(=O)n5ccccc5n4)cc3[nH]2)C1] | C | 2.58 | 418.5 |
| 87 | N-[(2-{[3-(tert-butoxy)azetidin-1-yl]methyl}-1H-indol-6-yl)methyl]-4-oxo-4H-pyrido[1,2-a]pyrimidine-2-carboxamide | 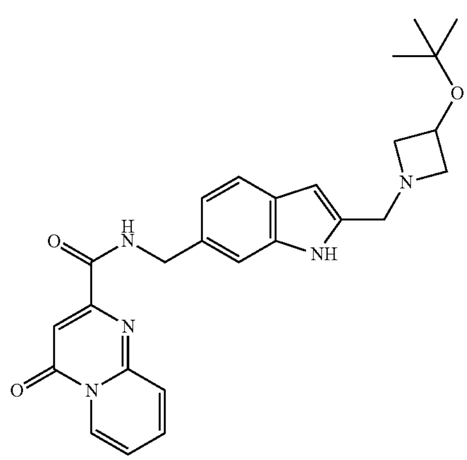 [SMILES: CC(C)(C)OC1CN(Cc2cc3ccc(CNC(=O)c4cc(=O)n5ccccc5n4)cc3[nH]2)C1] | C | 3.18 | 460.6 |

TABLE 1-continued

| Compound No | Name | Structure | LCMS method | LCMS Retention time | Mass Ion |
|---|---|---|---|---|---|
| 88 | 4-oxo-N-[(2-{[3-(trifluoromethyl)azetidin-1-yl]methyl}-1H-indol-6-yl)methyl]-4H-pyrido[1,2-a]pyrimidine-2-carboxamide | 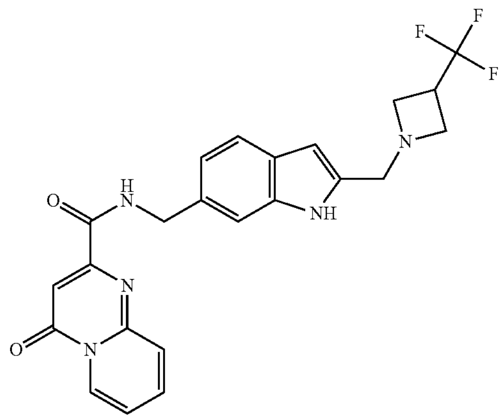 [SMILES: O=C(NCc1ccc2cc(CN3CC(C(F)(F)F)C3)[nH]c2c1)c1cc(=O)n2ccccc2n1] | C | 3.11 | 456.4 |
| 89 | N-({2-[(3-ethoxyazetidin-1-yl)methyl]-1H-indol-6-yl}methyl)-4-oxo-4H-pyrido[1,2-a]pyrimidine-2-carboxamide | 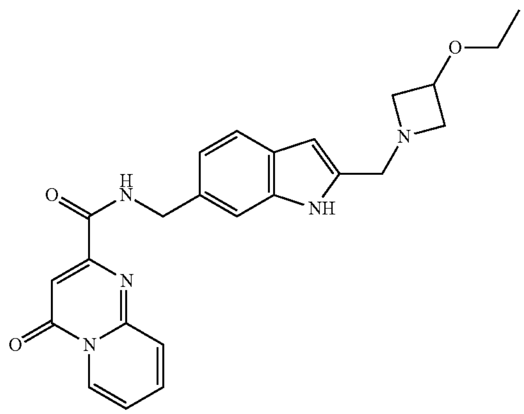 [SMILES: CCOC1CN(Cc2cc3ccc(CNC(=O)c4cc(=O)n5ccccc5n4)cc3[nH]2)C1] | C | 2.80 | 432.5 |
| 90 | N-{[2-({2-azaspiro[3.5]nonan-2-yl}methyl)-1H-indol-6-yl]methyl}-4-oxo-4H-pyrido[1,2-a]pyrimidine-2-carboxamide | 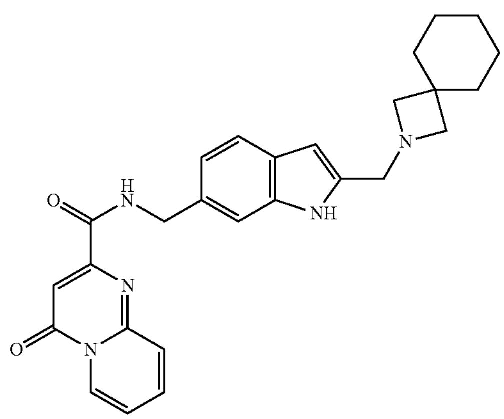 [SMILES: O=C(NCc1ccc2cc(CN3CC4(CCCCC4)C3)[nH]c2c1)c1cc(=O)n2ccccc2n1] | C | 3.77 | 456.5 |
| 91 | N-({2-[(2-methylazetidin-1-yl)methyl]-1H-indol-6-yl}methyl)-4-oxo-4H-pyrido[1,2-a]pyrimidine-2-carboxamide | 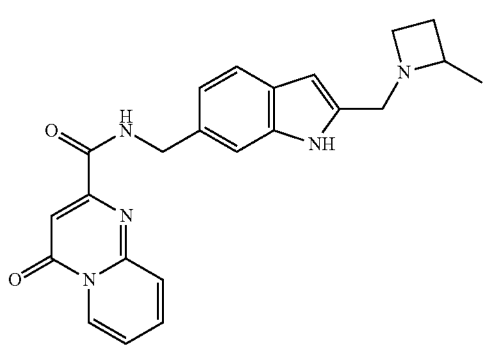 [SMILES: CC1CCN1Cc1cc2ccc(CNC(=O)c3cc(=O)n4ccccc4n3)cc2[nH]1] | C | 2.94 | 402.4 |

TABLE 1-continued

| Compound No | Name | Structure | LCMS method | LCMS Retention time | Mass Ion |
|---|---|---|---|---|---|
| 92 | N-({2-[(3,3-dimethyl-pyrrolidin-1-yl)methyl]-1H-indol-6-yl}methyl)-4-oxo-4H-pyrido[1,2-a]pyrimidine-2-carboxamide | 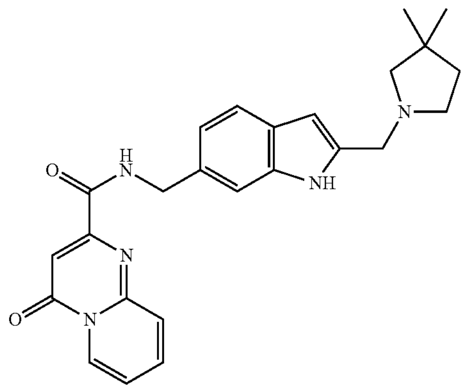 [SMILES: CC1(C)CCN(Cc2cc3ccc(CNC(=O)c4cc(=O)n5ccccc5n4)cc3[nH]2)C1] | C | 3.63 | 430.7 |
| 93 | N-{[2-({6-fluoro-2-azaspiro[3.3]heptanean-2-yl}methyl)-1H-indol-6-yl]methyl}-4-oxo-4H-pyrido[1,2-a]pyrimidine-2-carboxamide | 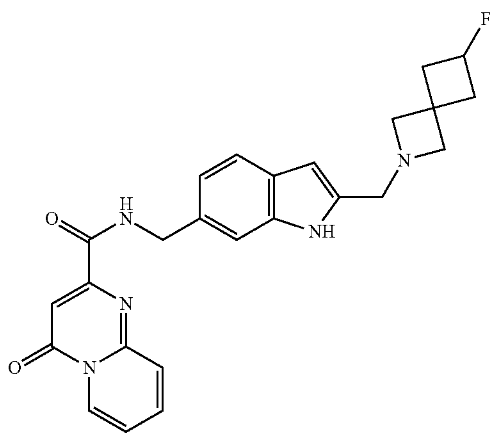 [SMILES: O=C(NCc1ccc2cc(CN3CC4(CC(F)C4)C3)[nH]c2c1)c1cc(=O)n2ccccc2n1] | C | 3.00 | 446.4 |
| 94 | N-[2-({6,6-difluoro-2-azaspiro[3.3]heptanean-2-yl}methyl)-1H-indol-6-yl]methyl}-4-oxo-4H-pyrido[1,2-a]pyrimidine-2-carboxamide | 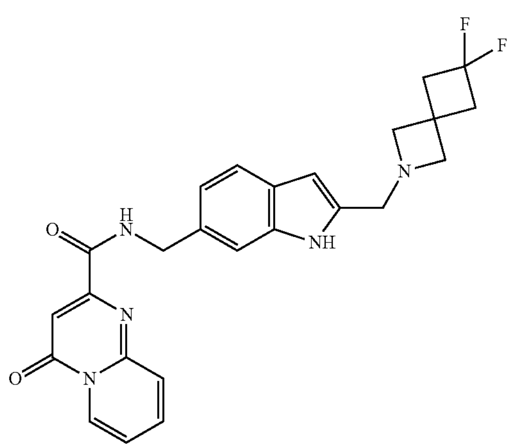 [SMILES: O=C(NCc1ccc2cc(CN3CC4(C3)CC(F)(F)C4)[nH]c2c1)c1cc(=O)n2ccccc2n1] | C | 3.10 | 464.595 |

TABLE 1-continued

| Compound No | Name | Structure | LCMS method | LCMS Retention time | Mass Ion |
|---|---|---|---|---|---|
| 95 | N-({2-[(3-cyclobutyl-azetidin-1-yl)methyl]-1H-indol-6-yl}methyl)-4-oxo-4H-pyrido[1,2-a]pyrimidine-2-carboxamide | 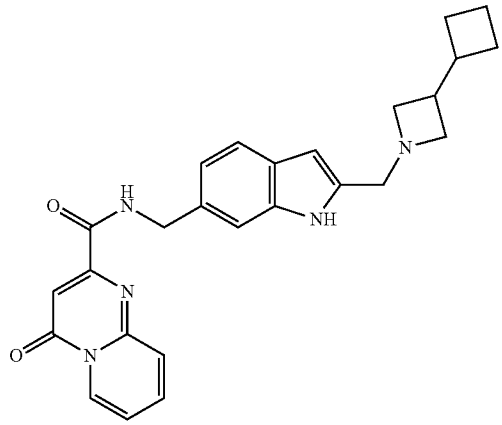 [SMILES: O=C(NCc1ccc2cc(CN3CC(C4CCC4)C3)[nH]c2c1)c1cc(=O)n2ccccc2n1] | C | 3.63 | 442.8 |
| 96 | N-({2-[(3-cyclopropyl-azetidin-1-yl)methyl]-1H-indol-6-yl}methyl)-4-oxo-4H-pyrido[1,2-a]pyrimidine-2-carboxamide | 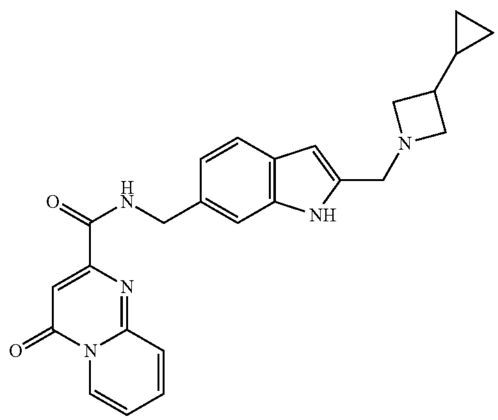 [SMILES: O=C(NCc1ccc2cc(CN3CC(C4CC4)C3)[nH]c2c1)c1cc(=O)n2ccccc2n1] | C | 3.31 | 429.1 |
| 97 | N-({2-[(3-tert-butylazetidin-1-yl)methyl]-1H-indol-6-yl}methyl)-4-oxo-4H-pyrido[1,2-a]pyrimidine-2-carboxamide | 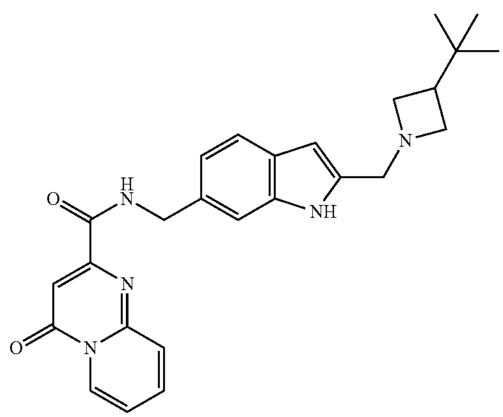 [SMILES: CC(C)(C)C1CN(Cc2cc3ccc(CNC(=O)c4cc(=O)n5ccccc5n4)cc3[nH]2)C1] | E | 1.94 | 444.5 |
| 98 | N-[(2-{[(1-tert-butylcyclopropyl)amino]methyl}-1H-indol-6-yl)methyl]-4-oxo-4H-pyrido[1,2-a]pyrimidine-2-carboxamide | 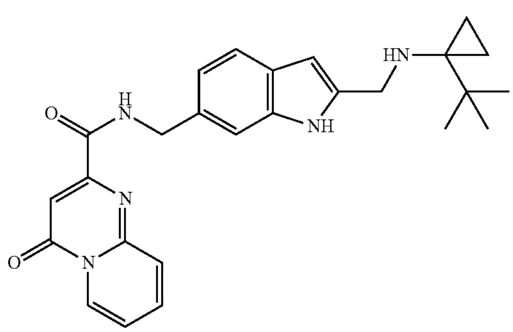 [SMILES: CC(C)(C)C1(NCc2cc3ccc(CNC(=O)c4cc(=O)n5ccccc5n4)cc3[nH]2)CC1] | C | 4.19 | 444.6 |

TABLE 1-continued

| Compound No | Name | Structure | LCMS method | LCMS Retention time | Mass Ion |
|---|---|---|---|---|---|
| | yl]}methyl}-4-oxo-4H-pyrido[1,2-a]pyrimidine-2-carboxamide | | | | |
| 106 | N-{[2-({octahydrocyclopenta[c]pyrrol-2-yl}methyl)-1H-indol-6-yl]methyl}-4-oxo-4H-pyrido[1,2-a]pyrimidine-2-carboxamide | 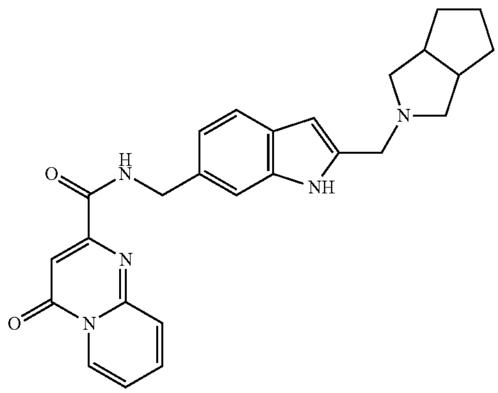 [SMILES: O=C(NCc1ccc2cc(CN3CC4CCCC4C3)[nH]c2c1)c1cc(=O)n2ccccc2n1] | C | 3.69 | 442.8 |
| 107 | N-{[2-({5-azaspiro[2.4]heptanean-5-yl}methyl)-1H-indol-6-yl]methyl}-4-oxo-4H-pyrido[1,2-a]pyrimidine-2-carboxamide | 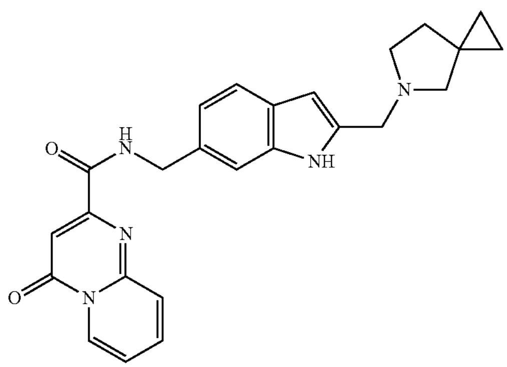 [SMILES: O=C(NCc1ccc2cc(CN3CCC4(CC4)C3)[nH]c2c1)c1cc(=O)n2ccccc2n1] | C | 3.28 | 428.5 |
| 108 | N-[(2-{[({3-methoxybicyclo[1.1.1]pentan-1-yl}methyl)amino]methyl}-1H-indol-6-yl)methyl]-4-oxo-4H-pyrido[1,2-a]pyrimidine-2-carboxamide | 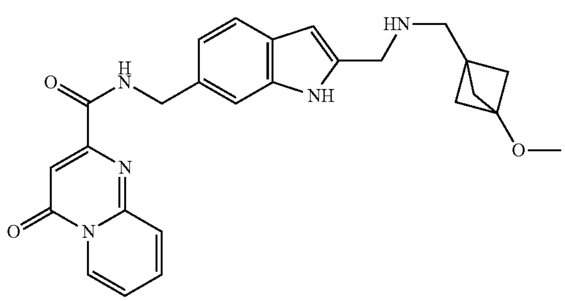 [SMILES: COC12CC(CNCc3cc4ccc(CNC(=O)c5cc(=O)n6ccccc6n5)cc4[nH]3)(C1)C2] | C | 2.96 | 458.6 |
| 109 | 4-oxo-N-[(2-{[({spiro[2.2]pentan-1-yl}methyl)amino]methyl}-1H-indol-6-yl)methyl]-4H-pyrido[1,2-a]pyrimidine-2-carboxamide | 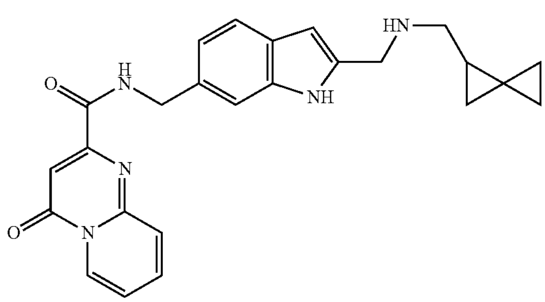 [SMILES: O=C(NCc1ccc2cc(CNCC3CC34CC4)[nH]c2c1)c1cc(=O)n2ccccc2n1] | C | 3.49 | 428.5 |

TABLE 1-continued

| Compound No | Name | Structure | LCMS method | LCMS Retention time | Mass Ion |
|---|---|---|---|---|---|
| 110 | 4-oxo-N-({2-[({spiro[2.3]hexan-1-yl}amino)methyl]-1H-indol-6-yl}methyl)-4H-pyrido[1,2-a]pyrimidine-2-carboxamide | 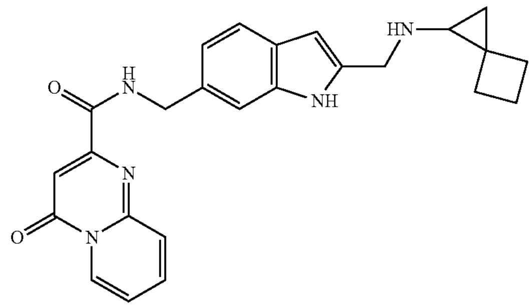 [SMILES: O=C(NCc1ccc2cc(CNC3CC34CCC4)[nH]c2c1)c1cc(=O)n2ccccc2n1] | C | 3.35 | 428.5 |
| 111 | N-[(2-{[({3-cyanobicyclo[1.1.1]pentan-1-yl}methyl)amino]methyl}-1H-indol-6-yl)methyl]-4-oxo-4H-pyrido[1,2-a]pyrimidine-2-carboxamide | 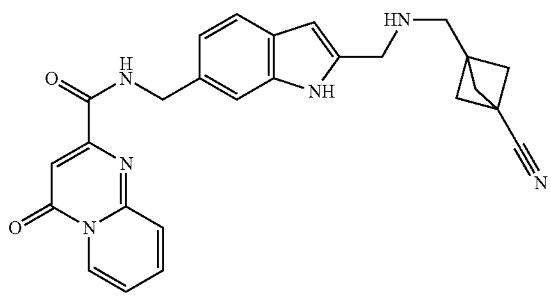 [SMILES: N#CC12CC(CNCc3cc4ccc(CNC(=O)c5cc(=O)n6ccccc6n5)cc4[nH]3)(C1)C2] | C | 2.89 | 453.5 |
| 112 | N-{[2-({1-oxa-6-azaspiro[3.4]octan-6-yl}methyl)-1H-indol-6-yl]methyl}-4-oxo-4H-pyrido[1,2-a]pyrimidine-2-carboxamide | 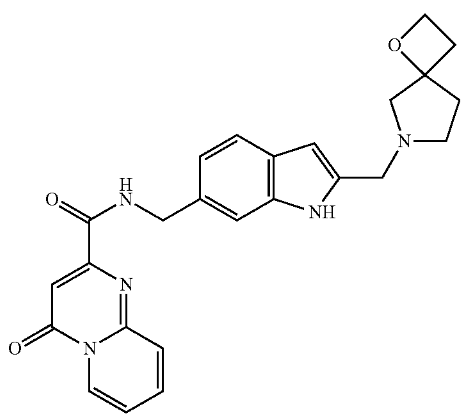 [SMILES: O=C(NCc1ccc2cc(CN3CCC4(CCO4)C3)[nH]c2c1)c1cc(=O)n2ccccc2n1] | C | 2.65 | 444.5 |
| 113 | N-{[2-({2-azaspiro[4.4]nonan-2-yl}methyl)-1H-indol-6-yl]methyl}-4-oxo-4H-pyrido[1,2-a]pyrimidine-2-carboxamide | 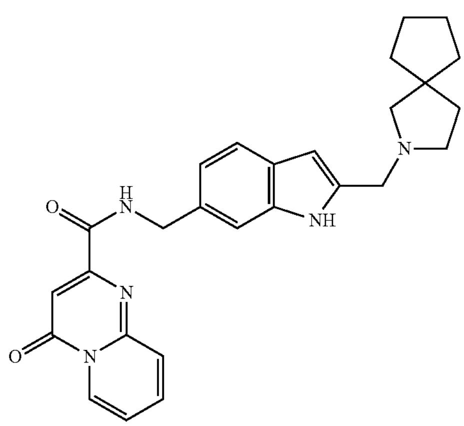 [SMILES: O=C(NCc1ccc2cc(CN3CCC4(CCCC4)C3)[nH]c2c1)c1cc(=O)n2ccccc2n1] | C | 3.88 | 456.5 |

| Compound No | Name | Structure | LCMS method | LCMS Retention time | Mass Ion |
|---|---|---|---|---|---|
| 139 | N-[[2-(2-azabicyclo[2.2.1]heptanean-2-ylmethyl)-1H-indol-6-yl]methyl]-4-oxo-pyrido[1,2-a]pyrimidine-2-carboxamide | 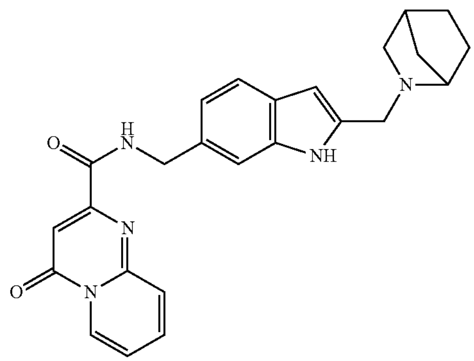 [SMILES: O=C(NCc1ccc2cc(CN3CC4CCC3C4)[nH]c2c1)c1cc(=O)n2ccccc2n1] | C | 3.39 | 428.4 |

Example 42: 4-oxo-N-[[2-[(2,2,2-trifluoroethyl-amino)methyl]-1H-indol-6-yl]methyl]pyrido[1,2-a]pyrimidine-2-carboxamide

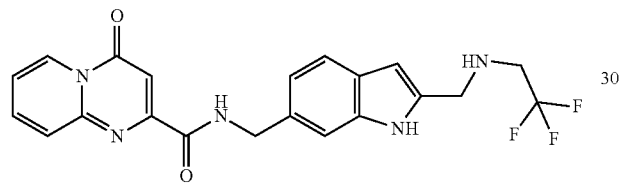

2,2,2-trifluoroethanamine (25 µL, 0.318 mmol) was added to a solution of N-[(2-formyl-1H-indol-6-yl)methyl]-4-oxo-pyrido[1,2-a]pyrimidine-2-carboxamide Example 2 Step 4 (55 mg, 0.159 mmol) in DCE (4 mL) and 1,1,1,3,3,3-Hexafluoro-2-propanol (2 mL) in a pressure vial, and the mixture was stirred at 50° C. for 1 h. The mixture was cooled to room temperature and retreated with 2,2,2-trifluoroethanamine (25 µL, 0.318 mmol) and left to stir at 50° C. for 2.5 h. The mixture was cooled to room temperature and added dropwise over 5 mins to a solution of NaBH$_4$ (18 mg, 0.476 mmol) in Ethanol (2 mL). The mixture was stirred at ambient temperature overnight. The mixture was retreated with NaBH$_4$ (18 mg, 0.476 mmol) and left to stir at ambient temperature for 1 h 15 mins. The mixture was quenched with water (30 mL) and extracted with DCM (3×40 mL). The combined organic layers were passed through an Isolute phase separator and concentrated in vacuo. The crude material was purified by preparative HPLC (Method B) to give the title compound (40.2 mg, 59%) as an off-white solid.

Method C: LC-MS (electrospray): m/z=430.3 (M+H)$^+$, RT=2.94 min

Example 70: N-[[2-[[cyclobutylmethyl(methyl)amino]methyl]-1H-indol-6-yl]methyl]-4-oxo-pyrido[1,2-a]pyrimidine-2-carboxamide

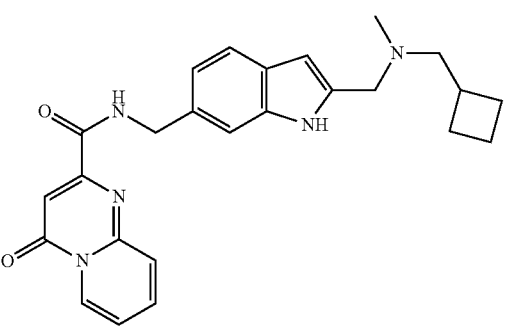 [SMILES: CN(Cc1cc2ccc(CNC(=O)c3cc(=O)n4ccccc4n3)cc2[nH]1)CC1CCC1]

To a solution of N-[[2-[(cyclobutylmethylamino)methyl]-1H-indol-6-yl]methyl]-4-oxo-pyrido[1,2-a]pyrimidine-2-carboxamide (200 mg, 0.481 mmol) in Chloroform (3 mL) and 2-Propanol (1 mL) was added N-ethyl-N-isopropyl-propan-2-amine (0.25 mL, 1.44 mmol) and methyl iodide (30 µL, 0.481 mmol) at ambient temperature and the mixture was stirred for 4 h. The mixture was concentrated under reduced pressure to dryness. The residue was dissolved in MeOH (3 mL) and purified by preparative HPLC (Method B). The product containing fraction were combined and concentrated to dryness at reduced pressure. The residue was dissolved in a 1:1 mixture of acetonitrile and water (4 mL) and lyophilsed to afford the title compound (65 mg, 31%) as pale yellow solid.

Method C: LC-MS (electrospray): m/z=430.4 (M+H)$^+$, RT=3.62 min

Example 43: N-[(2-{[N-(cyclobutylmethyl)acet-amido]methyl}-1H-indol-6-yl)methyl]-4-oxo-4H-pyrido[1,2-a]pyrimidine-2-carboxamide

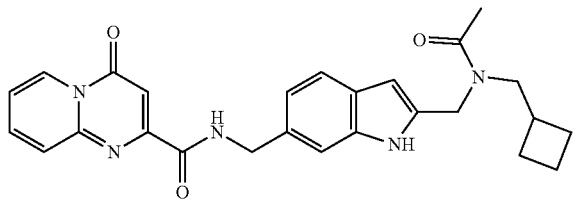

To a solution of N-[[2-[(cyclobutylmethylamino)methyl]-1H-indol-6-yl]methyl]-4-oxo-pyrido[1,2-a]pyrimidine-2-carboxamide Example 2 (150 mg, 0.350 mmol) and N-ethyl-N-isopropyl-propan-2-amine (0.18 mL, 1.05 mmol) in DCM (5 mL) was added acetic anhydride (36 µL, 0.385 mmol) at ambient temperature and the mixture was stirred for 2 h. The mixture was concentrated at reduced pressure to dryness. The residue was purified by preparative HPLC (Method B) to give the title compound (139 mg, 85.9%) as a white solid.

Method E: LC-MS (electrospray): m/z=458.2 (M+H)$^+$, RT=3.01 min

Example 44: 4-oxo-N-{[2-(piperidin-2-yl)-1H-indol-6-yl]methyl}-4H-pyrido[1,2-a]pyrimidine-2-carboxamide

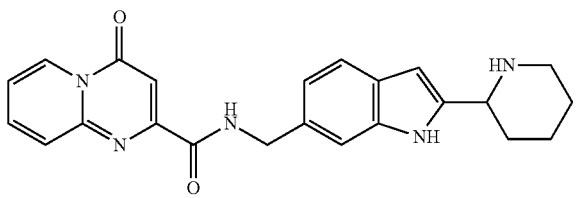

Step 1: tert-butyl 2-[2-(2-amino-4-cyano-phenyl)ethynyl]piperidine-1-carboxylate

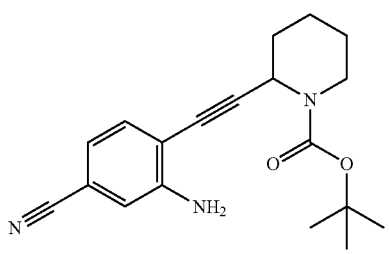 [SMILES: CC(C)(C)OC(=O)N1CCCCC1C#Cc1ccc(C#N)cc1N]

To a solution of 3-amino-4-iodobenzonitrile (1.05 g, 4.30 mmol) in THF-Anhydrous (5 mL) and triethylamine (10 mL, 71.7 mmol) was added Bis(triphenylphosphine)palladium (II) chloride (30 mg, 0.0430 mmol) and triphenylphosphine (23 mg, 0.0861 mmol) at room temperature. The solution was de-gassed by bubbling nitrogen into the solution for 15 minutes. Then copper(1) iodide (16 mg, 0.0861 mmol) and tert-butyl 2-ethynylpiperidine-1-carboxylate (0.99 g, 4.73 mmol) were added sequentially and the reaction was stirred under nitrogen atmosphere for 4 h. The precipitate (triethylamine hydroiodide) was collected by filtration and washed with EtOAc (~20 mL). The filtrate was concentrated at reduced pressure and the residue was purified by chromatography on SiO$_2$ (eluting with 0-50% EtOAc in heptane). The product containing fractions were combined and concentrated in vacuo. The orange solid was triturated with heptane. The resulting solid was collected by filtration, washed with hepatane (~25 mL) and dried in the vacuum oven at 45° C. for 2 h to afford the title compound (1.03 g, 70%) as a white solid.

Method C: LC-MS (electrospray): m/z=651.5 (2M+H)+, RT=4.21 min

Step 2: tert-butyl 2-(6-cyano-1H-indol-2-yl)piperidine-1-carboxylate

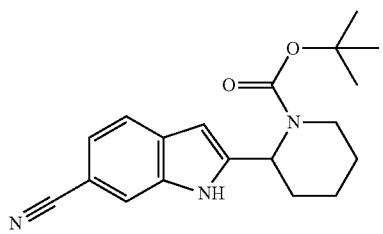

To a stirred solution of tert-butyl 2-[2-(2-amino-4-cyanophenyl)ethynyl]piperidine-1-carboxylate (1.00 g, 3.07 mmol) in NMP-Anhydrous (12 mL) was added potassium 2-methylpropan-2-olate (0.69 g, 6.15 mmol) at 0° C. (the colour of the solution turned from colourless to orange within seconds). After warming to room temperature for 16 h under a nitrogen atmosphere. Ammonium chloride (sat., 5 mL) was added and the resulting mixture was partitioned between EtOAc (100 mL) and water (80 mL). The organic layer was separated, and the aqueous layer was extracted with EtOAc (50 mL). The combined organic layers were washed with water (2×50 mL) and brine (30 mL), dried (Na$_2$SO$_4$), filtered and concentrated at reduced pressure. The residue (brown solid) was purified by chromatography on SiO$_2$ (eluting with 0-50% EtOAc in heptane). The product containing fractions were combined and concentrated in vacuo. The residue (orange solid) was triturated with heptane. The resulting solid was collected by vacuum filtration, washed with heptane (10 mL) and dried in the vacuum oven at 45° C. for 2 h to afford the title compound (875 mg, 87%) as white solid.

Method C: LC-MS (electrospray): m/z=326.3 (M+H)$^+$, RT=4.19 min

Step 3: tert-butyl 2-[6-(aminomethyl)-1H-indol-2-yl]piperidine-1-carboxylate

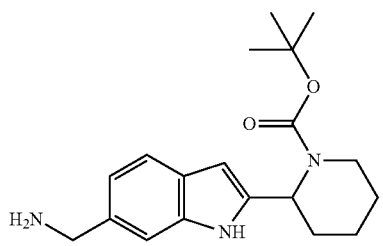 [SMILES: CC(C)(C)OC(=O)N1CCCCC1c1cc2ccc(CN)cc2[nH]1]

The title compound (785 mg, 83%) was prepared from tert-butyl 2-(6-cyano-1H-indol-2-yl)piperidine-1-carboxylate using the chemistry described in Example 2 Step 3.

Method E: LC-MS (electrospray): m/z=330.2 (M+H)$^+$, RT=2.22 min.

Step 4: tert-butyl 2-{6-[({4-oxo-4H-pyrido[1,2-a]pyrimidin-2-yl}formamido)methyl]-1H-indol-2-yl}piperidine-1-carboxylate

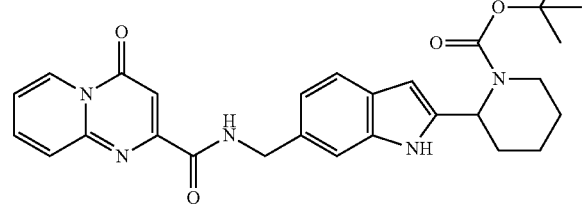

To a solution of 4-oxopyrido[1,2-a]pyrimidine-2-carboxylic acid (135 mg, 0.711 mmol) (Intermediate 1), N-ethyl-N-isopropyl-propan-2-amine (0.11 mL, 0.647 mmol) and tert-butyl 2-[6-(aminomethyl)-1H-indol-2-yl]piperidine-1-carboxylate (213 mg, 0.647 mmol) in DMF-Anhydrous (4 mL) was added HATU (246 mg, 0.647 mmol), the mixture was stirred at ambient temperature for 2 h. The mixture was partitioned between EtOAc (60 mL) and water (40 mL). The organic layer was separated, washed with water (40 mL) and brine (20 mL), dried (Na$_2$SO$_4$), filtered and concentrated in vacuo to dryness. The residue was purified by chromatography on SiO$_2$ (eluting with 0-100% EtOAc in heptane). The product containing fractions were combined and concentrated in vacuo to afford the title compound (313 mg, 92%) as yellow oil.

Method C: LC-MS (electrospray): m/z=502.4 (M+H)$^+$, RT=3.89 min

Step 5: 4-oxo-N-{[2-(piperidin-2-yl)-1H-indol-6-yl]methyl}-4H-pyrido[1,2-a]pyrimidine-2-carboxamide

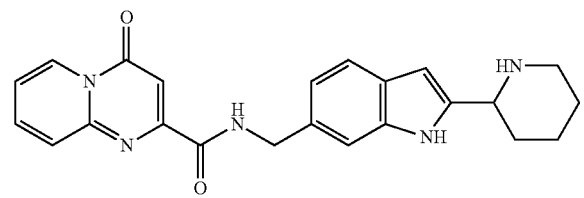

A solution of tert-butyl 2-{6-[({4-oxo-4H-pyrido[1,2-a]pyrimidin-2-yl}formamido)methyl]-1H-indol-2-yl}piperidine-1-carboxylate (96%, 313 mg, 0.599 mmol) in 4M HCl in dioxane (4.5 mL) was stirred at 40° C. for 2 h [the solution turned dark red and the production of gas ceased]. The mixture was cooled to room temperature and concentrated at reduced pressure to dryness. The residue was dissolved in MeOH (3 mL) and by preparative HPLC (Method B). The product containing fractions were combined and concentrated in vacuo to dryness. The residue was dissolved in acetonitrile (2 mL) and water (2 mL) and lyophilsed to afford the title compound (120 mg, 49%) as pale yellow solid.

Method C: LC-MS (electrospray): m/z=402.5 (M+H)$^+$, RT=2.77 min

Example 45: N-[(2-{[(cyclobutylmethyl)amino]methyl}-3-fluoro-1H-indol-6-yl)methyl]-4-oxo-4H-pyrido[1,2-a]pyrimidine-2-carboxamide

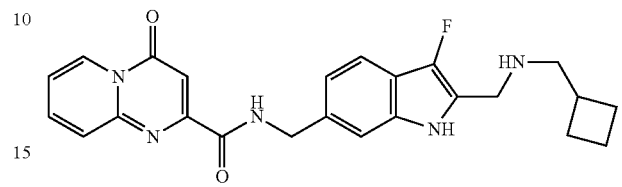

Step 1: N-[(3-fluoro-2-formyl-1H-indol-6-yl)methyl]-4-oxo-pyrido[1,2-a]pyrimidine-2-carboxamide

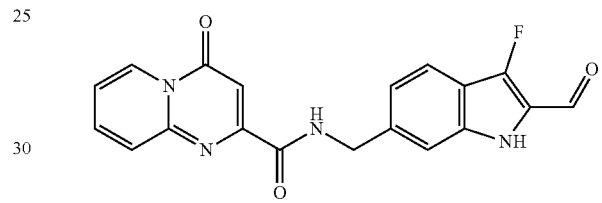

To a solution of N-[(2-formyl-1H-indol-6-yl)methyl]-4-oxo-pyrido[1,2-a]pyrimidine-2-carboxamide (95%, 530 mg, 1.45 mmol) in NMP-Anhydrous (10 mL) was added 1-Chloromethyl-4-fluoro-1,4-diazoniabicyclo[2.2.2]octane bis(tetrafluoroborate) (515 mg, 1.45 mmol) at room temperature and the mixture was stirred for 3 days. The mixture was diluted with EtOAc (100 mL), washed with water (50 mL) and brine (20 mL), dried (Na$_2$SO$_4$) and concentrated at reduced pressure. The residue was purified by preparative HPLC (Method B). The product containing fractions were combined and concentrated to dryness to afford the title compound (97 mg, 15%) as a beige solid.

Method C: LC-MS (electrospray): m/z=365.3 (M+H)$^+$, RT=2.60 min

Step 2: N-[(2-{[(cyclobutylmethyl)amino]methyl}-3-fluoro-1H-indol-6-yl)methyl]-4-oxo-4H-pyrido[1,2-a]pyrimidine-2-carboxamide

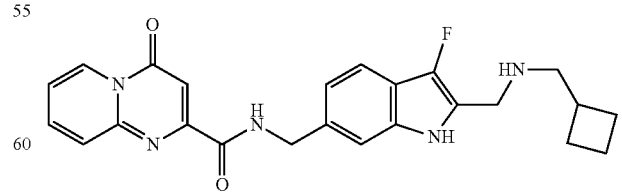

The title compound (40 mg, 43.5%) was prepared in the same manner as Example 2 Step 5.

Method C: LC-MS (electrospray): m/z=434.4 (M+H)$^+$, RT=3.29 min

Example 46: N-[(2-{[(cyclobutylmethyl)amino]methyl}-1-methyl-1H-indol-6-yl)methyl]-4-oxo-4H-pyrido[1,2-a]pyrimidine-2-carboxamide

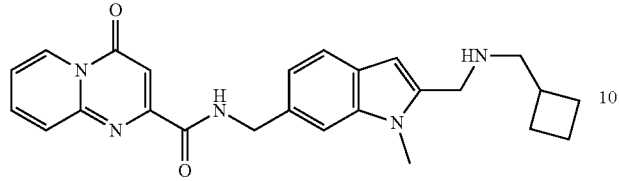

Step 1: 2-(diethoxymethyl)-1-methyl-1H-indole-6-carbonitrile

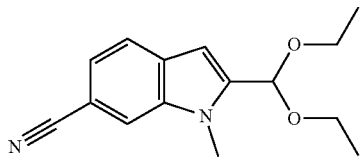 [SMILES: CCOC(OCC)c1cc2ccc(C#N)cc2n1C]

To a slurry of sodium hydride (60%, 266 mg, 6.65 mmol) in DMF (1 mL) at 0° C. was added a solution of 2-(diethoxymethyl)-1H-indole-6-carbonitrile (650 mg, 2.66 mmol) in DMF (1 mL). The reaction was warmed to room temperature for 10 minutes before cooling back to 0° C. Methyl iodide (0.33 mL, 5.32 mmol) was added dropwise to the slurry and the reaction stirred at 0° C. for 5 minutes before warming to room temperature. The reaction was stirred for 1 h. The mixture was cooled to 0° C. and quenched via dropwise addition of water (3 mL). The mixture was diluted with EtOAc (5 mL) and the layers separated. The aqueous layer was extracted twice more with EtOAc (2×5 mL). The organic layers were combined and washed with brine (5 mL), dried over MgSO$_4$, filtered and concentrated in vacuo to give the crude product as a yellow oil. The crude material was purified by chromatography on SiO$_2$ [0-50% EtOAc/heptane] to afford the title compound (624 mg, 90%) as a white solid.

Method B: LC-MS (electrospray): m/z=259.1 (M+H)$^+$, RT=0.68 min

Step 2: 1-[2-(diethoxymethyl)-1-methyl-1H-indol-6-yl]methanamine

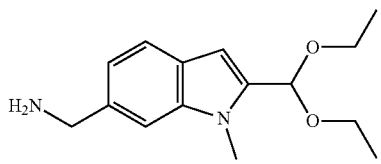 [SMILES: CCOC(OCC)c1cc2ccc(CN)cc2n1C]

The title compound (570 mg, 90%) was prepared in the same manner as Example 2 Step 3.

Method B: LC-MS (electrospray): m/z=263.3 (M+H)$^+$, RT=1.75 min

Step 3: N-[(2-formyl-1-methyl-indol-6-yl)methyl]-4-oxo-pyrido[1,2-a]pyrimidine-2-carboxamide

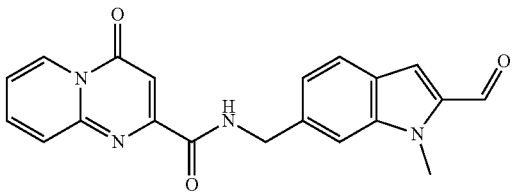 [SMILES: Cn1c(C=O)cc2ccc(CNC(=O)c3cc(=O)n4ccccc4n3)cc21]

T3P (50%, 1.6 mL, 2.61 mmol) was added to a mixture of 4-oxopyrido[1,2-a]pyrimidine-2-carboxylic acid (454 mg, 2.39 mmol) (Intermediate 1), [2-(diethoxymethyl)-1-methyl-indol-6-yl]methanamine (570 mg, 2.17 mmol) and DIPEA (1.9 mL, 10.9 mmol) in DMF (10 mL), and the mixture was stirred at ambient temperature overnight. The mixture was retreated with T3P (50%, 1.6 mL, 2.61 mmol) and DIPEA (1.9 mL, 10.9 mmol) and stirred at ambient temperature for 2 h The mixture was extracted with DCM and H$_2$O, the layers were separated, the mixture was extracted with DCM (3×10 mL), the organic layer was passed through a TELOS phase separator and concentrated. The crude material was purified by chromatography on SiO$_2$ [0-100% EtOAc/heptane] to afford the title compound (369 mg, 46%) as an off-white solid.

Method A: LC-MS (electrospray): m/z=361.1 (M+H)$^+$, RT=1.06 min

Step 4: N-[(2-{[(cyclobutylmethyl)amino]methyl}-1-methyl-1H-indol-6-yl)methyl]-4-oxo-4H-pyrido[1,2-a]pyrimidine-2-carboxamide

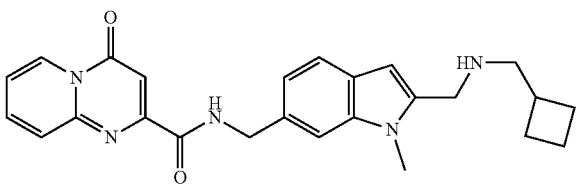 [SMILES: Cn1c(CNCC2CCC2)cc2ccc(CNC(=O)c3cc(=O)n4ccccc4n3)cc21]

1-cyclobutylmethanamine (87 mg, 1.02 mmol) was added to a solution of N-[(2-formyl-1-methyl-indol-6-yl)methyl]-4-oxo-pyrido[1,2-a]pyrimidine-2-carboxamide (184 mg, 0.511 mmol) in 1,1,1,3,3,3-Hexafluoro-2-propanol (18.437 mL), and the mixture was stirred at ambient temperature for 30 minutes. 1-cyclobutylmethanamine (87 mg, 1.02 mmol) was added, and the mixture was stirred at ambient temperature for 1 h, then the mixture was heated 40° C. for 2 h. A further 1-cyclobutylmethanamine (87 mg, 1.02 mmol) was added, and the mixture was stirred at ambient temperature overnight. NaBH$_4$ (58 mg, 1.53 mmol) was added to the mixture, followed by a few drops of MeOH and stirred at ambient temperature for 30 minutes. The mixture was quenched with MeOH (10 mL) at 0° C. and concentrated in vacuo. The residue was partitioned between sat. NaHCO$_3$ (aq) (10 mL) and DCM (10 mL) and the phases separated. The aqueous phase was extracted with DCM (2×10 mL) and the combined organic phases were passed through a TELOS phase separator and concentrated in vacuo. The residue was purified by preparative HPLC (Method B) to afford the title compound (119 mg, 54.3%) as a pale yellow solid.

Method C: LC-MS (electrospray): m/z=430.6 (M+H)⁺, RT=3.42 min

Example 47: N-[[2-[(Cyclobutylmethylamino)-dideuterio-methyl]-1H-indol-6-yl]methyl]-4-oxopyrido[1,2-a]pyrimidine-2-carboxamide

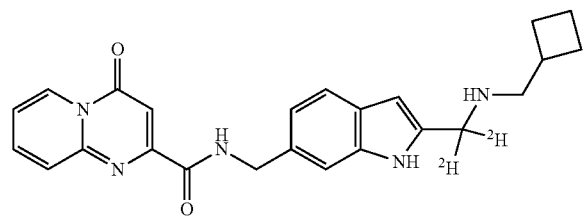 [SMILES: [2H]C([2H])(NCC1CCC1)c1cc2ccc(CNC(=O)c3cc(=O)n4ccccc4n3)cc2[nH]1]

Step 1: 6-cyano-1H-indole-2-carboxylic acid

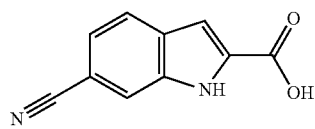 [SMILES: N#Cc1ccc2cc(C(=O)O)[nH]c2c1]

To a suspension of methyl 6-cyano-1H-indole-2-carboxylate (1.00 g, 5.00 mmol) in MeOH (15 mL) was added 1 M sodium hydroxide (7.5 mL, 7.49 mmol) at ambient temperature. The mixture was stirred at 40° C. for 2 h. After cooling to room temperature, the reaction was acidified with 2M HCl (5 mL) and water (20 mL) was added. The resulting precipitate was collected by vacuum filtration, washed with water (50 mL) and dried in the vacuum oven at 45° C. overnight to afford the title compound (926 mg, 95%) as pale yellow solid.

Method A: LC-MS (electrospray): m/z=185.2 (M−H)⁻, RT=0.98 min

Step 2: 6-Cyano-N-(cyclobutylmethyl)-1H-indole-2-carboxamide

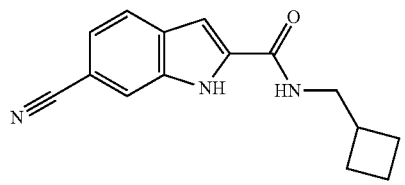 [SMILES: N#Cc1ccc2cc(C(=O)NCC3CCC3)[nH]c2c1]

To a solution of 6-cyano-1H-indole-2-carboxylic acid (97%, 626 mg, 3.26 mmol) in DMF (5 mL) was added di(imidazol-1-yl)methanone (529 mg, 3.26 mmol) at ambient temperature. The mixture was stirred at 70° C. (significant production of gas) for 1 h. The mixture was cooled to room temperature and 1-cyclobutylmethanamine (361 mg, 4.24 mmol) was added. The mixture was stirred at ambient temperature for 3 h. The mixture was diluted with EtOAc (10 mL) and the solid was filtered. To the filtrate were added water (50 mL) and diethyl ether (50 mL) with stirring. The resulting precipitate was collected by vacuum filtration, washed with water (20 mL) and diethyl ether (20 mL), and dried in the vacuum oven at 45° C. overnight to afford the title compound (550 mg, 63%) as an off-white solid.

Method A: LC-MS (electrospray): m/z=253.9 (M+H)⁺, RT=1.14 min

Step 3: 6-(aminomethyl)-N-(cyclobutylmethyl)-1H-indole-2-carboxamide

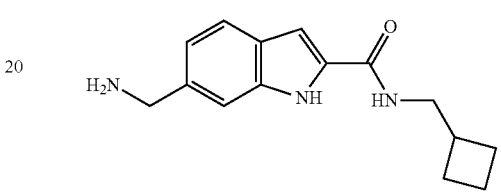

The title compound (487 mg, 94%) was prepared in the same manner as Example 2 Step 3.

Method C: LC-MS (electrospray): m/z=258.1 (M+H)⁺, RT=2.56 min

Step 4: 1-[6-(Aminomethyl)-1H-indol-2-yl]-N-(cyclobutylmethyl)-1,1-dideuterio-methanamine

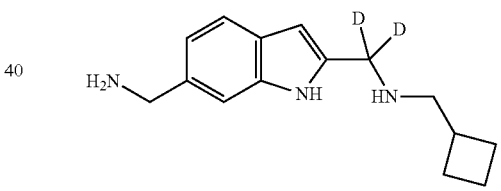

To a cooled (ice-bath) suspension of lithium tetrahydrido(²H₄)aluminate(1-) (221 mg, 5.83 mmol) in 1,4-Dioxane-Anhydrous (5 mL) was added 6-(aminomethyl)-N-(cyclobutylmethyl)-1H-indole-2-carboxamide (150 mg, 0.583 mmol) in one portion. The ice-bath was removed, and the mixture was stirred at reflux for 3 h (heating-block temperature 110° C.). The mixture was cooled to 0° C. (ice-bath) and quenched by drop-wise addition of a mixture of THF (10 mL) and water (1 mL), followed by 2M NaOH (0.2 mL). The mixture was stirred for 30 minutes at ambient temperature. The solids were removed by filtration (Kieselguhr) and washed with THF (20 mL). The filtrate was dried (Na₂SO₄), filtered and concentrated at reduced pressure to dryness. The residue was dissolved in chloroform (2 mL) and heptane (10 mL) was added. The resulting precipitate was collected by vacuum filtration, washed with heptane (5 mL) and dried in the vacuum oven at 45° C. for 2 h to afford the title compound (114 mg, 69%) as a pale yellow solid.

Method C: LC-MS (electrospray): m/z=246.2 (M+H)⁺, RT=2.96 min

Step 5: N-[[2-[(Cyclobutylmethylamino)-dideuterio-methyl]-1H-indol-6-yl]methyl]-4-oxo-pyrido[1,2-a]pyrimidine-2-carboxamide

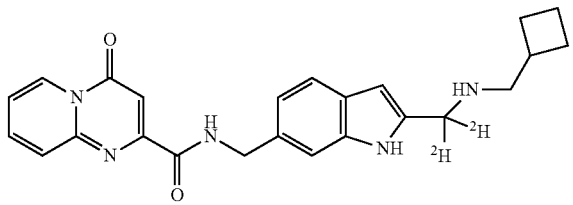 [SMILES: [2H]C([2H])(NCC1CCC1)c1cc2ccc(CNC(=O)c3cc(=O)n4ccccc4n3)cc2[nH]1]

To a solution of 4-oxopyrido[1,2-a]pyrimidine-2-carboxylic acid (78 mg, 0.408 mmol) (Intermediate 1), 1-[6-(aminomethyl)-1H-indol-2-yl]-N-(cyclobutylmethyl)-1,1-dideuterio-methanamine (86%, 116 mg, 0.408 mmol) and DIPEA (0.21 mL, 1.22 mmol) in DMF (3 mL) was added HATU (170 mg, 0.448 mmol). The reaction was stirred at ambient temperature overnight. The mixture was partitioned between EtOAc (600 mL) and sat. NaHCO$_3$ solution (20 mL). The organic layer was separated, washed with brine (10 mL), dried (Na$_2$SO$_4$), filtered and concentrated at reduced pressure. The residue was purified by open access prep HPLC method A. The product containing fractions were combined and concentrated in vacuo until the bulk of the acetonitrile was removed (water bath temperature 45° C., pressure 100 mbar). The clear solution was basified with sat. aq. sodium carbonate solution and extracted with 3:1 chloroform/2-propanol (3×40 mL). The combined extracts were washed with brine (40 mL), dried (Na$_2$SO$_4$), filtered and concentrated to dryness at reduced pressure. The residue was triturated with acetonitrile. The solid was collected by vacuum filtration, washed with acetonitrile (10 mL) and dried in the vacuum oven at 45° C. overnight to afford the title compound (63 mg 36%) as a white solid.

Method C: LC-MS (electrospray): m/z=418.5 (M+H)$^+$, RT=3.14 min

Example 48: N-[[2-[(cyclobutylmethylamino)methyl]-1H-indol-6-yl]methyl]-1H-indazole-4-carboxamide

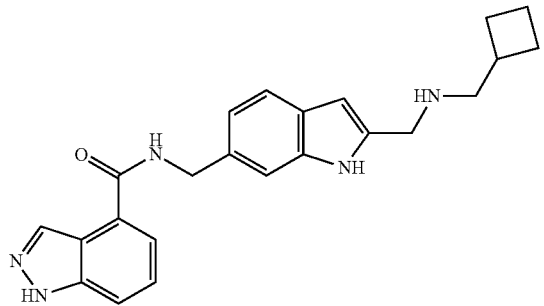 [SMILES: O=C(NCc1ccc2cc(CNCC3CCC3)[nH]c2c1)c1cccc2[nH]ncc12]

A pressure vial was charged with N-[(2-formyl-1H-indol-6-yl)methyl]-1-tetrahydropyran-2-yl-indazole-4-carboxamide (150 mg, 0.373 mmol), DCE (4.3 mL) and 1-cyclobutyl-methanamine (0.091 mL, 0.745 mmol) at ambient temperature. The vial was sealed, and the mixture was stirred at 65° C. for 2 h. After cooling to room temperature, sodium triacetoxyboranuide (184 mg, 0.866 mmol) was added and the mixture was heated to 65° C. for 2 h. The mixture was partitioned between EtOAc (40 mL) and saturated sodium bicarbonate solution (30 mL). The organic layer was separated, washed with brine (20 mL), dried (Na$_2$SO$_4$), filtered and concentrated at reduced pressure. The orange residue was purified via basic reversed phase chromatography (SNAP Ultra 30 g cartridge, MeCN+0.1% NH$_3$/H$_2$O+0.1% NH$_3$ 10 to 90%). The fractions containing pure product were concentrated in vacuo to give a beige residue. The crude material was redissolved in MeOH (1 mL) and DCM (4 mL) and 4M HCl in dioxane (1 mL) was added. The reaction was stirred at ambient temperature for 5 h. The solvent was removed in vacuo and the crude pink solid purified using a 2g-SCX cartridge eluting first with MeOH (10 mL) and then a 2M ammonia in MeOH solution (10 mL). The second filtrate was concentrated in vacuo to give the desired product as a an off-white solid. The compound was freeze dried overnight to afford the title compound (78 mg, 53%) as an off-white powder.

Method C: LC-MS (electrospray): m/z=388.3 (M+H)$^+$, RT=2.96 min

Intermediate 2: tert-Butyl N-(cyclobutylmethyl)-N-prop-2-ynyl-carbamate

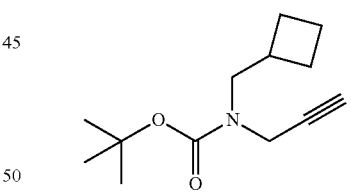

To a solution of tert-butyl prop-2-yn-1-ylcarbamate (3.00 g, 19.3 mmol) in DMF-Anhydrous (30 mL) was added sodium hydride (60%, 852 mg, 21.3 mmol) at 0° C. The mixture was left to stir for 10 min before addition of (bromomethyl)cyclobutane (2.4 mL, 21.3 mmol). The resulting mixture was then stirred at ambient temperature overnight. The mixture was diluted with water (50 mL) and extracted with diethyl ether (3×50 mL). The combined organic extracts were washed with water (80 mL) and brine (30 mL), dried over MgSO$_4$, filtered and concentrated under reduced pressure. The crude material was purified by chromatography on SiO$_2$ [Sfar silica D Cartridge 50 g; 0-20% EtOAc in heptane, 12 CVs]. The product containing fractions were combined and concentrated in vacuo to afford the title compound (3.12 g, 13.3 mmol, 69%) as a colourless oil.

Intermediate 3: tert-butyl 6-(azidomethyl)-2-[[tert-butoxycarbonyl(cyclobutylmethyl)amino]methyl]pyrrolo[3,2-b]pyridine-1-carboxylate

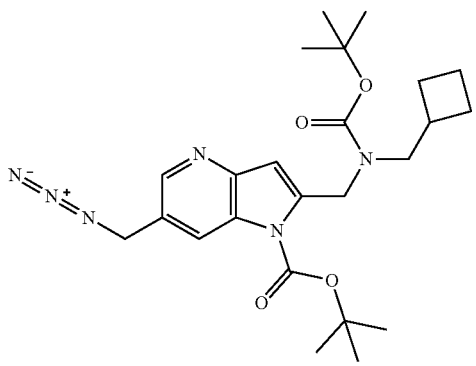 [SMILES: CC(C)(C)OC(=O)N(Cc1cc2ncc(CN=[N+]=[N-])cc2n1C(=O)OC(C)(C)C)CC1CCC1]

Step 1: methyl 5-amino-6-bromo-pyridine-3-carboxylate

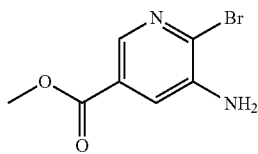

NBS (6434 mg, 36.1 mmol) was added to a solution of methyl 5-aminopyridine-3-carboxylate (5000 mg, 32.9 mmol) in DMF-Anhydrous (50 mL) and the mixture was stirred at room temperature over a weekend. The mixture was diluted with water (250 mL) and extracted with EtOAc (250 mL). The combined organics were washed with water (250 mL) and brine (250 mL), dried over magnesium sulfate and evaporated to dryness. The crude material was purified by chromatography on SiO$_2$ (Biotage; 100 g Sfar Duo; 0-100% EtOAc in heptane) to afford the title compound (2850 mg, 25%) as a yellow solid.

Method A: LC-MS (electrospray): m/z=231/233 (M+H)$^+$, RT=0.95 min

Step 2: methyl 6-bromo-5-[(2,2,2-trifluoroacetyl)amino]pyridine-3-carboxylate

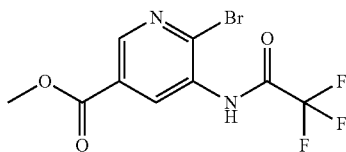

TFAA (4.5 mL, 32.2 mmol) was added to a solution of methyl 5-amino-6-bromo-pyridine-3-carboxylate (70%, 3540 mg, 10.7 mmol) in DCM (30 mL) and the RM was stirred at ambient temperature for 3 h. The RM was evaporated to dryness to afford methyl (5250 mg, 99%) as an orange oil.

Method A: LC-MS (electrospray): m/z=327/329 (M+H)$^+$, RT=1.10 min

Step 3: methyl 2-[[tert-butoxycarbonyl(cyclobutylmethyl)amino]methyl]-1H-pyrrolo[3,2-b]pyridine-6-carboxylate

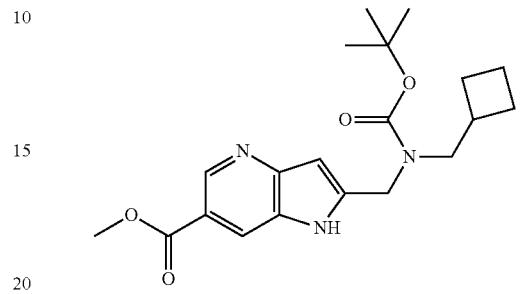

A solution of methyl 6-bromo-5-[(2,2,2-trifluoroacetyl)amino]pyridine-3-carboxylate (66%, 5250 mg, 10.6 mmol) in 1,4-Dioxane-Anhydrous (11 mL) was added to a suspension of tert-butyl N-(cyclobutylmethyl)-N-prop-2-ynyl-carbamate (95%, 2490 mg, 10.6 mmol) (Intermediate 2), CuI (304 mg, 1.59 mmol), potassium phosphate (4562 mg, 21.2 mmol) and triphenylphosphane (834 mg, 3.18 mmol) in 1,4-Dioxane-Anhydrous (55 mL). The resulting suspension was degassed with nitrogen for 10 min, then stirred at 110° C. for 2 h. The mixture was cooled and concentrated under reduced pressure. The residue was partitioned between water (30 mL) and EtOAc (30 mL). The organic phase was collected, and the aqueous phase was extracted with EtOAc (2×30 mL). The combined organic phases were dried over magnesium sulfate and concentrated to afford crude material as a brown oil. The crude material was purified by chromatography on SiO$_2$ (Biotage Isolera Four; 100 g Sfar Duo; 10-60% EtOAc in heptane), then repurified by chromatography on SiO$_2$ (Biotage Isolera Four; 55 g Sfar Amino D; 10-50% EtOAc in heptane) to afford the title compound (1180 mg, 30%) as a white solid.

Method A: LC-MS (electrospray): m/z=374.2 (M+H)$^+$, RT=1.07 min

Step 4: 1-tert-butyl 6-methyl 2-[[tert-butoxycarbonyl(cyclobutylmethyl)amino]methyl]pyrrolo[3,2-b]pyridine-1,6-dicarboxylate

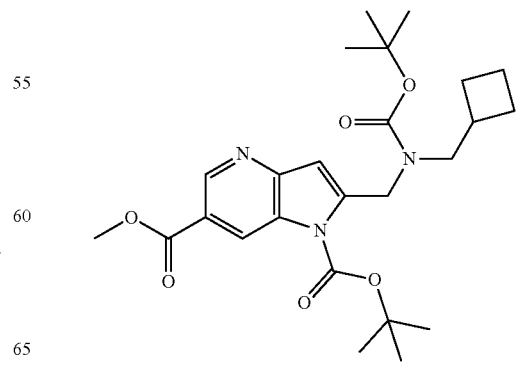

Boc anhydride (947 mg, 4.34 mmol) was added to an ice-cooled solution of methyl 2-[[tert-butoxycarbonyl(cyclobutylmethyl)amino]methyl]-1H-pyrrolo[3,2-b]pyridine-6-carboxylate (1350 mg, 3.61 mmol) in DCM (28.602 mL), followed by DMAP (44 mg, 0.361 mmol). The mixture was warmed to room temperature and stirred for 30 minutes. Water (50 mL) was added and the mixture was extracted with DCM (3×50 mL). The combined organics were dried over magnesium sulfate, evaporated to dryness and purified by chromatography on SiO$_2$ (55 g Sfar Amino D; 0-50% EtOAc in heptane) to afford the title compound (1630 mg, 95%) as a colourless oil.

Method B: LC-MS (electrospray): m/z=474.3 (M+H)$^+$, RT=2.28 min

Step 5: tert-butyl 2-[[tert-butoxycarbonyl(cyclobutylmethyl)amino]methyl]-6-(hydroxymethyl)pyrrolo[3,2-b]pyridine-1-carboxylate

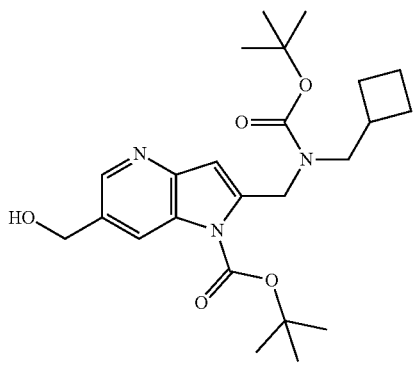 [SMILES: CC(C)(C)OC(=O)N(Cc1cc2ncc(CO)cc2n1C(=O)OC(C)(C)C)CC1CCC1]

1M DIBAL in DCM (14 mL, 13.5 mmol) was added to a solution of 1-tert-butyl 6-methyl 2-[[tert-butoxycarbonyl(cyclobutylmethyl)amino]methyl]pyrrolo[3,2-b]pyridine-1,6-dicarboxylate (1600 mg, 3.38 mmol) in DCM-Anhydrous (32 mL) at –78° C. The mixture was stirred at this temperature for 2 h. At –78° C. the reaction was quenched with water (10 mL). The mixture was stirred for 10 min, then warmed to room temperature. Water (50 mL) was added and the mixture was extracted with DCM (3×50 mL). The combined organic phases were dried over magnesium sulfate, evaporated to dryness and purified by chromatography on SiO$_2$ (Biotage Isolera Four; 55 g Sfar Amino D; 0-100% EtOAc in heptane) to afford the title compound (1160 mg, 74%) as a colourless oil.

Method A: LC-MS (electrospray): m/z=446.3 (M+H)$^+$, RT=1.25 min

Step 6: tert-butyl 6-(azidomethyl)-2-[[tert-butoxycarbonyl(cyclobutylmethyl)amino]methyl]pyrrolo[3,2-b]pyridine-1-carboxylate

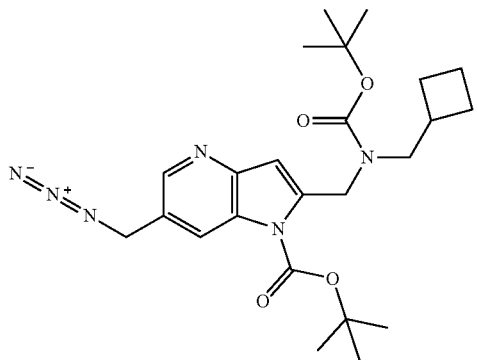 [SMILES: CC(C)(C)OC(=O)N(Cc1cc2ncc(CN=[N+]=[N-])cc2n1C(=O)OC(C)(C)C)CC1CCC1]

DPPA (241 μL, 1.12 mmol) was added to an ice-cooled solution of tert-butyl 2-[[tert-butoxycarbonyl(cyclobutylmethyl)amino]methyl]-6-(hydroxymethyl)pyrrolo[3,2-b]pyridine-1-carboxylate (250 mg, 0.561 mmol) and DBU (167 IL, 1.12 mmol) in DMF-Anhydrous (3.125 mL). The mixture was stirred at ambient temperature for 24 h A further amount of DPPA (241 μL, 1.12 mmol) was added and the mixture was stirred at ambient temperature for 18 h, then heated to 40° C. for 2 h. The mixture was diluted with water (25 mL) and extracted with EtOAc (3×20 mL). The combined organics were washed with brine (25 mL), dried over magnesium sulfate and evaporated to dryness. The crude material was purified by chromatography on SiO$_2$ (Biotage Isolera Four; 28 g Sfar Amino D; 0-100% EtOAc in heptane) to afford the title compound (140 mg, 0.24, 44%) as a colourless oil.

Method A: LC-MS (electrospray): m/z=471.3 (M+H)$^+$, RT=1.53 min

Example 49: N-[[2-[(cyclobutylmethylamino)methyl]-1H-pyrrolo[3,2-b]pyridin-6-yl]methyl]-4-oxo-pyrido[1,2-a]pyrimidine-2-carboxamide

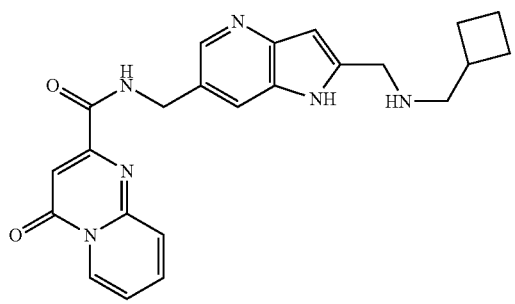 [SMILES: O=C(NCc1cnc2cc(CNCC3CCC3)[nH]c2c1)c1cc(=O)n2ccccc2n1]

Step 1: tert-butyl 6-(aminomethyl)-2-[[tert-butoxycarbonyl(cyclobutylmethyl)amino]methyl]pyrrolo[3,2-b]pyridine-1-carboxylate

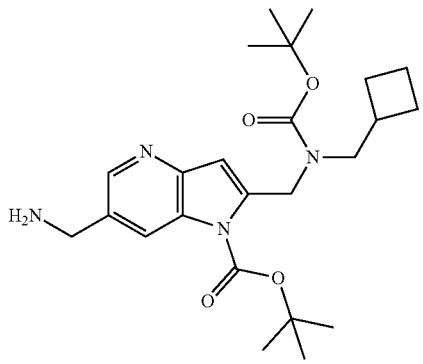 [SMILES: CC(C)(C)OC(=O)N(Cc1cc2ncc(CN)cc2n1C(=O)OC(C)(C)C)CC1CCC1]

Triphenylphosphane (524 mg, 2.00 mmol) was added to an ice-cooled solution of tert-butyl 6-(azidomethyl)-2-[[tert-butoxycarbonyl(cyclobutylmethyl)amino]methyl]pyrrolo[3,2-b]pyridine-1-carboxylate (94%, 500 mg, 0.999 mmol) (Intermediate 3) in THF (5 mL) and water (0.5 mL). The mixture was warmed to room temperature and stirred overnight. The mixture was evaporated to dryness and purified by basic reverse phase chromatography to afford (55 mg, 12%) as a colourless oil.

Method B: LC-MS (electrospray): m/z=445.3 (M+H)$^+$, RT=1.89 min

Step 2: tert-butyl 2-[[tert-butoxycarbonyl(cyclobutylmethyl)amino]methyl]-6-[[(4-oxopyrido[1,2-a]pyrimidine-2-carbonyl)amino]methyl]pyrrolo[3,2-b]pyridine-1-carboxylate

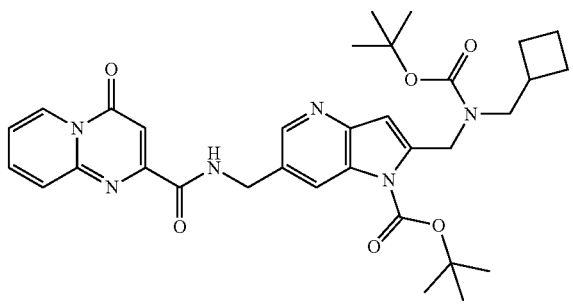 [SMILES: CC(C)(C)OC(=O)N(Cc1cc2ncc(CNC(=O)c3cc(=O)n4ccccc4n3)cc2n1C(=O)OC(C)(C)C)CC1CCC1]

A mixture of tert-butyl 6-(aminomethyl)-2-[[tert-butoxycarbonyl(cyclobutylmethyl)amino]methyl]pyrrolo[3,2-b]pyridine-1-carboxylate (55 mg, 0.124 mmol), 4-oxopyrido[1,2-a]pyrimidine-2-carboxylic acid (24 mg, 0.124 mmol) (Intermediate 1), DIPEA (65 µL, 0.371 mmol) and HATU (52 mg, 0.136 mmol) in DMF (1 mL) was stirred at ambient temperature over a weekend. The mixture was partitioned between sat. aq. NaHCO$_3$ (15 mL) and EtOAc (15 mL). The organic phase was collected, dried over magnesium sulfate and evaporated to dryness. The crude material was purified by chromatography on SiO$_2$ (11 g Sfar Amino D; 0-100% EtOAc in heptane) to afford the title compound (51 mg, 57%) as a yellow oil.

Method B: LC-MS (electrospray): m/z=617.4 (M+H)$^+$, RT=1.91 min

Step 3: N-[[2-[(cyclobutylmethylamino)methyl]-1H-pyrrolo[3,2-b]pyridin-6-yl]methyl]-4-oxo-pyrido[1,2-a]pyrimidine-2-carboxamide

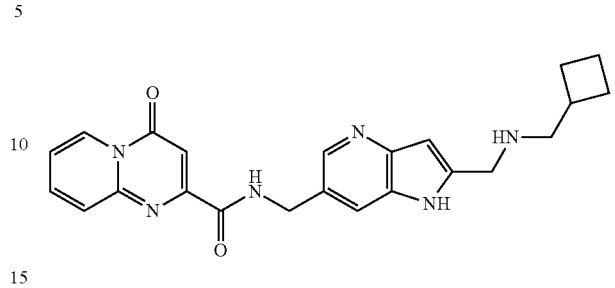

4 M HCl in dioxane (0.17 mL, 0.697 mmol) was added to a solution of tert-butyl 2-[[tert-butoxycarbonyl(cyclobutylmethyl)amino]methyl]-6-[[(4-oxopyrido[1,2-a]pyrimidine-2-carbonyl)amino]methyl]pyrrolo[3,2-b]pyridine-1-carboxylate (86%, 50 mg, 0.0697 mmol) in DCM (0.5 mL) and MeOH (0.5 mL). The mixture was stirred at 40° C. for 2 h, then room temperature overnight. The mixture was evaporated to dryness and purified by preparative HPLC (Method B) to afford the title compound (15 mg, 50%) as a white powder.

Method C: LC-MS (electrospray): m/z=417.3 (M+H)$^+$, RT=2.32 min

Intermediate 12: tert-butyl N-[[6-(aminomethyl)-1H-pyrrolo[2,3-b]pyridin-2-yl]methyl]-N-(cyclobutylmethyl)carbamate

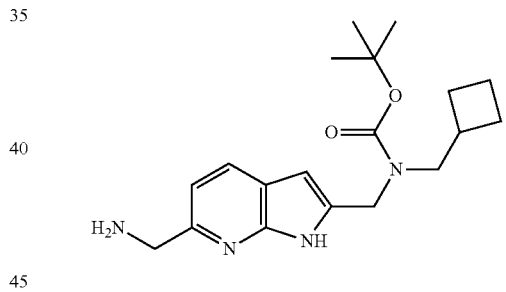

Step 1: tert-butyl N-[3-(2-amino-6-chloro-3-pyridyl)prop-2-ynyl]-N-(cyclobutylmethyl)carbamate

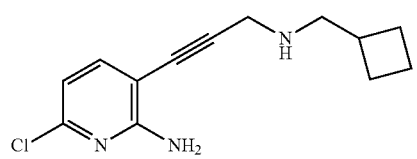 [SMILES: Nc1nc(Cl)ccc1C#CCNCC1CCC1]

To a solution of 6-chloro-3-iodopyridin-2-amine (0.96 g, 3.77 mmol) in THF-Anhydrous (5 mL) and triethylamine (9.0 mL, 64.6 mmol) was added palladium(2+) chloride-triphenylphosphane (1:2:2) (26 mg, 0.0377 mmol) and triphenylphosphane (20 mg, 0.0755 mmol) at ambient temperature. The solution was de-gassed by bubbling nitrogen into the solution for 15 minutes. Then copper(1+) iodide (14 mg, 0.0755 mmol) and tert-butyl N-(cyclobutylmethyl)-N-prop-2-ynyl-carbamate (1.01 g, 4.53 mmol) (Intermediate 2)

were added sequentially and the reaction was stirred under nitrogen atmosphere for 4 h. The precipitate (triethylamine hydroiodide) was collected by filtration and washed with EtOAc (~20 mL). The filtrate was concentrated at reduced pressure and the residue was purified by chromatography on SiO$_2$ [BIOTAGE Sfar Silica D-Duo 60 μm cartridge, 0-50% EtOAc in heptane 12CVs]. The product containing fractions were combined and concentrated in vacuo to afford the title compound (1.31 g, 92%) as orange oil, that solidified upon standing to give a brown solid.

Method C: LC-MS (electrospray): m/z=350.3 (M+H)$^+$, RT=4.54 min

Step 2: tert-butyl N-[(6-chloro-1H-pyrrolo[2,3-b]pyridin-2-yl)methyl]-N-(cyclobutylmethyl)carbamate

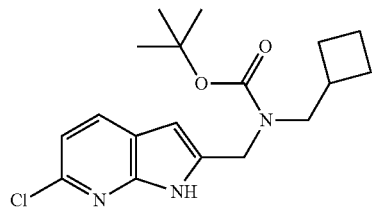 [SMILES: CC(C)(C)OC(=O)N(Cc1cc2ccc(Cl)nc2[nH]1)CC1CCC1]

To a stirred solution of tert-butyl N-[3-(2-amino-6-chloro-3-pyridyl)prop-2-ynyl]-N-(cyclobutylmethyl)carbamate (93%, 1.41 g, 3.74 mmol) in NMP-Anhydrous (15 mL) was added potassium 2-methylpropan-2-olate (0.84 g, 7.49 mmol) at 0° C. (the colour of the solution turned from orange to black within seconds). After warming to room temperature, the solution was stirred at ambient temperature for 16 h under nitrogen atmosphere. Saturated aqueous ammonium chloride solution (5 mL) was added and the resulting mixture was partitioned between EtOAc (100 mL) and water (80 mL). The organic layer was separated, and the aqueous layer was extracted with EtOAc (50 mL). The combined organic layers were washed with water (2×50 mL) and brine (30 mL), dried (Na$_2$SO$_4$), filtered and concentrated at reduced pressure. The residue was purified by chromatography on SiO$_2$ [BIOTAGE Sfar Silica D-Duo 60 μm cartridge 50 g, 0-50% EtOAc in heptane 12CVs]. The product containing fractions were combined and concentrated in vacuo. The residue (orange solid) was triturated with heptane. The resulting solid was collected by vacuum filtration, washed with heptane (10 mL) and dried in the vacuum oven at 45° C. for 2 h to afford the title compound (650 mg, 47%) as white solid.

Method C: LC-MS (electrospray): m/z=350.3/352.3 (M+H)$^+$, RT=4.60 min

Step 3: tert-butyl N-[(6-cyano-1H-pyrrolo[2,3-b]pyridin-2-yl)methyl]-N-(cyclobutylmethyl)carbamate

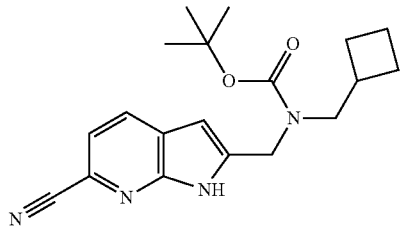 [SMILES: CC(C)(C)OC(=O)N(Cc1cc2ccc(C#N)nc2[nH]1)CC1CCC1]

To a de-gassed suspension of tert-butyl N-[(6-chloro-1H-pyrrolo[2,3-b]pyridin-2-yl)methyl]-N-(cyclobutylmethyl)carbamate (585 mg, 1.67 mmol) and zinc dicyanide (216 mg, 1.84 mmol) in NMP-Anhydrous (7 mL) in a pressure vial was added tBuXPhos Pd G3 (33 mg, 0.0418 mmol) at ambient temperature. The vial was sealed, and the reaction was stirred at 120° C.° C. for 2 h. After cooling to room temperature, the mixture was diluted with water (30 mL) and extracted with ethyl acetate (2×50 mL). The combined organic extracts were washed with water (50 mL), saturated NaHCO$_3$ (aq) solution (20 mL) and brine (20 mL), dried over (Na$_2$SO$_4$), filtered and concentrated at reduced pressure. The residue was purified by chromatography on SiO$_2$ [BIOTAGE Sfar Silica D-Duo 60 μm cartridge 25 g, 0-100% EtOAc in heptane 12CVs]. The product containing fraction (fraction 3) was concentrated in vacuo to afford the title compound (475 mg, 79%) as white solid.

Method C: LC-MS (electrospray): m/z=341.4 (M+H)$^+$, RT=4.22 min

Step 4: tert-butyl N-[[6-(aminomethyl)-1H-pyrrolo[2,3-b]pyridin-2-yl]methyl]-N-(cyclobutylmethyl)carbamate

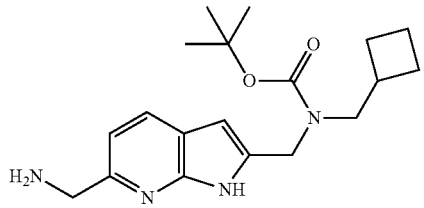 [SMILES: CC(C)(C)OC(=O)N(Cc1cc2ccc(CN)nc2[nH]1)CC1CCC1]

To a de-gassed suspension of tert-butyl N-[(6-cyano-1H-pyrrolo[2,3-b]pyridin-2-yl)methyl]-N-(cyclobutylmethyl)carbamate (475 mg, 1.40 mmol) in Ethanol (20 mL) were added 7 M ammonia in MeOH (5.0 mL, 35.0 mmol) and Raney-nickel (164 mg, 2.79 mmol) at ambient temperature. The mixture was degassed again and stirred under an atmosphere of hydrogen for 16 h. The catalyst was removed by filtration (Celite) and washed with ethanol (approximately 20 mL). The filtrate was concentrated at reduced pressure to dryness to afford the title compound (480 mg, 95) as a greenish oil.

Method C: LC-MS (electrospray): m/z=345.4 (M+H)$^+$, RT=3.58 min

Example 71: N-[[2-[(cyclobutylmethylamino)methyl]-1H-pyrrolo[2,3-b]pyridin-6-yl]methyl]-4-oxo-pyrido[1,2-a]pyrimidine-2-carboxamide

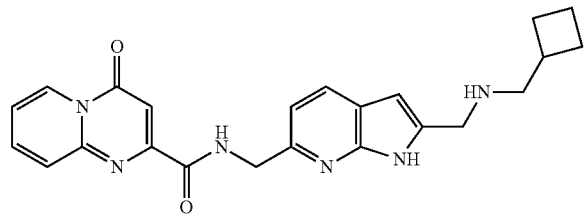 [SMILES: O=C(NCc1ccc2cc(CNCC3CCC3)[nH]c2n1)c1cc(=O)n2ccccc2n1]

Step 1: N-[[2-[(cyclobutylmethylamino)methyl]-1H-pyrrolo[2,3-b]pyridin-6-yl]methyl]-4-oxo-pyrido[1,2-a]pyrimidine-2-carboxamide

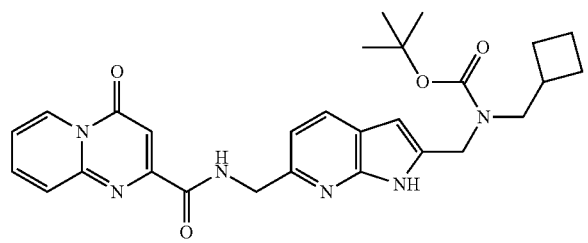 [SMILES: CC(C)(C)OC(=O)N(Cc1cc2ccc(CNC(=O)c3cc(=O)n4ccccc4n3)nc2[nH]1)CC1CCC1]

The title compound (345 mg, 64%) was prepared in the same manner as precursor in Example 42, using Intermediate 12.
Method C: LC-MS (electrospray): m/z=517.4 (M+H)$^+$, RT=3.92 min Step 2: N-[[2-[(cyclobutylmethylamino)methyl]-1H-pyrrolo[2,3-b]pyridin-6-yl]methyl]-4-oxo-pyrido[1,2-a]pyrimidine-2-carboxamide

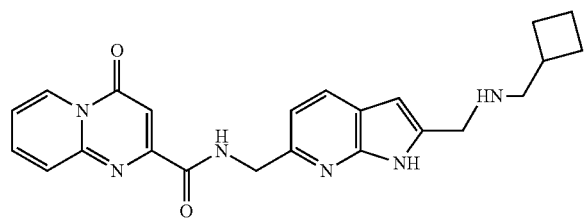 [SMILES: O=C(NCc1ccc2cc(CNCC3CCC3)[nH]c2n1)c1cc(=O)n2ccccc2n1]

To a solution of tert-butyl N-(cyclobutylmethyl)-N-[[6-[[(4-oxopyrido[1,2-a]pyrimidine-2-carbonyl)amino]methyl]-1H-pyrrolo[2,3-b]pyridin-2-yl]methyl]carbamate (90%, 730 mg, 1.27 mmol) in DCM (5 mL) was added TFA (5 mL) at ambient temperature. The mixture was stirred at ambient temperature until the production of gas ceased (~1 h). The mixture was concentrated to dryness at reduced pressure. The residue was dissolved in MeOH (6 mL) and purified by open access prep HPLC Method B. The product containing fractions were combined and concentrated in vacuo to dryness. The residue (colourless oil) was triturated with acetonitrile (5 mL). The resulting solid was collected by vacuum filtration, washed with acetonitrile (2 mL) and heptane (5 mL) and dried in the vacuum oven at 45° C. overnight to the title compound (345 mg, 64%) as a white solid.
Method C: LC-MS (electrospray): m/z=417.4 (M+H)$^+$, RT=2.85 min Example 72: N-[(2-{[(cyclobutylmethyl)amino]methyl}-1H-1,3-benzodiazol-6-yl)methyl]-4-oxo-4H-pyrido[1,2-a]pyrimidine-2-carboxamide

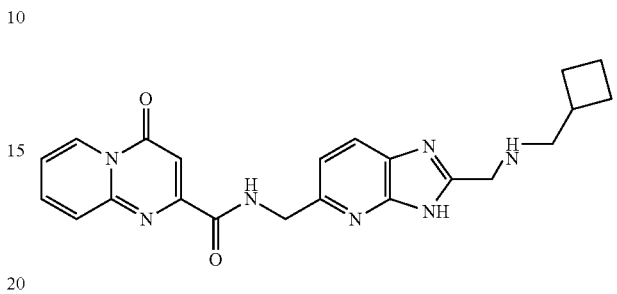

Step 1: tert-Butyl N-[(5-cyano-1H-benzimidazol-2-yl)methyl]carbamate

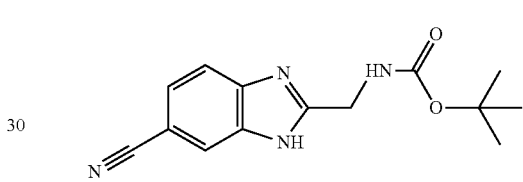

To a suspension of 3,4-diaminobenzonitrile (98%, 0.50 g, 3.68 mmol) and N-(tert-butoxycarbonyl)glycine (0.71 g, 4.05 mmol) in DCE (10 mL) was added N-ethyl-N-isopropyl-propan-2-amine (3.2 mL, 18.4 mmol) and T3P (50%, 4.4 mL, 7.36 mmol) in EtOAc at ambient temperature. The mixture was stirred in a pressure vial for 24 h at 100° C. After cooling to room temperature, the mixture was poured into saturated aqueous NaHCO$_3$ solution (25 mL). The organic layer was separated and the aqueous was extracted with DCE (2×20 mL). The combined organic layers were washed with brine (20 mL), dried (Na$_2$SO$_4$), filtered and concentrated at reduced pressure. The residue was purified by chromatography on SiO$_2$ [SNAP Cartridge KP-Sil 25 g; 0-100% EtOAc in heptane, 12 CVs]. The product containing fractions were combined and concentrated in vacuo to afford an orange oil. The product was re-purified by chromatography on SiO$_2$ [SNAP Cartridge KP-Sil 25 g; 0-100% EtOAc in DCM, 12 CVs]. The product containing fractions were combined and concentrated in vacuo. The residue was triturated with EtOAc/heptane to afford the title compound (260 mg, 25%) as a grey solid.
Method C: LC-MS (electrospray): m/z=273.1 (M–H)$^-$, RT=2.33 min Step 2: tert-Butyl N-[[6-(aminomethyl)-1H-benzimidazol-2-yl]methyl]carbamate

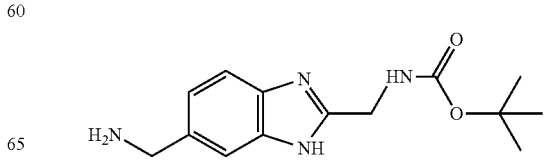

The title compound (255 mg, 95.5%) was prepared in the same manner as Example 2 Step 3.

Method C: LC-MS (electrospray): m/z=277.2 (M+H)⁺, RT=1.85 min

Step 3: tert-Butyl N-[[6-[[(4-oxopyrido[1,2-a]pyrimidine-2-carbonyl)amino]methyl]-1H-benzimidazol-2-yl]methyl]carbamate

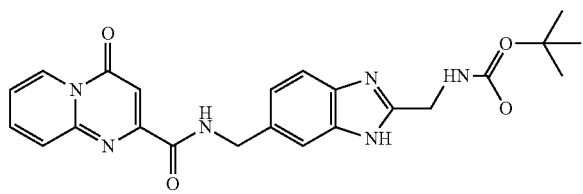

To a solution of 4-oxopyrido[1,2-a]pyrimidine-2-carboxylic acid (180 mg, 0.945 mmol) (Intermediate 1), tert-butyl N-[[6-(aminomethyl)-1H-benzimidazol-2-yl]methyl]carbamate (95%, 250 mg, 0.859 mmol) and DIPEA (0.45 mL, 2.58 mmol)) in DMF (7.5 mL) was added HATU (392 mg, 1.03 mmol). The reaction was stirred at ambient temperature overnight. The mixture was partitioned between EtOAc (80 mL) and sat. NaHCO₃ solution (500 mL). The organic layer was separated, washed with water (50 mL) and brine (20 mL), dried (Na₂SO₄), filtered and concentrated at reduced pressure. The residue was purified by preparative HPLC (Method B) to afford the title compound (220 mg, 55.9%) as a colourless solid.

Method C: LC-MS (electrospray): m/z=449.3 (M+H)⁺, RT=2.30 min

Step 4: N-[[2-(Aminomethyl)-3H-benzimidazol-5-yl]methyl]-4-oxo-pyrido[1,2-a]pyrimidine-2-carboxamide hydrochloride

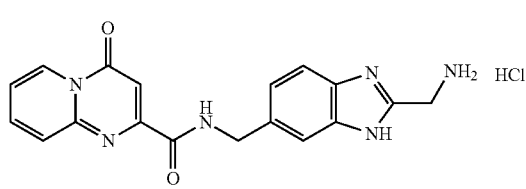 [SMILES: NCc1nc2ccc(CNC(=O)c3cc(=O)n4ccccc4n3)cc2[nH]1 ; Cl]

To a solution of tert-butyl N-[[6-[[(4-oxopyrido[1,2-a]pyrimidine-2-carbonyl)amino]methyl]-1H-benzimidazol-2-yl]methyl]carbamate (202 mg, 0.450 mmol) in THF (3 mL) was added 4 M hydrogen chloride in 1,4-dioxane (4.0 mL, 16.0 mmol) and the mixture was stirred at ambient temperature for 2 h. The volatiles were removed at reduced pressure. The residue was dissolved in MeOH (3 mL) and diethyl ether (20 mL) was added. The resulting precipitate was collected by vacuum filtration, washed with diethyl ether (10 mL) and dried in the vacuum oven at 45° C. for 2 h to afford the title compound (165 mg, 92%) as a white solid.

Method C: LC-MS (electrospray): m/z=449.3 (M+H)⁺, RT=2.30 min

Step 5: N-[(2-{[(cyclobutylmethyl)amino]methyl}-1H-1,3-benzodiazol-6-yl)methyl]-4-oxo-4H-pyrido[1,2-a]pyrimidine-2-carboxamide

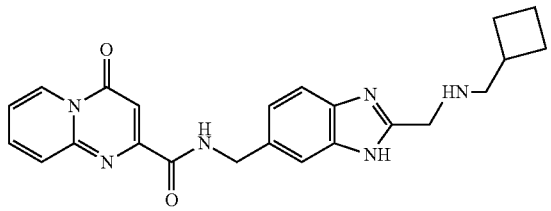 [SMILES: O=C(NCc1ccc2nc(CNCC3CCC3)[nH]c2c1)c1cc(=O)n2ccccc2n1]

A solution of N-[[2-(aminomethyl)-3H-benzimidazol-5-yl]methyl]-4-oxo-pyrido[1,2-a]pyrimidine-2-carboxamide hydrochloride (100 mg, 0.260 mmol), N-ethyl-N-isopropyl-propan-2-amine (0.14 mL, 0.780 mmol) and cyclobutanecarbaldehyde (95%, 23 mg, 0.260 mmol) in Ethanol (5 mL) was stirred at ambient temperature for 1 h. The mixture was then cooled to 0° C. (ice bath) and sodium boranuide (10 mg, 0.260 mmol) was added. The reaction was allowed to warm to room temperature and was stirred for 1 h. The reaction was partitioned between ethyl acetate (40 mL) and 2M aq. Na₂CO₃ solution (30 mL). The organic layer was separated, washed with brine (20 mL), dried (Na₂SO₄), filtered and concentrated at reduced pressure. The residue was purified by open access prep HPLC Method B. The product containing fractions were combined and concentrated to dryness. The residue was dissolved in a 1:1 (v/v) mixture of acetonitrile and water (4 mL). The resulting solution was lyophilised to afford the title compound (36 mg, 33%) as a white solid.

Method C: LC-MS (electrospray): m/z=417.3 (M+H)⁺, RT=2.28 min

Example 50: N-(1H-indol-6-ylmethyl)-4-oxo-pyrido[1,2-a]pyrimidine-2-carboxamide

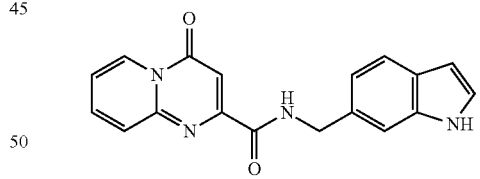

HATU (219 mg, 0.575 mmol) was added to the mixture of 4-oxopyrido[1,2-a]pyrimidine-2-carboxylic acid (109 mg, 0.575 mmol) (Intermediate 1) and DIPEA (0.24 mL, 1.37 mmol) in DMF (5.6 mL) and the mixture was stirred at DMF (5.6 mL). 1H-indol-6-ylmethanamine (70 mg, 0.479 mmol) was added after 10 min. and the reaction stirred at ambient temperature overnight. Water (15 mL) was added to the reaction and the mixture was extracted with DCM (15 mL). The organic phase was washed with brine (4×15 mL), dried, filtered and reduced in vacuo. The crude was purified by preparative HPLC (Method B) to afford the title compound (30 mg, 19%) as an off-white solid.

Method C: LC-MS (electrospray): m/z=319.2 (M+H)⁺, RT=2.55 min

Example 51: N-(1H-indol-2-ylmethyl)-4-oxo-pyrido[1,2-a]pyrimidine-2-carboxamide

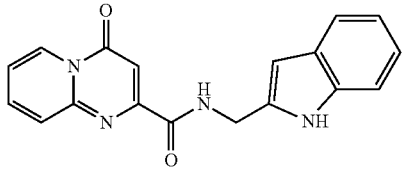 [SMILES: O=C(NCc1cc2ccccc2[nH]1)c1cc(=O)n2ccccc2n1]

The title compound was prepared in the same manner as Example 49, using DIPEA (0.36 mL, 2.05 mmol) as the amine was a salt.
Method C: LC-MS (electrospray): m/z=319.2 (M+H)$^+$, RT=2.75 min

Example 52: N-(indolizin-2-ylmethyl)-4-oxo-pyrido[1,2-a]pyrimidine-2-carboxamide

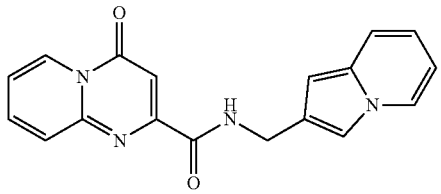 [SMILES: O=C(NCc1cc2ccccn2c1)c1cc(=O)n2ccccc2n1]

The title compound was prepared in the same manner as Example 49
Method C: LC-MS (electrospray): m/z=319.2 (M+H)$^+$, RT=2.74 min

Intermediate 4: 7-ethynyl-1-tetrahydropyran-2-yl-indazole

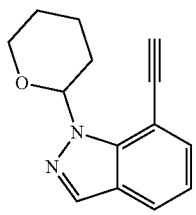

Step 1: 7-bromo-1-tetrahydropyran-2-yl-indazole

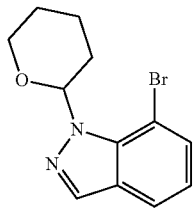 [SMILES: Brc1cccc2cnn(C3CCCCO3)c12]

7-bromo-1H-indazole (1 g, 5.08 mmol), TsOH, H$_2$O (193 mg, 1.02 mmol) and 3,4-dihydro-2H-pyran (923 µL, 10.2 mmol) were combined in DCM (50 mL) and the mixture stirred at ambient temperature overnight. The mixture was quenched with saturated NaHCO$_3$ (aq) (50 mL) and stirred briskly for 5 mins. The phases were separated, and the aqueous phase extracted with DCM (2×50 mL). The combined organic layers were dried over Na$_2$SO$_4$ and evaporated under vacuum. The residue was purified by chromatography on SiO$_2$ (50 g Sfar Duo, eluting with EtOAc/heptane 0-100%) to afford the title compound (543 mg, 36%).
Method B: LC-MS (electrospray): m/z=281.1/283.1 (M+H)$^+$, RT=1.77 min Step 2: trimethyl-[2-(1-tetrahydropyran-2-ylindazol-7-yl)ethynyl]silane

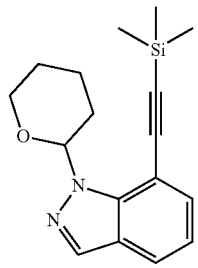 [SMILES: C[Si](C)(C)C#Cc1cccc2cnn(C3CCCCO3)c12]

A mixture of 4-bromo-1-tetrahydropyran-2-yl-indazole (2.50 g, 8.89 mmol) and triethylamine (5.9 mL, 42.5 mmol) in DMF-Anhydrous (15 mL) was degassed for 5 mins. Ethynyl(trimethyl)silane (3.7 mL, 26.7 mmol), CuI (170 mg, 0.889 mmol) and PdCl$_2$dppf (652 mg, 0.889 mmol) were added, the mixture was degassed for a further 5 mins before the mixture was stirred at 100° C. for 2 h. The mixture was allowed to cool to room temperature and was concentrated in vacuo to remove the DMF. The material was dissolved in DCM (10 mL), passed through a plug of Celite, washed with DCM (100 mL) and concentrated to give a crude brown solid. The crude material was dry loaded onto silica and purified by chromatography on SiO$_2$ (50 g, 0-30% EtOAc/heptane) to afford the title compound (2.38 g, 88%) as a brown oil.
Method B: LC-MS (electrospray): m/z=299.3 (M+H)$^+$, RT=2.15 min Step 3: 7-ethynyl-1-tetrahydropyran-2-yl-indazole

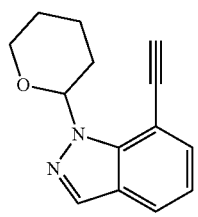 [SMILES: C#Cc1cccc2cnn(C3CCCCO3)c12]

Dipotassium carbonate (2.20 g, 15.9 mmol) was added to a solution of trimethyl-[2-(1-tetrahydropyran-2-ylindazol-4-yl)ethynyl]silane (2.38 g, 7.96 mmol) in MeOH (15 mL), and the brown mixture was stirred at ambient temperature for 2 h (K$_2$CO$_3$ was not entirely in solution). The solvent was removed in vacuo. The residue was diluted with DCM (20 mL) and H$_2$O (10 mL). The layers were separated, and the aqueous phase was extracted with DCM (3×15 mL). The combined organic extracts were washed with brine (20 mL), passed through a TELOS phase separator and concentrated in vacuo. The crude material was dry loaded onto a 30 g KP-Sil cartridge and purified by chromatography on SiO$_2$ (0-20% EtOAc/heptane) to afford the title compound (1.69 g, 89%) as a dark red solid.

Method J: LC-MS (electrospray): m/z=227.1 (M+H)$^+$, RT=0.62 min

Intermediate 5: O1-tert-butyl O2-methyl 6-(azidomethyl)indole-1,2-dicarboxylate

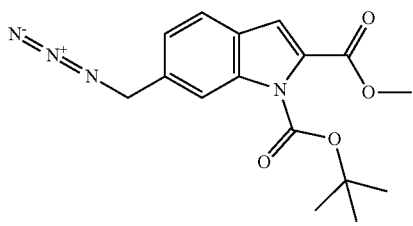 [SMILES: COC(=O)c1cc2ccc(CN=[N+]=[N-])cc2n1C(=O)OC(C)(C)C]

Step 1: O1-tert-butyl O2-methyl 6-methylindole-1,2-dicarboxylate

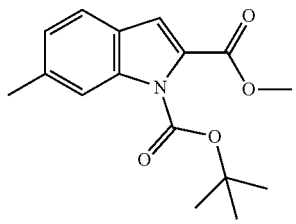

Boc anhydride (13.84 g, 63.4 mmol) was added to a mixture of methyl 6-methyl-1H-indole-2-carboxylate (10.00 g, 52.9 mmol) and DMAP (1.00 g, 8.19 mmol) in Acetonitrile (100 mL). The mixture was stirred at ambient temperature for 10 mins before being stirred at 45° C. overnight. The mixture was cooled to room temperature. The solvent was removed in vacuo to give an orange solid. The solid was dissolved in EtOAc (50 mL) and washed with H$_2$O (20 mL). The layers were separated, and the aqueous layer extracted with EtOAc (3×30 mL). The combined organic phases were washed with brine (50 mL), dried over MgSO$_4$, filtered and concentrated in vacuo. The crude material was purified by chromatography on SiO$_2$ (100 g KP-Sil, eluting with EtOAc/heptane 0-50%) to afford the title compound (14.21 g, 93%) as a pale orange solid.

Method B: LC-MS (electrospray): m/z=290.2 (M+H)$^+$, RT=2.01 min

Step 2: O1-tert-butyl O2-methyl 6-(bromomethyl)indole-1,2-dicarboxylate

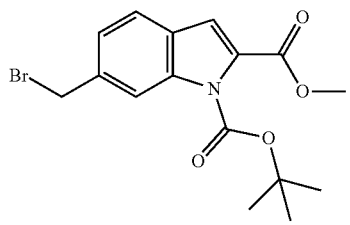 [SMILES: COC(=O)c1cc2ccc(CBr)cc2n1C(=O)OC(C)(C)C]

A 250 mL RBF was charged with O1-tert-butyl O2-methyl 6-methylindole-1,2-dicarboxylate (3.00 g, 10.4 mmol) in DCE (150 mL), 1-bromopyrrolidine-2,5-dione (1.75 g, 9.85 mmol) and 2,2F(E)-diazene-1,2-diylbis(2-methylpropanenitrile) (170 mg, 1.04 mmol) were added, and the mixture was stirred at 75° C. for 2 h. The mixture was cooled to room temperature, and the solvent was removed in vacuo. The crude material was purified by chromatography on SiO$_2$ (100 g KP-Sil, 0-10% EtOAc/heptane) to afford the title compound (3.12 g, 79%) as an off white solid.

Method B: LC-MS (electrospray): m/z=368.1/370.2 (M+H)$^+$, RT=1.99 min

Step 3: O1-tert-butyl O2-methyl 6-(azidomethyl)indole-1,2-dicarboxylate

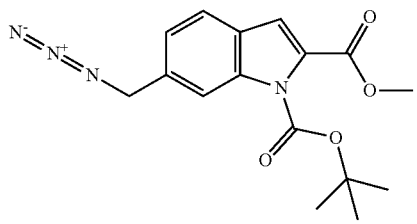 [SMILES: COC(=O)c1cc2ccc(CN=[N+]=[N-])cc2n1C(=O)OC(C)(C)C]

O1-tert-butyl O2-methyl 6-(bromomethyl)indole-1,2-dicarboxylate (1.80 g, 4.89 mmol) was dissolved in DMF (8.0488 mL) followed by addition of NaI (72 mg, 0.477 mmol) and NaN$_3$ (794 mg, 12.2 mmol), and the reaction was stirred at ambient temperature for 2 h. The mixture was quenched with H$_2$O (10 mL), and extracted with EtOAc (3×20 mL). The combined organic layers were washed with brine (2×50 mL), dried over MgSO$_4$, filtered and concentrated in vacuo. The crude material was purified by chromatography on SiO$_2$ (0-40% EtOAc/heptane) to afford the title compound (1.37 g, 78%) as a yellow oil.

Method B: LC-MS (electrospray): m/z=331.2 (M+H)$^+$, RT=1.97 min

229

Example 53: N-[(6-{[4-(1H-indazol-4-yl)-1H-1,2,3-triazol-1-yl]methyl}-1H-indol-2-yl)methyl]cyclopropanamine

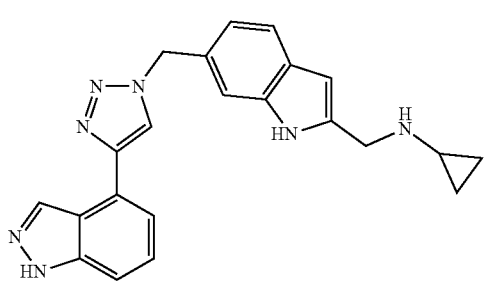 [SMILES: c1cc(-c2cn(Cc3ccc4cc(CNC5CC5)[nH]c4c3)nn2)c2cn[nH]c2c1]

Step 1: O1-tert-butyl O2-methyl 6-[[4-(1-tetrahydropyran-2-ylindazol-4-yl)triazol-1-yl]methyl]indole-1,2-dicarboxylate

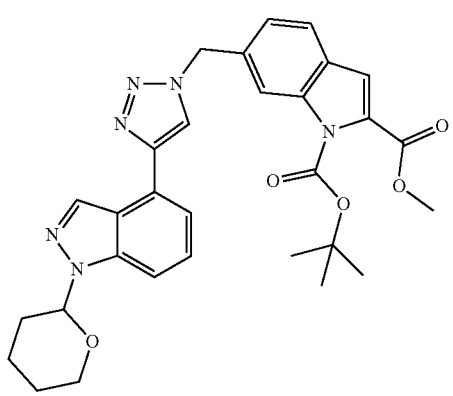 [SMILES: COC(=O)c1cc2ccc(Cn3cc(-c4cccc5c4cnn5C4CCCCO4)nn3)cc2n1C(=O)OC(C)(C)C]

Sodium ascorbate (1.24 g, 6.20 mmol) and CuSO$_4$ (41 mg, 0.254 mmol) were added to a mixture of 1-tert-butyl 2-methyl 6-(azidomethyl)indole-1,2-dicarboxylate (1.37 g, 4.14 mmol) (Intermediate 5) and 4-ethynyl-1-tetrahydropyran-2-yl-indazole (1.03 g, 4.55 mmol) (Intermediate 4) in DMF (25 mL) and water (10 mL), and the mixture was stirred at ambient temperature for 3.5 h A further amount of CuSO$_4$ (41 mg, 0.254 mmol) was added, and the mixture was stirred at ambient temperature overnight. The mixture was diluted with 3:1 chloroform/isopropanol (40 mL) and water (30 mL) and the phases separated. The aqueous phase was extracted with 3:1 chloroform/isopropanol (2×30 mL) and the combined organic layers washed with water (40 mL), passed through a TELOS phase separator and evaporated under vacuum. The crude material was purified by chromatography on SiO$_2$ (0-50% EtOAc/heptane, 50 g D Sfar) to afford the title compound (1.80 g, 71%) as an off white solid.

Method B: LC-MS (electrospray): m/z=557.3 (M+H)$^+$, RT=1.98 min

230

Step 2: tert-butyl 2-(hydroxymethyl)-6-[[4-(1-tetrahydropyran-2-ylindazol-4-yl)triazol-1-yl]methyl]indole-1-carboxylate

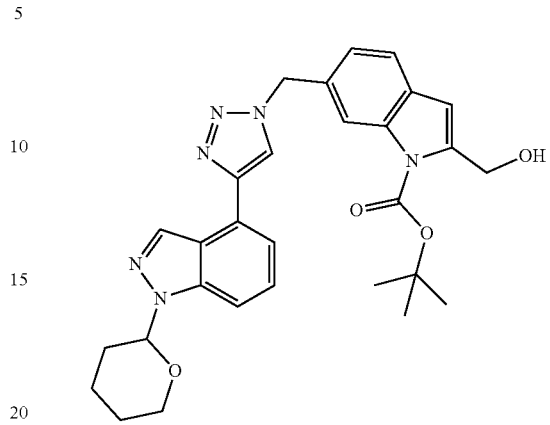

1 M DIBAL-H (1M in DCM) (6.5 mL, 6.47 mmol) was slowly added to a solution of O1-tert-butyl O2-methyl 6-[[4-(1-tetrahydropyran-2-ylindazol-4-yl)triazol-1-yl]methyl]indole-1,2-dicarboxylate (1.80 g, 3.24 mmol) in DCM-Anhydrous (40 mL) at −78° C., and the mixture was stirred at −78° C. for 1 h. The mixture was retreated with 1 M DIBAL-H (1M in DCM) (3.2 mL, 3.24 mmol) and was stirred at −78° C. for 1 h then stirred at −40° C. for 2 h. A further 1 M DIBAL-H (1.6 mL, 1.62 mmol) was added to the mixture and stirred at −40° C. for 1.5 h. The mixture was slowly quenched with MeOH (5 mL) at −40° C., stirred for 5 mins, then H$_2$O (5 mL) was added dropwise, and the mixture was vigorously stirred at ambient temperature for 10 mins. 1 M NaOH (aq) (5 mL) was added to help solubilise the mixture. The organic solvent was removed in vacuo. The mixture was diluted with DCM (40 mL) and H$_2$O (20 mL), the layers were separated, the mixture was extracted with DCM (3×10 mL), the organic layers were washed with brine, passed through a TELOS phase separator and concentrated. The crude material was purified by chromatography on SiO$_2$ (0-70% EtOAc/heptane) to afford the title compound (1.30 g, 74%) as a white solid.

Method B: LC-MS (electrospray): m/z=529.3 (M+H)$^+$, RT=1.79 min

Step 3: tert-butyl 2-formyl-6-[[4-(1-tetrahydropyran-2-ylindazol-4-yl)triazol-1-yl]methyl]indole-1-carboxylate

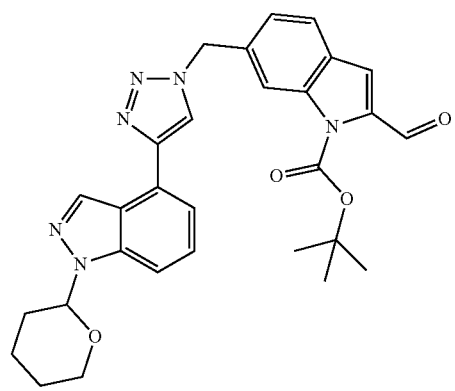 [SMILES: CC(C)(C)OC(=O)n1c(C=O)cc2ccc(Cn3cc(-c4cccc5c4cnn5C4CCCCO4)nn3)cc21]

A mixture of tert-butyl 2-(hydroxymethyl)-6-[[4-(1-tetrahydropyran-2-ylindazol-4-yl)triazol-1-yl]methyl]indole-1-carboxylate (1.45 g, 2.75 mmol) and dioxomanganese (2.39 g, 27.5 mmol) in DCE (80 mL) was stirred at reflux (90° C.) for 1 h. The reaction was cooled to room temperature and filtered through a pad of Celite to remove the solid. The solid was washed with EtOAc (50 mL). The filtrate was collected, and the solvent was removed in vacuo to afford the title compound (1.37 g, 87%) as a yellow foam.

Method B: LC-MS (electrospray): m/z=527.2 (M+H)$^+$, RT=1.93 min

Step 4: N-[(6-{[4-(1H-indazol-4-yl)-1H-1,2,3-triazol-1-yl]methyl}-1H-indol-2-yl)methyl]cyclopropanamine

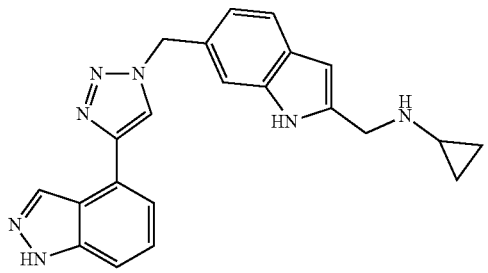 [SMILES: c1cc(-c2cn(Cc3ccc4cc(CNC5CC5)[nH]c4c3)nn2)c2cn[nH]c2c1]

cyclopropanamine (53 μL, 0.760 mmol) was added to a solution of tert-butyl 2-formyl-6-[[4-(1-tetrahydropyran-2-ylindazol-4-yl)triazol-1-yl]methyl]indole-1-carboxylate (200 mg, 0.380 mmol) in DCE (0.72 mL) and the mixture was stirred 60° C. for 1 h. The mixture was cooled to room temperature and added drop-wise over 5 min to a solution of NaBH$_4$ (14 mg, 0.380 mmol) in Ethanol (1.44 mL). The RM was stirred at ambient temperature overnight. A further amount of NaBH$_4$ (14 mg, 0.380 mmol) was added to the mixture, and stirred at ambient temperature for 2 h. The mixture was quenched with water and extracted with DCM (3×20 mL), the organic phases were passed through a TELOS phase separator and concentrated in vacuo. The mixture was diluted with MeOH (1.4 mL) and then treated with HCl (4M in dioxane, 1.4 mL), and the mixture was stirred at ambient temperature for 6 h. The mixture was stirred at room temperature overnight. The mixture was stirred at 45° C. for 30 mins, before being concentrated in vacuo. The crude material was purified by preparative HPLC (Method B) and a bespoke method to afford the title compound (32 mg, 22%) as a white solid.

Method C: LC-MS (electrospray): m/z=384.3 (M+H)$^+$, RT=2.84 min

The compounds in Table 2 were prepared in the same manner as Example 52 using commercial amines or described intermediates.

TABLE 2

| Compound No | Name | Structure | LCMS method | LCMS Retention time | Mass Ion |
|---|---|---|---|---|---|
| 54 | (1R,2S)-2-[[6-[[4-(1H-indazol-4-yl)triazol-1-yl]methyl]-1H-indol-2-yl]methylamino]cyclopentanol | 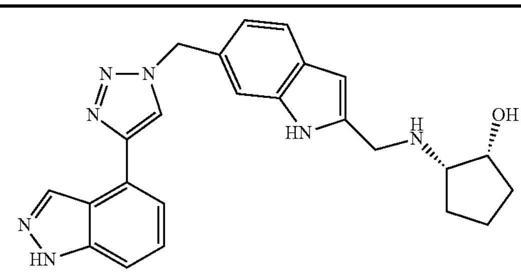 | C | 2.73 | 428.4 |
| 55 | N-[[6-[[4-(1H-indazol-4-yl)triazol-1-yl]methyl]-1H-indol-2-yl]methyl]cyclopentanamine | 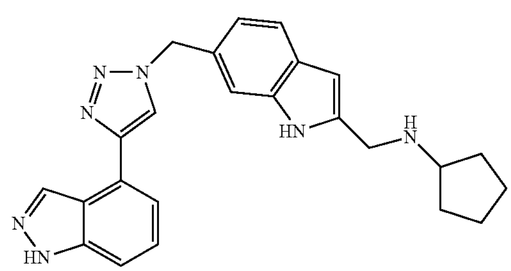 [SMILES: c1cc(-c2cn(Cc3ccc4cc(CNC5CCCC5)[nH]c4c3)nn2)c2cn[nH]c2c1] | C | 3.24 | 412.4 |
| 56 | N-(cyclopropylmethyl)-1-[6-[[4-(1H-indazol-4-yl)triazol-1-yl]methyl]-1H-indol-2-yl]methanamine | 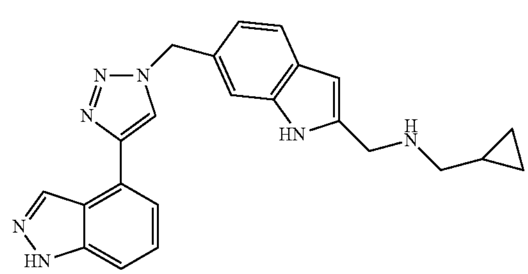 [SMILES: c1cc(-c2cn(Cc3ccc4cc(CNCC5CC5)[nH]c4c3)nn2)c2cn[nH]c2c1] | C | 2.98 | 398.4 |

TABLE 2-continued

| Compound No | Name | Structure | LCMS method | LCMS Retention time | Mass Ion |
|---|---|---|---|---|---|
| 57 | 1-[[[6-[[4-(1H-indazol-4-yl)triazol-1-yl]methyl]-1H-indol-2-yl]methylamino]methyl]cyclobutanol | 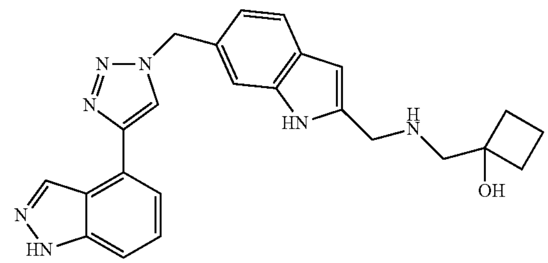 [SMILES: OC1(CNCc2cc3ccc(Cn4cc(-c5cccc6[nH]ncc56)nn4)cc3[nH]2)CCC1] | C | 2.67 | 428.5 |
| 122 | 4-(1-{[2-({2-azaspiro[3.3]heptanean-2-yl}methyl)-1H-indol-6-yl]methyl}-1H-1,2,3-triazol-4-yl)-1H-indazole | 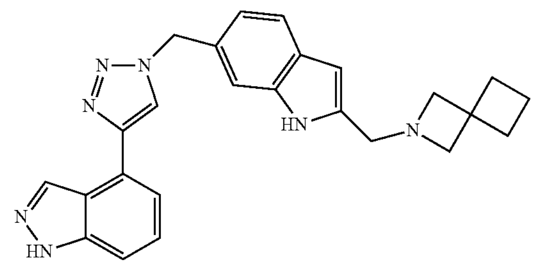 [SMILES: c1cc(-c2cn(Cc3ccc4cc(CN5CC6(CCC6)C5)[nH]c4c3)nn2)c2cn[nH]c2c1] | C | 3.46 | 424.5 |

Example 58: N-(cyclobutylmethyl)-1-[6-[[4-(1H-indazol-4-yl)triazol-1-yl]methyl]-1H-indol-2-yl]methanamine

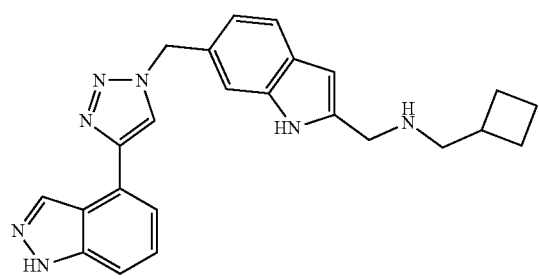 [SMILES: c1cc(-c2cn(Cc3ccc4cc(CNCC5CCC5)[nH]c4c3)nn2)c2cn[nH]c2c1]

tert-butyl 2-formyl-6-[[4-(1-tetrahydropyran-2-ylindazol-4-yl)triazol-1-yl]methyl]indole-1-carboxylate (50 mg, 0.10 mmol) and 1-cyclobutylmethanamine (16 mg, 0.19 mmol) were combined in 1,1,1,3,3,3-Hexafluoro-2-propanol (2 mL) and the mixture incubated at ambient temperature for 30 minutes. NaBH₄ (11 mg, 0.28 mmol) was added with a few drops MeOH and the mixture incubated briefly at ambient temperature. The reaction was quenched with MeOH (20 mL) and evaporated under vacuum. The residue was partitioned between saturated NaHCO₃ (aq) (10 mL) and DCM (10 mL) and the phases separated. The aqueous phase was extracted with DCM (2×15 mL) and the combined organic layers dried over Na₂SO₄ and evaporated under vacuum. The residue was redissolved in MeOH (5 mL) and treated with 4M HCl in Dioxane (5 mL) and incubated at ambient temperature overnight. The mixture was evaporated under vacuum and the residue purified by preparative HPLC (Method B) to afford the title compound (13 mg, 33%) as an off-white solid.

Method D: LC-MS (electrospray): m/z=412.3 (M+H)⁺, RT=4.12 min

Example 59: N-(cyclobutylmethyl)-1-[6-[[4-(1H-indazol-4-yl)triazol-1-yl]methyl]-1H-pyrrolo[3,2-b]pyridin-2-yl]methanamine

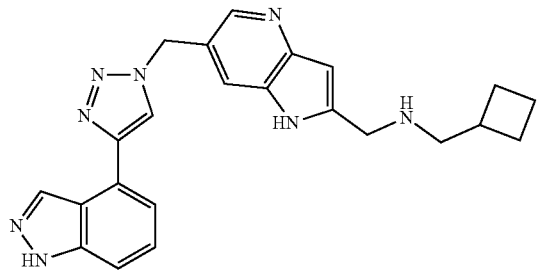 [SMILES: c1cc(-c2cn(Cc3cnc4cc(CNCC5CCC5)[nH]c4c3)nn2)c2cn[nH]c2c1]

Step 1: tert-butyl 2-[[tert-butoxycarbonyl(cyclobutylmethyl)amino]methyl]-6-[[4-(1-tetrahydropyran-2-ylindazol-4-yl)triazol-1-yl]methyl]pyrrolo[3,2-b]pyridine-1-carboxylate

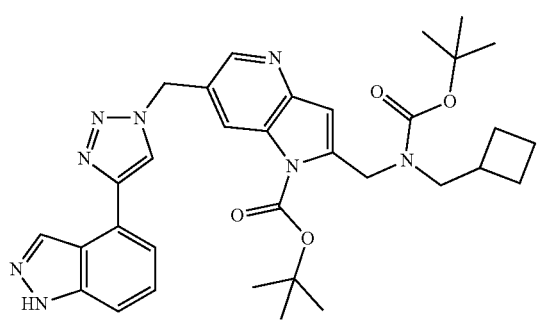 [SMILES: CC(C)(C)OC(=O)N(Cc1cc2ncc(Cn3cc(-c4cccc5[nH]ncc45)nn3)cc2n1C(=O)OC(C)(C)C)CC1CCC1]

A mixture of 4-ethynyl-1-tetrahydropyran-2-yl-indazole (19 mg, 0.0850 mmol) (Intermediate 4), tert-butyl 6-(azidomethyl)-2-[[tert-butoxycarbonyl(cyclobutylmethyl)amino]methyl]pyrrolo[3,2-b]pyridine-1-carboxylate (40 mg, 0.0850 mmol) (Intermediate 3), copper sulfate (2.7 mg, 0.0170 mmol) and sodium ascorbate (19 mg, 0.0935 mmol) in DMF (1 mL) and water (0.2 mL) was stirred at ambient temperature overnight. The mixture was diluted with water and 10% MeOH in DCM. The organic phase was collected using a Telos phase separator, evaporated to dryness under reduced pressure and purified by chromatography on SiO₂ (KP—NH; 0-100% EtOAc in heptane, then 0-20% MeOH in EtOAc) to afford the title compound (26 mg, 44%) as a colourless oil.

Method A: LC-MS (electrospray): m/z=697.5 (M+H)⁺, RT=1.81 min

Step 2: N-(cyclobutylmethyl)-1-[6-[[4-(1H-indazol-4-yl)triazol-1-yl]methyl]-1H-pyrrolo[3,2-b]pyridin-2-yl]methanamine

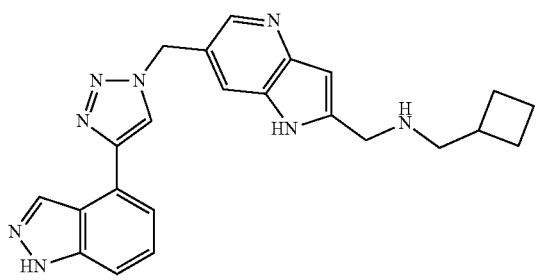 [SMILES: c1cc(-c2cn(Cc3cnc4cc(CNCC5CCC5)[nH]c4c3)nn2)c2cn[nH]c2c1]

4 M HCl in dioxane (0.19 mL, 0.746 mmol) was added to a solution of tert-butyl 2-[[tert-butoxycarbonyl(cyclobutylmethyl)amino]methyl]-6-[[4-(1-tetrahydropyran-2-ylindazol-4-yl)triazol-1-yl]methyl]pyrrolo[3,2-b]pyridine-1-carboxylate (26 mg, 0.0373 mmol) in MeOH (1 mL) and the mixture was stirred at room temperature over a weekend. The mixture was evaporated to dryness, purified by preparative HPLC (Method B) and freeze dried to afford the title compound (7.0 mg, 45%) as a white powder.

Method D: LC-MS (electrospray): m/z=413.4 (M+H)⁺, RT=2.45 min

Intermediate 6: tert-butyl N-[[6-(azidomethyl)-1H-pyrrolo[3,2-c]pyridin-2-yl]methyl]-N-(cyclobutylmethyl)carbamate

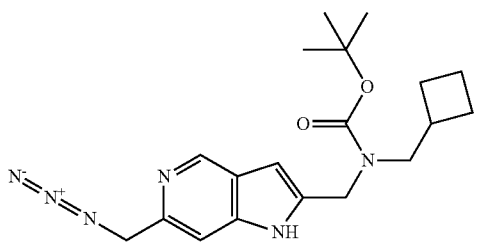 [SMILES: CC(C)(C)OC(=O)N(Cc1cc2cnc(CN=[N+]=[N-])cc2[nH]1)CC1CCC1]

Step 1: methyl 4-amino-5-bromo-pyridine-2-carboxylate

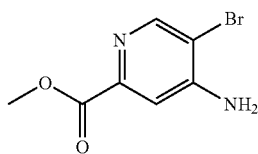

NBS (2.29 g, 12.9 mmol) was added to a solution of methyl 4-aminopyridine-2-carboxylate (98%, 2.00 g, 12.9 mmol) in DCE (60 mL) and the mixture was stirred at room temperature overnight. The mixture was diluted with water (50 mL) and extracted with EtOAc (3×50 mL). The combined organics were washed with brine (100 mL), dried over magnesium sulfate and evaporated to dryness to afford the title compound (2.47 g, 79%) as an off white solid.

Method B: LC-MS (electrospray): m/z=231.1/233.1 (M+H)⁺, RT=1.16 min

Step 2: methyl 5-bromo-4-[(2,2,2-trifluoroacetyl)amino]pyridine-2-carboxylate

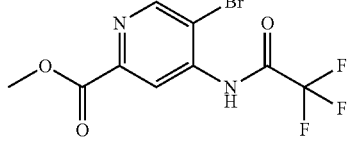

TFAA (4.5 mL, 32.0 mmol) was added to a solution of methyl 4-amino-5-bromo-pyridine-2-carboxylate (2.47 g, 10.7 mmol) in DCM (30 mL) and the mixture was stirred at ambient temperature overnight. Initially the white cloudy mixture was fully in solution and colourless by morning. The mixture was evaporated to dryness to afford product as a TFA salt (4.7 g, 97%). 55 mg of the salt was taken, diluted with DCM (2 mL) and sat. aq. NaHCO₃ (2 mL), the layers were separated, the aqueous layer was extracted with DCM (3×2 mL), the organic layers were passed through a TELOS phase separator and concentrated to give 32 mg of the title compound (32 mg, 0.85%) as a white solid.

Method B: LC-MS (electrospray): m/z=327.0/329.0 (M+H)⁺, RT=0.90 min

Step 3: methyl 2-[[tert-butoxycarbonyl(cyclobutylmethyl)amino]methyl]-1H-pyrrolo[3,2-c]pyridine-6-carboxylate

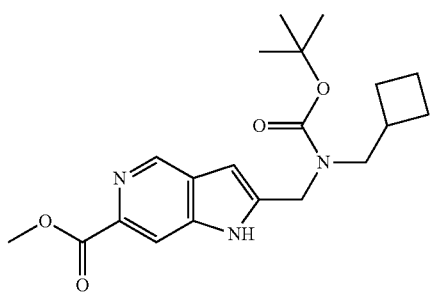 [SMILES: COC(=O)c1cc2[nH]c(CN(CC3CCC3)C(=O)OC(C)(C)C)cc2cn1]

A mixture of methyl 5-bromo-4-[(2,2,2-trifluoroacetyl)amino]pyridine-2-carboxylate (1.63 g, 4.99 mmol), tert-butyl N-(cyclobutylmethyl)-N-prop-2-ynyl-carbamate (1.34 g, 5.99 mmol) (Intermediate 2) and 1,1,3,3-tetramethylguanidine (1.9 mL, 15.0 mmol) in DMF-Anhydrous (27.668 mL) was degassed for 5 mins, iodocopper (96 mg, 0.499 mmol) and dichloropalladium triphenylphosphane (422 mg, 0.599 mmol) were added, the mixture was degassed for a further 5 mins before being stirred at 65° C. overnight. The mixture was re-treated with dichloropalladium triphenylphosphane (422 mg, 0.599 mmol) and iodocopper (96 mg, 0.499 mmol), the mixture was degassed for 10 mins, then the mixture was stirred at 65° C. for a further 2 h. The mixture was cooled to room temperature, filtered through Celite and washed with EtOAc (300 mL). The mixture was concentrated and purified by chromatography on SiO₂ (Sfar amino D Duo 55 g, 0-100% EtOAc/heptane) gave impure material with a large amount of triphenylphosphine oxide byproduct. The material was loaded onto a 5 g SCX cartridge, MeOH was passed through, followed by 2.5 M NH₃ in MeOH solution. The latter fractions were collected and concentrated to afford the title compound (784 mg, 21%) as a brown oil.

Step 4: tert-butyl N-(cyclobutylmethyl)-N-[[6-(hydroxymethyl)-1H-pyrrolo[3,2-c]pyridin-2-yl]methyl]carbamate

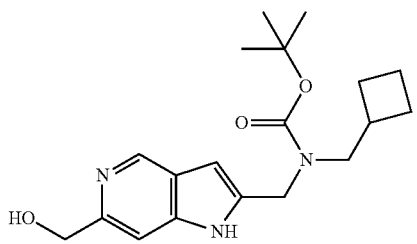 [SMILES: CC(C)(C)OC(=O)N(Cc1cc2cnc(CO)cc2[nH]1)CC1CCC1]

1 M DIBAL-H (1M in DCM) (2.2 mL, 2.25 mmol) was slowly added to a solution of methyl 2-[[tert-butoxycarbonyl(cyclobutylmethyl)amino]methyl]-1H-pyrrolo[3,2-c]pyridine-6-carboxylate (50%, 839 mg, 1.12 mmol) in DCM-Anhydrous (13.879 mL) at −78° C., and the mixture was stirred at −78° C. for 2 h. The mixture was warmed to −40° C., re-treated with 1 M DIBAL-H (1M in DCM) (1.1 mL, 1.12 mmol) and stirred at −40° C. for 3.5 h. The mixture was slowly quenched with MeOH (5 mL) at −40° C., stirred for 5 mins, then H₂O (5 mL) was added dropwise, and the mixture was vigorously stirred at ambient temperature for 10 mins. 1 M NaOH (aq) (5 mL) was added to help solubilise the mixture. The organic solvent was removed in vacuo. The mixture was diluted with DCM (40 mL) and H₂O (20 mL), the layers were separated, the mixture was extracted with DCM (3×10 mL), the organic layers were washed with brine, passed through a TELOS phase separator and concentrated in vauo.

The crude product was purified by chromatography on SiO₂ (0-70% EtOAc/heptane) to afford the title compound (128 mg, 31%) as a pale brown solid.

Method B: LC-MS (electrospray): m/z=346.3 (M+H)⁺, RT=1.61 min

Step 5: tert-butyl N-[[6-(azidomethyl)-1H-pyrrolo[3,2-c]pyridin-2-yl]methyl]-N-(cyclobutylmethyl)carbamate

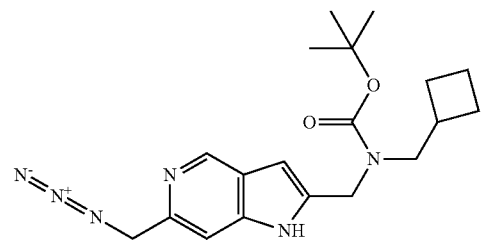 [SMILES: CC(C)(C)OC(=O)N(Cc1cc2cnc(CN=[N+]=[N-])cc2[nH]1)CC1CCC1]

diphenyl phosphorazidate (0.16 mL, 0.741 mmol) was added to an ice-cooled solution of tert-butyl N-(cyclobutylmethyl)-N-[[6-(hydroxymethyl)-1H-pyrrolo[3,2-c]pyridin-2-yl]methyl]carbamate (128 mg, 0.371 mmol) and DBU (0.11 mL, 0.741 mmol) in DMF-Anhydrous (1.9347 mL). The mixture was stirred at ambient temperature for 6 h. The mixture was stirred at 40° C. for 2 h, then at ambient temperature overnight. The mixture was re-treated with diphenyl phosphorazidate (0.16 mL, 0.741 mmol) and DBU (0.11 mL, 0.741 mmol) and was stirred at 40° C. for 2 h then at ambient temperature overnight. The mixture was diluted with water (25 mL) and extracted with EtOAc (3×20 mL). The combined organics were washed with brine (25 mL), dried over magnesium sulfate and evaporated to dryness. The crude material was purified by chromatography on SiO₂ (11 g Sfar Amino D; 0-100% EtOAc in heptane) to afford the title compound (36 mg, 24%) as a pale brown solid.

Method B: LC-MS (electrospray): m/z=371.3 (M+H)⁺, RT=1.83 min

Example 60: N-(cyclobutylmethyl)-1-[6-[[4-(1H-indazol-4-yl)triazol-1-yl]methyl]-1H-pyrrolo[3,2-c]pyridin-2-yl]methanamine

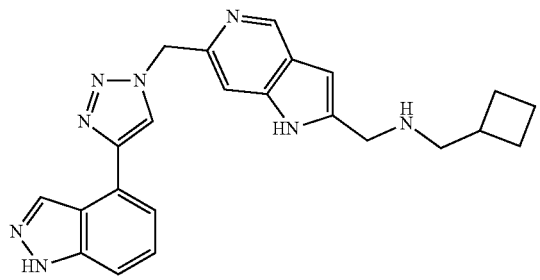 [SMILES: c1cc(-c2cn(Cc3cc4[nH]c(CNCC5CCC5)cc4cn3)nn2)c2cn[nH]c2c1]

Step 1: tert-butyl N-(cyclobutylmethyl)-N-[[6-[[4-(1-tetrahydropyran-2-ylindazol-4-yl)triazol-1-yl]methyl]-1H-pyrrolo[3,2-c]pyridin-2-yl]methyl]carbamate

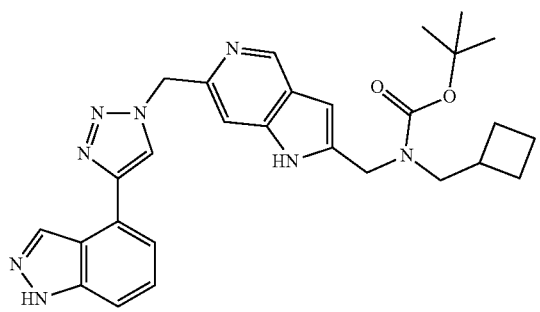 [SMILES: CC(C)(C)OC(=O)N(Cc1cc2cnc(Cn3cc(-c4cccc5[nH]ncc45)nn3)cc2[nH]1)CC1CCC1]

A mixture of 4-ethynyl-1-tetrahydropyran-2-yl-indazole (26 mg, 0.117 mmol), tert-butyl N-[[6-(azidomethyl)-1H-pyrrolo[3,2-c]pyridin-2-yl]methyl]-N-(cyclobutylmethyl)carbamate (36 mg, 0.0972 mmol) (Intermediate 6), copper sulfate (3.1 mg, 0.0194 mmol) and sodium ascorbate (21 mg, 0.107 mmol) in DMF (1.1432 mL) and water (0.2286 mL) was stirred at ambient temperature for 2 h. The mixture was diluted with water and a 3:1 mixture of CHCl$_3$/IPA. The layers were separated. The aqueous layer was extracted with CHCl$_3$/IPA (3×40 mL). The organic phase was collected using a Telos phase separator, evaporated to dryness under reduced pressure. The material was purified by SCX (1 g), loading with MeOH, flushing with MeOH then eluting with 2.5 M NH$_3$·MeOH solution and collecting and concentrating the latter fractions to afford the title compound (67 mg, 100%) as a pale brown solid.

Method B: LC-MS (electrospray): m/z=597.4 (M+H)$^+$, RT=1.96 min

Step 2: N-(cyclobutylmethyl)-1-[6-[[4-(1H-indazol-4-yl)triazol-1-yl]methyl]-1H-pyrrolo[3,2-c]pyridin-2-yl]methanamine

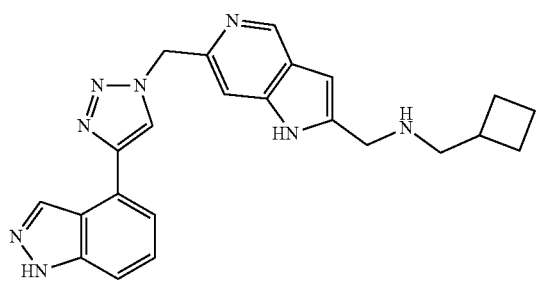 [SMILES: c1cc(-c2cn(Cc3cc4[nH]c(CNCC5CCC5)cc4cn3)nn2)c2cn[nH]c2c1]

A solution of tert-butyl N-(cyclobutylmethyl)-N-[[6-[[4-(1-tetrahydropyran-2-ylindazol-4-yl)triazol-1-yl]methyl]-1H-pyrrolo[3,2-c]pyridin-2-yl]methyl]carbamate (86%, 67 mg, 0.0966 mmol) in MeOH (0.5 mL) was treated with 4M HCl in dioxane (2 mL) and the mixture was stirred at ambient temperature overnight. The solvent was removed in vacuo. The crude material was purified by preparative HPLC (Method B) and freeze dried to afford the title compound (8.0 mg, 19%) as a white solid.

Method C: LC-MS (electrospray): m/z=413.4 (M+H)$^+$, RT=2.66 min

Intermediate 7: tert-butyl 6-(azidomethyl)-2-[[tert-butoxycarbonyl(cyclobutylmethyl)amino]methyl]indole-1-carboxylate

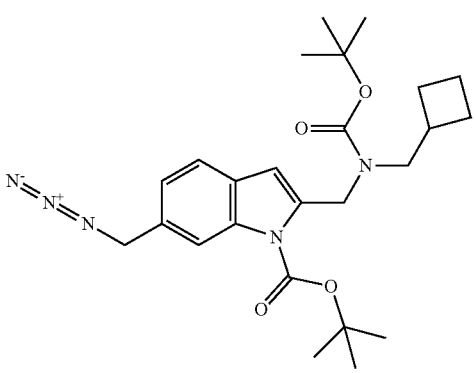 [SMILES: CC(C)(C)OC(=O)N(Cc1cc2ccc(CN=[N+]=[N-])cc2n1C(=O)OC(C)(C)C)CC1CCC1]

Step 1: methyl 4-iodo-3-[(2,2,2-trifluoroacetyl)amino]benzoate

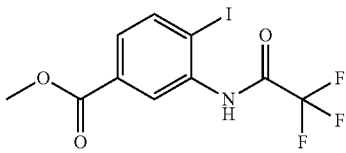 [SMILES: COC(=O)c1ccc(I)c(NC(=O)C(F)(F)F)c1]

A stirred suspension of methyl 3-amino-4-iodobenzoate (5.19 g, 18.7 mmol) in DCM (51.9 mL) was treated with (2,2,2-trifluoroacetyl) 2,2,2-trifluoroacetate (7.8 mL, 56.0 mmol). The resulting solution was stirred at ambient temperature overnight. The mixture was concentrated in vacuo to give an off white solid, which was redissolved in DCM (40 mL) and passed through a plug of silica in a plastic fritted tube. The silica was washed with DCM (450 mL) and the filtrate (~500 mL) was concentrated in vacuo and further dried in a vacuum oven at 45° C. for several h to afford the title compound (6.94 g, 98%) as an off white solid.

Method A: LC-MS (electrospray): m/z=371.9 (M+H)$^+$, RT=1.18 min

Step 2: methyl 2-[[tert-butoxycarbonyl(cyclobutylmethyl)amino]methyl]-1H-indole-6-carboxylate

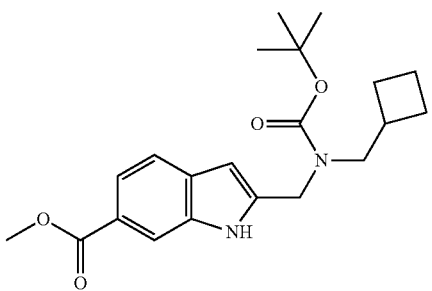 [SMILES: COC(=O)c1ccc2cc(CN(CC3CCC3)C(=O)OC(C)(C)C)[nH]c2c1]

A oven-dried three-neck 100 mL RBF equipped with a reflux condenser was flushed with nitrogen and charged with triphenylphosphane (0.68 g, 2.61 mmol), Copper (I) Iodide (0.25 g, 1.30 mmol), tripotassium phosphate (3.74 g, 17.4 mmol), methyl 4-iodo-3-[(2,2,2-trifluoroacetyl)amino]benzoate (98%, 3.31 g, 8.69 mmol) and 1,4-Dioxane-Anhydrous (40 mL). A solution of tert-butyl N-(cyclobutylmethyl)-N-prop-2-ynyl-carbamate (97%, 2.00 g, 8.69 mmol) (Intermediate 2) in 1,4-Dioxane-Anhydrous (8 mL) was added and the resulting thick suspension was de-oxygenated by passing a flow of nitrogen for 5 min. The mixture was placed in a pre-heated heating block at 110° C. and stirred rapidly at this temperature for 7.5 h. The reaction was allowed to stand at ambient temperature overnight. The mixture was heated to 110° C. for another 3 h the next day. The mixture was cooled down and concentrated. The resulting brown paste was partitioned between water (60 mL) and EtOAc (30 mL). The aqueous phase was extracted with EtOAc (3×30 mL). The combined organic phases were washed with brine (40 mL). The combined aqueous phases were back-extracted with EtOAc (20 mL). All the organics were combined, dried on magnesium sulfate and concentrated to give the crude product as a brown solid. Purification was carried out by chromatography on SiO$_2$ (0-70% EtOAc/heptane) (Kp-Sil 50 g cartridge) eluting in a gradient of EtOAc/heptane (0-100%). The product containing fractions were combined to afford the title compound (2.29 g, 71%) as a brown solid.

Method D: LC-MS (electrospray): m/z=373.3 (M+H)$^+$, RT=5.46 min

Step 3: 1-tert-butyl 6-methyl 2-({[(tert-butoxy)carbonyl](cyclobutylmethyl)amino}methyl)-1H-indole-1,6-dicarboxylate

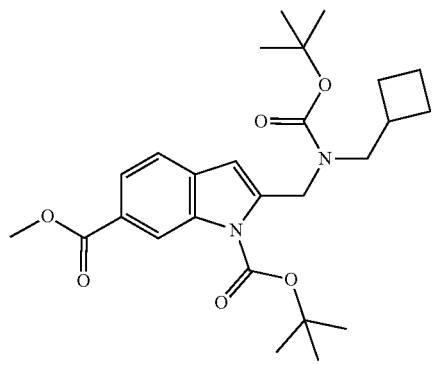 [SMILES: COC(=O)c1ccc2cc(CN(CC3CCC3)C(=O)OC(C)(C)C)n(C(=O)OC(C)(C)C)c2c1]

In a 250 mL RBF was prepared a solution containing methyl 2-[[tert-butoxycarbonyl(cyclobutylmethyl)amino]methyl]-1H-indole-6-carboxylate (2.29 g, 6.15 mmol) in DCM (30 mL). The flask was cooled in an ice bath and a solution containing di-tert-butyl dicarbonate (1.61 g, 7.38 mmol) in DCM (20 mL) was added, followed by N,N-dimethylpyridin-4-amine (75 mg, 0.615 mmol). The mixture was warmed to room temperature and stirred for 30 minutes. The mixture was washed with water (40 mL). The aqueous phase was separated and extracted with DCM (2×20 mL). The combined organic phases were washed with brine (20 mL), dried over magnesium sulfate and concentrated to give the crude product as a brown gum. Purification was carried out by chromatography on SiO$_2$ (KP-Sil 50 g cartridge) eluting in a gradient of EtOAc/heptane (0-50%). The product containing fractions were combined to afford the title compound (2.54 g, 86%) as a pale-yellow oil.

Method B: LC-MS (electrospray): m/z=473.3 (M+H)$^+$, RT=2.44 min

Step 4: tert-butyl 2-[[tert-butoxycarbonyl(cyclobutylmethyl)amino]methyl]-6-(hydroxymethyl)indole-1-carboxylate

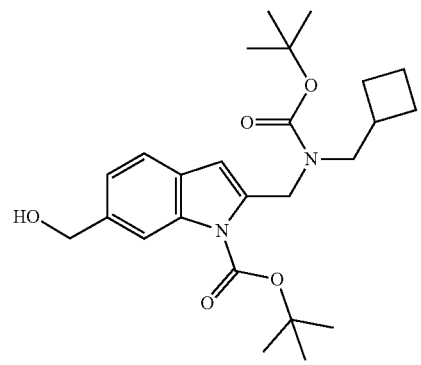 [SMILES: CC(C)(C)OC(=O)N(Cc1cc2ccc(CO)cc2n1C(=O)OC(C)(C)C)CC1CCC1]

A 50 mL oven-dried RBF was charged with 1-tert-butyl 6-methyl 2-[[tert-butoxycarbonyl(cyclobutylmethyl)amino]methyl]indole-1,6-dicarboxylate (2.54 g, 5.37 mmol), purged with nitrogen and then DCM-Anhydrous (20 mL) was added. The solution was kept under nitrogen and cooled using a dry ice/acetone cooling bath. 1 M diisobutylalumane in DCM (6 mL, 6 mmol) was added slowly, with stirring of the substrate solution, and addition of the reagent solution being carried out such that the solution is allowed to run down the side of the reaction flask for pre-cooling. The mixture was stirred at the dry ice/acetone bath temperature for 1 h 20 min. 1 M diisobutylalumane in DCM (7.5 mL, 7.5 mmol) was added in a similar manner to previous. The reaction was stirred at cold bath temperature for 1 h and 40 min. 1 M diisobutylalumane in DCM (7 mL, 7 mmol) was added. The mixture was stirred at cold bath temperature for 1 h and 45 min. At cold bath temperature, the reaction was quenched with water (2 mL). After gas evolution subsided, water was added (4 mL) and the reaction was allowed to warm up to room temperature. The emulsion formed was diluted with brine (50 mL) and extracted with DCM (3×50 mL). The remaining aqueous phase was diluted with a saturated Rochelle salt solution (50 mL) (improved phase separation) and extracted with DCM (50 mL). After standing overnight the solution was extracted again with DCM (50 mL), diluted with 1M NaOH solution (50 mL) and extracted with DCM (50 mL). The combined organics were dried on magnesium sulfate and concentrated to give the crude as a foam. Purification was carried out by chromatography on SiO$_2$ (50 g Kp-Sil cartridge) eluting in a gradient of EtOAc/heptane (0-100%). The product containing fractions were combined to afford the title compound (1.99 g, 83%) as a yellow oil.

Method D: LC-MS (electrospray): m/z=445.3 (M+H)$^+$, RT=5.67 min

243

Step 5: tert-butyl 6-(azidomethyl)-2-[[tert-butoxy-carbonyl(cyclobutylmethyl)amino]methyl]indole-1-carboxylate

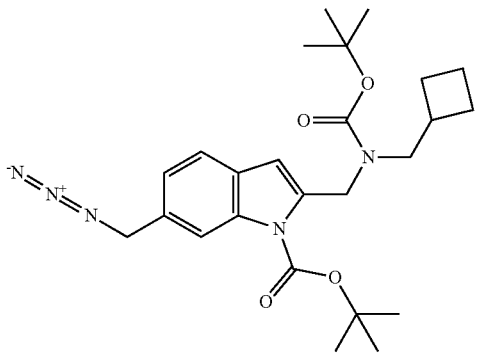 [SMILES: CC(C)(C)OC(=O)N(Cc1cc2ccc(CN=[N+]=[N-])cc2n1C(=O)OC(C)(C)C)CC1CCC1]

An oven-dried 10 mL RBF was charged with tert-butyl 2-[[tert-butoxycarbonyl(cyclobutylmethyl)amino]methyl]-6-(hydroxymethyl)indole-1-carboxylate (100%, 400 mg, 0.900 mmol) and DMF-Anhydrous (5 mL). DBU (269 µL, 1.80 mmol) was added and the resulting solution was cooled in an ice bath and stirred. Diphenyl phosphorazidate (388 µL, 1.80 mmol) was added and the mixture was stirred, allowing to warm up to room temperature, for 24 h. The mixture was diluted with water (5 mL) and extracted with DCM (2×10 mL). The aqueous phase was diluted with brine (20 mL) and extracted with DCM (2×10 mL). The organics were combined, washed with brine (5 mL), dried over magnesium sulfate and concentrated to give the crude as a brown oil. Purification was carried out by chromatography on SiO₂ (Sfar duo silica 25 g cartridge) eluting in a gradient of EtOAc/heptane 0-100%. The product containing fractions were combined to afford the title compound (377 mg, 83%) as a pale-yellow oil.

Method C: LC-MS (electrospray): m/z=470.4 (M+H)⁺, RT=5.44 min

244

Example 61: N-(cyclobutylmethyl)-1-[6-[[4-(1H-indazol-4-yl)triazol-1-yl]methyl]-1H-pyrrolo[3,2-c]pyridin-2-yl]methanamine

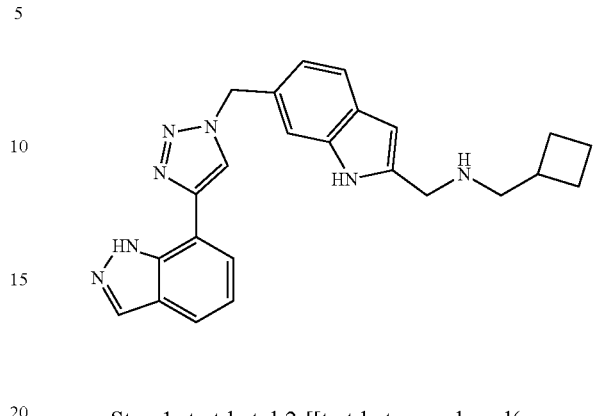

Step 1: tert-butyl 2-[[tert-butoxycarbonyl(cyclobutylmethyl)amino]methyl]-6-[[4-(1-tetrahydropyran-2-ylindazol-7-yl)triazol-1-yl]methyl]indole-1-carboxylate

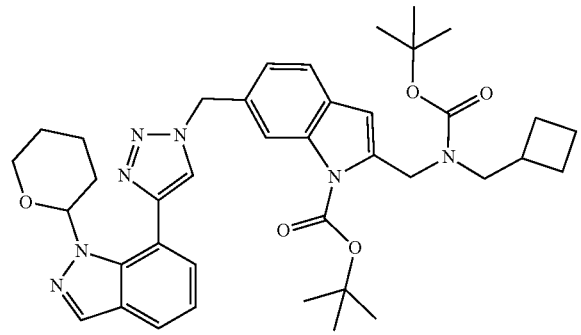

7-ethynyl-1-tetrahydropyran-2-yl-indazole (70 mg, 0.31 mmol) (Intermediate 4), tert-butyl 6-(azidomethyl)-2-[[tert-butoxycarbonyl(cyclobutylmethyl)amino]methyl]indole-1-carboxylate (145 mg, 0.31 mmol) (Intermediate 7) and sodium ascorbate (74 mg, 0.37 mmol) were combined in DMF (4 mL) and water (1 mL) and CuSO₄ (5 mg, 0.03 mmol) was added. The mixture was stirred at ambient temperature overnight. The mixture was diluted with EtOAc (40 mL) and washed with water (30 mL) and brine (5×30 mL). The organic layer was dried over Na₂SO₄ and evaporated under vacuum. The residue was purified by chromatography on SiO₂ (10 g Sfar Duo, eluting with EtOAc/heptane 0-100%) to afford the title compound (127 mg, 59%) as a pale yellow solid.

Method B: LC-MS (electrospray): m/z=696.5 (M+H)⁺, RT=2.41 min

Step 2: N-(cyclobutylmethyl)-1-[6-[[4-(1H-indazol-4-yl)triazol-1-yl]methyl]-1H-pyrrolo[3,2-c]pyridin-2-yl]methanamine

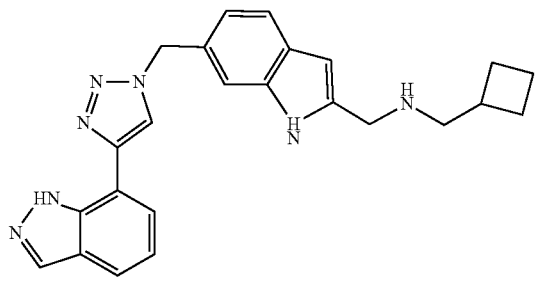 [SMILES: c1cc(-c2cn(Cc3ccc4cc(CNCC5CCC5)[nH]c4c3)nn2)c2[nH]ncc2c1]

Tert-butyl 2-[[tert-butoxycarbonyl(cyclobutylmethyl)amino]methyl]-6-[[4-(1-tetrahydropyran-2-ylindazol-7-yl)triazol-1-yl]methyl]indole-1-carboxylate (127 mg, 0.18 mmol) was dissolved in MeOH (5 mL) and treated with 4M HCl in Dioxane (2 mL). The mixture was incubated at ambient temperature for 5 h. The mixture was cooled to room temperature and evaporated under vacuum. The residue was purified by preparative HPLC (Method B) and the product-containing fractions combined and evaporated under vacuum to afford of the title compound (30 mg, 40%) as a white solid.

Method D: LC-MS (electrospray): m/z=412.3 (M+H)$^+$, RT=4.56 min

Example 62: 2-[1-[[2-[(cyclobutylmethylamino)methyl]-1H-indol-6-yl]methyl]triazol-4-yl]pyrido[1,2-a]pyrimidin-4-one

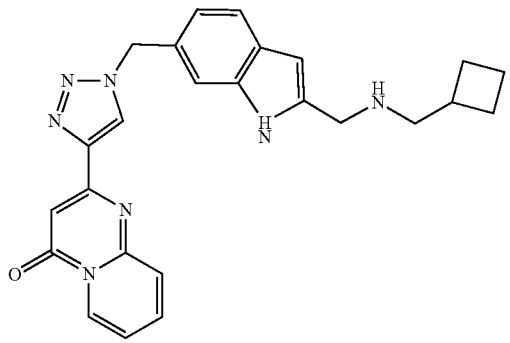

Step 1: 2-ethynylpyrido[1,2-a]pyrimidin-4-one

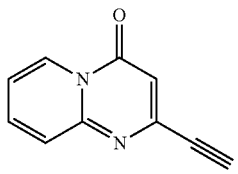

2-chloropyrido[1,2-a]pyrimidin-4-one (700 mg, 3.88 mmol), CuI (74 mg, 0.388 mmol), PdCl2dppf (284 mg, 0.388 mmol) and triethylamine (2.6 mL, 18.5 mmol) were combined in DMF-Anhydrous (4 mL) in a 20 mL pressure vial and the mixture sparged with nitrogen for 10 mins. Ethynyl(trimethyl)silane (1.6 mL, 11.6 mmol) was added and the mixture was sparged with nitrogen for a further 5 minutes. The mixture was heated at 100° C. overnight.

The mixture was cooled to room temperature and diluted with saturated NaHCO₃ (aq) (50 mL). The mixture was extracted with DCM (3×50 mL) and the combined organic extracts were washed with saturated NaHCO₃ (aq) (100 mL), dried over Na₂SO₄ and evaporated under vacuum. The residue was purified by chromatography on SiO₂ (KP—NH, eluting in 0-50% EtOAc/heptane). The crude material was re-purified by chromatography on SiO₂ (KP—NH, eluting in 0-50% EtOAc/heptane) to afford the title compound (302 mg, 46%) as a brown solid.

Method B: LC-MS (electrospray): m/z=171.2 (M+H)$^+$, RT=1.14 min

Step 2: tert-butyl 2-formyl-6-[[4-(4-oxopyrido[1,2-a]pyrimidin-2-yl)triazol-1-yl]methyl]indole-1-carboxylate

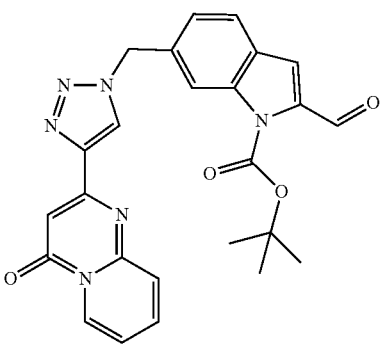

The title compound (181 mg, 72%) was prepared in the same manner as tert-butyl 2-formyl-6-[[4-(1-tetrahydropyran-2-ylindazol-4-yl)triazol-1-yl]methyl]indole-1-carboxylate in Example 52.

Method B: LC-MS (electrospray): m/z=471.3 (M+H)$^+$, RT=1.65 min

Step 3: 2-[1-[[2-[(cyclobutylmethylamino)methyl]-1H-indol-6-yl]methyl]triazol-4-yl]pyrido[1,2-a]pyrimidin-4-one

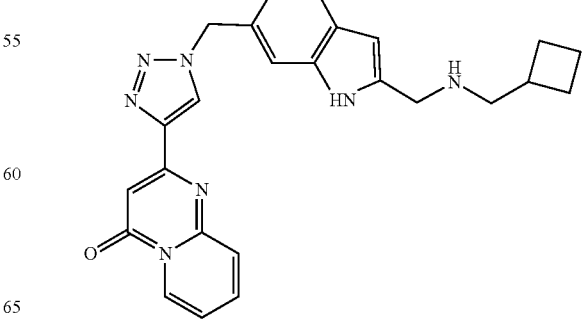

1-cyclobutylmethanamine (0.073 mL, 0.762 mmol) was added to a solution of tert-butyl 2-formyl-6-[[4-(4-oxopyrido[1,2-a]pyrimidin-2-yl)triazol-1-yl]methyl]indole-1-carboxylate (179 mg, 0.381 mmol) in 1,1,1,3,3,3-Hexafluoro-2-propanol (8 mL), and the mixture was stirred at room temperature for 30 minutes. NaBH$_4$ (43 mg, 1.14 mmol) was added, followed by a few drops of MeOH. The mixture was stirred at ambient temperature for 1.5 h. The mixture was quenched with MeOH (10 mL) at 0° C. (mild effervescence) and concentrated in vacuo. The residue was partitioned between saturated NaHCO$_3$ (aq) (20 mL) and DCM (20 mL) and the phases separated. The aqueous phase was extracted with DCM (3×20 mL) and the combined organic phases were dried over Na$_2$SO$_4$, filtered and concentrated. The crude material was diluted with 4M HCl in dioxane (7 mL) and MeOH (0.5 mL), and the mixture was stirred at ambient temperature for 2 h. The mixture was re-treated with 4M HCl in dioxane (5 mL) and MeOH (1 mL) and the mixture was stirred at ambient temperature overnight. The mixture was re-treated with 4M HCl in dioxane (3 mL) and MeOH (1 mL) and the mixture was stirred at ambient temperature for 2 h. The solvent from the mixture was removed in vacuo. The residue was purified by preparative HPLC (Method B) and the pure product containing fractions were combined, concentrated in vacuo and freeze dried overnight to afford the title compound (79 mg, 47%) as a white solid.

Method C: LC-MS (electrospray): m/z=440.4 (M+H)$^+$, RT=3.15 min

Example 63: N-(cyclobutylmethyl)-1-[6-[[4-(6-methoxyimidazo[1,5-a]pyridin-8-yl)triazol-1-yl]methyl]-1H-indol-2-yl]methanamine

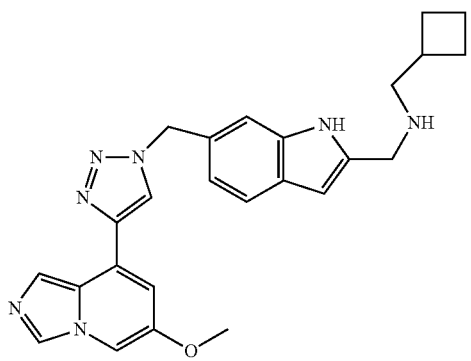 [SMILES: COc1cc(-c2cn(Cc3ccc4cc(CNCC5CCC5)[nH]c4c3)nn2)c2cncn2c1]

Step 1: 3-bromo-5-methoxy-pyridine-2-carbonitrile

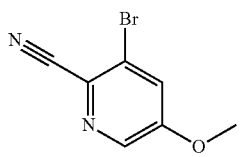

Sodium methoxide (296 mg, 5.47 mmol) was added to an ice-cooled solution of 3-bromo-5-fluoropyridine-2-carbonitrile (1000 mg, 4.98 mmol) in MeOH (15 mL). The RM was warmed to room temperature and stirred for 1.5 h. Sodium methoxide (296 mg, 5.47 mmol) was added and the RM was stirred at ambient temperature for 1 h, heated to 40° C. for 4 h, then at ambient temperature over the weekend. Sodium methoxide (150 mg) was added and the mixture was stirred at 60° C. for 4 h. The mixture was evaporated under reduced pressure, water was added, and the mixture was extracted with ethyl acetate. The combined organic extracts were washed with saturated brine and dried over anhydrous magnesium sulfate. The solvent was evaporated under reduced pressure. The residue was purified by chromatography on SiO$_2$ (25 g SNAP Duo; 0-100% EtOAc in heptane) to the title compound (1130 mg, 106%) as a white powder.

Method A: LC-MS (electrospray): m/z=213/215 (M+H)$^+$, RT=1.05 min

Step 2: (3-bromo-5-methoxy-2-pyridyl)methanamine

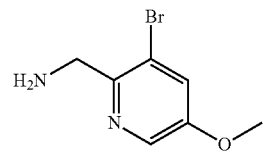

1 M DIBAL in DCM (16 mL, 15.9 mmol) was added to an ice-cooled solution of 3-bromo-5-methoxy-pyridine-2-carbonitrile (1130 mg, 5.30 mmol) in DCE (11 mL). The mixture was warmed to room temperature and stirred for 16 h. The mixture was cooled to 0° C., quenched with saturated NH$_4$Cl (aq), basified using 2 M NaOH and diluted with DCM. The organic phase was collected using a Telos phase separator and evaporated to dryness under reduced pressure to afford the title compound (840 mg, 69%) as an orange oil.

Method B: LC-MS (electrospray): m/z=217/219 (M+H)$^+$, RT=1.22 min

Step 3: tert-butyl N-[(3-bromo-5-methoxy-2-pyridyl)methyl]carbamate

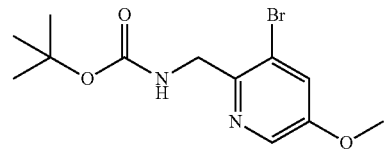 [SMILES: COc1cnc(CNC(=O)OC(C)(C)C)c(Br)c1]

A mixture of (3-bromo-5-methoxy-2-pyridyl)methanamine (830 mg, 3.82 mmol), boc anhydride (1001 mg, 4.59 mmol) and triethylamine (1.3 mL, 9.56 mmol) in Acetonitrile (26 mL) was stirred at reflux for 1 h. The mixture was evaporated to dryness, then water was added, and the mixture was extracted with DCM using a Telos phase separator. The organics were evaporated to dryness to afford the title compound (1130 mg, 75%) as a brown oil.

Method A: LC-MS (electrospray): m/z=317/319 (M+H)$^+$, RT=1.20 min

Step 4: 8-bromo-6-methoxy-imidazo[1,5-a]pyridine

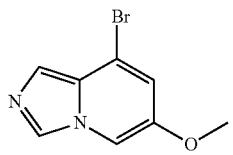

A mixture of tert-butyl N-[(3-bromo-5-methoxy-2-pyridyl)methyl]carbamate (500 mg, 1.58 mmol), trimethoxymethane (8.6 mL, 78.8 mmol) and TFA (0.47 mL, 6.31 mmol) was stirred at 100° C. for 0.5 h. The mixture was evaporated to dryness and purified by chromatography on $SiO_2$ (eluting with 0-100% EtOAc in heptane, then 10% MeOH in EtOAc) to afford the title compound (191 mg, 53%) as a light sticky solid.

Method A: LC-MS (electrospray): m/z=227/229 $(M+H)^+$, RT=0.80 min

Step 5: 2-(6-methoxyimidazo[1,5-a]pyridin-8-yl)ethynyl-trimethyl-silane

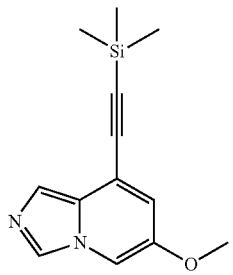 [SMILES: COc1cc(C#C[Si](C)(C)C)c2cncn2c1]

A mixture of 8-bromo-6-methoxy-imidazo[1,5-a]pyridine (790 mg, 3.48 mmol), ethynyl(trimethyl)silane (0.98 mL, 6.96 mmol), ethynyl(trimethyl)silane (0.98 mL, 6.96 mmol), $PdCl_2$ (dppf) (255 mg, 0.348 mmol) triethylamine (2.4 mL, 17.4 mmol) and CuI (66 mg, 0.348 mmol) in DMF-Anhydrous (5 mL) was stirred at 100° C. for 2 h. The mixture was cooled to room temperature, diluted with EtOAc (25 mL) and filtered through Celite. The filtrate was evaporated to dryness and purified by chromatography on $SiO_2$ (eluting with 0-100% EtOAc in heptane) to afford the title compound (250 mg, 25%) as a brown oil.

Method A: LC-MS (electrospray): m/z=245.1 $(M+H)^+$, RT=1.11 min

Step 6: 8-ethynyl-6-methoxy-imidazo[1,5-a]pyridine

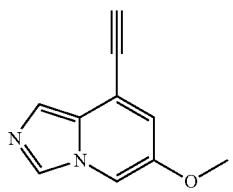

Potassium carbonate (163 mg, 1.18 mmol) was added to a solution of 2-(6-methoxyimidazo[1,5-a]pyridin-8-yl)ethynyl-trimethyl-silane (90%, 160 mg, 0.589 mmol) in MeOH (2.75 mL) at ambient temperature and the mixture was stirred at ambient temperature for 1 h. The solvent was removed under reduced pressure. 25% IPA in $CHCl_3$ (30 mL) and water (30 mL) were added and the organic phase was collected using a Telos phase separator and concentrated under reduced pressure to afford the title compound (90 mg, 63%) as a brown oil.

Method A: LC-MS (electrospray): m/z=173.1 $(M+H)^+$, RT=0.77 min

Step 7: tert-butyl 2-[[tert-butoxycarbonyl(cyclobutylmethyl)amino]methyl]-6-[[4-(6-methoxyimidazo[1,5-a]pyridin-8-yl)triazol-1-yl]methyl]indole-1-carboxylate

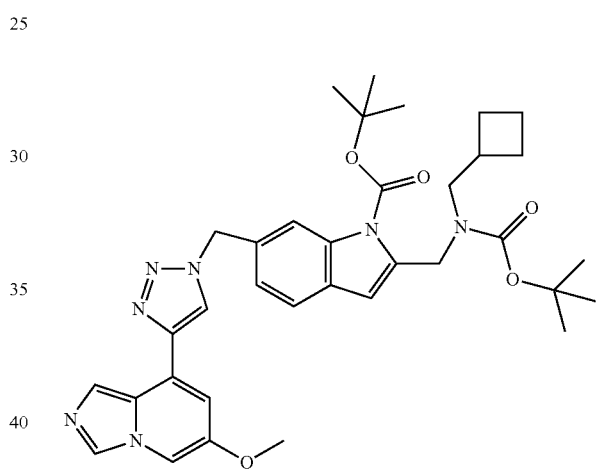

A mixture of 8-ethynyl-6-methoxy-imidazo[1,5-a]pyridine (70 mg, 0.407 mmol), tert-butyl 6-(azidomethyl)-2-[[tert-butoxycarbonyl(cyclobutylmethyl)amino]methyl]indole-1-carboxylate (191 mg, 0.407 mmol) (Intermediate 7), $CuSO_4$ (13 mg, 0.0813 mmol) and sodium ascorbate (89 mg, 0.447 mmol) in DMF (4.5 mL) and water (1 mL) was stirred at ambient temperature overnight. The mixture was diluted with water and DCM and the organic phase was collected using a Telos phase separator. The organics were evaporated to dryness under reduced pressure and purified by chromatography on $SiO_2$ (KP—NH; 0-100% EtOAc in heptane, then 0-20% MeOH in EtOAc) to afford the title compound (120 mg, 46%) as an orange solid.

Method J: LC-MS (electrospray): m/z=642.5 $(M+H)^+$, RT=0.82 min

Step 8: N-(cyclobutylmethyl)-1-[6-[[4-(6-methoxy-imidazo[1,5-a]pyridin-8-yl)triazol-1-yl]methyl]-1H-indol-2-yl]methanamine

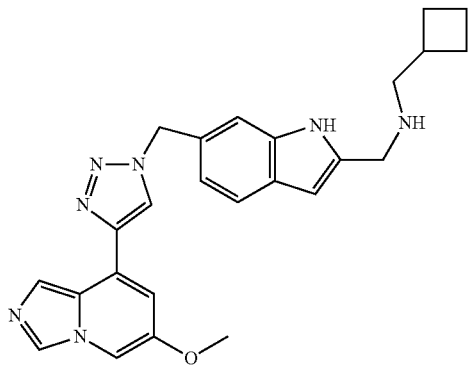 [SMILES: COc1cc(-c2cn(Cc3ccc4cc(CNCC5CCC5)[nH]c4c3)nn2)c2cncn2c1]

HCl (4M in dioxane, 0.47 mL, 1.87 mmol) was added to a solution of tert-butyl 2-[[tert-butoxycarbonyl(cyclobutylmethyl)amino]methyl]-6-[[4-(6-methoxyimidazo[1,5-a]pyridin-8-yl)triazol-1-yl]methyl]indole-1-carboxylate (120 mg, 0.187 mmol) in DCM (1.2 mL) and the mixture was stirred at room temperature for 16 h. The mixture was evaporated to dryness and purified by preparative HPLC (Method B). The product-containing fractions were combined, and the organic solvent removed under reduced pressure. The solid formed in the aqueous suspension thus obtained was collected by vacuum filtration and dried under vacuum to afford the title compound (26 mg, 31%) as a white powder.

Method C: LC-MS (electrospray): m/z=442.4 (M+H)$^+$, RT=3.28 min

Intermediate 8: 1-tert-butyl 2-methyl 6-(bromomethyl)-1H-indole-1,2-dicarboxylate

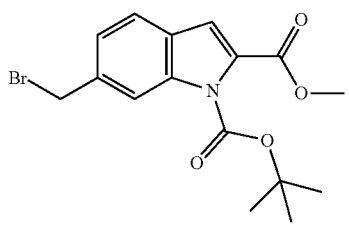 [SMILES: COC(=O)c1cc2ccc(CBr)cc2n1C(=O)OC(C)(C)C]

Step 1: 1-tert-butyl 2-methyl 6-methyl-1H-indole-1,2-dicarboxylate

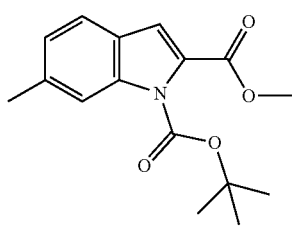

Methyl 6-methyl-1H-indole-2-carboxylate (5.25 g, 27.7 mmol) and DMAP (0.53 g, 4.30 mmol) were combined in Acetonitrile (80 mL) and Boc$_2$O (7.27 g, 33.3 mmol) was added. The reaction was stirred at ambient temperature for 10 minutes where upon the colour of the solution had changed from colourless to dark orange. The temperature was increased to 45° C. and stirred overnight. The mixture was cooled to room temperature and the solvent removed in vacuo to give an orange solid. The solid was dissolved in EtOAc (150 mL) and washed with water (100 mL). The layers were separated, and the aqueous layer extracted with EtOAc (100 mL). The combined organic phases were washed with brine (100 mL), dried over Na$_2$SO$_4$ and evaporated under vacuum to give the crude material as an orange residue. The residue was purified by chromatography on SiO$_2$ (100 g Kp-Sil, eluting with EtOAc/heptane 0-50%) to afford the title compound (8.20 g, 100%) as an off-white crystalline solid.

Method B: LC-MS (electrospray): m/z=290.2 (M+H)$^+$, RT=2.01 min

Step 2: 1-tert-butyl 2-methyl 6-(bromomethyl)indole-1,2-dicarboxylate

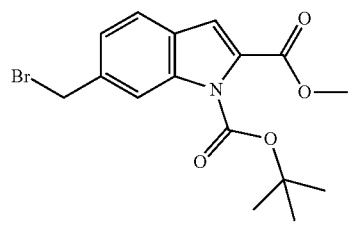 [SMILES: COC(=O)c1cc2ccc(CBr)cc2n1C(=O)OC(C)(C)C]

1-tert-butyl O2-methyl 6-methylindole-1,2-dicarboxylate (5.00 g, 17.3 mmol), 1-bromopyrrolidine-2,5-dione (2.92 g, 16.4 mmol) and AIBN (284 mg, 1.73 mmol) were combined in DCE (200 mL) and the mixture was stirred at 75° C. for 2 h. The mixture was cooled to room temperature and concentrated under vacuum. The residue was purified by chromatography on SiO$_2$ (0-10% EtOAc/heptane, KP-sil, 30 g, done in 2 batches), clean fractions were combined and concentrated to afford the title compound (4.00 g, 61%) as a colourless oil, which formed a white crystalline solid upon standing.

Method B: LC-MS (electrospray): m/z=368.1/370.1 (M+H)$^+$, RT=2.00 min

Intermediate 9: 4-(1H-imidazol-4-yl)-1-tetrahydropyran-2-yl-indazole

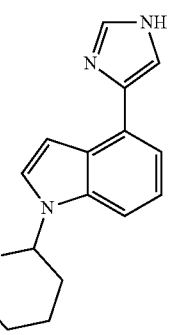

253

Step 1: 4-bromo-1-tetrahydropyran-2-yl-indazole

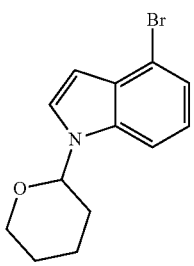 [SMILES: Brc1cccc2c1ccn2C1CCCCO1]

4-bromo-1H-indazole (6.1 g, 31.0 mmol) and tosic acid monohydrate (589 mg, 3.10 mmol) were combined in DCM (100 mL) and 3,4-dihydro-2H-pyran (4.24 mL, 46.4 mmol) was added. The mixture was stirred at ambient temperature for 3 h. The mixture was quenched with saturated NaHCO$_3$ (aq) (100 mL) and the mixture stirred vigorously for 5 minutes. The layers were separated, the aqueous phase was extracted with DCM (2×100 mL) and the combined organic layers dried over Na$_2$SO$_4$ and evaporated under vacuum. The residue was purified by chromatography on SiO$_2$ (100 g kp-Sil, eluting with EtOAc/heptane 0-100%) to afford the title compound (8.91 g, 96%) as a white solid.

Method A: LC-MS (electrospray): m/z=280.9/282.9 (M+H)$^+$, RT=1.31 min

Step 2: 1-tetrahydropyran-2-yl-4-(4,4,5,5-tetramethyl-1,3,2-dioxaborolan-2-yl)indazole

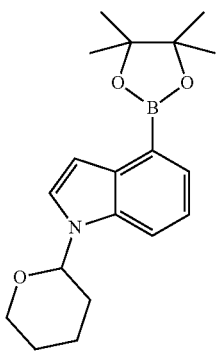 [SMILES: CC1(C)OB(c2cccc3c2ccn3C2CCCCO2)OC1(C)C]

4-bromo-1-tetrahydropyran-2-yl-indazole (3 g, 10.7 mmol), potassium acetate (4.76 g, 48.0 mmol), 4,4,5,5-tetramethyl-2-(4,4,5,5-tetramethyl-1,3,2-dioxaborolan-2-yl)-1,3,2-dioxaborolane (3.52 g, 13.9 mmol) and PdCl$_2$(dppf) (391 mg, 0.53 mmol) were combined in 1,4-Dioxane (40 mL) and the mixture sparged with nitrogen for 5 minutes. The mixture was heated at 100° C. (external) under nitrogen for 2.5 h. The mixture was cooled to room temperature, diluted with EtOAc (150 mL) and filtered. The residue was rinsed with EtOAc and the combined filtrates were washed with sat. NaHCO$_3$ (aq) (100 mL) and brine (100 mL). The organic layer was dried over Na$_2$SO$_4$ and evaporated under vacuum. The residue was purified by chromatography on SiO$_2$ (100 g kp-Sil, eluting with EtOAc/heptane 0-100%) to afford the title compound (3.21 g, 78 5) as a pale yellow wax.

254

Method A: LC-MS (electrospray): m/z=329.2 (M+H)$^+$, RT=1.39 min

Step 3: 4-(1H-imidazol-4-yl)-1-tetrahydropyran-2-yl-indazole

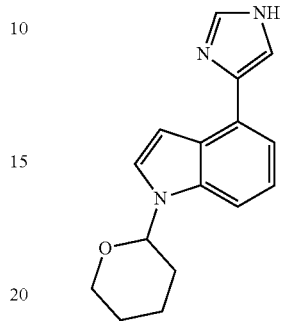

1-(oxan-2-yl)-4-(4,4,5,5-tetramethyl-1,3,2-dioxaborolan-2-yl)-1H-indazole (740 mg, 2.25 mmol), 4-bromo-1H-imidazole (440 mg, 2.93 mmol), Pd(OAc)$_2$ (101 mg, 0.45 mmol), APhos (287 mg, 1.08 mmol) and K$_2$CO$_3$ (aq) (1.2M aqueous, 5.6 mL, 6.76 mmol) were combined in 1,4-Dioxane (10 mL) and the mixture sparged with nitrogen for 5 mins. The vessel was sealed, and the mixture heated at 115° C. (external) for 2.5 h. The mixture was cooled to room temperature and stood overnight. The mixture was diluted with water (80 mL) and extracted with 3:1 chloroform/isopropanol (3×50 mL). The combined organic extracts were dried over Na$_2$SO$_4$ and evaporated under vacuum. The residue was purified by (chromatography on SiO$_2$ (kp-NH, eluting with EtOAc/heptane 0-100% followed by MeOH/EtOAc 0-20%) to afford the title compound (371 mg, 58%) as a white solid.

Method B: LC-MS (electrospray): m/z=296.2 (M+H)$^+$, RT=1.35 min

Example 64: N-(cyclobutylmethyl)-1-[6-[[4-(1H-indazol-4-yl)imidazol-1-yl]methyl]-1H-indol-2-yl]methanamine

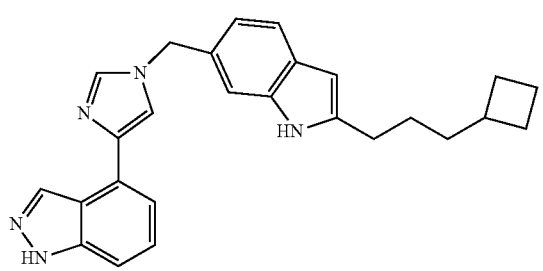 [SMILES: c1cc(-c2cn(Cc3ccc4cc(CCCC5CCC5)[nH]c4c3)cn2)c2cn[nH]c2c1]

Step 1: O1-tert-butyl O2-methyl 6-[[4-(1-tetrahydropyran-2-ylindazol-4-yl)imidazol-1-yl]methyl]indole-1,2-dicarboxylate

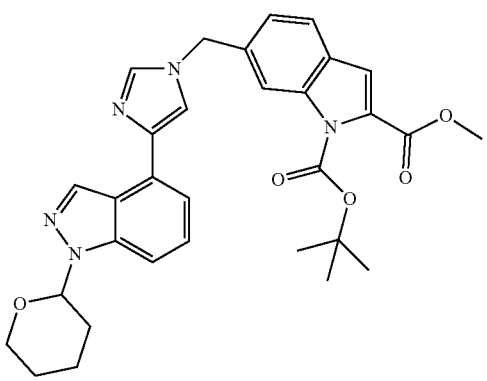 [SMILES: COC(=O)c1cc2ccc(Cn3cnc(-c4cccc5c4cnn5C4CCCCO4)c3)cc2n1C(=O)OC(C)(C)C]

4-(1H-imidazol-4-yl)-1-tetrahydropyran-2-yl-indazole (370 mg, 1.38 mmol) (Intermediate 9), O1-tert-butyl O2-methyl 6-(bromomethyl)indole-1,2-dicarboxylate (508 mg, 1.38 mmol) (Intermediate 8), Cs$_2$CO$_3$ (599 mg, 2.76 mmol) and NaI (21 mg, 0.14 mmol) were combined in DMF (10 mL) and the mixture heated at 90° C. (External). The mixture was cooled to room temperature, diluted with EtOAc (50 mL) and washed with sat. NaHCO$_3$ (aq) (30 mL) and brine (5×30 mL). The organic layer was dried over Na$_2$SO$_4$ and evaporated under vacuum. The residue was purified by chromatography on SiO$_2$ (25 g Sfar Duo, eluting with EtOAc/heptane 0-100% followed by MeOH/EtOAc 0-20%) to afford the title compound (336 mg, 21%) as a pale orange solid.

Method B: LC-MS (electrospray): m/z=556.3 (M+H)$^+$, RT=1.89 min

Step 2: tert-butyl 2-(hydroxymethyl)-6-[[4-(1-tetrahydropyran-2-ylindazol-4-yl)imidazol-1-yl]methyl]indole-1-carboxylate

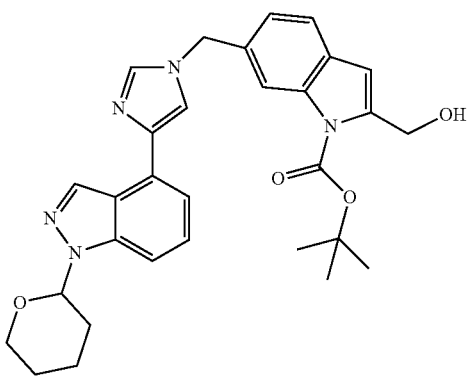 [SMILES: CC(C)(C)OC(=O)n1c(CO)cc2ccc(Cn3cnc(-c4cccc5c4cnn5C4CCCCO4)c3)cc21]

O1-tert-butyl O2-methyl 6-[[4-(1-tetrahydropyran-2-ylindazol-4-yl)imidazol-1-yl]methyl]indole-1,2-dicarboxylate (336 mg, 0.60 mmol) was dissolved in DCM-Anhydrous (10 mL) and cooled to −40° C. (external). DIBAL (1M in DCM, 1.21 mL, 1.21 mmol) was added dropwise and the mixture stirred at −40° C. for 1 h. DIBAL (1M in DCM, 1.21 mL, 1.21 mmol) was added and the mixture was stirred for 3 h. DIBAL (1M in DCM, 1.21 mL, 1.21 mmol) was added and the mixture was stirred for 5 h. The mixture was quenched by dropwise addition of MeOH (4 mL) and the mixture stirred under cooling for 5 mins, then allowed to warm to room temperature. The mixture was further diluted with 2M NaOH (aq) (4 mL), then water (10 mL) and the mixture stood overnight. The phases were separated, and the aqueous phase extracted with DCM (3×30 mL). The combined organic layers were dried over Na$_2$SO$_4$ and evaporated under vacuum to afford the title product (343 mg, 45%) as a brown residue, which was used without further purification.

Method B: LC-MS (electrospray): m/z=528.3 (M+H)$^+$, RT=1.73 min

Step 3: tert-butyl 2-formyl-6-[[4-(1-tetrahydropyran-2-ylindazol-4-yl)imidazol-1-yl]methyl]indole-1-carboxylate

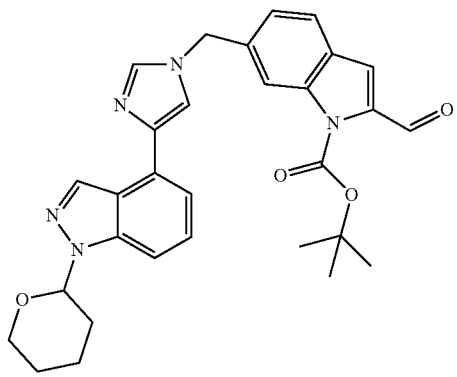 [SMILES: CC(C)(C)OC(=O)n1c(C=O)cc2ccc(Cn3cnc(-c4cccc5c4cnn5C4CCCCO4)c3)cc21]

tert-butyl 2-(hydroxymethyl)-6-[[4-(1-tetrahydropyran-2-ylindazol-4-yl)imidazol-1-yl]methyl]indole-1-carboxylate (343 mg, 0.65 mmol) was dissolved in DCE (10 mL) and MnO$_2$ (565 mg, 6.50 mmol) was added. The mixture was heated at reflux for 1 h. Further amounts of MnO$_2$ (565 mg, 6.50 mmol) added and reflux continued for a further 2 h. The mixture was cooled to room temperature and filtered through a plug of Celite. The residue was rinsed with MeOH and the combined filtrates evaporated under vacuum to afford the title compound (233 mg, 40%) compound as a pale yellow solid. The Material was used directly without purification.

Method B: LC-MS (electrospray): m/z=526.3 (M+H)$^+$, RT=1.88 min

Step 4: N-(cyclobutylmethyl)-1-[6-[[4-(1H-indazol-4-yl)imidazol-1-yl]methyl]-1H-indol-2-yl]methanamine

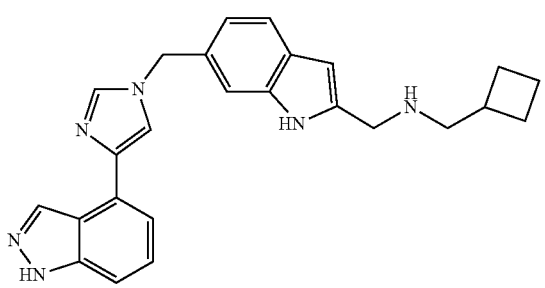 [SMILES: c1cc(-c2cn(Cc3ccc4cc(CNCC5CCC5)[nH]c4c3)cn2)c2cn[nH]c2c1]

tert-butyl 2-formyl-6-[[4-(1-tetrahydropyran-2-ylindazol-4-yl)imidazol-1-yl]methyl]indole-1-carboxylate (230 mg, 0.44 mmol) and 1-cyclobutylmethanamine (75 mg, 0.88 mmol) were combined in 1,1,1,3,3,3-Hexafluoro-2-propanol (5 mL) and the mixture incubated at ambient temperature for 30 minutes. NaBH$_4$ (50 mg, 1.31 mmol) was added with a few drops MeOH and the mixture stirred briefly at ambient temperature. The mixture was quenched with MeOH and the mixture evaporated under vacuum. The residue was partitioned between saturated NaHCO$_3$ (aq) (20 mL) and extracted with DCM (3×30 mL). The combined organic extracts were dried over Na$_2$SO$_4$ and evaporated under vacuum. The residue was redissolved in MeOH (5 mL) and 4M HCl in Dioxane (5 mL) and the mixture heated at 60° C. (external) for 3 h. The mixture was cooled to room temperature and evaporated under vacuum. The residue was loaded to an SCX-2 cartridge (5 g) and the cartridge rinsed with DCM and MeOH, then eluted with 7M NH$_3$/MeOH. The basic eluent was evaporated under vacuum. The crude material was purified by preparative HPLC (Method B) and the clean product containing fractions were combined and evaporated under vacuum to afford the title compound (19 mg, 11%) as a beige solid.

Method D: LC-MS (electrospray): m/z=411.3 (M+H)$^+$, RT=4.13 min

Intermediate 10: N|-hydroxy-1-tetrahydropyran-2-yl-indazole-4-carboxamidine

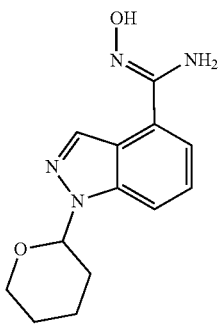 [SMILES: N/C(=N\O)c1cccc2c1cnn2C1CCCCO1]

Step 1: 4-bromo-1-tetrahydropyran-2-yl-indazole

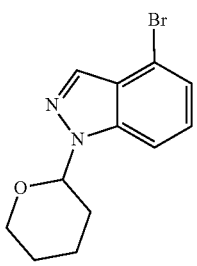 [SMILES: Brc1cccc2c1cnn2C1CCCCO1]

4-bromo-1H-indazole (8 g, 40.6 mmol), tosic acid monohydrate (772 mg, 4.06 mmol) and 3,4-dihydro-2H-pyran (5.56 mL, 60.9 mmol) were combined in DCM (80 mL) and the mixture stirred at ambient temperature for 3 h. The mixture was quenched with saturated NaHCO$_3$ (aq) (80 mL) and stirred vigorously for 5 mins. The phases were separated, the aqueous phase was extracted with DCM (2×50 mL) and the combined organic layers were dried over Na$_2$SO$_4$ and evaporated under vacuum. The residue was purified by chromatography on SiO$_2$ (350 g Sfar Duo, eluting with EtOAc/heptane 0-100%) to afford the title compound (11.16 g, 97%) as a colourless oil which solidified on standing to a white wax.

Method B: LC-MS (electrospray): m/z=281.1/283.1 (M+H)$^+$, RT=1.83 min

Step 2: 1-tetrahydropyran-2-ylindazole-4-carbonitrile

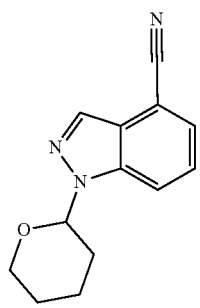 [SMILES: N#Cc1cccc2c1cnn2C1CCCCO1]

An oven-dried three-neck 25 mL RBF was charged with zinc cyanide (459 mg, 3.91 mmol), 4-bromo-1-tetrahydropyran-2-yl-indazole (1.00 g, 3.56 mmol), palladium-triphenylphosphane complex (1:4) (206 mg, 0.178 mmol) and DMF-Anhydrous (9 mL). The flask was equipped with a reflux condenser, the assembly flushed with nitrogen and then the mixture was de-oxygenated by passing a stream of nitrogen gas for 5 min. The mixture was placed in a pre-heated heating block at 100° C. and the reaction was stirred at this temperature for 3 h. The mixture was cooled to room temperature and diluted with EtOAc (30 mL) and water (20 mL). The aqueous phase was extracted with EtOAc (2×30 mL). The combined organics were washed with brine (10 mL), dried over magnesium sulfate and concentrated to give a reddish oily solid. Purification was carried out by chromatography on SiO$_2$ (Sfar silica duo 25 g cartridge) eluting in a gradient of EtOAc/heptane (0-100%). The product containing fractions were combined to afford the title compound (697 mg, 86%) as a white solid.

Method B: LC-MS (electrospray): m/z=228.3 (M+H)$^+$, RT=1.60 min

Step 3: N-hydroxy-1-tetrahydropyran-2-yl-indazole-4-carboxamidine

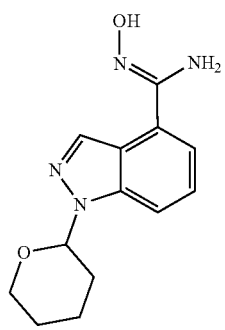 [SMILES: N/C(=N\O)c1cccc2c1cnn2C1CCCCO1]

1-tetrahydropyran-2-ylindazole-4-carbonitrile (100 mg, 0.440 mmol), Ethanol (5 mL) and 17 M hydroxylamine (50% in water) (0.13 mL, 2.20 mmol) were combined and heated under reflux at 80° C. for 3.5 h. The mixture was cooled to room temperature and concentrated. The resulting solid was washed with water (approx. 5 mL) and air-dried to afford a white solid. Purification was carried out by chromatography on $SiO_2$ (10 g sfar duo cartridge) eluting in a gradient of EtOAc/heptane 0-100%. The product containing fractions were combined to afford the title compound (93 mg, 77%) as an off-white solid.

Method B: LC-MS (electrospray): m/z=261.2 (M+H)$^+$, RT=1.26 min

Intermediate 11: 2-(1H-indol-6-yl)acetic acid

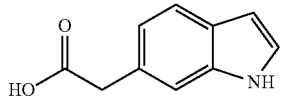 [SMILES: O=C(O)Cc1ccc2cc[nH]c2c1]

Step 1: tert-butyl 6-formylindole-1-carboxylate

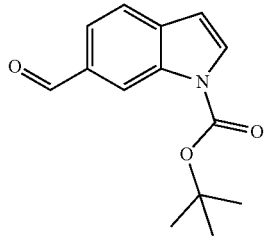 [SMILES: CC(C)(C)OC(=O)n1ccc2ccc(C=O)cc21]

1H-indole-6-carbaldehyde (4.52 g, 31.14 mmol), Boc$_2$O (8.15 g, 37.4 mmol) and DMAP (380 mg, 3.1 1 mmol) were combined in Acetonitrile (50 mL) and the mixture heated at reflux for 1 h. The mixture was cooled to room temperature and evaporated under vacuum. The residue was redissolved in EtOAc (150 mL) and washed with sat. NaHCO$_3$ (aq) (2×80 mL) and brine (80 mL). The organic layer was dried over Na$_2$SO$_4$ and evaporated under vacuum. The residue was purified by chromatography on SiO$_2$ (100 g Sfar Duo, eluting with EtOAc/heptane 0-100%) to afford the title compound (7.53 g, 95%) as a pale-yellow solid.

Method A: LC-MS (electrospray): m/z=246.0 (M+H)$^+$, RT=1.33 min

Step 2: 2-(1H-indol-6-yl)acetonitrile

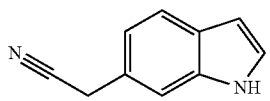 [SMILES: N#CCc1ccc2cc[nH]c2c1]

KOtBu (906 mg, 8.07 mmol) was suspended in THF-Anhydrous (25 mL) and cooled to −55° C. (External). A solution of 1-[(isocyanomethyl)sulfonyl]-4-methylbenzene (TosMIC; 946 mg, 4.48 mmol) in THF-Anhydrous (8 mL) was added slowly and the mixture stirred under cooling for 15 mins. A solution of tert-butyl 6-formylindole-1-carboxylate (1 g, 4.04 mmol) in THF-Anhydrous (10 mL) was then added dropwise over 15 mins, ensuring temperature <−50° C., giving a deep yellow solution and the mixture stirred at <−50° C. for 2 h. MeOH (50 mL) was added and the mixture heated at reflux for 15 mins. The mixture was cooled to room temperature and evaporated under vacuum. The residue was suspended in water (100 mL) and AcOH (4 mL) and extracted with DCM (3×80 mL). The combined organic extracts were dried over Na$_2$SO$_4$ and evaporated under vacuum. The residue was purified by chromatography on SiO$_2$ (25 g Sfar Duo, eluting with EtOAc/heptane 0-100%) to afford the title compound (532 mg, 84%) as an off-white solid.

Method A: LC-MS (electrospray): m/z=no ionisation (M+H)$^+$, RT=1.05 min

Step 3: 2-(1H-indol-6-yl)acetic acid

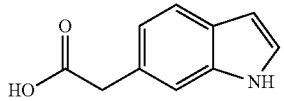

A flask was charged with 2-(1H-indol-6-yl)acetonitrile (508 mg, 3.25 mmol), IPA (40 mL) and water (40 mL). To the resulting solution was added lithium hydroxide (4059 mg, 0.163 mol). The mixture was stirred at 75° C. for 25 h, with solids deposited above the solvent level being occasionally re-introduced to the reaction. The mixture was cooled in an ice bath and neutralised with a 1M HCl solution until the pH was 4-5. The reaction was extracted with a mixture of IPA/CHCl$_3$ 1:3 (4×50 mL). The combined organics were dried over magnesium sulfate and concentrated to give a pink solid. Purification was carried out by chromatography on SiO$_2$ (25 g sfar duo) eluting in a gradient of DCM/MeOH 0-33%. Product containing fractions were collected to afford the title compound (407 mg, 69%) as a yellow solid.

Method L: LC-MS (electrospray): m/z=176.0 (M+H)$^+$, RT=0.6 min

Intermediate 13: +1-{3-fluorobicyclo[1.1.1]pentan-1-yl}ethan-1-amine

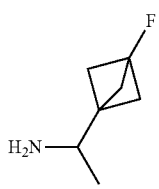

Step 1: 3-fluorobicyclo[1.1.1]pentane-1-carboxylic acid

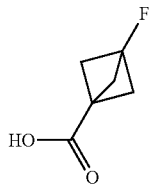

A 500 mL three-neck flask was charged with Selectfluor (17.02 g, 48.0 mmol), bicyclo[1.1.1]pentane-1,3-dicarboxylic acid (3.00 g, 19.2 mmol), silver nitrate (245 mg, 1.44 mmol) and water (96 mL), a small volume of which was used to achieve complete transfer of the silver nitrate. The reaction was equipped with a reflux condenser connected to an oil bubbler and an immersion thermometer. The reaction was de-oxygenated by passing a stream of nitrogen gas through the contents for 15 minutes. The reaction was kept under a flow of nitrogen and placed in a pre-heated heating block at 65° C. (external). The internal temperature of the reaction reached 60° C. in approximately 15 min, with gas evolution was observed above 50° C. The temperature control was adjusted, and the internal temperature stabilised at approximately 62-63° C. after another 15 minutes. Stirring was continued at this temperature for 2.5 h. The reaction was cooled to room temperature and extracted with diethyl ether (4×40 mL). The combined organics were dried over $Na_2SO_4$ and concentrated under vacuum to a small volume. The resulting oil was allowed to crystallise. The solids were re-dissolved in a small amount of diethyl ether (approx 15 mL) resulting in the separation of a white gel phase. The solution was filtered through a phase separator, dried over $Na_2SO_4$ and concentrated to give the title compound (1.85 g, 70%) as a white solid.

Method E: LC-MS (electrospray): m/z=129.2 (M−H)−, RT=1.44 min

Step 2: 3-fluoro-N-methoxy-N-methylbicyclo[1.1.1]pentane-1-carboxamide

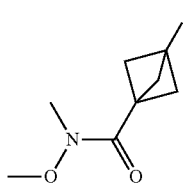

An oven-dried 25 mL flask was charged with 3-fluorobicyclo[1.1.1]pentane-1-carboxylic acid (359 mg, 2.62 mmol), purged with nitrogen and DCE (5 mL) and DMF-Anhydrous (18.032 μL) were added resulting in the formation of a clear solution. To the solution was slowly added N-methoxymethanamine hydrochloride (1.3 g, 13.1 mmol) resulting in gas evolution. The reaction was stirred at room temperature for 4 h and then was cooled in ice. Oxalyl chloride (0.45 mL, 5.24 mmol) was added (further gas evolution) followed by slow addition of N-ethyl-N-isopropyl-propan-2-amine (4.6 mL, 26.2 mmol) and the reaction was stirred at room temperature for 24 h. The mixture was diluted with DCM (20 mL) and washed with water (5 mL) and brine (5 mL), dried over $Na_2SO_4$ and concentrated to give a brown oil (~1.3 g). The material was re-dissolved in DCM (25 mL) washed with HCl (1M, 5 mL), water (5 mL) and brine (5 mL), dried over $Na_2SO_4$ and concentrated to give a brown oil (700 mg). The material was purified by chromatography on $SiO_2$ [eluting with 0-100% EtOAc/heptane] followed by 0-100% MeOH/EtOAc to give the title compound (347 mg, 73%) as a yellow oil.

Method J: LC-MS (electrospray): m/z=174.2 (M−H)−, RT=0.50 min

Step 3: 1-(3-fluoro-1-bicyclo[1.1.1]pentanyl)ethanone

A cooled (0° C.) solution of 3-fluoro-N-methoxy-N-methyl-bicyclo[1.1.1]pentane-1-carboxamide (130 mg, 0.71 mmol) in THF-Anhydrous (2 mL) was treated slowly with methyl magnesium bromide (1M in THF, 1.1 mL, 1.1 mmol) resulting in the formation of a cloudy solution which was stirred at 0-5° C. for 4 h and then treated with further methyl magnesium bromide (1M in THF, 1.1 mL, 1.1 mmol) and the reaction was stirred for 1 h and then quenched with $NH_4Cl$ (sat., 2 mL) and warmed to room temperature. The mixture was extracted with diethyl ether (20+10 mL) and the combined organics were filtered through a bed of $Na_2SO_4$ and concentrated under vacuum (at room temperature) to give the title compound (130 mg, 87%) as a yellow oil.

$^1$H NMR (400 MHz, DMSO) δ 2.31 (d, J=2.7 Hz, 6H), 2.15 (s, 3H)

Step 4: 1-(3-fluoro-1-bicyclo[1.1.1]pentanyl)ethanamine hydrochloride

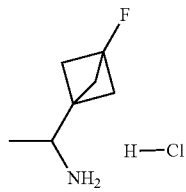

A solution of 1-(3-fluoro-1-bicyclo[1.1.1]pentanyl)ethanone (130 mg, 0.62 mmol), ammonium acetate (954 mg, 12.4 mmol) and sodium cyanoborohydride (389 mg, 6.2 mmol) in MeOH (2 mL) was stirred at room temperature for 20 h. The mixture was diluted with water (3 mL) and extracted with $CHCl_3$/IPA (3:1, 3×10 mL). The aqueous phase was saturated with sodium chloride and extracted with $CHCl_3$/IPA (3:1, 10 mL). The combined organics were washed with a mixture of water (1 mL) and brine (5 mL) and dried over $Na_2SO_4$. The resulting solution was cooled using an ice bath and treated with HCl (4M in dioxane, 4 mL). The mixture was allowed to warm up and stirred for 3 h before it was concentrated to give a yellow residue (104 mg). The material was dissolved in ethanol (2 mL) and diethyl ether (50 mL) was added. The resulting suspension was stirred for 5 minutes and filtered to give the title compound (36 mg, 33%) as a white solid.

Method K: LC-MS (electrospray): m/z=129.95 (M+H)$^+$, RT=0.45 min

Intermediate 14: 8-bromoimidazo[1,5-a]pyridine

A mixture of formaldehyde (37%, 16 mL, 0.22 mol) and ammonium acetate (20.7 g, 0.27 mol) in acetic acid (100 mL) was stirred at room temperature for 10 minutes before 3-bromopyridine-2-carbaldehyde (5.0 g, 26.9 mmol) was added portionwise over 2 h and the mixture was stirred at room temperature for 3 h. The mixture was partitioned between water (100 mL) and DCM (100 mL) and the phases separated. The aqueous phase was washed with DCM (3×100 mL), and the combined organic phases passed through an Isolute phase separator and concentrated under vacuum. The residue was purified by chromatography on SiO$_2$ (eluting with 0-100% EtOAc/heptane) to the title compound (2.51 g, 46%) as an off-white solid.

Method C: LC-MS (electrospray): m/z=196.9/198.9 (M+H)$^+$, RT=2.28 min

Intermediate 15: tert-butyl 6-(azidomethyl)-2-({[(tert-butoxy)carbonyl]({3-fluorobicyclo[1.1.1]pentan-1-yl}methyl)amino}methyl)-1H-indole-1-carboxylate

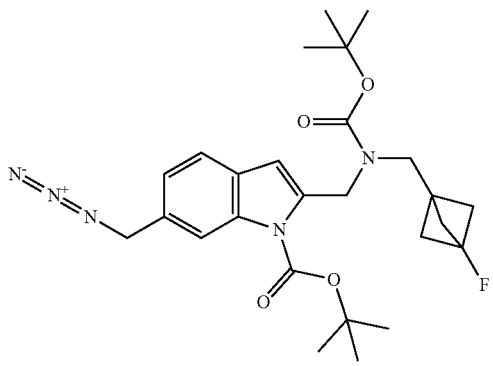 [SMILES: CC(C)(C)OC(=O)N(Cc1cc2ccc(CN=[N+]=[N-])cc2n1C(=O)OC(C)(C)C)CC12CC(F)(C1)C2]

The title compound was prepared from 1-{3-fluorobicyclo[1.1.1]pentan-1-yl}methanamine hydrochloride in an analogous manner to the procedures described for Intermediate 2 and intermediate 7 to give (72 mg, 25%) as a cloudy grey oil.

Method J: LC-MS (electrospray): m/z=500.6 (M+H)$^+$, RT=1.17 min

Intermediate 16: N-({2-formyl-1H-pyrrolo[3,2-c]pyridin-6-yl}methyl)-4-oxo-4H-pyrido[1,2-a]pyrimidine-2-carboxamide

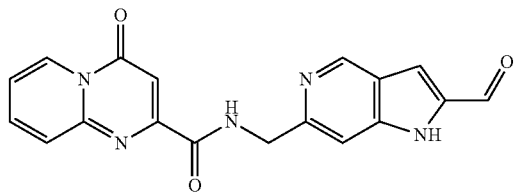 [SMILES: O=Cc1cc2cnc(CNC(=O)c3cc(=O)n4ccccc4n3)cc2[nH]1]

Step 1: 4-Amino-5-bromo-pyridine-2-carbonitrile

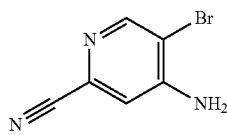

To a solution of 4-aminopyridine-2-carbonitrile (3.25 g, 27.3 mmol) in acetic acid (30 mL) and acetonitrile (30 mL) was added Benzyltrimethylammonium tribromide (10.64 g, 27.3 mmol) and potassium acetate (5.41 g, 54.6 mmol) at room temperature and the mixture was stirred for 24 h. The mixture was quenched by addition of Na$_2$SO$_3$ solution (sat., 2 mL) (colour changed from orange to yellow). The mixture was concentrated to dryness at reduced pressure. The residue was partitioned between EtOAc (200 mL) and Na$_2$CO$_3$ (sat., 100 mL).

The organic layer was separated, washed with brine (100 mL), dried (Na$_2$SO$_4$) and concentrated at reduced pressure. The residue was purified by chromatography on SiO$_2$ (eluting with 0-50% EtOAc in DCM) to afford the title compound (2.15 g, 39%) as beige solid solid.

Method C: LC-MS (electrospray): m/z=197.9/199.9 (M+H)$^+$, RT=1.85 min

Step 2: 4-amino-5-(3,3-diethoxyprop-1-ynyl)pyridine-2-carbonitrile

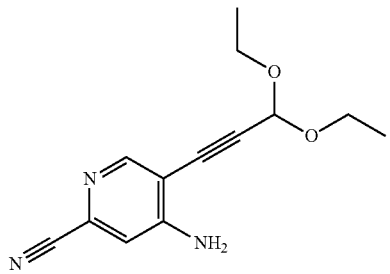 [SMILES: CCOC(C#Cc1cnc(C#N)cc1N)OCC]

A degassed mixture of 4-amino-5-bromo-pyridine-2-carbonitrile (480 mg, 2.42 mmol), 3,3-diethoxyprop-1-yne (0.42 mL, 2.91 mmol), triethylamine (5.7 mL, 41.2 mmol), triphenylphosphine (13 mg, 0.049 mmol), PdCl$_2$(PPh$_3$)$_2$ (17 mg, 0.024 mmol) and CuI (9.2 mg, 0.049 mmol) in DMF-Anhydrous (3.1 mL) was stirred at 80° C. for 18 h. More PdCl$_2$(PPh$_3$)$_2$ (17 mg, 0.024 mmol) and CuI (9.2 mg, 0.049 mmol) was added and the mixture was stirred at 80° C. for 2 h. More 3,3-diethoxypropyne (0.2 mL) was added and the mixture was stirred at 80° C. for 2 h. More 3,3-diethoxypropyne (0.4 mL) was added and the mixture was stirred at 80° C. for 18 h. The mixture was cooled to room temperature, filtered by vacuum filtration to remove the precipitate and washed with EtOAc (25 mL). The organic filtrate was washed with water (25 mL), NaHCO$_3$ (sat., 3×25 mL) and brine (25 mL) dried over magnesium sulfate. The solid residue in the filtrate was removed by filtration and the filtrate was evaporated to dryness under reduced pressure. The crude material was purified by chromatography on SiO$_2$ (eluting with 0-50% EtOAc in heptane) to afford the title compound (310 mg, 43%) as a brown solid.

Method A: LC-MS (electrospray): m/z=246.1 (M+H)$^+$, RT=1.05 min

Step 3: 2-(diethoxymethyl)-1H-pyrrolo[3,2-c]pyridine-6-carbonitrile

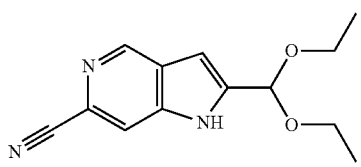 [SMILES: CCOC(OCC)c1cc2cnc(C#N)cc2[nH]1]

Potassium tert-butoxide (235 mg, 2.10 mmol) was added to a solution of 4-amino-5-(3,3-diethoxyprop-1-ynyl)pyridine-2-carbonitrile (310 mg, 1.05 mmol) in NMP-Anhydrous (3.2 mL), and the mixture was stirred at 60° C. for 2 h. The mixture was partitioned between EtOAc (25 mL) and water (25 mL). The organic phase was separated, and the aqueous phase was extracted with EtOAc (25 mL). The combined organics were washed with brine (3×30 mL), dried over magnesium sulfate, filtered and evaporated to dryness to afford the title compound (365 mg, 99%) as a brown oil.

Method J: LC-MS (electrospray): m/z=246.2 (M+H)$^+$, RT=0.65 min

Step 4: tert-butyl 6-cyano-2-(diethoxymethyl)pyrrolo[3,2-c]pyridine-1-carboxylate

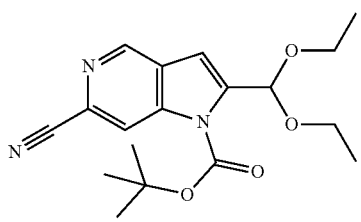 [SMILES: CCOC(OCC)c1cc2cnc(C#N)cc2n1C(=O)OC(C)(C)C]

Boc anhydride (273 mg, 1.25 mmol) was added to a solution of 2-(diethoxymethyl)-1H-pyrrolo[3,2-c]pyridine-6-carbonitrile (365 mg, 1.04 mmol) and DMAP (25 mg, 0.2 mmol) in acetonitrile (8 mL) and the mixture was stirred at room temperature for 18 h. The mixture was evaporated to dryness, partitioned between NaHCO$_3$ (sat., 10 mL), water (20 mL) and extracted with DCM (3×20 mL) using a Telos phase separator. The combined organics were evaporated to dryness and purified by chromatography on SiO$_2$ (eluting with 0-60% EtOAc in heptane) to afford the title compound (300 mg, 0.851 mmol, 82%) as a colourless oil.

Method A: LC-MS (electrospray): m/z=346.1 (M+H)$^+$, RT=1.40 min

Step 5: tert-butyl 6-(aminomethyl)-2-(diethoxymethyl)pyrrolo[3,2-c]pyridine-1-carboxylate

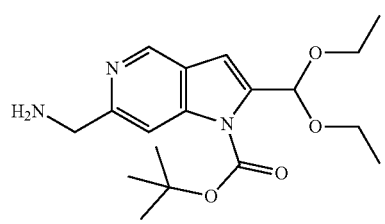 [SMILES: CCOC(OCC)c1cc2cnc(CN)cc2n1C(=O)OC(C)(C)C]

A mixture of tert-butyl 6-cyano-2-(diethoxymethyl)pyrrolo[3,2-c]pyridine-1-carboxylate (300 mg, 0.87 mmol) and Raney nickel (~51 mg, 0.87 mmol) in ammonia in MeOH (7M, 0.87 mL, 6.0 mmol) and ethanol (5.5 mL) was stirred at room temperature under a hydrogen atmosphere for 18 h. The catalyst was removed by filtration and washed with EtOH (50 mL). The filtrate was evaporated to dryness to afford the title compound (195 mg, 45%) as a colourless oil.

Method A: LC-MS (electrospray): m/z=350.1 (M+H)$^+$, RT=0.92 min

Step 6: tert-butyl 2-(diethoxymethyl)-6-[[(4-oxopyrido[1,2-a]pyrimidine-2-carbonyl)amino]methyl]pyrrolo[3,2-c]pyridine-1-carboxylate

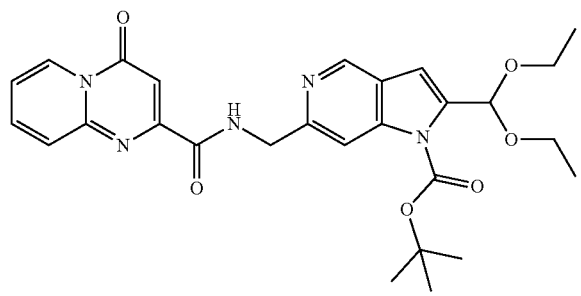 [SMILES: CCOC(OCC)c1cc2cnc(CNC(=O)c3cc(=O)n4ccccc4n3)cc2n1C(=O)OC(C)(C)C]

4-oxopyrido[1,2-a]pyrimidine-2-carboxylic acid Intermediate 1 (116 mg, 0.61 mmol) was added to a solution of tert-butyl 6-(aminomethyl)-2-(diethoxymethyl)pyrrolo[3,2-c]pyridine-1-carboxylate (190 mg, 0.54 mmol), T3P (50% in EtOAc, 0.39 mL, 0.65 mmol) and DIPEA (0.28 mL, 1.63 mmol) in DMF (2.5 mL) and the mixture was stirred at room temperature for 1 h. The mixture was partitioned between EtOAc (25 mL) and water (25 mL). The aqueous phase was basified to ~pH 10 using NaOH (1 M) and the organic phase was collected. The basic aqueous phase was extracted with EtOAc (2×25 mL). The combined organics were washed with brine (2×25 mL), dried over magnesium sulfate and evaporated to dryness under reduced pressure. The crude material was purified by chromatography on SiO$_2$ (eluting with 0-100% EtOAc in heptane, then 0-20% MeOH in EtOAc) to afford the title compound (250 mg, 43%) as a colourless oil.

Method A: LC-MS (electrospray): m/z=522.1 (M+H)+, RT=1.01 min

Step 7: N-({2-formyl-1H-pyrrolo[3,2-c]pyridin-6-yl}methyl)-4-oxo-4H-pyrido[1,2-a]pyrimidine-2-carboxamide

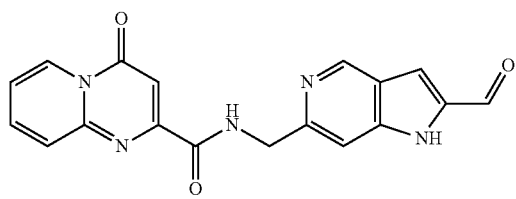 [SMILES: O=Cc1cc2cnc(CNC(=O)c3cc(=O)n4ccccc4n3)cc2[nH]1]

TFA (2.7 mL, 36.8 mmol) was added to a solution of tert-butyl 2-(diethoxymethyl)-6-[[(4-oxopyrido[1,2-a]pyrimidine-2-carbonyl)amino]methyl]pyrrolo[3,2-c]pyridine-1-carboxylate (240 mg, 0.46 mmol) in DCM (2.5 mL) and the mixture was stirred at room temperature for 1 h.

The mixture was evaporated to dryness and the residue was suspended in water (2 mL) and basified to ~pH 10 using NaOH (1M). The aqueous mixture was evaporated to dryness under reduced pressure. The residue was suspended in MeCN (5 mL) and the precipitate formed was collected by vacuum filtration, washed with water (3 mL) and dried under vacuum to afford (133 mg, 83%) as a brown solid.

Method A: LC-MS (electrospray): m/z=348.0 (M+H)+, RT=0.69 min

Intermediate 17:
5-amino-6-bromo-pyridine-3-carbonitrile

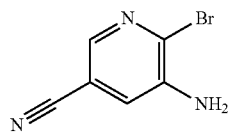

N-bromosuccinimide (3287 mg, 18.5 mmol) was added to a solution of 5-aminopyridine-3-carbonitrile (2000 mg, 16.8 mmol) in DMF-Anhydrous (20 mL) and the mixture was stirred at room temperature for 1 h. The mixture was diluted with water (100 mL) and extracted with EtOAc (100 mL). The organic phase was washed with water (100 mL) and brine (2×100 mL), dried over magnesium sulfate and evaporated to dryness. The crude material was purified by chromatography on SiO2 (eluting with 0-100% EtOAc in heptane) to afford the title compound (460 mg, 14%) as a yellow solid.

1H NMR (500 MHz, DMSO) δ 7.97 (d, J=2.1 Hz, 1H), 7.36 (d, J=2.1 Hz, 1H), 6.08 (s, 2H)

Intermediate 18: N-({2-formyl-1H-pyrrolo[3,2-c]pyridin-6-yl}methyl)-4-oxo-4H-pyrido[1,2-a]pyrimidine-2-carboxamide

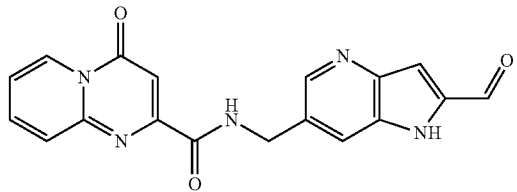 [SMILES: O=Cc1cc2ncc(CNC(=O)c3cc(=O)n4ccccc4n3)cc2[nH]1]

The title compound was prepared from Intermediate 17 in an analogous manner to Intermediate 16 to give (185 mg, 86%) as a light brown solid.

Method A: LC-MS (electrospray): m/z=348.0 (M+H)+, RT=0.76 min

Intermediate 19: tert-butyl 6-(bromomethyl)-2-[[tert-butoxycarbonyl(cyclobutylmethyl)amino]methyl]indole-1-carboxylate

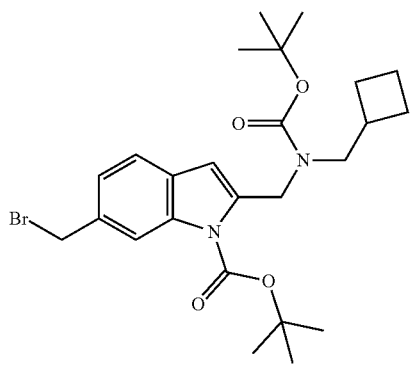 [SMILES: CC(C)(C)OC(=O)N(Cc1cc2ccc(CBr)cc2n1C(=O)OC(C)(C)C)CC1CCC1]

tert-butyl 2-[[tert-butoxycarbonyl(cyclobutylmethyl)amino]methyl]-6-(hydroxymethyl)indole-1-carboxylate Intermediate 7 Step 4 (1 g, 2.25 mmol) and tetrabromomethane (2.24 g, 6.75 mmol) were combined in THF (30 mL) and triphenylphosphine (1.77 g, 6.75 mmol) was added. Colour change to yellow-orange within 2 minutes, and formation of a precipitate was observed. The mixture was heated at 55° C. for 2 h. The mixture was cooled to room temperature filtered and the residue was washed with THF and the combined filtrates evaporated under vacuum. The residue was purified by chromatography on SiO2 (eluting with 0-100% TBME/heptane) to afford the title compound (452 mg, %) as a colourless residue.

Method A: LC-MS (electrospray): m/z=529.2/531.2 (M+H)+, RT=2.06 min

Intermediate 20: tert-butyl 4-bromoimidazole-1-carboxylate

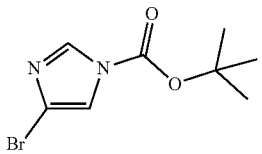

4-bromo-1H-imidazole (2 g, 13.3 mmol), DMAP (163 mg, 1.33 mmol) and Boc₂O (3.78 g, 17.3 mmol) were combined in THF (20 mL)—gas evolution noted—and the mixture was stirred at room temperature for 3 h. The mixture was evaporated under vacuum and the residue was purified by chromatography on SiO₂ (eluting with 0-100% EtOAc/heptane) to afford the title compound (3.04 g, 92%) as a colourless oil which solidified on standing to a white waxy solid.

Method B: LC-MS (electrospray): m/z=247.2/249.2 (M+H)⁺, RT=1.60 min

Intermediate 21: N-[(2-formyl-1H-indol-6-yl)methyl]-1H-pyrrolo[2,3-b]pyridine-5-carboxamide

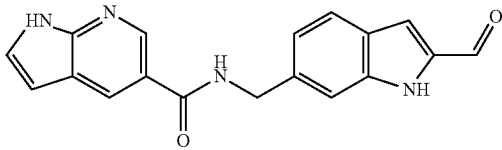 [SMILES: O=Cc1cc2ccc(CNC(=O)c3cnc4[nH]ccc4c3)cc2[nH]1]

The title compound was prepared from Example 2 Step 3 in a similar manner to that described for Example 2 Step 4 to give (445 mg, 56%) as a pale pink solid.

Method B: LC-MS (electrospray): m/z=319.2 (M+H)⁺, RT=1.32 min

Example 66: N-(cyclobutylmethyl)-1-[6-[[3-(1H-indazol-4-yl)-1,2,4-oxadiazol-5-yl]methyl]-1H-indol-2-yl]methanamine

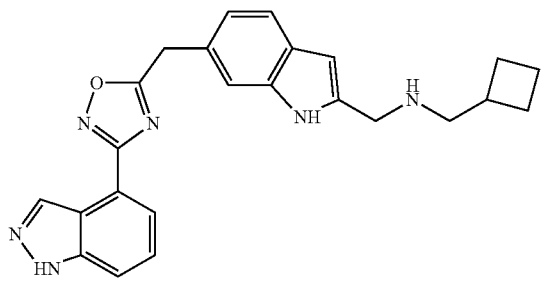 [SMILES: c1cc(-c2noc(Cc3ccc4cc(CNCC5CCC5)[nH]c4c3)n2)c2cn[nH]c2c1]

Step 1: 2-[2-[[tert-butoxycarbonyl(cyclobutylmethyl)amino]methyl]-1H-indol-6-yl]acetic acid

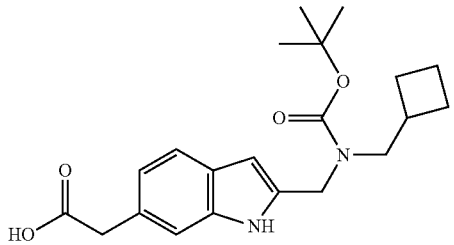 [SMILES: CC(C)(C)OC(=O)N(Cc1cc2ccc(CC(=O)O)cc2[nH]1)CC1CCC1]

The title compound (62 mg, 76%) was prepared in the same manner as Intermediate 11, using precursor from Intermediate 7 Step 3.

Method C: LC-MS (electrospray): m/z=373.2 (M+H)⁺, RT=3.86 min

Step 2: N-(cyclobutylmethyl)-1-[6-[[3-(1H-indazol-4-yl)-1,2,4-oxadiazol-5-yl]methyl]-1H-indol-2-yl]methanamine

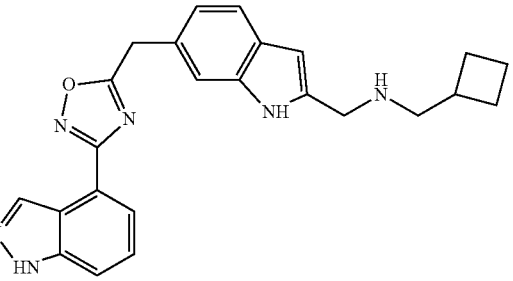

The title compound (7.6 mg, 14%) was prepared in the same manner as Example 64.

Method C: LC-MS (electrospray): m/z=413.4 (M+H)⁺, RT=3.71 min

Example 114: N-[(2-{[(1-methylcyclopentyl)amino]methyl}-1H-indol-6-yl)methyl]-4-oxo-4H-pyrido[1,2-a]pyrimidine-2-carboxamide

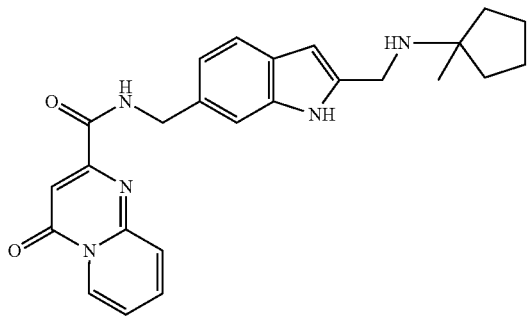 [SMILES: CC1(NCc2cc3ccc(CNC(=O)c4cc(=O)n5ccccc5n4)cc3[nH]2)CCCC1]

N-[(2-formyl-1H-indol-6-yl)methyl]-4-oxo-pyrido[1,2-a]pyrimidine-2-carboxamide (70 mg, 0.20 mmol), 1-methylcyclopentanamine hydrochloride (55 mg, 0.40 mmol) and triethylamine (83 µL, 0.61 mmol) were combined in 1,1,1,3,3,3-Hexafluoro-2-propanol (3 mL) and the mixture was stirred at room temperature for two days. NaBH₄ (76 mg, 2.02 mmol) was added with a few drops MeOH—gas evolution—and the mixture was stirred briefly. The mixture was quenched with MeOH—gas evolution—and evaporated under vacuum. The residue was suspended in NaHCO₃ (sat., 30 mL) and extracted with chloroform/isopropanol (3:1, 3×30 mL). The combined organic extracts were dried over Na₂SO₄ and evaporated under vacuum. The residue was purified by preparative HPLC (Method B) and the clean product-containing fractions combined and evaporated under vacuum to afford the title compound (50 mg, 57%) as a pale yellow solid.

Method C: LC-MS (electrospray): m/z=430.7 (M+H)⁺, RT=3.43 min

Example 115: N-{[2-(hydroxymethyl)-1H-indol-6-yl]methyl}-4-oxo-4H-pyrido[1,2-a]pyrimidine-2-carboxamide

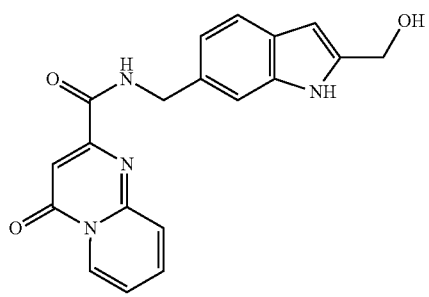 [SMILES: O=C(NCc1ccc2cc(CO)[nH]c2c1)c1cc(=O)n2ccccc2n1]

The title compound was isolated during the purification of Example 114 (18 mg, 25%) as an off-white solid.

Method C: LC-MS (electrospray): m/z=349.3 (M+H)⁺, RT=2.15 min

The compounds in Table 3 were prepared in the same manner as Example 114 using commercial amines or described intermediates.

TABLE 3

| Compound No | Name | Structure | LCMS method | LCMS Retention time | Mass Ion |
|---|---|---|---|---|---|
| 116 | N-[(2-{[(1-cyclobutylcyclopropyl)amino]methyl}-1H-indol-6-yl)methyl]-4-oxo-4H-pyrido[1,2-a]pyrimidine-2-carboxamide | 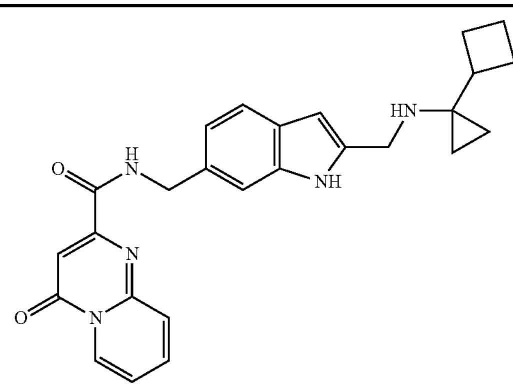 | C | 3.83 | 442.6 |
| 117 | N-{[2-({[(1-methylcyclobutyl)methyl]amino}methyl)-1H-indol-6-yl]methyl}-4-oxo-4H-pyrido[1,2-a]pyrimidine-2-carboxamide | 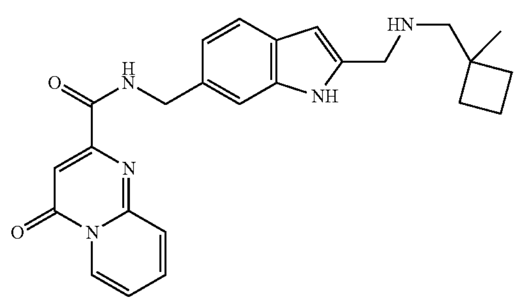 [SMILES: CC1(CNCc2cc3ccc(CNC(=O)c4cc(=O)n5ccccc5n4)cc3[nH]2)CCC1] | C | 3.46 | 430.6 |
| 118 | 4-oxo-N-[(2-{[({spiro[2.3]hexan-5-yl}methyl)amino]methyl}-1H-indol-6-yl)methyl]-4H-pyrido[1,2-a]pyrimidine-2-carboxamide | 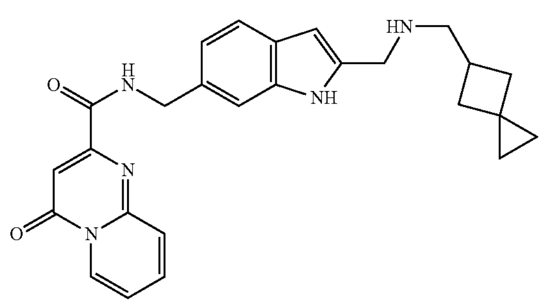 [SMILES: O=C(NCc1ccc2cc(CNCC3CC4(CC4)C3)[nH]c2c1)c1cc(=O)n2ccccc2n1] | C | 3.46 | 442.6 |

TABLE 3-continued

| Compound No | Name | Structure | LCMS method | LCMS Retention time | Mass Ion |
|---|---|---|---|---|---|
| 119 | N-({2-[({[3-(fluoromethyl)bicyclo[1.1.1]pentan-1-yl]methyl}amino)methyl]-1H-indol-6-yl}methyl)-4-oxo-4H-pyrido[1,2-a]pyrimidine-2-carboxamide | 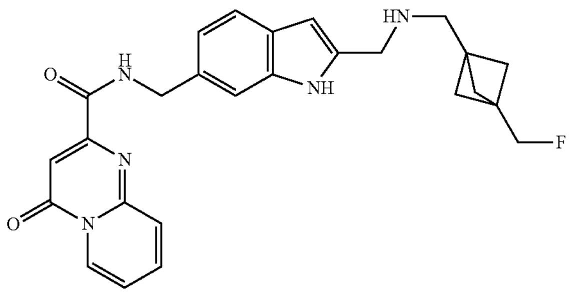 [SMILES: O=C(NCc1ccc2cc(CNCC34CC(CF)(C3)C4)[nH]c2c1)c1cc(=O)n2ccccc2n1] | C | 3.19 | 460.6 |
| 120 | N-[(2-{[(1-(3-fluorobicyclo[1.1.1]pentan-1-yl)ethyl)amino]methyl}-1H-indol-6-yl)methyl]-4-oxo-4H-pyrido[1,2-a]pyrimidine-2-carboxamide | 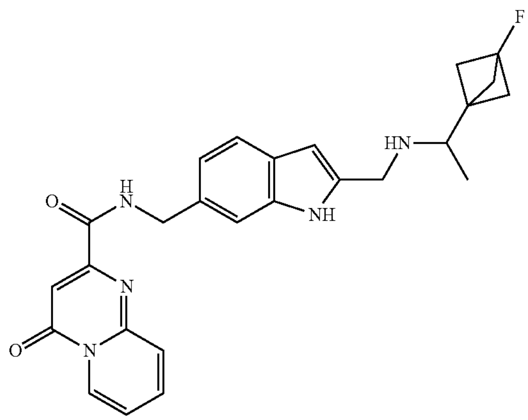 [SMILES: CC(NCc1cc2ccc(CNC(=O)c3cc(=O)n4ccccc4n3)cc2[nH]1)C12CC(F)(C1)C2] | C | 3.32 | 460.5 |

Example 121: N-({2-[(tert-butylamino)methyl]-1H-indol-6-yl}methyl)-4-oxo-4H-pyrido[1,2-a]pyrimidine-2-carboxamide

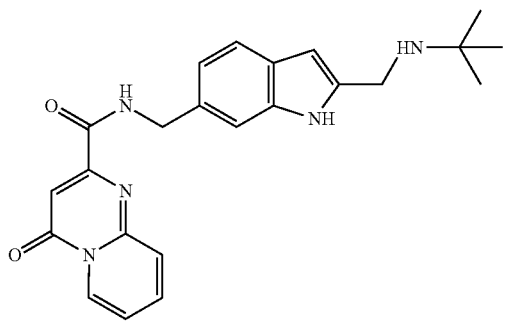 [SMILES: CC(C)(C)NCc1cc2ccc(CNC(=O)c3cc(=O)n4ccccc4n3)cc2[nH]1]

A suspension of tert butylamine (34 µL, 0.566 mmol) and N-[(2-formyl-1H-indol-6-yl)methyl]-4-oxo-pyrido[1,2-a]pyrimidine-2-carboxamide (100 mg, 0.28 mmol) in DCE (7 mL) was stirred at 60° C. for 65 h and left standing for a week. The mixture was diluted with ethanol (3 mL) and cautiously treated with NaBH$_4$ (32 mg, 0.85 mmol)—effervescence—and stirred for 16 h. The mixture was quenched with NaHCO$_3$ (sat., 5 mL) extracted with DCM (3×5 mL) and the extracts were concentrated under vacuum. The residue was purified by preparative HPLC (Method B) to give a pale gum which was triturated with MeCN to give an off-white solid 28 mg. The solid was recrystallized from MeCN, the solid was collected by filtration, washed with Et$_2$O and dried under vacuum oven to give the title compound (16 mg, 14%) as an off-white solid.

Method C: LC-MS (electrospray): m/z=404.5 (M+H)$^+$, RT=3.10 min

Example 123: N-{[2-(2-{2-azaspiro[3.3]heptanean-2-yl}ethyl)-1H-indol-6-yl]methyl}-4-oxo-4H-pyrido[1,2-a]pyrimidine-2-carboxamide

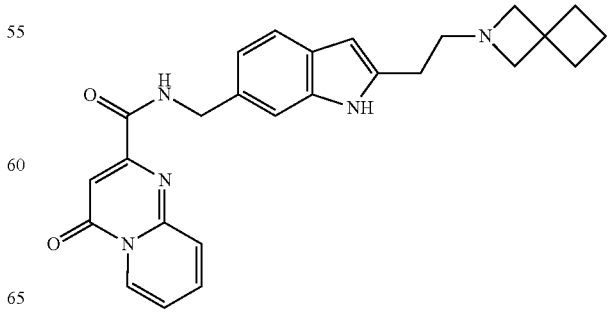

Step 1: N-(5-cyano-2-iodophenyl)-2,2,2-trifluoroacetamide

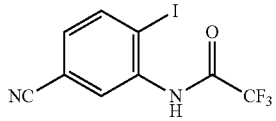 [SMILES: N#Cc1ccc(I)c(NC(=O)C(F)(F)F)c1]

3-amino-4-iodobenzonitrile (3.3 g, 13.52 mmol) was dissolved in DCM (40 mL) and trifluoroacetic anhydride (5.6 mL, 40.3 mmol) was added in a slow stream and the mixture was stirred at room temperature for 1 h. The mixture was evaporated directly onto silica. The solids were deposited on a short pad of silica (~5 cm diameter, 5 cm depth) and eluted with 0-100% DCM/heptane to afford the title compound (4.3 g, 93%) as a white solid.

Method B: LC-MS (electrospray): m/z=358.1 (M+H)$^+$, RT=0.98 min

Step 2: 2-(2-hydroxyethyl)-1H-indole-6-carbonitrile

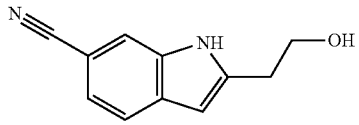 [SMILES: N#Cc1ccc2cc(CCO)[nH]c2c1]

N-(5-cyano-2-iodo-phenyl)-2,2,2-trifluoro-acetamide (4.3 g, 12.14 mmol), CuI (231 mg, 1.21 mmol) and PdCl$_2$(dppf) (888 mg, 1.21 mmol) were combined in triethylamine (30 mL) and the mixture was sparged with nitrogen for 5 minutes before but-3-yn-1-ol (1.84 mL, 24.3 mmol) was added, the mixture further sparged briefly and heated at 70° C. under nitrogen for 2 h. The mixture was cooled to room temperature, diluted with EtOAc (200 mL) and washed with NaHCO$_3$ (sat., 2×100 mL) and brine (100 mL). The organic phase was dried over Na$_2$SO$_4$ and evaporated under vacuum. The resultant residue was purified by chromatography on SiO$_2$ (eluting with 0-100% EtOAc/heptane) to afford the title compound (1.7 g, 74%) as a beige solid.

Method C: LC-MS (electrospray): m/z=187.1 (M+H)$^+$, RT=0.65 min

Step 3: 2-(6-cyano-1H-indol-2-yl)ethyl 4-methyl-benzene-1-sulfonate

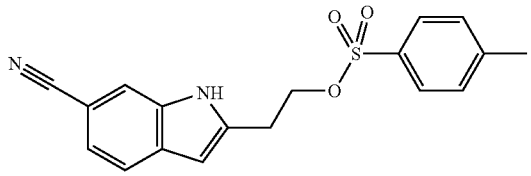 [SMILES: Cc1ccc(S(=O)(=O)OCCc2cc3ccc(C#N)cc3[nH]2)cc1]

4-Methylbenzenesulfonyl chloride (532 mg, 2.79 mmol) was added to a mixture of 2-(2-hydroxyethyl)-1H-indole-6-carbonitrile (400 mg, 2.15 mmol) and triethylamine (0.60 mL, 4.30 mmol) in DCM (26 mL) at 0° C. and the mixture was stirred at 0° C. for 20 minutes and at room temperature for 4 h. The mixture was retreated with 4-methylbenzenesulfonyl chloride (532 mg, 2.79 mmol) and was stirred at room temperature for 18 h. The mixture was concentrated under vacuum and the residue was purified by chromatography on SiO$_2$ to give the title compound (639 mg, 78%) as a yellow oil, which crystallised on standing to an off white solid.

Method A: LC-MS (electrospray): m/z=341.1 (M+H)$^+$, RT=1.24 min

Step 4: 2-[2-(2-azaspiro[3.3]heptanean-2-yl)ethyl]-1H-indole-6-carbonitrile

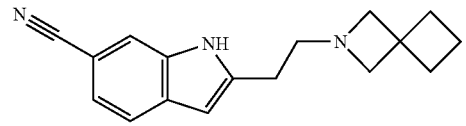 [SMILES: N#Cc1ccc2cc(CCN3CC4(CCC4)C3)[nH]c2c1]

2-(6-cyano-1H-indol-2-yl)ethyl 4-methylbenzenesulfonate (300 mg, 0.881 mmol), 2-azaspiro[3.3]heptane hydrochloride (0.37 mL, 1.32 mmol), sodium iodide (16 mg, 0.110 mmol) and N-ethyl-N-(propan-2-yl)propan-2-amine (0.31 mL, 1.76 mmol) were combined in DMSO (6.6 mL) and the mixture was stirred at 50° C. for 3 h. The mixture was cooled to room temperature, diluted with EtOAc (20 mL) and washed with NaHCO$_3$ (sat., 20 mL). A white insoluble solid was removed by filtration, the layers were separated, and the mixture was extracted with EtOAc (3×20 mL). The organics were washed with brine (50 mL), dried over MgSO$_4$, and concentrated under vacuum to a residue which was purified by chromatography on SiO$_2$ (eluting with 0-100% EtOAc/heptane then 0-20% MeOH/EtOAc) to give the title compound (62 mg, 19%) as an orange oil.

Method A: LC-MS (electrospray): m/z=266.3 (M+H)$^+$, RT=0.86 min

Step 5: [2-[2-(2-azaspiro[3.3]heptanean-2-yl)ethyl]-1H-indol-6-yl]methanamine

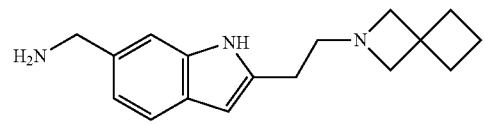 [SMILES: NCc1ccc2cc(CCN3CC4(CCC4)C3)[nH]c2c1]

A mixture of 2-[2-(2-azaspiro[3.3]heptanean-2-yl)ethyl]-1H-indole-6-carbonitrile (62 mg, 0.23 mmol) and ammonia in MeOH (7M, 0.61 mL, 4.29 mmol) in ethanol (2.4 mL) was degassed, a slurry of Raney-nickel (50%, 123 mg, 1.04 mmol) in H$_2$O was added, the mixture was degassed further and stirred under a hydrogen atmosphere for 4.5 h. The mixture was retreated with Raney-nickel (50%, 123 mg, 1.04 mmol) degassed and stirred under a hydrogen atmosphere for 16 h. The mixture was filtered through Celite, washing with MeOH (100 mL) and concentrated to give the title compound (44 mg, 50%) as a colourless oil.

Method J: LC-MS (electrospray): m/z=270.3 (M+H)$^+$, RT=0.69 min

Step 6: N-{[2-(2-{2-azaspiro[3.3]heptanean-2-yl}ethyl)-1H-indol-6-yl]methyl}-4-oxo-4H-pyrido[1,2-a]pyrimidine-2-carboxamide

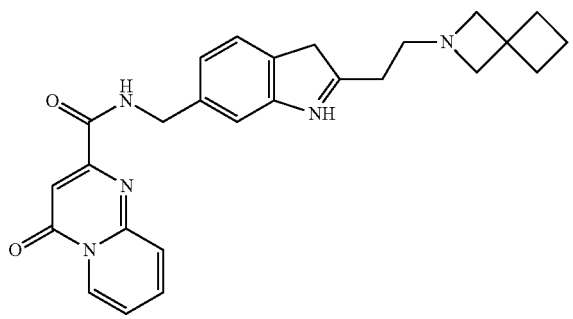 [SMILES: O=C(NCc1ccc2c(c1)N=C(CCN1CC3(CCC3)C1)C2)c1cc(=O)n2ccccc2n1]

HATU (85 mg, 0.223 mmol) was added to a mixture of 4-oxopyrido[1,2-a]pyrimidine-2-carboxylic acid Intermediate 1 (28 mg, 0.15 mmol) and DIPEA (0.13 mL, 0.74 mmol) in DMF (0.6 mL), and the mixture was stirred at room temperature for 10 minutes. [2-[2-(2-azaspiro[3.3]heptanean-2-yl)ethyl]-1H-indol-6-yl]methanamine (40 mg, 0.148 mmol) was added, and the mixture was stirred at room temperature for 90 minutes. The mixture was quenched with NaHCO$_3$ (sat., 50 mL) and extracted with EtOAc (3×50 mL). The combined organic phases were washed with water (50 mL) then brine (50 mL), dried (MgSO$_4$) and concentrated under vacuum. The crude material was purified by Preparative HPLC (Method B) to give the title product (4.1 mg, 6.1%) as an off white solid.

Method C: LC-MS (electrospray): m/z=442.7 (M+H)$^+$, RT=3.45 min

Example 124: ({3-fluorobicyclo[1.1.1]pentan-1-yl}methyl)({6-[(4-{imidazo[1,5-a]pyridin-8-yl}-1H-1,2,3-triazol-1-yl)methyl]-1H-indol-2-yl}methyl)amine

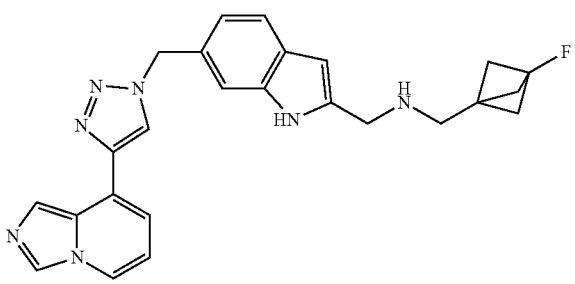 [SMILES: FC12CC(CNCc3cc4ccc(Cn5cc(-c6cccn7cncc67)nn5)cc4[nH]3)(C1)C2]

The title compound was prepared in an analogous manner to Example 63 using intermediates 14 and 15 giving (7 mg, 31%) as a brown solid.

Method E: LC-MS (electrospray): m/z=442.2 (M+H)$^+$, RT=1.36 min

Example 125: N-[(2-{[({3-fluorobicyclo[1.1.1]pentan-1-yl}methyl)amino]methyl}-1H-indol-6-yl)methyl]-5-oxo-5H-[1,3]thiazolo[3,2-a]pyrimidine-7-carboxamide

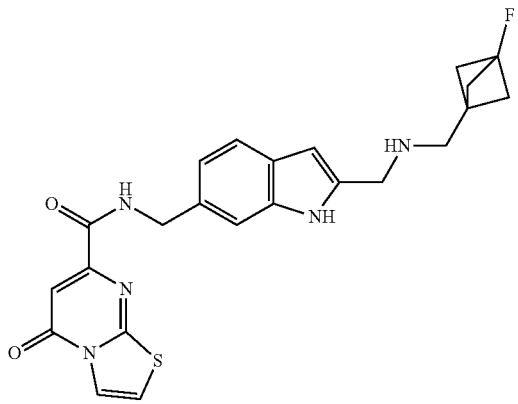 [SMILES: O=C(NCc1ccc2cc(CNCC34CC(F)(C3)C4)[nH]c2c1)c1cc(=O)n2ccsc2n1]

Step 1: tert-butyl N-{[2-(diethoxymethyl)-1H-indol-6-yl]methyl}carbamate

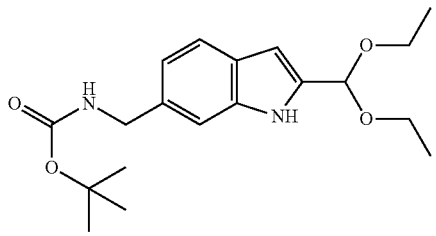 [SMILES: CCOC(OCC)c1cc2ccc(CNC(=O)OC(C)(C)C)cc2[nH]1]

2-(diethoxymethyl)-1H-indole-6-carbonitrile (Example 2 Step 3) (200 mg, 0.82 mmol), Boc anhydride (268 mg, 1.23 mmol) and NiCl$_2$ (11 mg, 0.08 mmol) were combined in MeOH (5 mL) and NaBH$_4$ (155 mg, 4.10 mmol) was added in three portions over 3 mins—strong gas evolution, black colour and the mixture was stirred at room temperature for 30 minutes. Further NaBH$_4$ (155 mg, 4.10 mmol) was added portionwise and the mixture was stirred for 1 h. The mixture was quenched with NaHCO$_3$ (sat., 20 mL) and extracted with DCM (3×30 mL). The combined organic extracts were dried over Na$_2$SO$_4$ and evaporated under vacuum. The residue was purified chromatography on SiO$_2$ (eluting with 0-100% EtOAc/heptane) to afford the title compound (135 mg, 43%) as a yellow residue.

Method J: LC-MS (electrospray): m/z=347.5 (M+H)$^+$, RT=0.87 min

Step 2: tert-butyl N-[(2-formyl-1H-indol-6-yl)methyl]carbamate

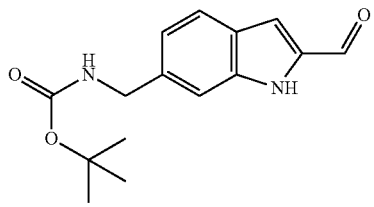 [SMILES: CC(C)(C)OC(=O)NCc1ccc2cc(C=O)[nH]c2c1]

Tert-butyl N-[[2-(diethoxymethyl)-1H-indol-6-yl]methyl]carbamate (135 mg, 0.39 mmol) was dissolved in THF (2 mL), water (2 mL) and acetic Acid (2 mL) and stirred at room temperature. The mixture was basified with NaHCO$_3$ (sat.) and extracted with DCM (3×30 mL). The combined organic extracts were dried over Na$_2$SO$_4$ and evaporated under vacuum. The residue was purified by chromatography on SiO$_2$ (eluting with 0-100% EtOAc/heptane) to afford the title compound (111 mg, 98%) as a white solid.

Method J: LC-MS (electrospray): m/z=273.4 (M−H)$^−$, RT=0.72 min

Step 3: tert-butyl N-[[2-[[(3-fluoro-1-bicyclo[1.1.1]pentanyl)methylamino]methyl]-1H-indol-6-yl]methyl]carbamate

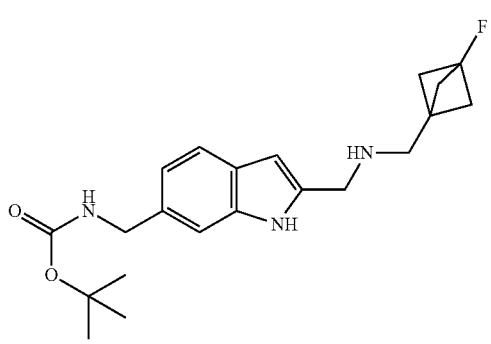 [SMILES: CC(C)(C)OC(=O)NCc1ccc2cc(CNCC34CC(F)(C3)C4)[nH]c2c1]

The title compound was prepared using the procedure described for Example 42 to give (92 mg, 67%) as a yellow residue.

Method A: LC-MS (electrospray): m/z=374.2 (M−H)$^−$, RT=0.93 min

Step 4: [2-[[(3-fluoro-1-bicyclo[1.1.1]pentanyl)methylamino]methyl]-1H-indol-6-yl]methanamine dihydrochloride

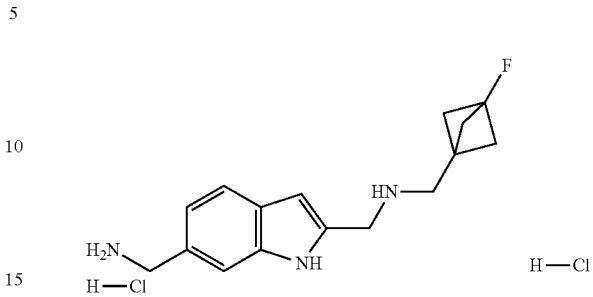

The title compound was prepared in a similar fashion to Example 44 Step 3 to give 90 mg (quant) as a pink solid.

Method A: LC-MS (electrospray): m/z=274.0 (M+H)$^+$, RT=0.21 min

Step 5: N-[(2-{[({3-fluorobicyclo[1.1.1]pentan-1-yl}methyl)amino]methyl}-1H-indol-6-yl)methyl]-5-oxo-5H-[1,3]thiazolo[3,2-a]pyrimidine-7-carboxamide

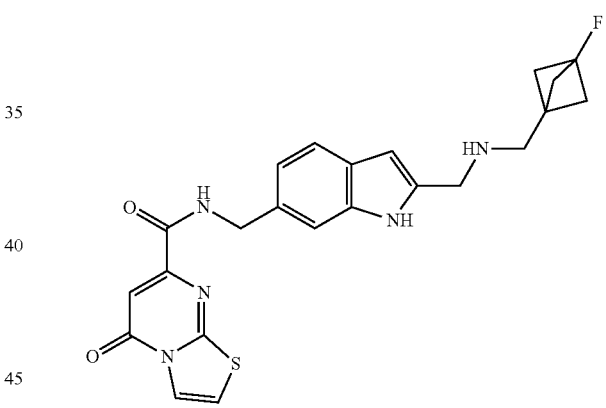

5-oxothiazolo[3,2-a]pyrimidine-7-carboxylic acid (56 mg, 0.28 mmol) was added to a stirred solution of DIPEA (136 µL, 0.8 mmol) and [2-[[(3-fluoro-1-bicyclo[1.1.1]pentanyl)methylamino]methyl]-1H-indol-6-yl]methanamine dihydrochloride (90 mg, 0.26 mmol) in DMF (2 mL) and the mixture was left to stir at room temperature for 10 mins. HATU (108 mg, 0.28 mmol) in DMF (2 mL) was added, and the mixture was stirred at room temperature for 2 h. The mixture was partitioned between NaHCO$_3$ (sat., 25 mL) and EtOAc (25 mL) and the layers separated. The pH of the aqueous layer was adjusted to pH 11 by addition of NaOH (1M) and the aqueous layer was extracted with EtOAc (3×25 mL). The combined organic layers were dried over Na$_2$SO$_4$ and concentrated under vacuum. The residue was purified by preparative HPLC (Method B) to give 11 mg of material. The product was further purified by basic preparative HPLC to give the title product (5.2 mg, 8.4%) as a white solid.

Method A LC-MS (electrospray): m/z=452.5 (M+H)$^+$, RT=3.00 min

Example 126: N-[(2-{[({bicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide

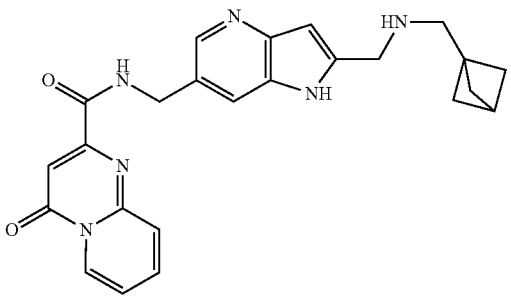

A mixture of N-[(2-formyl-1H-pyrrolo[3,2-b]pyridin-6-yl)methyl]-4-oxo-pyrido[1,2-a]pyrimidine-2-carboxamide (55 mg, 0.16 mmol), STAB (84 mg, 0.4 mmol) and bicyclo[1.1.1]pentan-1-ylmethanamine hydrochloride (23 mg, 0.17 mmol) in DCE (1.25 mL) was stirred at 50° C. for 1 h. The mixture was evaporated to dryness, dissolved in DMSO (1 mL), filtered and purified by preparative HPLC (Method B) to afford the title compound (24 mg, 35%) as a white solid.

Method C LC-MS (electrospray): m/z=429.4 (M+H)$^+$, RT=2.43 min

The compounds in Table 4 were prepared from either Intermediate 16 or Intermediate 18 in a similar manner to Example 126.

TABLE 4

| Compound No | Name | Structure | LCMS method | LCMS Retention time | Mass Ion |
|---|---|---|---|---|---|
| 127 | N-[(2-{[({3-fluorobicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide | 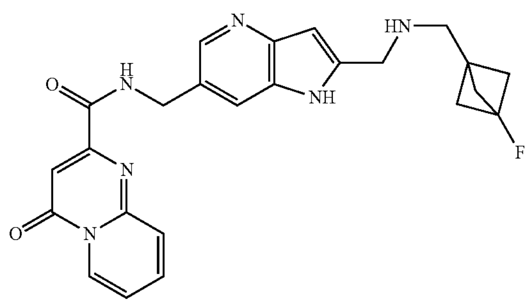 [SMILES: O=C(NCc1cnc2cc(CNCC34CC(F)(C3)C4)[nH]c2c1)c1cc(=O)n2ccccc2n1] | C | 2.27 | 447.4 |
| 129 | N-[(2-{[({3-methylbicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide | 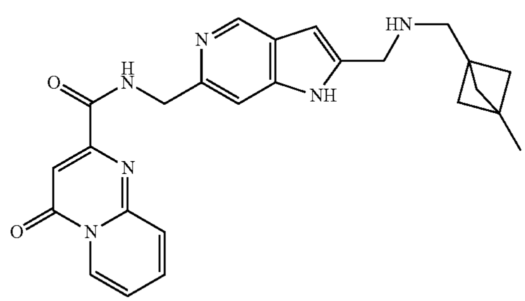 [SMILES: CC12CC(CNCc3cc4cnc(CNC(=O)c5cc(=O)n6ccccc6n5)cc4[nH]3)(C1)C2] | E | 1.08 | 443.3 |
| 130 | N-[(2-{[(cyclobutylmethyl)amino]methyl}-1H-pyrrolo[3,2-c]pyridin-6-yl)methyl]-4-oxo-4H-pyrido[1,2-a]pyrimidine-2-carboxamide | 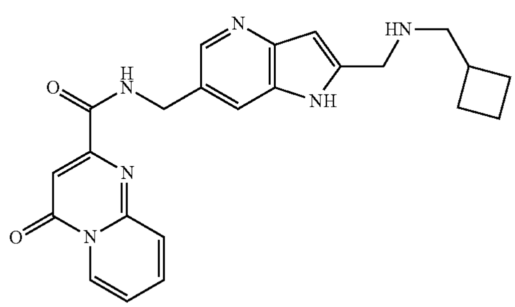 [SMILES: O=C(NCc1cnc2cc(CNCC3CCC3)[nH]c2c1)c1cc(=O)n2ccccc2n1] | C | 2.55 | 417.4 |

TABLE 4-continued

| Compound No | Name | Structure | LCMS method | LCMS Retention time | Mass Ion |
|---|---|---|---|---|---|
| 131 | N-[(2-{[({bicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide | 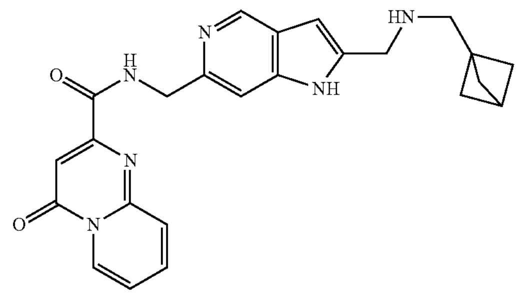 [SMILES: O=C(NCc1cc2[nH]c(CNCC34CC(C3)C4)cc2cn1)c1cc(=O)n2ccccc2n1] | C | 2.64 | 429.4 |
| 132 | N-[(2-{[({3-fluorobicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide | 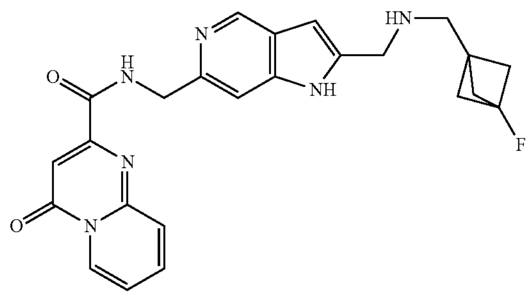 [SMILES: O=C(NCc1cc2[nH]c(CNCC34CC(F)(C3)C4)cc2cn1)c1cc(=O)n2ccccc2n1] | C | 2.48 | 447.5 |
| 145 | N-((2-((6-azaspiro[3.4]octan-6-yl)methyl)-1H-pyrrolo[3,2-c]pyridin-6-yl)methyl)-4-oxo-4H-pyrido[1,2-a]pyrimidine-2-carboxamide | 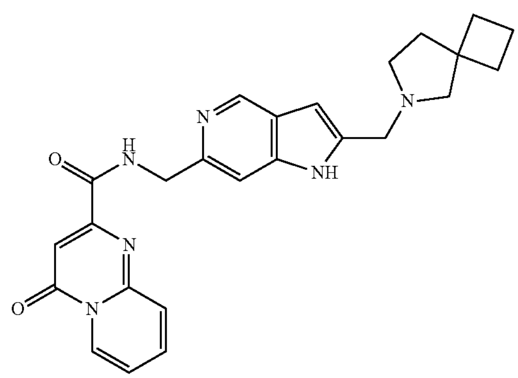 [SMILES: O=C(NCc1cc2[nH]c(CN3CCC4(CCC4)C3)cc2cn1)c1cc(=O)n2ccccc2n1] | C | 3.03 | 443.4 |

Example 133: N-[(2-{[(cyclobutylmethyl)amino]methyl}-1H-indol-6-yl)methyl]-4-oxo-4H,6H,7H,8H,9H-pyrido[1,2-a]pyrimidine-2-carboxamide

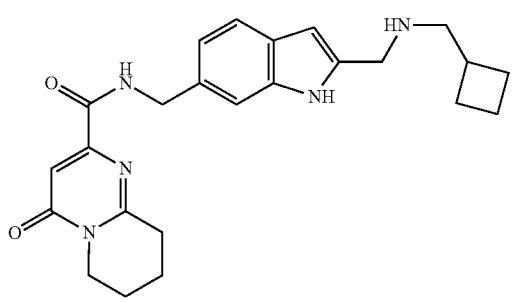 [SMILES: O=C(NCc1ccc2cc(CNCC3CCC3)[nH]c2c1)c1cc(=O)n2c(n1)CCCC2]

To a degassed solution of N-[[2-[(cyclobutylmethylamino)methyl]-1H-indol-6-yl]methyl]-4-oxo-pyrido[1,2-a]pyrimidine-2-carboxamide Example 2 (150 mg, 0.350 mmol) in ethanol (25 mL) was added Pd on C (10% Pd (50% wet) 200 mg, 0.188 mmol) at room temperature. The mixture was degassed again and stirred under an atmosphere of hydrogen for 6 h. The catalyst was removed by filtration (Celite) and washed with ethanol (approximately 20 mL). The filtrate was concentrated at reduced pressure to dryness to afford a yellow oil that was dissolved in MeOH (3 mL) and purified by preparative HPLC (Method B). The residue was dissolved in acetonitrile (2 mL) and water (2 mL) and lyophilsed to afford the title compound (85 mg, 57%) as pale yellow solid.

Method C LC-MS (electrospray): m/z=420.5 (M+H)$^+$, RT=3.17 min

Example 134: (cyclobutylmethyl)({6-[(4-{1H-pyr-rolo[2,3-b]pyridin-5-yl}-1H-imidazol-1-yl)methyl]-1H-indol-2-yl}methyl)amine

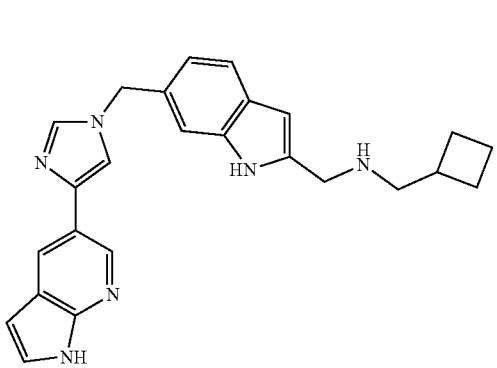 [SMILES: c1cc2cc(-c3cn(Cc4ccc5cc(CNCC6CCC6)[nH]c5c4)cn3)cnc2[nH]1]

Step 1: 1-(p-tolylsulfonyl)-5-(4,4,5,5-tetramethyl-1,3,2-dioxaborolan-2-yl)pyrrolo[2,3-b]pyridine

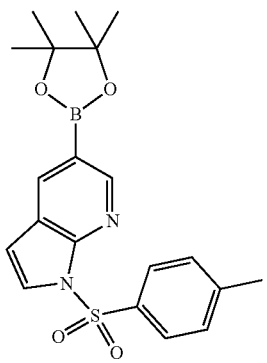 [SMILES: Cc1ccc(S(=O)(=O)n2ccc3cc(B4OC(C)(C)C(C)(C)O4)cnc32)cc1]

5-(4,4,5,5-tetramethyl-1,3,2-dioxaborolan-2-yl)-1H-pyrrolo[2,3-b]pyridine (500 mg, 2.05 mmol), DIPEA (714 µl, 4.10 mmol), DMAP (25 mg, 0.20 mmol) and TsCl (469 mg, 2.45 mmol) were combined in DCM (10 mL) and the mixture was stirred at room temperature for 20 h. The mixture was quenched with NaHCO₃ (sat., 20 mL) and the phases separated. The aqueous phase was extracted with DCM (2×20 mL) and the combined organic layers were dried over Na₂SO₄ and evaporated under vacuum. The residue was purified by chromatography on SiO₂ (eluting with 0-100% EtOAc/heptane) to afford the title compound (320 mg, 37%) as a white solid.

Method B LC-MS (electrospray): m/z=399.2 (M+H)⁺, RT=1.65 min

Step 2: 5-(1H-imidazol-4-yl)-1-(p-tolylsulfonyl)pyrrolo[2,3-b]pyridine

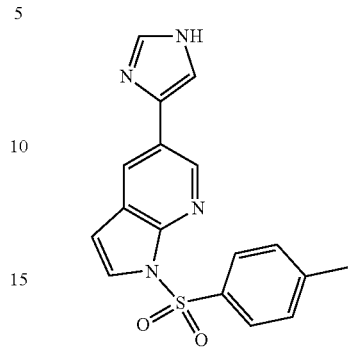

1-(p-tolylsulfonyl)-5-(4,4,5,5-tetramethyl-1,3,2-dioxaborolan-2-yl)pyrrolo[2,3-b]pyridine (320 mg, 0.76 mmol), tert-butyl 4-bromoimidazole-1-carboxylate Intermediate 20 (226 mg, 0.92 mmol) and K₂CO₃ (1.2M aqueous, 1.91 mL, 2.29 mmol) were combined in 1,4-Dioxane (5 mL) and the mixture sparged with nitrogen for 5 minutes. PdCl₂(dppf) (56 mg, 0.08 mmol) was added, the mixture further sparged briefly and the vessel sealed. The mixture was heated at 100° C. for 2 h. Further tert-butyl 4-bromoimidazole-1-carboxylate (120 mg, 0.49 mmol) was added and the heating was continued for 3 h. The mixture was cooled to room temperature, diluted with NaHCO₃ (sat., 30 mL) and extracted with DCM (2×30 mL) and chloroform/isopropanol (3:1, 2×30 mL). The combined organic extracts were dried over Na₂SO₄ and evaporated under vacuum. The residue was purified by chromatography on SiO₂ (kp-NH eluting with 0-100% EtOAc/heptane followed by 0-20% MeOH/EtOAc) to afford the title compound (163 mg, 57%) as a pale orange solid.

Method B LC-MS (electrospray): m/z=339.2 (M+H)⁺, RT=1.44 min

Step 3: tert-butyl 2-[[tert-butoxycarbonyl(cyclobutylmethyl)amino]methyl]-6-[[4-[1-(p-tolylsulfonyl)pyrrolo[2,3-b]pyridin-5-yl]imidazol-1-yl]methyl]indole-1-carboxylate

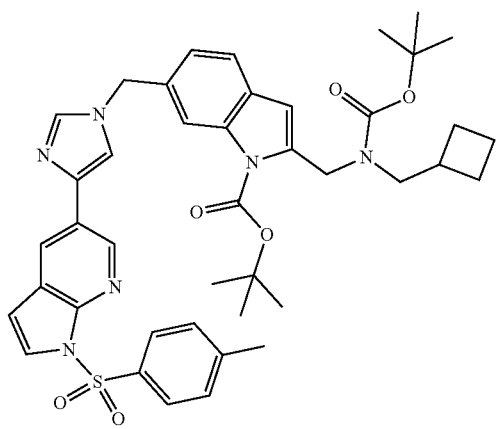 [SMILES: Cc1ccc(S(=O)(=O)n2ccc3cc(-c4cn(Cc5ccc6cc(CN(CC7CCC7)C(=O)OC(C)(C)C)n(C(=O)OC(C)(C)C)c6c5)cn4)cnc32)cc1]

5-(1H-imidazol-4-yl)-1-(p-tolylsulfonyl)pyrrolo[2,3-b]pyridine (162 mg, 0.48 mmol), tert-butyl 6-(bromomethyl)-

2-[[tert-butoxycarbonyl(cyclobutylmethyl)amino]methyl]indole-1-carboxylate Intermediate 19 (410 mg, 0.81 mmol), K$_2$CO$_3$ (199 mg, 1.4 mmol) and sodium iodide (7 mg, 0.05 mmol) were combined in DMF (8 mL) and the mixture was heated at 80° C. for 6 h. The mixture was cooled to room temperature and diluted with EtOAc (50 mL) and brine (50 mL). The phases were separated, and the organic phase washed with brine (4×50 mL). The organic layer was dried over Na$_2$SO$_4$ and evaporated under vacuum. The residue was purified by chromatography on SiO$_2$ (eluting with 0-100% EtOAc/heptane followed by 0-20% MeOH/EtOAc) to afford the title compound (128 mg, 26%) as a pale yellow solid.

Method M LC-MS (electrospray): m/z=765.35 (M+H)$^+$, RT=1.79 min

Step 4: (cyclobutylmethyl)({6-[(4-{1H-pyrrolo[2,3-b]pyridin-5-yl}-1H-imidazol-1-yl)methyl]-1H-indol-2-yl}methyl)amine

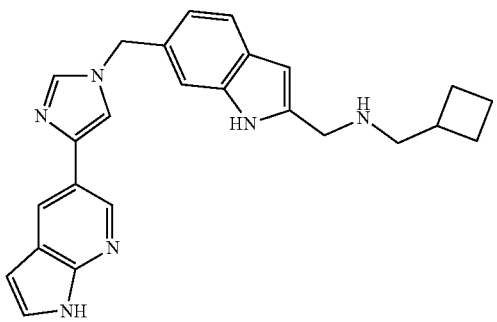 [SMILES: c1cc2cc(-c3cn(Cc4ccc5cc(CNCC6CCC6)[nH]c5c4)cn3)cnc2[nH]1]

tert-butyl 2-[[tert-butoxycarbonyl(cyclobutylmethyl)amino]methyl]-6-[[4-[1-(p-tolylsulfonyl)pyrrolo[2,3-b]pyridin-5-yl]imidazol-1-yl]methyl]indole-1-carboxylate (120 mg, 0.16 mmol) was dissolved in MeOH (5 mL) and NaOMe (90 mg, 1.67 mmol) was added. The vessel was sealed, and the mixture was heated at 90° C. for 2 h. The mixture was cooled to room temperature and HCl (4M in Dioxane, 5 mL) was added, and the mixture was stirred at room temperature for 4 h. The mixture was evaporated under vacuum. The residue was dissolved in MeOH and purified by Ion exchange (SCX-2 washing with MeOH and eluting with ammonia in MeoH). The basic eluent was evaporated under vacuum. The residue was purified by preparative HPLC (Method B) to afford the title compound (27 mg, 42%) as a pale-yellow solid.

Method D LC-MS (electrospray): m/z=411.2 (M+H)$^+$, RT=4.03 min

Example 135: (cyclobutylmethyl)({6-[(4-{imidazo[1,5-a]pyridin-8-yl}-1H-1,2,3-triazol-1-yl)methyl]-1H-indol-2-yl}methyl)amine

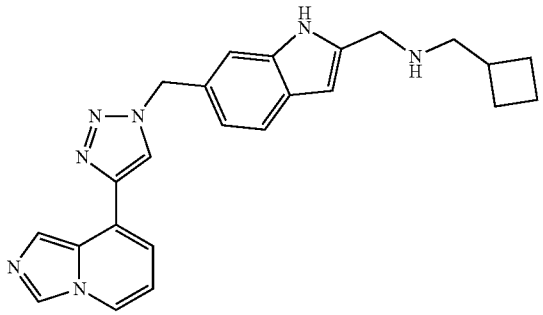 [SMILES: c1cc(-c2cn(Cc3ccc4cc(CNCC5CCC5)[nH]c4c3)nn2)c2cncn2c1]

The title compound was prepared in an analogous manner to Example 63 using intermediates 7 and 14 giving (192 mg, 74%) as a light yellow solid.

Method C: LC-MS (electrospray): m/z=412.4 (M+H)$^+$, RT=3.13 min

Example 136: N-[(2-{[(2,2-dimethylpropyl)amino]methyl}-1H-indol-6-yl)methyl]-1H-pyrrolo[2,3-b]pyridine-5-carboxamide

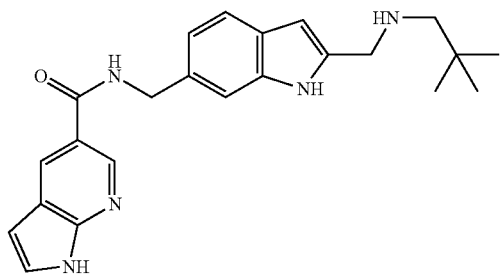 [SMILES: CC(C)(C)CNCc1cc2ccc(CNC(=O)c3cnc4[nH]ccc4c3)cc2[nH]1]

The title compound was prepared from Intermediate 21 using the procedure described for Example 2 Step 5 to give (30 mg, 23%) as an off-white solid.

Method C: LC-MS (electrospray): m/z=390.4 (M+H)$^+$, RT=3.16 min

Example 137: N-[(2-{[(cyclobutylmethyl)amino]methyl}-1H-indol-6-yl)methyl]-1H-pyrrolo[2,3-b]pyridine-5-carboxamide

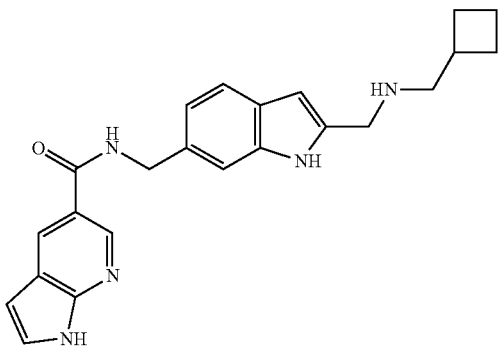 [SMILES: O=C(NCc1ccc2cc(CNCC3CCC3)[nH]c2c1)c1cnc2[nH]ccc2c1]

The title compound was prepared in the same manner as Example 136 to give (83 mg, 43%) as a white solid.
Method C: LC-MS (electrospray): m/z=388.4 (M+H)+, RT=2.95 min Example 138: (cyclobutylmethyl)({6-[(4-{1H-pyrrolo[2,3-b]pyridin-5-yl}-1H-1,2,3-triazol-1-yl)methyl]-1H-indol-2-yl}methyl)amine

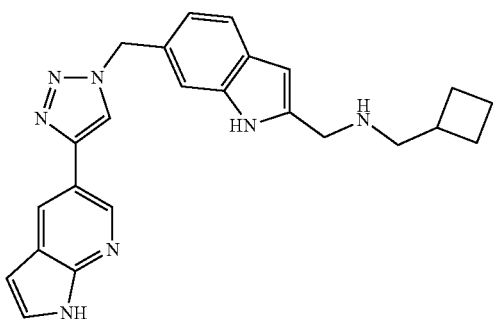 [SMILES: c1cc2cc(-c3cn(Cc4ccc5cc(CNCC6CCC6)[nH]c5c4)nn3)cnc2[nH]1]

Step 1: tert-butyl 2-[[tert-butoxycarbonyl(cyclobutylmethyl)amino]methyl]-6-[[4-(1H-pyrrolo[2,3-b]pyridin-5-yl)triazol-1-yl]methyl]indole-1-carboxylate

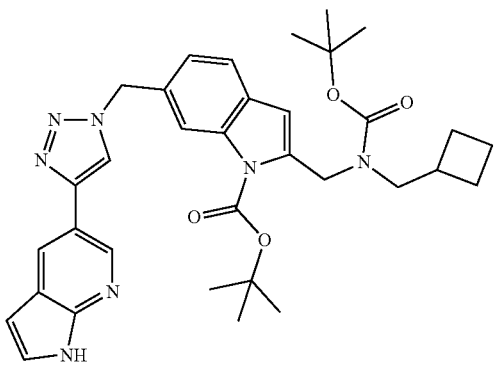 [SMILES: CC(C)(C)OC(=O)N(Cc1cc2ccc(Cn3cc(-c4cnc5[nH]ccc5c4)nn3)cc2n1C(=O)OC(C)(C)C)CC1CCC1]

Under a nitrogen atmosphere, 1H-pyrrolo[2,3-b]pyridine-5-carbaldehyde (60 mg, 0.411 mmol) was suspended in MeOH (dry, 1 mL) and THF (dry 1 mL), dimethyl (1-diazo-2-oxopropyl)phosphonate (0.12 mL, 0.821 mmol) and potassium carbonate (170 mg, 1.23 mmol) were added and the mixture was stirred at room for 3 h. Tert-Butyl 6-(azidomethyl)-2-[[tert-butoxycarbonyl(cyclobutylmethyl)amino]methyl]indole-1-carboxylate Intermediate 7 (193 mg, 0.411 mmol) and copper(1) iodide (16 mg, 0.0821 mmol) were added and the mixture was stirred at room temperature for 2 h. The mixture was diluted with water and extracted with DCM using a Telos phase separator. The organics were evaporated to dryness and purified by chromatography on SiO₂ (eluting with 0-60% EtOAc in heptane) to provide the title compound (90 mg, 36%) as a white solid.
Method B: LC-MS (electrospray): m/z=612.4 (M+H)+, RT=2.15 min Step 2: (cyclobutylmethyl)({6-[(4-{1H-pyrrolo[2,3-b]pyridin-5-yl}-1H-1,2,3-triazol-1-yl)methyl]-1H-indol-2-yl}methyl)amine

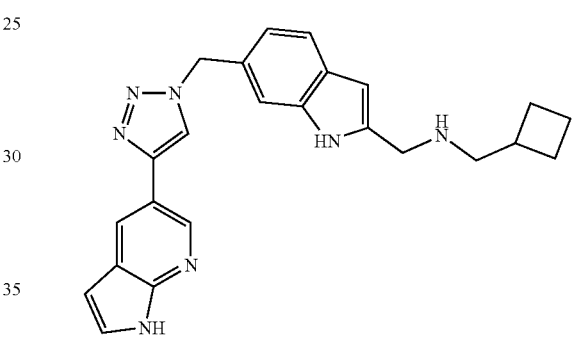

HCl in dioxane (4M in dioxane, 1 mL) was added to a solution of tert-butyl 2-[[tert-butoxycarbonyl(cyclobutylmethyl)amino]methyl]-6-[[4-(1H-pyrrolo[2,3-b]pyridin-5-yl)triazol-1-yl]methyl]indole-1-carboxylate (60 mg, 0.09 mmol) in MeOH (1 mL) and the mixture was stirred at 60° C. for 3 h. The mixture was evaporated to dryness and purified by preparative HPLC (Method B) to afford the title compound (19 mg, 44%) as a white solid.
Method C: LC-MS (electrospray): m/z=412.4 (M+H)+, RT=3.18 min Intermediate 22: 8-bromoimidazo[1,5-a]pyridine

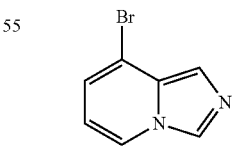

A mixture of formaldehyde (37%, 16 mL, 0.22 mol) and ammonium acetate (20.7 g, 0.27 mol) in acetic acid (100 mL) was stirred at room temperature for 10 minutes before 3-bromopyridine-2-carbaldehyde (5.0 g, 26.9 mmol) was added portionwise over 2 h and the mixture was stirred at room temperature for 3 h.

Intermediate 23: 8-ethynylimidazo[1,5-a]pyridine

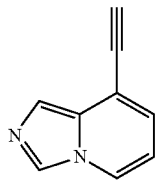

The title compound was prepared from Intermediate 22 using the procedures described in Example 63 steps 5 and 6 giving (1.29 g, 84%) as a brown solid.

Method C: LC-MS (electrospray): m/z=285.2 (2M+H)+, RT=2.01 min

Example 140: N-[(3-fluoro-1-bicyclo[1.1.1]pentanyl)methyl]-1-[6-[(4-imidazo[1,5-a]pyridin-8-yltriazol-1-yl)methyl]-1H-pyrrolo[3,2-c]pyridin-2-yl]methanamine

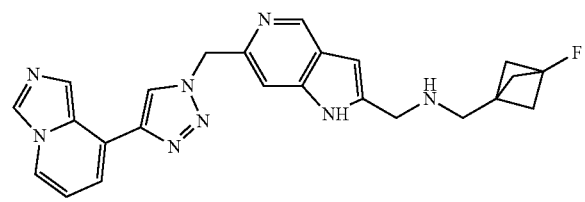 [SMILES: FC12CC(CNCc3cc4cnc(Cn5cc(-c6cccn7cncc67)nn5)cc4[nH]3)(C1)C2]

Step 1: 2-bromo-5-iodopyridin-4-amine

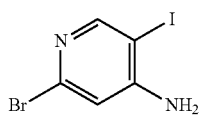

To a stirred solution of 2-bromopyridin-4-amine (25 g, 144.5 mmol) in acetonitrile (500 mL) was added N-iodosuccinimide (39.01 g, 173.4 mmol). The resulting reaction mixture was stirred at 80° C. for 16 h. The reaction was repeated in the same manner and combined for work up. The reaction was cooled to room temperature and concentrated under vacuum. The residue was dissolved in saturated solution of sodium thiosulfate (700 mL) and extracted with ethyl acetate (250 mL×3). The combined organic layers were dried over anhydrous $Na_2SO_4$ and concentrated under vacuum. The crude product was purified by chromatography on $SiO_2$ (eluting with 5% ethyl acetate in hexane) to afford the title compound (37 g 80%) as a yellow solid.

$^1$H NMR: (400 MHz, DMSO-d6) δ 8.16 (s, 1H), 6.77 (s, 1H), 6.50 (bs, 2H). LCMS: 3.709 min

Step 2: 2-bromo-5-(3,3-diethoxyprop-1-yn-1-yl)pyridin-4-amine

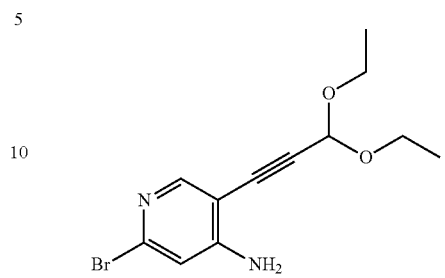

To a stirred solution of 2-bromo-5-iodopyridin-4-amine (18.5 g, 62.0 mmol) in THF (185 mL) were added triethyl amine (152.6 mL, 1086.4 mmol), triphenyl phosphine (0.32 g, 1.2 mmol) and $PdCl_2(PPh_3)_2$ (0.43 g, 0.62 mmol) at room temperature. The solution was de-gassed by bubbling nitrogen gas into the solution for 0.5 h. Then copper (1) iodide (0.23 g, 1.2 mmol) and 3,3-Diethoxyprop-1-yne (11.9 g, 93.1 mmol) were added and the reaction was stirred at 60° C. for 16 h. The reaction was repeated in the same manner and combined for work up. The reaction was cooled to room temperature and poured into saturated sodium bicarbonate (700 mL). The aqueous layer was extracted with ethyl acetate (250 mL×3). The combined organic layers were dried over anhydrous $Na_2SO_4$ and concentrated under vacuum. The crude product was purified by chromatography on $SiO_2$ (eluting with 12% ethyl acetate in hexane) to afford the title compound (33.5 g) as a brown solid.

$^1$H NMR: (400 MHz, $CDCl_3$) δ 8.14 (s, 1H), 6.78 (s, 1H), 5.52 (s, 1H), 4.82 (bs, 2H), 3.85-3.77 (m, 2H), 3.71-3.64 (m, 2H), 1.29 (t, J=6.8 Hz, 6H).

Step 3: 2-(dimethoxymethyl)-1H-pyrrolo[3,2-c]pyridine-6-carbaldehyde

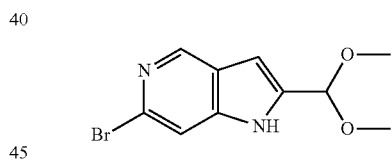

To a solution of 2-bromo-5-(3,3-diethoxyprop-1-yn-1-yl)pyridin-4-amine (16.5 g, 5.53 mmol) in NMP (165 mL) was added potassium tert-butoxide (12.42 g, 110.7 mmol). The reaction mixture was allowed to stir at 50° C. for 3 h. The reaction was repeated in the same manner and combined for work up. The reaction was cooled to room temperature and poured into cold water (500 mL). The aqueous layer was extracted with diethyl ether (250 mL×3). The combined organic layers were dried over anhydrous $Na_2SO_4$ and concentrated under vacuum to afford the title compound (35.0 g) as a yellow liquid.

$^1$H NMR: (400 MHz, $CDCl_3$) δ 8.78 (bs, 1H), 8.66 (s, 1H), 7.50 (s, 1H), 6.60 (s, 1H), 5.74 (s, 1H), 3.73-3.58 (m, 4H), 1.28 (t, J=7.2 Hz, 6H).

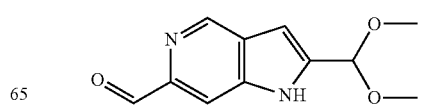

Sodium hydride (60%, 590 mg, 14.8 mmol) was added to an ice-cooled solution of 6-bromo-2-(dimethoxymethyl)-1H-pyrrolo[3,2-c]pyridine (1000 mg, 3.69 mmol) in THF-Anhydrous (32.5 mL) and the mixture was stirred under ice-cooling for 10 minutes. The mixture was cooled to −78° C. and t-BuLi (1.9M in pentane, 10 mL, 18.4 mmol) was added and the mixture was stirred at −78° C. for 1 h. Anhydrous DMF (1714 μL, 22.1 mmol) was added and the mixture was stirred at −78° C. for 45 minutes. The mixture was then quenched with saturated NH$_4$Cl (sat., 30 mL) and extracted with EtOAc (3×30 mL). The combined organic layers were washed with brine (2×40 mL), dried over MgSO$_4$, and concentrated under reduced pressure. The residue was purified by chromatography on SiO$_2$ (eluting with 20-100% EtOAc in heptane) to afford (650 mg, 78%) as a white solid.

Method C: LC-MS (electrospray): m/z=221.1 (M+H)+, RT=1.84 min

Step 4: tert-butyl 2-(dimethoxymethyl)-6-formyl-pyrrolo[3,2-c]pyridine-1-carboxylate

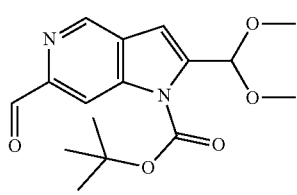 [SMILES: COC(OC)c1cc2cnc(C=O)cc2n1C(=O)OC(C)(C)C]

Boc anhydride (750 mg, 3.44 mmol) was added to a solution of 2-(dimethoxymethyl)-1H-pyrrolo[3,2-c]pyridine-6-carbaldehyde (650 mg, 2.86 mmol) and DMAP (70 mg, 0.573 mmol) in acetonitrile (21 mL) and the mixture was stirred at room temperature for 1 h. The mixture was evaporated to dryness, partitioned between NaHCO$_3$ (sat., 10 mL)/water (20 mL) and extracted with DCM (3×20 mL) using a Telos phase separator. The organics were evaporated to dryness and purified by chromatography on SiO$_2$ (eluting with 0-60% EtOAc in heptane) to afford (790 mg, 77%) as a colourless oil that solidified upon scratching to a white solid.

Method A: LC-MS (electrospray): m/z=321.0 (M+H)+, RT=1.14 min

Step 5: tert-butyl 2-(dimethoxymethyl)-6-(hydroxymethyl)pyrrolo[3,2-c]pyridine-1-carboxylate

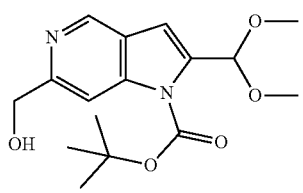 [SMILES: COC(OC)c1cc2cnc(CO)cc2n1C(=O)OC(C)(C)C]

NaBH$_4$ (71 mg, 1.87 mmol) was added to an ice-cooled solution of tert-butyl 2-(dimethoxymethyl)-6-formyl-pyrrolo[3,2-c]pyridine-1-carboxylate (500 mg, 1.56 mmol) in MeOH (16 mL) and the mixture was stirred for 15 minutes. The mixture was quenched with water (5 mL) and extracted with DCM (3×10 mL) using a Telos phase separator. The organic phase was evaporated to dryness to afford the title compound (380 mg, 73%) as a colourless oil that solidified upon scratching to a white solid.

Method A: LC-MS (electrospray): m/z=323.0 (M+H)+, RT=0.87 min

Step 6: tert-butyl 6-(azidomethyl)-2-(dimethoxymethyl)pyrrolo[3,2-c]pyridine-1-carboxylate

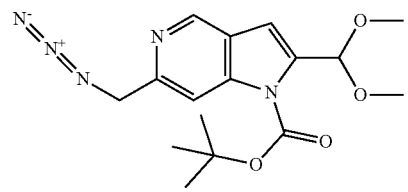 [SMILES: COC(OC)c1cc2cnc(CN=[N+]=[N-])cc2n1C(=O)OC(C)(C)C]

To a stirring solution of tert-butyl 2-(dimethoxymethyl)-6-(hydroxymethyl)pyrrolo[3,2-c]pyridine-1-carboxylate (390 mg, 1.14 mmol) and DBU (339 μL, 2.27 mmol) in DMF-Anhydrous (6.7 mL) under N$_2$ at 0° C. was added dropwise DPPA (489 μL, 2.27 mmol) and the mixture was stirred at room temperature for 72 h. The mixture was diluted with water (30 mL) and extracted with EtOAc (5×10 mL). The organics were washed with brine (10 mL), dried (MgSO$_4$) and concentrated to a pink oil. The crude was purified by chromatography on SiO$_2$ (eluting with 0%-100% EtOAc in heptane) to afford the title compound (394 mg, 99%) as a colourless oil.

Method J: LC-MS (electrospray): m/z=348.4 (M+H)+, RT=0.88 min

Step 7: 6-(azidomethyl)-1H-pyrrolo[3,2-c]pyridine-2-carbaldehyde

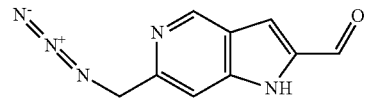 [SMILES: [N-]=[N+]=NCc1cc2[nH]c(C=O)cc2cn1]

A solution of tert-butyl 6-(azidomethyl)-2-(dimethoxymethyl)pyrrolo[3,2-c]pyridine-1-carboxylate (100 mg, 0.29 mmol) in THE (2 mL), water (2 mL) was stirred at room temperature.

Acetic acid (2 mL) was added and stirring was continued for a further 2 h. The mixture was then stirred at 50° C. for 16 h. The reaction was vigorously concentrated, and the residue was diluted with NaHCO$_3$ (sat., 15 mL) and extracted with IPA:CHCl$_3$ (1:3, 4×10 mL). The organics were dried (MgSO$_4$) and concentrated to give the title compound (94 mg, quant) as a beige solid.

Method J: LC-MS (electrospray): m/z=204.2 (M+H)+, RT=0.63 min

Step 8: 1-[6-(azidomethyl)-1H-pyrrolo[3,2-c]pyridin-2-yl]-N-[(3-fluoro-1-bicyclo[1.1.1]pentanyl)methyl]methanamine

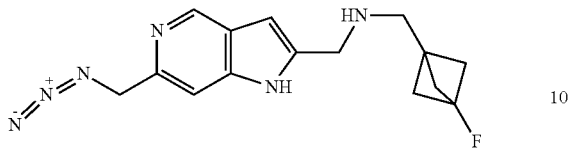

A solution of {3-fluorobicyclo[1.1.1]pentan-1-yl}methanamine hydrochloride (65 mg, 0.43 mmol), 6-(azidomethyl)-1H-pyrrolo[3,2-c]pyridine-2-carbaldehyde (94 mg, 0.29 mmol), STAB (362 mg, 1.71 mmol) and N-ethyl-N-isopropyl-propan-2-amine (0.15 mL, 0.86 mmol) in DCE (6 mL) under $N_2$ was stirred at 60° C. for 2 h. The mixture was diluted with $NaHCO_3$ (sat., 15 mL) and extracted with $IPA:CHCl_3$ (1:3, 5×5 mL). The organics were dried ($MgSO_4$) and concentrated to a yellow oil (0.3 g). The crude was purified by chromatography on $SiO_2$ (eluting with 15%-100% EtOAc in heptane then 0-12% MeOH in EtOAc) to afford the title compound (81 mg, 71%) as a colourless oil.

Method J: LC-MS (electrospray): m/z=301.3 (M+H)+, RT=0.63 min

Step 9: N-[(3-fluoro-1-bicyclo[1.1.1]pentanyl)methyl]-1-[6-[(4-imidazo[1,5-a]pyridin-8-yltriazol-1-yl)methyl]-1H-pyrrolo[3,2-c]pyridin-2-yl]methanamine

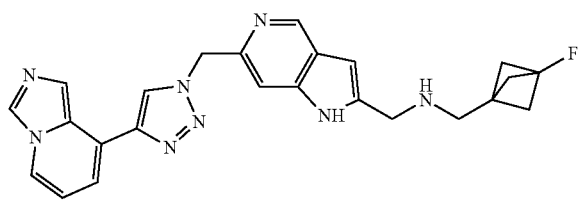 [SMILES: FC12CC(CNCc3cc4cnc(Cn5cc(-c6cccn7cncc67)nn5)cc4[nH]3)(C1)C2]

A solution of 1-[6-(azidomethyl)-1H-pyrrolo[3,2-c]pyridin-2-yl]-N-[(3-fluoro-1-bicyclo[1.1.1]pentanyl)methyl]methanamine (81 mg, 0.202 mmol) and 8-ethynylimidazo[1,5-a]pyridine Intermediate 23 (29 mg, 0.202 mmol) in DMF (1.7 mL) and water (0.6 mL) at room temperature was treated with sodium ascorbate (44 mg, 0.223 mmol) and $CuSO_4$ (7 mg, 0.041 mmol) and stirred at room temperature for 1 h. The mixture was concentrated and purified by preparative HPLC (Method B). The product containing fractions were concentrated gently to remove the MeCN and the remaining aqueous was extracted with $IPA:CHCl_3$ (1:3, 4×10 mL). The organics were dried ($MgSO_4$) and concentrated to a residue which was purified by acidic reverse-phase chromatography (Biotage Isolera Four; 6 g Sfar Duo C18-D; 10%-100% MeCN (0.1% formic acid) in water (0.1% formic acid)). The product fractions were basified using $NaHCO_3$ (sat, 5 mL) and concentrated to remove the MeCN, the remaining aqueous was extracted with IPA:$CHCl_3$ (1:4, 5×5 mL). The organics were dried ($MgSO_4$) and concentrated to give the title compound (11 mg, 12%) as an off-white solid.

Method C: LC-MS (electrospray): m/z=443.4 (M+H)+, RT=2.49 min

Intermediate 25: 4-azido-1-(oxan-2-yl)-1H-indazole

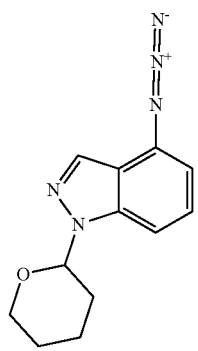 [SMILES: [N-]=[N+]=Nc1cccc2c1cnn2C1CCCCO1]

Step 1: 1H-indazol-4-amine

To a solution of 4-nitro-1H-indazole (50.0 g, 153.33 mmol) in MeOH (500 mL) was added Pd/C (50% wet) (10%, 5.00 g) at room temperature. The reaction mixture was placed under an atmosphere of hydrogen and stirred at room temperature for 5 h. The reaction mixture was filtered through celite pad and washed with additional MeOH (3×200 mL). The combined filtrate was concentrated under vacuum to afford the title compound (14.0 g, 34%).

Method G: LC-MS (electrospray): m/z=134.0 (M+H)+, RT=0.49 min

Step 2: 4-azido-1H-indazole

To a solution of 1H-indazol-4-amine (0.50 g, 3.14 mmol) in acetonitrile (5 mL) was added tert butyl nitrite (1.16 g, 12.57 mmol) followed by addition of sodium azide (0.97 g, 15.7 mmol) at 0° C. The resulting reaction mixture was stirred at 60° C. for 16 h. The reaction mixture was cooled to room temperature. This procedure was repeated five times and the combined reactions were poured into water (250 mL). The mixture was extracted with ethyl acetate (3×100 mL). The combined organic layers were dried (Na₂SO₄) and concentrated under vacuum. The crude material was purified by chromatography on SiO₂ (60-120) eluting with 15% EtOAc in hexane to afford the title compound (0.90 g, 25%). LCMS: 1.504 min, MS: ES+160.1 (M+1);

Method G: LC-MS (electrospray): m/z=160.1 (M+H)⁺, RT=1.50 min

Step 3: 4-azido-1-(tetrahydro-2H-pyran-2-yl)-1H-indazole

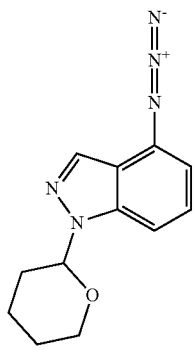 [SMILES: [N-]=[N+]=Nc1cccc2c1cnn2C1CCCCO1]

To a solution of 4-azido-1H-indazole (1.0 g, 6.3 mmol) in EtOAc (10 mL) was added dihydropyran (1.30 g, 15.5 mmol) followed by TFA (0.07 g, 0.63 mmol) at 0° C. and the resulting reaction mixture was stirred at 70° C. temperature for 4 h. The reaction mixture was allowed to cool to room temperature, poured into saturated NaHCO₃ (sat, 100 mL) and extracted with ethyl acetate (2×50 mL). The organic layer was dried (Na₂SO₄) and concentrated under vacuum. The crude material was purified by chromatography on SiO₂ (60-120) eluting with 8% EtOAc in hexane to afford the title compound (0.9 g, 59%).

Method G: LC-MS (electrospray): m/z=244.1 (M+H)⁺, RT=2.07 min

Intermediate 26: tert-butyl 2-(((tert-butoxycarbonyl)(cyclobutylmethyl)amino)methyl)-6-(prop-2-yn-1-yl)-1H-indole-1-carboxylate

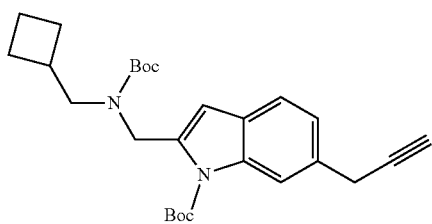 [SMILES: C#CCc1ccc2cc(CN(CC3CCC3)C(=O)OC(C)(C)C)n(C(=O)OC(C)(C)C)c2c1]

Step 1: 1-(6-bromo-1H-indol-2-yl)-N-(cyclobutylmethyl)methanamine

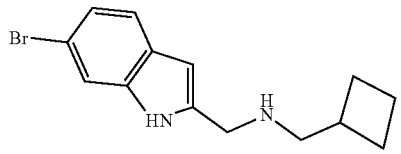 [SMILES: Brc1ccc2cc(CNCC3CCC3)[nH]c2c1]

To a stirred solution of 6-bromo-1H-indole-2-carbaldehyde (4.00 g, 17.80 mmol) and cyclobutylmethylamine (3.04 g, 35.70 mmol) in DCE/MeOH (200 mL, 4:1) was added sodium triacetoxy borohydride (11.32 g, 53.40 mmol) portionwise at 0° C. The resulting solution was then stirred at room temperature for 16 h. The reaction was repeated in the same manner and combined for work up. The reaction was poured into water (100 mL) and the aqueous layer was extracted with dichloromethane (70 mL×3). The combined organic layers were dried over anhydrous Na₂SO₄ and concentrated under vacuum. The crude product was purified by chromatography on SiO₂ (eluting with 2.2% MeOH in DCM) to afford the title compound (7.0 g).

¹H-NMR (400 MHz, DMSO-d₆) δ 11.12 (s, 1H), 7.49 (s, 1H), 7.39 (d, J=8.4 Hz, 1H), 7.05 (dd, J=8.4, 2.0 Hz, 1H), 6.28 (s, 1H), 3.79 (s, 2H), 2.45-2.37 (m, 1H), 2.02-1.94 (m, 2H), 1.91 (s, 2H), 1.86-1.75 (m, 2H), 1.68-1.58 (m, 2H).

Step 2: tert-butyl 6-bromo-2-(((tert-butoxycarbonyl)(cyclobutylmethyl)amino)methyl)-1H-indole-1-carboxylate

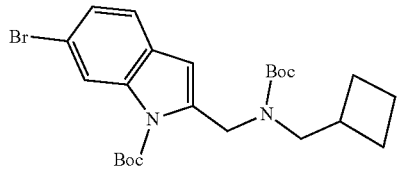 [SMILES: CC(C)(C)OC(=O)N(Cc1cc2ccc(Br)cc2n1C(=O)OC(C)(C)C)CC1CCC1]

To a stirred solution of 1-(6-bromo-1H-indol-2-yl)-N-(cyclobutylmethyl)methanamine (4.00 g, 13.60 mmol) in THF (50 mL) was added LiHMDS in (1M in THF, 41.00 mL, 41.00 mmol) followed by the addition of Boc-anhydride (11.87 g, 54.40 mmol) at room temperature. The mixture was heated at 70° C. for 16 h, cooled to room temperature and poured into water (100 mL). The aqueous layer was extracted with ethyl acetate (50 mL×3). The combined organic layers were dried over anhydrous Na₂SO₄ and concentrated under vacuum. The crude product was purified by chromatography on SiO₂ (eluting with 8% ethyl acetate in hexane) to afford the title compound (5.0 g, 30%).

Method LC04_ABF3: LC-MS (electrospray): m/z=493.6/495.6 (M+H)⁺, RT=2.81 min

MS (ESI-MS): m/z calcd for C₂₄H₃₃BrN₂O₄[MH]+ 492.16, found 493.63 & 495.63 [M+1 & M+3].

Step 3: tert-butyl 2-(((tert-butoxycarbonyl)(cyclobutylmethyl)amino)methyl)-6-(4,4,5,5-tetramethyl-1,3,2-dioxaborolan-2-yl)-1H-indole-1-carboxylate

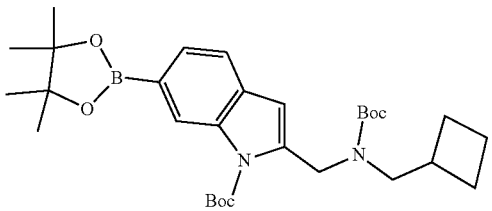 [SMILES: CC(C)(C)OC(=O)N(Cc1cc2ccc(B3OC(C)(C)C(C)(C)O3)cc2n1C(=O)OC(C)(C)C)CC1CCC1]

To a stirred solution of tert-butyl 6-bromo-2-(((tert-butoxycarbonyl)(cyclobutylmethyl)amino)methyl)-1H-indole-1-carboxylate (5.00 g, 10.16 mmol), in 1,4-dioxane (50 mL) were added potassium acetate (3.00 g, 30.40 mmol) and bispinacolatediborane (10.32 g, 40.60 mmol). The solution was de-gassed by bubbling nitrogen gas into the solution for 0.5 h and PdCl$_2$(dppf) (0.740 g, 1.01 mmol) was added at room temperature. The resulting reaction mixture was heated at 90° C. for 2 h, cooled to room temperature and poured into water (50 mL). The aqueous layer was extracted with ethyl acetate (50 mL×3). The combined organic layers were dried over anhydrous Na$_2$SO$_4$ and concentrated under vacuum. The crude product was purified by chromatography on SiO$_2$ (eluting with 10% ethyl acetate in hexane) to afford the title compound (5.0 g, 92%).

Method LC04-ABR2: LC-MS (electrospray): m/z=542.18 (M+H)$^+$, RT=3.42 min

MS (ESI-MS): m/z calcd for C$_{30}$H$_{45}$BN$_2$O$_6$[MH]+ 540.34, found 542.18 [M+1].

Step 4: tert-butyl 2-(((tert-butoxycarbonyl) (cyclobutylmethyl)amino)methyl)-6-(3-(trimethylsilyl)prop-2-yn-1-yl)-1H-indole-1-carboxylate

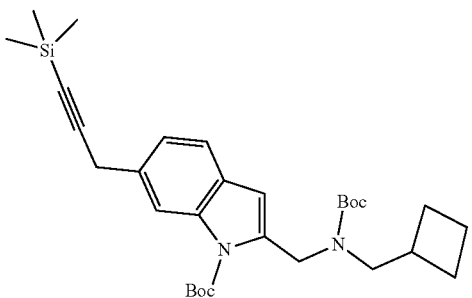 [SMILES: CC(C)(C)OC(=O)N(Cc1cc2ccc(CC#C[Si](C)(C)C)cc2n1C(=O)OC(C)(C)C)CC1CCC1]

To a stirred mixture of tert-butyl 2-(((tert-butoxycarbonyl)(cyclobutylmethyl)amino)methyl)-6-(4,4,5,5-tetramethyl-1,3,2-dioxaborolan-2-yl)-1H-indole-1-carboxylate (5.00 g, 9.25 mmol) in 1,4-dioxane (50 mL) & water (2.5 mL) were added potassium carbonate (3.84 g, 27.70 mmol) and 3-bromo-1-(trimethylsilyl)-1-propyne (5.30 g, 27.70 mmol). The solution was de-gassed by bubbling nitrogen gas into the solution for 0.5 h and PdCl$_2$(dppf) (0.680 g, 0.92 mmol) was added at room temperature. The reaction was heated at 80° C. for 5 h, cooled to room temperature and poured into water (50 mL). The aqueous layer was extracted with ethyl acetate (50 mL×3). The combined organic layers were dried over anhydrous Na$_2$SO$_4$, filtered and concentrated under vacuum. The crude product was purified by column chromatography on SiO$_2$ (eluting with 60% ethyl acetate in hexane) to afford the title compound (1.2 g, 24%).

1H NMR: (400 MHz, dmso-d$_6$) 8.10 (s, 1H), 7.49 (d, J=8.4 Hz, 1H), 7.13 (d, J=8.0 Hz, 1H), 6.26 (s, 1H), 4.66 (s, 2H), 3.81 (s, 2H), 1.99-1.90 (m, 2H), 1.82-1.76 (m, 2H), 1.70-1.66 (m, 10H), 1.47 (s, 9H), 0.16 (s, 9H).

Step 5: tert-butyl 2-(((tert-butoxycarbonyl)(cyclobutylmethyl)amino)methyl)-6-(prop-2-yn-1-yl)-1H-indole-1-carboxylate

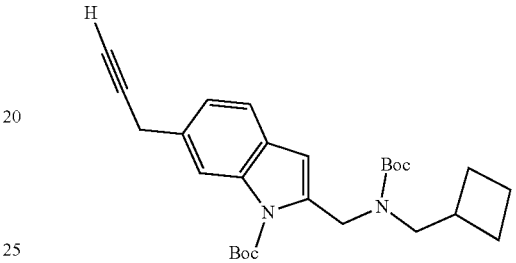

To a stirred solution of tert-butyl 2-(((tert-butoxycarbonyl)(cyclobutylmethyl)amino)methyl)-6-(3-(trimethylsilyl)prop-2-yn-1-yl)-1H-indole-1-carboxylate (3.00 g, 5.70 mmol) in THF (20 mL) was added TBAF (1M in THF, 5.70 mL, 5.70 mmol) at 0° C. The reaction was stirred at 0° C. for 30 min. before being poured into water (30 mL) and extracted with ethyl acetate (50 mL×3). The combined organic layers were dried over anhydrous Na$_2$SO$_4$ and concentrated under vacuum to afford the title compound (1.5 g, 57%).

Method LC03_ABR2: LC-MS (electrospray): m/z=493.6/495.6 (M+H)$^+$, RT=3.27 min

MS (ESI-MS): m/z calcd for C$_{27}$H$_{36}$N$_2$O$_4$[MH]+452.27, found 453.91 [M+1]. (LCMS: 90.21%, rt: 3.27 min).

Intermediate 27: tert-butyl 2-(tert-butoxycarbonyl)((3,3-difluorocyclobutyl) methyl) amino) methyl)-6-(prop-2-yn-1-yl)-1H-indole-1-carboxylate

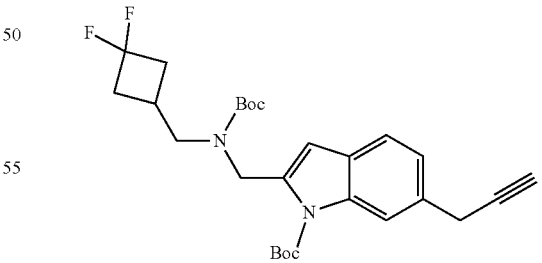

The title compound was prepared from 1-(3,3-difluorocyclobutyl)methanamine in the same manner as Intermediate 26 to afford the title compound (0.36 g, 69%).

$^1$H NMR: (DMSO-d$_6$, 400 MHz) δ 8.10 (s, 1H), 7.48 (d, J=7.6 Hz, 1H), 7.13 (d, J=7.6 Hz, 1H), 6.26 (s, 1H), 4.69 (br s, 2H), 3.75 (br s, 2H), 3.43 (d, J=6.4 Hz, 3H), 3.12 (d, J=2.0 Hz, 1H), 2.66-2.32 (m, 4H), 1.65 (s, 9H) 1.44 (s, 9H)

301
Intermediate 28

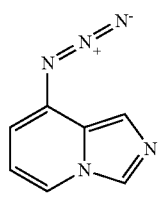

Step 1: tert-butyl (2-chloropyridin-3-yl) carbamate

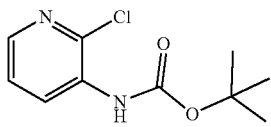

To a stirred solution of 2-chloropyridin-3-amine (10.00 g, 78.00 mmol) in DCM (50 mL) were added Et$_3$N (23.7 mL, 234.0 mmol), Boc anhydride (25.5 g, 117.0 mmol) and DMAP (0.95 g, 7.8 mmol) at room temperature. The resulting reaction mixture was stirred at room temperature for 16 h. The reaction mixture was poured in to water (100 mL) and the aqueous layer was extracted with dichloromethane (100 mL×3). The combined organic layers were dried over anhydrous Na$_2$SO$_4$ and concentrated under vacuum. The crude product was purified by chromatography on SiO$_2$ (eluting with 11% ethyl acetate in hexane) to afford the title compound (8.5 g, 47%).

MS (ESI-MS): m/z calcd for C$_{10}$H$_{13}$ClN$_2$O$_2$ [MH]+ 228.07, found 229.1 & 231.1 [M+1 & M+3].

Step 2: tert-butyl (2-cyanopyridin-3-yl)carbamate

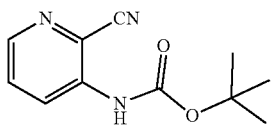 [SMILES: CC(C)(C)OC(=O)Nc1cccnc1C#N]

To a solution of tert-butyl (2-chloropyridin-3-yl)carbamate (8.50 g, 37.10 mmol) in DMF (50 mL) were added zinc dust (0.29 g, 4.40 mmol) and zinc cyanide (2.61 g, 22.20 mmol). The solution was de-gassed by bubbling nitrogen gas into the solution for 0.5 h followed by addition of PdCl$_2$ (dppf) (0.54 g, 0.74 mmol) and Pd$_2$(dba)$_3$ (0.34 g, 0.37 mmol). The resulting reaction mixture was stirred at 90° C. for 8 h. The reaction was then poured into ice-cold water (500 mL). The aqueous layer was extracted with ethyl acetate (100 mL×3). The combined organic layers were dried over anhydrous Na$_2$SO$_4$ and concentrated under vacuum. The crude product was purified by chromatography on SiO$_2$ (eluting with 15% ethyl acetate in hexane) to afford the title compound (4.5 g, 55%).

$^1$H-NMR (400 MHz, DMSO-d$_6$) δ 9.72 (s, 1H), 8.49 (dd, J=4.4, 1.2 Hz, 1H), 7.97 (dd, J=8.4, 1.2 Hz, 1H), 7.70 (dd, J=8.4, 4.4 Hz, 1H), 1.49 (s, 9H).

302
Step 3: tert-butyl (2-(aminomethyl)pyridin-3-yl)carbamate

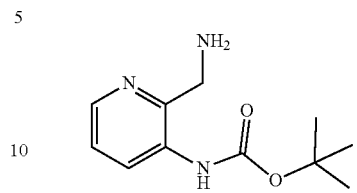

To a stirred solution of 1-(tert-butyl (2-cyanopyridin-3-yl) carbamate (3.80 g, 17.30 mmol) in ethyl acetate (100 mL) was added Raney nickel (0.76 mL, 20%). The reaction was stirred at room temperature for 6 h under hydrogen (40 bar). The mixture was then filtered through a Celite pad and the filtrate was concentrated under vacuum to afford the title compound (4.3 g).

MS (ESI-MS): m/z calcd for C$_{11}$H$_{17}$N$_3$O$_2$ [MH]+223.13, found 224.52 [M+1].

Step 4: tert-butyl (2-(formamidomethyl)pyridin-3-yl)carbamate

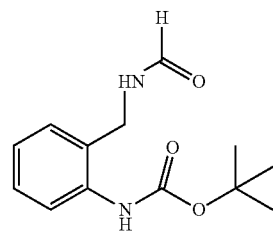 [SMILES: CC(C)(C)OC(=O)Nc1ccccc1CNC=O]

Tert-butyl (2-(aminomethyl) pyridin-3-yl) carbamate (4.30 g, 19.20 mmol) in ethyl formate (100 mL) was heated at 65° C. for 16 h. The reaction mixture was cooled to room temperature and concentrated under vacuum. The crude product was purified by chromatography on SiO$_2$ (eluting with 2.5% MeOH in DCM) to afford the title compound (2.80 g, 11.14 mmol).

$^1$H-NMR (400 MHz, DMSO-d$_6$) δ 9.13 (s, 1H), 8.65 (s, 1H), 8.29 (dd, J=4.8, 1.6 Hz, 1H), 8.10 (d, J=1.6 Hz, 1H), 7.87 (dd, J=7.6 Hz, 1H), 7.31 (q, J=8.0 Hz, 4.4 Hz, 1H), 4.38 (d, J=6.0 Hz, 2H), 1.47 (s, 9H).

Step 5: tert-butyl imidazo[1,5-a]pyridin-8-ylcarbamate

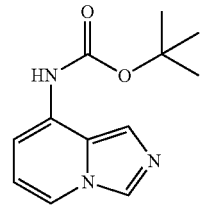 [SMILES: CC(C)(C)OC(=O)Nc1cccn2cncc12]

To a stirred solution of tert-butyl (2-(formamidomethyl) pyridin-3-yl) carbamate (2.80 g, 11.10 mmol) in DCM (50 mL) was added TEA (4.7 mL, 33.3 mmol) at room temperature. POCl$_3$ was then added drop wise at 0° C. The resulting reaction mixture was allowed to stir at 0° C. for 1 h before being poured into NaHCO$_3$ (sat., 50 mL). The aqueous layer was extracted with dichloromethane (250 mL×2). The combined organic layers were dried over anhydrous Na$_2$SO$_4$ and concentrated under vacuum to afford the title compound (3.5 g, 57%).

Step 6: imidazo[1,5-a]pyridin-8-amine hydrochloride

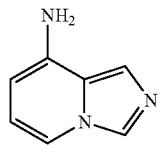

To a stirred solution of tert-butyl imidazo [1,5-a]pyridin-8-ylcarbamate (3.50 g, 15.00 mmol) in DCM (30 mL) was added HCl (4M in dioxane, 35 mL) at room temperature. The resulting reaction mixture was allowed to stir at room temperature for 2 h. The solution was then concentrated under vacuum to afford the title compound (4.00 g).

$^1$H-NMR (400 MHz, DMSO-d$_6$) δ 10.65 (s, 1H), 9.58 (s, 1H), 8.25 (s, 1H), 7.88 (d, J=6.8 Hz, 1H), 6.92 (t, J=7.2 Hz, 1H), 6.11 (d, J=7.6 Hz, 1H).

Step 7: 8-azidoimidazo [1,5-a]pyridine

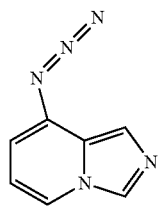

To a stirred solution of imidazo[1,5-a]pyridin-8-amine hydrochloride (0.50 g, 3.70 mmol) in acetonitrile (10 mL) was added t-butyl nitrite (1.2 g, 11.2 mmol) at 0° C. and stirring was continued for 5 min at 0° C. A solution of NaN$_3$ (0.96 g, 14.8 mmol) in water (0.5 mL) was added at 0° C. The reaction was then stirred at 0° C. for 1 h. The reaction was repeated in the same manner, combined and was poured into water (10 mL). The aqueous layer was extracted with ethyl acetate (30 mL×2). The combined organic layers were dried over Na$_2$SO$_4$ and concentrated under vacuum to afford the title compound (0.05 g, 10%).

$^1$H-NMR (400 MHz, DMSO-d$_6$) δ 8.46 (s, 1H), 8.21-8.19 (m, 1H), 7.38 (s, 1H), 6.71-6.65 (m, 2H).

Intermediate 29: 4-azidoisoquinoline

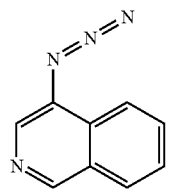

To a stirred solution of isoquinolin-4-amine (1.00 g, 6.90 mmol) in acetic acid (10 mL) was added NaNO$_2$ (0.96 g, 13.80 mmol) in water (3 mL). The addition was drop-wise at 0° C. after which the reaction was stirred for a further 15 minutes at 0° C. An additional aliquot of NaN$_3$ (0.90 g, 13.80 mmol) in water (3 mL) was added drop-wise at 0° C. The reaction was then stirred at room temperature for 2 h. before being poured into water (30 mL). The aqueous layer was extracted with ethyl acetate (30 mL×3). The organic layers were dried over Na$_2$SO$_4$ and concentrated under vacuum. The crude product was purified by chromatography on SiO$_2$ (eluting with 20% ethyl acetate in hexane) to afford the title compound (0.35 g, 30%).

$^1$H-NMR (400 MHz, DMSO-d$_6$) δ 9.16 (s, 1H), 8.56 (s, 1H), 8.17 (d, J=8.0 Hz, 1H), 8.01 (d, J=8.0 Hz, 1H), 7.85 (td, J=6.8, 1.2 Hz, 1H), 7.77 (td, J=8.0, 0.8 Hz, 1H).

Example 141: (cyclobutylmethyl)[(6-{[1-(1H-indazol-4-yl)-1H-1,2,3-triazol-4-yl]methyl}-1H-indol-2-yl)methyl]amine

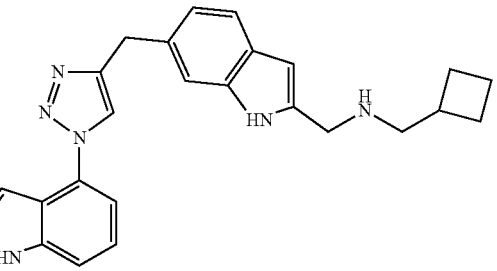

Step 1: tert-butyl 2-({[(tert-butoxy)carbonyl](cyclobutylmethyl)amino}methyl)-6-({1-[1-(oxan-2-yl)-1H-indazol-4-yl]-1H-1,2,3-triazol-4-yl}methyl)-1H-indole-1-carboxylate

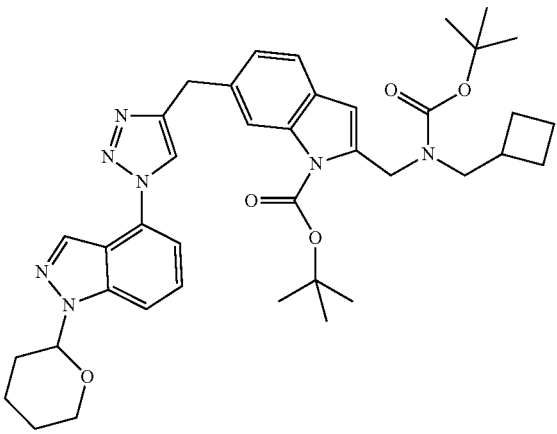 [SMILES: CC(C)(C)OC(=O)N(Cc1cc2ccc(Cc3cn(-c4cccc5c4cnn5C4CCCCO4)nn3)cc2n1C(=O)OC(C)(C)C)CC1CCC1]

A mixture of tert-butyl 2-(((tert-butoxycarbonyl)(cyclobutylmethyl)amino)methyl)-6-(prop-2-yn-1-yl)-1H-indole-1-carboxylate Intermediate 26 (0.200 g, 0.440 mmol), 4-azido-1-(oxan-2-yl)-1H-indazole Intermediate 25 (0.107 g, 0.440 mmol), sodium ascorbate (0.035 g, 0.176 mmol) and CuSO$_4$ (0.028 g, 0.176 mmol) in tert-butanol:water (1:1, 2 mL) was heated at 70° C. for 1 h. The reaction was cooled to room temperature and poured into water (150 mL). The aqueous layer was extracted with ethyl acetate (50 mL×3). The combined organic layers were dried over Na$_2$SO$_4$ and concentrated under vacuum. The crude product was purified by chromatography on SiO$_2$ (eluting with (34% ethyl acetate in hexane) to afford the title compound (0.150 g, 48%).

Method G: LC-MS (electrospray): m/z=696.8 (M+H)$^+$, RT=3.38 min

Step 2: (cyclobutylmethyl)[(6-{[1-(1H-indazol-4-yl)-1H-1,2,3-triazol-4-yl]methyl}-1H-indol-2-yl)methyl]amine

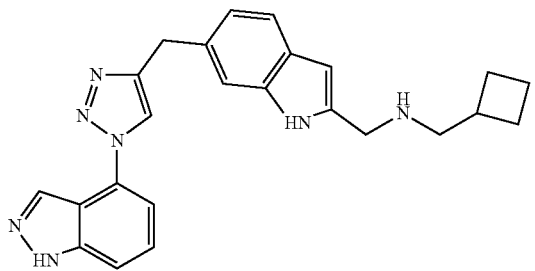 [SMILES: c1cc(-n2cc(Cc3ccc4cc(CNCC5CCC5)[nH]c4c3)nn2)c2cn[nH]c2c1]

To a stirred solution of 2-(((tert-butoxycarbonyl)(cyclobutylmethyl)amino)methyl)-6-((1-(1-(tetrahydro-2H-pyran-2-yl)-1H-indazol-4-yl)-1H-1,2,3-triazol-4-yl)methyl)-1H-indole-1-carboxylate (0.150 g, 0.21 mmol) in 1,4-dioxane (1.5 mL) was added HCl (4M in dioxane, 5.00 mL) drop-wise at room temperature. The resulting mixture was allowed to stir at room temperature for 16 h. The mixture was poured into Na$_2$CO$_3$ solution (sat., 100 mL) and extracted with ethyl acetate (3×30 mL). The combined organic layers were dried over Na$_2$SO$_4$ and concentrated under vacuum. The crude product was purified by chromatography on SiO$_2$ eluting with (6% MeOH in dichloromethane) to afford the title compound (0.015 g, 16%).

Method G: LC-MS (electrospray): m/z=412 (M+H)+, RT=1.34 min $^1$H NMR: (MeOD, 400 MHz) δ 8.46 (d, J=4.4 Hz, 2H), 7.67 (d, J=8.0 Hz, 1H), 7.56-7.49 (m, 3H), 7.40 (s, 1H), 7.11 (d, J=8.0 Hz, 1H), 6.61 (s, 1H), 4.31 (d, J=8.8 Hz, 4H), 3.08 (d, J=7.6 Hz, 2H), 2.72-2.66 (m, 1H), 2.21-2.14 (m, 2H), 2.04-1.81 (m, 4H)

The compounds in Table 5 were prepared from the appropriate intermediates in a similar manner to Example 141.

TABLE 5

| Compound No | Name | Structure | LCMS method | LCMS Retention time | Mass Ion |
|---|---|---|---|---|---|
| 142 | [(3,3-difluorocyclobutyl)methyl][(6-{[1-(1H-indazol-4-yl)-1H-1,2,3-triazol-4-yl]methyl}-1H-indol-2-yl)methyl]amine | 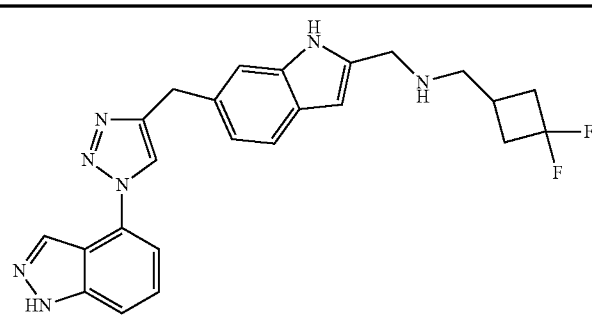 | G | 1.36 | 448.2 |
| 143 | (cyclobutylmethyl)[(6-{[1-(isoquinolin-4-yl)-1H-1,2,3-triazol-4-yl]methyl}-1H-indol-2-yl)methyl]amine | 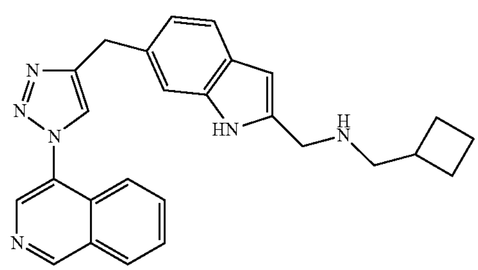 [SMILES: c1ccc2c(-n3cc(Cc4ccc5cc(CNCC6CCC6)[nH]c5c4)nn3)cncc2c1] | C | 3.53 | 423.4 |
| 144 | (cyclobutylmethyl)({6-[(1-{imidazo[1,5-a]pyridin-8-yl}-1H-1,2,3-triazol-4-yl)methyl]-1H-indol-2-yl}methyl)amine | 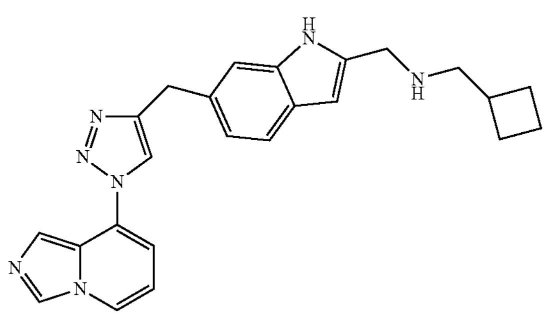 [SMILES: c1cc(-n2cc(Cc3ccc4cc(CNCC5CCC5)[nH]c4c3)nn2)c2cncn2c1] | C | 3.17 | 412.4 |

Intermediate 30: 3-ethynyl-5-methoxypyridine-2-carbonitrile

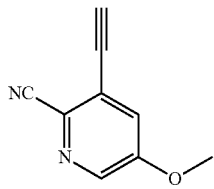

The title compound was prepared from 3-bromo-5-methoxy-pyridine-2-carbonitrile (Example 63 Step 1) using procedures similar to those described in Example 63 Steps 5 and 6 to provide the title compound (564 mg, 97%) as a beige solid.

Method A: LC-MS (electrospray): m/z=159.0 (M+H)⁺, RT=0.98 min

Intermediate 33: 3-ethynyl-5-fluoropyridine-2-carbonitrile

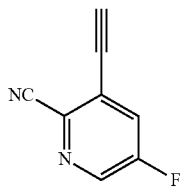

The title compound was prepared from 3-bromo-5-fluoropyridine-2-carbonitrile using procedures similar to those described in Example 63 Steps 5 and 6 to provide the title compound (306 mg, 97%) as a pale brown solid.

1H NMR (400 MHz, CDCl3) δ 8.54 (d, J=2.7 Hz, 1H), 7.62 (dd, J=7.9, 2.7 Hz, 1H), 3.70 (s, 1H).

Intermediate 34: 3-ethynyl-5-methoxypyridine

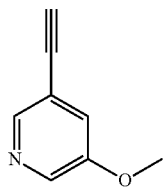

The title compound was prepared from 3-bromo-5-methoxypyridine using procedures similar to those described in Example 63 Steps 5 and 6 to provide the title compound (306 mg, 97%) as a brown solid.

Method A: LC-MS (electrospray): m/z=134.0 (M+H)⁺, RT=0.86 min

Intermediate 31: 6-(azidomethyl)-1H-indole-2-carbaldehyde

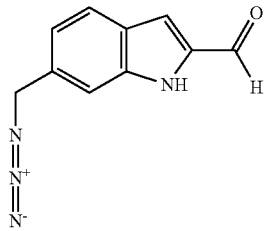 [SMILES: [N-]=[N+]=NCc1ccc2cc(C=O)[nH]c2c1]

Step 1: 6-bromo-2-(dimethoxymethyl)-1H-indole

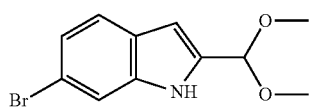

A suspension of 6-bromo-1H-indole-2-carbaldehyde (500 mg, 2.23 mmol) and trimethoxymethane (3.9 mL, 35.7 mmol) in methanol (1.5 mL) was treated with 4-methylbenzenesulfonic acid hydrate (4.2 mg, 0.02 mmol) and the mixture was stirred at room temperature for 30 minutes which resulted in formation of a black solution.

The mixture was diluted with NaHCO₃ (sat., 5 mL) and extracted with DCM (3×10 mL). The combined organics were washed with brine (10 mL), dried over magnesium sulfate and concentrated to give a brown oil which was purified by chromatography on SiO₂ (eluting with 0-100% EtOAc in heptane) to afford the title compound (570 mg, 91%) as an orange oil.

Method J: LC-MS (electrospray): m/z=268.2/270.2 (M+H)⁺, RT=0.81 min

Step 2: 2-(dimethoxymethyl)-1H-indole-6-carbaldehyde

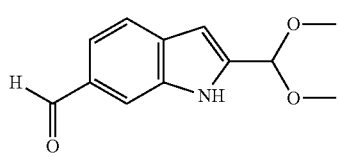 [SMILES: COC(OC)c1cc2ccc(C=O)cc2[nH]1]

Sodium hydride (60%, 397 mg, 9.92 mmol) was added to an ice-cooled solution of 6-bromo-2-(dimethoxymethyl)-1H-indole (670 mg, 2.48 mmol) in THF-Anhydrous (20 mL) and the mixture was stirred under ice-cooling for 10 minutes. The mixture was cooled to −78° C. and 2.5 M n-BuLi in hexanes (5.0 mL, 12.4 mmol) was added. The reaction mixture was stirred and allowed to warm slowly to −10° C. over 3 hours.

Anhydrous DMF (1.2 mL, 14.9 mmol) was added at −10° C. and the reaction mixture was stirred and allowed to warm to 0° C. over 30 minutes.

The mixture was then quenched with NH₄Cl (sat., 30 mL) and extracted with EtOAc (3×30 mL). The combined organic layers were washed with brine (2×40 mL), dried (MgSO₄) and concentrated under reduced pressure. The crude material was purified by chromatography on SiO₂ (eluting with 0-100% EtOAc in heptane) to afford the title compound (440 mg, 78%) as an off-white solid.

Method J: LC-MS (electrospray): m/z=220.2 (M+H)⁺, RT=0.62 min

Step 3: 6-(azidomethyl)-1H-indole-2-carbaldehyde

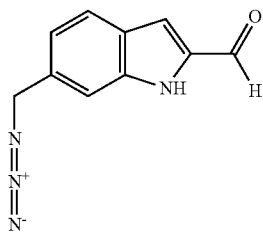 [SMILES: [N-]=[N+]=NCc1ccc2cc(C=O)[nH]c2c1]

The title compound was prepared from 2-(dimethoxymethyl)-1H-indole-6-carbaldehyde using procedures similar to those described in Example 140 Steps 4-7 to provide (155 mg, 70%) as an off-white solid.

Method J: LC-MS (electrospray): m/z=199.4 (M+H)⁺, RT=0.66 min

Intermediate 32: 3-[1-[(2-formyl-1H-indol-6-yl)methyl]triazol-4-yl]-5-methoxy-pyridine-2-carbonitrile

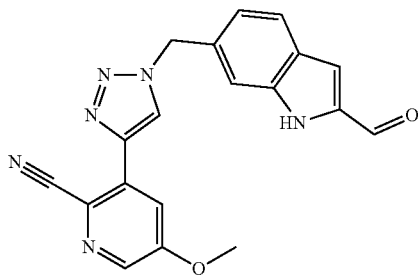 [SMILES: COc1cnc(C#N)c(-c2cn(Cc3ccc4cc(C=O)[nH]c4c3)nn2)c1]

The title compound was prepared from Intermediate 31 and intermediate 30 using the procedure described in Example 14 step 9 to give (588 mg, 78%) as a pale brown solid.

Method A: LC-MS (electrospray): m/z=359.0 (M+H)⁺, RT=1.07 min

Example 146: 3-[1-({2-[(4,4-Dimethyl-1-piperidyl)methyl]-1H-indol-6-yl}methyl)-1H-1,2,3-triazol-4-yl]-5-methoxy-2-pyridinecarbonitrile

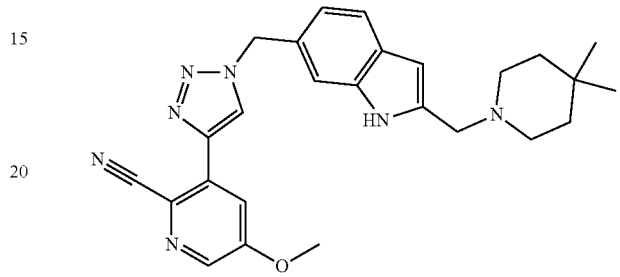

3-[1-[(2-formyl-1H-indol-6-yl)methyl]triazol-4-yl]-5-methoxy-pyridine-2-carbonitrile (Intermediate 32) (100 mg, 0.15 mmol), 4,4-dimethylpiperidine hydrochloride (65 mg, 0.44 mmol) and triethylamine (81 µl, 0.58 mmol) were combined in DCE (3 ml) and the mixture was heated at 70° C. for 10 minutes before sodium triacetoxyborohydride (154 mg, 0.73 mmol) was added—slight gas evolution—and the mixture was heated at 70° C. for 3 hours.

The mixture was cooled to room temperature, quenched with NaHCO₃(Aq) (sat., 20 ml) and extracted with chloroform/isopropanol (3:1, 3×30 ml) and the combined organic extracts were dried over sodium sulfate and evaporated under vacuum.

The residue was purified by reverse phase chromatography (30 g Sfar C18, eluting with acetonitrile+0.1% NH3/Water+0.1% NH3 10-100%) to afford the title compound (34 mg, 51%) as an off-white solid.

Method C: LC-MS (electrospray): m/z=456.4 (M+H), RT=4.14 min

TABLE 6

The compounds in Table 6 were prepared in the same fashion as Example XXX using the appropriate amine.

| Compound No | Name | Structure | LCMS method | LCMS Retention time | Mass Ion |
|---|---|---|---|---|---|
| 147 | 3-{(1-[(2-{(6-Aza-6-spiro[3.4]octyl)methyl}-1H-indol-6-yl)methyl]-1H-1,2,3-triazol-4-yl}-5-methoxy-2-pyridinecarbonitrile | 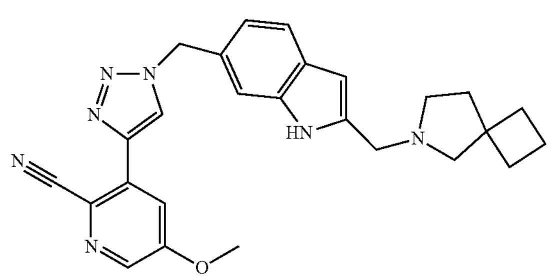 [SMILES: COc1cnc(C#N)c(-c2cn(Cc3ccc4cc(CN5CCC6(CCC6)C5)[nH]c4c3)nn2)c1] | C | 4.03 | 454.4 |

TABLE 6-continued

The compounds in Table 6 were prepared in the same fashion as Example XXX using the appropriate amine.

| Compound No | Name | Structure | LCMS method | LCMS Retention time | Mass Ion |
|---|---|---|---|---|---|
| 148 | 3-[1-(2-[({(Bicyclo[1.1.1]pent-1-yl)methyl}amino)methyl]-1H-indol-6-yl}methyl)-1H-1,2,3-triazol-4-yl]-5-methoxy-2-pyridinecarbonitrile | 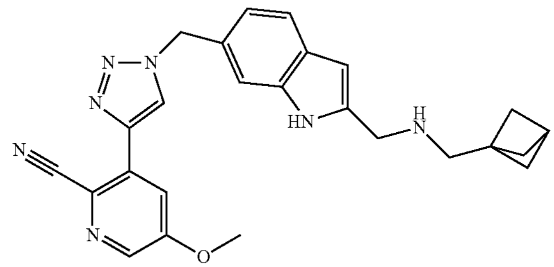 [SMILES: COc1cnc(C#N)c(-c2cn(Cc3ccc4cc(CNCC56CC(C5)C6)[nH]c4c3)nn2)c1] | C | 3.70 | 440.4 |
| 149 | 3-[1-({2-[({(3-Fluorobicyclo[1.1.1]pent-1-yl)methyl}amino)methyl]-1H-indol-6-yl}methyl)-1H-1,2,3-triazol-4-yl]-5-methoxy-2-pyridinecarbonitrile | 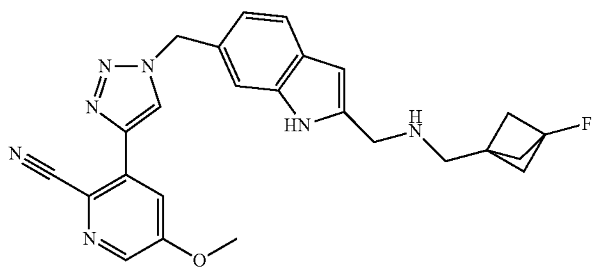 [SMILES: COc1cnc(C#N)c(-c2cn(Cc3ccc4cc(CNCC56CC(F)(C5)C6)[nH]c4c3)nn2)c1] | C | 3.45 | 458.5 |
| 150 | 5-Methoxy-3-[1-({2-[({(3-methylbicyclo[1.1.1]pent-1-yl)methyl}amino)methyl]-1H-indol-6-yl}methyl)-1H-1,2,3-triazol-4-yl]-2-pyridinecarbonitrile | 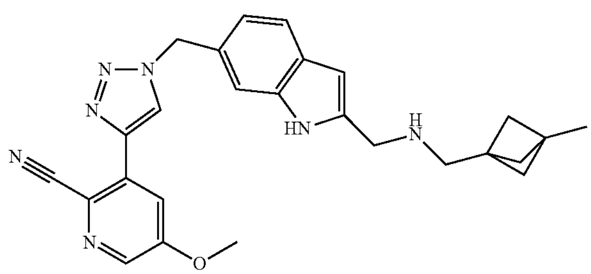 [SMILES: COc1cnc(C#N)c(-c2cn(Cc3ccc4cc(CNCC56CC(C)(C5)C6)[nH]c4c3)nn2)c1] | C | 3.90 | 454.6 |

Example 151: 3-{1-[(2-{[(Cyclobutylmethyl)amino]methyl}-1H-indol-6-yl)methyl]-1H-1,2,3-triazol-4-yl}-5-methoxy-2-pyridinecarbonitrile Example 152: 3-(1-((2-(((cyclobutylmethyl)amino)methyl)-1H-indol-6-yl)methyl)-1H-1,2,3-triazol-4-yl)-5-fluoropicolinonitrile

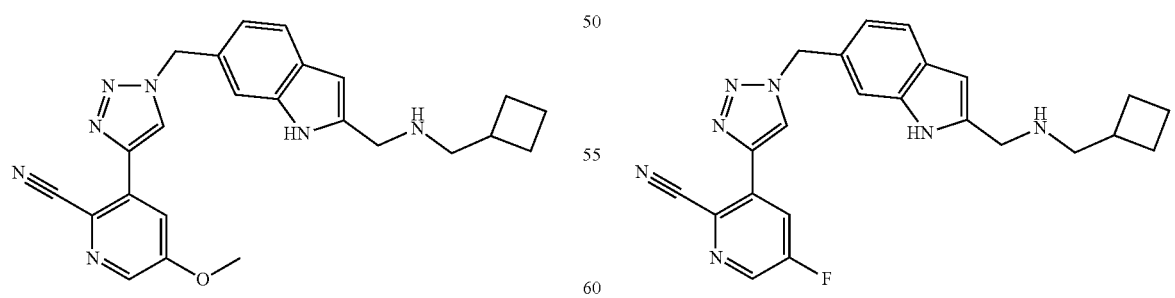

The title compound was prepared from Intermediate 7 and Intermediate 30 using the procedures described in Example 141 to give (146 mg, 67%) as a white solid.

Method C: LC-MS (electrospray): m/z=428.5 (M+H)$^+$, RT=3.54 min

The title compound was prepared from Intermediate 7 and Intermediate 33 using the procedures described in Example 141 to give (97 mg, 46%) as a white solid.

Method C: LC-MS (electrospray): m/z=416.4 (M+H)$^+$, RT=3.71 min

Example 153: 1-cyclobutyl-N-((6-((4-(5-methoxypyridin-3-yl)-1H-1,2,3-triazol-1-yl)methyl)-1H-indol-2-yl)methyl)methanamine

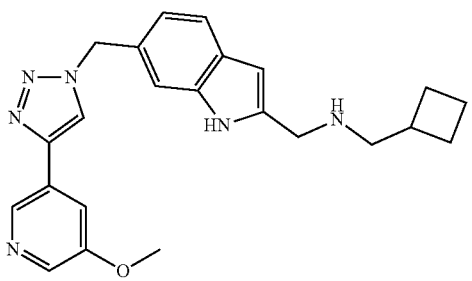 [SMILES: COc1cncc(-c2cn(Cc3ccc4cc(CNCC5CCC5)[nH]c4c3)nn2)c1]

The title compound was prepared from Intermediate 7 and Intermediate 34 using the procedures described in Example 141 to give (50 mg, 33%) as an off-white solid.

Method C: LC-MS (electrospray): m/z=403.4 (M+H)$^+$, RT=3.27 min

Example 154: 5-chloro-3-(1-((2-(((cyclobutylmethyl)amino)methyl)-1H-indol-6-yl)methyl)-1H-1,2,3-triazol-4-yl)picolinonitrile

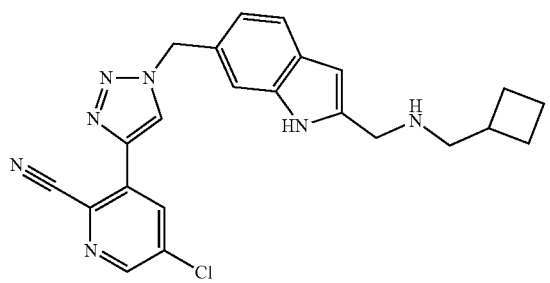 [SMILES: N#Cc1ncc(Cl)cc1-c1cn(Cc2ccc3cc(CNCC4CCC4)[nH]c3c2)nn1]

Step 1: tert-butyl 2-[[tert-butoxycarbonyl(cyclobutylmethyl)amino]methyl]-6-[[4-(6-methyl-4,8-dioxo-1,3,6,2-dioxazaborocan-2-yl)triazol-1-yl]methyl]indole-1-carboxylate

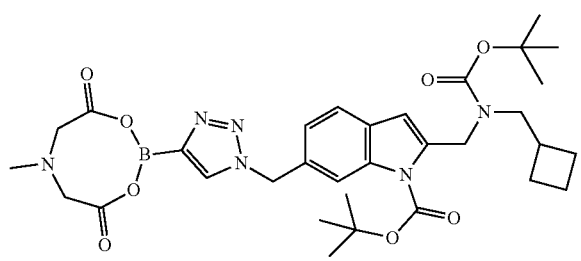 [SMILES: CN1CC(=O)OB(c2cn(Cc3ccc4cc(CN(CC5CCC5)C(=O)OC(C)(C)C)n(C(=O)OC(C)(C)C)c4c3)nn2)OC(=O)C1]

A mixture of ethynylboronic acid MIDA ester (77 mg, 0.426 mmol), tert-butyl 6-(azidomethyl)-2-[[tert-butoxycarbonyl(cyclobutylmethyl)amino]methyl]indole-1-carboxylate Intermediate 7 (200 mg, 0.426 mmol) and Cu(OAc)$_2$·H$_2$O (8.5 mg, 0.04 mmol) was diluted with acetonitrile (4 mL) and heated at 60° C. for 18 hours.

The blue suspension was evaporated under vacuum (blast shield) and the residue was purified by chromatography on SiO$_2$ (eluting with 40-100% EtOAc in heptane followed by 10% MeOH in EtOAc) to give the title compound (204 mg, 53%) as a white foam.

Method J: LC-MS (electrospray): m/z=651.6 (M+H)$^+$, RT=0.99 min

Step 2: tert-butyl 2-[[tert-butoxycarbonyl(cyclobutylmethyl)amino]methyl]-6-[[4-(5-chloro-2-cyano-3-pyridyl)triazol-1-yl]methyl]indole-1-carboxylate

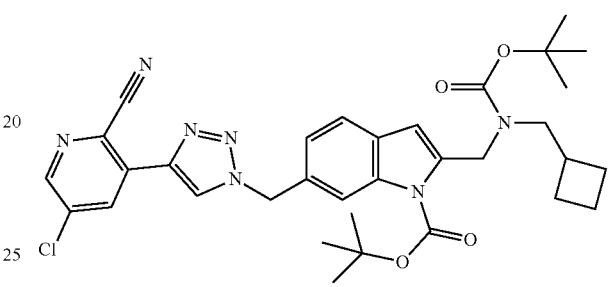

A microwave vial containing tert-butyl 2-[[tert-butoxycarbonyl(cyclobutylmethyl)amino]methyl]-6-[[4-(6-methyl-4,8-dioxo-1,3,6,2-dioxazaborocan-2-yl)triazol-1-yl]methyl]indole-1-carboxylate (100 mg, 0.111 mmol), 3-bromo-5-chloropyridine-2-carbonitrile (30 mg, 0.138 mmol), K$_2$CO$_3$ (107 mg, 0.78 mmol), Cu(OAc)$_2$·H$_2$O (11 mg, 0.0553 mmol) and Palladium-Xphos G2 (4.4 mg, 5.53 µmol) was sealed, diluted with MeCN (2 mL) and IPA (0.5 mL) and heated under microwave irradiation at 120° C. for 2×20 minutes.

The mixture diluted with DCM and a little water to dissolve the few solids and concentrated under vacuum. The residue was diluted with water and extracted with DCM. The extracts were evaporated under vacuum to a brown gum which was purified by chromatography on SiO$_2$ (eluting with EtOAc) to give the desired product (contaminated with ~20% of de-chlorinated side product) (33 mg, 47%) as a clear gum.

Method J: LC-MS (electrospray): m/z=632.6 (M+H)$^+$, RT=1.19 min

Step 3: 5-chloro-3-(1-((2-(((cyclobutylmethyl)amino)methyl)-1H-indol-6-yl)methyl)-1H-1,2,3-triazol-4-yl)picolinonitrile

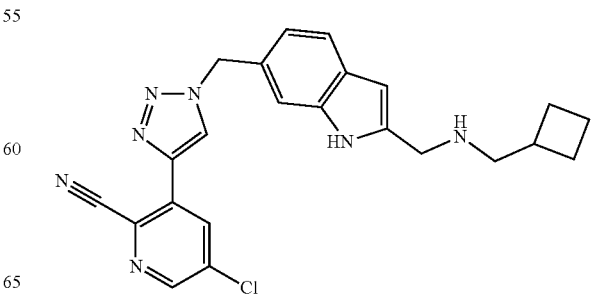

A solution of tert-butyl 2-[[tert-butoxycarbonyl(cyclobutylmethyl)amino]methyl]-6-[[4-(5-chloro-2-cyano-3-pyridyl)triazol-1-yl]methyl]indole-1-carboxylate (33 mg, 0.05 mmol) in MeOH (0.3108 mL) was treated with HCl (4M in dioxane, 0.6 mL), and the resulting mixture was stirred at room temperature for one hour. Further HCl (4M in dioxane, 0.6 mL) was added and the mixture was stirred at room temperature for 36 hours.

The reaction mixture was retreated with HCl (4M in dioxane, 0.6 mL), and the mixture left to stir at room temperature for 18 hours.

The pink mixture was evaporated under vacuum and the residue was purified by preparative HPLC (method B), and the product containing fractions were combined, concentrated in vacuo and freeze dried to give the title compound (8.6 mg, 38% Yield) as a white solid.

Method C: LC-MS (electrospray): m/z=432.5 (M+H)$^+$, RT=3.78 min

Example 155: 2-((6-azaspiro[3.4]octan-6-yl)methyl)-6-((4-(imidazo[1,5-a]pyridin-8-yl)-1H-1,2,3-triazol-1-yl)methyl)-1H-pyrrolo[3,2-c]pyridine

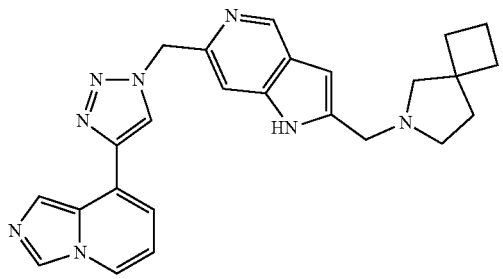 [SMILES: c1cc(-c2cn(Cc3cc4[nH]c(CN5CCC6(CCC6)C5)cc4cn3)nn2)c2cncn2c1]

The title compound was prepared from 6-azaspiro[3.4]octane in a similar manner to Example 140 to give the title compound (24 mg, 40%) as a beige solid.

Method C: LC-MS (electrospray): m/z=439.4 (M+H)$^+$, RT=2.95 min

METTL3/14 Methyltransferase Assay
Biochemical Assay

The enzymatic assay was established to determine IC50 values for inhibition of RNA methyltransferase activity. The enzyme used was full-length his-tagged METTL3 co-expressed with full length FLAG-tagged METTL14 in a baculovirus expression system. Enzymatic reactions were performed at room temperature in 384-well plates using a final reaction volume of 20 μL containing 20 mM TrisCl pH 7.6, 1 mM DTT, 0.01% Tween-20. 5 nM final concentration of METTL3/14 was pre-incubated with various compound concentrations for 10 minutes, followed by addition of 0.2 μM final concentration synthetic RNA substrate (5'P-uacacucgaucuggacuaaagcugcuc-3') and 0.5 μM final concentration S-adenosyl-methionine (SAM). The reaction was incubated for further 60 minutes at room temperature, and then quenched by the addition of 40 μL 7.5% TCA with two internal product standards (D$_4$-SAH and $^{13}$C$_{10}$-SAH). After termination, plates were sealed, centrifuged and stored at 4° C. until analysis.

Mass Spectrometry Analysis

RNA methyltransferase activity was measured label free using the RapidFire™ mass spectrometry (RF/MS) platform. Stopped and stable assay plates were analyzed on the Agilent RF300 integrated autosampler/solid-phase extraction (SPE) system coupled to an ABSciex 4000 mass spectrometer for the generation of the product S-adenosyl homocysteine (SAH) and normalized to the ratio of signal of the two internal product standards, respectively. Solvent A was water containing 0.1% (v/v) TCA. Solvent B was acetonitrile/0.1% ammonium acetate (8:2, v/v). More specifically, plates were centrifuged at 4350 rpm for 10 min, samples were aspirated under vacuum for 600 ms, then loaded onto a C18 solid-phase extraction cartridge and washed for 3 s with solvent A at a flow rate of 1.5 mL/min. Retained product and internal standards were eluted with solvent B at a flow rate of 1 mL/min for 3 s and finally the cartridge was reequilibrated with solvent A for 500 ms. The mass transition for the product (SAH) was 384.9/135.9 Da. Transitions of the two internal product standards (IS1: D$_4$-SAH and IS2: $^{13}$C$_{10}$-SAH) were 389.1/135.8 Da and 395.0/134.2 Da, respectively. Ratios of SAH/IS1 and SAH/IS2 were used for normalization of matrix effects. IC50 values were calculated based on dilution series of individual compounds. Potency of a compound was measured at varied inhibitor concentrations and normalized to control wells without RNA substrate and without inhibition (DMSO only).

Results:

TABLE 6

| Example No | METTL3_14 IC50 nM |
|---|---|
| 1 | 3.84 |
| 2 | 6.1 |
| 3 | 6.1 |
| 4 | 6.1 |
| 5 | 17.6 |
| 6 | 6.1 |
| 7 | 88.6 |
| 8 | 9.53 |
| 9 | 228 |
| 10 | 603 |
| 11 | 6.1 |
| 12 | 26.8 |
| 13 | 14 |
| 14 | 15.1 |
| 15 | 6.1 |
| 16 | 15.6 |
| 17 | 70.8 |
| 18 | 19.2 |
| 19 | 66.4 |
| 20 | 66.4 |
| 21 | 6.62 |
| 22 | 6.28 |
| 23 | 6.1 |
| 24 | 11.7 |
| 25 | 11.7 |
| 26 | 6.1 |
| 27 | 6.1 |
| 28 | 9.32 |
| 29 | 8.64 |
| 30 | 6.1 |
| 31 | 10.7 |
| 32 | 636 |
| 33 | 8.11 |
| 34 | 6.1 |
| 35 | 6.1 |
| 36 | 6.1 |
| 37 | 10.7 |
| 38 | 6.1 |
| 39 | 10.2 |
| 40 | 12.29 |
| 41 | 6.1 |
| 42 | 1220 |
| 43 | 1160 |
| 44 | 756 |
| 45 | 6.1 |
| 46 | 5080 |
| 47 | 6.1 |
| 48 | 12.5 |
| 49 | 6.86 |

TABLE 6-continued

| Example No | METTL3_14 IC50 nM |
|---|---|
| 50 | 1090 |
| 51 | 6680 |
| 52 | 5080 |
| 53 | 22.1 |
| 54 | 7.83 |
| 55 | 6.1 |
| 56 | 11.6 |
| 57 | 6.1 |
| 58 | 6.1 |
| 59 | 6.1 |
| 60 | 6.1 |
| 61 | 10.6 |
| 62 | 6.1 |
| 63 | 8.14 |
| 64 | 6.82 |
| 65 | 16100 |
| 66 | 15.9 |
| 67 | 6.1 |
| 68 | 9.86 |
| 69 | 17.2 |
| 70 | 11.3 |
| 71 | 192 |
| 72 | 32.1 |
| 73 | 199 |
| 74 | 260 |
| 75 | 35.2 |
| 76 | 6.1 |
| 77 | 6.1 |
| 78 | 75.3 |
| 79 | 488 |
| 80 | 445 |
| 81 | 6.1 |
| 82 | 374 |
| 83 | 9.32 |
| 84 | 150 |
| 85 | 67.8 |
| 86 | 158 |
| 87 | 309 |
| 88 | 106 |
| 89 | 113 |
| 90 | 6.1 |
| 123 | 118 |
| 122 | 6.1 |
| 121 | 80.9 |
| 91 | 638 |
| 92 | 6.1 |
| 93 | 6.1 |
| 94 | 6.1 |
| 95 | 6.1 |
| 96 | 9.24 |
| 97 | 7.2 |
| 98 | 14.8 |
| 99 | 6.66 |
| 100 | 6.99 |
| 124 | 6.1 |
| 101 | 193 |
| 102 | 6.1 |
| 115 | 564 |
| 103 | 185 |
| 114 | 6.1 |
| 104 | 6.1 |
| 116 | 6.1 |
| 105 | 71.6 |
| 106 | 6.1 |
| 120 | 6.1 |
| 117 | 6.1 |
| 118 | 9.22 |
| 119 | 8.97 |
| 107 | 13.5 |
| 108 | 17.8 |
| 125 | 6.1 |
| 113 | 6.1 |
| 112 | 125 |
| 111 | 7.54 |
| 110 | 6.1 |
| 109 | 6.1 |
| 129 | 6.1 |
| 130 | 6.1 |
| 131 | 6.1 |
| 132 | 6.1 |
| 126 | 6.1 |
| 127 | 6.1 |
| 133 | 11.4 |
| 134 | 6.1 |
| 135 | 6.3 |
| 136 | 18.8 |
| 137 | 6.1 |
| 138 | 6.1 |
| 139 | 24.4 |
| 140 | 6.53 |
| 141 | 7.02 |
| 142 | 7.91 |
| 143 | 495 |
| 144 | 19.3 |
| 145 | <6.1 |
| 146 | 26.8 |
| 147 | 26.4 |
| 148 | <6.1 |
| 149 | 6.91 |
| 151 | 34.6 |
| 152 | 259 |
| 153 | 6.8 |
| 154 | 71.04 |
| 155 | <6.1 |

Kasumi Cell Assay

Cell culture: KASUMI-1 cells (ACC20, Leibniz-Institut DSMZ Deutsche Sammlung von Mikroorganismen und Zellkulturen GmbH) were grown in RPMI 1640 (31870-025, Gibco) supplemented with 20% fetal bovine serum (F1524, Gibco), 1 mM sodium pyruvate (11360-039, Gibco) and 2 mM Glutamax (35050-038, Gibco) in a 5% CO2 humidified incubator at 37° C.

Cell treatment and cell growth assessment: KASUMI-1 hours were seeded in ultra-low attachment 384-well culture plate (MS-9384WZ, SBio) at a final concentration of 250000 cells/ml (35 µL/well) and treated for 120 hours with compounds inhibiting the METTL3/14 activity (10 serial semi-log dilutions, 30 µM as top concentration). Upon treatment, Kasumi1 cells were incubated for 10 min at RT with the CellTiter-Glo reagent (G7571, Promega). Measurement of the luminescence signal was performed on a microplate reader (Ensight, PerkinElmer).

TABLE 7

Results:

| Example No | KASUMI1 cells IC50 nM |
|---|---|
| 2 | 586.7 |
| 23 | 262.9 |
| 38 | 2306 |
| 41 | 309 |
| 45 | 764 |
| 47 | 343.8 |
| 60 | 2177 |
| 63 | 868.9 |
| 67 | 1723 |
| 70 | 4895 |
| 76 | 698 |
| 77 | 1765 |
| 81 | 1030 |
| 83 | 3679 |
| 90 | 1247 |
| 92 | 1610 |
| 93 | 1330 |
| 94 | 2237 |
| 95 | 3188 |
| 97 | 3094 |

TABLE 7-continued

Results:

| Example No | KASUMI1 cells IC50 nM |
|---|---|
| 99 | 3256 |
| 100 | 2544 |
| 102 | 524.7 |
| 104 | 661.1 |
| 106 | 1828 |
| 109 | 1474 |
| 110 | 1145 |
| 111 | 2287 |
| 113 | 1653 |
| 114 | 1458 |
| 116 | 5072 |
| 117 | 1726 |
| 120 | 446.9 |
| 122 | 1105 |
| 124 | 662.1 |
| 125 | 504 |
| 126 | 3069 |
| 129 | 2903 |
| 130 | 3155 |
| 131 | 1140 |
| 132 | 784.9 |
| 140 | 1086 |
| 145 | 717.2 |
| 151 | 7215 |
| 152 | 9963 |
| 155 | 546.7 |

CTG Assay (Caov3 Cell Line)

Cell culture: Caov-3 cells (HTB-75, Lot number: 70016791, ATCC) were grown in DMEM (11960-04431053-028, Gibco) supplemented with 10% fetal bovine serum (1600-44, Gibco), 1 mM sodium pyruvate (11360-039, Gibco) and 2 mM Glutamax (35050-038, Gibco) at 37° C. with 5% CO2.

Cell treatment and cell growth assessment: 18 hours post-seeding in white 384-Viewplate (6007480, PerkinElmer) at 1500 cells/well, Caov3 cells were treated for 120 hours with compounds inhibiting the METTL3/14 activity (10 serial semi-log dilutions, 30 μM as top concentration). Upon treatment, Coav-3 cells were incubated for 10 min at RT with the CellTiter-Glo reagent (G7571, Promega). Measurement of the luminescence signal was performed on a microplate reader (Ensight, PerkinElmer).

Caov3 CTG Assay—Proliferation Assay

TABLE 8

| Example No | Caov3 cells IC50 nM |
|---|---|
| 1 | 260 |
| 2 | 237.1 |
| 6 | 756.5 |
| 11 | 606.8 |
| 15 | 657.6 |
| 21 | 745.6 |
| 23 | 80.1 |
| 25 | 732.4 |
| 26 | 274 |
| 27 | 419.7 |
| 31 | 933 |
| 34 | 988 |
| 35 | 118 |
| 36 | 973.1 |
| 38 | 458.1 |
| 40 | 1030 |
| 41 | 191.7 |
| 45 | 574.2 |
| 47 | 185.5 |
| 49 | 1056 |
| 54 | 837.4 |
| 55 | 763.8 |
| 57 | 1060 |
| 58 | 702 |
| 59 | 523.9 |
| 60 | 422.9 |
| 62 | 695.5 |
| 63 | 256.8 |
| 64 | 922.5 |
| 67 | 481.8 |
| 76 | 241.9 |
| 77 | 700.7 |
| 81 | 564 |
| 90 | 601.5 |
| 92 | 597.5 |
| 93 | 452.6 |
| 94 | 681 |
| 95 | 959.6 |
| 97 | 1025 |
| 99 | 1090 |
| 100 | 685.4 |
| 102 | 229.7 |
| 104 | 237.3 |
| 106 | 911 |
| 109 | 608.4 |
| 110 | 411.5 |
| 113 | 574.6 |
| 114 | 679 |
| 117 | 502.4 |
| 120 | 203.4 |
| 122 | 524.6 |
| 124 | 266.2 |
| 125 | 212.3 |
| 126 | 522.8 |
| 127 | 623.6 |
| 128 | 1056 |
| 129 | 699.3 |
| 130 | 457.3 |
| 131 | 237.3 |
| 132 | 268 |
| 135 | 268.7 |
| 137 | 1080 |
| 140 | 296.9 |
| 145 | 201.2 |
| 151 | 9055 |
| 152 | 5431 |
| 155 | 472.9 |

Numbered Paragraphs

The following numbered paragraphs are not claims, but serve to define particular aspects and embodiments of the invention:

1. A compound of formula (I) shown below, or a pharmaceutically acceptable salt thereof:

X—Y—Z  (I)

wherein:
wherein:
X is selected from:

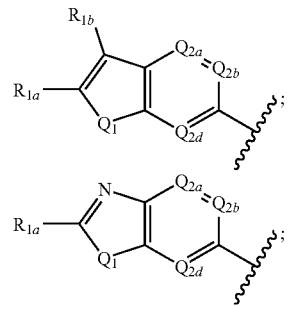

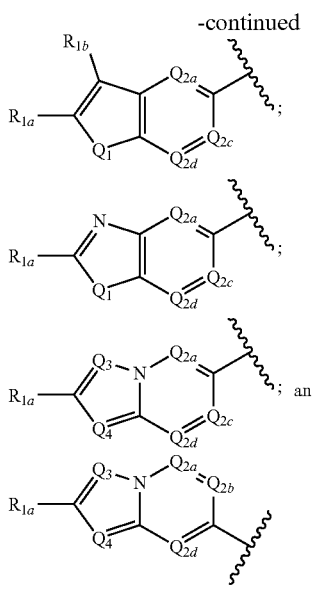

wherein
Q$_1$ is selected from NH, N—C$_{1-4}$alkyl, O or S;
Q$_{2a}$ is selected from N or CR$_{2a}$;
Q$_{2b}$ is selected from N or CR$_{2b}$;
Q$_{2c}$ is selected from N or CR$_{2c}$;
Q$_{2d}$ is selected from N or CR$_{2d}$;
Q$_3$ is selected from N or CR$_{1b}$;
Q$_4$ is selected from N or CR$_{1x}$;
subject to the proviso that no more than 3 of Q$_1$, Q$_{2a}$, Q$_{2b}$, Q$_{2c}$, Q$_{2d}$, Q$_3$ and Q$_4$ are nitrogen;
R$_{1a}$ is selected from:
(i) C$_{1-4}$alkyl or C$_{1-4}$alkoxy, each of which being optionally substituted by halo, cyano, hydroxy, C$_{3-6}$cycloalkyl, C$_{1-4}$alkoxy, C$_{1-4}$haloalkoxy, aryl or heteroaryl; or
(ii) a group of the formula:

—(CR$_{1c}$R$_{1d}$)$_p$—NR$_{1e}$R$_{1f}$;

wherein
p is an integer selected from 0, 1, 2 or 3
R$_{1c}$ and R$_{1d}$ are independently selected from:
(i) hydrogen (including deuterium),
(ii) C$_{1-6}$alkyl which is optionally substituted by one more substituents selected from cyano, oxo, hydroxy, C$_{1-4}$alkoxy, halo, C$_{1-4}$haloalkoxy, C$_{3-6}$cycloalkyl, —O—C$_{3-6}$cycloalkyl, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl; and wherein C$_{3-6}$cycloalkyl and —O—C$_{3-6}$cycloalkyl are optionally further substituted with halo, cyano or hydroxy;
(iii) C$_{3-4}$cycloalkyl or 3 to 5 membered heterocyclyl, each of which is optionally substituted by C$_{1-4}$alkyl, C$_{1-4}$haloalkyl, cyano, hydroxy, C$_{1-2}$alkoxy, halo, C$_{1-2}$haloalkoxy, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl; and;
(iv) or R$_{1c}$ and R$_{1d}$ are linked together such that, together with the carbon atom to which they are attached, they form a 3- to 6-membered cycloalkyl or heterocyclic ring, or a spirocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl;

R$_{1e}$ and R$_{1f}$ are each independently selected from:
(i) hydrogen (including deuterium);
(ii) C$_{1-6}$alkyl which is optionally substituted by one more substituents selected from cyano, hydroxy, C$_{1-2}$alkoxy, halo, C$_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or C$_{1-2}$alkyl;
(iii) a group with the formula:

—(CR$_{1g}$R$_{1h}$)$_q$-T$_1$ wherein:
q is 0, 1, 2, 3, 4, 5 or 6; R$_{1g}$ and R$_{1h}$ are independently selected from:
e) hydrogen;
f) C$_{1-6}$alkyl which is optionally substituted by one more substituents selected from cyano, oxo, hydroxy, C$_{1-4}$alkoxy, halo, C$_{1-4}$haloalkoxy, —O—C$_{3-6}$cycloalkyl, NR$_{1ga}$R$_{1ha}$ or —S(O)$_{0-2}$R$_{1ga}$R$_{1ha}$, wherein R$_{1ga}$ and R$_{1h}$a are H or C$_{1-2}$alkyl; and wherein —O—C$_{3-6}$cycloalkyl is optionally substituted with halo, cyano or hydroxy;
g) an aryl-C$_{1-6}$alkyl, heteroarylC$_{1-6}$alkyl, C$_{3-6}$-cycloalkyl or C$_{3-6}$cycloalkylC$_{1-6}$alkyl group, each of which is optionally substituted by one or more substituents selected from C$_{1-2}$alkyl, cyano, C$_{1-2}$haloalkyl, hydroxy, C$_{1-2}$alkoxy, halo, C$_{1-2}$-haloalkoxy, NR$_{1ga}$R$_{1ha}$ or —S(O)$_{0-2}$R$_{1ga}$R$_{1ha}$, wherein R$_{1ga}$ and R$_{1ha}$ are H or C$_{1-2}$alkyl; or
h) or R$_{1g}$ and R$_{1h}$ are optionally linked together such that, together with the carbon atom to which they are attached, they form a 3- to 6-membered cycloalkyl or heterocyclic ring which is optionally substituted by one or more substituents selected from C$_{1-2}$alkyl, cyano, C$_{1-2}$haloalkyl, hydroxy, C$_{1-2}$ alkoxy, halo, C$_{1-2}$haloalkoxy, NR$_{1ga}$R$_{1ha}$ or —S(O)$_{0-2}$R$_{1ga}$R$_{1ha}$, wherein R$_{1ga}$ and R$_{1ha}$ are H or C$_{1-2}$alkyl;
and T$_1$ is selected from hydrogen, cyano, hydroxy, NR$_{1t}$R$_{2t}$ or —S(O)$_{0-2}$R$_{1t}$R$_{2t}$ (wherein R$_{1t}$ and R$_{2t}$ are H or C$_{1-4}$alkyl), C$_{3-8}$cycloalkyl, C$_{2-3}$alkenyl, C$_{2-3}$alkynyl, aryl, heterocyclyl, heteroaryl, a spirocyclic carbocyclic or heterocyclic ring system, a bridged C$_{3-8}$cycloalkyl, a bridged bicyclic C$_{5-12}$cycloalkyl, or a bridged heterocyclic ring system, each of which is optionally substituted by one or more substituents selected from C$_{1-2}$alkyl, C$_{1-2}$-haloalkyl, cyano, hydroxy, C$_{1-2}$alkoxy, halo, C$_{1-2}$-haloalkoxy, NR$_{3t}$R$_{4t}$ or —S(O)$_{0-2}$R$_{3t}$R$_{4t}$, wherein R$_{3t}$ and R$_{4t}$ are H or C$_{1-2}$alkyl;
(iv) or R$_{1e}$ and R$_{1f}$ are linked such that, together with the nitrogen atom to which they are attached, they form a mono- or bicyclic-heterocyclic ring, which is optionally substituted by one or more substituents selected from C$_{1-4}$alkyl, C$_{1-4}$haloalkyl, cyano, hydroxy, C$_{1-4}$alkoxy, halo, C$_{1-4}$haloalkoxy, NR$_{1i}$R$_{1j}$ or —S(O)$_{0-2}$R$_{1i}$R$_{1j}$, wherein R$_{1i}$ and R$_{1j}$ are H or C$_{1-4}$alkyl, and/or the mono- or bicyclic heterocyclic ring formed by R$_{1e}$ and R$_{1f}$ is optionally spiro-fused to a C$_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$ alkoxy, halo, $C_{1-4}$haloalkoxy, $NR_{1i}R_{1j}$ or $-S(O)_{0-2}$ $R_{1i}R_{1j}$), wherein $R_{1i}$ and $R_{1j}$ are H or $C_{1-4}$alkyl;

$R_{1b}$ is selected from hydrogen, cyano, halo or $C_{1-3}$ alkyl;
$R_{1x}$ is selected from hydrogen, cyano, halo or $C_{1-3}$ alkyl;
$R_{2a}$, $R_{2b}$, $R_{2c}$ and $R_{2d}$ are independently selected from hydrogen, cyano, halo or a group of the formula:

-$L_{2a}$-$L_{2b}$-$Q_2$ wherein
$L_{2a}$ is absent or $C_{1-3}$alkylene optionally substituted by $C_{1-2}$ alkyl or oxo;
$L_{2b}$ is absent or selected from O, S, SO, $SO_2$, $N(R_n)$, C(O), C(O)O, OC(O), $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_yR_p$ (where y is 0, 1 or 2), $SO_2N(R_p)R_q$, $N(R_r)SO_2R_p$ or $(CH_2)_z$ $NR_pR_q$ (where z is 1, 2 or 3), wherein $R_p$ and $R_q$ are each independently selected from hydrogen or $C_{1-4}$alkyl;

Y is selected from:

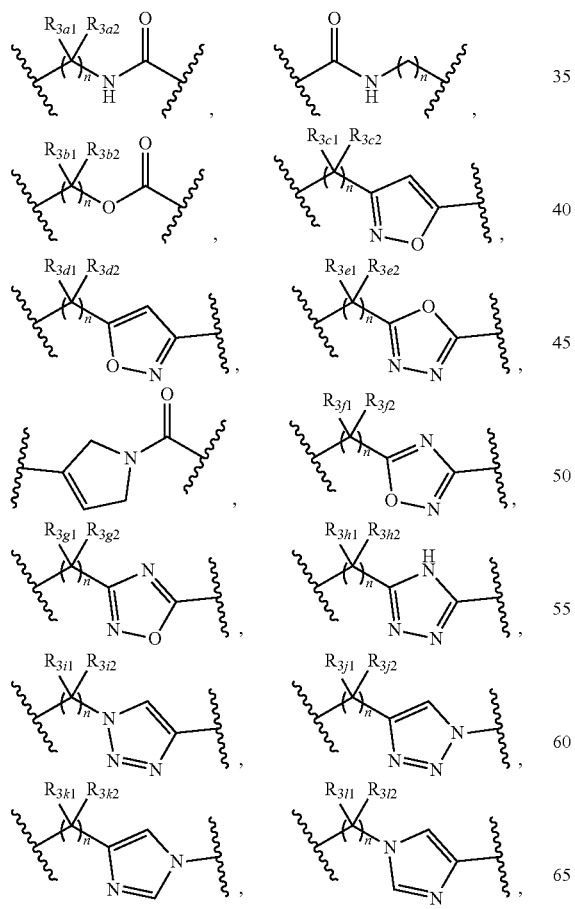

-continued

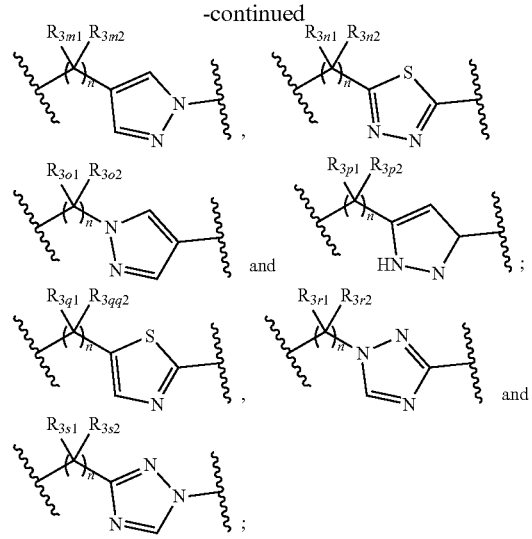

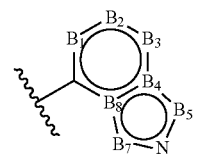

wherein:
$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen or halo;

with the proviso that $R_{3a1}$, $R_{3b1}$, $R_{3i1}$, $R_{3j1}$, $R_{3o1}$, $R_{3r1}$, $R_{3a2}$, $R_{3b2}$, $R_{3i2}$, $R_{3j2}$, $R_{3o2}$ and $R_{3s1}$ cannot be halo when n=1 or when n=2 and the carbon atom to which they are attached is linked to an oxygen or nitrogen atom;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$ and $R_{3f2}$, $R_{3a1}$ and $R_{3g2}$, $R_{3h1}$ and $R_{3h2}$, $R_{3i1}$ and $R_{3i2}$, $R_{3j1}$ and $R_{3j2}$, $R_{3k1}$ and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, or $R_{3r1}$ and $R_{3r2}$ or $R_{3s1}$ and $R_{3s2}$ may be linked such that, together with the carbon atom to which they are attached, they form a spiro-fused $C_{3-4}$cycloalkyl which is optionally substituted with one or more substituents selected from halo, methyl, amino, cyano, and hydroxy;

n is 0, 1 or 2

Z is selected from one of the following structures:

i)

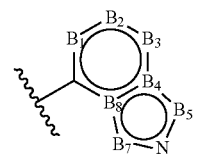

wherein:
$B_1$ is $A_5$, wherein $A_5$ is selected from $CR_{16}$ and N, wherein $R_{16}$ is selected from hydrogen, halo, cyano, $C_{1-4}$ alkyl, $C_{2-4}$ alkenyl, $C_{2-4}$ alkynyl, a 5- or 6-membered heteroaryl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$B_2$ is $A_6$, wherein $A_6$ is selected from N or $CR_{17}$, wherein $R_{17}$, $R_{H2}$, $R_{H4}$ and $R_{H5}$ are selected from hydrogen, hydroxy, halo, cyano, $C_{1-5}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, —O—$C_{3-6}$cycloalkyl, heterocyclyl, —O-heterocyclyl (carbon-linked), —(OCH$_2$CH$_2$)$_m$—NR$_q$R$_r$, —(OCH$_2$CH$_2$)$_m$—OCH$_3$ wherein m is an integer from 1 to 6, NR$_q$R$_r$, —C(O)—NR$_q$R$_r$, —C(O)OR$_q$, wherein $R_q$ and $R_r$ are each independently hydrogen, $C_{1-5}$ alkyl, $C_{3-6}$cycloalkyl, a 3- to 6-membered carbon-linked heterocyclyl, or $R_q$ and $R_r$ are linked together such that, together with the nitrogen atom to which they are attached, they form a 3- to 6-membered heterocyclic ring;

wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, —O—$C_{3-6}$cycloalkyl, heterocyclyl or —O— heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl;

$B_3$ is N or $CR_{Z1}$, wherein $R_{Z1}$ is selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

$B_4$ is selected from C or N;

$B_5$ is selected from $CR_{Zi1b}$ or NR$_{B5N}$, wherein:
$R_{Zi1b}$ is selected from hydrogen, $C_{1-4}$alkyl, cyano, halo, NH$_2$ and $C_{1-4}$alkoxy; and
$R_{B5N}$ is selected from hydrogen or $C_{1-4}$alkyl;

$B_7$ is N, NR$_{Z2N}$ or C—R$_{Z2}$, wherein R$_{Z2}$ is selected from hydrogen, $C_{1-4}$alkyl, cyano, halo, NH$_2$ and $C_{1-4}$alkoxy;

$B_8$ is selected from C or N;

with the proviso that no more than four of $B_1$ to $B_8$ are N.

ii)

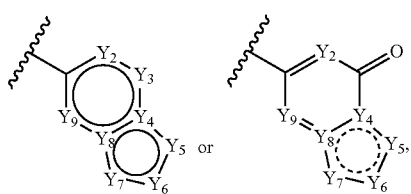

$Y_2$ is $A_7$, wherein $A_7$ is selected from $CR_{18}$ and N; wherein $R_{18}$ is selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$cycloalkoxy;

$Y_3$ is N or $CR_{Z1a}$ wherein $R_{Z1a}$, is selected from hydrogen, hydroxy, $C_{1-4}$alkyl, cyano, halo, $C_{1-4}$ haloalkyl, $C_{1-4}$haloalkoxy, $C_{1-4}$alkoxy, $C_{3-6}$cycloalkyl and —O—$C_{3-6}$cycloalkyl, wherein $C_{3-6}$cycloalkyl and —O—$C_{3-6}$cycloalkyl are optionally substituted by one or more of halo, methyl or methoxy;

$Y_4$ is C or N $Y_5$ is $CR_{Y5}$ or NR$_{Y5N}$, wherein:
$R_{Y5}$ is selected from hydrogen, $C_{1-4}$alkyl, cyano, halo, NH$_2$ and $C_{1-4}$alkoxy;
$R_{Y5N}$ is selected from hydrogen or $C_{1-4}$alkyl;

$Y_6$ is C—R$_{Zi2e}$ or N, wherein R$_{Zi2e}$ is selected from hydrogen, $C_{1-4}$alkyl, cyano, halo, NH$_2$ and $C_{1-4}$alkoxy $Y_7$ is O, S, $CR_{Z2a}$ or N, wherein $R_{Z2a}$ is selected from hydrogen, $C_{1-4}$alkyl, cyano, halo, NH$_2$ and $C_{1-4}$alkoxy;

$Y_8$ is C or N;

$Y_9$ is $CR_{Z3a}$ or N; wherein
$R_{Z3a}$ is selected from hydrogen, $C_{1-4}$alkyl, cyano, halo, NH$_2$ and $C_{1-4}$alkoxy;

with the proviso that no more than four of $Y_1$ to $Y_8$ are N.

(iii)

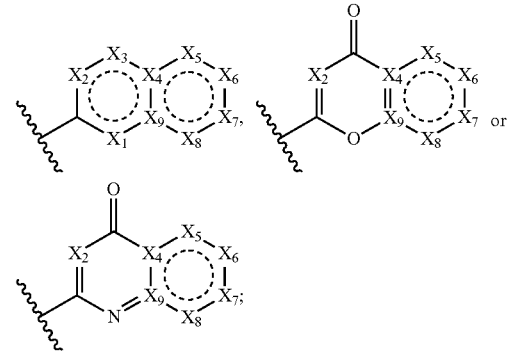

$X_1$ is N or C—$R_{Z9}$, wherein $R_{Z9}$ is selected from hydrogen, halo, cyano, $C_{1-4}$ alkyl, $C_{1-4}$ haloalkyl, $C_{1-4}$alkoxy, $C_{1-4}$ haloalkoxy;

$X_2$ is selected from N or $CR_4$ wherein:
$R_4$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl);

$X_3$ is N;

$X_4$ is N or C;

$X_5$ is selected from N, $CR_5$ and $CRx_{5a}Rx_{5b}$ wherein:
$R_5$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);
$Rx_{5a}$ and $Rx_{5b}$ are independently selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl);

either:
$X_6$ is $A_1$ and $X_7$ is $A_2$; or
$X_6$ is $A_8$ and $X_7$ is $A_9$ or $A_{11}$, wherein:
$A_1$ is selected from $CR_{12}$ and N; wherein
$R_{12}$ is selected from selected from hydrogen, halo, cyano, $C_{1-4}$ alkyl, $C_{1-4}$ haloalkyl, $C_{1-4}$alkoxy and $C_{1-4}$ haloalkoxy (e.g. hydrogen, halo, cyano and $C_{1-4}$ alkyl);

$A_2$ is selected from $CR_{13}$ and N, wherein
$R_{13}$ selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano, methoxy and methyl);

$A_8$ is selected from $CR_{19}R_{20}$ and NR$_{21}$; wherein
$R_{19}$ and $R_{20}$ are independently selected from hydrogen, halo, cyano, $C_{1-4}$ alkyl, $C_{1-4}$ haloalkyl, $C_{1-4}$alkoxy, $C_{1-4}$ haloalkoxy (e.g hydrogen, halo, cyano and $C_{1-4}$ alkyl);

$R_{21}$ is hydrogen or $C_{1-4}$alkyl.

$A_9$ is selected from $CR_{22}R_{23}$ and $NR_{24}$;
  wherein $R_{22}$ and $R_{23}$ are independently selected from selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and methyl);
  $R_{24}$ is selected from hydrogen or $C_{1-4}$alkyl $A_{11}$ is selected from $CR_{28}R_{29}$ and $NR_{30}$;
  $R_{28}$ and $R_{29}$ are selected from hydrogen, halo, methoxy and methyl;
  $R_{30}$ is selected from hydrogen or $C_{1-4}$alkyl.

$X_8$ is selected from $CR_6$, N or $CR_{X6a}R_{X6b}$;
  wherein $R_6$ is selected from hydrogen, halo, cyano, $C_{1-4}$ alkyl, $C_{1-4}$ haloalkyl, $C_{1-4}$alkoxy and $C_{1-4}$ haloalkoxy;
  $R_{X6a}$ and $R_{X6b}$ are each independently selected from hydrogen, halo, cyano, $C_{1-4}$ alkyl, $C_{1-4}$ haloalkyl, $C_{1-4}$alkoxy and $C_{1-4}$ haloalkoxy;

$X_9$ is N or C;

with the proviso that no more than four of $X_2$ to $X_9$ are N.

(iv)

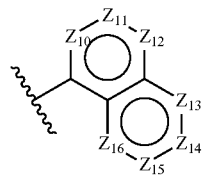

$Z_{10}$ is N or C—$R_{Z10}$, wherein $R_{Z10}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{11}$, is N or C—$R_{Z11}$, wherein $R_{Z11}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{12}$ is N or C—$R_{Z12}$, wherein $R_{Z12}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{13}$ is N or C—$R_{Z13}$, wherein $R_{Z13}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{14}$ is N or C—$R_{Z14}$, wherein $R_{Z14}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{15}$ is N or C—$R_{Z15}$, wherein $R_{Z15}$ is selected from hydrogen, halo, cyano, $C_{1-4}$ alkyl, $C_{1-4}$ haloalkyl, $C_{1-4}$alkoxy, $C_{1-4}$ haloalkoxy;

$Z_{16}$ is N or C—$R_{Z16}$, wherein $R_{Z16}$ is selected from hydrogen, halo, cyano, $C_{1-4}$ alkyl, $C_{1-4}$ haloalkyl, $C_{1-4}$alkoxy, $C_{1-4}$ haloalkoxy;

with the proviso that no more than three of $Z_{10}$ to $Z_{16}$ are N;

(v)

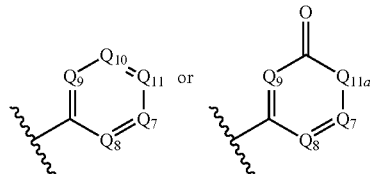

$Q_7$ is $CR_7$ or N;
$Q_8$ is $CR_8$ or N;
$Q_9$ is $CR_9$ or N;
$Q_{10}$ is $CR_{10}$ or N;
$Q_{11}$ is $CR_{11}$ or N;
$Q_{11a}$ is $NR_{11N}$ or $CR_{11a}R_{11b}$;

wherein $R_7$, $R_8$, $R_9$, $R_{10}$, $R_{11}$, $R_{11a}$ and $R_{11b}$ are each independently selected from hydrogen, $NH_2$, halo, cyano, $C_{1-4}$ alkoxy, $C_{1-4}$ haloalkoxy, $C_{1-6}$ alkyl, —$CH_2OCH_3$, —$CH_2SO_2CH_3$, —$SO_2CH_3$, —$NHC(O)CH_3$ and —$C(O)NR_{v1}R_{v2}$, wherein $R_{v1}$ and $R_{v2}$ are independently selected from hydrogen and methyl and;
and $R_{11N}$ is selected from hydrogen, $NH_2$, halo, cyano, and $C_{1-6}$ alkyl;

or $R_9$ and $R_{10}$ may be linked together such that, together to the atoms to which they are attached, they form a fused 5- or 6-membered saturated or unsaturated ring system, or $R_{10}$ and $R_{11}$ may be linked together such that, together to the atoms to which they are attached, they form a fused 5- or 6-membered saturated or unsaturated ring system, wherein either of the fused 5- or 6-membered saturated or unsaturated ring system may be optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ia}R_{1ja}$ or —$S(O)_{0-2}R_{1ia}R_{1ja}$, wherein $R_{1ia}$ and $R_{1ja}$ are H or $C_{1-2}$alky;

with the proviso that no more than three of $Q_7$ to $Q_{11}$ are N.

2. A compound of Formula (I) according to paragraph 1, or a pharmaceutically acceptable salt thereof, $$X—Y—Z \qquad (I)$$

wherein:
X is selected from:

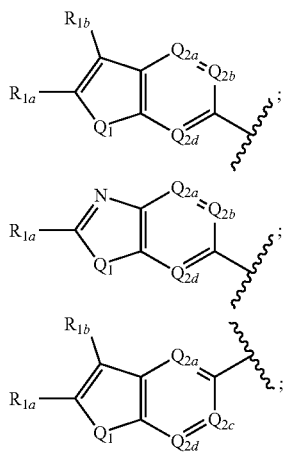

-continued

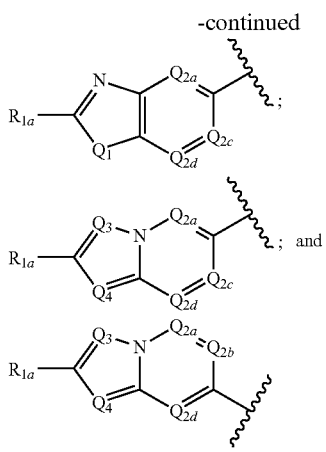

wherein
Q$_1$ is selected from NH, N—C$_{1-4}$alkyl, O or S;
Q$_{2a}$ is selected from N or CR$_{2a}$;
Q$_{2b}$ is selected from N or CR$_{2b}$;
Q$_{2c}$ is selected from N or CR$_{2c}$;
Q$_{2d}$ is selected from N or CR$_{2d}$;
Q$_3$ is selected from N or CR$_{1b}$;
Q$_4$ is selected from N or CR$_{1x}$;
subject to the proviso that no more than 3 of Q$_1$, Q$_{2a}$, Q$_{2b}$, Q$_{2c}$, Q$_{2d}$, Q$_3$ and Q$_4$ are nitrogen;
R$_{1a}$ is selected from:
  (i) C$_{1-4}$alkyl or C$_{1-4}$alkoxy, each of which being optionally substituted by halo, cyano, hydroxy, C$_{3-6}$cycloalkyl, a 3 to 6 membered heterocyclyl C$_{1-4}$alkoxy, C$_{1-4}$haloalkoxy, aryl or heteroaryl; or
  (ii) a group of the formula:

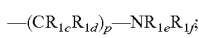

wherein
  p is an integer selected from 0, 1, 2 or 3
  R$_{1c}$ and R$_{1d}$ are independently selected from:
    (i) hydrogen (including deuterium),
    (ii) C$_{1-6}$alkyl which is optionally substituted by one more substituents selected from cyano, oxo, hydroxy, C$_{1-4}$alkoxy, halo, C$_{1-4}$haloalkoxy, C$_{3-6}$cycloalkyl, —O—C$_{3-6}$cycloalkyl, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl; and wherein C$_{3-6}$cycloalkyl and —O—C$_{3-6}$ cycloalkyl are optionally further substituted with halo, cyano or hydroxy;
    (iii) C$_{3-4}$cycloalkyl or 3 to 5 membered heterocyclyl, each of which is optionally substituted by C$_{1-4}$alkyl, C$_{1-4}$haloalkyl, cyano, hydroxy, C$_{1-2}$alkoxy, halo, C$_{1-2}$haloalkoxy, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl; and;
    (iv) or R$_{1c}$ and R$_{1d}$ are linked together such that, together with the carbon atom to which they are attached, they form a 3- to 6-membered cycloalkyl or heterocyclic ring, or a spirocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy, NR$_{1ca}$R$_{1da}$ or —S(O)$_{0-2}$R$_{1ca}$R$_{1da}$, wherein R$_{1ca}$ and R$_{1da}$ are H or C$_{1-2}$alkyl;

R$_{1e}$ and R$_{1f}$ are each independently selected from:
  (i) hydrogen (including deuterium);
  (ii) C$_{1-6}$alkyl which is optionally substituted by one more substituents selected from cyano, oxo, hydroxy, C$_{1-2}$alkoxy, halo, C$_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or C$_{1-2}$alkyl;
  (iii) a group with the formula:

wherein:
    q is 0, 1, 2, 3, 4, 5 or 6;
    R$_{1g}$ and R$_{1h}$ are independently selected from:
    a) hydrogen;
    b) C$_{1-6}$alkyl which is optionally substituted by one more substituents selected from cyano, hydroxy, C$_{1-4}$alkoxy, halo, C$_{1-4}$-haloalkoxy, —O—C$_{3-6}$cycloalkyl, NR$_{1ga}$R$_{1ha}$ or —S(O)$_{0-2}$R$_{1ga}$R$_{1ha}$, wherein R$_{1ga}$ and R$_{1ha}$ are H or C$_{1-2}$alkyl; and wherein —O—C$_{3-6}$cycloalkyl is optionally substituted with halo, cyano or hydroxy;
    c) an aryl-C$_{1-6}$alkyl, heteroarylC$_{1-6}$alkyl, C$_{3-6}$cycloalkyl or C$_{3-6}$cycloalkylC$_{1-6}$alkyl group, each of which is optionally substituted by one or more substituents selected from C$_{1-2}$alkyl, cyano, C$_{1-2}$-haloalkyl, hydroxy, C$_{1-2}$alkoxy, halo, C$_{1-2}$haloalkoxy, NR$_{1ga}$R$_{1ha}$ or —S(O)$_{0-2}$R$_{1ga}$R$_{1ha}$, wherein R$_{1ga}$ and R$_{1ha}$ are H or C$_{1-2}$alkyl; or
    d) or R$_{1g}$ and R$_{1h}$ are optionally linked together such that, together with the carbon atom to which they are attached, they form a 3- to 6-membered cycloalkyl or heterocyclic ring which is optionally substituted by one or more substituents selected from C$_{1-2}$alkyl, cyano, C$_{1-2}$haloalkyl, hydroxy, C$_{1-2}$alkoxy, halo, C$_{1-2}$haloalkoxy, NR$_{1ga}$R$_{1ha}$ or —S(O)$_{0-2}$R$_{1ga}$R$_{1ha}$, wherein R$_{1ga}$ and R$_{1h}$a are H or C$_{1-2}$alkyl; and
    T$_1$ is selected from hydrogen, halo, C$_{1-4}$alkyl, C$_{1-4}$haloalkyl, cyano, hydroxy, NR$_{1t}$R$_{2t}$ or —S(O)$_{0-2}$R$_{1t}$R$_{2t}$ (wherein R$_{1t}$ and R$_{2t}$ are H or C$_{1-4}$alkyl), C$_{3-8}$cycloalkyl, C$_{2-3}$alkenyl, C$_{2-3}$alkynyl, aryl, heterocyclyl, a mono- or bicyclic heteroaryl, a spirocyclic carbocyclic or heterocyclic ring system, a bridged C$_{3-8}$cycloalkyl, a bridged bicyclic C$_{5-12}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$-haloalkoxy, C$_{3-6}$cycloalkyl, NR$_{3t}$R$_{4t}$ or —S(O)$_{0-2}$R$_{3t}$R$_{4t}$, wherein R$_{3t}$ and R$_{4t}$ are H or C$_{1-2}$alkyl;
  (iv) or R$_{1e}$ and R$_{1f}$ are linked such that, together with the nitrogen atom to which they are attached, they form a mono- or bicyclic-heterocyclic ring, which is optionally substituted by one or more substituents selected from C$_{1-4}$alkyl, C$_{1-4}$haloalkyl, C$_{3-6}$cycloalkyl, cyano, hydroxy, C$_{1-4}$alkoxy, halo, C$_{1-4}$haloalkoxy, NR$_{1i}$R$_{1j}$ or —S(O)$_{0-2}$R$_{1i}$R$_{1j}$, wherein R$_{1i}$ and R$_{1j}$ are H or C$_{1-4}$alkyl, and/or the mono- or bicyclic heterocyclic ring formed by R$_{1e}$ and R$_{1f}$ is optionally spiro-fused to a C$_{3-6}$cycloalkyl or a heterocyclic ring, which in turn is optionally substituted by one or more substituents selected from C$_{1-4}$alkyl, C$_{1-4}$haloalkyl, C$_{3-6}$cycloalkyl, cyano, hydroxy, C$_{1-4}$alkoxy, halo, C$_{1-4}$haloalkoxy, NR$_{1i}$R$_{1j}$ or —S(O)$_{0-2}$R$_{1i}$R$_{1j}$, wherein $R_{1i}$ and $R_{1j}$ are H or $C_{1-4}$alkyl; wherein any wherein any alkyl, alkoxy or $C_{3-6}$cycloalkyl is further optionally substituted by one or more substituents selected from cyano, hydroxy, halo, $NR_{1k}R_{1l}$ or $-S(O)_{0-2}R_{1k}R_{1l}$, wherein $R_{1k}$ and $R_{1l}$, are H or $C_{1-4}$alkyl $R_{1b}$ is selected from hydrogen, cyano, halo or $C_{1-3}$ alkyl;

$R_{1x}$ is selected from hydrogen, cyano, halo or $C_{1-3}$ alkyl;

$R_{2a}$, $R_{2b}$, $R_{2c}$ and $R_{2d}$ are independently selected from hydrogen, cyano, halo or a group of the formula:

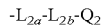

wherein $L_{2a}$ is absent or $C_{1-3}$alkylene optionally substituted by $C_{1-2}$ alkyl or oxo;

$L_{2b}$ is absent or selected from O, S, SO, $SO_2$, $N(R_n)$, C(O), C(O)O, OC(O), $C(O)N(R_n)$, $N(R_n)C(O)$, $N(R_n)C(O)N(R_o)$, $S(O)_2N(R_n)$, or $N(R_n)SO_2$, wherein $R_n$ and $R_o$ are each independently selected from hydrogen or $C_{1-2}$alkyl; and $Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, $C(O)OR_p$, $OC(O)R_p$, $C(O)N(R_p)R_q$, $N(R_r)C(O)R_p$, $S(O)_y R_p$ (where y is 0, 1 or 2), $SO_2N(R_p)R_q$, $N(R_r)SO_2R_p$ or $(CH_2)_zNR_pR_q$ (where z is 1, 2 or 3), wherein $R_p$ and $R_q$ are each independently selected from hydrogen or $C_{1-4}$alkyl;

Y is selected from:

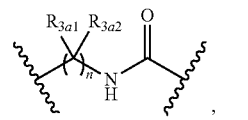,
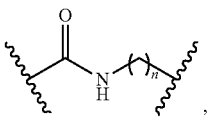,
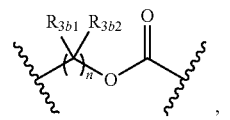,
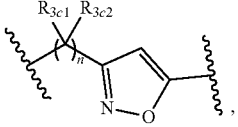,
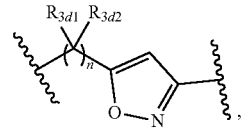,
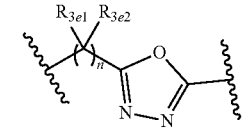,
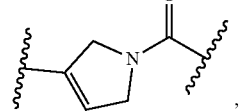,
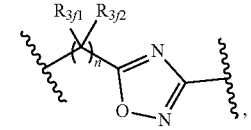,
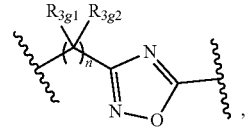,
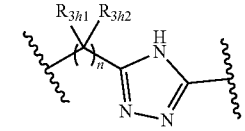,
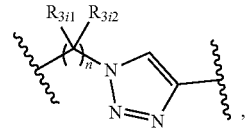,
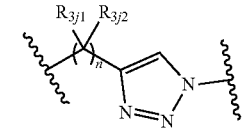,

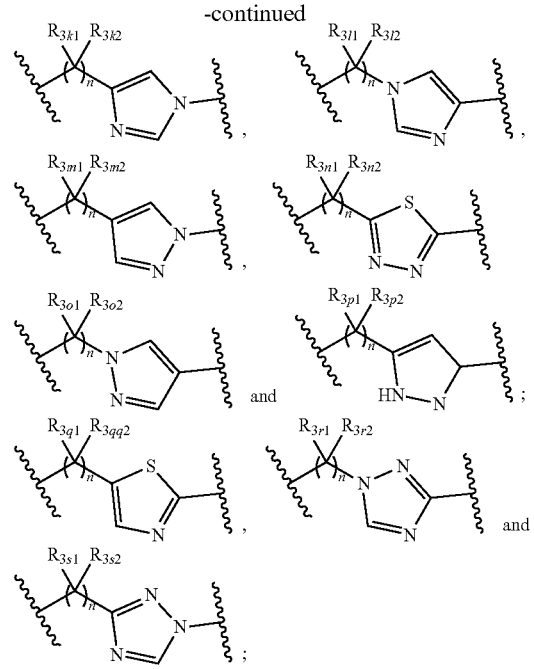

wherein:

$R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl, $C_{3-4}$ cycloalkyl, hydroxy, and halo; and wherein $C_{1-6}$alkyl, or $C_{3-4}$ cycloalkyl is optionally substituted with one or more substituents selected from halo, amino, cyano, and hydroxy;

$R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen or halo;

with the proviso that $R_{3a1}$, $R_{3b1}$, $R_{3i1}$, $R_{3l1}$, $R_{3o1}$, $R_{3r1}$, $R_{3a2}$, $R_{3b2}$, $R_{3i2}$, $R_{3l2}$, $R_{3o2}$ and $R_{3s1}$ cannot be halo when n=1 or when n=2 and the carbon atom to which they are attached is linked to an oxygen or nitrogen atom;

or $R_{3a1}$ and $R_{3a2}$, $R_{3b1}$ and $R_{3b2}$, $R_{3c1}$ and $R_{3c2}$, $R_{3d1}$ and $R_{3d2}$, $R_{3e1}$ and $R_{3e2}$, $R_{3f1}$, and $R_{3f2}$, $R_{3g1}$ and $R_{3g2}$, $R_{3h1}$ and $R_{3h2}$, $R_{3i1}$ and $R_{3i2}$, $R_{3j1}$ and $R_{3j2}$, $R_{3k1}$, and $R_{3k2}$, $R_{3l1}$ and $R_{3l2}$, $R_{3m1}$ and $R_{3m2}$, $R_{3n1}$ and $R_{3n2}$, $R_{3o1}$ and $R_{3o2}$, $R_{3p1}$ and $R_{3p2}$, $R_{3q1}$ and $R_{3q2}$, or $R_{3r1}$ and $R_{3r2}$ or $R_{3s1}$ and $R_{3s2}$ may be linked such that, together with the carbon atom to which they are attached, they form a spiro-fused $C_{3-4}$cycloalkyl which is optionally substituted with one or more substituents selected from halo, methyl, amino, cyano, and hydroxy;

n is 0, 1 or 2

Z is selected from:

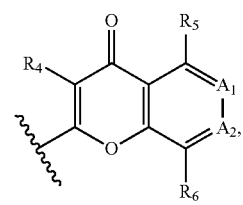 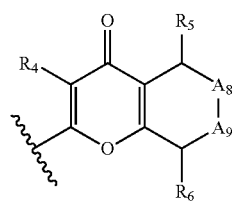

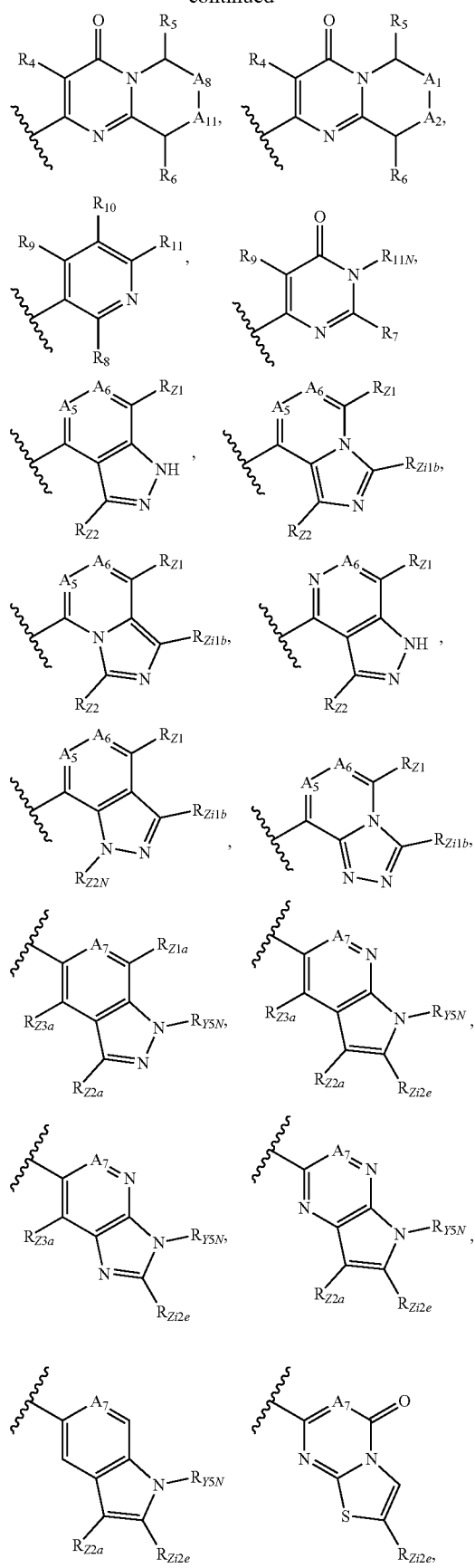
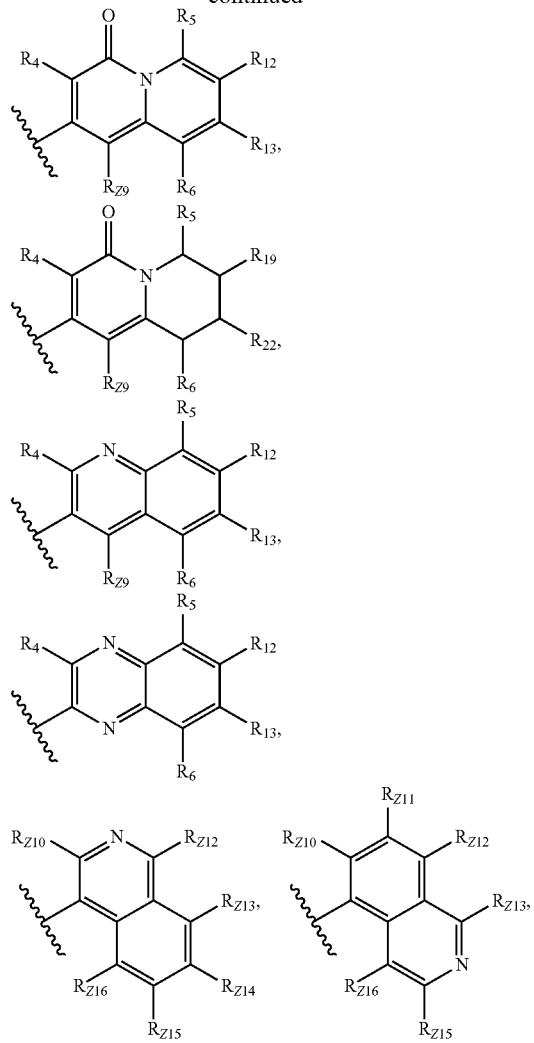

wherein:

$R_4$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);

$R_5$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);

$R_6$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl);

$R_8$, $R_9$, $R_{10}$ and $R_{11}$ are independently selected from hydrogen, $NH_2$, halo, cyano, $C_{1-4}$ alkoxy, $C_{1-4}$ haloalkoxy, $C_{1-6}$ alkyl, —$CH_2OCH_3$, —$CH_2SO_2CH_3$, —$SO_2CH_3$, —$NHC(O)CH_3$ and —$C(O)NR_{v1}R_{v2}$, wherein $R_{v1}$ and $R_{v2}$ are independently selected from hydrogen and methyl; or $R_9$ and $R_{10}$ may be linked together such that, together to the atoms to which they are attached, they form a fused 5- or 6-membered saturated or unsaturated ring system, or $R_{10}$ and $R_{11}$ may be linked together such that, together to the atoms to which they are attached, they form a fused 5- or 6-membered saturated or unsaturated ring system, wherein either of the fused 5- or 6-membered saturated or unsaturated ring system may be optionally substituted by one or more substituents selected from $C_{1-2}$ alkyl, cyano, $C_{1-2}$haloalkyl, hydroxy, $C_{1-2}$alkoxy, halo, $C_{1-2}$haloalkoxy, $NR_{1ia}R_{1ja}$ or $-S(O)_{0-2}R_{1ia}R_{1ja}$, wherein $R_{1ia}$ and $R_{1ja}$ are H or $C_{1-2}$alky;

$R_7$ and $R_{11N}$ are independently selected from hydrogen, $NH_2$, halo, cyano, and $C_{1-6}$ alkyl;

$R_{Z1}$ and $R_{Z1a}$ selected from hydrogen, $C_{1-4}$alkyl, cyano, halo, $C_{1-4}$haloalkyl, $C_{1-4}$ haloalkoxy, $C_{1-4}$alkoxy, $C_{3-6}$cycloalkyl and $-O-C_{3-6}$cycloalkyl, wherein $C_{3-6}$cycloalkyl and $-O-C_{3-6}$cycloalkyl are optionally substituted by one or more of halo, methyl or methoxy;

$R_{Z2}$ and $R_{Z2a}$ are selected from hydrogen, $C_{1-4}$alkyl, cyano, halo, $NH_2$ and $C_{1-4}$alkoxy;

$R_{Z3a}$ is selected from hydrogen, $C_{1-4}$alkyl, cyano, halo, $NH_2$ and $C_{1-4}$alkoxy;

$R_{Zi1b}$ is selected from hydrogen, $C_{1-4}$alkyl, cyano, halo, $NH_2$ and $C_{1-4}$alkoxy;

$R_{Zi2e}$ is selected from hydrogen, $C_{1-4}$alkyl, cyano, halo, $NH_2$ and $C_{1-4}$alkoxy;

$R_{Y5N}$ and $R_{Z2N}$ are selected from hydrogen or $C_{1-4}$alkyl;

$R_{Z9}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z10}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z11}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z12}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z13}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z14}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z15}$ is selected from hydrogen, halo, cyano, $C_{1-4}$ alkyl, $C_{1-4}$ haloalkyl, $C_{1-4}$alkoxy, $C_{1-4}$ haloalkoxy;

$R_{Z16}$ is selected from hydrogen, halo, cyano, $C_{1-4}$ alkyl, $C_{1-4}$ haloalkyl, $C_{1-4}$alkoxy, $C_{1-4}$ haloalkoxy;

$A_1$ is selected from $CR_{12}$ and N;
$A_2$ is selected from $CR_{13}$ and N;
$A_5$ is selected from $CR_{16}$ and N;
$A_6$ is selected from $CR_{17}$ and N;
$A_7$ is selected from $CR_{18}$ and N;
$A_8$ is selected from $CR_{19}R_{20}$ and $NR_{21}$;
$A_9$ is selected from $CR_{22}R_{23}$ and $NR_{24}$;
$A_{11}$ is selected from $CR_{28}R_{29}$ and $NR_{30}$;

$R_{12}$ is selected from hydrogen, halo, cyano, $C_{1-4}$ alkyl, $C_{1-4}$ haloalkyl, $C_{1-4}$alkoxy, $C_{1-4}$ haloalkoxy (e.g. hydrogen, halo, cyano and $C_{1-4}$ alkyl);

$R_{13}$ is selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano, methoxy and methyl);

$R_{16}$ and $R_{18}$ are selected from hydrogen, halo, cyano, $C_{1-4}$ alkyl, $C_{1-4}$ alkoxy, $C_{1-4}$haloalkyl, $C_{1-4}$haloalkoxy, $C_{3-4}$cycloalkyl, a 3- to 4-membered heterocyclyl and $C_{3-4}$-cycloalkoxy;

$R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, phenyl, a 5- or 6-membered or heteroaryl, $C_{3-6}$cycloalkyl, $-O-C_{3-6}$cycloalkyl, heterocyclyl, $-O$-heterocyclyl (carbon-linked), $-(OCH_2CH_2)_m-OCH_3$ wherein m is an integer from 1 to 6, $NR_qR_r$, wherein $R_q$ and $R_r$ are each independently hydrogen, $C_{1-5}$ alkyl, $C_{3-6}$cycloalkyl, a 3- to 6-membered carbon-linked heterocyclyl, or $R_q$ and $R_r$ are linked together such that, together with the nitrogen atom to which they are attached, they form a 3- to 6-membered heterocyclic ring; wherein any $C_{1-5}$alkyl, $C_{1-4}$ alkoxy, $C_{2-4}$alkenyl, $C_{2-4}$alkynyl, phenyl, 5- or 6-membered or heteroaryl, $C_{3-6}$cycloalkyl, $-O-C_{3-6}$cycloalkyl, heterocyclyl or $-O-$heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ea}R_{1fa}$ or $-S(O)_{0-2}R_{1ea}R_{1fa}$, wherein $R_{1ea}$ and $R_{1fa}$ are H or $C_{1-2}$alkyl;

$R_{19}$ and $R_{20}$, $R_{25}$ and $R_{26}$ are selected from hydrogen, halo, cyano and $C_{1-4}$ alkyl;

$R_{22}$ and $R_{23}$ are selected from hydrogen, halo, cyano, $C_{1-4}$ alkyl, $C_{1-4}$ haloalkyl, $C_{1-4}$ alkoxy, $C_{1-4}$ haloalkoxy (e.g. hydrogen, halo, cyano and methyl;

$R_{28}$ and $R_{29}$ are selected from hydrogen, halo, methoxy and methyl;

$R_{21}$, $R_{24}$ and $R_{30}$ are hydrogen or $C_{1-4}$alkyl.

3. A compound according to paragraph 1 or 2, wherein X is selected from:

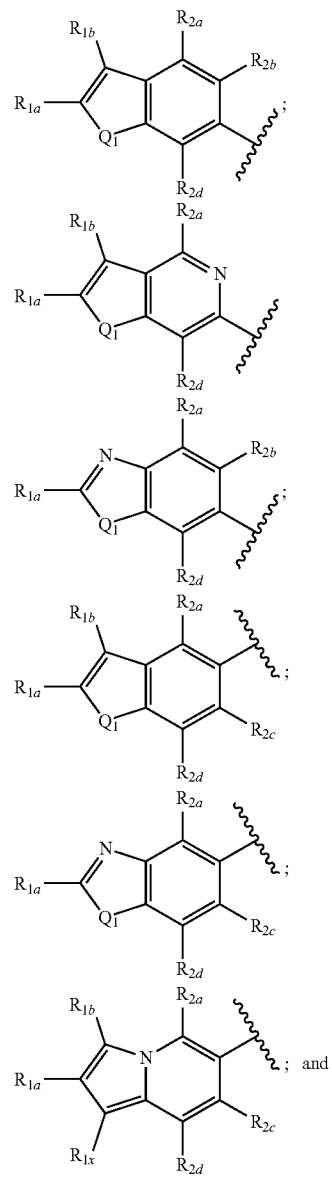

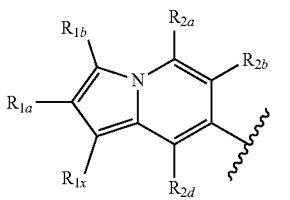

wherein $Q_1$, $R_{1a}$, $R_{1b}$, $R_{1x}$, $R_{2a}$, $R_{2b}$, $R_{2c}$, $R_{2d}$ are as defined in paragraph 1.

3. A compound according to paragraph 1 2, or a pharmaceutically acceptable salt thereof, wherein X is selected from:

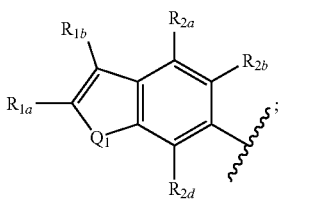

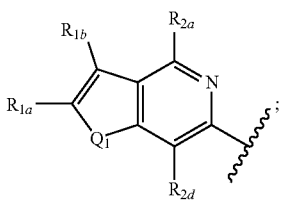

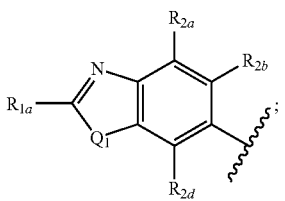

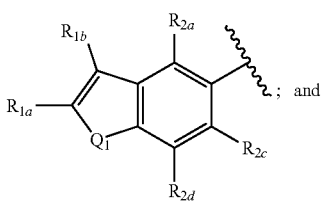

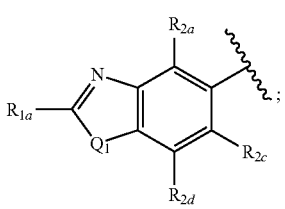

wherein $Q_1$, $R_{1a}$, $R_{1b}$, $R_{2a}$, $R_{2b}$, $R_{2c}$ and $R_{2d}$ are as defined in paragraph 1.

4. A compound according to any one of the preceding paragraphs, or a pharmaceutically acceptable salt thereof, wherein X is selected from:

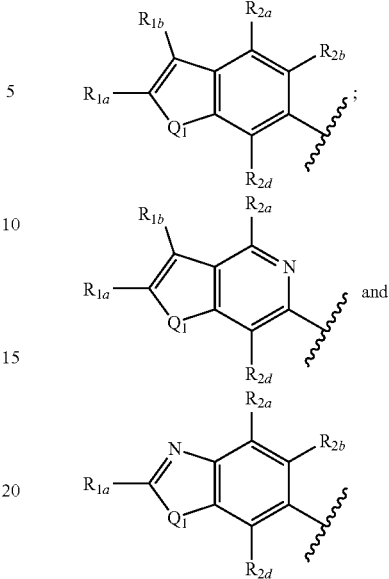

wherein $Q_1$, $R_{1a}$, $R_{1b}$, $R_{2a}$, $R_{2b}$ and $R_{2d}$ are as defined in paragraph 1.

5. A compound according to any one of the preceding paragraphs, or a pharmaceutically acceptable salt thereof, wherein X is:

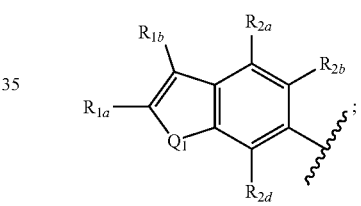

wherein $Q_1$, $R_{a1}$, $R_{1b}$, $R_{2a}$, $R_{2b}$ and $R_{2d}$ are as defined in paragraph 1.

6. A compound according to any one of paragraphs 1 to 3, or a pharmaceutically acceptable salt thereof, wherein $Q_1$ is selected from NH or N—$C_{1-4}$alkyl.

7. A compound according to paragraph 1 or paragraph 2, or a pharmaceutically acceptable salt thereof, wherein X is selected from:

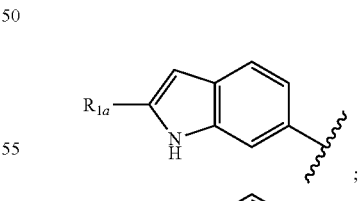

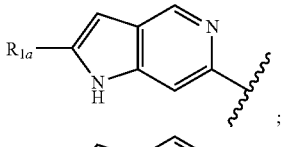

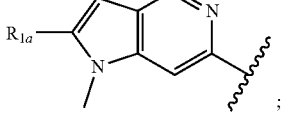

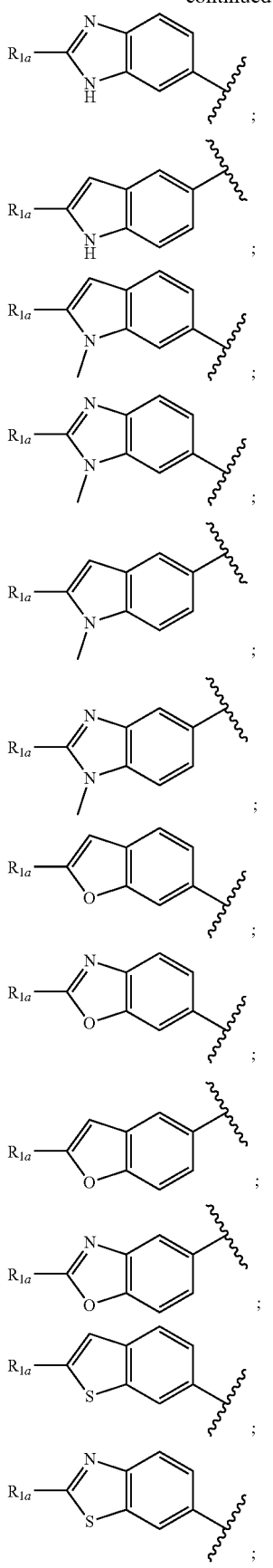

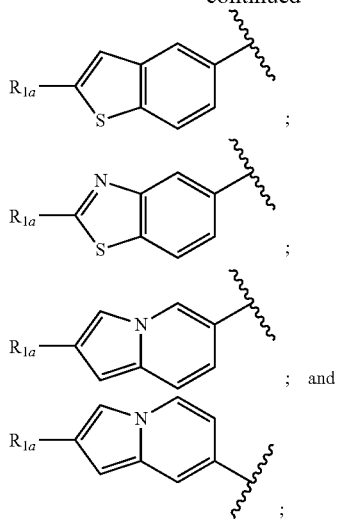

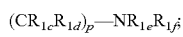

wherein $R_{1a}$ is as defined in paragraph 1 or paragraph 2.

8. A compound according to any preceding paragraph, or a pharmaceutically acceptable salt thereof, wherein $R_{1a}$ is selected from:
(i) $C_{1-4}$alkyl optionally substituted by halo, cyano, hydroxy, $C_{3-6}$cycloalkyl, a 3 to 6 membered heterocyclyl, $C_{1-4}$alkoxy, $C_{1-4}$haloalkoxy, aryl or heteroaryl; or
(ii) a group of the formula:

$$(CR_{1c}R_{1d})_p\text{—}NR_{1e}R_{1f};$$

wherein
p is an integer selected from 1 or 2;
$R_{1c}$ and $R_{1d}$ are independently selected from:
(i) hydrogen (including deuterium),
(ii) $C_{1-3}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —S(O)$_{0-2}$$R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally substituted with halo, cyano or hydroxy;
(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$ alkoxy, halo, $C_{1-2}$haloalkoxy, $NR_{1ca}R_{1da}$ or —S(O)$_{0-2}R_{1ca}R_{1da}$, wherein $R_{1ca}$ and $R_{1da}$ are H or $C_{1-2}$alkyl; and;
(iv) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{1ca}R_{1da}$ or —S(O)$_{0-2}R_{1ca}R_{1da}$, wherein $R_{1ca}$ and $R_{1da}$ are H or $C_{1-2}$alkyl;
$R_{1e}$ and $R_{1f}$ are each independently selected from:
(i) hydrogen (including deuterium);
(ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1fa}$ or —S(O)$_{0-2}R_{1ea}R_{1fa}$, wherein $R_{1ea}$ and $R_{1fa}$ are H or $C_{1-2}$alkyl;
(iii) a group with the formula:

—$(CR_{1g}R_{1h})_q$-$T_1$ wherein:

q is 0, 1, 2 or 3;

$R_{1g}$ and $R_{1h}$ are independently selected from:
a) hydrogen (including deuterium); or
b) $C_{1-3}$alkyl which is optionally substituted by one more substituents selected from cyano, oxo, hydroxy, $C_{1-3}$alkoxy, halo, $C_{1-4}$haloalkoxy, —O—$C_{3-4}$cycloalkyl, wherein —O—$C_{3-4}$cycloalkyl is optionally substituted with halo, cyano or hydroxy, $NR_{1ca}R_{1da}$ or —$S(O)_{0-2}$$R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl;
c) or $R_{1g}$ and $R_{1h}$ are optionally linked together such that, together with the carbon atom to which they are attached, they form a 3- to 6-membered cycloalkyl or heterocyclic ring which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

(iv) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

9. A compound according to any preceding paragraph, or a pharmaceutically acceptable salt thereof, wherein $R_{1a}$ is a group of the formula:

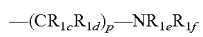—$(CR_{1c}R_{1d})_p$—$NR_{1e}R_{1f}$ wherein p is an integer selected from 1 or 2;

$R_{1c}$ and $R_{1d}$ are independently selected from:
(i) hydrogen (including deuterium),
(ii) $C_{1-3}$alkyl which is optionally substituted by one more substituents selected from cyano, oxo, hydroxy, $C_{1-3}$alkoxy, halo, $C_{1-43}$haloalkoxy, —O—$C_{3-4}$cycloalkyl, or $NH_2$; wherein —O—$C_{3-6}$cycloalkyl is optionally substituted with halo, cyano or hydroxy,
(iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{1e}$ is selected from:
(i) hydrogen (including deuterium);
(ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

and $R_{1f}$ is selected from:
(i) $C_{1-6}$alkyl which is optionally substituted by one more substituents selected from cyano, oxo, hydroxy, $C_{1-2}$alkoxy, halo, $C_{1-2}$haloalkoxy and $NH_2$;
(ii) a group with the formula:

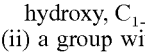—$(CR_{1g}R_{1h})_q$-$T_1$ wherein:

q is 1, 2 or 3;

$R_{1g}$ and $R_{1h}$ are independently selected from:
a) hydrogen (including deuterium); or
b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;
c) or $R_{1g}$ and $R_{1h}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$-haloalkyl, cyano, hydroxy, $C_{1-2}$alkoxy, halo, $C_{1-2}$-haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$ alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $C_{3-6}$ cycloalkyl, $NR_{3t}R_{4t}$ or —$S(O)_{0-2}R_{3t}R_{4t}$, wherein $R_{3t}$ and $R_{4c}$ are H or $C_{1-2}$ alkyl;

(iii) or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$ haloalkyl, $C_{3-6}$cycloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring; which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or $—S(O)_{0-2}R_{1k}R_{1l}$, wherein $R_{1k}$ and $R_{1l}$ are H or $C_{1-4}$alkyl.

10. A compound according to any preceding paragraph, or a or a pharmaceutically acceptable salt thereof, wherein $R_{1a}$ is a group of the formula:

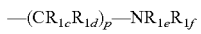

wherein
p is an integer selected from 1 or 2;
$R_{1c}$ and $R_{1d}$ are independently selected from:
  (i) hydrogen (including deuterium),
  (ii) $C_{1-3}$alkyl which is optionally substituted by one more substituents selected from cyano, oxo, hydroxy, $C_{1-3}$alkoxy, halo, $C_{1-3}$haloalkoxy, $—O—C_{3-4}$cycloalkyl, or $NH_2$; wherein $—O—C_{3-6}$cycloalkyl is optionally substituted with halo, cyano or hydroxy,
  (iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;
$R_{1e}$ is selected from:
  (i) hydrogen (including deuterium);
  (ii) $C_{1-3}$alkyl which is optionally substituted by one more substituents selected from cyano, oxo, hydroxy, $C_{1-2}$alkoxy, halo, $C_{1-2}$haloalkoxy and $NH_2$;
$R_{1f}$ is a group with the formula:

wherein:
q is 1, 2 or 3;
$R_{1g}$ and $R_{1h}$ are independently selected from:
a) hydrogen (including deuterium); or
b) $C_{1-3}$alkyl which is optionally substituted by one more substituents selected from cyano, oxo, hydroxy, $C_{1-4}$alkoxy, halo, $C_{1-4}$haloalkoxy, $—O—C_{3-6}$cycloalkyl, wherein $—O—C_{3-6}$cycloalkyl is optionally substituted with halo, cyano or hydroxy;
c) or $R_{1g}$ and $R_{1h}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$-haloalkyl, cyano, hydroxy, $C_{1-2}$alkoxy, halo or $C_{1-2}$-haloalkoxy;
and $T_1$ is selected from halo, $C_{1-4}$alkyl, $C_{1-4}$haloalkyl, cyano, hydroxy, $NR_{1t}R_{2t}$ or $—S(O)_{0-2}R_{1t}R_{2t}$ (wherein $R_{11}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $C_{3-6}$cycloalkyl, $NR_{3t}R_{4t}$ or $—S(O)_{0-2}R_{3t}R_{4t}$, wherein $R_{3t}$ and $R_{4t}$ are H or $C_{1-2}$alkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or $—S(O)_{0-2}R_{1k}R_{1l}$, wherein $R_{1k}$ and $R_{1l}$ are H or $C_{1-4}$alkyl.

11. A compound according to any preceding paragraph, or a pharmaceutically acceptable salt thereof, wherein $R_{1a}$ is a group of the formula:

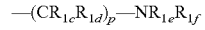

wherein
p is an integer selected from 1 or 2;
$R_{1c}$ and $R_{1d}$ are independently selected from:
  (i) hydrogen (including deuterium),
  (ii) $C_{1-3}$alkyl which is optionally substituted by one more substituents selected from cyano, oxo, hydroxy, $C_{1-3}$alkoxy, halo, $C_{1-3}$haloalkoxy, $—O—C_{3-4}$cycloalkyl, or $NH_2$; wherein $—O—C_{3-6}$cycloalkyl is optionally substituted with halo, cyano or hydroxy,
  (iii) or $R_{1c}$ and $R_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;
$R_{1e}$ is selected from:
  (i) hydrogen (including deuterium);
  (ii) $C_{1-3}$alkyl which is optionally substituted by one more substituents selected from cyano, oxo, hydroxy, $C_{1-2}$alkoxy, halo, $C_{1-2}$haloalkoxy and $NH_2$;
$R_{1f}$ is a group with the formula:

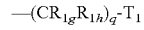

wherein:
q is 1 or 2;
$R_{1g}$ and $R_{1h}$ are independently selected from:
a) hydrogen (including deuterium); or
b) $C_{1-3}$alkyl, which is optionally substituted by one more substituents selected from cyano, oxo, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy;

and $T_1$ is selected from $C_{1-4}$alkyl, $C_{3-8}$cycloalkyl, aryl, heterocyclyl, heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$), wherein $R_{1i}$ and $R_{1j}$ are H or $C_{1-2}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{3-6}$cycloalkyl, cyano, hydroxy, $C_{1-2}$alkoxy, halo, $C_{1-2}$haloalkoxy, $NR_{1i}R_{1j}$; or —$S(O)_{0-2}R_{1i}R_{1j}$, wherein $R_{1i}$ and $R_{1j}$ are H or $C_{1-2}$alkyl;

wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

12. A compound according to any preceding paragraph, or a pharmaceutically acceptable salt thereof, wherein $R_{1a}$ is a group of the formula:

—$(CR_{1c}R_{1d})_p$—$NR_{1e}R_{1f}$ p is an integer selected from 1 or 2;

$R_{1c}$ and $R_{1d}$ are independently selected from:
(i) hydrogen (including deuterium) or
(ii) $C_{1-3}$alkyl which is optionally substituted by one more substituents selected from cyano, oxo, hydroxy, $C_{1-2}$alkoxy, halo, $C_{1-2}$haloalkoxy, —O—$C_3$cycloalkyl;

$R_{1e}$ is selected from hydrogen (including deuterium) or $C_{1-2}$alkyl; and $R_{1f}$ is a group with the formula:

—$(CR_{1g}R_{1h})_q$-$T_1$ wherein:
q is 1 or 2;
$R_{1g}$ and $R_{1h}$ are independently selected from:
a) hydrogen (including deuterium); or
b) $C_{1-2}$alkyl, which is optionally substituted by one more substituents selected from cyano, oxo, hydroxy, $C_{1-2}$alkoxy, halo or $C_{1-2}$haloalkoxy;

and $T_1$ is selected from $C_{1-4}$alkyl, $C_{3-8}$cycloalkyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy or $C_{3-6}$cycloalkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$-haloalkyl, $C_{3-6}$cycloalkyl, cyano, hydroxy, $C_{1-2}$alkoxy, halo or $C_{1-2}$haloalkoxy; wherein any wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

13. A compound according to any preceding paragraph, or a pharmaceutically acceptable salt thereof, wherein $R_{1a}$ is a group of the formula:

—$(CR_{1c}R_{1d})_p$—$NR_{1e}R_{1f}$ wherein
p is an integer selected from 1 or 2;
$R_{1c}$ and $R_{1d}$ are independently selected from hydrogen (including deuterium) or $C_{1-2}$alkyl;
$R_{1e}$ is selected from hydrogen (including deuterium) or $C_{1-2}$alkyl; and
$R_{1f}$ is a group with the formula:

—$(CR_{1g}R_{1h})_q$-$T_1$ wherein:
q is 1 or 2;
$R_{1g}$ and $R_{1h}$ are independently selected from hydrogen (including deuterium) or $C_{1-2}$alkyl;

and $T_1$ is selected from $C_{1-4}$alkyl, $C_{3-4}$cycloalkyl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

14. A compound according to any preceding paragraph, or a pharmaceutically acceptable salt thereof, wherein $R_{1a}$ is a group of the formula:

—$(CR_{1c}R_{1d})_p$—$NR_{1e}R_{1f}$ wherein
p is 1;
$R_{1c}$ and $R_{1d}$ are independently selected from hydrogen (including deuterium) or $C_{1-2}$alkyl;
$R_{1e}$ is selected from hydrogen (including deuterium) or $C_{1-2}$alkyl; and R$_{1f}$ is a group with the formula:

—(CR$_{1g}$R$_{1h}$)$_q$-T$_1$ wherein:
q is 1 or 2;
R$_{1g}$ and R$_{1h}$ are independently selected from hydrogen (including deuterium) or C$_{1-2}$alkyl;
and T$_1$ is selected from C$_{3-4}$cycloalkyl, heterocyclyl, a mono- or bicyclic heteroaryl, a spirocyclic carbocyclic or heterocyclic ring system, a bridged C$_{3-8}$cycloalkyl, a bridged bicyclic C$_{5-12}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy or C$_{3-6}$cycloalkyl;

or R$_{1e}$ and R$_{1f}$ are linked such that, together with the nitrogen atom to which they are attached, they form a mono- or bicyclic-heterocyclic ring, which is optionally substituted by one or more substituents selected from C$_{1-2}$alkyl, C$_{1-2}$haloalkyl, C$_{3-6}$cycloalkyl, cyano, hydroxy, C$_{1-2}$alkoxy, halo or C$_{1-2}$haloalkoxy, and/or the mono- or bicyclic heterocyclic ring formed by R$_{1e}$ and R$_{1f}$ is optionally spiro-fused to a C$_{3-6}$cycloalkyl or a heterocyclic ring; which in turn is optionally substituted by one or more substituents selected from C$_{1-2}$alkyl, C$_{1-2}$-haloalkyl, C$_{3-6}$cycloalkyl, cyano, hydroxy, C$_{1-2}$alkoxy, halo or C$_{1-2}$haloalkoxy, wherein any alkyl, alkoxy or C$_{3-6}$cycloalkyl is further optionally substituted by one or more substituents selected from cyano, hydroxy, halo, NR$_{1k}$R$_{1l}$ or —S(O)$_{0-2}$R$_{1k}$R$_{1l}$, wherein R$_{1k}$ and R$_{1l}$ are H or C$_{1-4}$alkyl.

15. A compound according to any preceding paragraph, or a pharmaceutically acceptable salt thereof, wherein R$_{1a}$ is a group of the formula:

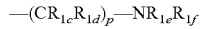
—(CR$_{1c}$R$_{1d}$)$_p$—NR$_{1e}$R$_{1f}$ wherein
R$_{1c}$ and R$_{1d}$ are independently selected from hydrogen (including deuterium) or C$_{1-2}$alkyl;
R$_{1e}$ is selected from hydrogen (including deuterium) or C$_{1-2}$alkyl; and
R$_{1f}$ is a group with the formula:

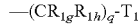
—(CR$_{1g}$R$_{1h}$)$_q$-T$_1$ wherein:
q is 1;
R$_{1g}$ and R$_{1h}$ are independently selected from hydrogen (including deuterium) or C$_{1-2}$alkyl;
and T$_1$ is selected from C$_{3-4}$cycloalkyl, heterocyclyl, a spirocyclic carbocyclic or heterocyclic ring system, a bridged C$_{3-8}$cycloalkyl, a bridged bicyclic C$_{5-12}$cycloalkyl, or a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy or C$_{3-6}$cycloalkyl,
wherein any alkyl or alkoxy is optionally further substituted by one or more substituents selected from cyano, hydroxy or halo.

16. A compound according to any preceding paragraph, or a or a pharmaceutically acceptable salt thereof, wherein R$_{1a}$ is a group of the formula:

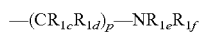
—(CR$_{1c}$R$_{1d}$)$_p$—NR$_{1e}$R$_{1f}$ wherein
p is 1;
R$_{1c}$ and R$_{1d}$ are independently selected from hydrogen (including deuterium) or C$_{1-2}$alkyl; and
R$_{1e}$ and R$_{1f}$ are linked such that, together with the nitrogen atom to which they are attached, they form a mono- or bicyclic-heterocyclic ring, which is optionally substituted by one or more substituents selected from C$_{1-2}$alkyl, C$_{1-2}$haloalkyl, C$_{3-6}$cycloalkyl, cyano, hydroxy, C$_{1-2}$alkoxy, halo or C$_{1-2}$haloalkoxy, and/or the mono- or bicyclic heterocyclic ring formed by R$_{1e}$ and R$_{1f}$ is optionally spiro-fused to a C$_{3-6}$cycloalkyl or a heterocyclic ring, which in turn is optionally substituted by one or more substituents selected from C$_{1-2}$alkyl, C$_{1-2}$haloalkyl, cyano, hydroxy, C$_{1-2}$alkoxy, halo or C$_{1-2}$haloalkoxy.

17. A compound according to any preceding paragraph, or a or a pharmaceutically acceptable salt thereof, wherein R$_{1a}$ is

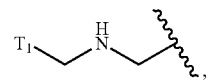

wherein T$_1$ is as defined in any of paragraphs 1 to 16.

18. A compound according to any preceding paragraph, wherein R$_{1a}$ is selected from methoxy;

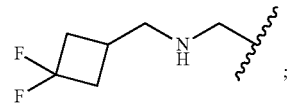
;

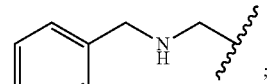
;

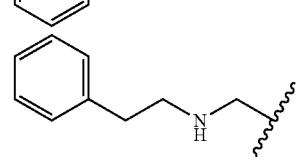
;

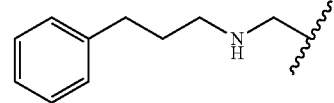
;

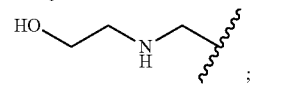
;

;

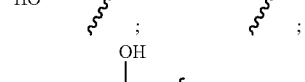
;

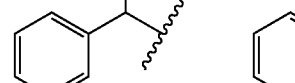
;

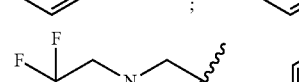
;

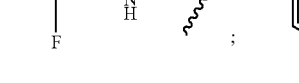
;

;

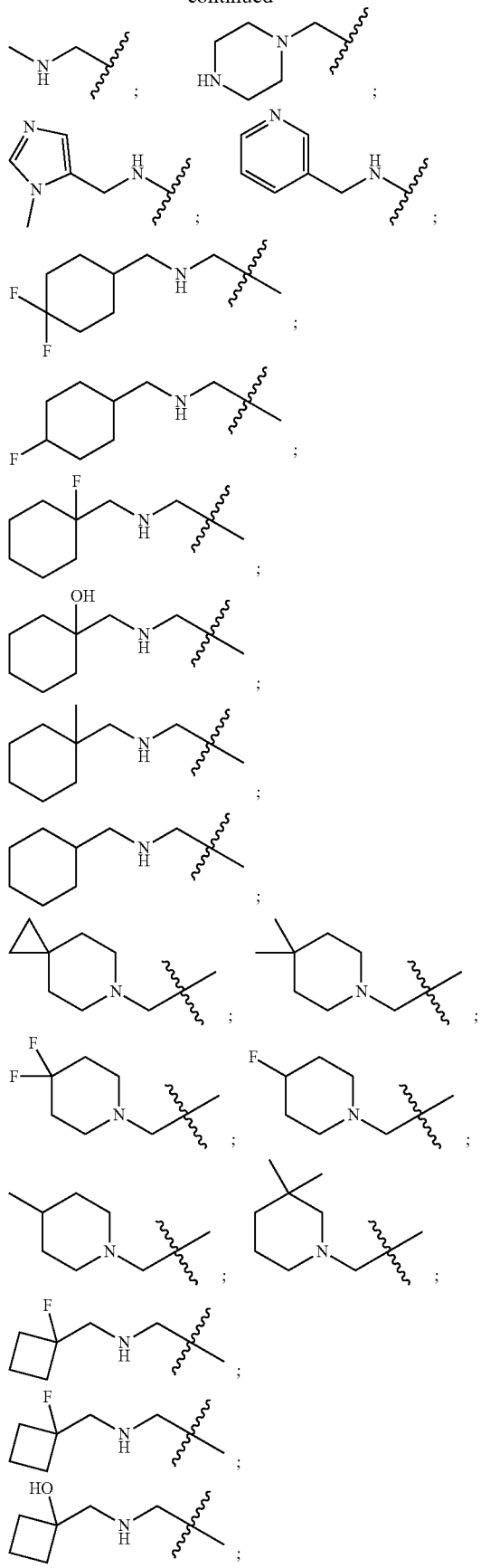
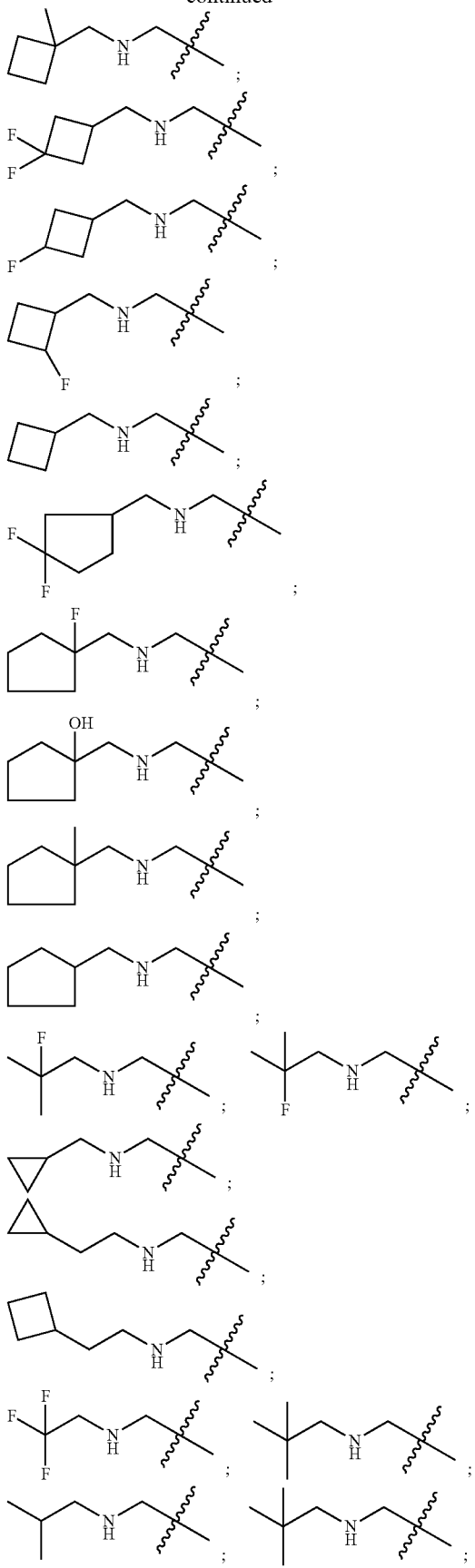

351 -continued

352 -continued

353
-continued
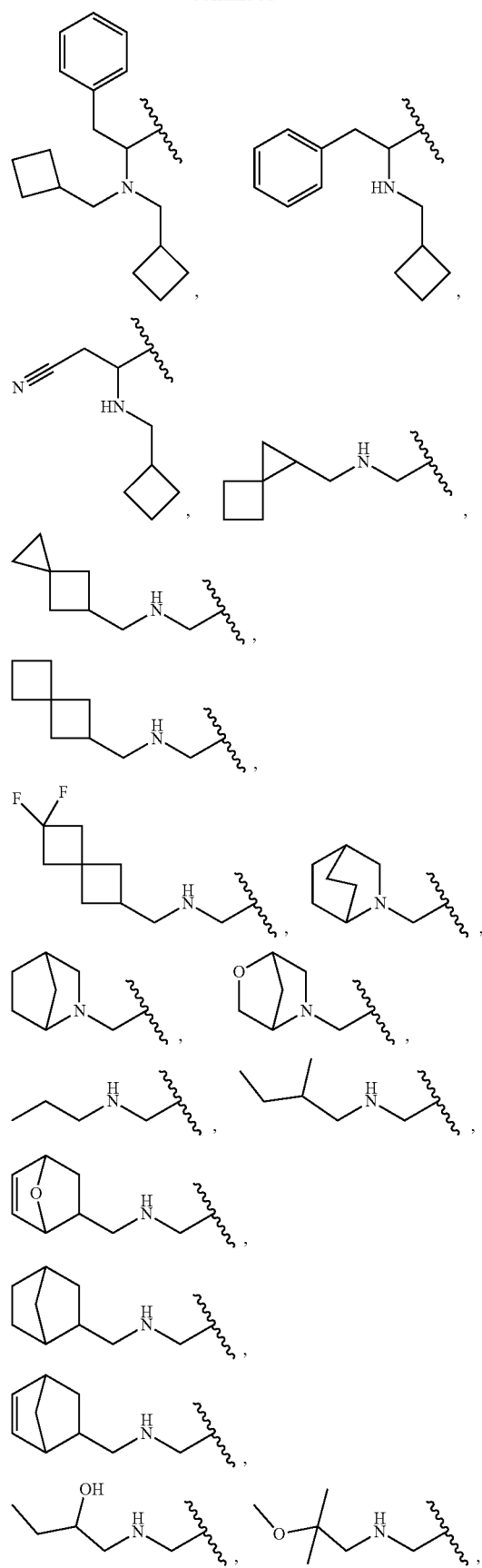
354
-continued
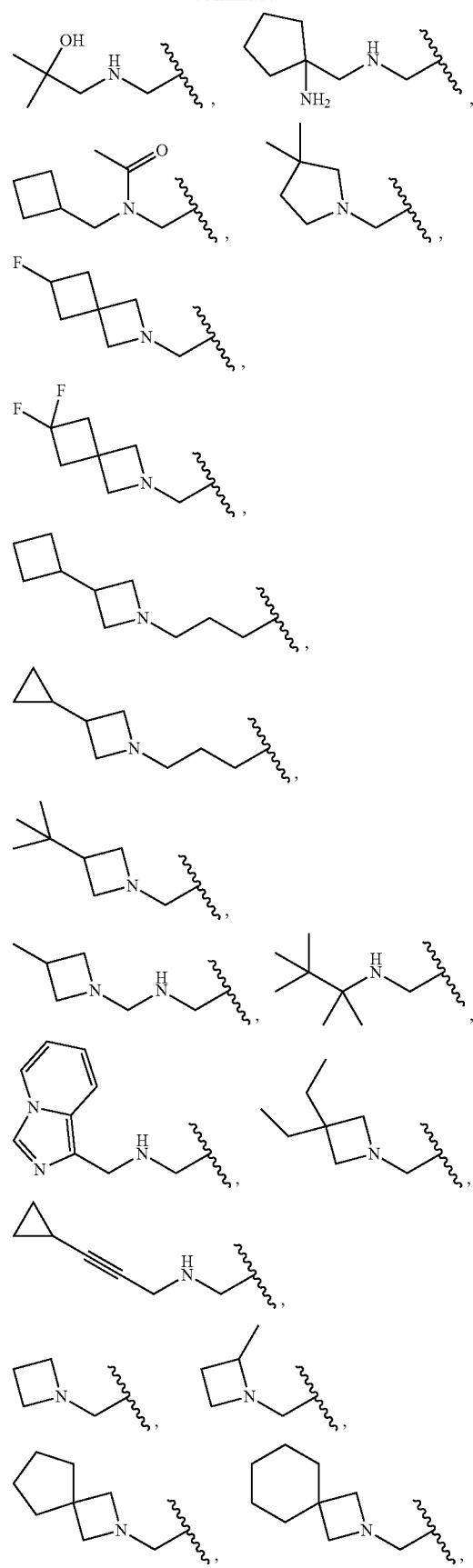

355
-continued
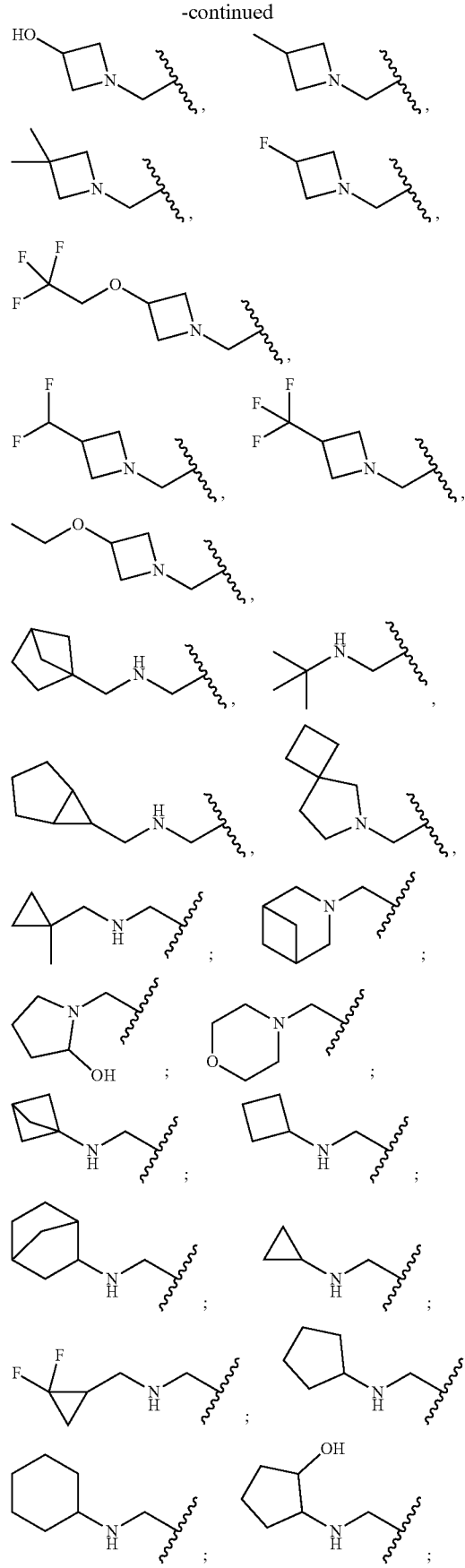
356
-continued
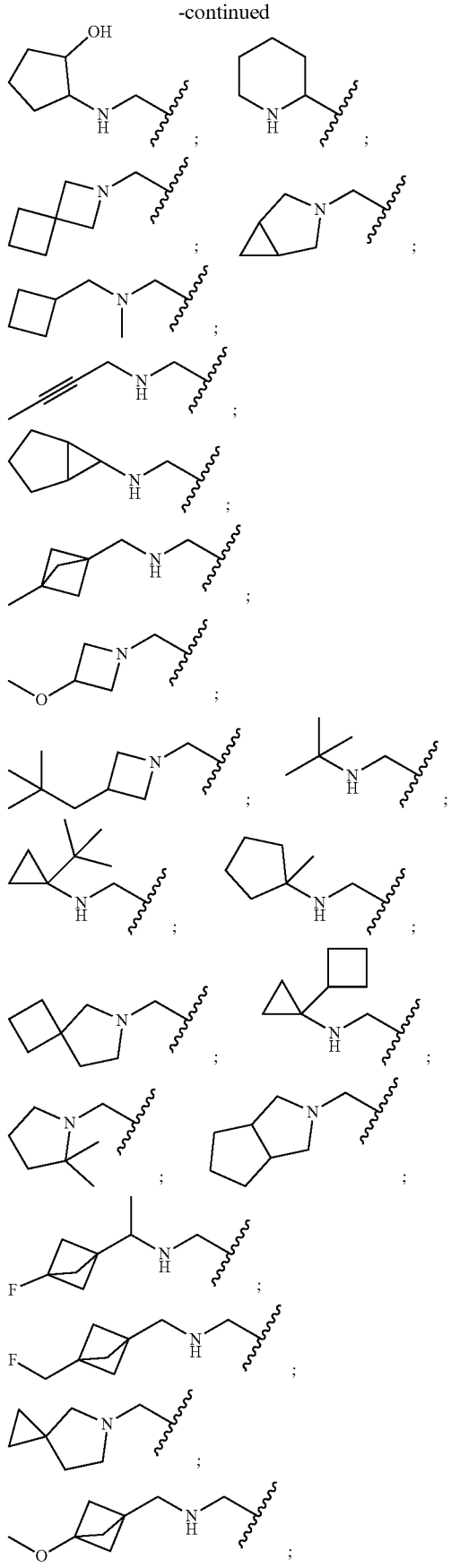

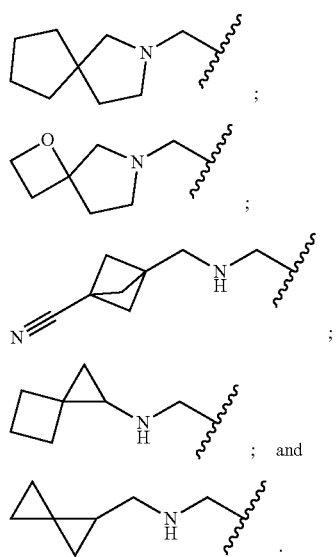
19. A compound according to any preceding paragraph, or a or a pharmaceutically acceptable salt thereof, wherein $R_{1a}$ is selected from:
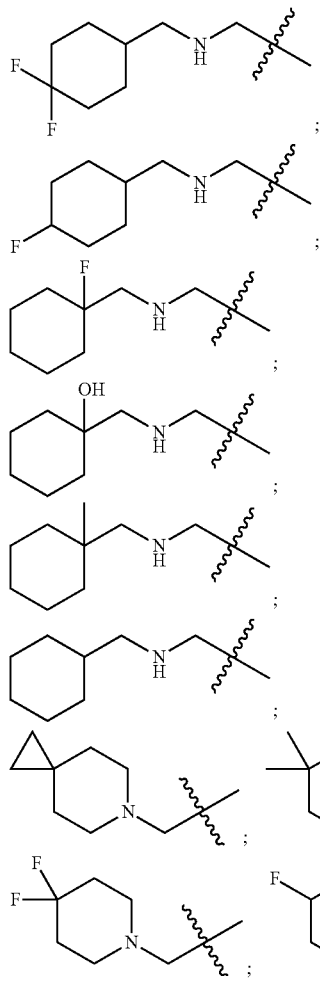
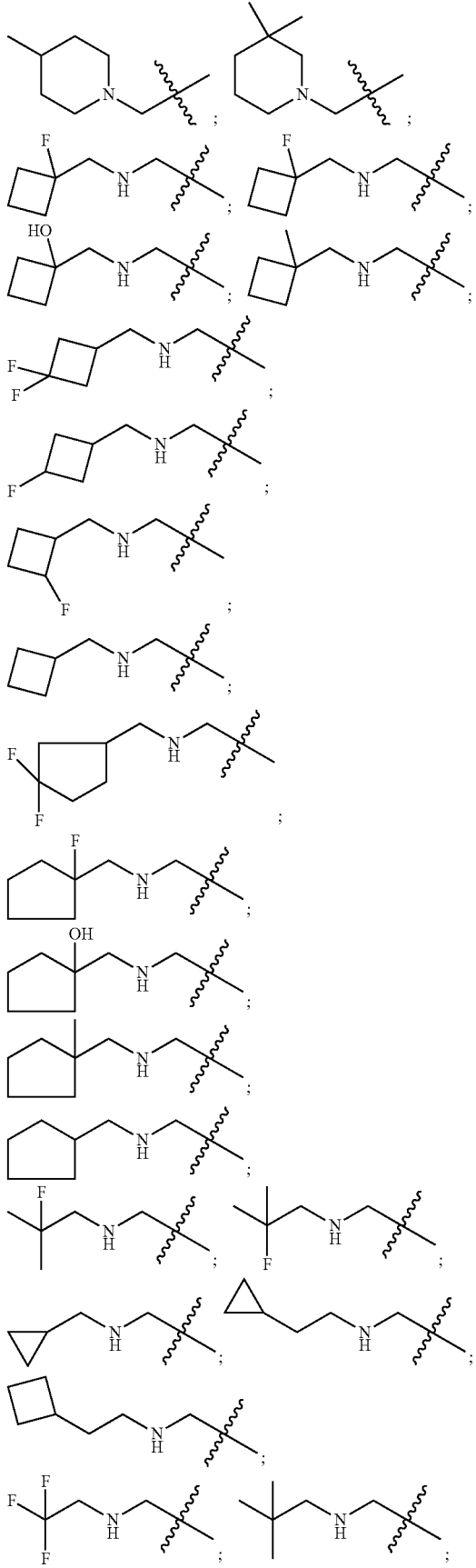

359
-continued
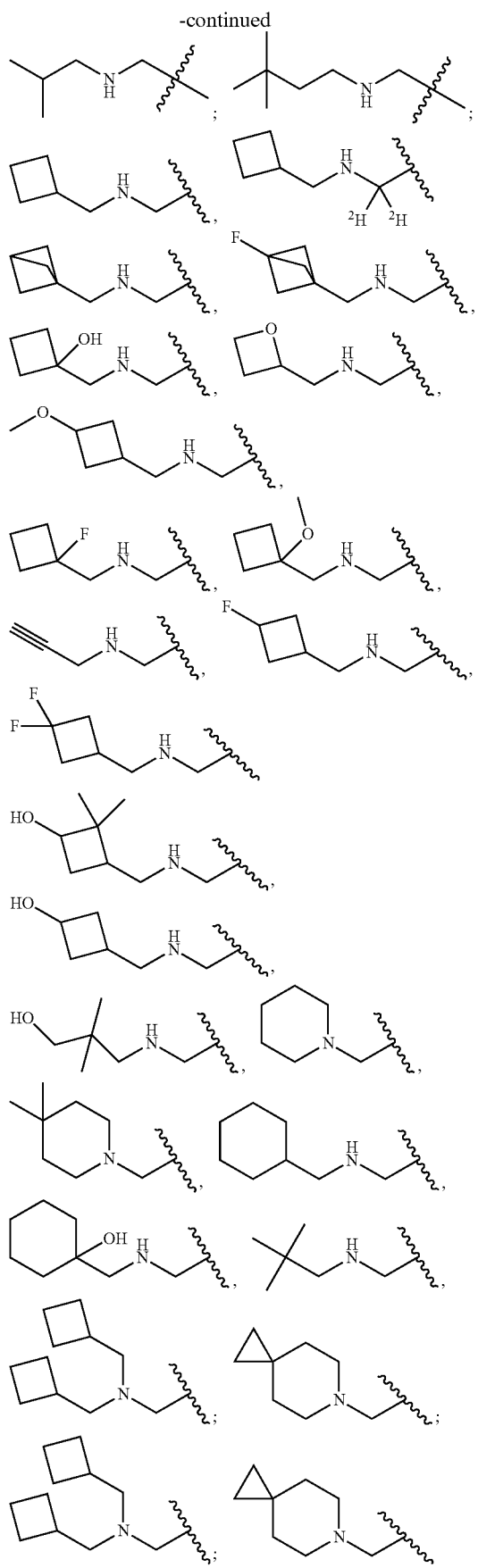
360
-continued
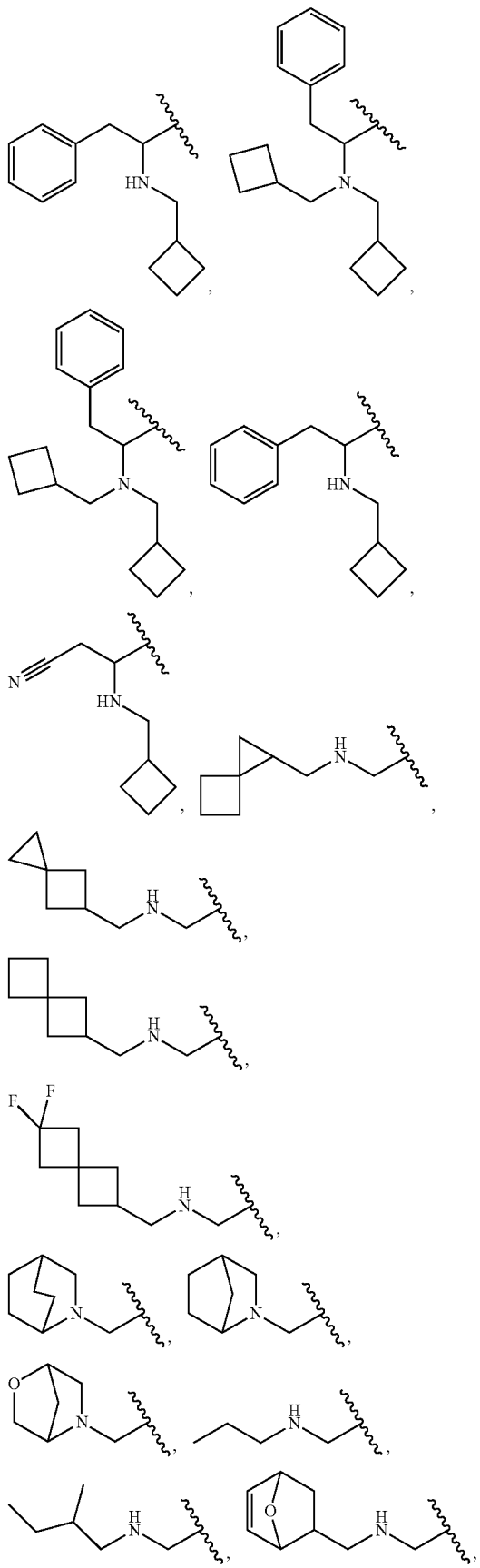

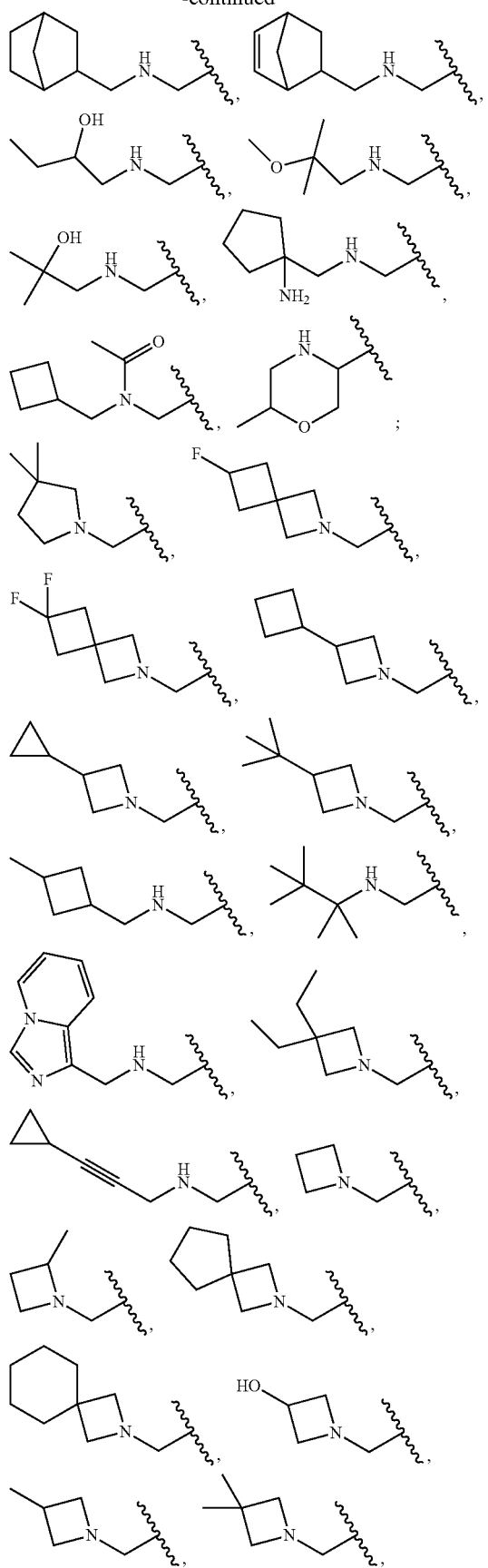
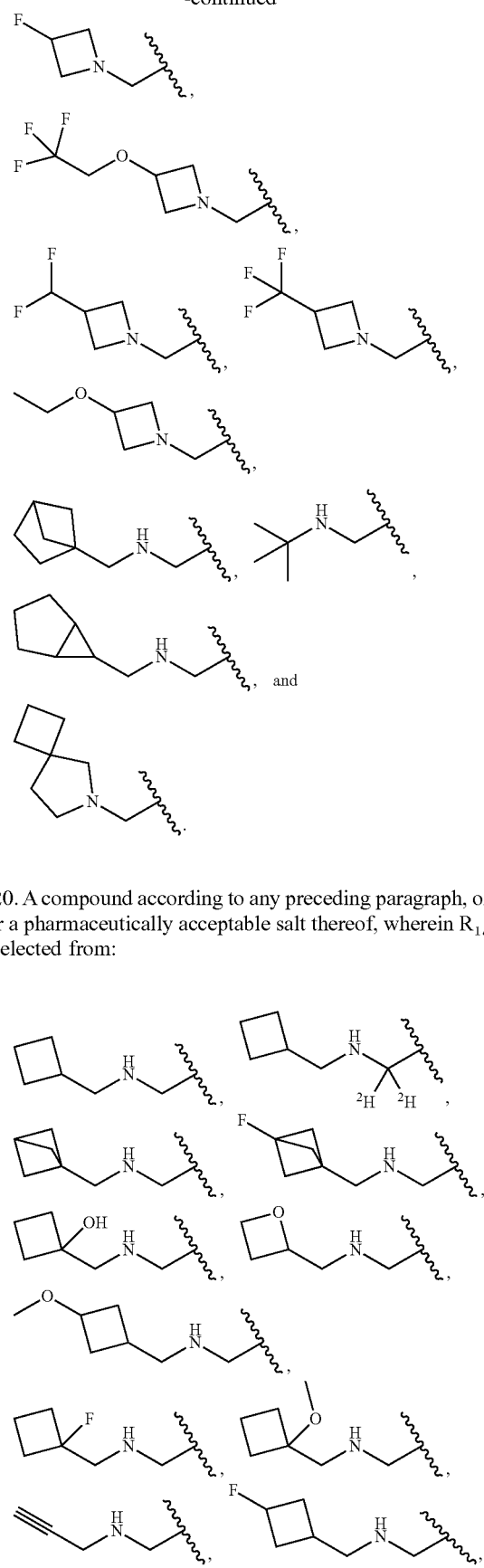
20. A compound according to any preceding paragraph, or a or a pharmaceutically acceptable salt thereof, wherein $R_{1a}$ is selected from:

363
-continued
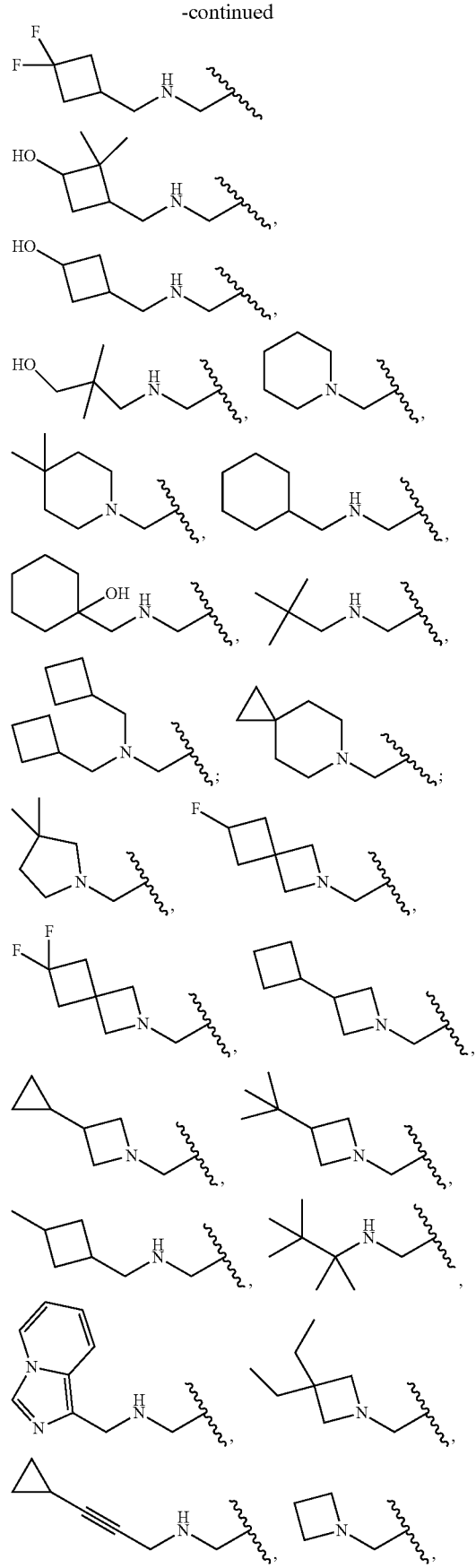
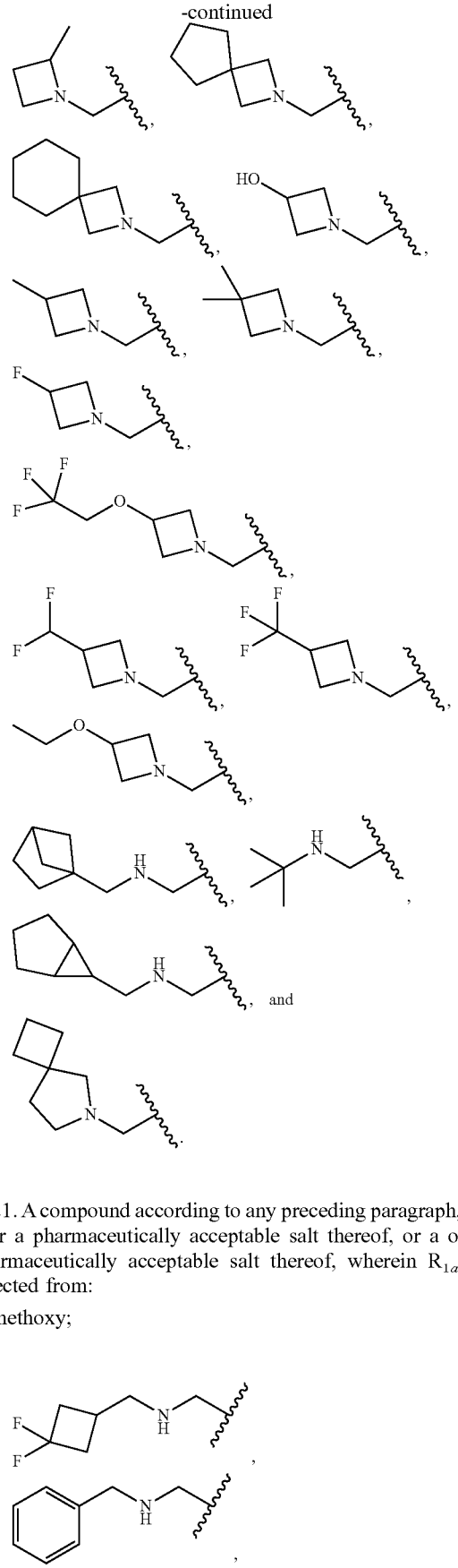
21. A compound according to any preceding paragraph, or a or a pharmaceutically acceptable salt thereof, or a or a pharmaceutically acceptable salt thereof, wherein $R_{1a}$ is selected from:
methoxy;
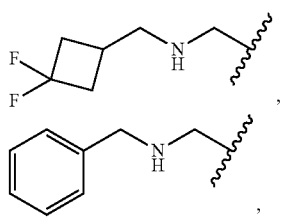

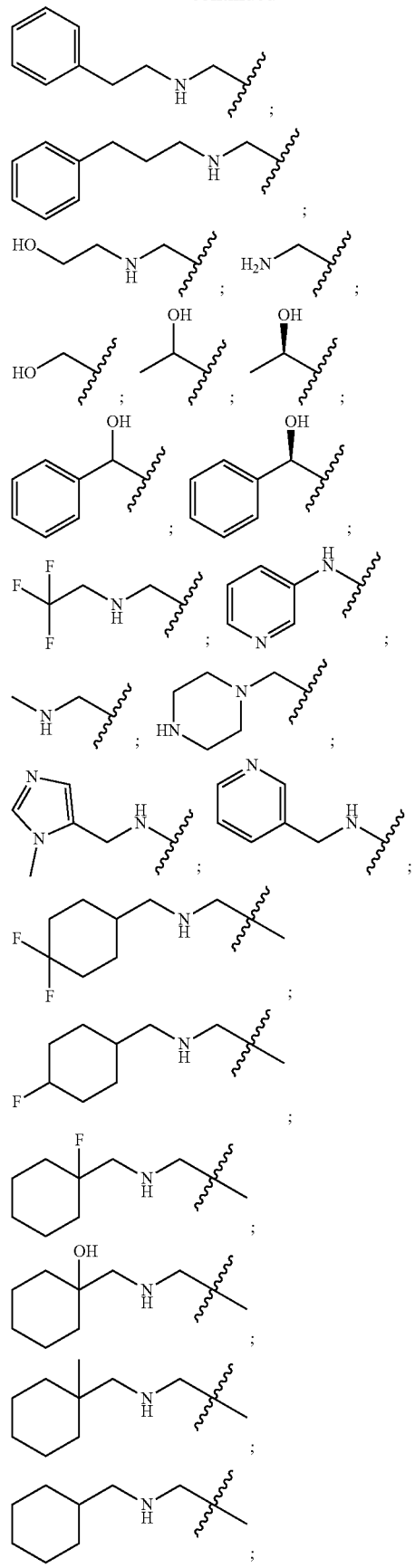
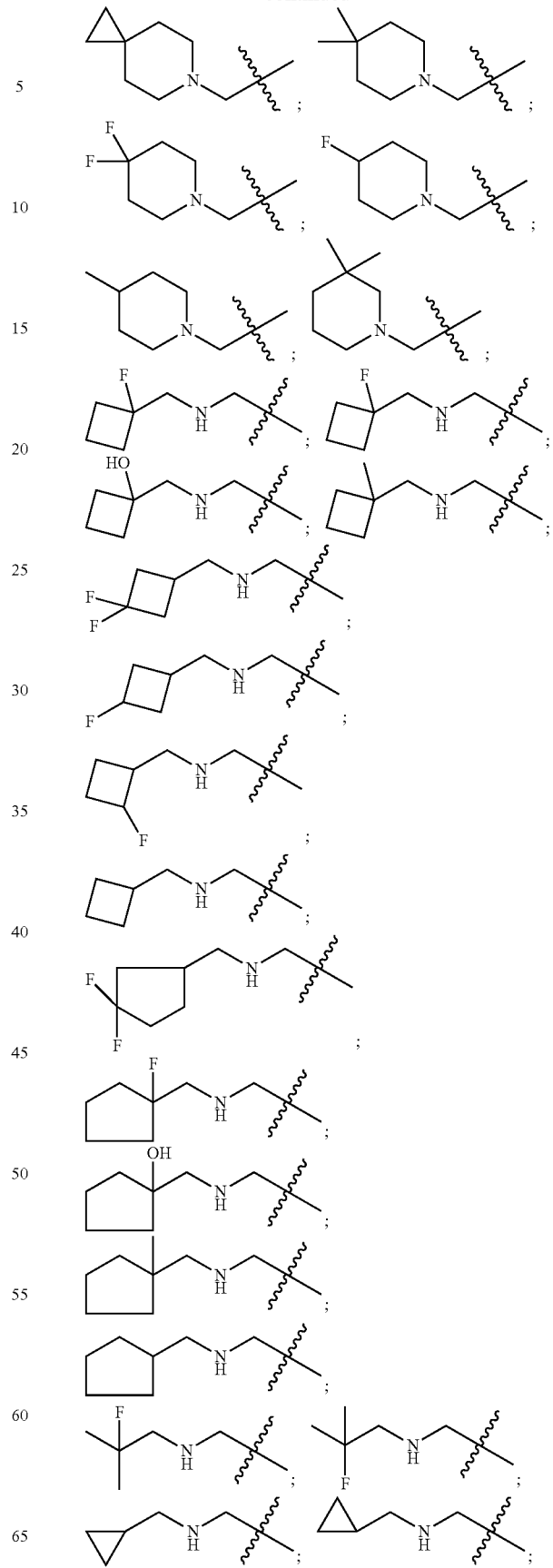

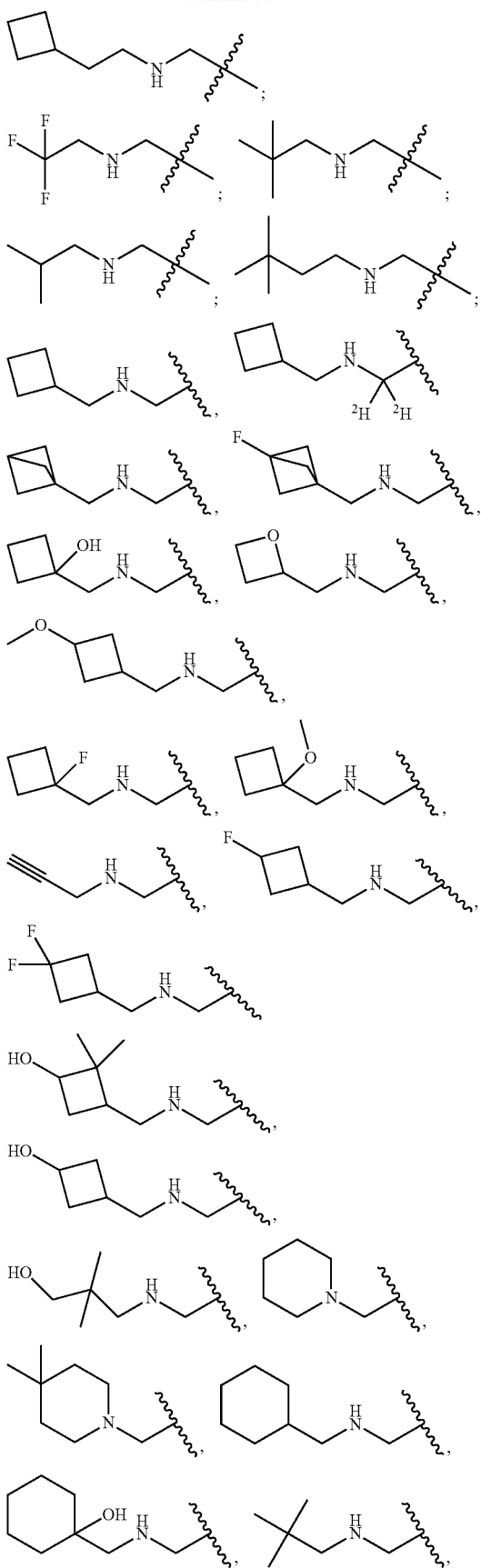
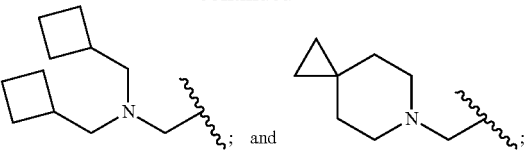

22. A compound according to any preceding paragraph, or a pharmaceutically acceptable salt thereof, wherein $R_{1b}$ is selected from hydrogen, halo or $C_{1-2}$ alkyl.

23. A compound according to any preceding paragraph, or a pharmaceutically acceptable salt thereof, wherein $R_{2a}$, $R_{2b}$, $R_{2c}$ and $R_{2d}$ are independently selected from hydrogen, cyano, halo or a group of the formula:

-$L_{2a}$-$L_{2b}$-$Q_2$ wherein
$L_{2a}$ is absent or $C_{1-3}$alkylene optionally substituted by $C_{1-2}$ alkyl or oxo;
$L_{2b}$ is absent or selected from O, S, N($R_n$), C(O), C(O)O, OC(O), C(O)N($R_n$), N($R_n$)C(O), N($R_n$)C(O)N($R_o$), wherein $R_n$ and $R_o$ are each independently selected from hydrogen or $C_{1-2}$alkyl; and
$Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, $C_{1-4}$alkyl, $NR_pR_q$, $OR_p$, $C(O)R_p$, wherein $R_p$ and $R_q$ are each independently selected from hydrogen or $C_{1-4}$alkyl.

24. A compound according to any preceding paragraph, or a pharmaceutically acceptable salt thereof, wherein $R_{2a}$, $R_{2b}$, $R_{2c}$ and $R_{2d}$ are independently selected from hydrogen, cyano, halo or a group of the formula:

-$L_{2a}$-$L_{2b}$-$Q_2$ wherein
$L_{2a}$ is absent or $C_{1-3}$alkylene optionally substituted by $C_{1-2}$ alkyl;
$L_{2b}$ is absent or selected from O, S, N($R_n$), C(O); and
$Q_2$ is hydrogen, cyano, $C_{1-6}$alkyl, $C_{3-6}$cycloalkyl, aryl, heterocyclyl or heteroaryl, each of which is optionally substituted by one or more substituents selected from halo, trifluoromethyl, trifluoromethoxy, amino, cyano and hydroxy.

25. A compound according to any preceding paragraph, or a pharmaceutically acceptable salt thereof, wherein $R_{2a}$, $R_{2b}$, $R_{2c}$ and $R_{2d}$ are independently selected from hydrogen, cyano, $C_{1-6}$ alkoxy, $C_{1-6}$ haloalkoxy, halo, $C_{1-6}$alkyl, $C_{1-6}$haloalkyl, $C_{3-6}$cycloalkyl, aryl, heterocyclyl or heteroaryl, each of which is optionally substituted by one or more substituents selected from halo, trifluoromethyl, trifluoromethoxy, amino, cyano and hydroxy.

26. A compound according to any preceding paragraph, or a pharmaceutically acceptable salt thereof, wherein $R_{2a}$, $R_{2b}$, $R_{2c}$ and $R_{2d}$ are independently selected from hydrogen, cyano, halo or $C_{1-3}$alkyl.

27. A compound according to any preceding paragraph, or a pharmaceutically acceptable salt thereof, wherein $R_{2a}$, $R_{2b}$, $R_{2c}$ and $R_{2d}$ are hydrogen.

28. A compound according to any preceding paragraph, or a pharmaceutically acceptable salt thereof, wherein $R_{3a1}$, $R_{3b1}$, $R_{3c1}$, $R_{3d1}$, $R_{3e1}$, $R_{3f1}$, $R_{3g1}$, $R_{3h1}$, $R_{3i1}$, $R_{3j1}$, $R_{3k1}$, $R_{3l1}$, $R_{3m1}$, $R_{3n1}$, $R_{3o1}$, $R_{3p1}$, $R_{3q1}$, $R_{3r1}$ and $R_{3s1}$ are independently selected from hydrogen (including deuterium), $C_{1-6}$alkyl; wherein $C_{1-6}$alkyl is optionally substituted with one or more substituents selected from halo, amino, cyano, and hydroxy.

29. A compound according to any one of the preceding paragraphs, or a pharmaceutically acceptable salt thereof, wherein $R_{3a2}$, $R_{3b2}$, $R_{3c2}$, $R_{3d2}$, $R_{3e2}$, $R_{3f2}$, $R_{3g2}$, $R_{3h2}$, $R_{3i2}$, $R_{3j2}$, $R_{3k2}$, $R_{3l2}$, $R_{3m2}$, $R_{3n2}$, $R_{3o2}$, $R_{3p2}$, $R_{3q2}$, $R_{3r2}$ and $R_{3s2}$ are hydrogen.

30. A compound according to any one of the preceding paragraphs, or a pharmaceutically acceptable salt thereof, wherein n is 1.

31. A compound according to any one of the preceding paragraphs, or a pharmaceutically acceptable salt thereof, wherein Y is selected from:

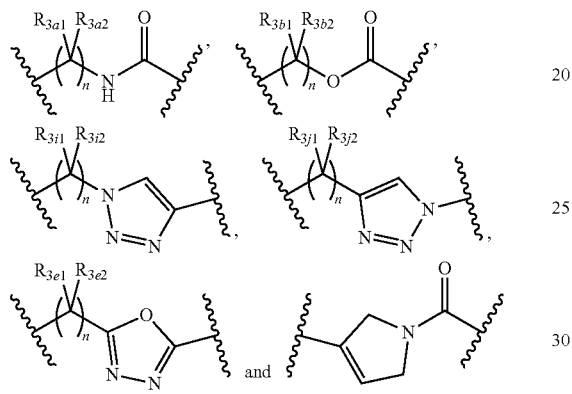

wherein n, $R_{3a1}$, $R_{3a2}$, $R_{3b1}$, $R_{3b2}$, $R_{3e1}$, $R_{3e2}$, $R_{3i1}$, $R_{3i2}$, $R_{3j1}$, and $R_{3j2}$ are as defined in any preceding paragraph.

32. A compound according to any one of the preceding paragraphs, or a pharmaceutically acceptable salt thereof, wherein Y is selected from:

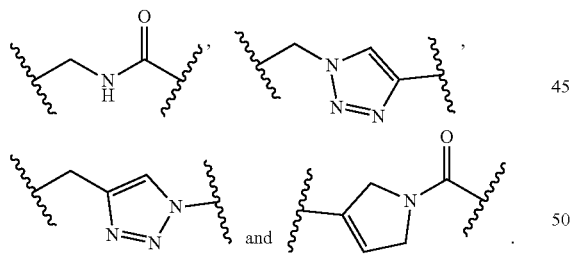

33. A compound according to any one of the preceding paragraphs, or a pharmaceutically acceptable salt thereof, wherein Y is selected from

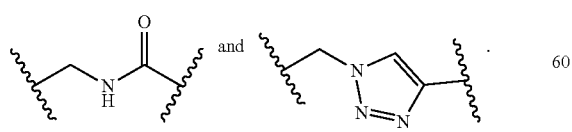

34. A compound according to any one of the preceding paragraphs, or a pharmaceutically acceptable salt thereof, wherein Z is selected from:

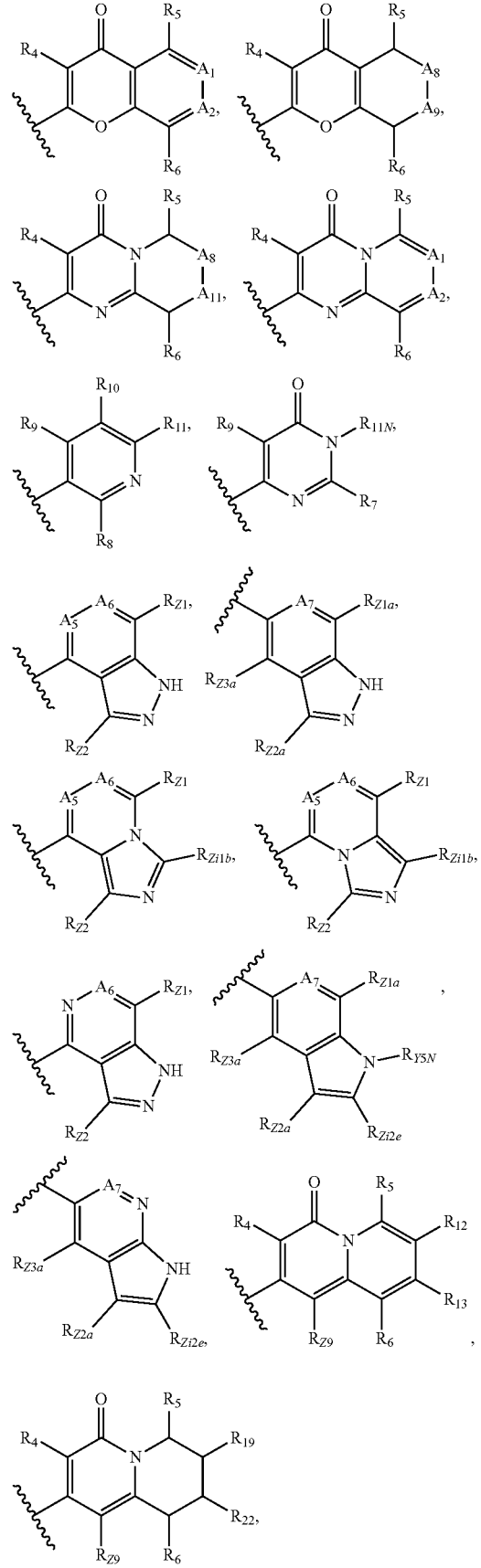

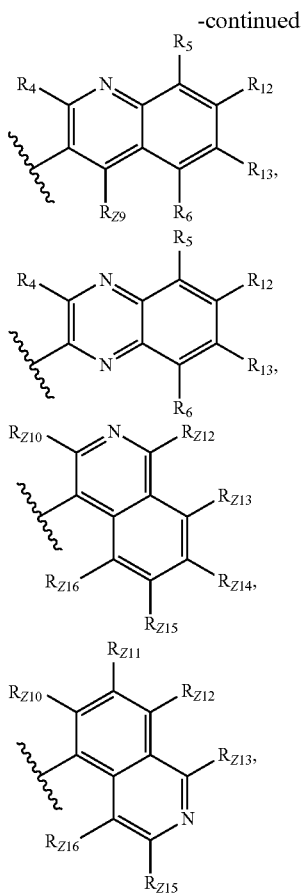

wherein:
R$_4$ is selected from hydrogen, halo, cyano and methyl;
R$_5$ is selected from hydrogen, halo, cyano and methyl;
R$_6$ is selected from hydrogen, halo, cyano and methyl;
R$_8$, R$_9$, R$_{10}$ and R$_{11}$ are independently selected from hydrogen, NH$_2$, halo, cyano, and C$_{1-6}$ alkyl; or
R$_9$ and R$_{10}$ may be linked together such that, together to the atoms to which they are attached, they form a fused 5- or 6-membered saturated or unsaturated ring system, or R$_{10}$ and R$_{11}$ may be linked together such that, together to the atoms to which they are attached, they form a fused 5- or 6-membered saturated or unsaturated ring system, wherein either of the fused 5- or 6-membered saturated or unsaturated ring system may be optionally substituted by one or more substituents selected from C$_{1-2}$alkyl, cyano, C$_{1-2}$haloalkyl, hydroxy, C$_{1-2}$alkoxy, halo, C$_{1-2}$haloalkoxy, NR$_{1ia}$R$_{1ja}$ or —S(O)$_{0-2}$R$_{1ia}$R$_{1ja}$, wherein R$_{1ia}$ and R$_{1ja}$ are H or C$_{1-2}$alky;
R$_7$ and R$_{11N}$ are independently selected from hydrogen, NH$_2$, halo, cyano, and C$_{1-6}$ alkyl;
R$_{Z1}$ and R$_{Z1a}$ are selected from hydrogen, C$_{1-4}$alkyl, cyano, halo, C$_{1-4}$haloalkyl, C$_{1-4}$haloalkoxy, C$_{1-4}$alkoxy, C$_{3-6}$cycloalkyl and —O—C$_{3-6}$cycloalkyl, wherein C$_{3-6}$cycloalkyl and —O—C$_{3-6}$cycloalkyl are optionally substituted by one or more of halo, methyl or methoxy;
R$_{Z2}$ and R$_{Z2a}$ are selected from hydrogen, C$_{1-4}$alkyl, cyano, halo, NH$_2$ and C$_{1-4}$alkoxy;
R$_{Z3a}$ is selected from C$_{1-4}$alkyl, cyano, halo, NH$_2$ and C$_{1-4}$alkoxy;
R$_{Zi1b}$ is selected from hydrogen, C$_{1-4}$alkyl, cyano, halo, NH$_2$ and C$_{1-4}$alkoxy;
R$_{Zi2e}$ is selected from hydrogen, C$_{1-4}$alkyl, cyano, halo, NH$_2$ and C$_{1-4}$alkoxy; R$_{Z9}$ is selected from hydrogen, halo, cyano, C$_{1-4}$ alkyl, C$_{1-4}$ haloalkyl, C$_{1-4}$alkoxy, C$_{1-4}$ haloalkoxy;
R$_{Z10}$ is independently selected from hydrogen, halo, cyano, C$_{1-4}$ alkyl, C$_{1-4}$ haloalkyl, C$_{1-4}$alkoxy, C$_{1-4}$ haloalkoxy;
R$_{Z11}$ is selected from hydrogen, halo, cyano, C$_{1-4}$ alkyl, C$_{1-4}$ haloalkyl, C$_{1-4}$alkoxy, C$_{1-4}$ haloalkoxy;
R$_{Z12}$ is independently selected from hydrogen, halo, cyano, C$_{1-4}$ alkyl, C$_{1-4}$ haloalkyl, C$_{1-4}$alkoxy, C$_{1-4}$ haloalkoxy;
R$_{Z13}$ is independently selected from hydrogen, halo, cyano, C$_{1-4}$ alkyl, C$_{1-4}$ haloalkyl, C$_{1-4}$alkoxy, C$_{1-4}$ haloalkoxy;
R$_{Z14}$ is selected from hydrogen, halo, cyano, C$_{1-4}$ alkyl, C$_{1-4}$ haloalkyl, C$_{1-4}$alkoxy, C$_{1-4}$ haloalkoxy;
R$_{Z15}$ is independently selected from hydrogen, halo, cyano, C$_{1-4}$ alkyl, C$_{1-4}$ haloalkyl, C$_{1-4}$alkoxy, C$_{1-4}$ haloalkoxy;
R$_{Z16}$ is independently selected from hydrogen, halo, cyano, C$_{1-4}$ alkyl, C$_{1-4}$ haloalkyl, C$_{1-4}$alkoxy, C$_{1-4}$ haloalkoxy;
A$_1$ is selected from CR$_{12}$ and N;
A$_2$ is selected from CR$_{13}$ and N;
A$_5$ is selected from CR$_{16}$ and N;
A$_6$ is selected from CR$_{17}$ and N;
A$_7$ is selected from CR$_{18}$, and N;
A$_8$ is selected from CR$_{19}$R$_{20}$ and NR$_{21}$;
A$_9$ is selected from CR$_{22}$R$_{23}$ and NR$_{24}$;
A$_{11}$ is selected from CR$_{28}$R$_{29}$ and NR$_{30}$;
R$_{12}$ is selected from hydrogen, halo, cyano, C$_{1-4}$ alkyl, C$_{1-4}$ haloalkyl, C$_{1-4}$alkoxy, C$_{1-4}$ haloalkoxy (e.g. hydrogen, halo, cyano and C$_{1-4}$ alkyl);
R$_{13}$ is selected from hydrogen, halo, cyano, C$_{1-4}$ alkyl, C$_{1-4}$ haloalkyl, C$_{1-4}$alkoxy, C$_{1-4}$ haloalkoxy (e.g. hydrogen, halo, cyano, methoxy and methyl);
R$_{16}$ and R$_{18}$ are selected from hydrogen, halo, cyano, C$_{1-4}$ alkyl, C$_{1-4}$ alkoxy, C$_{1-4}$haloalkyl, C$_{1-4}$haloalkoxy, C$_{3-4}$cycloalkyl, a 3- to 4-membered heterocyclyl and C$_{3-4}$-cycloalkoxy;
R$_{17}$ is selected from hydrogen, halo, cyano, C$_{1-4}$ alkyl, C$_{1-4}$ haloalkyl, C$_{1-4}$ alkoxy, C$_{1-4}$ haloalkoxy, C$_{2-4}$ alkenyl, C$_{2-4}$ alkynyl, phenyl, a 5- or 6-membered or heteroaryl, C$_{3-6}$ cycloalkyl, —O—C$_{3-6}$cycloalkyl, heterocyclyl, —O-heterocyclyl (carbon-linked), —(OCH$_2$CH$_2$)$_m$—OCH$_3$ wherein m is an integer from 1 to 6, NR$_q$R$_r$, wherein R$_q$ and R$_r$ are each independently hydrogen, C$_{1-5}$ alkyl, C$_{3-6}$cycloalkyl, a 3- to 6-membered carbon-linked heterocyclyl, or R$_q$ and R$_r$ are linked together such that, together with the nitrogen atom to which they are attached, they form a 3- to 6-membered heterocyclic ring; wherein any C$_{1-5}$alkyl, C$_{1-4}$ alkoxy, C$_{2-4}$alkenyl, C$_{2-4}$alkynyl, phenyl, 5- or 6-membered or heteroaryl, C$_{3-6}$cycloalkyl, —O—C$_{3-6}$ cycloalkyl, heterocyclyl or —O— heterocyclyl (carbon-linked) is optionally further substituted by one or more substituents selected from C$_{1-2}$alkyl, cyano, C$_{1-2}$haloalkyl, hydroxy, C$_{1-2}$alkoxy, halo, C$_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or C$_{1-2}$alkyl;
R$_{19}$ and R$_{20}$ are selected from hydrogen, halo, cyano and C$_{1-4}$ alkyl;
R$_{22}$ and R$_{23}$ are selected from selected from hydrogen, halo, cyano, C$_{1-4}$ alkyl, C$_{1-4}$ haloalkyl, C$_{1-4}$alkoxy, C$_{1-4}$ haloalkoxy (e.g. hydrogen, halo, cyano and methyl);

$R_{28}$ and $R_{29}$ are selected from hydrogen, halo, methoxy and methyl;
$R_{21}$, $R_{24}$ and $R_{30}$ are hydrogen or $C_{1-4}$alkyl.

34. A compound according to any preceding paragraph, or a pharmaceutically acceptable salt thereof, wherein:
(i) $R_4$, $R_5$, $R_{X5a}$, $R_{X5b}$, $R_{Y5}$, $R_6$, $R_7$, $R_8$, $R_9$, $R_{10}$, $R_{11}$, $R_{11a}$, $R_{11b}$, $R_{Z2}$, $R_{Z2a}$, $R_{Z3a}$, $R_{Z1b}$, $R_{Zi2e}$, $R_{Z9}$, $R_{Z10}$, $R_{Z11}$, $R_{Z12}$, $R_{Z12a}$, $R_{Z13}$, $R_{Z14}$, $R_{Z15}$ and $R_{Z16}$ are independently selected from hydrogen, methyl, cyano or halo; and
$R_{B5N}$, $R_{Y5N}$, and $R_{11N}$ are selected from methyl or hydrogen;
(ii) $R_{Z1}$ and $R_{Z1}a$ are selected from hydrogen, $C_{1-4}$alkyl, cyano, halo, $C_{1-4}$haloalkyl, $C_{1-4}$haloalkoxy, $C_{1-4}$alkoxy, $C_{3-6}$cycloalkyl and —O—$C_{3-8}$cycloalkyl;
(iii) $R_{12}$, $R_{13}$, $R_{16}$, $R_{18}$, $R_{19}$, $R_{20}$, $R_{21}$, $R_{22}$, $R_{23}$, $R_{24}$ and $R_{30}$ are independently selected from hydrogen, halo, cyano and methyl;
(iv) $R_{17}$ is selected from hydrogen, halo, cyano, $C_{1-4}$alkyl, $C_{1-4}$haloalkyl, $C_{1-4}$alkoxy, $C_{1-4}$haloalkoxy, $C_{2-4}$alkenyl, $C_{2-4}$alkynyl, phenyl a 5- or 6-membered or heteroaryl, $C_{3-6}$cycloalkyl, —O—$C_{3-6}$cycloalkyl, heterocyclyl, —(OCH$_2$CH$_2$)$_m$—OCH$_3$ wherein m is an integer from 1 to 6, NR$_q$R$_r$, wherein R$_q$ and R$_r$ are each independently hydrogen, $C_{1-4}$ alkyl or R$_q$ and R$_r$ are linked together such that, together with the nitrogen atom to which they are attached, they form a 3- to 6-membered heterocyclic ring; wherein any $C_{1-4}$ alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl.
(v) $R_{21}$, $R_{24}$ and $R_{30}$, are independently selected from hydrogen or methyl;
(vi) $R_{28}$ and $R_{29}$ are selected from hydrogen or halo, methoxy and methyl.

35. A compound according to any preceding paragraph, or a pharmaceutically acceptable salt thereof, wherein:
(i) $R_4$, $R_5$, $R_{X5a}$, $R_{X5b}$, $R_{Y5}$, $R_{B5N}$, $R_{Y5N}$, $R_6$, $R_7$, $R_8$, $R_9$, $R_{10}$, $R_{11}$, $R_{11a}$, $R_{11b}$, $R_{11N}$, $R_{Z2}$, $R_{Z2a}$, $R_{Z3a}$, $R_{Zi1b}$, $R_{Zi2e}$, $R_{Z9}$, $R_{Z10}$, $R_{Z11}$, $R_{Z12}$, $R_{Z12a}$, $R_{Z13}$, $R_{Z14}$, $R_{Z15}$ and $R_{Z16}$ are hydrogen;
(ii) $R_{Z1}$ and $R_{Z1a}$ are selected from hydrogen, cyano, halo, $C_{1-2}$haloalkyl, $C_{1-2}$haloalkoxy, $C_{1-2}$alkoxy, $C_{3-6}$cycloalkyl and —O—$C_{3-6}$cycloalkyl;
(iii) $R_{12}$, $R_{13}$, $R_{16}$, $R_{18}$, $R_{19}$, $R_{20}$, $R_{21}$, $R_{22}$, $R_{23}$, $R_{24}$ and $R_{30}$ are hydrogen;
(iv) $R_{17}$ is selected from hydrogen, halo, cyano, $C_{1-2}$alkyl, $C_{1-2}$haloalkyl, $C_{1-2}$alkoxy, $C_{1-2}$haloalkoxy, $C_{2-3}$alkenyl, $C_{2-3}$alkynyl, phenyl a 5- or 6-membered or heteroaryl, $C_{3-6}$cycloalkyl, —O—$C_{3-6}$cycloalkyl, heterocyclyl, —(OCH$_2$CH$_2$)$_m$—OCH$_3$ wherein m is an integer from 1 to 6, NR$_q$R$_r$, wherein R$_q$ and R$_r$ are each independently hydrogen, $C_{1-2}$ alkyl or R$_q$ and R$_r$ are linked together such that, together with the nitrogen atom to which they are attached, they form a 3- to 6-membered heterocyclic ring; wherein any $C_{1-4}$ alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl
(v) $R_{21}$, $R_{24}$ and $R_{30}$, are hydrogen;
(vi) $R_{28}$ and $R_{29}$ are hydrogen.

36. A compound according to any one of the preceding paragraphs, wherein
when $X_6$ is $A_1$, $A_1$ is $CR_{12}$;
when $X_7$ is $A_2$, $A_2$ is $CR_{13}$;
$B_1$ is $A_5$, wherein $A_5$ is $CR_{16}$;
$B_2$ is $A_6$, wherein $A_6$ is $CR_{17}$;
$Y_2$ is $A_7$, wherein is $CR_{18}$;
when $X_6$ is $A_8$, $A_8$ is $CR_{18}R_{20}$;
when $X_7$ is $A_9$, $A_9$ is $CR_{22}R_{23}$;
when $X_7$ is $A_{11}$, $A_{11}$ is $CR_{28}R_{29}$;
and wherein $R_{12}$, $R_{13}$, $R_{16}$, $R_{17}$, $R_{16}$, $R_{19}$, $R_{20}$, $R_{21}$, $R_{22}$, $R_{23}$, $R_{28}$ and $R_{29}$ are as defined in any one of the preceding paragraphs.

37. A compound according to any preceding paragraph, or a pharmaceutically acceptable salt thereof, wherein $R_{17}$ is selected from hydrogen, halo, cyano, $C_{1-2}$ alkyl, $C_{1-2}$ haloalkyl, $C_{1-2}$ alkoxy, $C_{1-2}$ haloalkoxy, $C_{2-3}$ alkenyl, $C_{2-3}$ alkynyl, phenyl a 5- or 6-membered or heteroaryl, $C_{3-6}$cycloalkyl, —O—$C_{3-6}$cycloalkyl, heterocyclyl, —O-heterocyclyl (carbon-linked), —(OCH$_2$CH$_2$)$_m$—OCH$_3$ wherein m is an integer from 1 to 6, NR$_q$R$_r$, wherein R$_q$ and R$_r$ are each independently hydrogen, $C_{1-2}$ alkyl or R$_q$ and R$_r$ are linked together such that, together with the nitrogen atom to which they are attached, they form a 3- to 6-membered heterocyclic ring;
wherein any $C_1$-alkyl, $C_{2-4}$ alkenyl, $C_{2-4}$ alkynyl, phenyl, 5- or 6-membered or heteroaryl, $C_{3-6}$cycloalkyl, —O—$C_{3-6}$cycloalkyl, heterocyclyl or —O-heterocyclyl (carbon-linked) is optionally further substituted by one or more substituents selected from $C_{1-2}$alkyl, cyano, $C_{1-2}$haloalkyl, hydroxy, $C_{1-2}$alkoxy, halo, $C_{1-2}$haloalkoxy, NR$_{1ea}$R$_{1fa}$ or —S(O)$_{0-2}$R$_{1ea}$R$_{1fa}$, wherein R$_{1ea}$ and R$_{1fa}$ are H or $C_{1-2}$alkyl.

38. A compound according to any preceding paragraph, or a pharmaceutically acceptable salt thereof, wherein $R_{17}$ is selected from hydrogen, halo, cyano, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{3-6}$cycloalkyl, —O—$C_{3-4}$cycloalkyl, heterocyclyl, —(OCH$_2$CH$_2$)$_m$—OCH$_3$ wherein m is 1, 2 or 3, NR$_q$R$_r$, wherein R$_q$ and R$_r$ are each independently hydrogen or $C_{1-2}$ alkyl;
wherein any $C_{1-4}$ alkyl, $C_{2-4}$ alkenyl, $C_{2-4}$ alkynyl, $C_{3-6}$cycloalkyl, —O—$C_{3-4}$cycloalkyl, heterocyclyl, system is optionally further substituted by one or more substituents selected from $C_{1-2}$alkyl, $C_{1-2}$haloalkyl, cyano, hydroxy, $C_{1-2}$alkoxy, halo and $C_{1-2}$haloalkox.

39. A compound according to any one of the preceding paragraphs, or a pharmaceutically acceptable salt thereof, wherein $R_{Z1}$ and $R_{Z1a}$ are selected from hydrogen, cyano or halo.

40. A compound according to any one of the preceding paragraphs, or a pharmaceutically acceptable salt thereof, wherein Z is selected from:

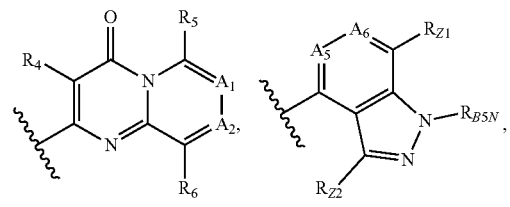

[Structures shown]

$A_1$, $A_2$, $A_5$, $A_6$, $A_7$, $A_8$, $A_9$, $A_{11}$, $R_4$, $R_5$, $R_6$, $R_7$, $R_8$, $R_9$, $R_{10}$, $R_{11}$, $R_{Y5N}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined in any one of the preceding paragraphs.

41. A compound according to any one of the preceding paragraphs, or a pharmaceutically acceptable salt thereof, wherein Z is selected from:

[Structures shown]

wherein $A_1$, $A_2$, $A_5$, $A_6$, $A_7$, $A_8$, $A_9$, $A_{11}$, $R_4$, $R_5$, $R_6$, $R_7$, $R_8$, $R_9$, $R_{10}$, $R_{11}$, $R_{Y5N}$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Z1a}$, $R_{Zi1b}$ and $R_{Zi2e}$ are as defined in any one of the preceding paragraphs.

42. A compound according to any one of the preceding paragraphs, or a pharmaceutically acceptable salt thereof, wherein Z is selected from:

[Structures shown]

wherein $R_8$, $R_{10}$, $R_{17}$, $R_{18}$ and $R_{Z1}$, are as defined herein in any one of the preceding paragraphs.

43. A compound according to any one of the preceding paragraphs, or a pharmaceutically acceptable salt thereof, wherein Z is selected from:

[Structures shown]

377
-continued
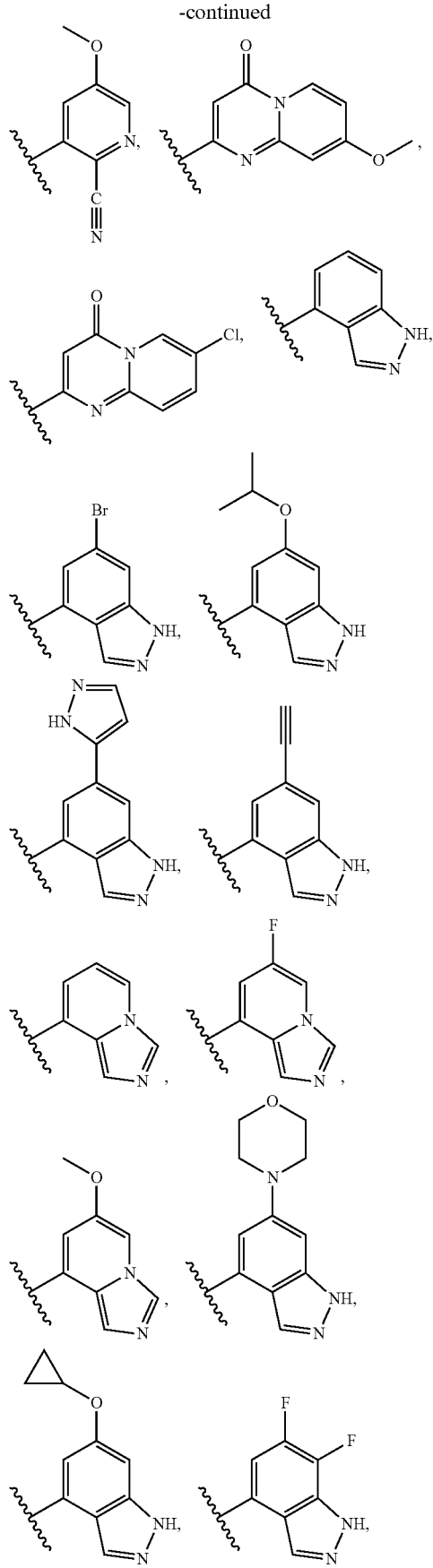
378
-continued
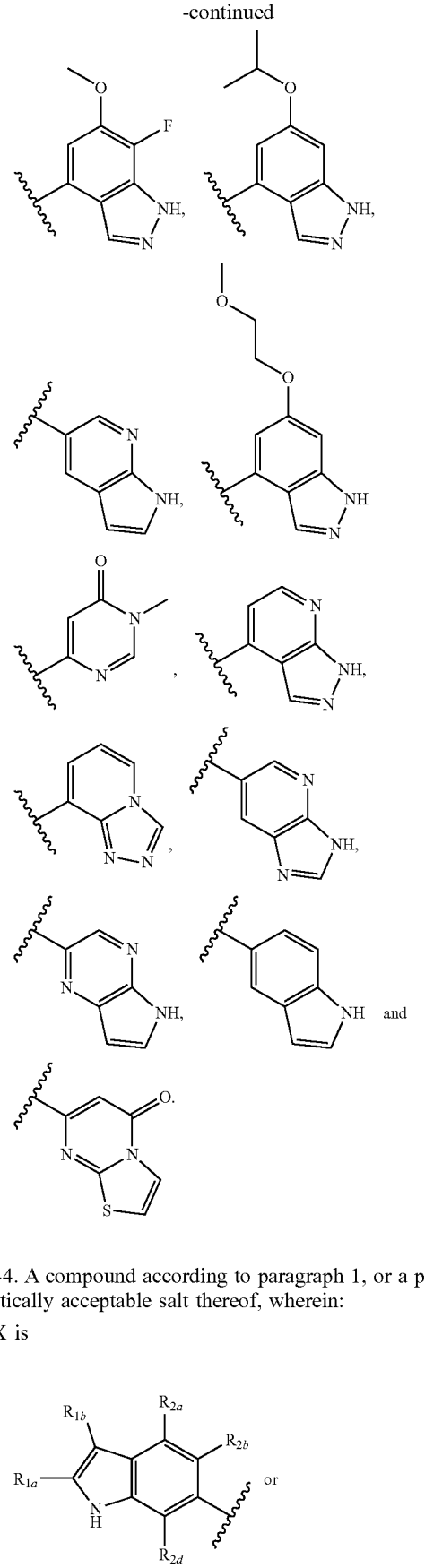
44. A compound according to paragraph 1, or a pharmaceutically acceptable salt thereof, wherein:
X is
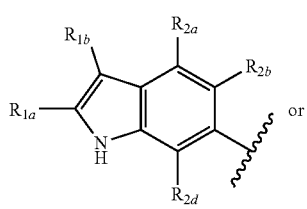
or -continued

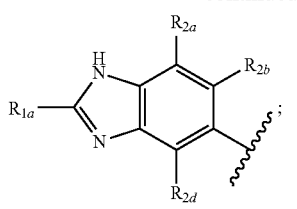

Y is selected from:

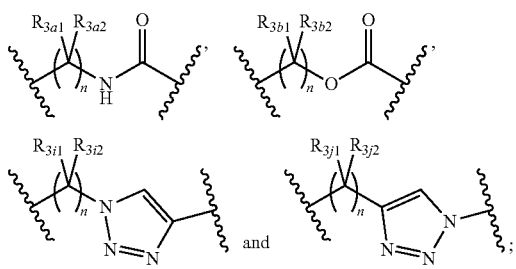

Z is selected from:

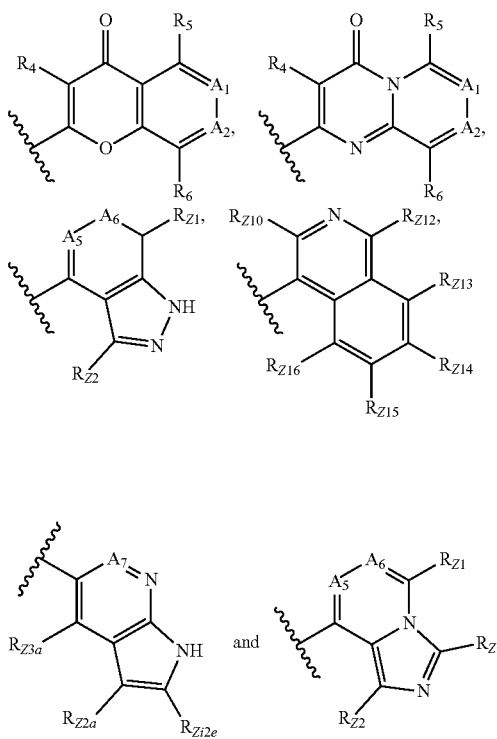

wherein:

(i) $R_{1a}$, $R_{1b}$, $R_{2a}$, $R_{2b}$ and $R_{2d}$ are as defined in any preceding paragraph;

(ii) $R_{3a1}$, $R_{3a2}$, $R_{3b1}$, $R_{3b2}$, $R_{3i1}$, $R_{3i2}$, $R_{3j1}$, $R_{3j2}$ and n are as defined in any preceding paragraph; and (iii) $A_1$, $A_2$, $A_5$, $A_6$, $A_7$, $R_4$, $R_5$, $R_6$, $R_{Z1}$, $R_{Z2}$, $R_{Z10}$, $R_{Z12}$, $R_{Z13}$, $R_{Z14}$, $R_{Z15}$, $R_{Z16}$, $R_{Z2a}$, $R_{Z3a}$, $R_{Zi2e}$, $R_{Zi1b}$ and $R_{Z2}$ are as defined in any preceding paragraph.

45. A compound according to paragraph 44, or a pharmaceutically acceptable salt thereof, wherein:

X is

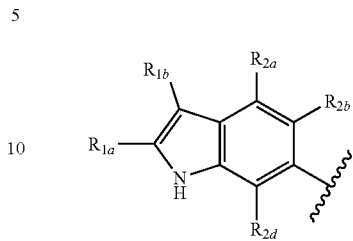

Y is

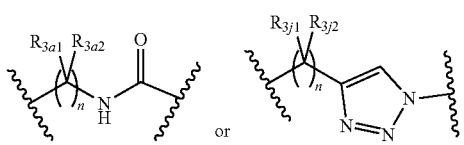

Z is

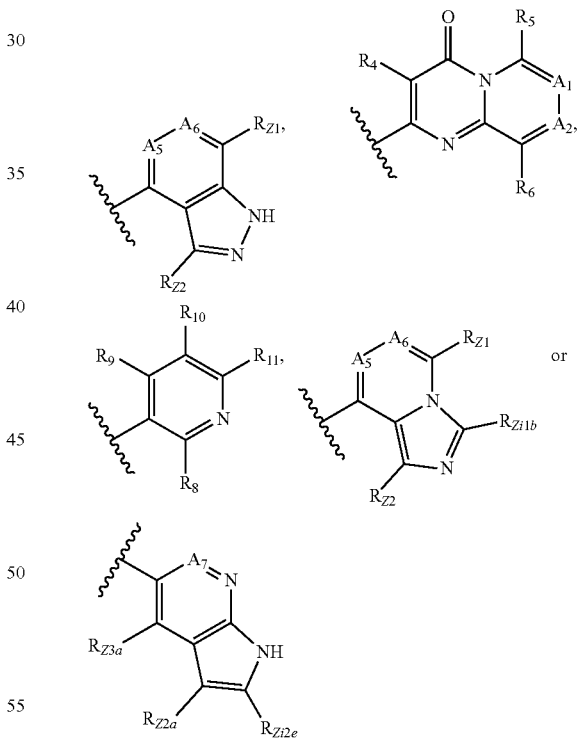

wherein:

(i) $R_{1a}$, $R_{1b}$, $R_{2a}$, $R_{2b}$ and $R_{2d}$ are as defined in any preceding paragraph;

(ii) n, $R_{3a1}$, $R_{3a2}$, $R_{3j1}$, $R_{3j2}$, are as defined in any preceding paragraph; and (iii) $A_1$, $A_2$, $A_5$, $A_6$, $A_7$, $R_4$, $R_5$, $R_6$, $R_8$, $R_9$, $R_{10}$, $R_{11}$, $R_{Z1}$, $R_{Z2}$, $R_{Z2a}$, $R_{Z3a}$, $R_{Zi2e}$, $R_{Zi1b}$ are as defined in any preceding paragraph.

46. A compound according to paragraph 44, or a pharmaceutically acceptable salt thereof, wherein:
X is

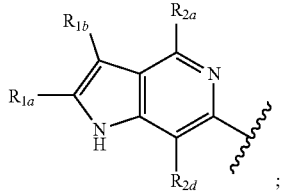

Y is

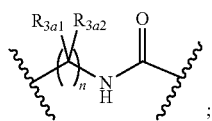

and
Z is

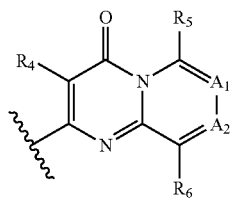

(i) wherein $R_{1a}$, $R_{1b}$, $R_{2a}$, $R_{2b}$ and $R_{2d}$ are as defined in any preceding paragraph;
(ii) n, $R_{3a1}$ and $R_{3a2}$ are as defined in any preceding paragraph; and
(iii) $A_1$, $A_2$, $R_4$, $R_5$ and $R_6$ are as defined in any preceding paragraph.

47. A compound, or a pharmaceutically acceptable salt thereof, selected from any one of the following:

N-({2-[(4,4-dimethylpiperidin-1-yl)methyl]-1H-indol-6-yl}methyl)-4-oxo-4H-pyrido[1,2-a]pyrimidine-2-carboxamide N-[(2-{[(cyclobutylmethyl)amino]methyl}-1H-indol-6-yl)methyl]-4-oxo-4H-pyrido[1,2-a]pyrimidine-2-carboxamide N-[[2-[[(3,3-difluorocyclobutyl)methylamino]methyl]-1H-indol-6-yl]methyl]-4-oxo-pyrido[1,2-a]pyrimidine-2-carboxamide N-[[2-[[(1-hydroxycyclobutyl)methylamino]methyl]-1H-indol-6-yl]methyl]-4-oxo-pyrido[1,2-a]pyrimidine-2-carboxamide N-[[2-[[(1-fluorocyclobutyl)methylamino]methyl]-1H-indol-6-yl]methyl]-4-oxo-pyrido[1,2-a]pyrimidine-2-carboxamide N-[[2-[[(1-methylcyclopropyl)methylamino]methyl]-1H-indol-6-yl]methyl]-4-oxo-pyrido[1,2-a]pyrimidine-2-carboxamide.

N-[[2-(2-azabicyclo[2.1.1]hexan-2-ylmethyl)-1H-indol-6-yl]methyl]-4-oxo-pyrido[1,2-a]pyrimidine-2-carboxamide N-[[2-(3-azabicyclo[3.1.1]heptanean-3-ylmethyl)-1H-indol-6-yl]methyl]-4-oxo-pyrido[1,2-a]pyrimidine-2-carboxamide N-[[2-[[2-(hydroxymethyl)pyrrolidin-1-yl]methyl]-1H-indol-6-yl]methyl]-4-oxo-pyrido[1,2-a]pyrimidine-2-carboxamide N-[[2-(morpholinomethyl)-1H-indol-6-yl]methyl]-4-oxo-pyrido[1,2-a]pyrimidine-2-carboxamide N-[[2-[(1-adamantylamino)methyl]-1H-indol-6-yl]methyl]-4-oxo-pyrido[1,2-a]pyrimidine-2-carboxamide 4-oxo-N-[[2-(1-piperidylmethyl)-1H-indol-6-yl]methyl]pyrido[1,2-a]pyrimidine-2-carboxamide N-[[2-[(4-fluoro-1-piperidyl)methyl]-1H-indol-6-yl]methyl]-4-oxo-pyrido[1,2-a]pyrimidine-2-carboxamide 4-oxo-N-[[2-[[[rac-(1S,2S,4S)-7-oxabicyclo[2.2.1]heptane-5-en-2-yl]methylamino]methyl]-1H-indol-6-yl]methyl]pyrido[1,2-a]pyrimidine-2-carboxamide N-[[2-[[(1-hydroxycyclopentyl)methylamino]methyl]-1H-indol-6-yl]methyl]-4-oxo-pyrido[1,2-a]pyrimidine-2-carboxamide 4-oxo-N-[[2-[[[rac-(1S,2R,4S)-7-oxabicyclo[2.2.1]heptane-5-en-2-yl]methylamino]methyl]-1H-indol-6-yl]methyl]pyrido[1,2-a]pyrimidine-2-carboxamide N-[[2-[(1-bicyclo[1.1.1]pentanylamino)methyl]-1H-indol-6-yl]methyl]-4-oxo-pyrido[1,2-a]pyrimidine-2-carboxamide N-[[2-[(cyclobutylamino)methyl]-1H-indol-6-yl]methyl]-4-oxo-pyrido[1,2-a]pyrimidine-2-carboxamide N-({2-[({bicyclo[2.2.1]heptanean-2-yl}amino)methyl]-1H-indol-6-yl}methyl)-4-oxo-4H-pyrido[1,2-a]pyrimidine-2-carboxamide N-[[2-[(cyclopropylamino)methyl]-1H-indol-6-yl]methyl]-4-oxo-pyrido[1,2-a]pyrimidine-2-carboxamide N-[[2-(2-azabicyclo[2.2.2]octan-2-ylmethyl)-1H-indol-6-yl]methyl]-4-oxo-pyrido[1,2-a]pyrimidine-2-carboxamide N-[[2-[[(2,2-difluorocyclopropyl)methylamino]methyl]-1H-indol-6-yl]methyl]-4-oxo-pyrido[1,2-a]pyrimidine-2-carboxamide N-[(2-{[({3-fluorobicyclo[1.1.1]pentan-1-yl}methyl)amino]methyl}-1H-indol-6-yl)methyl]-4-oxo-4H-pyrido[1,2-a]pyrimidine-2-carboxamide N-[[2-[(cyclohexylmethylamino)methyl]-1H-indol-6-yl]methyl]-4-oxo-pyrido[1,2-a]pyrimidine-2-carboxamide N-[[2-[[(1-hydroxycyclohexyl)methylamino]methyl]-1H-indol-6-yl]methyl]-4-oxo-pyrido[1,2-a]pyrimidine-2-carboxamide N-[[2-[(cyclopentylamino)methyl]-1H-indol-6-yl]methyl]-4-oxo-pyrido[1,2-a]pyrimidine-2-carboxamide N-[[2-[(cyclopentylmethylamino)methyl]-1H-indol-6-yl]methyl]-4-oxo-pyrido[1,2-a]pyrimidine-2-carboxamide N-[[2-[[(1-methoxycyclobutyl)methylamino]methyl]-1H-indol-6-yl]methyl]-4-oxo-pyrido[1,2-a]pyrimidine-2-carboxamide N-[[2-[(isobutylamino)methyl]-1H-indol-6-yl]methyl]-4-oxo-pyrido[1,2-a]pyrimidine-2-carboxamide N-[[2-[(cyclohexylamino)methyl]-1H-indol-6-yl]methyl]-4-oxo-pyrido[1,2-a]pyrimidine-2-carboxamide N-[[2-[(cyclopropylmethylamino)methyl]-1H-indol-6-yl]methyl]-4-oxo-pyrido[1,2-a]pyrimidine-2-carboxamide 4-oxo-N-[[2-[(prop-2-ynylamino)methyl]-1H-indol-6-yl]methyl]pyrido[1,2-a]pyrimidine-2-carboxamide N-[[2-[(oxetan-2-ylmethylamino)methyl]-1H-indol-6-yl]methyl]-4-oxo-pyrido[1,2-a]pyrimidine-2-carboxamide N-[[2-[(2,2-dimethylpropylamino)methyl]-1H-indol-6-yl]methyl]-4-oxo-pyrido[1,2-a]pyrimidine-2-carboxamide N-[[2-[(1-bicyclo[1.1.1]pentanylmethylamino)methyl]-1H-indol-6-yl]methyl]-4-oxo-pyrido[1,2-a]pyrimidine-2-carboxamide N-{[2-({[(1S,2S)-2-hydroxycyclopentyl]amino}methyl)-1H-indol-6-yl]methyl}-4-oxo-4H-pyrido[1,2-a]pyrimidine-2-carboxamide N-{[2-({[(1R,2R)-2-hydroxycyclopentyl]amino}methyl)-1H-indol-6-yl]methyl}-4-oxo-4H-pyrido[1,2-a]pyrimidine-2-carboxamide N-{[2-({[(1S,2R)-2-hydroxycyclopentyl]amino}methyl)-1H-indol-6-yl]methyl}-4-oxo-4H-pyrido[1,2-a]pyrimidine-2-carboxamide N-{[2-({[(1R,2S)-2-hydroxycyclopentyl]amino}methyl)-1H-indol-6-yl]methyl}-4-oxo-4H-pyrido[1,2-a]pyrimidine-2-carboxamide N-[[2-[(cyclopropylmethylamino)methyl]-5-fluoro-1H-indol-6-yl]methyl]-4-oxo-pyrido[1,2-a]pyrimidine-2-carboxamide N-[[2-[(cyclobutylmethylamino)methyl]-5-fluoro-1H-indol-6-yl]methyl]-4-oxo-pyrido[1,2-a]pyrimidine-2-carboxamide 4-oxo-N-[[2-[(2,2,2-trifluoroethylamino)methyl]-1H-indol-6-yl]methyl]pyrido[1,2-a]pyrimidine-2-carboxamide N-(2-{[N-(cyclobutylmethyl)acetamido]methyl}-1H-indol-6-yl)methyl]-4-oxo-4H-pyrido[1,2-a]pyrimidine-2-carboxamide 4-oxo-N-{[2-(piperidin-2-yl)-1H-indol-6-yl]methyl}-4H-pyrido[1,2-a]pyrimidine-2-carboxamide N-(2-{[(cyclobutylmethyl)amino]methyl}-3-fluoro-1H-indol-6-yl)methyl]-4-oxo-4H-pyrido[1,2-a]pyrimidine-2-carboxamide N-(2-{[(cyclobutylmethyl)amino]methyl}-1-methyl-1H-indol-6-yl)methyl]-4-oxo-4H-pyrido[1,2-a]pyrimidine-2-carboxamide N-[[2-[(Cyclobutylmethylamino)-dideuterio-methyl]-1H-indol-6-yl]methyl]-4-oxo-pyrido[1,2-a]pyrimidine-2-carboxamide N-[[2-[(cyclobutylmethylamino)methyl]-1H-indol-6-yl]methyl]-1H-indazole-4-carboxamide N-[[2-[(cyclobutylmethylamino)methyl]-1H-pyrrolo[3,2-b]pyridin-6-yl]methyl]-4-oxo-pyrido[1,2-a]pyrimidine-2-carboxamide N-(1H-indol-6-ylmethyl)-4-oxo-pyrido[1,2-a]pyrimidine-2-carboxamide N-(1H-indol-2-ylmethyl)-4-oxo-pyrido[1,2-a]pyrimidine-2-carboxamide N-(indolizin-2-ylmethyl)-4-oxo-pyrido[1,2-a]pyrimidine-2-carboxamide N-[(6-{[4-(1H-indazol-4-yl)-1H-1,2,3-triazol-1-yl]methyl}-1H-indol-2-yl)methyl]cyclopropanamine (1R,2S)-2-[[6-[[4-(1H-indazol-4-yl)triazol-1-yl]methyl]-1H-indol-2-yl]methylamino]cyclopentanol N-[[6-[[4-(1H-indazol-4-yl)triazol-1-yl]methyl]-1H-indol-2-yl]methyl]cyclopentanamine N-(cyclopropylmethyl)-1-[6-[[4-(1H-indazol-4-yl)triazol-1-yl]methyl]-1H-indol-2-yl]methanamine 1-[[[6-[[4-(1H-indazol-4-yl)triazol-1-yl]methyl]-1H-indol-2-yl]methylamino]methyl]cyclobutanol N-(cyclobutylmethyl)-1-[6-[[4-(1H-indazol-4-yl)triazol-1-yl]methyl]-1H-indol-2-yl]methanamine N-(cyclobutylmethyl)-1-[6-[[4-(1H-indazol-4-yl)triazol-1-yl]methyl]-1H-pyrrolo[3,2-b]pyridin-2-yl]methanamine N-(cyclobutylmethyl)-1-[6-[[4-(1H-indazol-4-yl)triazol-1-yl]methyl]-1H-pyrrolo[3,2-c]pyridin-2-yl]methanamine N-(cyclobutylmethyl)-1-[6-[[4-(1H-indazol-4-yl)triazol-1-yl]methyl]-1H-pyrrolo[3,2-c]pyridin-2-yl]methanamine 2-[1-[[2-[(cyclobutylmethylamino)methyl]-1H-indol-6-yl]methyl]triazol-4-yl]pyrido[1,2-a]pyrimidin-4-one N-(cyclobutylmethyl)-1-[6-[[4-(6-methoxyimidazo[1,5-a]pyridin-8-yl)triazol-1-yl]methyl]-1H-indol-2-yl]methanamine N-(cyclobutylmethyl)-1-[6-[[4-(1H-indazol-4-yl)imidazol-1-yl]methyl]-1H-indol-2-yl]methanamine N-(cyclobutylmethyl)-1-[6-[[3-(1H-indazol-4-yl)-1,2,4-oxadiazol-5-yl]methyl]-1H-indol-2-yl]methanamine N-[[2-(2-azaspiro[3.3]heptanean-2-ylmethyl)-1H-indol-6-yl]methyl]-4-oxo-pyrido[1,2-a]pyrimidine-2-carboxamide N-[[2-[(benzylamino)methyl]-1H-indol-6-yl]methyl]-4-oxo-pyrido[1,2-a]pyrimidine-2-carboxamide N-[[2-(3-azabicyclo[3.1.0]hexan-3-ylmethyl)-1H-indol-6-yl]methyl]-4-oxo-pyrido[1,2-a]pyrimidine-2-carboxamide N-[[2-[[cyclobutylmethyl(methyl)amino]methyl]-1H-indol-6-yl]methyl]-4-oxo-pyrido[1,2-a]pyrimidine-2-carboxamide N-[[2-[(cyclobutylmethylamino)methyl]-1H-pyrrolo[2,3-b]pyridin-6-yl]methyl]-4-oxo-pyrido[1,2-a]pyrimidine-2-carboxamide N-[(2-{[(cyclobutylmethyl)amino]methyl}-1H-1,3-benzodiazol-6-yl)methyl]-4-oxo-4H-pyrido[1,2-a]pyrimidine-2-carboxamide N-[(2-{[(but-2-yn-1-yl)amino]methyl}-1H-indol-6-yl)methyl]-4-oxo-4H-pyrido[1,2-a]pyrimidine-2-carboxamide N-[(2-{[(3-cyclopropylprop-2-yn-1-yl)amino]methyl}-1H-indol-6-yl)methyl]-4-oxo-4H-pyrido[1,2-a]pyrimidine-2-carboxamide N-({2-[({bicyclo[3.1.0]hexan-6-yl}amino)methyl]-1H-indol-6-yl}methyl)-4-oxo-4H-pyrido[1,2-a]pyrimidine-2-carboxamide N-[(2-{[({bicyclo[2.1.1]hexan-1-yl}methyl)amino]methyl}-1H-indol-6-yl)methyl]-4-oxo-4H-pyrido[1,2-a]pyrimidine-2-carboxamide N-[(2-{[({3-methylbicyclo[1.1.1]pentan-1-yl}methyl)amino]methyl}-1H-indol-6-yl)methyl]-4-oxo-4H-pyrido[1,2-a]pyrimidine-2-carboxamide N-({2-[(3-methylazetidin-1-yl)methyl]-1H-indol-6-yl}methyl)-4-oxo-4H-pyrido[1,2-a]pyrimidine-2-carboxamide N-({2-[(3-fluoroazetidin-1-yl)methyl]-1H-indol-6-yl}methyl)-4-oxo-4H-pyrido[1,2-a]pyrimidine-2-carboxamide N-({2-[(azetidin-1-yl)methyl]-1H-indol-6-yl}methyl)-4-oxo-4H-pyrido[1,2-a]pyrimidine-2-carboxamide N-{[2-({2-azaspiro[3.4]octan-2-yl}methyl)-1H-indol-6-yl]methyl}-4-oxo-4H-pyrido[1,2-a]pyrimidine-2-carboxamide N-({2-[(3-hydroxyazetidin-1-yl)methyl]-1H-indol-6-yl}methyl)-4-oxo-4H-pyrido[1,2-a]pyrimidine-2-carboxamide N-({2-[(3,3-dimethylazetidin-1-yl)methyl]-1H-indol-6-yl}methyl)-4-oxo-4H-pyrido[1,2-a]pyrimidine-2-carboxamide 4-oxo-N-[(2-{[3-(2,2,2-trifluoroethoxy)azetidin-1-yl]methyl}-1H-indol-6-yl)methyl]-4H-pyrido[1,2-a]pyrimidine-2-carboxamide N-[(2-{[3-(difluoromethyl)azetidin-1-yl]methyl}-1H-indol-6-yl)methyl]-4-oxo-4H-pyrido[1,2-a]pyrimidine-2-carboxamide N-({2-[(3-methoxyazetidin-1-yl)methyl]-1H-indol-6-yl}methyl)-4-oxo-4H-pyrido[1,2-a]pyrimidine-2-carboxamide N-[(2-{[3-(tert-butoxy)azetidin-1-yl]methyl}-1H-indol-6-yl)methyl]-4-oxo-4H-pyrido[1,2-a]pyrimidine-2-carboxamide 4-oxo-N-[(2-{[3-(trifluoromethyl)azetidin-1-yl]methyl}-1H-indol-6-yl)methyl]-4H-pyrido[1,2-a]pyrimidine-2-carboxamide N-({2-[(3-ethoxyazetidin-1-yl)methyl]-1H-indol-6-yl}methyl)-4-oxo-4H-pyrido[1,2-a]pyrimidine-2-carboxamide N-{[2-({2-azaspiro[3.5]nonan-2-yl}methyl)-1H-indol-6-yl]methyl}-4-oxo-4H-pyrido[1,2-a]pyrimidine-2-carboxamide N-({2-[(2-methylazetidin-1-yl)methyl]-1H-indol-6-yl}methyl)-4-oxo-4H-pyrido[1,2-a]pyrimidine-2-carboxamide N-({2-[(3,3-dimethylpyrrolidin-1-yl)methyl]-1H-indol-6-yl}methyl)-4-oxo-4H-pyrido[1,2-a]pyrimidine-2-carboxamide N-{[2-({6-fluoro-2-azaspiro[3.3]heptanean-2-yl}methyl)-1H-indol-6-yl]methyl}-4-oxo-4H-pyrido[1,2-a]pyrimidine-2-carboxamide N-{[2-({6,6-difluoro-2-azaspiro[3.3]heptanean-2-yl}methyl)-1H-indol-6-yl]methyl}-4-oxo-4H-pyrido[1,2-a]pyrimidine-2-carboxamide N-({2-[(3-cyclobutylazetidin-1-yl)methyl]-1H-indol-6-yl}methyl)-4-oxo-4H-pyrido[1,2-a]pyrimidine-2-carboxamide N-({2-[(3-cyclopropylazetidin-1-yl)methyl]-1H-indol-6-yl}methyl)-4-oxo-4H-pyrido[1,2-a]pyrimidine-2-carboxamide N-({2-[(3-tert-butylazetidin-1-yl)methyl]-1H-indol-6-yl}methyl)-4-oxo-4H-pyrido[1,2-a]pyrimidine-2-carboxamide N-[(2-{[(1-tert-butylcyclopropyl)amino]methyl}-1H-indol-6-yl)methyl]-4-oxo-4H-pyrido[1,2-a]pyrimidine-2-carboxamide N-{[2-({[(3-methylcyclobutyl)methyl]amino}methyl)-1H-indol-6-yl]methyl}-4-oxo-4H-pyrido[1,2-a]pyrimidine-2-carboxamide 4-oxo-N-[(2-{[(2,3,3-trimethylbutan-2-yl)amino]methyl}-1H-indol-6-yl)methyl]-4H-pyrido[1,2-a]pyrimidine-2-carboxamide N-[(2-{[({imidazo[1,2-a]pyridin-2-yl}methyl)amino]methyl}-1H-indol-6-yl)methyl]-4-oxo-4H-pyrido[1,2-a]pyrimidine-2-carboxamide N-({2-[(3,3-diethylazetidin-1-yl)methyl]-1H-indol-6-yl}methyl)-4-oxo-4H-pyrido[1,2-a]pyrimidine-2-carboxamide 4-oxo-N-[(2-{[(pent-3-yn-1-yl)amino]methyl}-1H-indol-6-yl)methyl]-4H-pyrido[1,2-a]pyrimidine-2-carboxamide N-{[2-({6-azaspiro[3.4]octan-6-yl}methyl)-1H-indol-6-yl]methyl}-4-oxo-4H-pyrido[1,2-a]pyrimidine-2-carboxamide N-({2-[(2,2-dimethylpyrrolidin-1-yl)methyl]-1H-indol-6-yl}methyl)-4-oxo-4H-pyrido[1,2-a]pyrimidine-2-carboxamide N-{[2-({octahydrocyclopenta[c]pyrrol-2-yl}methyl)-1H-indol-6-yl]methyl}-4-oxo-4H-pyrido[1,2-a]pyrimidine-2-carboxamide N-{[2-({5-azaspiro[2.4]heptanean-5-yl}methyl)-1H-indol-6-yl]methyl}-4-oxo-4H-pyrido[1,2-a]pyrimidine-2-carboxamide N-[(2-{[({3-methoxybicyclo[1.1.1]pentan-1-yl}methyl)amino]methyl}-1H-indol-6-yl)methyl]-4-oxo-4H-pyrido[1,2-a]pyrimidine-2-carboxamide 4-oxo-N-[(2-{[({spiro[2.2]pentan-1-yl}methyl)amino]methyl}-1H-indol-6-yl)methyl]-4H-pyrido[1,2-a]pyrimidine-2-carboxamide 4-oxo-N-({2-[({spiro[2.3]hexan-1-yl}amino)methyl]-1H-indol-6-yl}methyl)-4H-pyrido[1,2-a]pyrimidine-2-carboxamide N-[(2-{[({3-cyanobicyclo[1.1.1]pentan-1-yl}methyl)amino]methyl}-1H-indol-6-yl)methyl]-4-oxo-4H-pyrido[1,2-a]pyrimidine-2-carboxamide N-{[2-({1-oxa-6-azaspiro[3.4]octan-6-yl}methyl)-1H-indol-6-yl]methyl}-4-oxo-4H-pyrido[1,2-a]pyrimidine-2-carboxamide N-{[2-({2-azaspiro[4.4]nonan-2-yl}methyl)-1H-indol-6-yl]methyl}-4-oxo-4H-pyrido[1,2-a]pyrimidine-2-carboxamide N-[(2-{[(1-methylcyclopentyl)amino]methyl}-1H-indol-6-yl)methyl]-4-oxo-4H-pyrido[1,2-a]pyrimidine-2-carboxamide N-{[2-(hydroxymethyl)-1H-indol-6-yl]methyl}-4-oxo-4H-pyrido[1,2-a]pyrimidine-2-carboxamide N-[(2-{[(1-cyclobutylcyclopropyl)amino]methyl}-1H-indol-6-yl)methyl]-4-oxo-4H-pyrido[1,2-a]pyrimidine-2-carboxamide N-{[2-({[(1-methylcyclobutyl)methyl]amino}methyl)-1H-indol-6-yl]methyl}-4-oxo-4H-pyrido[1,2-a]pyrimidine-2-carboxamide 4-oxo-N-[(2-{[({spiro[2.3]hexan-5-yl}methyl)amino]methyl}-1H-indol-6-yl)methyl]-4H-pyrido[1,2-a]pyrimidine-2-carboxamide N-({2-[({[3-(fluoromethyl)bicyclo[1.1.1]pentan-1-yl]methyl}amino)methyl]-1H-indol-6-yl}methyl)-4-oxo-4H-pyrido[1,2-a]pyrimidine-2-carboxamide N-[(2-{[(1-{3-fluorobicyclo[1.1.1]pentan-1-yl}ethyl)amino]methyl}-1H-indol-6-yl)methyl]-4-oxo-4H-pyrido[1,2-a]pyrimidine-2-carboxamide N-({2-[(tert-butylamino)methyl]-1H-indol-6-yl}methyl)-4-oxo-4H-pyrido[1,2-a]pyrimidine-2-carboxamide 4-(1-{[2-({2-azaspiro[3.3]heptanean-2-yl}methyl)-1H-indol-6-yl]methyl}-1H-1,2,3-triazol-4-yl)-1H-indazole N-{[2-(2-{2-azaspiro[3.3]heptanean-2-yl}ethyl)-1H-indol-6-yl]methyl}-4-oxo-4H-pyrido[1,2-a]pyrimidine-2-carboxamide ({3-fluorobicyclo[1.1.1]pentan-1-yl}methyl)({6-[(4-{imidazo[1,5-a]pyridin-8-yl}-1H-1,2,3-triazol-1-yl)methyl]-1H-indol-2-yl}methyl)amine N-[(2-{[({3-fluorobicyclo[1.1.1]pentan-1-yl}methyl)amino]methyl}-1H-indol-6-yl)methyl]-5-oxo-5H-[1,3]thiazolo[3,2-a]pyrimidine-7-carboxamide N-[(2-{[({bicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide N-[(2-{[({3-fluorobicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide N-[(2-{[(cyclobutylmethyl)amino]methyl}-1H-pyrrolo[3,2-b]pyridin-6-yl)methyl]-4-oxo-4H-pyrido[1,2-a]pyrimidine-2-carboxamide N-[(2-{[({3-methylbicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide N-[(2-{[(cyclobutylmethyl)amino]methyl}-1H-pyrrolo[3,2-c]pyridin-6-yl)methyl]-4-oxo-4H-pyrido[1,2-a]pyrimidine-2-carboxamide N-[(2-{[({bicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide N-[(2-{[({3-fluorobicyclo[1.1.1]pentan-1-yl}methyl) amino]methyl}-1H-pyrrolo[3,2-c]465yridine-6-yl) methyl]-4-oxo-4H-pyrido[1,2-a]pyrimidine-2-carboxamide N-[(2-{[(cyclobutylmethyl)amino]methyl}-1H-indol-6-yl) methyl]-4-oxo-4H,6H,7H,8H,9H-pyrido[1,2-a]pyrimidine-2-carboxamide (cyclobutylmethyl)({6-[(4-{1H-pyrrolo[2,3-b]pyridin-5-yl}-1H-imidazol-1-yl)methyl]-1H-indol-2-yl}methyl) amine (cyclobutylmethyl)({6-[(4-{imidazo[1,5-a]pyridin-8-yl}-1H-1,2,3-triazol-1-yl)methyl]-1H-indol-2-yl}methyl) amine N-[(2-{[(2,2-dimethylpropyl)amino]methyl}-1H-indol-6-yl)methyl]-1H-pyrrolo[2,3-b]pyridine-5-carboxamide N-[(2-{[(cyclobutylmethyl)amino]methyl}-1H-indol-6-yl) methyl]-1H-pyrrolo[2,3-b]pyridine-5-carboxamide (cyclobutylmethyl)({6-[(4-{1H-pyrrolo[2,3-b]pyridin-5-yl}-1H-1,2,3-triazol-1-yl)methyl]-1H-indol-2-yl}methyl) amine N-[[2-(2-azabicyclo[2.2.1]heptanean-2-ylmethyl)-1H-indol-6-yl]methyl]-4-oxo-pyrido[1,2-a]pyrimidine-2-carboxamide N-[(3-fluoro-1-bicyclo[1.1.1]pentanyl)methyl]-1-[6-[(4-imidazo[1,5-a]pyridin-8-yltriazol-1-yl)methyl]-1H-pyrrolo[3,2-c]pyridin-2-yl]methanamine (cyclobutylmethyl)[(6-{[1-(1H-indazol-4-yl)-1H-1,2,3-triazol-4-yl]methyl}-1H-indol-2-yl)methyl]amine

[(3,3-difluorocyclobutyl)methyl][(6-{[1-(1H-indazol-4-yl)-1H-1,2,3-triazol-4-yl]methyl}-1H-indol-2-yl)methyl] amine (cyclobutylmethyl)[(6-{[1-(isoquinolin-4-yl)-1H-1,2,3-triazol-4-yl]methyl}-1H-indol-2-yl)methyl]amine (cyclobutylmethyl)({6-[(1-{imidazo[1,5-a]pyridin-8-yl}-1H-1,2,3-triazol-4-yl)methyl]-1H-indol-2-yl}methyl) amine.

3-[1-({2-[({(Bicyclo[1.1.1]pent-1-yl}methyl)amino) methyl]-1H-indol-6-yl}methyl)-1H-1,2,3-triazol-4-yl]-5-methoxy-2-pyridinecarbonitrile;

3-[1-({2-[({(3-Fluorobicyclo[1.1.1]pent-1-yl) methyl}amino)methyl]-1H-indol-6-yl}methyl)-1H-1,2,3-triazol-4-yl]-5-methoxy-2-pyridinecarbonitrile;

5-Methoxy-3-[1-({2-[({(3-methylbicyclo[1.1.1]pent-1-yl) methyl}amino)methyl]-1H-indol-6-yl}methyl)-1H-1,2,3-triazol-4-yl]-2-pyridinecarbonitrile;

3-{1-[(2-{[(Cyclobutylmethyl)amino]methyl}-1H-indol-6-yl)methyl]-1H-1,2,3-triazol-4-yl}-5-methoxy-2-pyridinecarbonitrile;

3-{1-[(2-{(6-Aza-6-spiro[3.4]octyl)methyl}-1H-indol-6-yl) methyl]-1H-1,2,3-triazol-4-yl}-5-methoxy-2-pyridinecarbonitrile;

3-[1-({2-[(4,4-Dimethyl-1-piperidyl)methyl]-1H-indol-6-yl}methyl)-1H-1,2,3-triazol-4-yl]-5-methoxy-2-pyridinecarbonitrile;

N-((2-((6-azaspiro[3.4]octan-6-yl)methyl)-1H-pyrrolo[3,2-c]pyridin-6-yl)methyl)-4-oxo-4H-pyrido[1,2-a]pyrimidine-2-carboxamide;

3-(1-((2-(((cyclobutylmethyl)amino)methyl)-1H-indol-6-yl) methyl)-1H-1,2,3-triazol-4-yl)-5-fluoropicolinonitrile;

1-cyclobutyl-N-((6-((4-(5-methoxypyridin-3-yl)-1H-1,2,3-triazol-1-yl)methyl)-1H-indol-2-yl)methyl)methanamine;

5-chloro-3-(1-((2-(((cyclobutylmethyl)amino)methyl)-1H-indol-6-yl)methyl)-1H-1,2,3-triazol-4-yl)picolinonitrile; and 2-((6-azaspiro[3.4]octan-6-yl)methyl)-6-((4-(imidazo[1,5-a]pyridin-8-yl)-1H-1,2,3-triazol-1-yl)methyl)-1H-pyrrolo[3,2-c]pyridine.

48. A compound, or a pharmaceutically acceptable salt thereof, selected from any one of the following:

N-[[2-[[(1-hydroxycyclobutyl)methylamino]methyl]-1H-indol-6-yl]methyl]-4-oxo-pyrido[1,2-a]pyrimidine-2-carboxamide;

N-[[2-[[(1-fluorocyclobutyl)methylamino]methyl]-1H-indol-6-yl]methyl]-4-oxo-pyrido[1,2-a]pyrimidine-2-carboxamide;

N-[[2-[(4,4-dimethyl-1-piperidyl)methyl]-1H-indol-6-yl] methyl]-4-oxo-pyrido[1,2-a]pyrimidine-2-carboxamide N-[[2-[(cyclobutylmethylamino)methyl]-1H-indol-6-yl] methyl]-4-oxo-pyrido[1,2-a]pyrimidine-2-carboxamide N-[[2-[(cyclobutylmethylamino)methyl]-1H-indol-6-yl] methyl]-1H-pyrrolo[2,3-b]pyridine-5-carboxamide N-(cyclobutylmethyl)-1-[6-[[4-(1H-pyrazolo[4,3-c]pyridin-4-yl)triazol-1-yl]methyl]-1H-indol-2-yl]methanamine N-(cyclobutylmethyl)-1-[6-[[4-(1H-indazol-4-yl)triazol-1-yl]methyl]-1H-indol-2-yl]methanamine N-(cyclobutylmethyl)-1-[6-[[4-(1H-pyrrolo[2,3-b]pyridin-5-yl)triazol-1-yl]methyl]-1H-indol-2-yl]methanamine N-[[2-[(2,2-dimethylpropylamino)methyl]-1H-indol-6-yl] methyl]-4-oxo-pyrido[1,2-a]pyrimidine-2-carboxamide N-[[2-[(1-bicyclo[1.1.1]pentanylmethylamino)methyl]-1H-indol-6-yl]methyl]-4-oxo-pyrido[1,2-a]pyrimidine-2-carboxamide 1-[[[6-[[4-(1H-indazol-4-yl)triazol-1-yl]methyl]-1H-indol-2-yl]methylamino]methyl]cyclobutanol N-[[2-[[(3-fluoro-1-bicyclo[1.1.1]pentanyl)methylamino] methyl]-1H-indol-6-yl]methyl]-4-oxo-pyrido[1,2-a]pyrimidine-2-carboxamide N-[[2-[[(3,3-difluorocyclobutyl)methylamino]methyl]-1H-indol-6-yl]methyl]-4-oxo-pyrido[1,2-a]pyrimidine-2-carboxamide N-[(3,3-difluorocyclobutyl)methyl]-1-[6-[[1-(1H-indazol-4-yl)triazol-4-yl]methyl]-1H-indol-2-yl]methanamine N-[[2-[(oxetan-2-ylmethylamino)methyl]-1H-indol-6-yl] methyl]-4-oxo-pyrido[1,2-a]pyrimidine-2-carboxamide N-[[2-[(cyclobutylmethylamino)methyl]-1H-indol-6-yl] methyl]-1H-indazole-4-carboxamide N-[[2-[[(1-fluorocyclobutyl)methylamino]methyl]-1H-indol-6-yl]methyl]-4-oxo-pyrido[1,2-a]pyrimidine-2-carboxamide N-[[2-[(cyclobutylmethylamino)methyl]-3H-benzimidazol-5-yl]methyl]-4-oxo-pyrido[1,2-a]pyrimidine-2-carboxamide N-(cyclobutylmethyl)-1-[6-[[1-(4-isoquinolyl)triazol-4-yl] methyl]-1H-indol-2-yl]methanamine 4-oxo-N-[[2-[(prop-2-ynylamino)methyl]-1H-indol-6-yl] methyl]pyrido[1,2-a]pyrimidine-2-carboxamide N-[[2-[(2,2-dimethylpropylamino)methyl]-1H-indol-6-yl] methyl]-1H-pyrrolo[2,3-b]pyridine-5-carboxamide N-[[2-[(cyclopropylmethylamino)methyl]-1H-indol-6-yl] methyl]-4-oxo-pyrido[1,2-a]pyrimidine-2-carboxamide N-[[2-[(isobutylamino)methyl]-1H-indol-6-yl]methyl]-4-oxo-pyrido[1,2-a]pyrimidine-2-carboxamide N-[[2-[(cyclohexylamino)methyl]-1H-indol-6-yl]methyl]-4-oxo-pyrido[1,2-a]pyrimidine-2-carboxamide.

49. A pharmaceutical composition comprising a compound according to any one of paragraphs 1 to 48, or a pharmaceutically acceptable salt thereof, and one or more pharmaceutically acceptable excipients.

50. A compound according to any one of paragraphs 1 to 48, or a pharmaceutically acceptable salt thereof, or a pharmaceutical composition according to paragraph 49, for use in therapy.

51. A compound according to any one of paragraphs 1 to 47, or a pharmaceutically acceptable salt thereof, or a pharmaceutical composition according to paragraph 49, for use in the treatment of a proliferative condition.

52. A compound according to any one of paragraphs 1 to 48, or a pharmaceutically acceptable salt thereof, or a pharmaceutical composition according to paragraph 49, for use in the treatment of cancer.

53. A compound according to any one of paragraphs 1 to 48, or a pharmaceutically acceptable salt thereof, or a pharmaceutical composition according to paragraph 49, for use in the treatment of leukaemia.

54. A compound according to any one of paragraphs 1 to 48, or a pharmaceutically acceptable salt thereof, or a pharmaceutical composition according to paragraph 49, for use in the treatment of AML leukaemia or chronic myeloid leukaemia.

55. A compound according to any one of paragraphs 1 to 48, or a pharmaceutically acceptable salt thereof, or a pharmaceutical composition according to paragraph 49, for use in the inhibition of METTL3 activity.

56. A compound according to any one of paragraphs 1 to 48, or a pharmaceutically acceptable salt thereof, or a pharmaceutical composition according to paragraph 49, for use in the treatment of an autoimmune disease, a neurological disease, an inflammatory disease or an infectious disease.

57. Use of a compound according to any one of paragraphs 1 to 48, or a pharmaceutically acceptable salt thereof, in the manufacture of a medicament for the treatment of a proliferative condition.

58. Use of a compound according to any one of paragraphs 1 to 48, or a pharmaceutically acceptable salt thereof, in the manufacture of a medicament for the treatment of cancer.

59. Use of a compound according to any one of paragraphs 1 to 48, or a pharmaceutically acceptable salt thereof, in the manufacture of a medicament for the treatment of leukaemia.

60. Use of a compound according to any one of paragraphs 1 to 48, or a pharmaceutically acceptable salt thereof, in the manufacture of a medicament for the treatment of AML leukaemia or chronic myeloid leukaemia.

61. Use of a compound according to any one of paragraphs 1 to 48, or a pharmaceutically acceptable salt thereof, in the manufacture of a medicament for the treatment of an autoimmune disease, a neurological disease, an inflammatory disease or an infectious disease.

62. Use of a compound according to any one of paragraphs 1 to 48, or a pharmaceutically acceptable salt thereof, in the manufacture of a medicament for the inhibition of METTL3 activity.

63. A method of treating a proliferative disorder, said method comprising administering to a subject in need thereof a therapeutically effective amount of a compound according to any one of paragraphs 1 to 48, or a pharmaceutically acceptable salt thereof, or a pharmaceutical composition according to paragraph 49.

64. A method of treating cancer, said method comprising administering to a subject in need thereof a therapeutically effective amount of a compound according to any one of paragraphs 1 to 45, or a pharmaceutically acceptable salt thereof, or a pharmaceutical composition according to paragraph 46.

65. A method of treating leukaemia, said method comprising administering to a subject in need thereof a therapeutically effective amount of a compound according to any one of paragraphs 1 to 48, or a pharmaceutically acceptable salt thereof, or a pharmaceutical composition according to paragraph 49.

66. A method of treating AML leukaemia or chronic myeloid leukaemia, said method comprising administering to a subject in need thereof a therapeutically effective amount of a compound according to any one of paragraphs 1 to 48, or a pharmaceutically acceptable salt thereof, or a pharmaceutical composition according to paragraph 49.

67. A method of treating an autoimmune disease, a neurological disease, an inflammatory disease or an infectious disease, said method comprising administering to a subject in need thereof a therapeutically effective amount of a compound according to any one of paragraphs 1 to 48, or a pharmaceutically acceptable salt thereof, or a pharmaceutical composition according to paragraph 49.

68. A method of inhibiting METTL3 activity in vitro or in vivo, said method comprising contacting a cell with an effective amount of a compound according to any one of paragraphs 1 to 48, or a pharmaceutically acceptable salt thereof, or a pharmaceutical composition according to paragraph 49.

69. A method of inhibiting metastasis in vitro or in vivo, said method comprising contacting a cell with an effective amount of a compound according to any one of paragraphs 1 to 48, or a pharmaceutically acceptable salt thereof, or a pharmaceutical composition according to paragraph 49.

The invention claimed is:

1. A compound of formula (I) shown below, or a pharmaceutically acceptable salt thereof:

$$X—Y—Z \qquad (I)$$

wherein:

X is selected from:

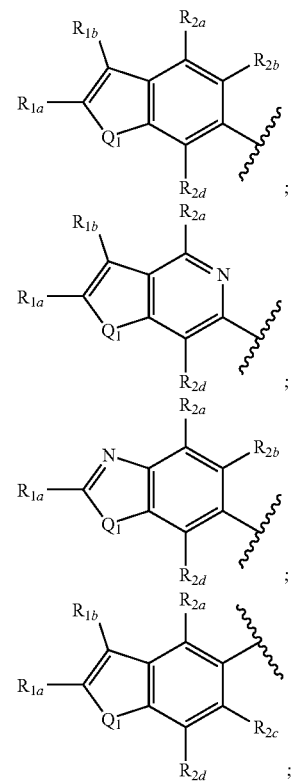

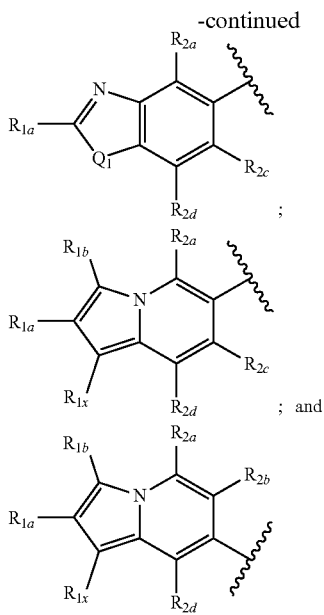

wherein
Q$_1$ is selected from NH, N—C$_{1-4}$alkyl, O and S;
R$_{1a}$ is a group of the formula:

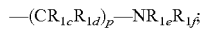

wherein
p is an integer selected from 1 and 2;
R$_{1c}$ and R$_{1d}$ are independently selected from:
(i) hydrogen (including deuterium),
(ii) C$_{1-3}$alkyl which is optionally substituted by one more substituents selected from cyano, oxo, hydroxy, C$_{1-3}$alkoxy, halo, C$_{1-3}$haloalkoxy, —O—C$_{3-4}$cycloalkyl, and NH$_2$; wherein —O—C$_{3-4}$cycloalkyl is optionally substituted with halo, cyano, or hydroxy, and
(iii) R$_{1c}$ and R$_{1d}$ are linked together such that, together with the carbon atom to which they are attached, they form a 3- to 5-membered cycloalkyl or heterocyclic ring, or a spirocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy, NR$_{1ca}$R$_{1da}$ and —S(O)$_{0-2}$R$_{1ca}$R$_{1da}$, wherein R$_{1ca}$ and R$_{1da}$ are H or C$_{1-2}$alkyl;
R$_{1e}$ and R$_{1f}$ are each independently selected from:
(i) hydrogen (including deuterium);
(ii) C$_{1-6}$alkyl which is optionally substituted by one more substituents selected from cyano, hydroxy, C$_{1-2}$alkoxy, halo, C$_{1-2}$haloalkoxy and NH$_2$;
(iii) a group with the formula:

wherein:
q is 0, 1, 2 or 3;
R$_{1g}$ and R$_{1h}$ are independently selected from:
a) hydrogen (including deuterium);
b) C$_{1-6}$alkyl which is optionally substituted by one more substituents selected from cyano, hydroxy, C$_{1-4}$alkoxy, halo, C$_{1-4}$haloalkoxy, —O—C$_{3-6}$cycloalkyl, NR$_{1ca}$R$_{1da}$ and —S(O)$_{0-2}$R$_{1ca}$R$_{1da}$, wherein R$_{1ca}$ and R$_{1da}$ are H or C$_{1-2}$alkylNR$_{1ga}$R$_{1ha}$ or —S(O)$_{0-2}$R$_{1ga}$R$_{1ha}$, wherein R$_{1ga}$ and R$_{1ha}$ are H or C$_{1-2}$alkyl; and
wherein —O—C$_{3-6}$cycloalkyl is optionally substituted with halo, cyano or hydroxy; and
c) R$_{1g}$ and R$_{1h}$ are optionally linked together such that, together with the carbon atom to which they are attached, they form a 3- to 6-membered cycloalkyl or heterocyclic ring which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy, NR$_{1ga}$R$_{1ha}$ and —S(O)$_{0-2}$R$_{1ga}$R$_{1ha}$, wherein R$_{1ga}$ and R$_{1ha}$ are H or C$_{1-2}$alkyl;
and T$_1$ is selected from hydrogen, halo, C$_{1-4}$alkyl, C$_{1-4}$haloalkyl, cyano, hydroxy, NR$_{1t}$R$_{2t}$ or —S(O)$_{0-2}$R$_{1t}$R$_{2t}$ (wherein R$_{1t}$ and R$_{2t}$ are H or C$_{1-4}$alkyl), C$_{3-8}$cycloalkyl, C$_{2-3}$alkenyl, C$_{2-3}$alkynyl, aryl, heterocyclyl, a mono- or bicyclic heteroaryl, a spirocyclic carbocyclic or heterocyclic ring system, a bridged C$_{3-8}$cycloalkyl, a bridged bicyclic C$_{5-12}$cycloalkyl, and a bridged heterocyclic ring system, each of which is optionally substituted by one or more substituents selected from C$_{1-2}$alkyl, C$_{1-2}$haloalkyl, cyano, hydroxy, C$_{1-2}$alkoxy, halo, C$_{1-2}$haloalkoxy, C$_{3-6}$cycloalkyl, NR$_{3t}$R$_{4t}$ and —S(O)$_{0-2}$R$_{3t}$R$_{4t}$, wherein R$_{3t}$ and R$_{4t}$ are H or C$_{1-2}$alkyl; and
(iv) R$_{1e}$ and R$_{1f}$ are linked such that, together with the nitrogen atom to which they are attached, they form a mono- or bicyclic-heterocyclic ring, which is optionally substituted by one or more substituents selected from C$_{1-4}$alkyl, C$_{1-4}$haloalkyl, C$_{3-6}$cycloalkyl, cyano, hydroxy, C$_{1-4}$alkoxy, halo, C$_{1-4}$haloalkoxy, NR$_{1i}$R$_{1j}$ and —S(O)$_{0-2}$R$_{1i}$R$_{1j}$, wherein R$_{1i}$ and R$_{1j}$ are H or C$_{1-4}$alkyl, and/or the mono- or bicyclic heterocyclic ring formed by R$_{1e}$ and R$_{1f}$ is optionally spiro-fused to a C$_{3-6}$cycloalkyl or a heterocyclic ring, which in turn is optionally substituted by one or more substituents selected from C$_{1-4}$alkyl, C$_{1-4}$haloalkyl, C$_{3-6}$cycloalkyl, cyano, hydroxy, C$_{1-4}$alkoxy, halo, C$_{1-4}$haloalkoxy, NR$_{1i}$R$_{1j}$ and —S(O)$_{0-2}$R$_{1i}$R$_{1j}$, wherein R$_{1i}$ and R$_{1j}$ are H or C$_{1-4}$alkyl; and
p is an integer selected from 1 and 2;
R$_{1b}$ is selected from hydrogen, cyano, halo and C$_{1-3}$ alkyl;
R$_{1x}$ is selected from hydrogen, cyano, halo and C$_{1-3}$ alkyl;
R$_{2a}$, R$_{2b}$, R$_{2c}$ and R$_{2d}$ are independently selected from hydrogen, cyano, C$_{1-6}$ alkoxy, C$_{1-6}$haloalkoxy, halo, C$_{1-6}$alkyl, C$_{1-6}$haloalkyl, C$_{3-6}$cycloalkyl, aryl, heterocyclyl and heteroaryl, each of which is optionally substituted by one or more substituents selected from halo, trifluoromethyl, trifluoromethoxy, amino, and hydroxy;
Y is selected from:

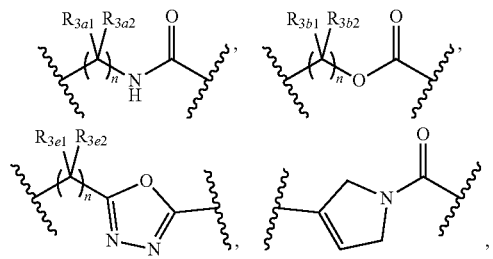

-continued

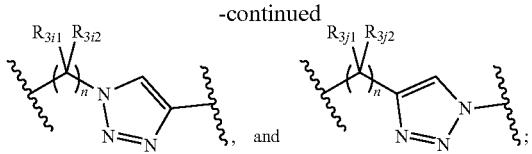

wherein:
R$_{3a1}$, R$_{3b1}$, R$_{3e1}$, R$_{3i1}$ and R$_{3j1}$ are selected from hydrogen and methyl;
R$_{3a2}$, R$_{3b2}$, R$_{3e2}$, R$_{3i2}$ and R$_{3j2}$ are hydrogen; and
n is 1 or 2;
Z is selected from:

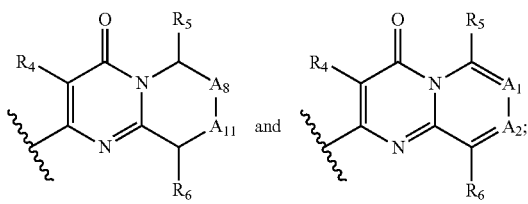

wherein:
A$_1$ is selected from CR$_{12}$ and N;
A$_2$ is selected from CR$_{13}$ and N;
A$_8$ is selected from CR$_{19}$R$_{20}$ and NR$_{21}$;
A$_{11}$ is selected from CR$_{28}$R$_{29}$ and NR$_{30}$;
(i) R$_4$, R$_5$, and R$_6$ are independently selected from hydrogen, methyl, cyano and halo;
(ii) R$_{12}$, R$_{13}$, R$_{18}$, R$_{19}$, and R$_{20}$ are independently selected from hydrogen, halo, cyano and methyl;
(iii) R$_{21}$ and R$_{30}$ are independently selected from hydrogen and methyl; and
(iv) R$_{28}$ and R$_{29}$ are selected from hydrogen, halo, methoxy and methyl.

2. A compound according to claim 1, or a pharmaceutically acceptable salt thereof, wherein X is selected from:

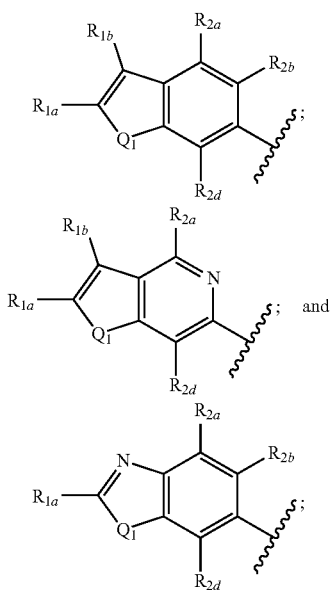

wherein Q$_1$, R$_{1a}$, R$_{1b}$, R$_{2a}$, R$_{2b}$, R$_{2d}$ are as defined in claim 1.

3. A compound according to claim 1, wherein X is selected from:

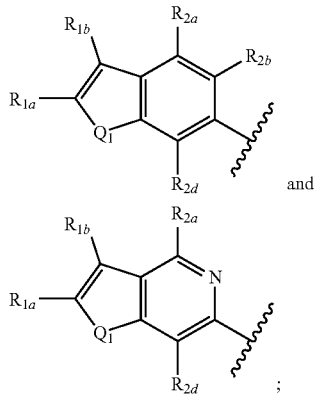

wherein Q$_1$, R$_{1a}$, R$_{1b}$, R$_{2a}$, R$_{2b}$ and R$_{2d}$ are as defined in claim 1.

4. A compound according to claim 1, or a pharmaceutically acceptable salt thereof, wherein Q$_1$ is selected from NH and N—C$_{1-4}$alkyl.

5. A compound according to claim 1, or a pharmaceutically acceptable salt thereof, wherein X is selected from:

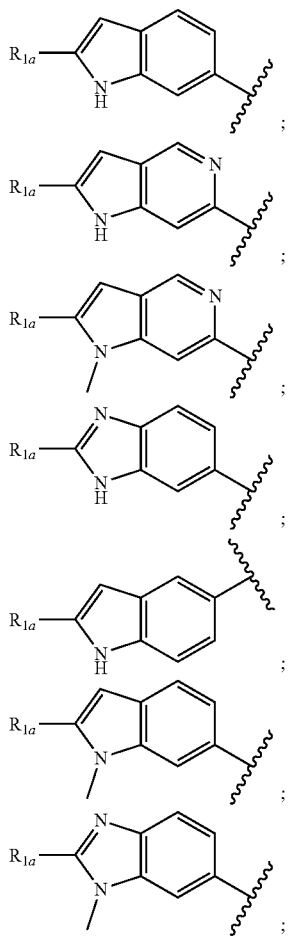

-continued

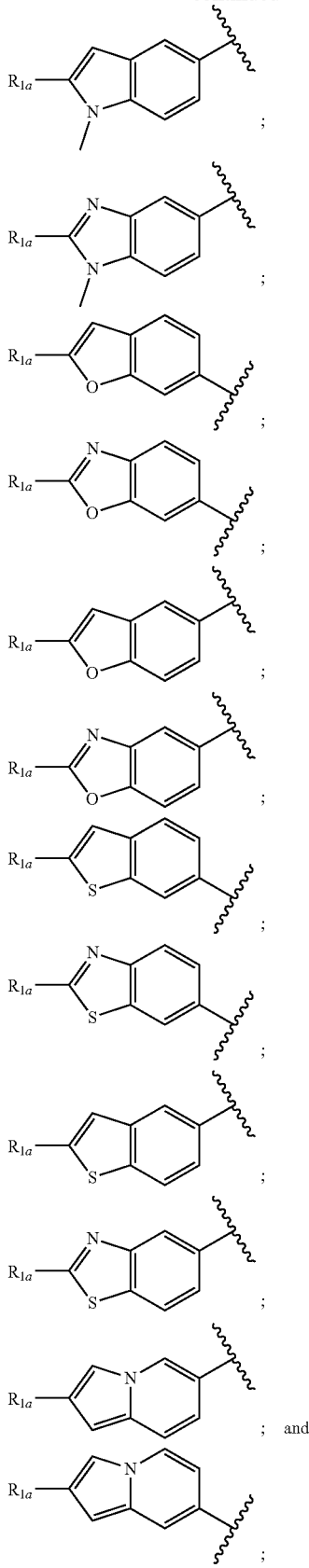

wherein $R_{1a}$ is as defined in claim 1.

6. A compound according to claim 1, or a pharmaceutically acceptable salt thereof, wherein $R_{1a}$ is a group of the formula:

$$-(CR_{1c}R_{1d})_p-NR_{1e}R_{1f}$$

wherein
p is an integer selected from 1 and 2;
$R_{1c}$ and $R_{1d}$ are independently selected from:
(i) hydrogen (including deuterium);
(ii) $C_{1-3}$alkyl which is optionally substituted by one more substituents selected from cyano, oxo, hydroxy, $C_{1-2}$alkoxy, halo, $C_{1-2}$haloalkoxy, and —O—$C_{3-6}$cycloalkyl;
$R_{1e}$ is selected from hydrogen (including deuterium) and $C_{1-2}$alkyl; and
$R_{1f}$ is
a group with the formula:

$$-(CR_{1g}R_{1h})_q-T_1$$

wherein:
q is 1 or 3;
$R_{1g}$ and $R_{1h}$ are independently selected from:
a) hydrogen (including deuterium); and
b) $C_{1-2}$alkyl which is optionally substituted by one more substituents selected from cyano, hydroxy, $C_{1-2}$alkoxy, halo, and $C_{1-2}$haloalkoxy;
and $T_1$ is selected from $C_{1-4}$alkyl, $C_{1-4}$haloalkyl, aryl, heterocyclyl, a mono- or bicyclic heteroaryl, a spirocyclic carbocyclic or heterocyclic ring system, a bridged $C_{3-8}$ cycloalkyl, a bridged bicyclic $C_{5-12}$cycloalkyl, and a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, and $C_{3-6}$cycloalkyl;
or $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo and $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo and $C_{1-2}$haloalkoxy.

7. A compound according to claim 1, or a pharmaceutically acceptable salt thereof, wherein $R_{1a}$ is a group of the formula:

$$-(CR_{1c}R_{1d})_p-NR_{1e}R_{1f}$$

wherein
p is an integer selected from 1 and 2;
$R_{1c}$ and $R_{1d}$ are independently selected from:
(i) hydrogen (including deuterium); and
(ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, and $NH_2$; wherein —O—$C_{3-4}$ cycloalkyl is optionally substituted with halo, cyano and hydroxy,
$R_{1e}$ and $R_{1f}$ are each independently selected from:
(i) hydrogen (including deuterium);
(ii) $C_{1-6}$alkyl which is optionally substituted by one more substituents selected from cyano, hydroxy, $C_{1-2}$alkoxy, halo, $C_{1-2}$haloalkoxy and $NH_2$;

(iii) a group with the formula:

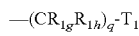

wherein:

q is 0, 1, 2 or 3;

$R_{1g}$ and $R_{1h}$ are independently selected from:

a) hydrogen (including deuterium); and b) $C_{1-6}$alkyl which is optionally substituted by one more substituents selected from cyano, hydroxy, $C_{1-4}$alkoxy, halo, $C_{1-4}$haloalkoxy, —O—$C_{3-6}$cycloalkyl, $NR_{1ca}R_{1da}$ and —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;

and $T_1$ is selected from $C_{1-4}$alkyl, $C_{1-4}$haloalkyl, cyano, hydroxy, $C_{3-8}$cycloalkyl, aryl, heterocyclyl, a mono- or bicyclic heteroaryl, a spirocyclic carbocyclic or heterocyclic ring system, a bridged $C_{3-8}$cycloalkyl, a bridged bicyclic $C_{5-12}$cycloalkyl, and a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ and —$S(O)_{0-2}R_{3t}R_{4t}$, wherein $R_{3t}$ and $R_{4t}$ are H or $C_{1-2}$alkyl; and (iv) $R_{1e}$ and $R_{1f}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ and —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ and —$S(O)_{0-2}R_{1i}R_{1j}$, wherein $R_{1i}$ and $R_{1j}$ are H or $C_{1-4}$alkyl.

8. A compound according to claim 1, or a pharmaceutically acceptable salt thereof, wherein $R_{1a}$ is a group of the formula:

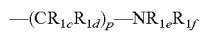

wherein $R_{1c}$ and $R_{1d}$ are independently selected from hydrogen (including deuterium) and $C_{1-2}$alkyl;

$R_{1e}$ is selected from hydrogen (including deuterium) and $C_{1-2}$alkyl; and $R_{1f}$ is a group with the formula:

wherein:

q is 1;

$R_{1g}$ and $R_{1h}$ are independently selected from hydrogen (including deuterium) and $C_{1-2}$alkyl;

and $T_1$ is selected from $C_{3-4}$cycloalkyl, heterocyclyl, a spirocyclic carbocyclic or heterocyclic ring system, a bridged $C_{3-8}$cycloalkyl, a bridged bicyclic $C_{5-12}$cycloalkyl, and a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy and $C_{3-6}$cycloalkyl, wherein any alkyl or alkoxy is optionally further substituted by one or more substituents selected from cyano, hydroxy and halo.

9. A compound according to claim 1, wherein $R_{1a}$ is a group of the formula:

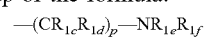

wherein p is 1;

$R_{1c}$ and $R_{1d}$ are independently selected from hydrogen (including deuterium) and $C_{1-2}$alkyl; and $R_{1e}$ and $R_{1f}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo and $C_{1-2}$haloalkoxy, and/or the mono- or bicyclic heterocyclic ring formed by $R_{1e}$ and $R_{1f}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, cyano, hydroxy, $C_{1-2}$alkoxy, halo and $C_{1-2}$haloalkoxy.

10. A compound according to claim 1, wherein $R_{1a}$ is selected from

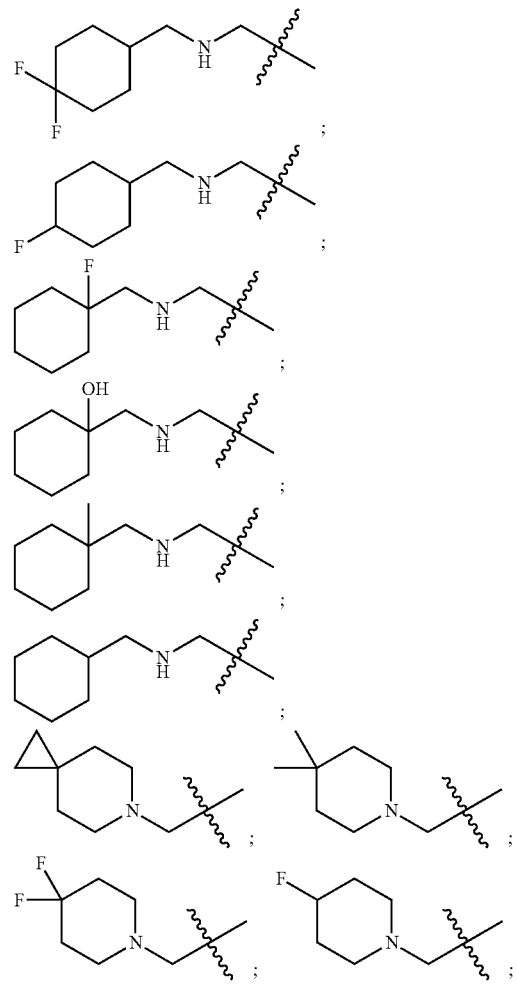

-continued
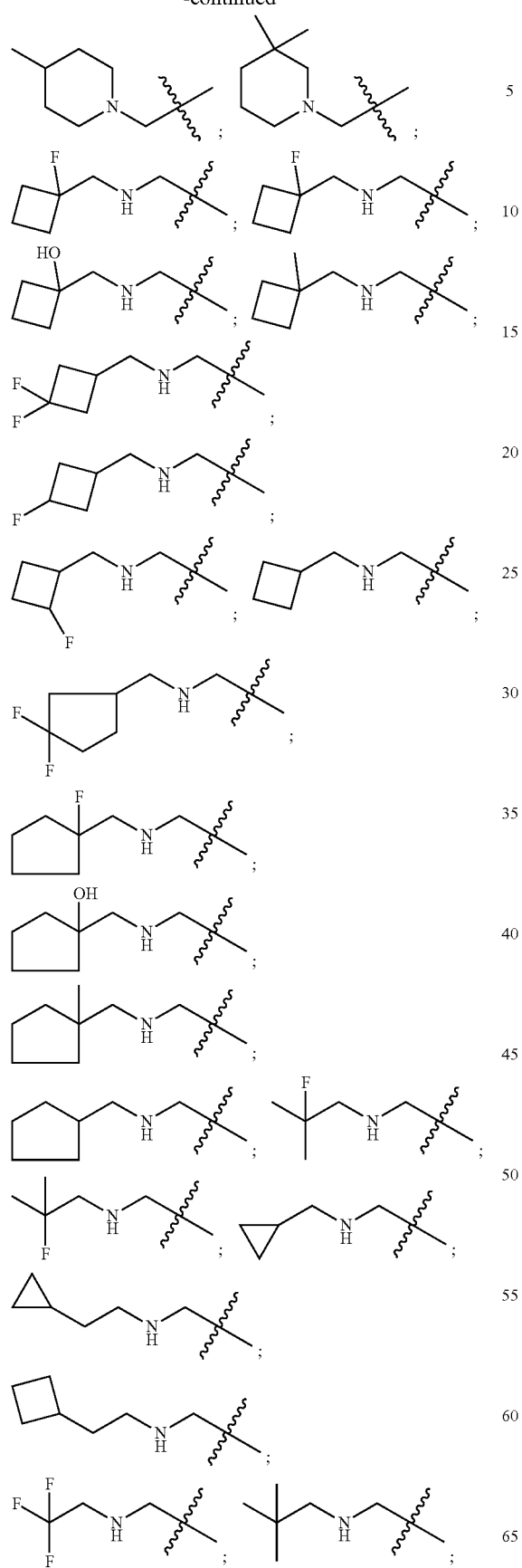
-continued
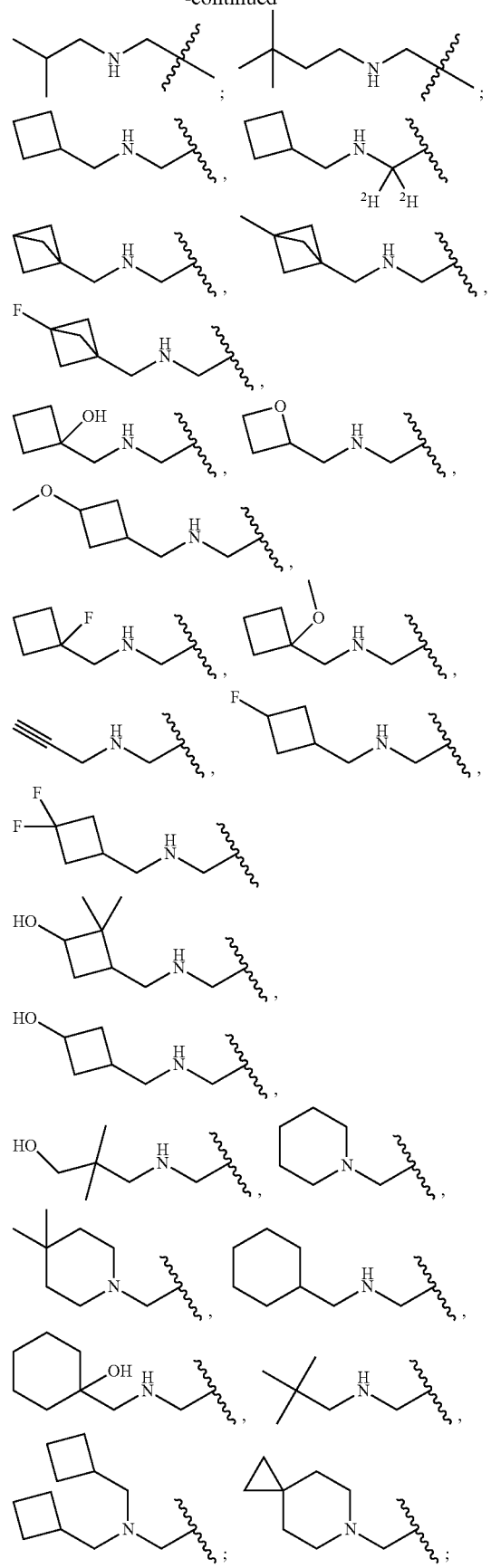

401
-continued
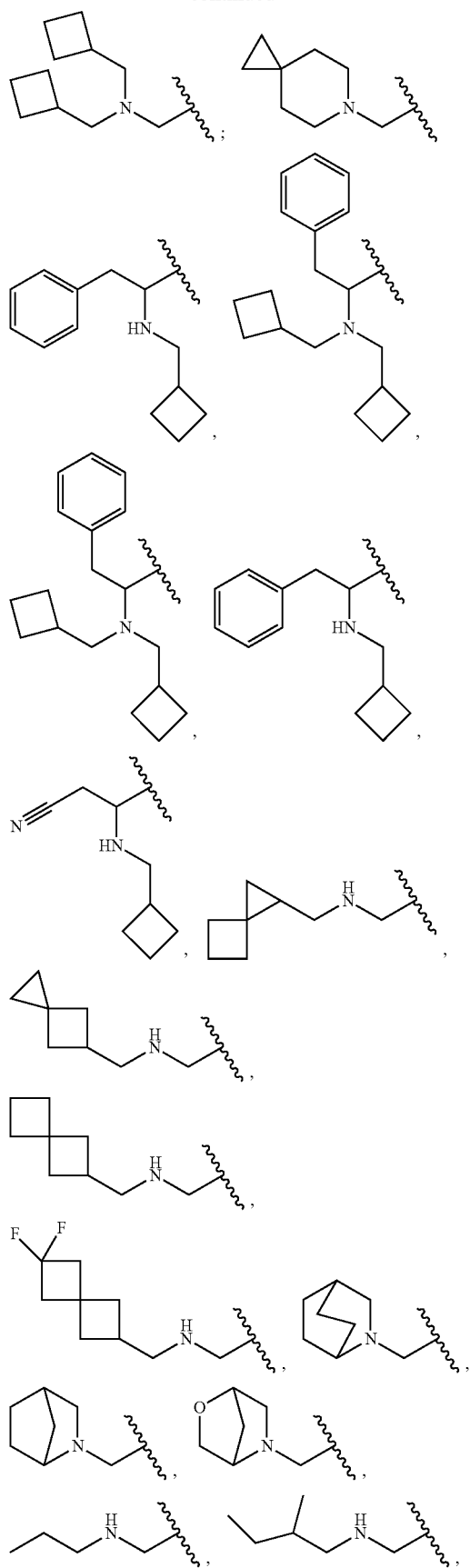
402
-continued
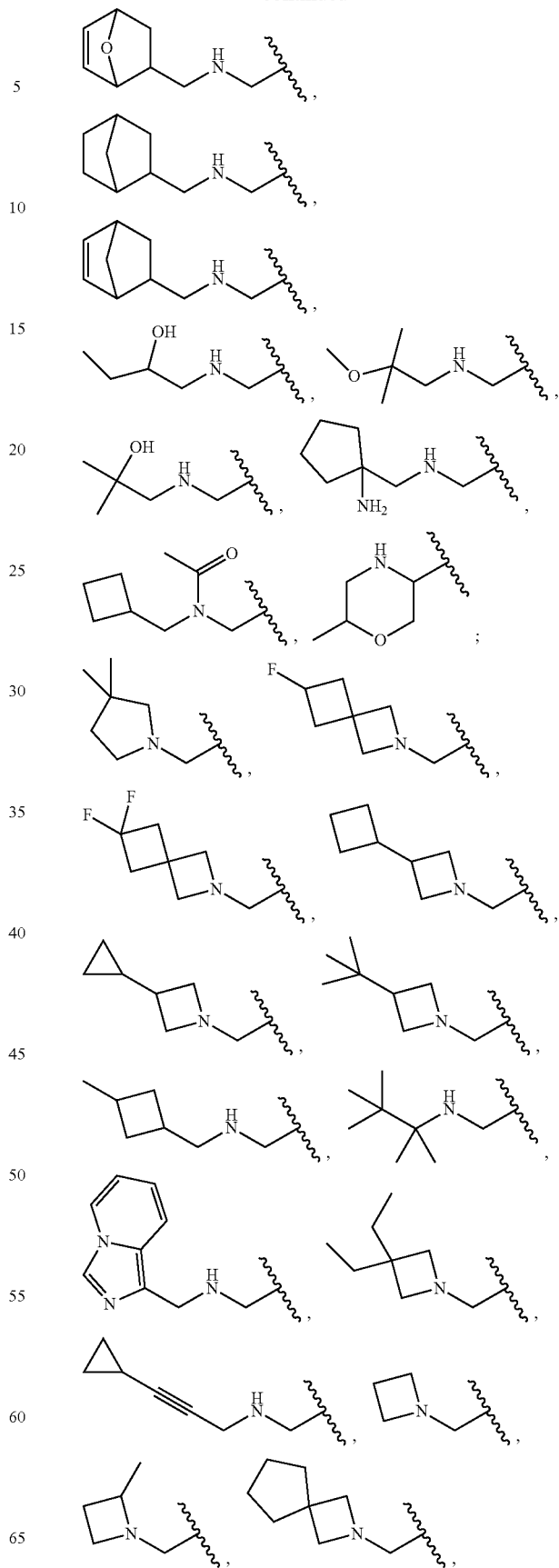

-continued

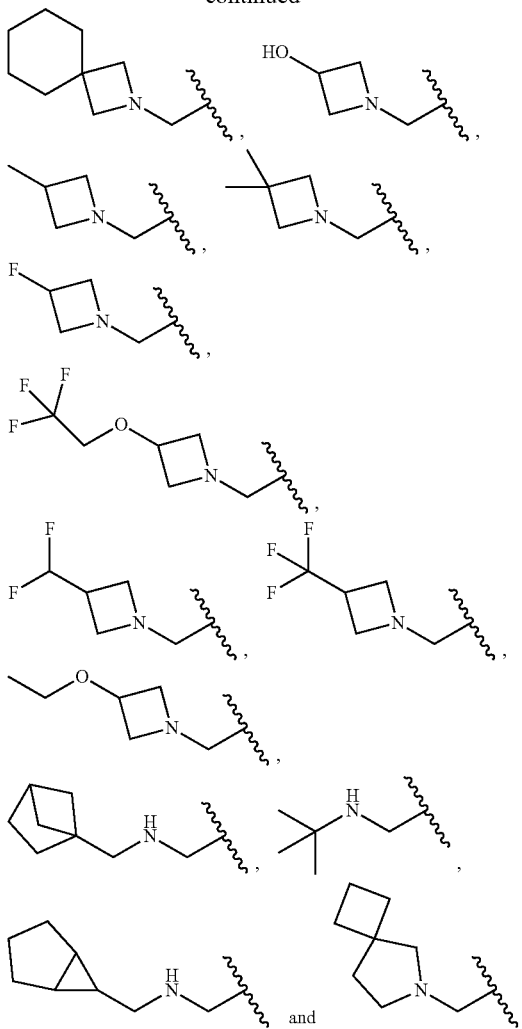

11. A compound according to claim 1, or a pharmaceutically acceptable salt thereof, wherein $R_{1b}$ is selected from hydrogen, halo and $C_{1-2}$ alkyl.

12. A compound according to claim 1, or a pharmaceutically acceptable salt thereof, wherein $R_{2a}$, $R_{2b}$, $R_{2c}$ and $R_{2d}$ are independently selected from hydrogen, cyano, halo and $C_{1-3}$alkyl.

13. A compound according to claim 1, or a pharmaceutically acceptable salt thereof, wherein Y is selected from:

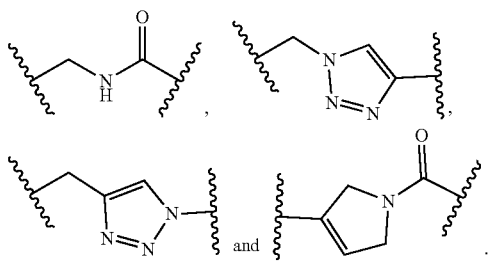

14. A compound according to claim 1, or a pharmaceutically acceptable salt thereof, wherein:
 (i) $R_4$, $R_5$, and $R_6$ are hydrogen;
 (ii) $R_{12}$, $R_{13}$, $R_{18}$, $R_{19}$, and $R_{20}$ are hydrogen;
 (iii) $R_{21}$ and $R_{30}$ are hydrogen; and
 (iv) $R_{28}$ and $R_{29}$ are hydrogen.

15. A compound according to claim 1, or a pharmaceutically acceptable salt thereof, wherein Z is:

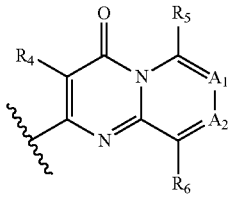

wherein $A_1$, $A_2$, $R_4$, $R_5$, and $R_6$ are as defined in claim 1.

16. A compound according to claim 1, or a pharmaceutically acceptable salt thereof, wherein:

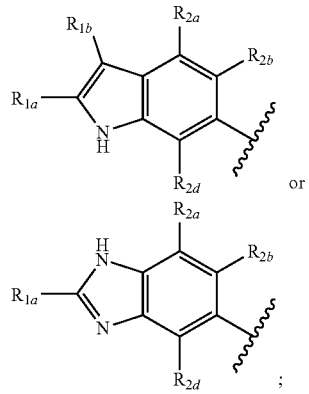

Y is selected from:

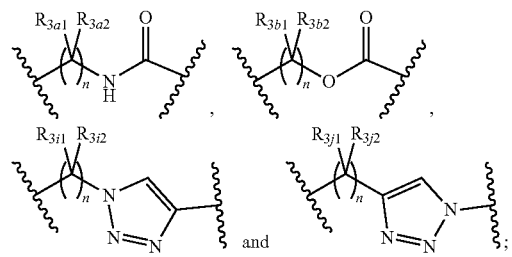

and
Z is:

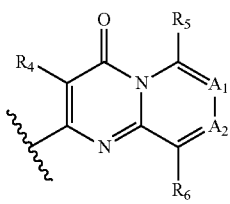

wherein:
 (i) $R_{1a}$, $R_{1b}$, $R_{2a}$, $R_{2b}$ and $R_{2d}$ are as defined in claim 1;
 (ii) $R_{3a1}$, $R_{3a2}$, $R_{3b1}$, $R_{3b2}$, $R_{3i1}$, $R_{3i2}$, $R_{3j1}$, $R_{3j2}$ and n are as defined in claim 1; and
 (iii) $A_1$, $A_2$, $R_4$, $R_5$, and $R_6$ are as defined in claim 1.

17. A compound according to claim 1, or a pharmaceutically acceptable salt thereof, wherein:

X is

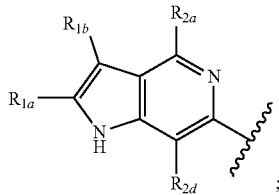

Y is

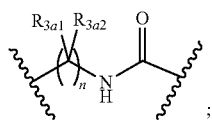

and

Z is

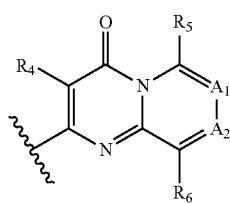

(i) wherein $R_{1a}$, $R_{1b}$, $R_{2a}$, and $R_{2d}$ are as defined in claim 1;
(ii) n, $R_{3a1}$ and $R_{3a2}$ are as defined in claim 1; and
(iii) $A_1$, $A_2$, $R_4$, $R_5$ and $R_6$ are as defined in claim 1.

18. A compound, or a pharmaceutically acceptable salt thereof, selected from any one of the following:

N-({2-[(4,4-dimethylpiperidin-1-yl)methyl]-1H-indol-6-yl}methyl)-4-oxo-4H-pyrido[1,2-a]pyrimidine-2-carboxamide;

N-[(2-{[(cyclobutylmethyl)amino]methyl}-1H-indol-6-yl)methyl]-4-oxo-4H-pyrido[1,2-a]pyrimidine-2-carboxamide;

N-[[2-1[[(3,3-difluorocyclobutyl)methylamino]methyl]-1H-indol-6-yl]methyl]-4-oxo-pyrido[1,2-a]pyrimidine-2-carboxamide;

N-[[2-[[(1-hydroxycyclobutyl)methylamino]methyl]-1H-indol-6-yl]methyl]-4-oxo-pyrido[1,2-a]pyrimidine-2-carboxamide;

N-[[2-[[(1-fluorocyclobutyl)methylamino]methyl]-1H-indol-6-yl]methyl]-4-oxo-pyrido[1,2-a]pyrimidine-2-carboxamide;

N-[[2-[[(1-methylcyclopropyl)methylamino]methyl]-1H-indol-6-yl]methyl]-4-oxo-pyrido[1,2-a]pyrimidine-2-carboxamide;

N-[[2-(2-azabicyclo[2.1.1]hexan-2-ylmethyl)-1H-indol-6-yl]methyl]-4-oxo-pyrido[1,2-a]pyrimidine-2-carboxamide;

N-[[2-(3-azabicyclo[3.1.1]heptanean-3-ylmethyl)-1H-indol-6-yl]methyl]-4-oxo-pyrido[1,2-a]pyrimidine-2-carboxamide;

N-[[2-[[2-(hydroxymethyl)pyrrolidin-1-yl]methyl]-1H-indol-6-yl]methyl]-4-oxo-pyrido[1,2-a]pyrimidine-2-carboxamide;

N-[[2-(morpholinomethyl)-1H-indol-6-yl]methyl]-4-oxo-pyrido[1,2-a]pyrimidine-2-carboxamide;

N-[[2-[(1-adamantylamino)methyl]-1H-indol-6-yl]methyl]-4-oxo-pyrido[1,2-a]pyrimidine-2-carboxamide;

4-oxo-N-[[2-(1-piperidylmethyl)-1H-indol-6-yl]methyl]pyrido[1,2-a]pyrimidine-2-carboxamide;

N-[[2-1[(4-fluoro-1-piperidyl)methyl]-1H-indol-6-yl]methyl]-4-oxo-pyrido[1,2-a]pyrimidine-2-carboxamide;

4-oxo-N-[[2-[[[rac-(1S,2S,4S)-7-oxabicyclo[2.2.1]heptane-5-en-2-yl]methylamino]methyl]-1H-indol-6-yl]methyl]pyrido[1,2-a]pyrimidine-2-carboxamide;

N-[[2-1[[(1-hydroxycyclopentyl)methylamino]methyl]-1H-indol-6-yl]methyl]-4-oxo-pyrido[1,2-a]pyrimidine-2-carboxamide;

4-oxo-N-[[2-[[[rac-(1S,2R,4S)-7-oxabicyclo[2.2.1]heptane-5-en-2-yl]methylamino]methyl]-1H-indol-6-yl]methyl]pyrido[1,2-a]pyrimidine-2-carboxamide;

N-[[2-[(1-bicyclo[1.1.1]pentanylamino)methyl]-1H-indol-6-yl]methyl]-4-oxo-pyrido[1,2-a]pyrimidine-2-carboxamide;

N-[[2-[(cyclobutylamino)methyl]-1H-indol-6-yl]methyl]-4-oxo-pyrido[1,2-a]pyrimidine-2-carboxamide;

N-({2-[({bicyclo[2.2.1]heptanean-2-yl}amino)methyl]-1H-indol-6-yl}methyl)-4-oxo-4H-pyrido[1,2-a]pyrimidine-2-carboxamide;

N-[[2-[(cyclopropylamino)methyl]-1H-indol-6-yl]methyl]-4-oxo-pyrido[1,2-a]pyrimidine-2-carboxamide;

N-[[2-(2-azabicyclo[2.2.2]octan-2-ylmethyl)-1H-indol-6-yl]methyl]-4-oxo-pyrido[1,2-a]pyrimidine-2-carboxamide;

N-[[2-[[(2,2-difluorocyclopropyl)methylamino]methyl]-1H-indol-6-yl]methyl]-4-oxo-pyrido[1,2-a]pyrimidine-2-carboxamide;

N-[(2-{[({3-fluorobicyclo[1.1.1]pentan-1-yl}methyl)amino]methyl}-1H-indol-6-yl)methyl]-4-oxo-4H-pyrido[1,2-a]pyrimidine-2-carboxamide;

N-[[2-[(cyclohexylmethylamino)methyl]-1H-indol-6-yl]methyl]-4-oxo-pyrido[1,2-a]pyrimidine-2-carboxamide;

N-[[2-1[[(1-hydroxycyclohexyl)methylamino]methyl]-1H-indol-6-yl]methyl]-4-oxo-pyrido[1,2-a]pyrimidine-2-carboxamide;

N-[[2-[(cyclopentylamino)methyl]-1H-indol-6-yl]methyl]-4-oxo-pyrido[1,2-a]pyrimidine-2-carboxamide;

N-[[2-[(cyclopentylmethylamino)methyl]-1H-indol-6-yl]methyl]-4-oxo-pyrido[1,2-a]pyrimidine-2-carboxamide;

N-[[2-1[[(1-methoxycyclobutyl)methylamino]methyl]-1H-indol-6-yl]methyl]-4-oxo-pyrido[1,2-a]pyrimidine-2-carboxamide;

N-[[2-[(isobutylamino)methyl]-1H-indol-6-yl]methyl]-4-oxo-pyrido[1,2-a]pyrimidine-2-carboxamide;

N-[[2-[(cyclohexylamino)methyl]-1H-indol-6-yl]methyl]-4-oxo-pyrido[1,2-a]pyrimidine-2-carboxamide;

N-[[2-[(cyclopropylmethylamino)methyl]-1H-indol-6-yl]methyl]-4-oxo-pyrido[1,2-a]pyrimidine-2-carboxamide;

4-oxo-N-[[2-[(prop-2-ynylamino)methyl]-1H-indol-6-yl]
methyl]pyrido[1,2-a]pyrimidine-2-carboxamide;
N-[[2-[(oxetan-2-ylmethylamino)methyl]-1H-indol-6-yl]
methyl]-4-oxo-pyrido[1,2-a]pyrimidine-2-carboxam-
ide;
N-[[2-[(2,2-dimethylpropylamino)methyl]-1H-indol-6-
yl]methyl]-4-oxo-pyrido[1,2-a]pyrimidine-2-carbox-
amide;
N-[[2-[(1-bicyclo[1.1.1]pentanylmethylamino)methyl]-
1H-indol-6-yl]methyl]-4-oxo-pyrido[1,2-a]pyrimi-
dine-2-carboxamide;
N-{[2-({[(1S,2S)-2-hydroxycyclopentyl]amino}methyl)-
1H-indol-6-yl]methyl}-4-oxo-4H-pyrido[1,2-a]pyrimi-
dine-2-carboxamide;
N-{[2-({[(1R,2R)-2-hydroxycyclopentyl]
amino}methyl)-1H-indol-6-yl]methyl}-4-oxo-4H-
pyrido[1,2-a]pyrimidine-2-carboxamide;
N-{[2-({[(1S,2R)-2-hydroxycyclopentyl]amino}methyl)-
1H-indol-6-yl]methyl}-4-oxo-4H-pyrido[1,2-a]pyrimi-
dine-2-carboxamide;
N-{[2-({[(1R,2S)-2-hydroxycyclopentyl]amino}methyl)-
1H-indol-6-yl]methyl}-4-oxo-4H-pyrido[1,2-a]pyrimi-
dine-2-carboxamide;
N-[[2-[(cyclopropylmethylamino)methyl]-5-fluoro-1H-
indol-6-yl]methyl]-4-oxo-pyrido[1,2-a]pyrimidine-2-
carboxamide;
N-[[2-[(cyclobutylmethylamino)methyl]-5-fluoro-1H-in-
dol-6-yl]methyl]-4-oxo-pyrido[1,2-a]pyrimidine-2-
carboxamide;
4-oxo-N-[[2-[(2,2,2-trifluoroethylamino)methyl]-1H-in-
dol-6-yl]methyl]pyrido[1,2-a]pyrimidine-2-carboxam-
ide;
N-[(2-{[N-(cyclobutylmethyl)acetamido]methyl}-1H-in-
dol-6-yl)methyl]-4-oxo-4H-pyrido[1,2-a]pyrimidine-
2-carboxamide;
4-oxo-N-{[2-(piperidin-2-yl)-1H-indol-6-yl]methyl}-4H-
pyrido[1,2-a]pyrimidine-2-carboxamide;
N-[(2-{[(cyclobutylmethyl)amino]methyl}-3-fluoro-1H-
indol-6-yl)methyl]-4-oxo-4H-pyrido[1,2-a]pyrimi-
dine-2-carboxamide;
N-[(2-{[(cyclobutylmethyl)amino]methyl}-1-methyl-1H-
indol-6-yl)methyl]-4-oxo-4H-pyrido[1,2-a]pyrimi-
dine-2-carboxamide;
N-[[2-[(Cyclobutylmethylamino)-dideuterio-methyl]-1H-
indol-6-yl]methyl]-4-oxo-pyrido[1,2-a]pyrimidine-2-
carboxamide;
N-[[2-[(cyclobutylmethylamino)methyl]-1H-pyrrolo[3,2-
b]pyridin-6-yl]methyl]-4-oxo-pyrido[1,2-a]pyrimi-
dine-2-carboxamide;
N-(1H-indol-6-ylmethyl)-4-oxo-pyrido[1,2-a]pyrimi-
dine-2-carboxamide;
N-(1H-indol-2-ylmethyl)-4-oxo-pyrido[1,2-a]pyrimi-
dine-2-carboxamide;
N-(indolizin-2-ylmethyl)-4-oxo-pyrido[1,2-a]pyrimi-
dine-2-carboxamide;
2-[1-[[2-[(cyclobutylmethylamino)methyl]-1H-indol-6-
yl]methyl]triazol-4-yl]pyrido[1,2-a]pyrimidin-4-one;
N-[[2-(2-azaspiro[3.3]heptanean-2-ylmethyl)-1H-indol-
6-yl]methyl]-4-oxo-pyrido[1,2-a]pyrimidine-2-carbox-
amide;
N-[[2-[(benzylamino)methyl]-1H-indol-6-yl]methyl]-4-
oxo-pyrido[1,2-a]pyrimidine-2-carboxamide;
N-[[2-(3-azabicyclo[3.1.0]hexan-3-ylmethyl)-1H-indol-
6-yl]methyl]-4-oxo-pyrido[1,2-a]pyrimidine-2-carbox-
amide;
N-[[2-[[cyclobutylmethyl(methyl)amino]methyl]-1H-in-
dol-6-yl]methyl]-4-oxo-pyrido[1,2-a]pyrimidine-2-
carboxamide;
N-[[2-[(cyclobutylmethylamino)methyl]-1H-pyrrolo[2,3-
b]pyridin-6-yl]methyl]-4-oxo-pyrido[1,2-a]pyrimi-
dine-2-carboxamide;
N-[(2-{[(cyclobutylmethyl)amino]methyl}-1H-1,3-ben-
zodiazol-6-yl)methyl]-4-oxo-4H-pyrido[1,2-a]pyrimi-
dine-2-carboxamide;
N-[(2-{[(but-2-yn-1-yl)amino]methyl}-1H-indol-6-yl)
methyl]-4-oxo-4H-pyrido[1,2-a]pyrimidine-2-carbox-
amide;
N-[(2-{[(3-cyclopropylprop-2-yn-1-yl)amino]methyl}-
1H-indol-6-yl)methyl]-4-oxo-4H-pyrido[1,2-a]pyrimi-
dine-2-carboxamide;
N-({2-[({bicyclo[3.1.0]hexan-6-yl}amino)methyl]-1H-
indol-6-yl}methyl)-4-oxo-4H-pyrido[1,2-a]pyrimi-
dine-2-carboxamide;
N-[(2-{[({bicyclo[2.1.1]hexan-1-yl}methyl)amino]
methyl}-1H-indol-6-yl)methyl]-4-oxo-4H-pyrido[1,2-
a]pyrimidine-2-carboxamide;
N-[(2-{[({3-methylbicyclo[1.1.1]pentan-1-yl}methyl)
amino]methyl}-1H-indol-6-yl)methyl]-4-oxo-4H-
pyrido[1,2-a]pyrimidine-2-carboxamide;
N-({2-[(3-methylazetidin-1-yl)methyl]-1H-indol-6-
yl}methyl)-4-oxo-4H-pyrido[1,2-a]pyrimidine-2-car-
boxamide;
N-({2-[(3-fluoroazetidin-1-yl)methyl]-1H-indol-6-
yl}methyl)-4-oxo-4H-pyrido[1,2-a]pyrimidine-2-car-
boxamide;
N-({2-[(azetidin-1-yl)methyl]-1H-indol-6-yl}methyl)-4-
oxo-4H-pyrido[1,2-a]pyrimidine-2-carboxamide;
N-{[2-({2-azaspiro[3.4]octan-2-yl}methyl)-1H-indol-6-
yl]methyl}-4-oxo-4H-pyrido[1,2-a]pyrimidine-2-car-
boxamide;
N-({2-[(3-hydroxyazetidin-1-yl)methyl]-1H-indol-6-
yl}methyl)-4-oxo-4H-pyrido[1,2-a]pyrimidine-2-car-
boxamide;
N-({2-[(3,3-dimethylazetidin-1-yl)methyl]-1H-indol-6-
yl}methyl)-4-oxo-4H-pyrido[1,2-a]pyrimidine-2-car-
boxamide;
4-oxo-N-[(2-{[3-(2,2,2-trifluoroethoxy)azetidin-1-yl]
methyl}-1H-indol-6-yl)methyl]-4H-pyrido[1,2-a]py-
rimidine-2-carboxamide;
N-[(2-{[3-(difluoromethyl)azetidin-1-yl]methyl}-1H-in-
dol-6-yl)methyl]-4-oxo-4H-pyrido[1,2-a]pyrimidine-
2-carboxamide;
N-({2-[(3-methoxyazetidin-1-yl)methyl]-1H-indol-6-
yl}methyl)-4-oxo-4H-pyrido[1,2-a]pyrimidine-2-car-
boxamide;
N-[(2-{[3-(tert-butoxy)azetidin-1-yl]methyl}-1H-indol-
6-yl)methyl]-4-oxo-4H-pyrido[1,2-a]pyrimidine-2-car-
boxamide;
4-oxo-N-[(2-{[3-(trifluoromethyl)azetidin-1-yl]methyl}-
1H-indol-6-yl)methyl]-4H-pyrido[1,2-a]pyrimidine-2-
carboxamide;
N-({2-[(3-ethoxyazetidin-1-yl)methyl]-1H-indol-6-
yl}methyl)-4-oxo-4H-pyrido[1,2-a]pyrimidine-2-car-
boxamide;
N-{[2-({2-azaspiro[3.5]nonan-2-yl}methyl)-1H-indol-6-
yl]methyl}-4-oxo-4H-pyrido[1,2-a]pyrimidine-2-car-
boxamide;
N-({2-[(2-methylazetidin-1-yl)methyl]-1H-indol-6-
yl}methyl)-4-oxo-4H-pyrido[1,2-a]pyrimidine-2-car-
boxamide;

N-({2-[(3,3-dimethylpyrrolidin-1-yl)methyl]-1H-indol-6-yl}methyl)-4-oxo-4H-pyrido[1,2-a]pyrimidine-2-carboxamide;

N-{[2-({6-fluoro-2-azaspiro[3.3]heptanean-2-yl}methyl)-1H-indol-6-yl]methyl}-4-oxo-4H-pyrido[1,2-a]pyrimidine-2-carboxamide;

N-{[2-({6,6-difluoro-2-azaspiro[3.3]heptanean-2-yl}methyl)-1H-indol-6-yl]methyl}-4-oxo-4H-pyrido[1,2-a]pyrimidine-2-carboxamide;

N-({2-[(3-cyclobutylazetidin-1-yl)methyl]-1H-indol-6-yl}methyl)-4-oxo-4H-pyrido[1,2-a]pyrimidine-2-carboxamide;

N-({2-[(3-cyclopropylazetidin-1-yl)methyl]-1H-indol-6-yl}methyl)-4-oxo-4H-pyrido[1,2-a]pyrimidine-2-carboxamide;

N-({2-[(3-tert-butylazetidin-1-yl)methyl]-1H-indol-6-yl}methyl)-4-oxo-4H-pyrido[1,2-a]pyrimidine-2-carboxamide;

N-[(2-{1[(1-tert-butylcyclopropyl)amino]methyl}-1H-indol-6-yl)methyl]-4-oxo-4H-pyrido[1,2-a]pyrimidine-2-carboxamide;

N-{[2-({[(3-methylcyclobutyl)methyl]amino}methyl)-1H-indol-6-yl]methyl}-4-oxo-4H-pyrido[1,2-a]pyrimidine-2-carboxamide;

4-oxo-N-[(2-{1[(2,3,3-trimethylbutan-2-yl)amino]methyl}-1H-indol-6-yl)methyl]-4H-pyrido[1,2-a]pyrimidine-2-carboxamide;

N-[(2-{[({imidazo[1,2-a]pyridin-2-yl}methyl)amino]methyl}-1H-indol-6-yl)methyl]-4-oxo-4H-pyrido[1,2-a]pyrimidine-2-carboxamide;

N-({2-[(3,3-diethylazetidin-1-yl)methyl]-1H-indol-6-yl}methyl)-4-oxo-4H-pyrido[1,2-a]pyrimidine-2-carboxamide;

4-oxo-N-[(2-{[(pent-3-yn-1-yl)amino]methyl}-1H-indol-6-yl)methyl]-4H-pyrido[1,2-a]pyrimidine-2-carboxamide;

N-{[2-({6-azaspiro[3.4]octan-6-yl}methyl)-1H-indol-6-yl]methyl}-4-oxo-4H-pyrido[1,2-a]pyrimidine-2-carboxamide;

N-({2-[(2,2-dimethylpyrrolidin-1-yl)methyl]-1H-indol-6-yl}methyl)-4-oxo-4H-pyrido[1,2-a]pyrimidine-2-carboxamide;

N-{[2-({octahydrocyclopenta[c]pyrrol-2-yl}methyl)-1H-indol-6-yl]methyl}-4-oxo-4H-pyrido[1,2-a]pyrimidine-2-carboxamide;

N-{[2-({5-azaspiro[2.4]heptanean-5-yl}methyl)-1H-indol-6-yl]methyl}-4-oxo-4H-pyrido[1,2-a]pyrimidine-2-carboxamide;

N-[(2-{[({3-methoxybicyclo[1.1.1]pentan-1-yl}methyl)amino]methyl}-1H-indol-6-yl)methyl]-4-oxo-4H-pyrido[1,2-a]pyrimidine-2-carboxamide;

4-oxo-N-[(2-{[({spiro[2.2]pentan-1-yl}methyl)amino]methyl}-1H-indol-6-yl)methyl]-4H-pyrido[1,2-a]pyrimidine-2-carboxamide;

4-oxo-N-({2-[({spiro[2.3]hexan-1-yl}amino)methyl]-1H-indol-6-yl}methyl)-4H-pyrido[1,2-a]pyrimidine-2-carboxamide;

N-[(2-{[({3-cyanobicyclo[1.1.1]pentan-1-yl}methyl)amino]methyl}-1H-indol-6-yl)methyl]-4-oxo-4H-pyrido[1,2-a]pyrimidine-2-carboxamide;

N-{[2-({1-oxa-6-azaspiro[3.4]octan-6-yl}methyl)-1H-indol-6-yl]methyl}-4-oxo-4H-pyrido[1,2-a]pyrimidine-2-carboxamide;

N-{[2-({2-azaspiro[4.4]nonan-2-yl}methyl)-1H-indol-6-yl]methyl}-4-oxo-4H-pyrido[1,2-a]pyrimidine-2-carboxamide;

N-[(2-{[(1-methylcyclopentyl)amino]methyl}-1H-indol-6-yl)methyl]-4-oxo-4H-pyrido[1,2-a]pyrimidine-2-carboxamide;

N-{[2-(hydroxymethyl)-1H-indol-6-yl]methyl}-4-oxo-4H-pyrido[1,2-a]pyrimidine-2-carboxamide;

N-[(2-{[(1-cyclobutylcyclopropyl)amino]methyl}-1H-indol-6-yl)methyl]-4-oxo-4H-pyrido[1,2-a]pyrimidine-2-carboxamide;

N-{[2-({[(1-methylcyclobutyl)methyl]amino}methyl)-1H-indol-6-yl]methyl}-4-oxo-4H-pyrido[1,2-a]pyrimidine-2-carboxamide;

4-oxo-N-[(2-{[({spiro[2.3]hexan-5-yl}methyl)amino]methyl}-1H-indol-6-yl)methyl]-4H-pyrido[1,2-a]pyrimidine-2-carboxamide;

N-({2-[({[3-(fluoromethyl)bicyclo[1.1.1]pentan-1-yl]methyl}amino)methyl]-1H-indol-6-yl}methyl)-4-oxo-4H-pyrido[1,2-a]pyrimidine-2-carboxamide;

N-[(2-{[(1-{3-fluorobicyclo[1.1.1]pentan-1-yl}ethyl)amino]methyl}-1H-indol-6-yl)methyl]-4-oxo-4H-pyrido[1,2-a]pyrimidine-2-carboxamide;

N-({2-[(tert-butylamino)methyl]-1H-indol-6-yl}methyl)-4-oxo-4H-pyrido[1,2-a]pyrimidine-2-carboxamide;

N-{[2-(-{2-azaspiro[3.3]heptanean-2-yl}ethyl)-1H-indol-6-yl]methyl}-4-oxo-4H-pyrido[1,2-a]pyrimidine-2-carboxamide;

N-[(2-{[({bicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide;

N-[(2-{[({3-fluorobicyclo[1.1.1]pentan-1-yl}methyl)amino]methyl}-1H-pyrrolo[3,2-b]pyridin-6-yl)methyl]-4-oxo-4H-pyrido[1,2-a]pyrimidine-2-carboxamide;

N-[(2-{[(cyclobutylmethyl)amino]methyl}-1H-pyrrolo[3,2-b]pyridin-6-yl)methyl]-4-oxo-4H-pyrido[1,2-a]pyrimidine-2-carboxamide;

N-[(2-{[({3-methylbicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide;

N-[(2-{[(cyclobutylmethyl)amino]methyl}-1H-pyrrolo[3,2-c]pyridin-6-yl)methyl]-4-oxo-4H-pyrido[1,2-a]pyrimidine-2-carboxamide;

N-[(2-{[({bicyclo[1.1.1]pentan-1-yl}methyl)amino]methyl}-1H-pyrrolo[3,2-c]pyridin-6-yl)methyl]-4-oxo-4H-pyrido[1,2-a]pyrimidine-2-carboxamide;

N-[(2-{[({3-fluorobicyclo[1.1.1]pentan-1-yl}methyl)amino]methyl}-1H-pyrrolo[3,2-c]3]yridin-6-yl)methyl]-4-oxo-4H-pyrido[1,2-a]pyrimidine-2-carboxamide;

N-[(2-{[(cyclobutylmethyl)amino]methyl}-1H-indol-6-yl)methyl]-4-oxo-4H,6H,7H,8H,9H-pyrido[1,2-a]pyrimidine-2-carboxamide;

N-[(2-{[(2,2-dimethylpropyl)amino]methyl}-1H-indol-6-yl)methyl]-1H-pyrrolo[2,3-b]pyridine-5-carboxamide;

N-[(2-{[(cyclobutylmethyl)amino]methyl}-1H-indol-6-yl)methyl]-1H-pyrrolo[2,3-b]pyridine-5-carboxamide;

N-[[2-(2-azabicyclo[2.2.1]heptanean-2-ylmethyl)-1H-indol-6-yl]methyl]-4-oxo-pyrido[1,2-a]pyrimidine-2-carboxamide; and N-((2-((6-azaspiro[3.4]octan-6-yl)methyl)-1H-pyrrolo[3,2-c]pyridin-6-yl)methyl)-4-oxo-4H-pyrido[1,2-a]pyrimidine-2-carboxamide.

19. A pharmaceutical composition comprising a compound according to claim 1, or a pharmaceutically acceptable salt thereof, and one or more pharmaceutically acceptable excipients.

20. A method of treating:
a) lung cancer, renal cancer, solid organ cancer, pancreatic cancer or leukaemia;
b) AML leukaemia or chronic myeloid leukaemia;
c) an autoimmune disease selected from colitis, multiple sclerosis, rheumatoid arthritis, lupus, cirrhosis, or dermatitis;
d) a RNA viral infection; or
e) Rett syndrome;
said method comprising administering to a subject in need thereof a therapeutically effective amount of a compound according to claim 1, or a pharmaceutically acceptable salt thereof.

21. A method of treating:
a) lung cancer, renal cancer, solid organ cancer, pancreatic cancer or leukaemia;
b) AML leukaemia or chronic myeloid leukaemia;
c) an autoimmune disease selected from colitis, multiple sclerosis, rheumatoid arthritis, lupus, cirrhosis, or dermatitis;
d) a RNA viral infection; or
e) Rett syndrome;
said method comprising administering to a subject in need thereof a therapeutically effective amount of a pharmaceutical composition according to claim 19.

* * * * *

UNITED STATES PATENT AND TRADEMARK OFFICE
CERTIFICATE OF CORRECTION

PATENT NO. : 12,195,458 B2
APPLICATION NO. : 17/778701
DATED : January 14, 2025
INVENTOR(S) : Wesley Peter Blackaby et al.

It is certified that error appears in the above-identified patent and that said Letters Patent is hereby corrected as shown below:

In the Claims

In Claim 16 at Column 404, Line number 18, please cancel:
"--tically acceptable salt thereof, wherein:"
And insert the following:
--tically acceptable salt thereof, wherein X is--

In Claim 18 at Column 405, Line number 49, please cancel:
"N-[[2-1[[(3,3-difluorocyclobutyl)methylamino]methyl]-"
And insert the following:
--N-[[2-[1][[(3,3-difluorocyclobutyl)methylamino]methyl]- --

In Claim 18 at Column 406, Line number 11, please cancel:
"N-[[2-1[(4-fluoro-1-piperidyl)methyl]-1H-indol-6-yl]-"
And insert the following:
--N-[[2-[1][(4-fluoro-1-piperidyl)methyl]-1H-indol-6-yl]- --

In Claim 18 at Column 406, Line number 48, please cancel:
"N-[[2-1[[(1-hydroxycyclohexyl)methylamino]methyl]"
And insert the following:
--N-[[2-[1][[(1-hydroxycyclohexyl)methylamino]methyl]- --

In Claim 18 at Column 406, Line number 57, please cancel:
"N-[[2-1[[(1-methoxycyclobutyl)methylamino]methyl]"
And insert the following:
--N-[[2-[1][[(1-methoxycyclobutyl)methylamino]methyl]- --

In Claim 18 at Column 410, Line number 48, please cancel:
"-amino]methyl}-1H-pyrrolo[3,2-c]31yridine-6-yl)"

Signed and Sealed this
Thirteenth Day of May, 2025

Coke Morgan Stewart
*Acting Director of the United States Patent and Trademark Office*

And insert the following:
--amino]methyl}-1H-pyrrolo[3,2-c]pyridine-6-yl)- --